US010660950B2

(12) United States Patent
Barbero Calzado et al.

(10) Patent No.: US 10,660,950 B2
(45) Date of Patent: *May 26, 2020

(54) VIRUS PURIFICATION

(71) Applicant: Valneva SE, Nantes (FR)

(72) Inventors: Jana Barbero Calzado, Vienna (AT); Mario Nebenführ, Vienna (AT); Robert Schlegl, Siegenfeld (AT); Michael Weber, Vienna (AT); Jürgen Heindl-Wruss, Vienna (AT)

(73) Assignee: Valneva SE, Nantes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/781,959

(22) PCT Filed: Dec. 23, 2016

(86) PCT No.: PCT/EP2016/082663
§ 371 (c)(1),
(2) Date: Jun. 6, 2018

(87) PCT Pub. No.: WO2017/109224
PCT Pub. Date: Jun. 29, 2017

(65) Prior Publication Data
US 2018/0362937 A1    Dec. 20, 2018

(30) Foreign Application Priority Data

| Dec. 23, 2015 | (EP) | ................................. 15202585 |
| Mar. 18, 2016 | (EP) | ................................. 16161068 |
| Jun. 23, 2016 | (EP) | ................................. 16176025 |
| Jun. 23, 2016 | (EP) | ................................. 16176049 |
| Aug. 4, 2016  | (EP) | ................................. 16182845 |

(51) Int. Cl.
| C12N 7/02  | (2006.01) |
| A61K 39/12 | (2006.01) |
| A61P 31/14 | (2006.01) |
| C07K 14/18 | (2006.01) |
| C12N 7/06  | (2006.01) |
| C12N 7/00  | (2006.01) |
| A61K 39/39 | (2006.01) |
| A61K 39/00 | (2006.01) |

(52) U.S. Cl.
CPC .............. *A61K 39/12* (2013.01); *A61K 39/39* (2013.01); *A61P 31/14* (2018.01); *C07K 14/18* (2013.01); *C07K 14/1825* (2013.01); *C12N 7/00* (2013.01); *C12N 7/02* (2013.01); *C12N 7/06* (2013.01); *A61K 2039/5252* (2013.01); *A61K 2039/5254* (2013.01); *A61K 2039/5258* (2013.01); *A61K 2039/55505* (2013.01); *C12N 2770/24134* (2013.01); *C12N 2770/24151* (2013.01); *C12N 2770/24163* (2013.01); *Y02A 50/383* (2018.01); *Y02A 50/386* (2018.01); *Y02A 50/388* (2018.01); *Y02A 50/39* (2018.01); *Y02A 50/392* (2018.01)

(58) Field of Classification Search
CPC .... A61K 2039/5258; A61K 2039/6068; A61K 2039/70; A61K 2039/5254; A61K 31/00; C12N 2770/24151; C12N 2770/24121; C12N 15/86; C12N 2710/24143; C12N 2770/24161; C12N 2840/203; C12N 15/113; C12N 2770/24111; C12N 2770/24221; C12N 2770/36151; Y02A 50/386; Y02A 50/53; Y02A 50/60; Y02A 50/385; Y02A 50/387; Y02A 50/393; Y02A 50/51; Y02A 50/389; Y02A 50/395

See application file for complete search history.

(56) References Cited

U.S. PATENT DOCUMENTS

| 6,309,650    | B1  | 10/2001 | Kim et al.                    |
| 7,871,814    | B2* | 1/2011  | Andino-Pavlovsky ..................... C07K 14/005 435/320.1 |
| 8,765,148    | B2  | 7/2014  | Wizel et al.                  |
| 9,499,588    | B2* | 11/2016 | Mason ................. C07K 14/005 |
| 10,086,061   | B2* | 10/2018 | Thomas ................. A61K 39/12 |
| 10,537,630   | B2  | 1/2020  | Barbero Calzado et al.        |
| 2018/0362936 | A1  | 12/2018 | Barbero Calzado et al.        |
| 2018/0369359 | A1  | 12/2018 | Barbero Calzado et al.        |
| 2018/0371027 | A1  | 12/2018 | Barbero Calzado et al.        |
| 2019/0008945 | A1  | 1/2019  | Barbero Calzado et al.        |

FOREIGN PATENT DOCUMENTS

| CN | 105749268 A        | 7/2016  |
| WO | WO 1999/011762 A1  | 3/1999  |
| WO | WO 2001/092552 A2  | 12/2001 |
| WO | WO 2013/083726 A1  | 6/2013  |
| WO | WO 2016/145149 A1  | 9/2016  |

OTHER PUBLICATIONS

U.S. Appl. No. 16/062,245, filed Jun. 14, 2018, Barbero Calzado et al.
PCT/EP2016/082663, Jul. 5, 2018, International Preliminary Report and Patentability.
PCT/EP2016/082663, Apr. 19, 2017, International Search Report and Written Opinion.
PCT/EP2016/082662, Jul. 5, 2018, International Preliminary Report and Patentability.
PCT/EP2016/082662, Apr. 18, 2017, International Search Report and Written Opinion.
U.S. Appl. No. 16/702,764, filed Dec. 4, 2019, Barbero Calzado et al.
[No Author Listed] Valneva Reports Excellent Final Phase 1 Results for its Chikungunya Vaccine Candidate, Confirms Plans. Press release. Nov. 18, 2019.
[No Author Listed] Centers for Disease Control and Prevention. Ingredients of vaccines fact sheet; continuously updated; https://www.cdc.gov/vaccines/vac-gen/additives.htm.

(Continued)

*Primary Examiner* — Bao Q Li

(74) *Attorney, Agent, or Firm* — Wolf, Greenfield & Sacks, P.C.

(57) ABSTRACT

Described herein are processes for purifying infectious virus particles and uses of protamine in such processes.

14 Claims, 35 Drawing Sheets

Specification includes a Sequence Listing.

(56) References Cited

OTHER PUBLICATIONS

[No Author Listed] Japanese Encephalitis Vaccine. Centers for Disease Control and Prevention, 2016. Retrieved from https://www.cdc.gov/japaneseencephalitis/vaccine/ on Jun. 16, 2016.

[No Author Listed] Pan-American Health Organization, 2015. Number of Reported Cases of Chikungunya Fever in the Americas, by Country or Territory 2013-2014. Cumulative Cases (Updated Oct. 23, 2015).

[No Author Listed] Protamine sulfate. Wikimedia Foundation, Inc., 2015. Retrieved from https://en.wikipedia.org/wiki/Protamine_sulfate; updated Sep. 30, 2015 on Nov. 26, 2015.

[No Author Listed] Valneva Announces Successful Generation of a Highly-purified Zika Vaccine Candidate Using its FDA-EMA Approved Japanese Encephalitis Platform. Press release. Jul. 7, 2016.

[No Author Listed] World Health Organization, 2016Zika Situation Report Feb. 5, 2016.

[No Author Listed] World Health Organization, 2016Zika Virus Fact Sheet 2016. Retrieved from http://www.who.int/mediacentre/factsheets/zika/en/ on Mar. 11, 2016.

[No Author Listed] Zika virus, strain H/PF/2013. European virus archive, 2016.

Abbink et al., Durability and correlates of vaccine protection against Zika virus in rhesus monkeys. Sci. Transl. Med. 9, eaao4163 (2017).

Altschul et al., Basic Local Alignment Search Tool. J. Mol. Biol. 1990;215:403-410.

Altschul et al., Gapped BLAST and PSI-BLAST: a new generation of protein database search programs. Nuc. Acids Res. 1997;25(17):3389-3402.

Baronti et al., Complete Coding Sequence of Zika Virus from a French Polynesia Outbreak in 2013. Genome Announc. May-Jun. 2014; 2(3):e00500-14. Abstract.

Bender et al., Zika Virus Vaccine Candidate VLA1601: Cooperation Valneva & Emergent. Presentation at World Vaccine Congress Apr. 4, 2018.

Cohen, Infectious Disease. The race for a Zika vaccine is on. Science. Feb. 5, 2016;351(6273):543-4. doi: 10.1126/science.351.6273.543.

Cox et al., Predicting Zika virus structural biology:Challenges and opportunities for intervention. Antivir Chem Chemother. Aug. 2015;24(3-4):118-26. doi: 10.1177/2040206616653873. Epub Jun. 13, 2016.

Dowall et al., A susceptible mouse model for Zika virus infection. PLOS Neglected Tropical Diseases.10(5):e0004658. May 5, 2016. DOI:10.1371/journal.pntd.0004658.

Fritsche et al., Vaccine hypersensitivity—update and overview. Swiss Med Wkly. 2010;140(17-18):238-246.

Gardner et al., Deliberate Attenuation of Chikungunya Virus by Adaptation to Heparan Sulfate-Dependent Infectivity: A Model of Rational Arboviral Vaccine Design. PLOS Neglected Tropical Diseases. 2014;8(2):e2719.

Geradin et al., Chikungunya virus-associated encephalitis: A cohort study on La Réunion Island. 2005-2009. Neurology. 86(1):94-102.

Gubler et al., Fields Virology. Knipe DM, Howley PM, editors. Lippincott-Raven Publishers; Philadelphia: 2007. pp. 1153-1252.

Haddow et al., Genetic Characterization of Zika Virus Strains: Geographic Expansion of the Asian Lineage. PLoS Negl Trop Dis 6(2): e1477. doi:10.1371/journal.pntd.0001477.

Hallengard et al., Novel Attenuated Chikungunya Vaccine Candidates Elicit Protective Immunity in C57BL/6 mice. J. Virology 88(5):2858-2866.

Hallengard et al., Prime-Boost Immunization Strategies against Chikungunya Virus. J. Virology. 88(22):13333-13343.

Hombach et al., Report on a WHO consultation on immunological endpoints for evaluation of new Japanese encephalitis vaccines, WHO, Geneva, Sep. 2-3, 2004. Vaccine. 2005; 23(45):5205-5211.

Hutornojs et al., Comparison of ultracentrifugation methods for concentration of recombinant alphaviruses: sucrose and iodixanol cushions. Environmental Experimental Biology. 2012;10:117-123.

Katoh et al., Recent developments in the MAFFT multiple sequence alignment program. Briefings in Bioinformatics. 2008;9(4):286-298.

Kim et al., Design of Chimeric Alphaviruses with a Programmed, Attenuated, Cell Type-Restricted Phenotype. J Virol. 2011;85(9):4363-4376.

Konishi et al., Studies on structural proteins of Chikungunya Virus. I. Separation of three species of proteins and their preliminary characterization. Microbiol Immunol. 1980;24(5):419-28.

Larkin et al., Clustal W and Clustal X version 2.0. Bioinformatics. 2007;23(21):2947-2948.

Larocca et al., Vaccine protection against Zika virus from Brazil. Nature. 2016;536:474-478. doi:10.1038/nature18952. Methods.

Lindenbach et al., Fields Virology. Knipe DM, Howley PM, editors. Lippincott-Raven Publishers; Philadelphia: 2007. pp. 1101-1152.

Malone et al., Zika Virus: Medical Countermeasure Development Challenges. PLoS Negl Trop Dis. 2016;10(3):e0004530. doi:10.1371/journal.pntd.0004530.

Modjarrad et al., Preliminary aggregate safety and immunogenicity results from three trials of a purified inactivated Zika virus vaccine candidate: phase 1, randomised, double-blind, placebo-controlled clinical trials. Dec. 4, 2017.

Monath, Yellow fever: an update. Lancet Infect Dis. 2001;1(1):11-20.

Needleman et al., A general method applicable to the search for similarities in the amino acid sequence of two proteins. J. Mol. Biol. 1970;48(3):443-453.

Patkar et al., Yellow Fever virus NS3 plays an essential role in virus assembly independent of its known enzymatic functions. J Virol. Apr. 2008;82(7):3342-52. doi: 10.1128/JVI.02447-07. Epub Jan. 16, 2008.

Pearson et al., Improved tools for biological sequence comparison. Proc. Natl. Acad. Sci. USA. 1988;85(8):2444-8.

Pellerin, Walter Reed Scientists Test Zika Vaccine Candidate. U.S. Department of Defense. Jun. 9, 2016.

Pinto et al., A Temporal Role of Type I Interferon Signaling in CD8+ T Cell Maturation during Acute West Nile Virus Infection. PLoS Pathog. Dec. 2011;7(12): e1002407.

Plevka et al., Maturation of flaviviruses starts from one or more icosahedrally independent nucleation centres. EMBO reports. 2011;12(6):602-606.

Reed et al., A simple method of estimating fifty percent endpoints. American J Hygiene. May 1938;27:493-497.

Rocha et al., Microcephaly: normality parameters and its determinants in northeastern Brazil: a multicentre prospective cohort study. Bull World Health Organ, E-pub: Feb. 8, 2016. doi:http://dx.doi.org/10.2471/BLT.16.171215.

Rozen-Gagnon et al., Alphavirus Mutator Variants Present Host-Specific Defects and Attenuation in Mammalian and Insect Models, PLOS Pathogens, 10(1):e1003877.

Schlegl et al., Influence of elemental impurities in aluminum hydroxide adjuvant on the stability of inactivated Japanese Encephalitis vaccine, IXIARO®. Vaccine. 2015;33(44):5989-5996.

Shustov et al., Efficient, trans-complementing packaging systems for chimeric, pseudoinfectious dengue 2/yellow fever viruses. Virology. Apr. 25, 2010;400(1):8-17. doi: 10.1016/j.virol.2009.12.015.

Simizu et al., Structural Proteins of Chikungunya Virus, J Virol. 1984;51(1): 254-258.

Smith et al., Comparison of Biosequences. Adv. Appl. Math. 1981;2:482-489.

Srivastava et al., A purified inactivated Japanese encephalitis virus vaccine made in vero cells. Vaccine. 2001;19:4557-4565.

Tiwari et al., Assessment of immunogenic potential of Vero adapted formalin inactivated vaccine derived from novel ECSA genotype of Chikungunya virus. Vaccine. Apr. 21, 2009;27(18):2513-22. doi: 10.1016/j.vaccine.2009.02.062. Epub Feb. 27, 2009.

Vega-Rua et al., Chikungunya Virus Transmission Potential by Local Aedes Mosquitoes in the Americas and Europe. PLOS Neglected Tropical Diseases. 2015;9(5):e000378

Waterhouse et al., Jalview Version 2—a multiple sequence alignment editor and analysis workbench. Bioinformatics. 2009;25(9):1189-1191.

(56) References Cited

OTHER PUBLICATIONS

Way et al., Comparative Studies of some African Arboviruses in Cell Culture and in Mice, J Gen. Virol. 1976;30:123-130.
Weaver et al., Arrival of Chiungunya Virus in the New Word: Prospects for Spread and Impact on Public Health. PLoS Negl Trop Dis. 2014;8(6): e2921. doi:10.1371/journal.pntd.0002921.

* cited by examiner

| | | 0 | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|---|
| 0 | DVV_1.NC_001477.1 | 100.0 | 70.7 | 70.8 | 67.8 | 60.5 | 60.4 | 60.5 | 60.5 | 60.7 | 55.8 | 60.6 | 60.3 | 60.5 | 58.0 | 57.9 | 57.9 | 58.0 | 62.3 | 62.3 | 62.3 | 61.3 |
| 1 | DVV_16681.NC_001474.2 | 70.7 | 100.0 | 70.9 | 68.6 | 60.5 | 60.5 | 60.6 | 60.6 | 60.7 | 54.9 | 60.9 | 60.3 | 60.4 | 58.3 | 58.3 | 58.3 | 58.3 | 62.7 | 62.8 | 62.8 | 62.2 |
| 2 | DVV_3.NC_001475.2 | 70.5 | 70.9 | 100.0 | 68.9 | 60.2 | 60.1 | 60.1 | 60.1 | 60.1 | 55.8 | 60.3 | 60.0 | 60.1 | 57.6 | 57.6 | 57.5 | 57.5 | 62.7 | 62.7 | 62.7 | 62.5 |
| 3 | DVV_4.NC_002640.1 | 67.8 | 68.0 | 68.9 | 100.0 | 60.5 | 60.6 | 60.6 | 60.6 | 60.4 | 55.4 | 60.8 | 60.3 | 60.5 | 58.0 | 57.9 | 57.9 | 57.9 | 62.1 | 62.0 | 62.0 | 62.1 |
| 4 | JEV_SA14-14-2.AF315119.1 | 60.5 | 60.5 | 60.6 | 60.5 | 100.0 | 99.8 | 99.4 | 99.5 | 98.6 | 56.5 | 70.6 | 70.5 | 70.5 | 57.7 | 57.9 | 57.9 | 58.0 | 61.9 | 61.8 | 61.8 | 61.4 |
| 5 | JEV_SA14-14-2.D90195.1 | 60.4 | 60.5 | 60.6 | 60.6 | 99.8 | 100.0 | 99.4 | 99.5 | 98.4 | 56.6 | 70.5 | 70.4 | 70.5 | 57.9 | 57.9 | 57.9 | 58.0 | 61.8 | 61.8 | 61.8 | 61.5 |
| 6 | JEV_SA14.D90194.1 | 60.5 | 60.6 | 60.6 | 60.6 | 99.4 | 99.4 | 100.0 | 99.8 | 98.6 | 56.6 | 70.3 | 70.3 | 70.4 | 58.0 | 58.0 | 58.0 | 58.0 | 61.9 | 61.8 | 61.8 | 61.6 |
| 7 | JEV_virus.M55506.1 | 60.6 | 60.6 | 60.6 | 60.6 | 99.5 | 99.5 | 99.8 | 100.0 | 98.6 | 56.7 | 70.3 | 70.4 | 70.4 | 58.0 | 58.1 | 58.0 | 58.1 | 61.9 | 61.8 | 61.8 | 61.6 |
| 8 | JEV_virus.NC_001437.1 | 60.7 | 60.7 | 60.4 | 60.4 | 98.6 | 98.4 | 98.6 | 98.6 | 100.0 | 56.6 | 70.5 | 70.4 | 70.5 | 58.0 | 58.3 | 58.3 | 58.3 | 62.1 | 62.0 | 62.0 | 61.7 |
| 9 | TEV_virus.NC_001672.1 | 55.8 | 54.9 | 55.8 | 55.4 | 56.5 | 56.6 | 56.6 | 56.7 | 56.6 | 100.0 | 56.2 | 56.7 | 56.6 | 56.9 | 57.0 | 57.0 | 57.0 | 56.7 | 56.7 | 56.7 | 56.7 |
| 10 | WNV_956.NC_001563.2 | 60.6 | 60.9 | 60.3 | 60.8 | 70.5 | 70.4 | 70.3 | 70.3 | 70.5 | 56.2 | 100.0 | 79.6 | 85.0 | 58.1 | 58.0 | 58.1 | 58.2 | 62.4 | 62.3 | 62.1 | 62.2 |
| 11 | WNV_Chin-01.AY490240.2 | 60.3 | 60.3 | 60.0 | 60.3 | 70.4 | 70.4 | 70.4 | 70.4 | 70.4 | 56.7 | 79.6 | 100.0 | 95.2 | 58.2 | 58.0 | 58.2 | 58.2 | 62.0 | 62.1 | 62.1 | 62.7 |
| 12 | WNV_NY99_isol-385-99.NC_009942.1 | 60.6 | 60.4 | 60.1 | 60.5 | 70.5 | 70.5 | 70.4 | 70.4 | 70.5 | 56.6 | 85.0 | 95.2 | 100.0 | 57.8 | 57.8 | 57.8 | 57.8 | 62.0 | 62.0 | 62.0 | 62.4 |
| 13 | YFV_17D_vaccine_strain.NC_002031.1 | 58.0 | 58.3 | 58.0 | 58.0 | 57.7 | 57.9 | 58.0 | 58.0 | 58.3 | 56.9 | 58.1 | 58.2 | 57.8 | 100.0 | 99.4 | 99.4 | 99.9 | 58.5 | 58.5 | 58.5 | 58.2 |
| 14 | YFV_ASIB.AY640589.1 | 57.9 | 58.3 | 57.9 | 58.0 | 57.9 | 58.0 | 58.0 | 58.1 | 58.3 | 57.0 | 58.0 | 58.2 | 57.8 | 99.4 | 100.0 | 99.4 | 99.4 | 58.4 | 58.4 | 58.4 | 58.1 |
| 15 | YFV_Pasteur_17D-204.X15062.1 | 57.9 | 58.3 | 57.5 | 57.9 | 58.0 | 57.9 | 58.0 | 58.0 | 58.4 | 57.0 | 58.1 | 58.2 | 57.8 | 99.4 | 99.4 | 100.0 | 99.9 | 58.4 | 58.4 | 58.4 | 58.2 |
| 16 | YFV_vaccine_strain_17D-213.U17067.1 | 58.0 | 58.3 | 57.5 | 57.9 | 58.0 | 58.0 | 58.0 | 58.1 | 58.3 | 57.0 | 58.2 | 58.2 | 57.8 | 99.9 | 99.4 | 99.9 | 100.0 | 58.4 | 58.4 | 58.4 | 58.1 |
| 17 | ZVV_MR766-NIID.LC002520.1 | 62.3 | 62.7 | 62.1 | 61.9 | 61.9 | 61.8 | 61.9 | 61.9 | 62.1 | 56.7 | 62.4 | 62.0 | 62.0 | 58.5 | 58.5 | 58.4 | 58.4 | 100.0 | 99.7 | 99.7 | 88.9 |
| 18 | ZVV_MR_766.AY632535.2 | 62.3 | 62.8 | 62.0 | 61.8 | 61.8 | 61.8 | 61.8 | 61.8 | 62.0 | 56.7 | 62.3 | 62.1 | 62.0 | 58.5 | 58.4 | 58.4 | 58.4 | 99.7 | 100.0 | 100.0 | 88.8 |
| 19 | ZVV_MR_766.NC_012532.1 | 62.3 | 62.8 | 62.0 | 61.8 | 61.8 | 61.8 | 61.8 | 61.8 | 62.0 | 56.7 | 62.3 | 62.1 | 62.0 | 58.5 | 58.4 | 58.4 | 58.4 | 99.7 | 100.0 | 100.0 | 88.8 |
| 20 | ZVV_ZikaSPH2015.KU321639.1 | 61.3 | 62.2 | 62.5 | 62.1 | 61.4 | 61.5 | 61.6 | 61.6 | 61.7 | 56.7 | 62.2 | 62.7 | 62.4 | 58.2 | 58.1 | 58.2 | 58.1 | 88.9 | 88.8 | 88.8 | 100.0 |

60 % Identity and higher
70 % Identity and higher
80 % Identity and higher

Figure 3

JEV_SA14.D90194.1
JEV_virus.NC_001437.1
JEV_virus.M55506.1
JEV_SA14-14-2.AF315119.1
JEV_SA14-14-2.D90195.1
WNV_956.NC_001563.2
WNV_NY99_isol-385-99.NC_009942.1
WNV_Chin-01.AY490240.2
DVV_1.NC_001477.1
DVV_3_isol-D3%H%IMTSSA-SRI%2000%1266.NC_001475.2
DVV_16681.NC_001474.2
DVV_4.NC_002640.1
ZVV_MR766-NIID.LC002520.1
ZVV_MR_766.NC_012532.1
ZVV_MR_766.AY632535.2
ZVV_ZikaSPH2015.KU321639.1
ZVV_BeH818995.KU365777.1
YFV_ASIBI.AY640589.1
YFV_17D_vaccine_strain.NC_002031.1
YFV_virus_isol-Pasteur_17D-204_yellow_fever_vaccine.X15062.1
YFV_vaccine_strain_17D-213.U17067.1
TEV_virus.NC_001672.1

Figure 4

Figure 7 (Part 1 of 3)

Figure 7 (Part 2 of 3)

Figure 7 (Part 3 of 3)

| Lane | Sample |
|---|---|
| 1 | Marker Seeblueplus2 |
| 2 | CHIKV lot20150812_WVB2015-01_Filtered harvest0.2μ_24hpi |
| 3 | CHIKV lot20150812_WVB2015-01_Filtered harvest0.2μ_48hpi |
| 4 | 20150812_CHIKV_DSP_UF/DF_Load |
| 5 | 20150812_CHIKV_DSP_UF/DF_conc.10x |
| 6 | 20150813_CHIKV_DSP_UF/DF_conc.&dia. 11x |
| 7 | 20150813_CHIKV_DSP_PStreatment |
| 8 | 20150813_CHIKV_DSP_PS&CC700treatment |
| 9 | 20150813_CHIKV_DSP_SGCFrac F5 |
| 10 | 20150813_CHIKV_DSP_SGCFrac F6 |
| 11 | 20150813_CHIKV_DSP_SGCPoolF7-F10 |
| 12 | 20150813_CHIKV_DSP_SGCPoolF7-F11 (final pool) |
| 13 | 20150813_CHIKV_DSP_SGCPoolF7-F12 |
| 14 | 20150813_CHIKV_DSP_SGCFrac F13 |
| 15 | 20150813_CHIKV_DSP_SGCFrac F14 |

Figure 11C

Figure 16 (Part 1 of 2)

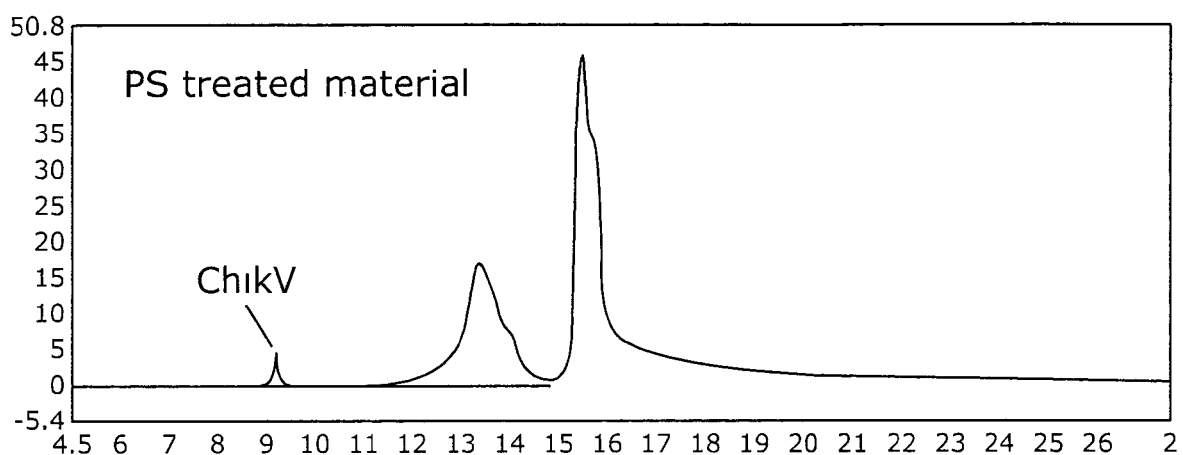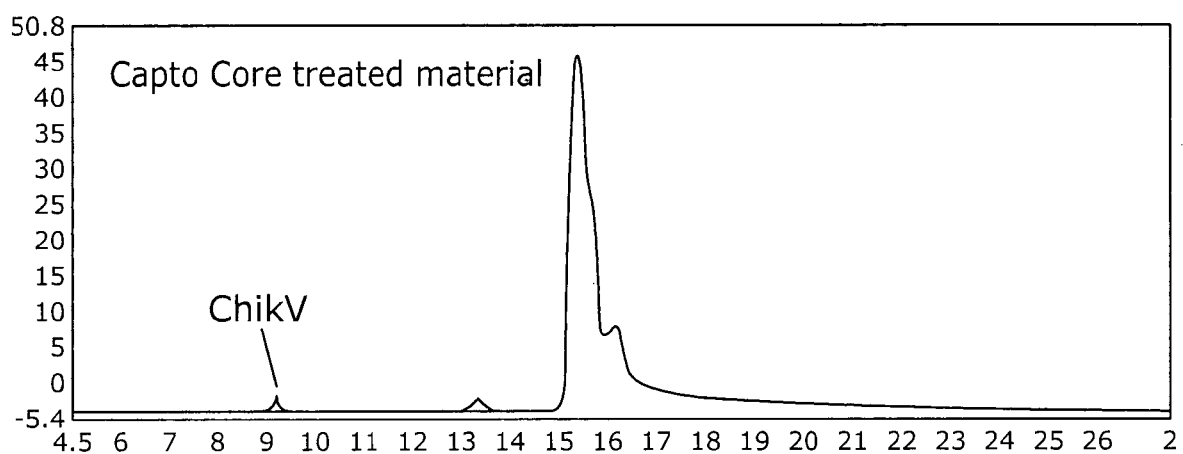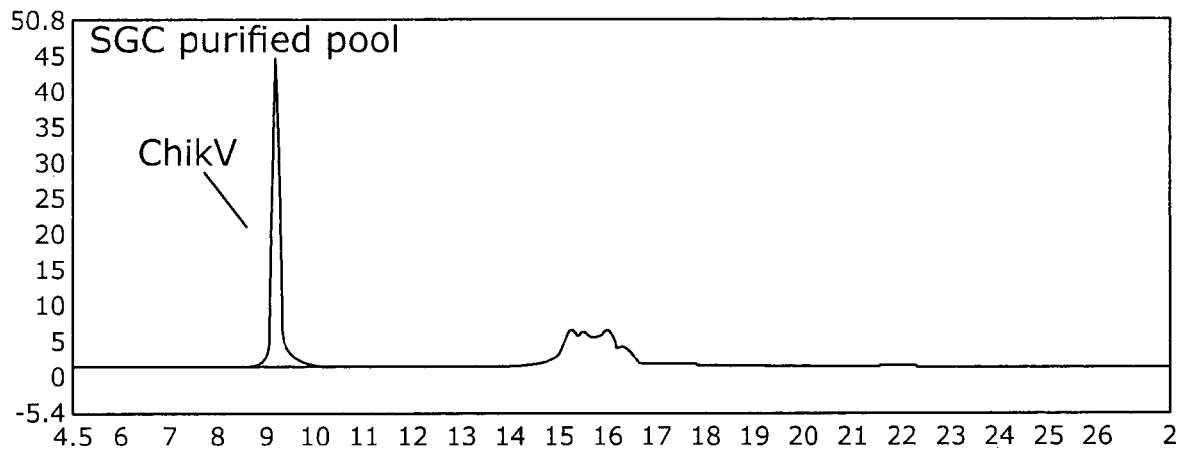
Figure 16 (Part 2 of 2)

Figure 22 rms radius vs. time

— UV_Zika NIV 20160601002 [VLA78-1601_160621]

Monomer ZikaV (Peak 1)

Multimer ZikaV (Peak 2)

Distribution Analysis

Cumulative weight fraction

Differential rms radius

Figure 26

VIRUS PURIFICATION

RELATED APPLICATION

This application is a national stage filing under 35 U.S.C. § 371 of International Patent Application Serial No. PCT/EP2016/082663, filed Dec. 23, 2016, the contents of which is incorporated herein by reference in its entirety.

FIELD OF THE INVENTION

The disclosure relates to methods for the purification of viruses for use in vaccines.

BACKGROUND OF THE INVENTION

Regulatory agencies such as the World Health Organization establish standards and guidelines for the production of pharmaceutical compositions administered to humans, such as vaccines, that limit quantity and components of the compositions. Meeting these standards is particularly challenging with regard to production of vaccines containing biological agents, such as viruses, which must be propagated on cell substrates. Such vaccine preparations must be sterile (i.e., free from independently replicating organisms) and may contain no more than 10 ng of host cell DNA per human dose, among other requirements. These standards are in place in order to ensure safety of the composition for human administration, but may introduce challenges in the development of processes used to produce such compositions.

Protamine was originally isolated from the sperm of salmon and other species of fish but is now produced primarily through recombinant biotechnology. It is a highly cationic peptide that binds to negatively charged molecules such as nucleic acids to form a stable ion pair. Its use in removing host cell nucleic acid is well document.

SUMMARY

During the course of routine virus purification, it was observed that addition of protamine sulfate to a virus harvest produced on a cell substrate removed not only contaminating DNA derived from host cells, as expected, but surprisingly also virtually eliminated immature and otherwise non-infectious virus particles from the preparation. This finding provides a streamlined, gentle, reproducible and broadly-applicable process for obtaining highly-purified infectious virus particles for applications such as vaccine preparation; furthermore, the process is not dependent on the charge of the virus particle.

Disclosed herein are downstream processes for purifying virus particles from a crude preparation. The downstream process can be applied to either a virus which has not adapted for propagation on a particular cell substrate or for a partial/fully cell substrate adapted virus particle.

Aspects of the invention provide processes for the purification of infectious virus particles comprising the steps of (a) providing a crude harvest (a) comprising virus particles and impurities, wherein the impurities are generated from growing said virus particles on a cell substrate; (b) reducing impurities from the crude harvest (a) by precipitation with an agent comprising a protamine salt, preferably a protamine sulphate, to obtain a virus preparation (b); and further purifying the virus preparation (b) by method or methods selecting for size of the virus particles, such as e.g. a sucrose density gradient centrifugation to obtain a virus preparation (c) comprising the infectious virus particles.

In some embodiments, the concentration of protamine sulphate in step (b) is about 1 to 10 mg/ml, more preferably about 1 to 5 mg/ml, more preferably about 1 to 2 mg/ml. In one embodiment, the concentration of protamine sulphate in step (b) is about 2 mg/mL. In one embodiment, the concentration of protamine sulphate is 1.2 to 1.8 mg/ml, more preferably 1.4 to 1.6 mg/ml. In a preferred embodiment, the concentration of protamine sulphate in step (b) is about 1.6 mg/ml or about 2 mg/ml.

In some embodiments, the residual host cell DNA of the virus preparation (e) is less than 1 µg/mL, especially less than 900, 800, 700, 600, 500, 400, 300 or 200 ng/mL, preferably less than 100 ng/mL. In a preferred embodiment, the residual host cell DNA of the virus preparation (c) is less than 10 ng/mL. In some embodiments, the residual host cell protein of the final virus preparation (c) is less than 10 µg/mL, especially less than 9, 8, 7, 6, 5, 4, 3 or 2 µg/mL, preferably less than 1 µg/mL. In a preferred embodiment, the residual host cell protein of the virus preparation (c) is less than 100 ng/mL. In some embodiments, the residual non-infectious virus particles of the final virus preparation (c) is less than 10 g/mL, especially less than 9, 8, 7, 6, 5, 4, 3 or 2 µg/mL, preferably less than 1 µg/mL. In a preferred embodiment, the residual non-infectious virus particles of the virus preparation (c) is less than 100 ng/mL.

In some embodiments, the residual protamine is less than 1 µg/mL, especially less than 900, 800, 700, 600, 500, 400, 300 or 200 ng/mL, preferably less than 100 ng/mL, more preferably is below the detection limit of HPLC, in particular below the detection limit in the final drug substance. In some embodiments, the PS content is tested by HPLC or size exclusion chromatography (SEC). For example, HPLC is validated for PS determination in JEV sucrose gradient pool samples as a routine release assay and is very sensitive (i.e., LOQ 3 µg/mL; LOD 1 µg/mL). In the current invention, PS content in virus DS samples was <LOD. In one embodiment, the HPLC assessment of PS content can be performed on a Superdex Peptide 10/300GL column (GE: 17-5176-01) using 30% Acetonitrile, 0.1% Trifluoroacetic acid as solvent with a flow rate of 0.6 ml/min at 25° C. and detection at 214 nm. A more sensitive method of measurement for residual protamine in a purified virus preparation is mass spectrometry (MS). In some embodiments, the residual PS levels in a virus preparation are tested by MS or other such highly sensitive method, e.g., nuclear magnetic resonance (NMR). With this method, residual PS, as well as fragments and/or break-down products of PS, can be detected at trace amounts, such as levels as low as, for example, $10^6$, $10^7$ or $10^8$ molecules per typical sample load. In some embodiments, the PS levels are tested in the sucrose gradient pool. In some embodiments, the PS levels are tested in the drug product. In some embodiments, the PS levels are tested in the drug substance.

In some embodiments, the crude harvest (a) comprising the virus particles and impurities is subjected to one or more pre-purification step(s) prior to step (b). In some embodiments, the one or more pre-purification step(s) comprises digesting host cell genomic DNA in the crude harvest (a) comprising the virus particles and impurities by enzymatic treatment. In some embodiments, the one or more pre-purification step(s) comprises filtration, ultrafiltration, concentration, buffer exchange and/or diafiltration. In some embodiments, the one or more pre-purification steps is filtration using a filter having a pore size equal to or less than 1 µm. In some embodiments, the filter has a pore size equal to or less than 0.2 µm. In a preferred embodiment, the filter has a pore size of 0.2 µm. In some embodiments, the concentration and/or ultra/diafiltration and/or buffer exchange is performed by tangential flow filtration (TFF). In some embodiments, ultra/diafiltration of the crude harvest (a) comprising the virus particles and impurities is performed using a hollow fiber membrane having a cut-off of equal to or less than 300 kDa. In a preferred embodiment, the hollow fiber membrane has a cut-off of 100 kDa.

In some embodiments, the virus particle is a live virus, a chimeric virus, an attenuated live virus, a modified live virus, or a recombinant live virus. In a further step, the virus particles of the invention may by optionally inactivated. In some embodiments, the virus particle is an attenuated form of the virus particle. For example, the virus may have reduced infectivity, virulence, and/or replication in a host, as compared to a wild-type virus. In some embodiments, the virus is a mutated or modified virus, for example the nucleic acid of the virus may contain at least one mutation relative to the wild-type virus. In some embodiments, the virus is a recombinant live virus, meaning a virus that is generated recombinantly and may contain nucleic acid from different sources.

In some embodiments, the virus particle is a live virus, an attenuated live virus, a modified live virus, or a recombinant live virus. In some embodiments, the virus belongs to a virus family selected from the group consisting of Paramyxoviridae, Orthomyxoviridae, Flaviviridae, Filoviridae, Arenaviridae, Rhabdoviridae, and Coronaviridae. In some embodiments, the virus belongs to a virus family selected from the group consisting of Togaviridae (being live or inactivated), such as alphaviruses, or Flaviviridae (being live or inactivated). In some embodiments, the virus is a virus of the family Flaviviridae, i.e. a flavivirus. In other embodiments, the virus is a Zika virus or Yellow Fever virus. In preferred embodiments, the virus is a Zika virus. In a most preferred embodiment, the Zika virus is a Zika virus from the Asian lineage.

In some embodiments, the relative reduction of impurity of the final virus preparation relative to the liquid medium (a) comprising the virus particles and impurities is in a range from 60 to 95%. In some embodiments, the residual impurity of the final virus preparation is less than 1%. We observed a decrease in the HCP peaks and the non-infectious aggregate peaks in the HPLC-SEC or SDS-PAGE. An exact quantification is difficult but one can measure the density of the SDS-PAGE bands and other methods.

In some embodiments, the filtration of step in (b)(ii) of claim 1 is performed using a filter having a pore size equal to or greater than 1 μm. In some embodiments, the filter has a pore size equal to or greater than 0.2 μm. In a preferred embodiment, the filter has a pore size of 0.2 μm.

In some embodiments, the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line. In some embodiments, said cell line is a duck cell line. In some embodiments, said cell line is a diploid avian cell line. In some embodiments, said cell line is EB66 cell line. In a preferred embodiment, said cell line is a Vero cell line.

Aspects of the invention provide a use of any of the processes described herein for manufacturing a composition for immunization against a viral infection. In a preferred embodiment, the composition is a vaccine. In one embodiment, the composition or vaccine is directed against Chikungunya virus. In one embodiment, the composition or vaccine is directed against a flavivirus. In one embodiment, the composition or vaccine is directed against Yellow Fever virus. In one embodiment, the composition or vaccine is directed against Zika virus such as e.g. a Zika virus of the Asian lineage.

Other aspects provide compositions comprising the virus particles obtainable by any of the processes described herein for treating and/or preventing a viral infection. In one embodiment, the viral infection is caused by Chikungunya virus. In one embodiment, the viral infection is caused by a flavivirus. In one embodiment, the viral infection is caused by Yellow Fever virus. In one embodiment, the viral infection is caused by Zika virus such as e.g. a Zika virus of the Asian lineage.

In some embodiments, the attenuated form of ChikV is derived from the LR2006-OPY1 ChikV infectious clone (La Reunion isolate). In some embodiments, the attenuated form of ChikV is the Δ5nsP3 mutant as described by Hallengird et al. (Novel Attenuated Chikungunya Vaccine Candidates Elicit Protective Immunity in C57BL/6 mice (2014) Journal of Virology 88(5):2858-2866) or an immunogenic variant thereof. The immunogenic variant of the Δ5nsP3 ChikV mutant is herein defined as having at least 80% sequence identity to the nucleotide sequence of the Δ5nsP3 mutant sequence as provided by SEQ ID NO: 77, especially at least 81%, 82%, 83%, 84%, 85%, 86%, 87%, 88% 89%, 90%, 91%, 92%, 93%, 94%, 95%, 96%, 97%, 98% or at least 99% sequence identity to SEQ ID NO: 77.

In some embodiments, the Zika virus is derived from the Asian lineage. In some embodiments, the Zika virus is a Zika virus as described partially or fully in Sequence section of this application, i.e. any of sequences SEQ ID Nos 2 to 69 or 78, in particular all partly or fully described Zika viruses of the Asian lineages or an immunogenic variant thereof. The immunogenic variants of the Zika virus or Zika virus of the Asian lineages are herein defined as having at least 80% sequence identity to the nucleotide sequence of the sequences described in any of sequences SEQ ID Nos 2 to 69 or 78, especially at least 81%, 82%, 83%, 84%, 85%, 86%, 87%, 88% 89%, 90%, 91%, 92%, 93%, 94%, 95%, 96%, 97%, 98% or at least 99% sequence identity.

In some embodiments, the process of the invention results in an enrichment of infectious virus particles from the crude harvest comprising infectious virus particles and non-infectious virus particles and other virus products such that the enrichment of the infectious virus particles is at least 50%, at least 60%, at least 70%, at least 80%, at least 90%, at least 95%, preferably at least 80%, especially 85% relative to the total virus particle content of the crude harvest (a) comprising the virus particles and impurities.

In some embodiments, the residual impurity of the final virus preparation with respect to all impurities in the crude harvest is less than 10%, 9%, 8%, 7%, 6%, 5%, 4%, 3%, 2%, 1%, preferably less than 5% as determined by SEC-HPLC (Size Exclusion Chromatography—HPLC).

In some embodiments, the filtration step of the virus preparation (b) after contact with the solid-phase matrix is performed using a filter having a pore size equal to or greater than 1 Lm. In some embodiments, the filter has a pore size equal to or greater than 0.2 Lm. In a preferred embodiment, the filter has a pore size of about 0.2 μm, such as 0.22 μm.

In some embodiments, the Zika virus, or Chikungunya virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line. In some embodiments, said cell line is a duck cell line. In some embodiments, said cell line is a diploid avian cell line. In some embodiments, said cell line is EB66 cell line. In a preferred embodiment, said cell line is a Vero cell line.

Aspects of the invention provide a use of any of the processes described herein for manufacturing a composition for immunization against a Zika virus, Yellow Fever, or Chikungunya virus infection. In a preferred embodiment, the composition is a vaccine. In preferred embodiments, the vaccine is administered to the subject once, twice or three or more times. In a preferred embodiment, the vaccine is administered once or twice. In a preferred embodiment, the vaccine is administered only once.

The herein disclosed in vivo data regarding immunogenicity of the inactivated Zika virus vaccine of the current invention indicates that the virus is surprisingly potently immunogenic and also highly cross-protective (very similar immunogenicity in African and Asian strains). Data indicate that immunogenicity was unexpectedly higher than the recently reported inactivated Zika virus vaccine candidate (Larocca, et. al, 2016, Nature doi:10.1038/nature18952.). Inactivated viruses are among the safest vaccines and especially preferred for delivery to populations where safety is especially concerning, such as pregnant women, children and immunocompromised individuals, which makes the herein disclosed inactivated Zika virus particularly suitable. Obtaining a high titer of inactivated virus is a challenge in the field. The herein disclosed process for purifying inactivated Zika virus results in not only a high yield, but also a very pure drug substance.

Other aspects provide compositions comprising the virus particles obtainable by any of the processes described herein for treating and/or preventing a Chikungunya virus infection.

BRIEF DESCRIPTION OF THE DRAWINGS

The accompanying drawings are not intended to be drawn to scale. The figures are illustrative only and are not required for enablement of the disclosure. For purposes of clarity, not every component may be labeled in every drawing, alignments were performed with the multi alignment package Jalview (Waterhouse et al., 2009, Bioinformatics 25 (9) 1189-1191). In the drawings:

FIG. 3: Pairwise alignment-Jalview (% identity, nt), complete genomes.

FIG. 4: Average distance tree (by % identity, aa), E-protein.

Figure 7:
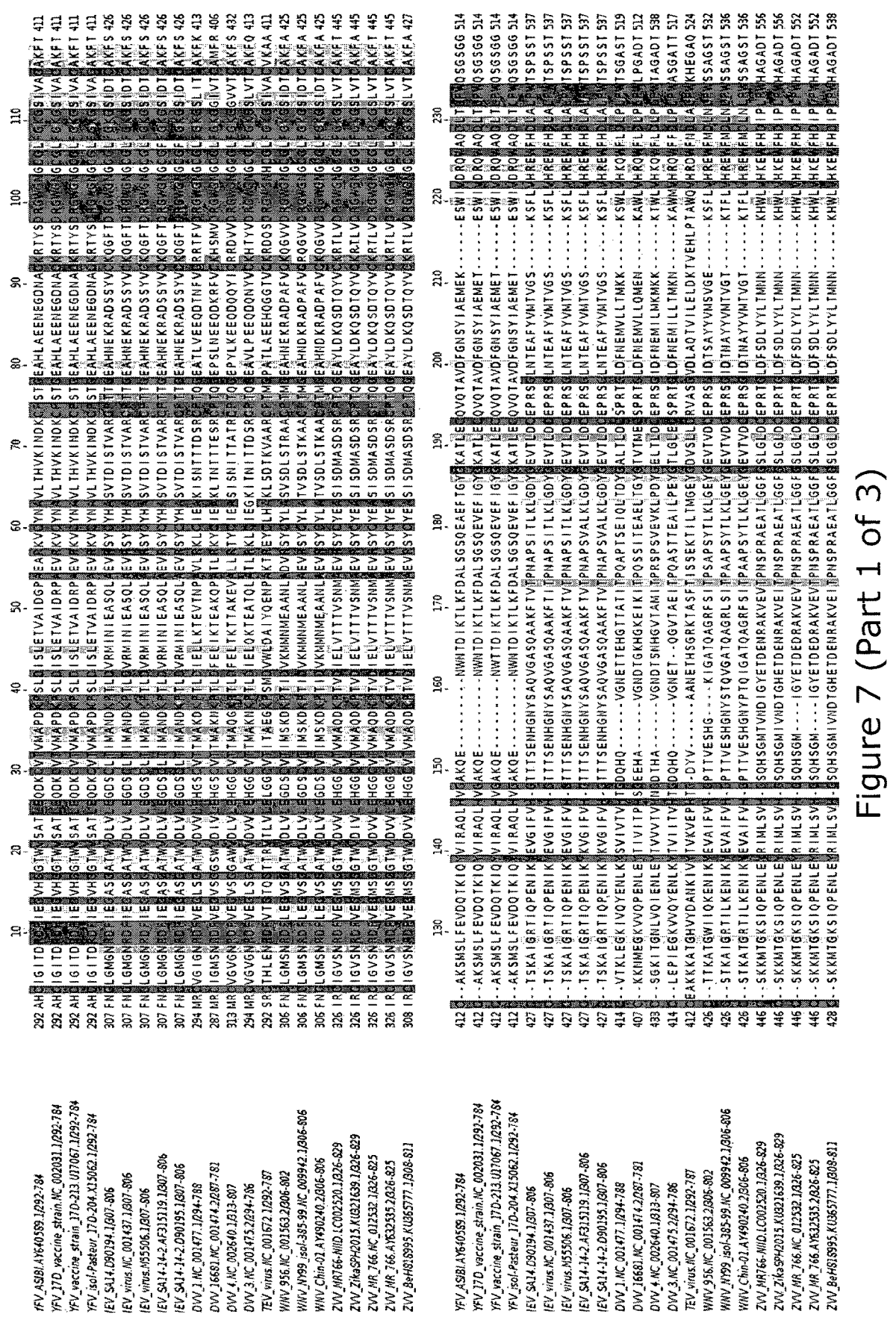
Figure 7:
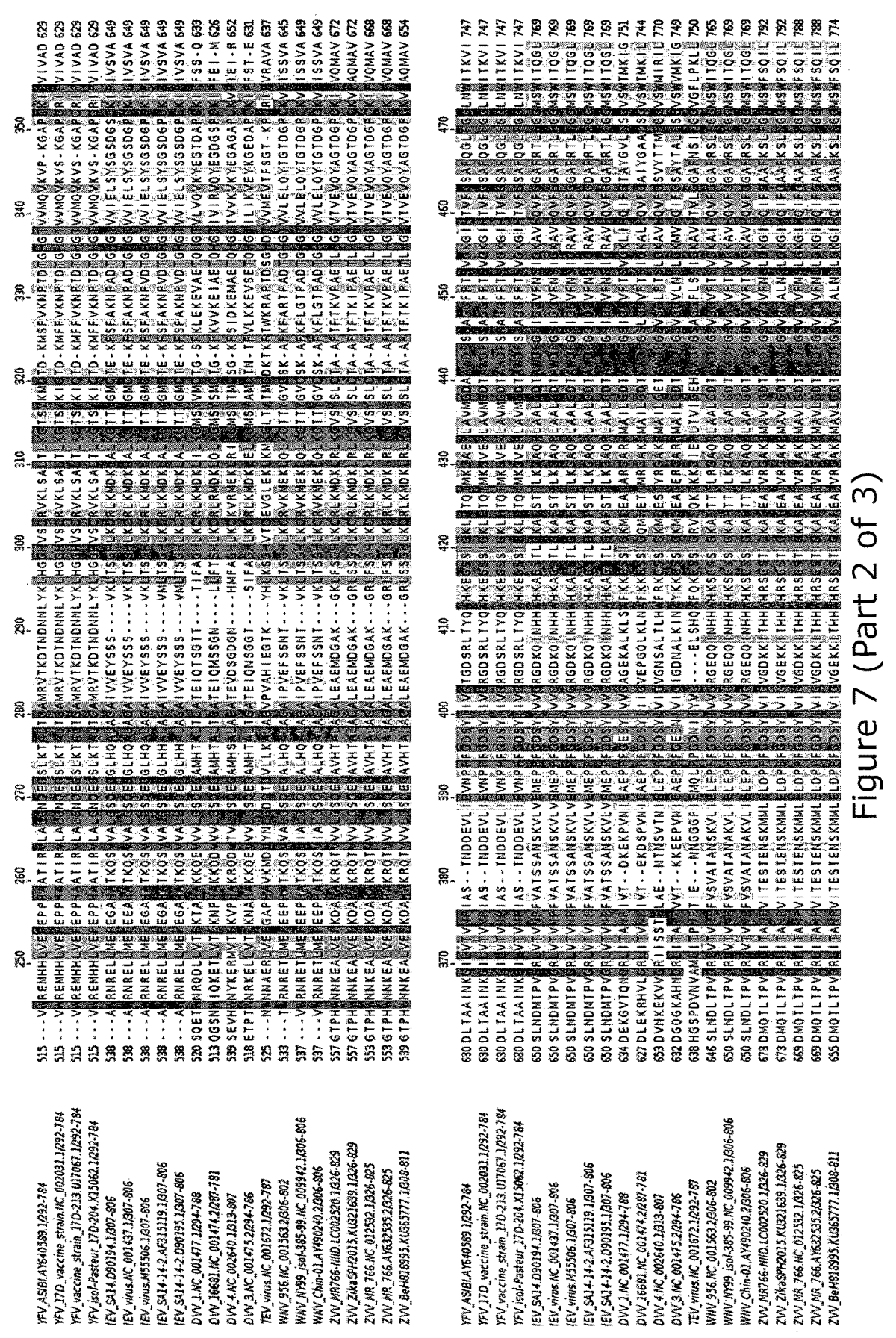
Figure 7:
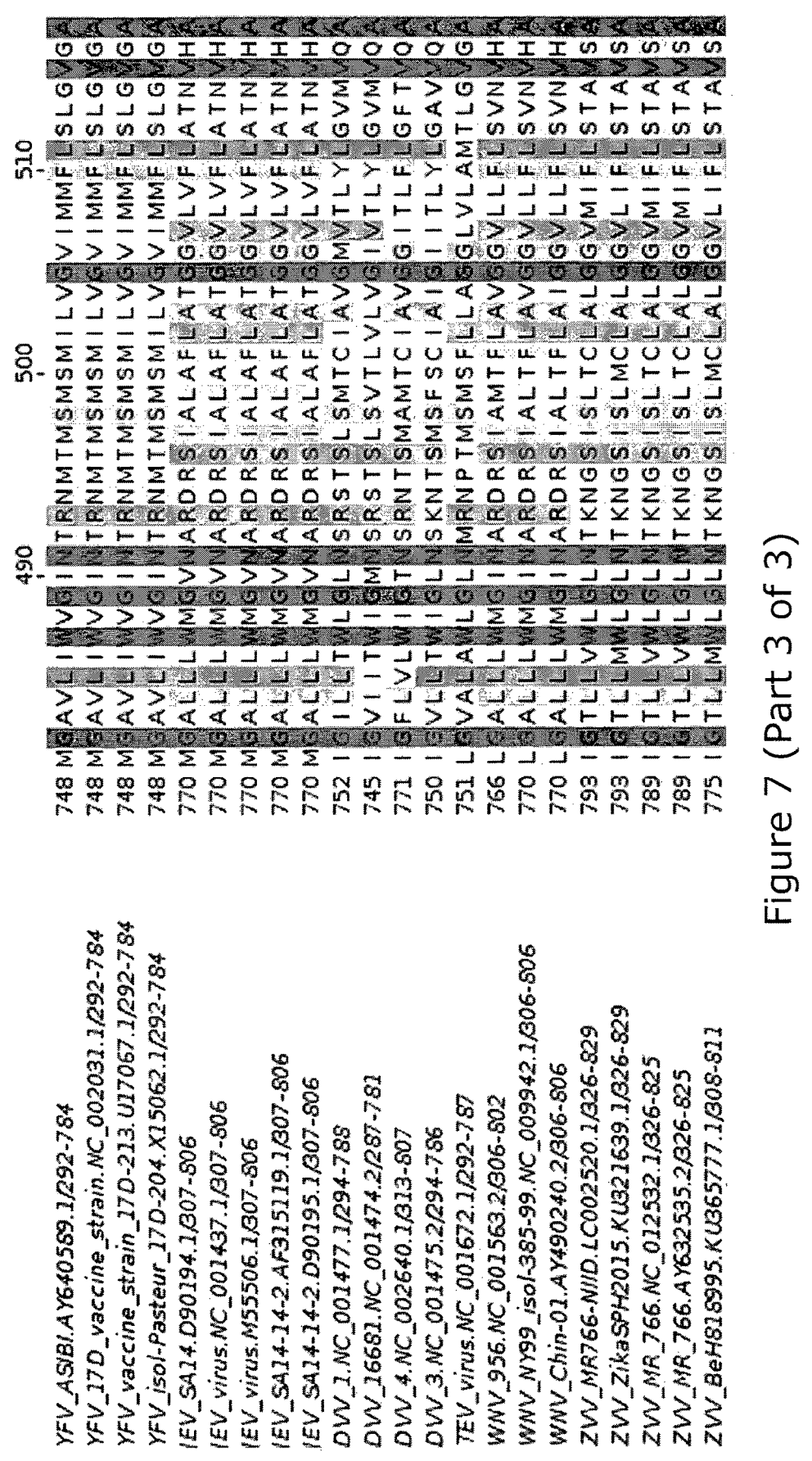

FIG. 7: Alignment (shading: % identity, aa), E-protein.

sucrose. PS SEC showed acceptable separation of PS from CHIKV, however a slight overlap is still present. C: CHIKV load material containing 10% sucrose was loaded on top of a two layer system consisting of a 50% (w/w) sucrose bottom layer and a second 25% (w/w) sucrose layer. Determination of sucrose content in the fractions showed the formation of a linear gradient. SEC showed concentration of CHIKV within a sucrose concentration range from 40-30% (w/w) sucrose. PS SEC showed a good separation of PS from CHIKV. D: CHIKV load material containing 10% sucrose was loaded on top of a three layer system consisting of a 50% (w/w) sucrose bottom layer as well as a 35% and a 15% (w/w) sucrose layer. Determination of sucrose content in the fractions showed the formation of a linear gradient and SEC showed concentration of CHIKV within a sucrose concentration range from 40-30% (w/w) sucrose. PS SEC showed a very good separation of PS and residual contaminants from CHIKV. Of the four tested sucrose layer systems the combination of 3 layers (shown in FIG. 16D) showed the best separation of the virus particles from residual contaminants and was therefore used for further DSP development.

Figure 16:
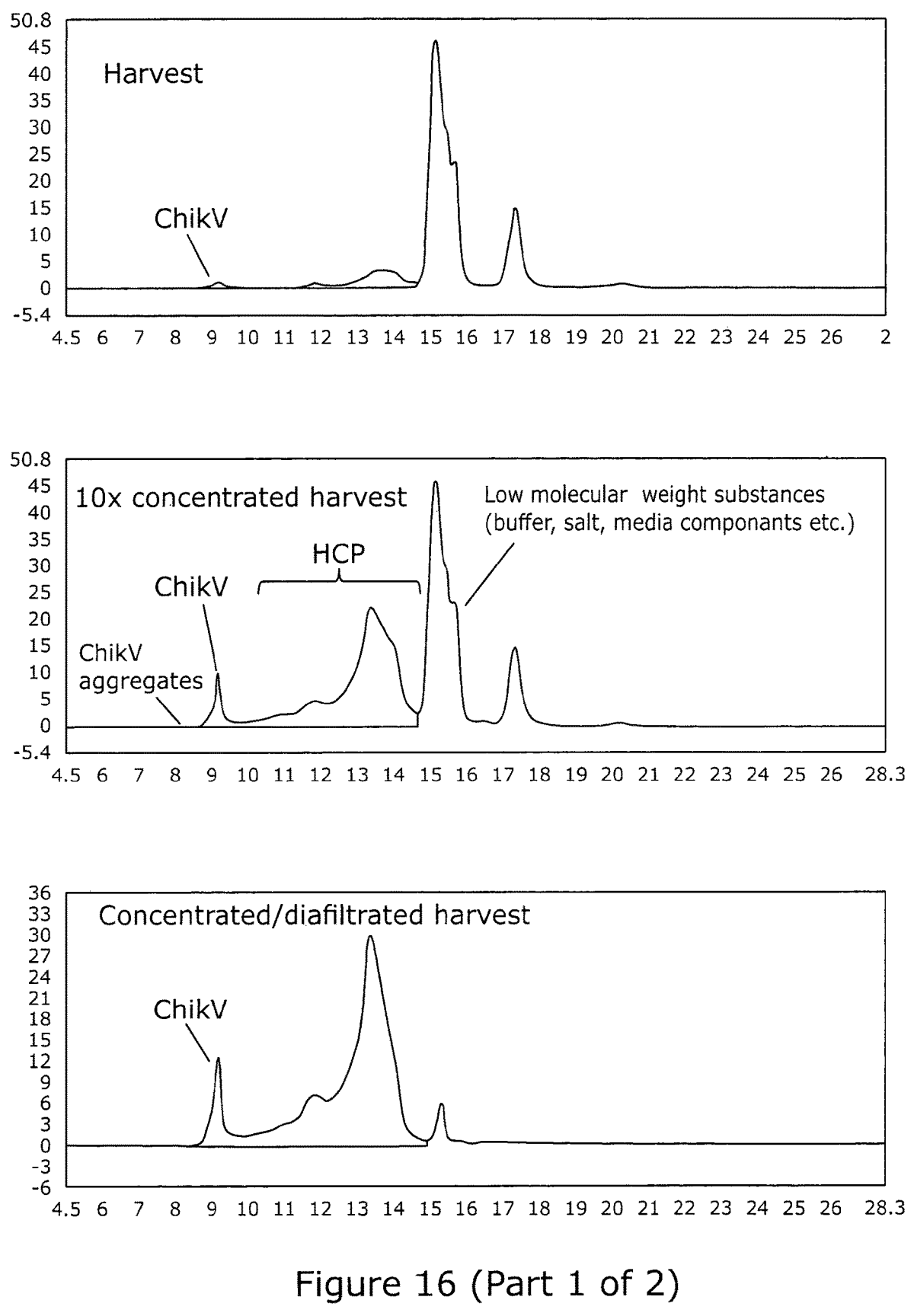

FIG. 16: Relative amounts of attenuated Δ5nsP3 ChikV particles and other components by SEC-HPLC analysis at the different steps of the process of the invention including, from top to bottom: crude harvest (a); 10× concentrated harvest; diafiltrated concentrated harvest; PS treated material; CC700-treated material and SGC purified pool.

Figure 17A:
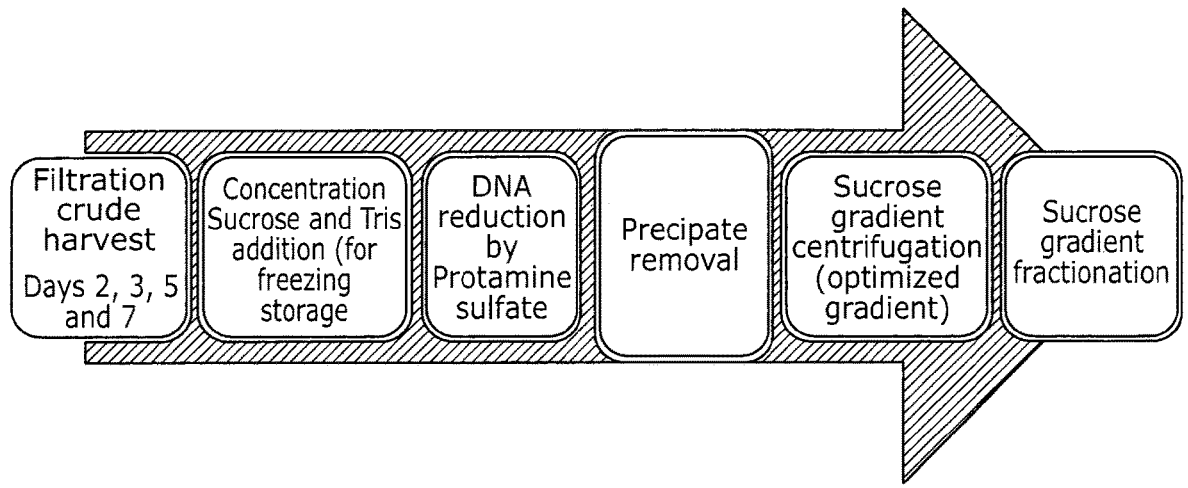
Figure 17B:
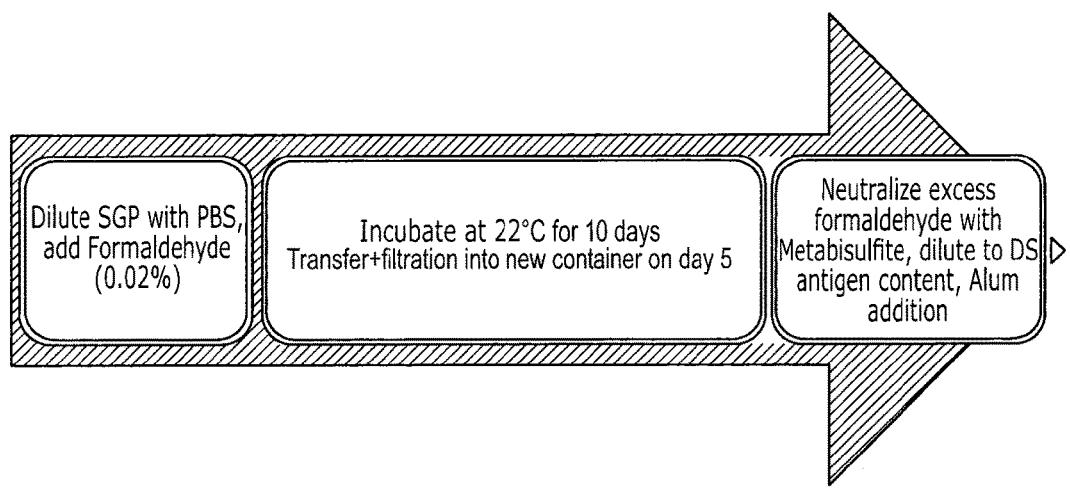

FIG. 17: An exemplary downstream virus purification process from the crude harvest to formulation of the drug substance (vaccine), a preferred embodiment of the process of the invention (A). A flow-chart of an exemplary virus inactivation process is shown in (B).

Figure 18:
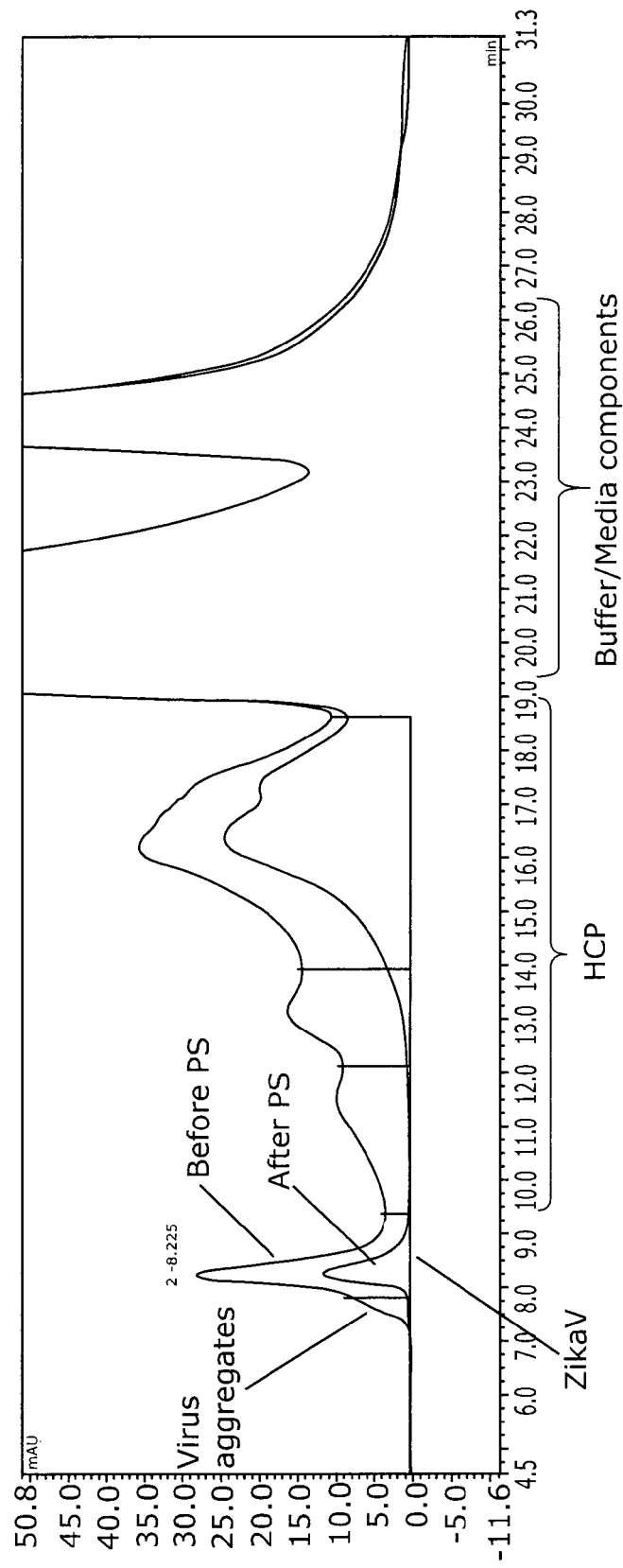

FIG. 18: PS treatment results in selective removal of Zika virus aggregates and Vero HCP and LMW impurities (SEC-HPLC of 30× concentrated Zika Virus harvest day 5).

Figure 19:
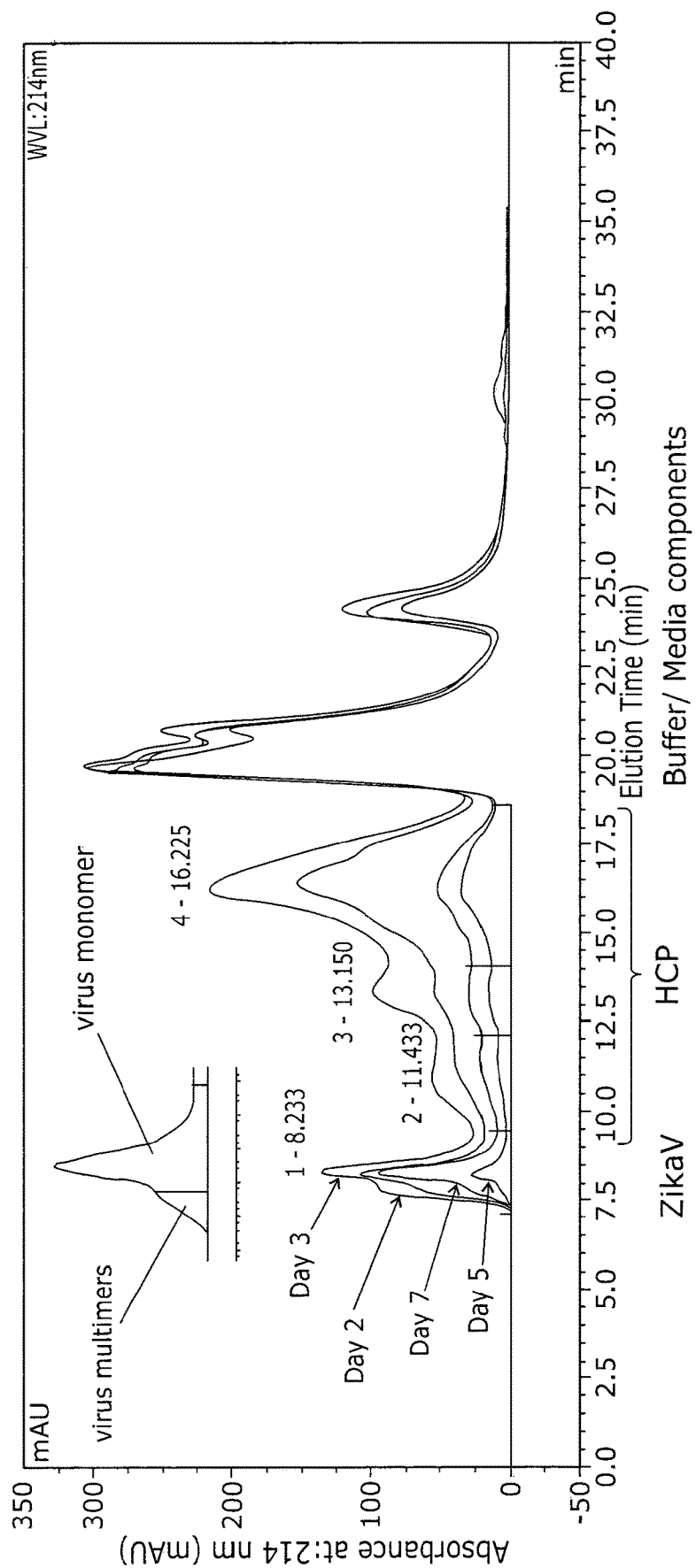

FIG. 19: SEC-HPLC of individual 30× concentrated Zika harvest prior PS treatment at different time points.

Figure 20:
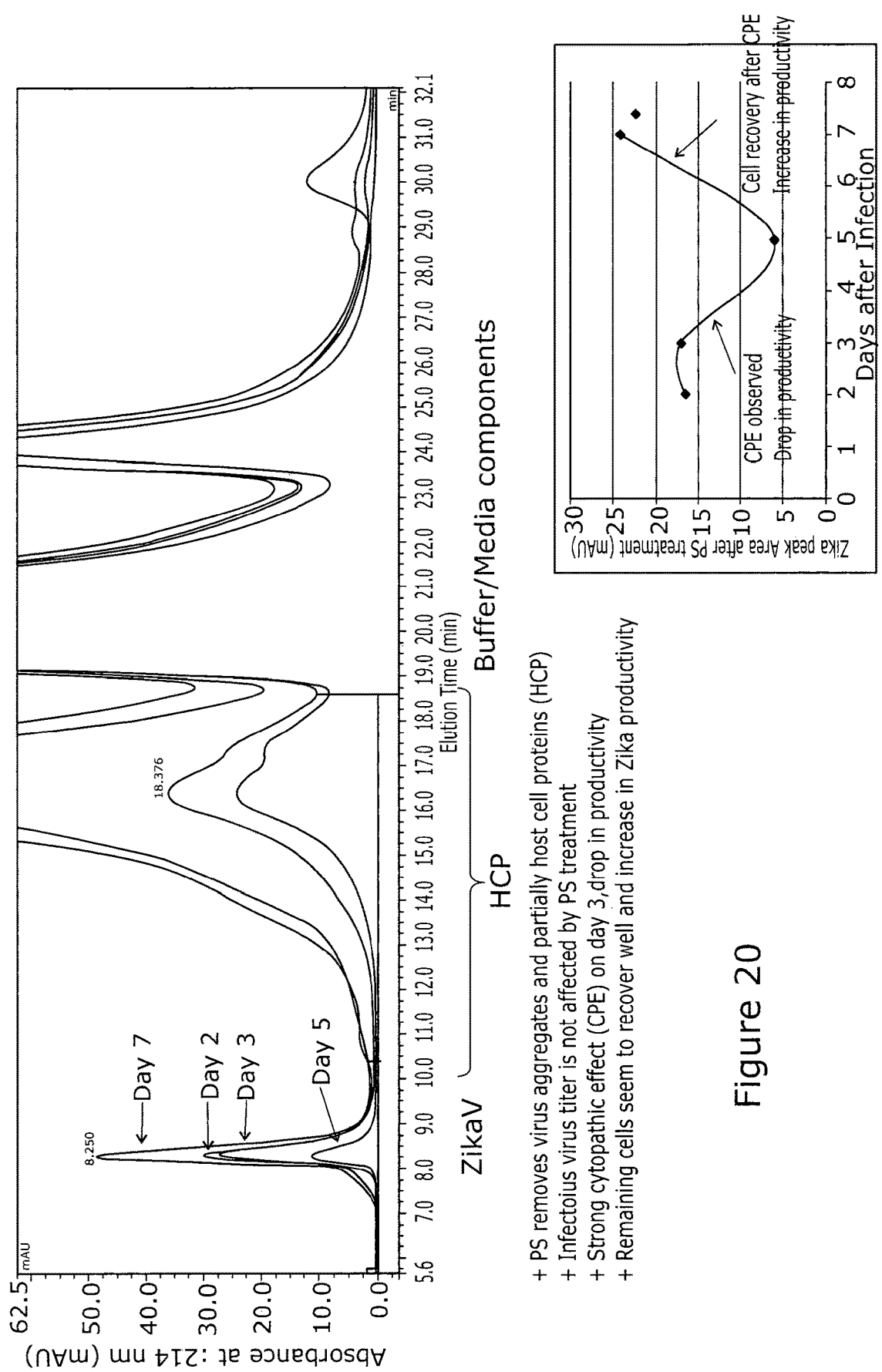

FIG. 20: SEC-HPLC of individual 30× concentrated Zika harvest post PS treatment at different time points.

Figure 21:
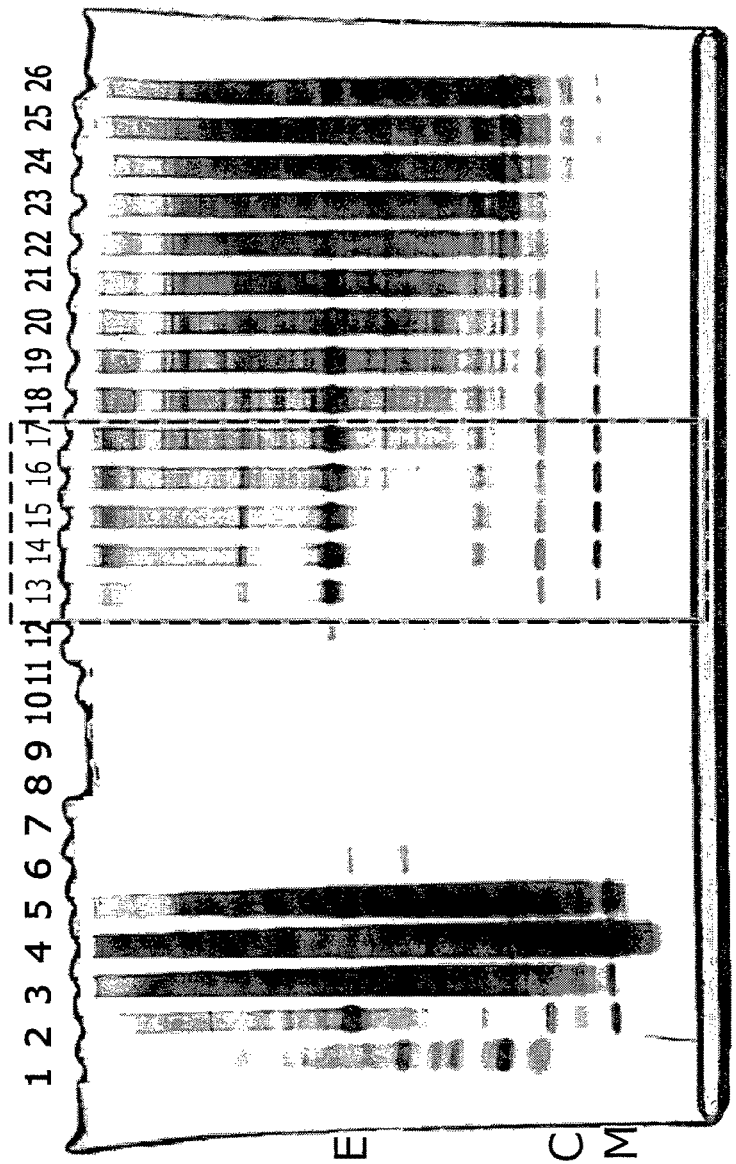

FIG. 21: Representative SDS-PAGE from the sucrose gradient harvest of a Zika purification is shown.

Figure 22:
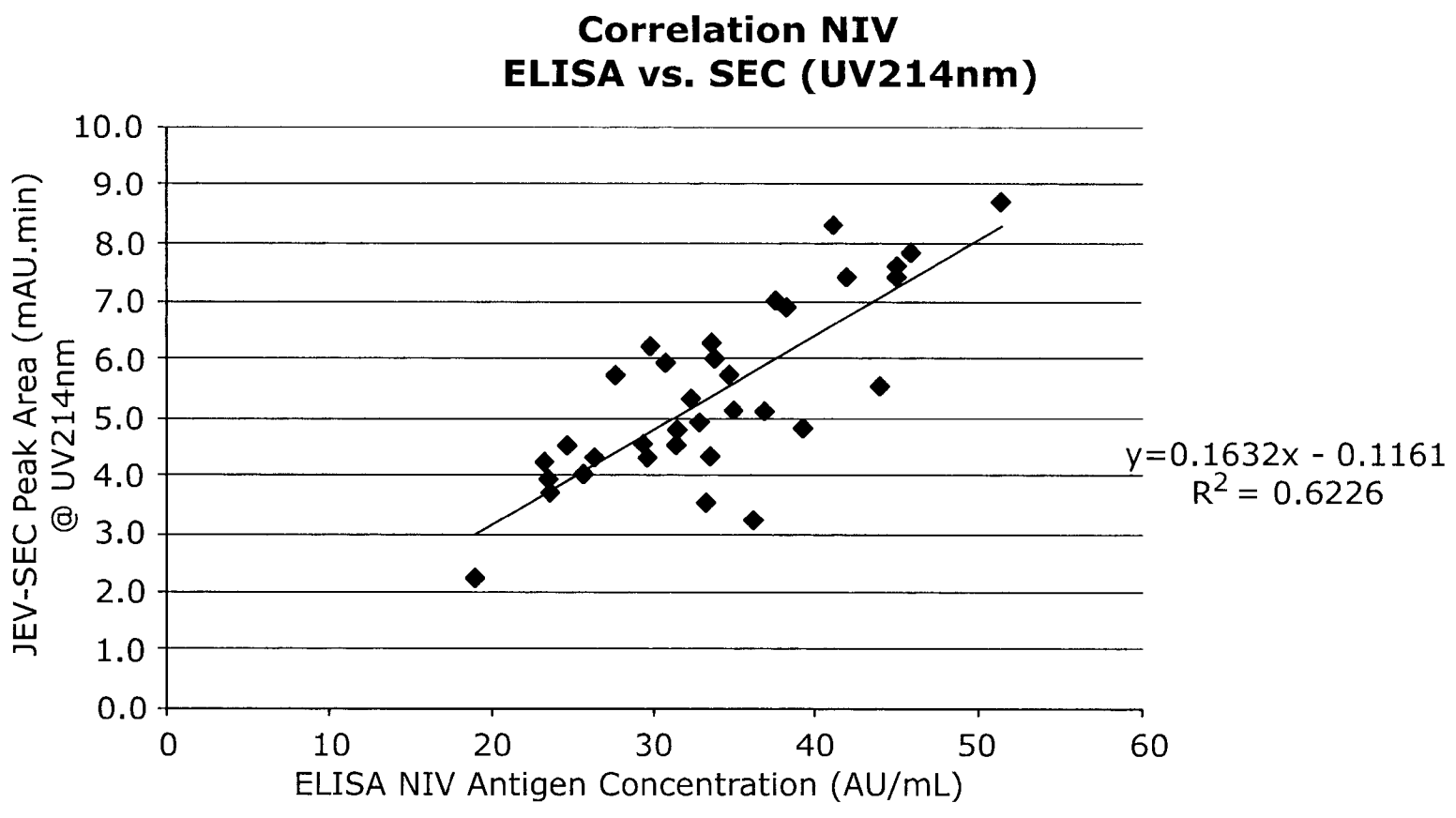

FIG. 22: Correlation between JEV Antigen content in NIV analysed by ELISA and SEC-HPLC (Dionex Ultimate 3000, Superose 6 column).

Figure 23:
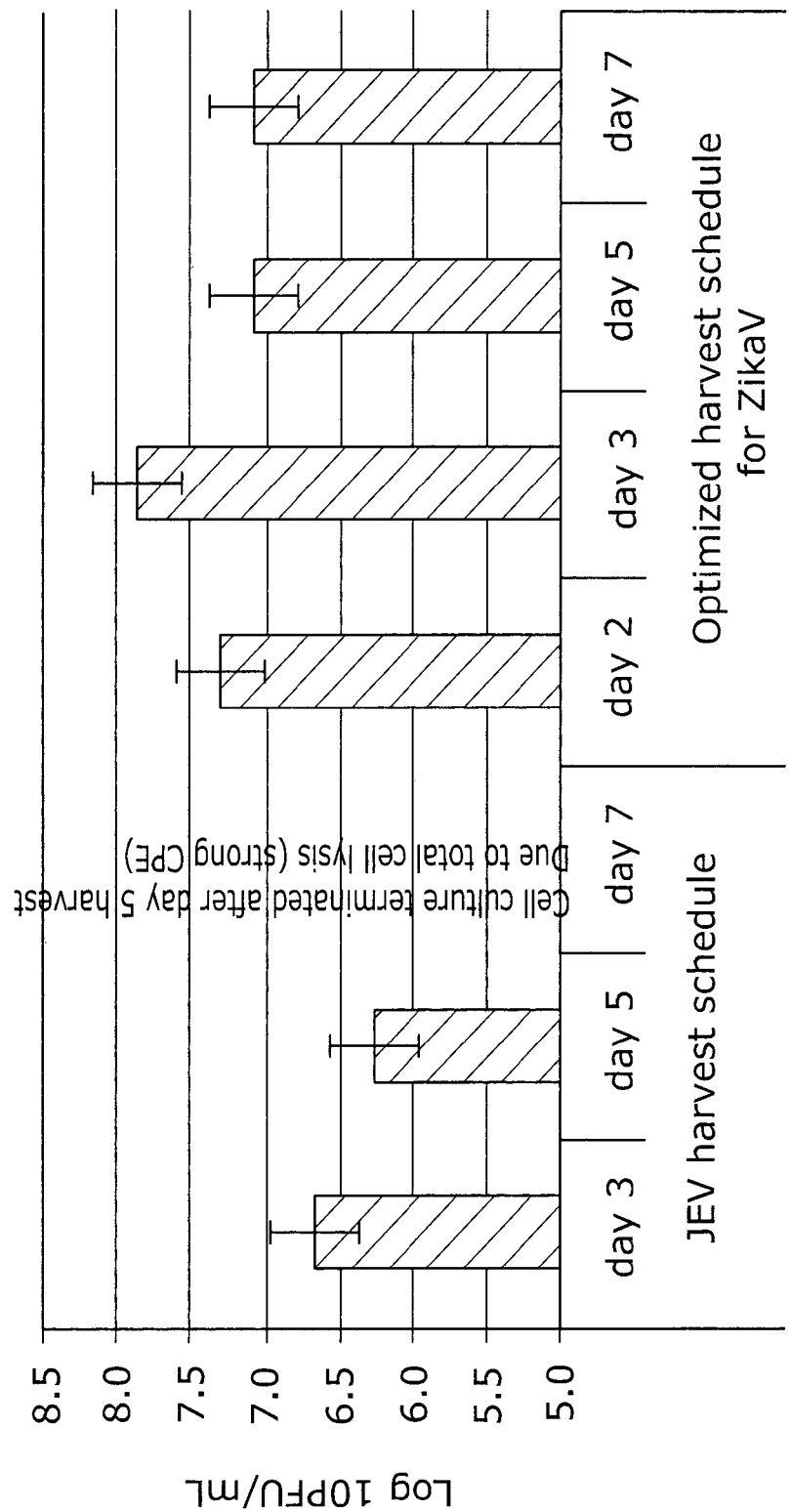

FIG. 23: Comparison of JEV and ZikaV harvest schedules/yields.

Figure 24:
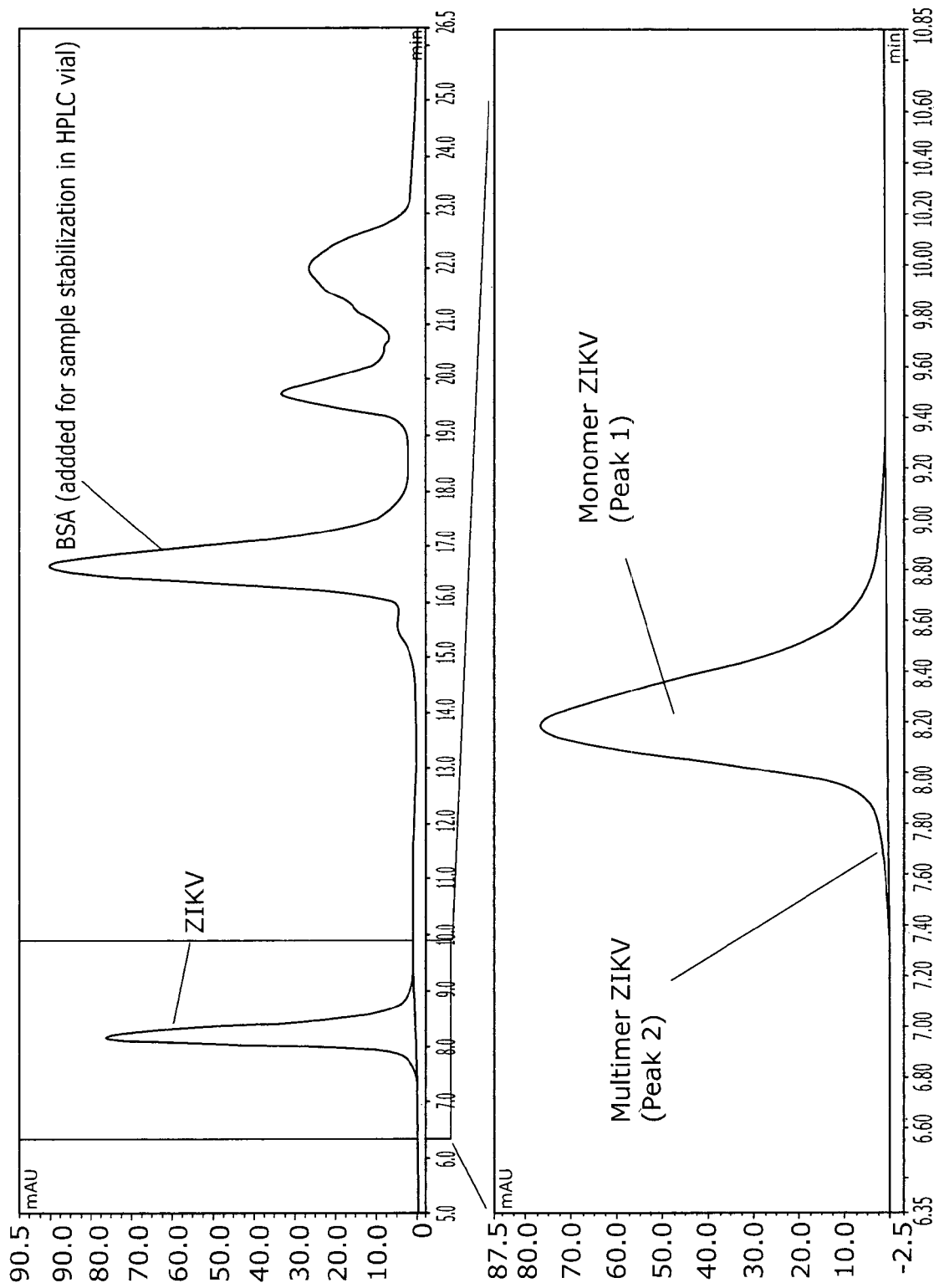

FIG. 24: SEC-HPLC elution profile of ZikaV NIV. Data were processed on Dionex Ultimate 3000/Superose 6 Increase column. Both panels are from the same chromatogram. The upper graph is the complete elution profile; the lower graph is an enlargement of the ZIKAV elution peak.

FIG. 25: SEC-MALLS analysis of inactivated ZikaV.

FIG. 26: Cumulative particle size distribution of Zika NIV.

Figure 27:
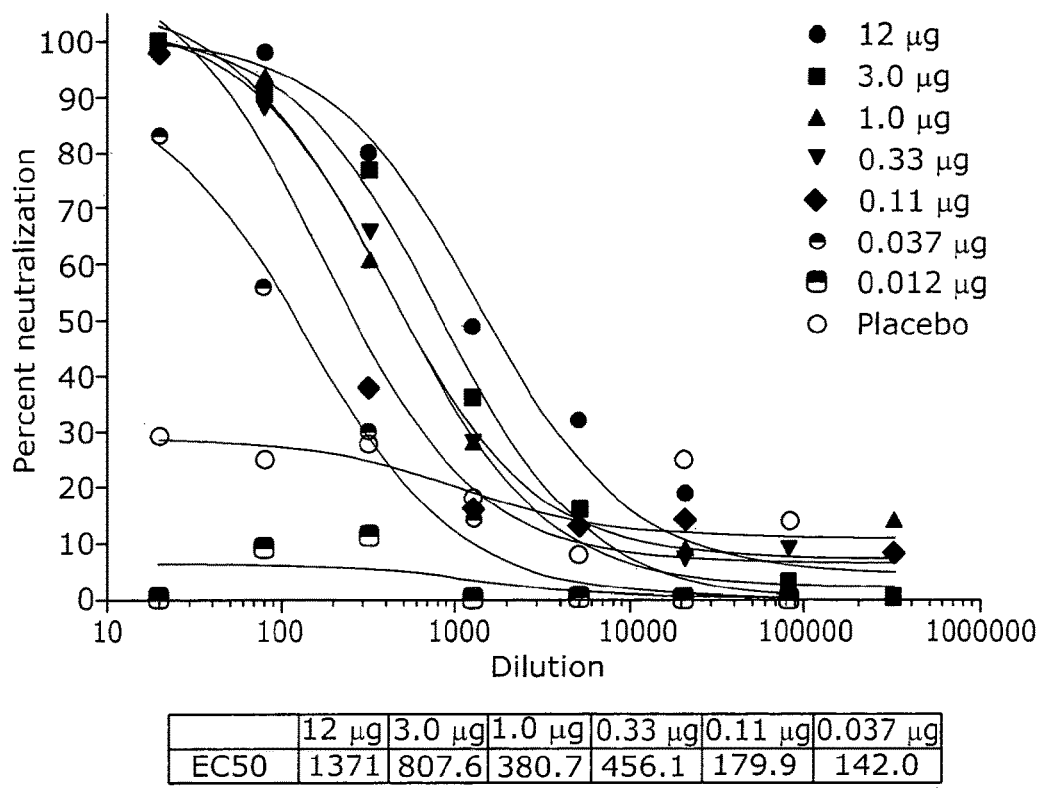

FIG. 27: Graphical representation of the neutralization of the Zika virus H/PF/2013 with pooled mouse sera. The number of plaques without serum was set to 100%. The EC50 was calculated with the 3-parameter method.

Figure 28:
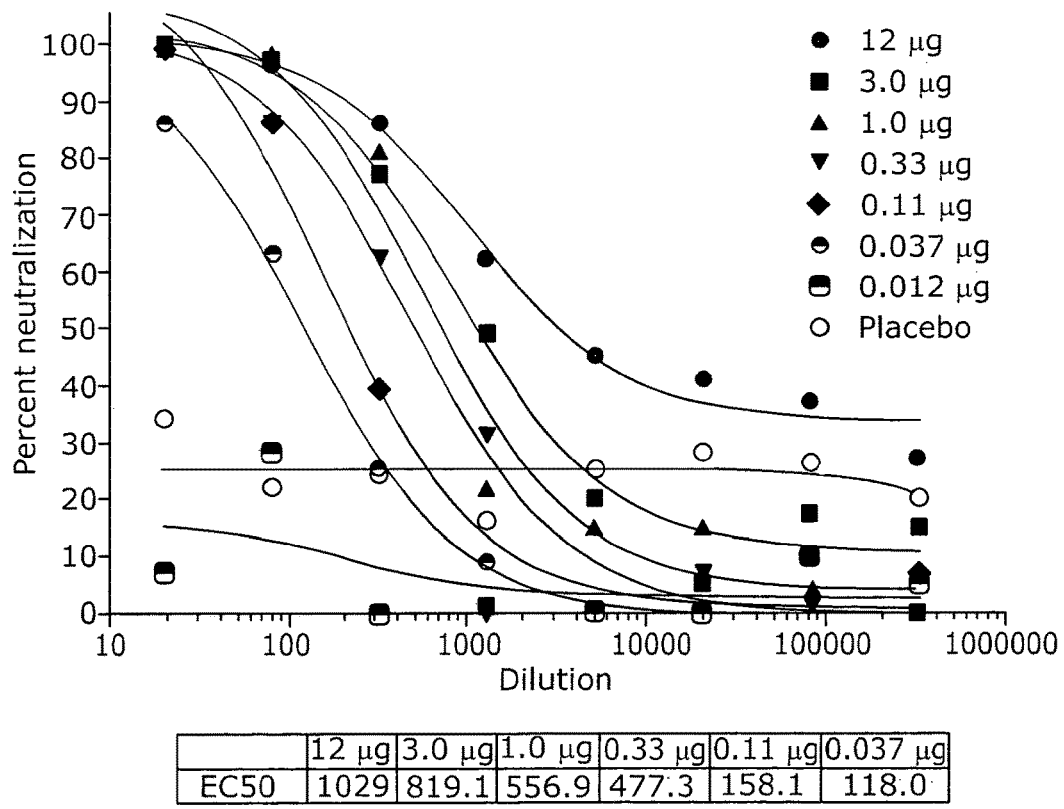

FIG. 28: Graphical representation of the neutralization of the Zika virus MR766 with pooled mouse sera. The number of plaques without serum was set to 100%. The EC50 was calculated with the 3-parameter method.

Figure 29:
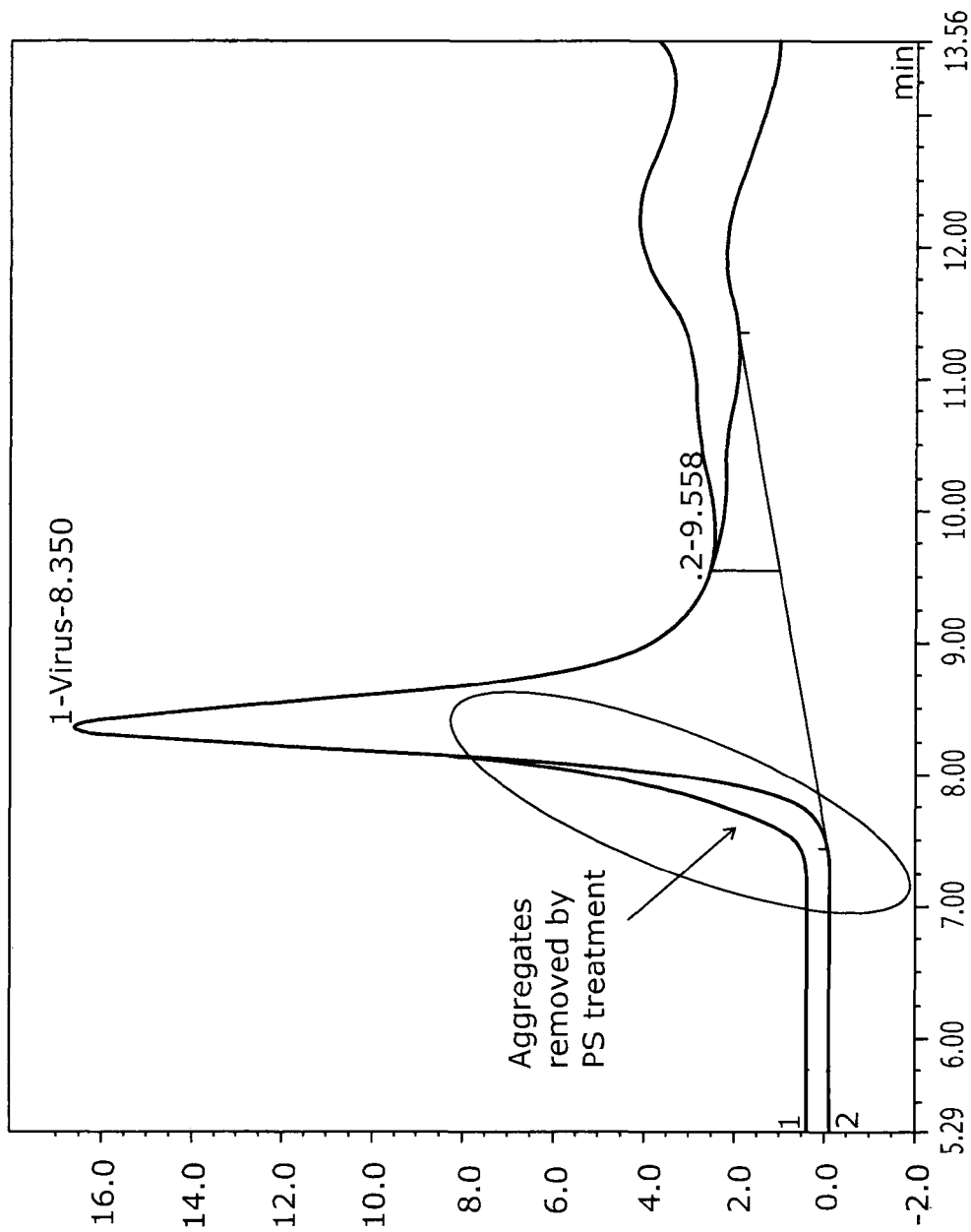

FIG. 29: Change in SEC profile of Yellow fever virus peak after PS addition according to the invention showing a complete removal of large size aggregates and LMW impurities.

DETAILED DESCRIPTION OF THE INVENTION

Disclosed herein are processes for the purification of infectious virus particles, i.e., mature, functional virus particles, e.g. flavivirus particles (Yellow Fever, Zika Virus, Japanese Encephalitis virus, Dengue virus) and/or alphavirus particles (Chikungunya virus). The processes disclosed are characterized by the removal of undesired by-products of virus production on host cells, such as non-infectious virus particles and aggregated and immature virus by-products. The processes provided herein allow the production of highly-purified virus preparations comprising mostly infectious virus particles. During the course of the invention, it was observed that protamine sulphate (PS), added to remove contaminating DNA during virus purification, resulted not only in removal of contaminating DNA, but also in the loss of a high percentage of total virus particles present in the preparation. Surprisingly, however, quantification of total infectious virus particles by TCID50 before and after PS treatment revealed that the absolute number of infectious virus particles did not change following this loss of total virus particles. This observation clearly shows that treatment with PS can facilitate selective removal of non-infectious, aggregated and immature viral by-products, leaving behind the infectious Chikungunya virus particles or other infectious virus particles. Because by-products produced during virus growth on host cells may have different (and undesirable) immunological properties or other unwanted side-effects or safety issues, a simple and robust way to remove these by-products is of high importance for the quality and safety of the final product.

Protamines are small arginine-rich nuclear proteins, present in high amounts in the sperm of fish, which have an important role in DNA packaging during spermatogenesis. Protamine sulfate (or "protamine" or "PS") can form a stable ion pair with heparin and is thus commonly used during certain surgeries when the anti-coagulation effect of heparin is no longer needed. In large doses, protamine sulfate administered alone can also have a weak anticoagulant effect ("Protamine sulfate". Wikipedia: The Free Encyclopedia. Wikimedia Foundation, Inc. 30 Sep. 2015 Web. 26 Nov. 2015<https://en.wikipedia.org/wiki/Protamine_sulfate>). Protamine Sulphate is additionally routinely used in biotechnology applications such as DNA precipitation (e.g., removal of host cell DNA from cell culture processes), purification of DNA binding proteins and retroviral-mediated gene transfer.

Protamine is obtained from salmon sperm or produced recombinantly and is used as a sulphate salt. The four major peptides, which constitute almost the entire nitrogen-containing material in salmon protamine, have been fully characterized and found to be polypeptides of 30-32 amino acids in length, of which 21-22 residues are arginine. The average molecular mass is in the range of 4250 Da for the following sequence: PRRRRSSSRP VRRRRRPRVS RRRRRRGGRR RR (SEQ ID NO: 1). Herein, protamine is also referred to as protamine salt, or preferably protamine sulphate.

Figure 1:
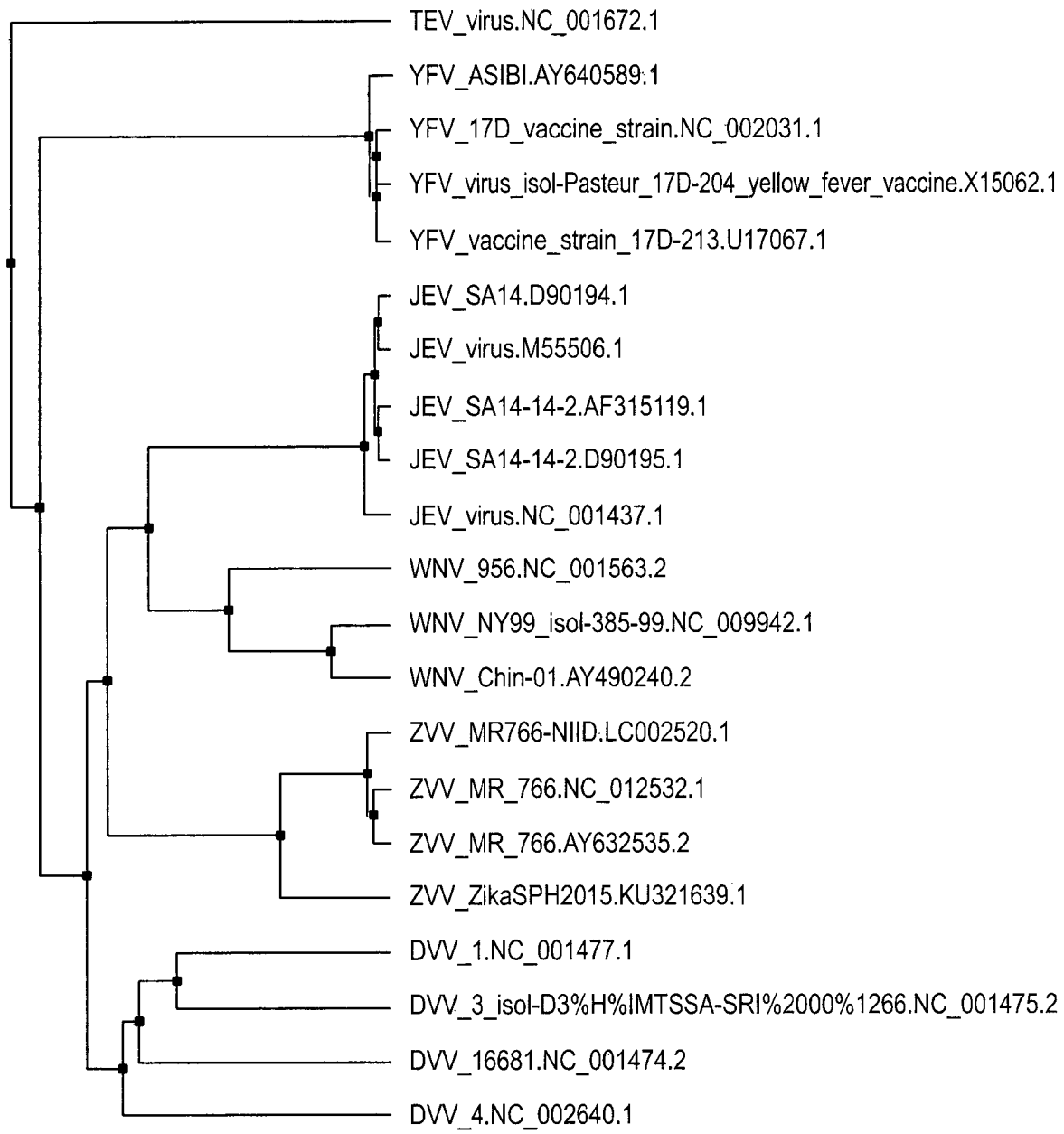
FIG. 1: Average distance tree (by % identity, nt), complete genomes.
Figure 2:
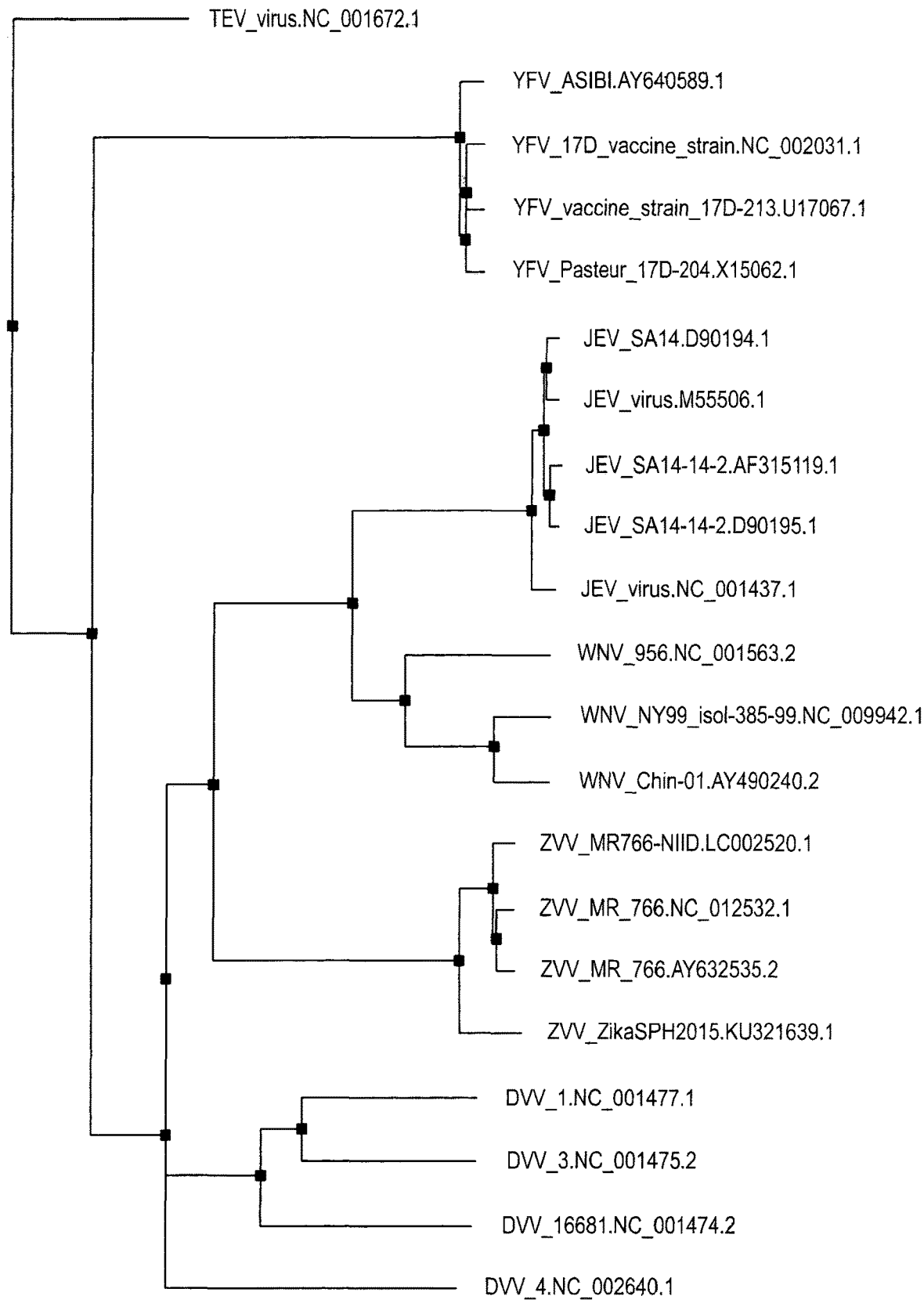
FIG. 2: Neighbor joining tree (by % identity, nt), complete genomes.
Figure 5:
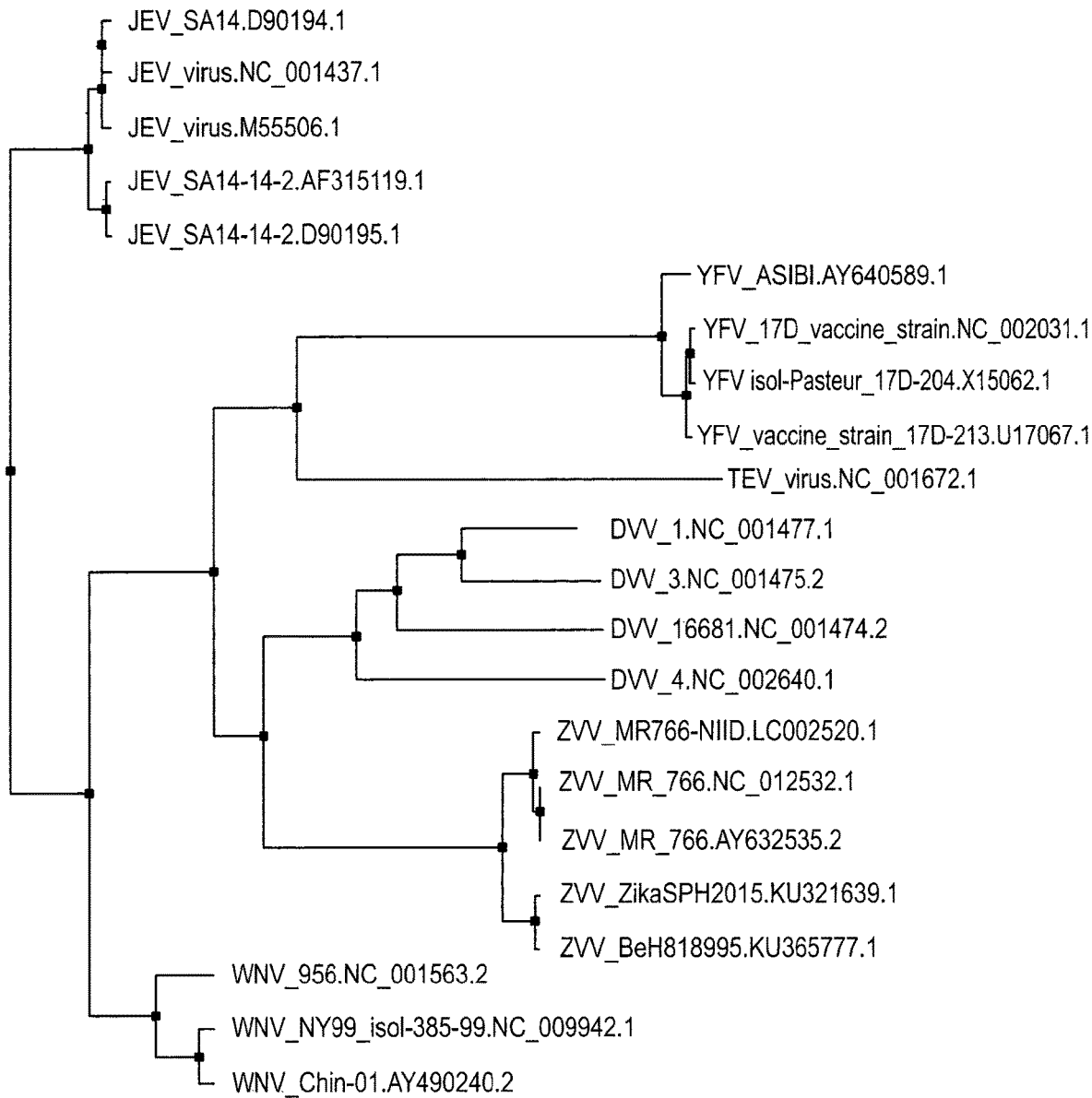
FIG. 5: Neighbor joining tree (by % identity. aa), E-protein.
Figure 6:
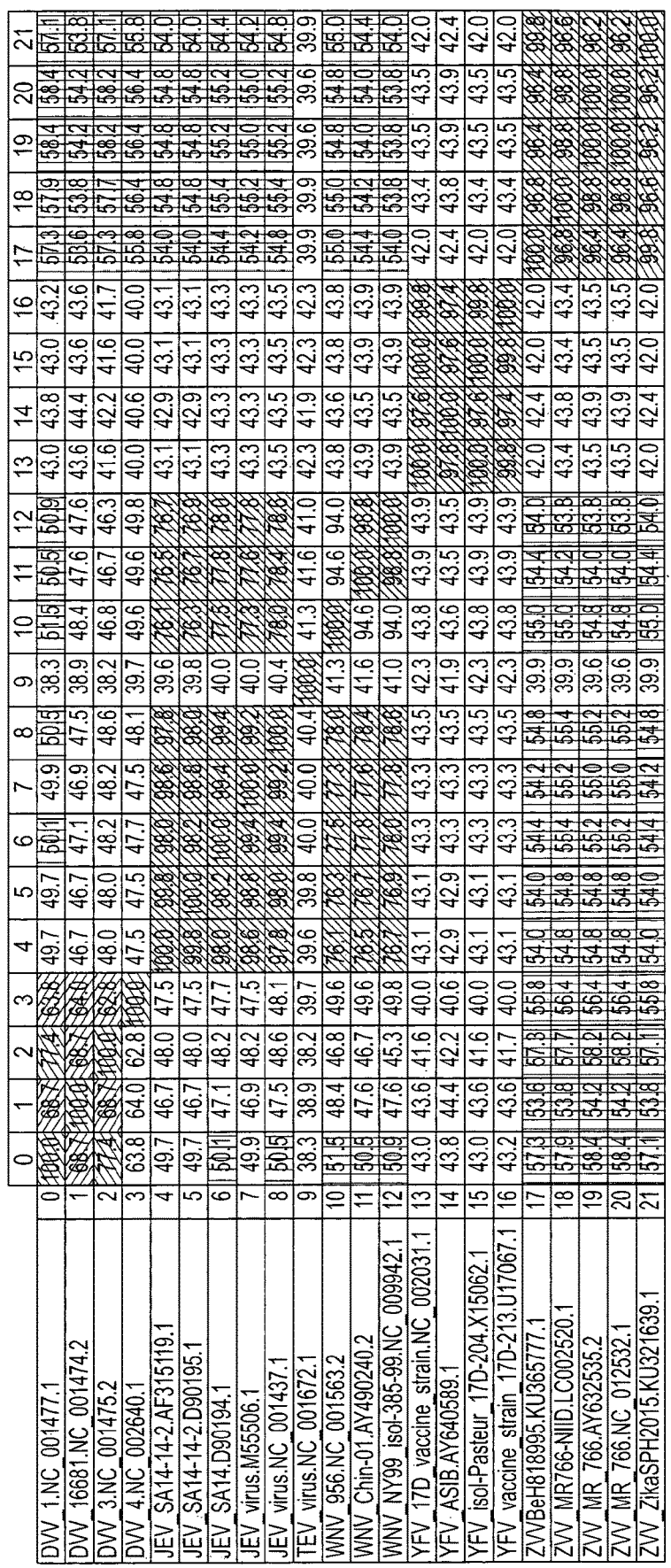
FIG. 6: Pairwise alignment-Jalview (% identity, aa), E-protein.
Figure 8:
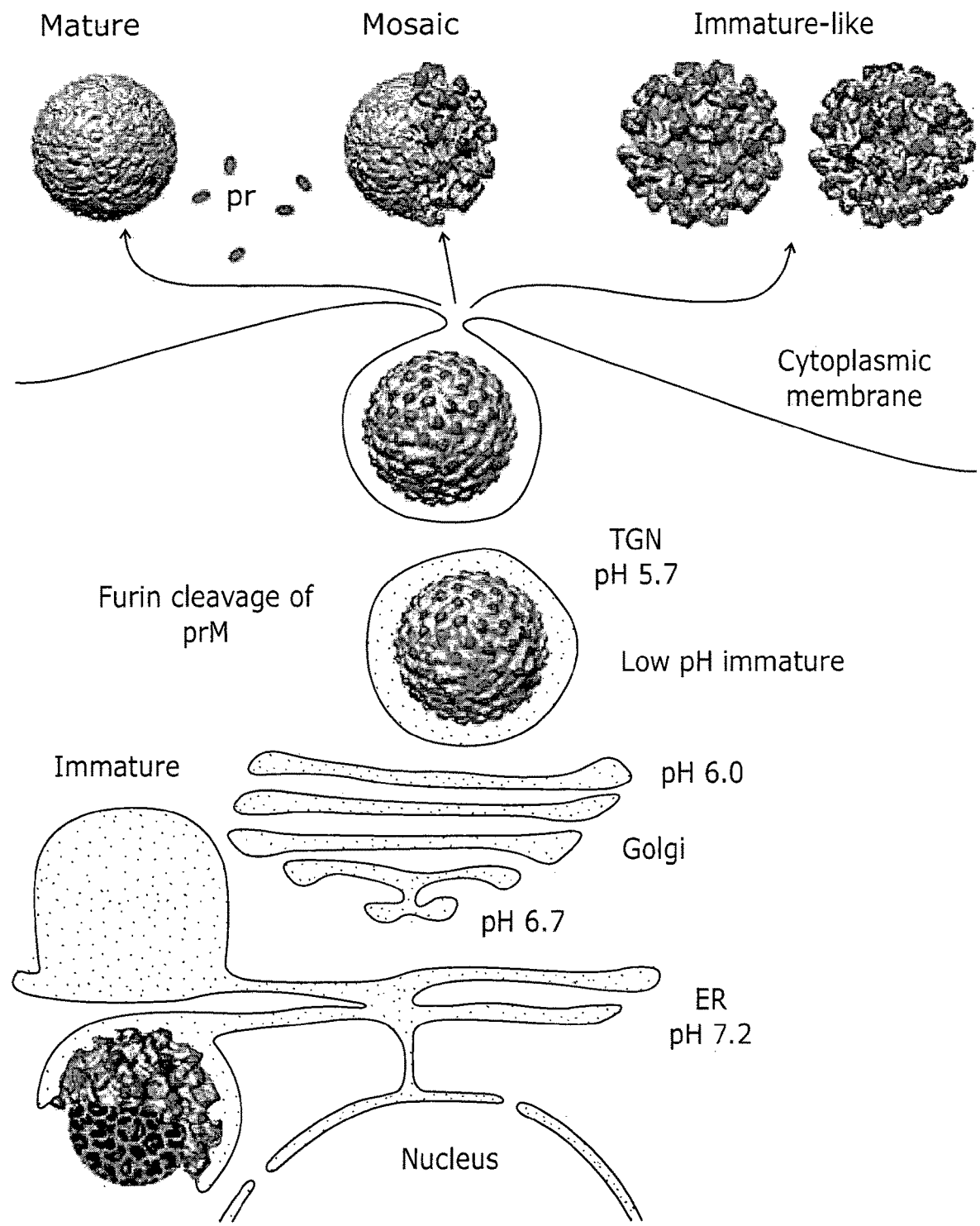
FIG. 8: An example of virus particle maturation in the host cell. As observed in flaviviruses, full maturation of the particles requires proteolytic cleavage of the precursor membrane glycoprotein (prM) by the host protease furin. Not all prM molecules are cleaved, resulting in the release of mature, mosaic or immature-like conformations from the cells. Mosaic and immature forms are generally not infectious-only mature virions are infective and have hemagglutinin (HA)/TCID50 activity. (Figure adapted from Plevka, et al., Maturation of flaviviruses starts from one or more icosahedrally independent nucleation centres, EMBO reports (2011) 12, 602-606).

The present invention relates to the use of protamine sulphate (PS) in a process of purification of a live virus, wherein the protamine sulphate facilitates the removal of impurities from a crude virus harvest, including non-infectious virus particles and aggregates. As seen in FIG. 8 using flaviviruses as an example, virus production in the host cell can result in the release of virus products which are not mature, and non-infectious particles, which can also be considered impurities according to the present invention. As such, the present invention also relates to the enrichment of infectious virus particles from a crude harvest containing a mixture of virus particles and other viral products in various stages of maturation.

The use of protamine sulphate can follow crude cell lysis or any further step after cell lysis (e.g. including after a pre-purification with filtration, chromatography etc) wherein the virus particles are further enriched or concentrated and/or other impurities are removed and/or buffer components are exchanged. The further steps may comprise filtration or concentration of the crude cell lysate.

The protamine sulphate may comprise the sequence PRRRRSSSRP VRRRRRPRVS RRRRRRGGRR RR (SEQ ID NO: 1) or a variant thereof wherein the amino acid sequence comprises from 28-35 amino acids, preferably 29-34, more preferably 30-33 amino acids, most preferably 31 or 32 amino acids. The protamine sulphate preferably comprises at least 19 arginine residues, more preferably at least 20 arginine residues, more preferably at least 21 arginine residues, even more preferably at least 22 residues, most preferably 20 or 21 arginine residues. Further, other protamine sulphate-like compounds or variants thereof may be used. Therefore, the use of the term "protamine salt" herein shall serve to encompass natural variations on SEQ ID NO: 1, preferably, but not limited to, the protamine sulphate forms.

The process according to the current invention may also comprise the use of a sucrose gradient, preferably an optimized sucrose gradient. The sucrose gradient is preferably optimized for the removal of protamine sulfate, also for the removal of immature viral particles or other viral particles which are non-infectious or host cell proteins or nucleic acids (DNA, RNA, mRNA, etc) or other host cell debris. In the current invention the optimized sucrose gradient comprises at least two, at least three, at least four layers of sucrose solutions with different densities. In one embodiment, the virus preparation to be purified is provided in a sucrose solution which has a density of about 8%, about 9%, about 10%, about 11%, about 12% sucrose (w/w), preferably about 10%. In one embodiment, one sucrose solution in the gradient has a density of about 45%, about 46%, about 47%, about 48%, about 49%, about 50%, about 51%, about 52%, about 53%, about 54%, about 55% sucrose (w/w), preferably about 50%. In one embodiment, one sucrose solution in the gradient has a density of about 30%, about 31%, about 32%, about 33%, about 34%, about 35%, about 36%, about 37%, about 38%, about 39%, about 40% sucrose (w/w), preferably about 35%. In one embodiment, one sucrose solution in the gradient has a density of about 10%, about 11%, about 12%, about 13%, about 14%, about 15%, about 16%, about 17%, about 18%, about 19%, about 20% sucrose (w/w), preferably about 15% sucrose. In a preferred embodiment, the sucrose gradient comprises three layers of sucrose solutions of about 50%, about 35% and about 15% (w/w) sucrose and the virus composition to be purified is contained in about 10% (w/w) sucrose. Because the invention provided for means to not only test for host cell DNA but also immature viral particles, the skilled person in the art is able to more precisely optimize the sucrose gradient for most efficient purification and include additional tools such as PRNT assay to monitor purification success.

The process comprising the use of protamine sulphate of the invention can be applied to purification of any virus for use in pharmaceutical compositions, for example, for a pharmaceutical composition such as a vaccine where it is important that the virus is in its infectious form. The virus to be purified may be any live virus, any live attenuated virus or any live chimeric virus, preferably a live wild type virus such as a Zika virus of the Asian lineage. In one embodiment, the virus particle is also be later inactivated. In a preferred embodiment, the virus is inactivated with formaldehyde.

In a preferred embodiment, the produced Zika virus is derived from the Asian lineage (which includes the strains found in South America and all strains derived from any Asian lineage). In some other embodiments, the produced Zika virus is a Zika virus as described in the Sequence section of this application (SEQ ID NO: 2 to 69 or 78).

Figure 9:
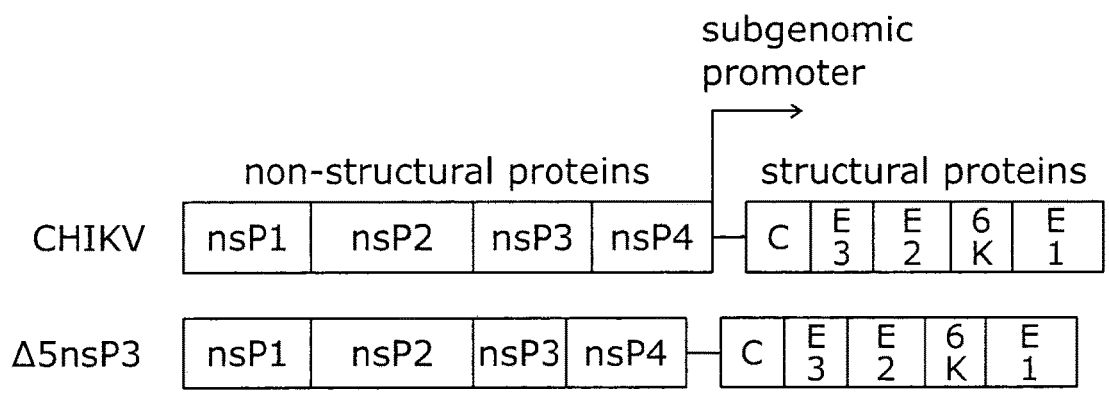
FIG. 9: CHIKV schematic genome, including non-structural and structural proteins (labeled "CHIKV") as well as a schematic representation of the Δ5nsP3 attenuated Chikungunya virus used to exemplify the purification process of the current invention (labeled "Δ5nsP3"). The black triangle indicates the approximate location of the deletion in the nsP3 coding region. (Figure adapted from Hallengird et al. 2014, supra.)

In another preferred embodiment, the live attenuated Chikungunya virus is the protective ChikV-ICRES1-Δ5nsP3 described by Hallengärd et al. (Novel Attenuated Chikungunya Vaccine Candidates Elicit Protective Immunity in C57BL/6 mice (2014) J. Virology, 88(5):2858-2866). Briefly, the ChikV genome carries a positive-sense single-stranded RNA genome of 11 Kb containing two open reading frames encoding nonstructural proteins (nsP1 to nsP4) and structural proteins (C, E3, E2, 6K, and E1), respectively (see FIG. 9, top construct). The attenuated virus Δ5nsP3, based on the La Reunion ChikV strain LR2006-OPY1, was obtained by the substitution of amino acid residues 1656 to 1717 of the P1234 polyprotein with a small linker (aa sequence AYRAAAG) in the hypervariable region of the nsP3 protein (see FIG. 9, bottom construct). The Δ5nsP3 ChikV mutant was shown to be infectious, highly immunogenic and protective against challenge with wild type ChikV (Hallengärd, et al., supra and Hallengärd, et al., Prime-Boost Immunization Strategies against Chikungunya Virus (2014) J. Virology, 88(22):13333-13343). In one embodiment, the live attenuated Chikungunya virus may be a variant of the ChikV-ICRES1-Δ5nsP3 attenuated mutant virus.

Figure 10:
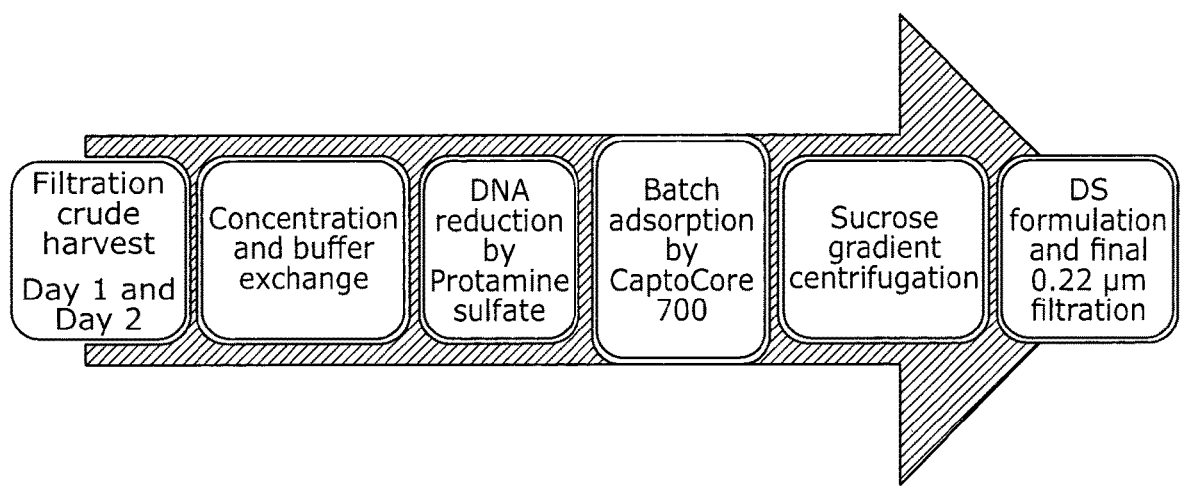
FIG. 10: Flow-chart showing an exemplary downstream Δ5nsP3 CHIK virus purification process from the crude harvest to formulation of the (vaccine) drug substance, a preferred embodiment of the process of the invention.

A preferred embodiment of the process of the current invention is shown in FIG. 10 (Chikungunya virus) and FIG. 17A (Zika virus).

TABLE 1

Overview of process buffers and stock solutions

| Buffer | Composition | Final pH | Final conductivity [mS/cm] |
|---|---|---|---|
| A | 0.5M NaOH | | n.a. |
| B | 0.1M NaOH | | n.a. |
| C | 25 mM Tris, 150 mM NaCl | 7.4 ± 0.2 | 16.5 |
| D | 1M Tris | 7.4 ± 0.2 | n.a. |
| E | 4.5M NaCl | n.a. | n.a. |
| F | 1M NaCl | n.a. | n.a. |
| G | 1% SDS | n.a. | n.a. |
| H | 50% (w/w) Sucrose in 25 mM Tris, 150 mM NaCl | 7.4 ± 0.2 | n.a. |
| I | 35% (w/w) Sucrose in 25 mM Tris, 150 mM NaCl | 7.4 ± 0.2 | n.a. |
| J | 15% (w/w) Sucrose in 25 mM Tris, 150 mM NaCl | 7.4 ± 0.2 | n.a. |
| K | 10× PBS | 7.4 ± 0.2 | n.a. |
| L | 50 mg/mL Protamine sulphate | 7.4 ± 0.2 | n.a. |
| M | Drug substance formulation buffer (10 mM Tris(hydroxymethyl)-aminomethan, 5% Sucrose, 1% (10 mg/mL) rHSA) | 7.4 ± 0.2 | 1.3 |

TABLE 2

Abbreviations

| | |
|---|---|
| °Bx | Degrees Brix = sugar content (w/w) of an aqueous solution |
| BSA | Bovine serum albumin |
| CC700 | Capto ™ Core 700 |
| ChikV | Chikungunya virus |
| CPE | Cytopathic effect |
| EtOH | Ethanol |
| EU | Endotoxin units |
| DS | Drug Substance |
| DP | Drug Product |
| DSP | Downstream Process |
| HCP | Host cell protein |
| hcDNA | Host cell DNA |
| hpi | Hours post infection |
| HPLC | High Performance Liquid Chromatography |
| ID | Inner diameter |
| JEV | Japanese Encephalitis virus |
| LAL | Limulus amebocyte lysate |
| LDS buffer | Lithium dodecyl sulfate sample loading buffer |
| LOD | Limit of detection |
| LOQ | Limit of quantitation |
| MALLS | Multiangle light scattering |
| mAU | Milli absorbance units |
| MS | Mass spectroscopy |
| NIV | Neutralized inactivated virus |
| PBS | Phosphate buffered saline |
| PD | Process development |
| PFU | Plaque forming units |

TABLE 2-continued

Abbreviations

| | |
|---|---|
| °Bx | Degrees Brix = sugar content (w/w) of an aqueous solution |
| p.i. | Post-infection |
| PS | Protamine sulphate or protamine sulfate |
| rcf | Relative centrifugal force |
| rHSA | Recombinant human serum albumin |
| Rms radius | Root mean square radius |
| rMSB | Research master seed bank |
| RSD | Relative standard deviation |
| SEC | Size exclusion chromatography |
| SGC | Sucrose gradient centrifugation |
| SGP | Sucrose gradient purified |
| SDS | Sodium dodecyl sulphate |
| TBS | Tris buffered saline |
| TFF | Tangential flow filtration |
| TCID50 | Tissue culture infectious dose 50% |
| UF/DF | Ultrafiltration/diafiltration |
| WFI | Water for injection |
| ZikaV | Zika virus |

Brix:

Degrees Brix (° Bx) is the sugar content of an aqueous solution. One degree Brix is 1 gram of sucrose in 100 grams of solution and represents the strength of the solution as percentage by mass. ° Bx corresponds to the sucrose content in % (w/w), eg. 45° Bx equals 45% (w/w) sucrose.

TABLE A

Primers for Zika virus sequencing: lower case letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
| 1 | 9320_Zika_PF_1F | SEQ ID NO: 80 ttaggatccGTTGTTGATCTGTGTGAAT | 69.9 | 74.6 | 707 |
| | 9321_Zika_PF_1R | SEQ ID NO: 81 taactcgagCGTACACAACCCAAGTT | 69.3 | 75.6 | |
| 2 | 9322_Zika_PF_2F | SEQ ID NO: 82 ttaggatccTCACTAGACGTGGGAGTG | 70 | 73.9 | 704 |
| | 9323_Zika_PF_2R | SEQ ID NO: 83 taactcgagAAGCCATGTCYGATATTGAT | 69.8 | 73.7 | |
| 3 | 9324_Zika_PF_3F | SEQ ID NO: 84 ttaggatccGCATACAGCATCAGGTG | 72.3 | 74.5 | 712 |
| | 9325_Zika_PF_3R | SEQ ID NO: 85 taactcgagTGTGGAGTTCCGGTGTCT | 72 | 76.4 | |
| 4 | 9326_Zika_PF_4F | SEQ ID NO: 86 ttaggatccGAATAGAGCGAARGTTGAGATA | 70.9 | 74 | 712 |
| | 9327_Zika_PF_4R | SEQ ID NO: 87 taactcgAGTGGTGGGTGATCTTCTTCT | 70.5 | 73.7 | |
| 5 | 9328_Zika_PF_5F | SEQ ID NO: 88 ttaggatcCAGTCACAGTGGAGGTACAGTAC | 70.3 | 75 | 704 |
| | 9329_Zika_PF_5R | SEQ ID NO: 89 taactcgagCRCAGATACCATCTTCCC | 71.5 | 77.3 | |
| 6 | 9330_Zika_PF_6F | SEQ ID NO: 90 ttaggatCCCTTATGTGCTTGGCCTTAG | 70.7 | 72.7 | 698 |
| | 9331_Zika_PF_6R | SEQ ID NO: 91 taactcgagTCTTCAGCCTCCATGTG | 70.4 | 76.9 | |
| 7 | 9332_Zika_PF_7F | SEQ ID NO: 92 ttaggatccAATGCCCACTCAAACATAGA | 71.9 | 75 | 716 |
| | 9333_Zika_PF_7R | SEQ ID NO: 93 taactcgagTCATTCTCTTCTTCAGCCCTT | 71 | 74 | |

TABLE A-continued

Primers for Zika virus sequencing: lower case letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
| 8 | 9334_Zika_PF_8F | SEQ ID NO: 94<br>ttaggatccAAGGGTGATCGAGGAAT | 70.9 | 75.2 | 703 |
|  | 9335_Zika_PF_8R | SEQ ID NO: 95<br>taactcgagTTCCCTTCAGAGAGGAGC | 71.9 | 73.4 |  |
| 9 | 9336_Zika_PF_9F | SEQ ID NO: 96<br>ttaggatccTCTTTTGCAAACTGCGATC | 71.9 | 75 | 699 |
|  | 9337_Zika_PF_9R | SEQ ID NO: 97<br>taactcgagTCCAGCTGCAAAGGGTAT | 71 | 74.9 |  |
| 10 | 9338_Zika_PF_10F | SEQ ID NO: 98<br>ttaggatccGTGTGGACATGTACATTGA | 71.4 | 75.8 | 706 |
|  | 9339_Zika_PF_10R | SEQ ID NO: 99<br>taactcgagCCCATTGCCATAAAGTC | 70.4 | 75.8 |  |
| 11 | 9340_Zika_PF_11F | SEQ ID NO: 100<br>ttaggatccTCATACTGTGGTCCATGGA | 71.6 | 78.1 | 692 |
|  | 9341_Zika_PF_11R | SEQ ID NO: 101<br>taactcgagGCCCATCTCAACCCTTG | 74 | 78 |  |
| 12 | 9342_Zika_PF_12F | SEQ ID NO: 102<br>ttaggatccTAGAGGGCTTCCAGTGC | 70.9 | 74 | 707 |
|  | 9343_Zika_PF_12R | SEQ ID NO: 103<br>taactcgAGATACTCATCTCCAGGTTTGTTG | 70.2 | 72.2 |  |
| 13 | 9344_Zika_PF_13F | SEQ ID NO: 104<br>ttaggatccGAAAACAAAACATCAAGAGTG | 70.6 | 75.4 | 726 |
|  | 9345_Zika_PF_13R | SEQ ID NO: 105<br>taactcgagGAATCTCTCTGTCATGTGTCCT | 71.9 | 75.6 |  |
| 14 | 9346_Zika_PF_14F | SEQ ID NO: 106<br>ttaggatccTTGATGGCACGACCAAC | 73.1 | 75.6 | 715 |
|  | 9347_Zika_PF_14R | SEQ ID NO: 107<br>ttaggatccGTTGTTGATCTGTGTGAAT | 70.8 | 77.9 |  |
| 15 | 9348_Zika_PF_15F | SEQ ID NO: 108<br>taactcgagCAGGTCAATGTCCATTG | 71.9 | 75.4 | 719 |
|  | 9349_Zika_PF_15R | SEQ ID NO: 109<br>ttaggatccTGTTGTGTTCCTATTGCTGGT | 73.9 | 77.2 |  |
| 16 | 9350_Zika_PF_16F | SEQ ID NO: 110<br>taactcgaGTGATCAGRGCCCCAGC | 72.3 | 75.4 | 703 |
|  | 9351_Zika_PF_16R | SEQ ID NO: 111<br>ttaggatccTGCTGCCCAGAAGAGAA | 72 | 76.3 |  |
| 17 | 9352_Zika_PF_17F | SEQ ID NO: 112<br>taactcgaGCACCAACAYGGGTTCTT | 73.6 | 76 | 705 |
|  | 9353_Zika_PF_17R | SEQ ID NO: 113<br>ttaggatcCTCAAGGACGGTGTGGC | 72 | 75.5 |  |
| 18 | 9354_Zika_PF_18F | SEQ ID NO: 114<br>taactcgagCAATGATCTTCATGTTGGG | 71.7 | 75.8 | 699 |
|  | 9355_Zika_PF_18R | SEQ ID NO: 115<br>ttaggatccTATGGGGGAGGACTGGT | 71 | 74.1 |  |
| 19 | 9356_Zika_PF_19F | SEQ ID NO: 116<br>taactcGAGCCCAGAACCTTGGATC | 73.3 | 75.5 | 711 |
|  | 9357_Zika_PF_19R | SEQ ID NO: 117<br>ttaggatcCAGACCCCCAAGAAGGC | 71.3 | 76.9 |  |
| 20 | 9358_Zika_PF_20F | SEQ ID NO: 118<br>taactcgagCCCCTTTGGTCTTGTCT | 71.7 | 75 | 706 |
|  | 9359_Zika_PF_20R | SEQ ID NO: 119<br>ttaggatccAGGAAGGATGTATGCAGATG | 71.9 | 73.9 |  |
| 21 | 9360_Zika_PF_21F | SEQ ID NO: 120<br>taactcgagACATTTGCGCATATGATTTTG | 70.4 | 75.7 | 709 |
|  | 9361_Zika_PF_21R | SEQ ID NO: 121<br>ttaggatccAGGAAGGACACACAAGAGT | 71.8 | 75 |  |

TABLE A-continued

Primers for Zika virus sequencing: lower case letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
| 22 | 9362_Zika_PF_22F | SEQ ID NO: 122 taactcgagACAGGCTGCACAGCTTT | 70 | 79.1 | 581 |
|  | 9363_Zika_PF_22R | SEQ ID NO: 123 ttaggatccTCTCTCATAGGGCACAGAC | 74.8 | 81.1 |  |

Sequences

A typical form of protamine
SEQ ID NO: 1
PRRRRSSSRP VRRRRRPRVS RRRRRRGGRR RR

Provided below are examples of nucleic acid sequences of the genomes of Zika viruses that may be used in the methods, compositions, and/or vaccines described herein.

```
KU321639.1 Zika virus strain ZikaSPH2015, Brazil, complete genome (SEQ ID NO: 2)
                                                                                      SEQ ID NO: 2
GTTGTTACTGTTGCTGACTCAGACTGCGACAGTTCGAGTTTGAAGCGAAAGCTAGCAACAGTATCAACAGGTTTTATTTGGATT TGGAAACGAGAGTTTCTGGTCATGAAAAACCCAAAAAAGAAATCCGGAGGATTCCGGATTGTCAATATGCTAAAACGCGGAG TAGCCCGTGTGAGCCCCTTTGGGGGCTTGAAGAGGCTGCCAGCCGGACTTCTGCTGGGTCATGGGCCCATCAGGATGGTCTTG GCAATTCTAGCCTTTTTGAGATTCACGGCAATCAAGCCATCACTGGGTCTCATCAATAGATGGGGTTCAGTGGGAAAAAAGA GGCTATGGAAATAATAAAGAAGTTCAAGAAAGATCTGGCTGCCATGCTGAGAATAATCAATGCTAGGAAGGAGAAGAAGAG ACGGGGCGCAGATACTAGTGTCGGAATTGTTGGCCTCCTGCTGACCACAGCTATGGCAGCGGAGGTCACTAGACGTGGGAGT GCATACTATATGTACTTGGACAGAAACGATGCTGGGGAGGCCATATCTTTTCCAACCACATTGGGGATGAATAAGTGTTATAT ACAGATCATGGATCTTGGACACATGTGTGATGCCACCATGAGCTATGAATGCCCTATGCTGGATGAGGGGGTGGAACCAGAT GACGTCGATTGTTGGTGCAACACGACGTCAACTTGGGTTGTGTACGGAACCTGCCATCACAAAAAAGGTGAAGCACGGAGAT CTAGAAGAGCTGTGACGCTCCCCTCCCATTCCACTAGGAAGCTGCAAACGCGGTCGCAAACCTGGTTGGAATCAAGAGAATAC ACAAAGCACTTGATTAGAGTCGAAAATTGGATATTCAGGAACCCTGGCTTCGCGTTAGCAGCAGCTGCCATCGCTTGGCTTTTG GGAAGCTCAACGAGCCAAAAAGTCATATACTTGGTCATGATACTGCTGATTGCCCCGGCATACAGCATCAGGTGCATAGGAGT CAGCAATAGGGACTTTGTGGAAGGTATGTCAGGTGGGACTTGGGTTGATATTGTCTTGGAACATGGAGGTTGTGTCACCGTA ATGGCACAGGACAAACCGACTGTCGACATAGAGCTGGTTACAACAACAGTCAGCAACATGGCGGAGGTAAGATCCTACTGCT ATGAGGCATCAATATCAGACATGGCTTCGGACAGCCGCTGCCCAACACAAGGTGAAGCCTACCTTGACAAGCAATCAGACACT CAATATGTCTGCAAAAGAACGTTAGTGGACAGAGGCTGGGGAAATGGATGTGGACTTTTTGGCAAAGGGAGTCTGGTGACAT GCGCTAAGTTTGCATGCTCCAAGAAAATGACCGGGAAGAGCATCCAGCCAGAGAATCTGGAGTACCGGATAATGCTGTCAGT TCATGGCTCCCAGCACAGTGGGATGATCGTTAATGACACAGGACATGAAACTGATGAGAATAGAGCGAAGGTTGAGATAACG CCCAATTCACCAAGAGCCGAAGCCACCCTGGGGGGTTTTGGAAGCCTAGGACTTGATTGTGAACCGAGGACAGGCCTTGACTT TTCAGATTTGTATTACTTGACTATGAATAACAAGCACTGGTTGGTTCACAAGGAGTGGTTCCACGACATTCCATTACCTTGGCAC GCTGGGGCAGACACCGGAACTCCACACTGGAACAACAAAGAAGCACTGGTAGAGTTCAAGGACGCACATGCCAAAAGGCAA ACTGTCGTGGTTCTAGGGAGTCAAGAAGGAGCAGTTCACACGGCCCTTGCTGGAGCTCTGGAGGCTGAGATGGATGGTGCAA AGGGAAGGCTGTCCTCTGGCCACTTGAAATGTCGCCTGAAAATGGATAAACTTAGATTGAAGGGCGTGTCATACTCCTTGTGT ACCGCAGCGTTCACATTCACCAAGATCCCGGCTGAAACACTGCACGGGACAGTCACAGTGGAGGTACAGTACGCAGGGACAG ATGGACCTTGCAAGGTTCCAGCTCAGATGGCGGTGGACATGCAAACTCTGACCCCAGTTGGGAGGTTGATAACCGCTAACCCC
```

-continued

```
GTAATCACTGAAAGCACTGAGAACTCTAAGATGATGCTGGAACTTGATCCACCATTTGGGGACTCTTACATTGTCATAGGAGTC

GGGGAGAAGAAGATCACCCACCACTGGCACAGGAGTGGCAGCACCATTGGAAAAGCATTTGAAGCCACTGTGAGAGGTGCC

AAGAGAATGGCAGTCTTGGGAGACACAGCCTGGGACTTTGGATCAGTTGGAGGCGCTCTCAACTCATTGGGCAAGGGCATCC

ATCAAATTTTTGGAGCAGCTTTCAAATCATTGTTTGGAGGAATGTCCTGGTTCTCACAAATTCTCATTGGAACGTTGCTGATGTG

GTTGGGTCTGAACACAAAGAATGGATCTATTTCCCTTATGTGCTTGGCCTTAGGGGAGTGTTGATCTTCTTATCCACAGCCGT

CTCTGCTGATGTGGGGTGCTCGGTGGACTTCTCAAAGAAGGAGACGAGATGCGGTACAGGGGTGTTCGTCTATAACGACGTT

GAAGCCTGGAGGGACAGGTACAAGTACCATCCTGACTCCCCCCGTAGATTGGCAGCAGCAGTCAAGCAAGCCTGGGAAGATG

GTATCTGCGGGATCTCCTCTGTTTCAAGAATGGAAAACATCATGTGGAGATCAGTAGAAGGGGAGCTCAACGCAATCCTGGAA

GAGAATGGAGTTCAACTGACGGTCGTTGTGGGATCTGTAAAAAACCCCATGTGGAGAGGTCCACAGAGATTGCCCGTGCCTG

TGAACGAGCTGCCCCACGGCTGGAAGGCTTGGGGGAAATCGCACTTCGTCAGAGCAGCAAAGACAAATAACAGCTTTGTCGT

GGATGGTGACACACTGAAGGAATGCCCACTCAAACATAGAGCATGGAACAGCTTTCTTGTGGAGGATCATGGGTTCGGGGTA

TTTCACACTAGTGTCTGGCTCAAGGTTAGAGAAGATTATTCATTAGAGTGTGATCCAGCCGTTATTGGAACAGCTGTTAAGGGA

AAGGAGGCTGTACACAGTGATCTAGGCTACTGGATTGAGAGTGAGAAGAATGACACATGGAGGCTGAAGAGGGCCCATCTG

ATCGAGATGAAAACATGTGAATGGCCAAAGTCCCACACATTGTGGACAGATGGAATAGAAGAGAGTGATCTGATCATACCCA

AGTCTTTAGCTGGGCCACTCAGCCATCACAATACCAGAGAGGGCTACAGGACCCAAATGAAAGGGCATGGCACAGTGAAGA

GCTTGAAATTCGGTTTGAGGAATGCCCAGGCACTAAGGTCCACGTGGAGGAAACATGTGGAACAAGAGGACCATCTCTGAGA

TCAACCACTGCAAGCGGAAGGGTGATCGAGGAATGGTGCTGCAGGGAGTGCACAATGCCCCACTGTCGTTCCGGGCTAAAG

ATGGCTGTTGGTATGGAATGGAGATAAGGCCCAGGAAAGAACCAGAAAGCAACTTAGTAAGGTCAATGGTGACTGCAGGATC

AACTGATCACATGGATCACTTCTCCCTTGGAGTGCTTGTGATTCTGCTCATGGTGCAGGAAGGGCTGAAGAAGAGAATGACCA

CAAAGATCATCATAAGCACATCAATGGCAGTGCTGGTAGCTATGATCCTGGGAGGATTTTCAATGAGTGACCTGGCTAAGCTT

GCAATTTTGATGGGTGCCACCTTCGCGGAAATGAACACTGGAGGAGATGTAGCTCATCTGGCGCTGATAGCGGCATTCAAAGT

CAGACCAGCGTTGCTGGTATCTTTCATCTTCAGAGCTAATTGGACACCCCGTGAAAGCATGCTGCTGGCCTTGGCCTCGTGTCT

TTTGCAAACTGCGATCTCCGCCTTGGAAGGCGACCTGATGGTTCTCATCAATGGTTTTGCTTTGGCCTGGTTGGCAATACGAGC

GATGGTTGTTCCACGCACTGATAACATCACCTTGGCAATCCTGGCTGCTCTGACACCACTGGCCCGGGGCACACTGCTTGTGGC

GTGGAGAGCAGGCCTTGCTACTTGCGGGGGGTTTATGCTCCTCTCTCTGAAGGGAAAAGGCAGTGTGAAGAAGAACTTACCA

TTTGTCATGGCCCTGGGACTAACCGCTGTGAGGCTGGTCGACCCCATCAACGTGGTGGGGCTGCTGTTGCTCACAAGGAGTGG

GAAGCGGAGCTGGCCCCCTAGCGAAGTACTCACAGCTGTTGGCCTGATATGCGCATTGGCTGGAGGGTTCGCCAAGGCAGAT

ATAGAGATGGCTGGGCCCATGGCCGCGGTCGGTCTGCTAATTGTCAGTTACGTGGTCTCAGGAAAGAGTGTGGACATGTACA

TTGAAAGAGCAGGTGACATCACATGGGAAAAGATGCGGAAGTCACTGGAAACAGTCCCCGGCTCGATGTGGCGCTAGATGA

GAGTGGTGATTTCTCCCTGGTGGAGGATGACGGTCCCCCCATGAGAGAGATCATACTCAAGGTGGTCCTGATGACCATCTGTG

GCATGAACCCAATAGCCATACCCTTTGCAGCTGGAGCGTGGTACGTATACGTGAAGACTGGAAAAAGGAGTGGTGCTCTATG

GGATGTGCCTGCTCCCAAGGAAGTAAAAAAGGGGGAGACCACAGATGGAGTGTACAGAGTAATGACTCGTAGACTGCTAGG

TTCAACACAAGTTGGAGTGGGAGTTATGCAAGAGGGGGTCTTTCACACTATGTGGCACGTCACAAAAGGATCCGCGCTGAGA

AGCGGTGAAGGGAGACTTGATCCATACTGGGGAGATGTCAAGCAGGATCTGGTGTCATACTGTGGTCCATGGAAGCTAGATG

CCGCCTGGGACGGGCACAGCGAGGTGCAGCTCTTGGCCGTGCCCCCCGGAGAGAGAGCGAGGAACATCCAGACTCTGCCCG

GAATATTTAAGACAAAGGATGGGGACATTGGAGCGGTTGCGCTGGATTACCCAGCAGGAACTTCAGGATCTCCAATCCTAGA

CAAGTGTGGGAGAGTGATAGGACTTTATGGCAATGGGGTCGTGATCAAAAATGGGAGTTATGTTAGTGCCATCACCCAAGGG

AGGAGGGAGGAAGAGACTCCTGTTGAGTGCTTCGAGCCTTCGATGCTGAAGAAGAAGCAGCTAACTGTCTTAGACTTGCATC

CTGGAGCTGGGAAAACCAGGAGAGTTCTTCCTGAAATAGTCCGTGAAGCCATAAAAACAAGACTCCGTACTGTGATCTTAGCT

CCAACCAGGGTTGTCGCTGCTGAAATGGAGGAAGCCCTTAGAGGGCTTCCAGTGCGTTATATGACAACAGCAGTCAATGTCAC

CCACTCTGGAACAGAAATCGTCGACTTAATGTGCCATGCCACCTTCACTTCACGTCTACTACAGCCAATCAGAGTCCCCAACTAT
```

-continued

```
AATCTGTATATTATGGATGAGGCCCACTTCACAGATCCCTCAAGTATAGCAGCAAGAGGATACATTTCAACAAGGGTTGAGAT

GGGCGAGGCGGCTGCCATCTTCATGACCGCCACGCCACCAGGAACCCGTGACGCATTTCCGGACTCCAACTCACCAATTATGG

ACACCGAAGTGGAAGTCCCAGAGAGAGCCTGGAGCTCAGGCTTTGATTGGGTGACGGATTATTCTGGAAAAACAGTTTGGTT

TGTTCCAAGCGTGAGGAACGGCAATGAGATCGCAGCTTGTCTGACAAAGGCTGGAAAACGGGTCATACAGCTCAGCAGAAAG

ACTTTTGAGACAGAGTTCCAGAAAACAAAACATCAAGAGTGGGACTTTGTCGTGACAACTGACATTTCAGAGATGGGCGCCAA

CTTTAAAGCTGACCGTGTCATAGATTCCAGGAGATGCCTAAAGCCGGTCATACTTGATGGCGAGAGAGTCATTCTGGCTGGAC

CCATGCCTGTCACACATGCCAGCGCTGCCCAGAGGAGGGGCGCATAGGCAGGAATCCCAACAAACCTGGAGATGAGTATCT

GTATGGAGGTGGGTGCGCAGAGACTGACGAAGACCATGCACACTGGCTTGAAGCAAGAATGCTCCTTGACAATATTTACCTCC

AAGATGGCCTCATAGCCTCGCTCTATCGACCTGAGGCCGACAAAGTAGCAGCCATTGAGGGAGAGTTCAAGCTTAGGACGGA

GCAAAGGAAGACCTTTGTGGAACTCATGAAAAGAGGAGATCTTCCTGTTTGGCTGGCCTATCAGGTTGCATCTGCCGGAATAA

CCTACACAGATAGAAGATGGTGCTTTGATGGCACGACCAACAACACCATAATGGAAGACAGTGTGCCGGCAGAGGTGTGGAC

CAGACACGAGAGAAAGAGTGCTCAAACCGAGGTGGATGGACGCCAGAGTTTGTTCAGATCATGCGGCCCTGAAGTCATTC

AAGGAGTTTGCCGCTGGGAAAAGAGGAGCGGCTTTTGGAGTGATGGAAGCCCTGGGAACACTGCCAGGACACATGACAGAG

AGATTCCAGGAAGCCATTGACAACCTCGCTGTGCTCATGCGGGCAGAGACTGGAAGCAGGCCTTACAAAGCCGCGGCGCCC

AATTGCCGGAGACCCTAGAGACCATTATGCTTTTGGGGTTGCTGGGAACAGTCTCGCTGGGAATCTTTTTCGTCTTGATGAGG

AACAAGGGCATAGGGAAGATGGGCTTTGGAATGGTGACTCTTGGGGCCAGCGCATGGCTCATGTGGCTCTCGGAAATTGAGC

CAGCCAGAATTGCATGTGTCCTCATTGTTGTGTTCCTATTGCTGGTGGTGCTCATACCTGAGCCAGAAAAGCAAAGATCCCCC

AGGACAACCAAATGGCAATCATCATCATGGTAGCAGTAGGTCTTCTGGGCTTGATTACCGCCAATGAACTCGGATGGTTGGAG

AGAACAAAGAGTGACCTAAGCCATCTAATGGGAAGGAGAGAGGAGGGGGCAACCATGGGATTCTCAATGGACATTGACCTG

CGGCCAGCCTCAGCTTGGGCCATCTATGCTGCCTTGACAACTTTCATTACCCCAGCCGTCCAACATGCAGTGACCACTTCATACA

ACAACTACTCCTTAATGGCGATGGCCACGCAAGCTGGAGTGTTGTTTGGTATGGGCAAAGGGATGCCATTCTACGCATGGGAC

TTTGGAGTCCCGCTGCTAATGATAGGTTGCTACTCACAATTAACGCCCCTGACCCTAATAGTGGCCATCATTTTGCTCGTGGCG

CACTACATGTACTTGATCCCAGGGCTGCAGGCAGCAGCTGCGCGTGCTGCCCAGAAGAGAACGGCAGCTGGCATCATGAAGA

ACCCTGTTGTGGATGGAATAGTGGTGACTGACATTGACACAATGACAATTGACCCCCAAGTGGAGAAAAAGATGGGACAGGT

GCTACTCATGGCAGTAGCCGTCTCCAGCGCCATACTGTCGCGGACCGCCTGGGGGTGGGGGAGGCTGGGGCCCTGATCACA

GCCGCAACTTCCACTTTGTGGGAAGGCTCTCCGAACAAGTACTGGAACTCCTCTACAGCCACTTCACTGTGTAACATTTTTAGG

GGAAGTTACTTGGCTGGAGCTTCTCTAATCTACACAGTAACAAGAAACGCTGGCTTGGTCAAGAGACGTGGGGGTGGAACAG

GAGAGACCCTGGGAGAGAAATGGAAGGCCCGCTTGAACCAGATGTCGGCCCTGGAGTTCTACTCCTACAAAAAGTCAGGCAT

CACCGAGGTGTGCAGAGAAGAGGCCCGCCGCGCCCTCAAGGACGGTGTGGCAACGGGAGGCCATGCTGTGTCCCGAGGAAG

TGCAAAGCTGAGATGGTTGGTGGAGCGGGATACCTGCAGCCCTATGGAAAGGTCATTGATCTTGGATGTGGCAGAGGGGG

CTGGAGTTACTACGCCGCCACCATCCGCAAAGTTCAAGAAGTGAAAGGATACACAAAAGGAGGCCCTGGTCATGAAGAACCC

GTGTTGGTGCAAAGCTATGGGTGGAACATAGTCCGTCTTAAGAGTGGGGTGGACGTCTTTCATATGGCGGCTGAGCCGTGTG

ACACGTTGCTGTGTGACATAGGTGAGTCATCATCTAGTCCTGAAGTGGAAGAAGCACGGACGCTCAGAGTCCTCTCCATGGTG

GGGGATTGGCTTGAAAAAAGACCAGGAGCCTTTTGTATAAAAGTGTTGTGCCCATACACCAGCACTATGATGGAAACCCTGGA

GCGACTGCAGCGTAGGTATGGGGAGGACTGGTCAGAGTGCCACTCTCCCGCAACTCTACACATGAGATGTACTGGGTCTCT

GGAGCGAAAAGCAACACCATAAAAAGTGTGTCCACCACGAGCCAGCTCCTCTTGGGGCGCATGGACGGGCCTAGGAGGCCA

GTGAAATATGAGGAGGATGTGAATCTCGGCTCTGGCACGCGGGCTGTGGTAAGCTGCGCTGAAGCTCCCAACATGAAGATCA

TTGGTAACCGCATTGAAAGGATCCGCAGTGAGCACGCGGAAACGTGGTTCTTTGACGAGAACCACCCATATAGGACATGGGC

TTACCATGGAAGCTATGAGGCCCCCACACAAGGGTCAGCGTCCTCTCTAATAAACGGGGTTGTCAGGCTCCTGTCAAAACCCT

GGGATGTGGTGACTGGAGTCACAGGAATAGCCATGACCGACACCACACCGTATGGTCAGCAAAGAGTTTTCAAGGAAAAAGT

GGACACTAGGGTGCCAGACCCCCAAGAAGGTACTCGTCAGGTTATGAGCATGGTCTCTTCCTGGTTGTGGAAAGAGCTAGGC
```

-continued

AAACACAAACGGCCACGAGTCTGTACCAAAGAAGAGTTCATCAACAAGGTTCGTAGCAATGCAGCATTAGGGGCAATATTTGA
AGAGGAAAAAGAGTGGAAGACTGCAGTGGAAGCTGTGAACGATCCAAGGTTCTGGGCTCTAGTGGACAAGGAAAGAGAGCA

CCACCTGAGAGGAGAGTGCCAGAGTTGTGTGTACAACATGATGGGAAAAAGAGAAAAGAAACAAGGGGAATTTGGAAAGGC

CAAGGGCAGCCGCGCCATCTGGTATATGTGGCTAGGGGCTAGATTTCTAGAGTTCGAAGCCCTTGGATTCTTGAACGAGGATC
ACTGGATGGGGAGAGAGAACTCAGGAGGTGGTGTTGAAGGGCTGGGATTACAAAGACTCGGATATGTCCTAGAAGAGATGA
GTCGCATACCAGGAGGAAGGATGTATGCAGATGACACTGCTGGCTGGGACACCCGCATCAGCAGGTTTGATCTGGAGAATGA
AGCTCTAATCACCAACCAAATGGAGAAAGGGCACAGGGCCTTGGCATTGGCCATAATCAAGTACACATACCAAAACAAAGTG
GTAAAGGTCCTTAGACCAGCTGAAAAAGGGAAAACAGTTATGGACATTATTTCGAGACAAGACCAAAGGGGGAGCGGACAA
GTTGTCACTTACGCTCTTAACACATTTACCAACCTAGTGGTGCAACTCATTCGGAATATGGAGGCTGAGGAAGTCCTAGAGATG
CAAGACTTGTGGCTGCTGCGGAGGTCAGAGAAAGTGACCAACTGGTTGCAGAGCAACGGATGGGATAGGCTCAAACGAATG
GCAGTCAGTGGAGATGATTGCGTTGTGAAGCCAATTGATGATAGGTTTGCACATGCCCTCAGGTTCTTGAATGATATGGGAAA
AGTTAGGAAGGACACACAAGAGTGGAAACCCTCAACTGGATGGGACAACTGGGAAGAAGTTCCGTTTTGCTCCCACCACTTCA
ACAAGCTCCATCTCAAGGACGGGAGGTCCATTGTGGTTCCCTGCCGCCACCAAGATGAACTGATTGGCCGGGCCCGCGTCTCT
CCAGGGGCGGGATGGAGCATCCGGGAGACTGCTTGCCTAGCAAAATCATATGCGCAAATGTGGCAGCTCCTTTATTTCCACAG
AAGGGACCTCCGACTGATGGCCAATGCCATTTGTTCATCTGTGCCAGTTGACTGGGTTCCAACTGGGAGAACTACCTGGTCAAT
CCATGGAAAGGGAGAATGGATGACCACTGAAGACATGCTTGTGGTGTGGAACAGAGTGTGGATTGAGGAGAACGACCACAT
GGAAGACAAGACCCCAGTTACGAAATGGACAGACATTCCCTATTTGGGAAAAAGGGAAGACTTGTGGTGTGGATCTCTCATA
GGGCACAGACCGCGCACCACCTGGGCTGAGAACATTAAAAACACAGTCAACATGGTGCGCAGGATCATAGGTGATGAAGAAA
AGTACATGGACTACCTATCCACCCAAGTTCGCTACTTGGGTGAAGAAGGGTCTACACCTGGAGTGCTGTAAGCACCAATCTTA
ATGTTGTCAGGCCTGCTAGTCAGCCACAGCTTGGGGAAAGCTGTGCAGCCTGTGACCCCCCCAGGAGAAGCTGGGAAACCAA
GCCTATAGTCAGGCCGAGAACGCCATGGCACGGAAGAAGCCATGCTGCCTGTGAGCCCCTCAGAGGACACTGAGTCAAAAAA
CCCCACGCGCTTGGAGGCGCAGGATGGGAAAAGAAGGTGGCGACCTTCCCCACCCTTCAATCTGGGGCCTGAACTGGAGATC
AGCTGTGGATCTCCAGAAGAGGGACTAGTGGTTAGAGGAGA

KU497555.1 Zika virus isolate Brazil-ZKV2015, Brazil, complete genome

SEQ ID NO: 3

CCAATCTGTGAATCAGACTGCGACAGTTCGAGTTTGAAGCGAAAGCTAGCAACAGTATCAACAGGTTTTATTTTGGATTTGGA

AACGAGAGTTTCTGGTCATGAAAAACCCAAAAAAGAAATCCGGAGGATTCCGGATTGTCAATATGCTAAAACGCGGAGTAGC

CCGTGTGAGCCCCTTTGGGGGCTTGAAGAGGCTGCCAGCCGGACTTCTGCTGGGTCATGGGCCCATCAGGATGGTCTTGGCG

ATTCTAGCCTTTTTGAGATTCACGGCAATCAAGCCATCACTGGGTCTCATCAATAGATGGGGTTCAGTGGGGAAAAAAGAGGC

TATGGAAATAATAAAGAAGTTCAAGAAAGATCTGGCTGCCATGCTGAGAATAATCAATGCCAGGAAGGAGAAGAAGAGACG

AGGCGCAGATACTAGTGTCGGAATCGTTGGCCTCCTGCTGACCACAGCTATGGCAGCGGAGGTCACTAGACGTGGGAGTGCA

TACTATATGTACTTGGACAGAAACGATGCTGGGGAGGCCATATCTTTTCCAACCACATTGGGGATGAATAAGTGTTATATACA

GATCATGGATCTTGGACACATGTGTGATGCCACCATGAGCTATGAATGCCCTATGCTGGATGAGGGGGTGGAACCAGATGAC

GTCGATTGTTGGTGCAACACGACGTCAACTTGGGTTGTGTACGGAACCTGCCATCACAAAAAAGGTGAAGCACGGAGATCTA

GAAGAGCTGTGACGCTCCCCTCCCATTCCACTAGGAAGCTGCAAACGCGGTCGCAAACCTGGTTGGAATCAAGAGAATACACA

AAGCACTTGATTAGAGTCGAAAATTGGATATTCAGGAACCCTGGCTTCGCGTTAGCAGCAGCTGCCATCGCTTGGCTTTTGGG

AAGCTCAACGAGCCAAAAAGTCATATACTTGGTCATGATACTGCTGATTGCCCCGGCATACAGCATCAGGTGCATAGGAGTCA

GCAATAGGGACTTTGTGGAAGGTATGTCAGGTGGGACTTGGGTTGATGTTGTCTTGGAACATGGGGGTTGTGTCACCGTAAT

GGCACAGGACAAACCGACTGTCGACATAGAGCTGGTTACAACAACAGTCAGCAACATGGCGGAGGTAAGATCCTACTGCTAT

GAGGCATCAATATCAGACATGGCTTCGGACAGCCGCTGCCCAACACAAGGTGAAGCCTACCTTGACAAGCAATCAGACACTCA

ATATGTCTGCAAAAGAACGTTAGTGGACAGAGGCTGGGGAAATGGATGTGGACTTTTTGGCAAAGGGAGCCTGGTGACATGC

GCTAAGTTTGCATGCTCCAAGAAAATGACCGGGAAGAGCATCCAGCCAGAGAATCTGGAGTACCGGATAATGCTGTCAGTTC

-continued

```
ATGGCTCCCAGCACAGTGGGATGATCGTTAATGACACAGGACATGAAACTGATGAGAATAGAGCGAAGGTTGAGATAACGCC

CAATTCACCAAGAGCCGAAGCCACCCTGGGGGGTTTTGGAAGCTTAGGACTTGATTGTGAACCGAGGACAGGCCTTGACTTTT

CAGATTTGTATTACTTGACTATGAATAACAAGCACTGGTTGGTTCACAAGGAGTGGTTCCACGACATTCCATTACCTTGGCACG

CTGGGGCAGACACCGGAACTCCACACTGGAACAACAAAGAAGCACTGGTAGAGTTCAAGGACGCACATGCCAAAAGGCAAA

CTGTCGTGGTTCTAGGGACTCAAGAAGGAGCAGTTCACACGGCCCTTGCTGGAGCTCTGGAGGCTGAGATGGATGGTGCAAA

GGGAAGGCTGTCCTCTGGCCACTTGAAATGTCGCCTGAAAATGGATAAACTTAGATTGAAGGGCGTGTCATACTCCTTGTGTA

CCGCAGCGTTCACATTCACCAAGATCCCGGCTGAAACACTGCACGGGACAGTCACAGTGGAGGTACAGTACGCAGGGACAGA

TGGACCTTGCAAGGTTCCAGCTCAGATGGCGGTGGACATGCAAACTCTGACCCCAGTTGGGAGGTTGATAACCGCTAACCCCG

TAATCACTGAAAGCACTGAGAACTCTAAGATGATGCTGGAACTTGATCCACCATTTGGGGACTCTTACATTGTCATAGGAGTCG

GGGAGAAGAAGATCACCCACCACTGGCACAGGAGTGGCAGCACCATTGGAAAAGCATTTGAAGCCACTGTGAGAGGTGCCA

AGAGAATGGCAGTCTTGGGAGACACAGCCTGGGACTTTGGATCAGTTGGAGGCGCTCTCAACTCATTGGGCAAGGGCATCCA

TCAAATTTTTGGAGCAGCTTTCAAATCATTGTTTGGAGGAATGTCCTGGTTCTCACAAATTCTCATTGGAACGTTGCTGATGTGG

TTGGGTCTGAACACAAAGAATGGATCTATTTCCCTTATGTGCTTGGCCTTAGGGGGAGTGTTGATCTTCTTATCCACAGCCGTC

TCTGCTGATGTGGGGTGCTCGGTGGACTTCTCAAAGAAGGAGACGAGATGTGGTACAGGGGTGTTCGTCTATAACGACGTTG

AAGCCTGGAGGGACAGGTACAAGTACCATCCTGACTCTCCCCGTAGATTGGCAGCAGCAGTCAAGCAAGCCTGGGAAGATGG

TATCTGCGGGATCTCCTCTGTTTCAAGAATGGAAAACATCATGTGGAGATCAGTAGAAGGGGAGCTTAACGCAATCCTGGAAG

AGAATGGAGTTCAACTGACGGTCGTTGTGGGATCTGTAAAAAACCCCATGTGGAGAGGTCCACAGAGATTGCCCGTGCCTGT

GAACGAGCTGCCCCACGGCTGGAAGGCTTGGGGGAAATCGTACTTCGTCAGAGCAGCAAAGACAAATAACAGCTTTGTCGTG

GATGGTGACACACTGAAGGAATGCCCACTCAAACATAGAGCATGGAACAGCTTTCTTGTGGAGGATCATGGGTTCGGGGTAT

TTCACACTAGTGTCTGGCTCAAGGTTAGAGAAGATTATTCATTAGAGTGTGATCCAGCCGTTATTGGAACAGCTGTTAAGGGA

AAGGAGGCTGTACACAGTGATCTAGGCTACTGGATTGAGAGTGAGAAGAATGACACATGGAGGCTGAAGAGGGCCCATCTG

ATCGAGATGAAAACATGTGAATGGCCAAAGTCCCACACATTGTGGACAGATGGAATAGAAGAGAGTGATCTGATCATACCCA

AGTCTTTAGCTGGGCCACTCAGCCATCACAATACCAGAGAGGGCTACAGGACCCAAATGAAAGGGCCATGGCACAGTGAAGA

GCTTGAAATTCGGTTTGAGGAATGCCCAGGCACTAAGGTCCACGTGGAGGAAACATGTGGAACAAGAGGACCATCTCTGAGA

TCAACCACTGCAAGCGGAAGGGTGATCGAGGAATGGTGCTGCAGGGAGTGCACAATGCCCCACTGTCGTTCCGGGCTAAAG

ATGGCTGTTGGTATGGAATGGAGATAAGGCCCAGGAAAGAACCAGAAAGCAACTTAGTAAGGTCAATGGTGACTGCAGGATC

AACTGATCACATGGATCACTTCTCCCTTGGAGTGCTTGTGATTCTGCTCATGGTGCAGGAAGGGCTGAAGAAGAGAATGACCA

CAAAGATCATCATAAGCACATCAATGGCAGTGCTGGTAGCTATGATCCTGGGAGGATTTTCAATGAGTGACCTGGCTAAGCTT

GCAATTTTGATGGGTGCCACCTTCGCGGAAATGAACACTGGAGGAGATGTAGCTCATCTGGCGCTGATAGCGGCATTCAAAGT

CAGACCAGCGTTGCTGGTATCTTTCATCTTCAGAGCTAATTGGACACCCCGTGAAAGCATGCTGCTGGCCTTGGCCTCGTGTTT

TTTGCAAACTGCGATCTCCGCCTTGGAAGGCGACCTGATGGTTCTCATCAATGGTTTTGCTTTGGCCTGGTTGGCAATACGAGC

GATGGTTGTTCCACGCACTGACAACATCACCTTGGCAATCCTGGCTGCTCTGACACCACTGGCCCGGGGCACACTGCTTGTGGC

GTGGAGAGCAGGCCTTGCTACTTGCGGGGGGTTTATGCTCCTCTCTCTGAAGGGAAAAGGCAGTGTGAAGAAGAACTTACCA

TTTGTCATGGCCCTGGGACTAACCGCTGTGAGGCTGGTCGACCCCATCAACGTGGTGGGACTGCTGTTGCTCACAAGGAGTGG

GAAGCGGAGCTGGCCCCTAGCGAAGTACTCACAGCTGTTGGCCTGATATGCGCATTGGCTGGAGGGTTCGCCAAGGCAGAT

ATAGAGATGGCTGGGCCCATGGCCGCGGTCGGTCTGCTAATTGTCAGTTACGTGGTCTCAGGAAAGAGTGTGGACATGTACA

TTGAAAGAGCAGGTGACATCACATGGGAAAAGATGCGGAAGTCACTGGAAACAGTCCCCGGCTCGATGGCGCTAGATGA

GAGTGGTGACTTCTCCCTGGTGGAGGATGACGGTCCCCCCATGAGAGAGATCATACTCAAGGTGGTCCTGATGACCATCTGTG

GCATGAACCCAATAGCCATACCCTTTGCAGCTGGAGCGTGGTACGTATACGTGAAGACTGGAAAAAGGAGTGGTGCTCTATG

GGATGTGCCTGCTCCCAAGGAAGTAAAAAAGGGGGAGACCACAGATGGAGTGTACAGAGTAATGACTCGTAGACTGCTAGG

TTCAACACAAGTTGGAGTGGGAGTTATGCAAGAGGGGGTCTTTCACACTATGTGGCACGTCACAAAAGGATCCGCGCTGAGA
```

-continued

```
AGCGGTGAAGGGAGACTTGATCCATACTGGGGAGATGTCAAGCAGGATCTGGTGTCATACTGTGGTCCATGGAAGCTAGATG
CCGCCTGGGACGGGCACAGCGAGGTGCAGCTCTTGGCCGTGCCCCCCGGAGAGAGAGCGAGGAACATCCAGACTCTGCCCG
GAATATTTAAGACAAAGGATGGGGACATTGGAGCGGTTGCGCTGGATTACCCAGCAGGAACTTCAGGATCTCCAATCCTAGA
CAAGTGTGGGAGAGTGATAGGACTTTATGGCAATGGGGTCGTGATAAAAAATGGGAGTTATGTTAGTGCCATCACCCAAGGG
AGGAGGGAGGAAGAGACTCCTGTTGAGTGCTTCGAGCCTTCGATGCTGAAGAAGAAGCAGCTAACTGTCTTAGACTTGCATC
CTGGAGCTGGGAAAACCAGGAGAGTTCTTCCTGAAATAGTCCGTGAAGCCATAAAAACAAGACTCCGTACTGTGATCTTAGCT
CCAACCAGGGTTGTCGCTGCTGAAATGGAGGAAGCCCTTAGAGGGCTTCCAGTGCGTTATATGACAACAGCAGTCAATGTCAC
CCACTCTGGAACAGAAATCGTCGACTTAATGTGCCATGCCACCTTCACTTCACGTCTACTACAGCCAATCAGAGTCCCCAACTAT
AATCTGTATATTATGGATGAGGCCCACTTCACAGATCCCTCAAGCATAGCAGCAAGAGGATACATTTCAACAAGGGTTGAGAT
GGGCGAGGCGGCTGCCATCTTCATGACCGCCACGCCACCAGGAACCCGTGACGCATTTCCGGACTCCAACTCACCAATTATGG
ACACCGAAGTGGAAGTCCCAGAGAGAGCCTGGAGCTCAGGCTTTGATTGGGTGACGGATCATTCTGGAAAAACAGTTTGGTT
TGTTCCAAGCGTGAGGAACGGCAATGAGATCGCAGCTTGTCTGACAAAGGCTGGAAAACGGGTCATACAGCTCAGCAGAAAG
ACTTTTGAGACAGAGTTCCAGAAAACAAAACATCAAGAGTGGGACTTTGTCGTGACAACTGACATTTCAGAGATGGGCGCCAA
CTTTAAAGCTGACCGTGTCATAGATTCCAGGAGATGCCTAAAGCCGGTCATACTTGATGGCGAGAGAGTCATTCTGGCTGGAC
CCATGCCTGTCACACATGCCAGCGCTGCCCAGAGGAGGGGGCGCATAGGCAGGAATCCCAACAAACCTGGAGATGAGTACCT
GTATGGAGGTGGGTGCGCAGAGACTGACGAAGACCATGCACACTGGCTTGAAGCAAGAATGCTCCTTGACAATATTTACCTCC
AAGATGGCCTCATAGCCTCGCTCTATCGACCTGAGGCCGACAAAGTAGCAGCCATTGAGGGAGAGTTCAAGCTTAGGACGGA
GCAAAGGAAGACCTTTGTGGAACTCATGAAAAGAGGAGATCTTCCTGTTTGGCTGGCCTATCAGGTTGCATCTGCCGGAATAA
CCTACACAGATAGAAGATGGTGCTTTGATGGCACGACCAACAACACCATAATGGAAGACAGTGTGCCGGCAGAGGTGTGGAC
CAGACACGGAGAGAAAAGAGTGCTCAAACCGAGGTGGATGGACGCCAGAGTTTGTTCAGATCATGCGGCCCTGAAGTCATTC
AAGGAGTTTGCCGCTGGGAAAAGAGGAGCGGCTTTTGGAGTGATGGAAGCCCTGGGAACACTGCCAGGACACATGACAGAG
AGATTCCAGGAAGCCATTGACAACCTCGCTGTGCTCATGCGGGCAGAGACTGGAAGCAGGCCTTACAAAGCCGCGGCGGCCC
AATTGCCGGAGACCCTAGAGACCATTATGCTTTTGGGGTTGCTGGGAACAGTCTCGCTGGGAATCTTTTTCGTCTTGATGAGG
AACAAGGGCATAGGGAAGATGGGCTTTGGAATGGTGACTCTTGGGGCCAGCGCATGGCTCATGTGGCTCTCGGAAATTGAGC
CAGCCAGAATTGCATGTGTCCTCATTGTTGTGTTCCTATTGCTGGTGGTGCTCATACCTGAGCCAGAAAAGCAAAGATCCCCC
AGGACAACCAAATGGCAATCATCATCATGGTAGCAGTAGGTCTTCTGGGCTTGATTACCGCCAATGAACTCGGATGGTTGGAG
AGAACAAAGAGTGACCTAAGCCATCTAATGGGAAGGAGAGAGGAGGGGGCAACCATAGGATTCTCAATGGACATTGACCTG
CGGCCAGCCTCAGCTTGGGCCATCTATGCTGCCTTGACAACTTTCATTACCCCAGCCGTCCAACATGCAGTGACCACTTCATACA
ACAACTACTCCTTAATGGCGATGGCCACGCAAGCTGGAGTGTTGTTTGGTATGGGCAAAGGGATGCCATTCTACGCATGGGAC
TTTGGAGTCCCGCTGCTAATGATAGGTTGCTACTCACAATTAACACCCCTGACCCTAATAGTGGCCATCATTTTGCTCGTGGCGC
ACTACATGTACTTGATCCCAGGGCTGCAGGCAGCAGCTGCGCGTGCTGCCCAGAAGAGAACGGCAGCTGGCATCATGAAGAA
CCCTGTTGTGGATGGAATAGTGGTGACTGACATTGACACAATGACAATTGACCCCCAAGTGGAGAAAAAGATGGGACAGGTG
CTACTCATAGCAGTAGCCGTCTCCAGCGCCATACTGTCGCGGACCGCCTGGGGGTGGGGGAGGCTGGGGCCCTGATCACAG
CCGCAACTTCCACTTTGTGGGAAGGCTCTCCGAACAAGTACTGGAACTCCTCTACAGCCACTTCACTGTGTAACATTTTTAGGG
GAAGTTACTTGGCTGGAGCTTCTCTAATCTACACAGTAACAAGAAACGCTGGCTTGGTCAAGAGACGTGGGGGTGGAACAGG
AGAGACCCTGGGAGAGAAATGGAAGGCCCGCTTGAACCAGATGTCGGCCCTGGAGTTCTACTCCTACAAAAAGTCAGGCATC
ACCGAGGTGTGCAGAGAAGAGGCCCGCCGCGCCCTCAAGGACGGTGTGGCAACGGGAGGCCATGCTGTGTCCCGAGGAAGT
GCAAAGCTGAGATGGTTGGTGGAGCGGGGATACCTGCAGCCCTATGGAAAGGTCATTGATCTTGGATGTGGCAGAGGGGC
TGGAGTTACTACGCCGCCACCATCCGCAAAGTTCAAGAAGTGAAAGGATACACAAAAGGAGGCCCTGGTCATGAAGAACCCG
TGTTGGTGCAAAGCTATGGGTGGAACATAGTCCGTCTTAAGAGTGGGGTGGACGTCTTTCATATGGCGGCTGAGCCGTGTGA
CACGTTGCTGTGTGACATAGGTGAGTCATCATCTAGTCCTGAAGTGGAAGAAGCACGGACGCTCAGAGTCCTCTCCATGGTGG
```

```
GGGATTGGCTTGAAAAAAGACCAGGAGCCTTTTGCATAAAAGTGTTGTGCCCATACACCAGCACTATGATGGAAACCCTGGAG

CGACTGCAGCGTAGGTATGGGGGAGGACTGGTCAGAGTGCCACTCTCCCGCAACTCTACACATGAGATGTACTGGGTCTCTG

GAGCGAAAAGCAACACCATAAAAAGTGTGTCCACCACGAGCCAGCTCCTCTTGGGGCGCATGGACGGGCCTAGGAGGCCAGT

GAAATATGAGGAGGATGTGAATCTCGGCTCTGGCACGCGGGCTGTGGTAAGCTGCGCTGAAGCTCCCAACATGAAGATCATT

GGTAACCGCATTGAAAGGATCCGCAGTGAGCACGCGGAAACGTGGTTCTTTGACGAAAACCACCCATATAGGACATGGGCTT

ACCATGGAAGCTATGTGGCCCCCACACAAGGGTCAGCGTCCTCTCTAATAAACGGGGTTGTCAGGCTCCTGTCAAACCCTGG

GATGTGGTGACTGGAGTCACAGGAATAGCCATGACCGACACCACACCGTATGGTCAGCAAAGAGTTTTCAAGGAAAAAGTGG

ACACTAGGGTGCCAGACCCCCAAGAAGGCACTCGTCAGGTTATGAGCATGGTCTCTTCCTGGTTGTGGAAAGAGCTAGGCAA

ACACAAACGACCACGAGTCTGTACCAAAGAAGAGTTCATCAACAAGGTTCGTAGCAATGCAGCATTAGGGGCAATATTTGAAG

AGGAAAAAGAGTGGAAGACTGCAGTGGAAGCTGTGAACGATCCAAGGTTCTGGGCTCTAGTGGACAAGGAAAGAGAGCACC

ACCTGAGAGGAGAGTGCCAGAGTTGTGTGTACAACATGATGGGAAAAAGAGAAAAGAAACAAGGGGAATTTGGAAAGGCCA

AGGGCAGCCGCGCCATCTGGTATATGTGGCTAGGGGCTAGATTTCTAGAGTTCGAAGCCCTTGGATTCTTGAACGAGGATCAC

TGGATGGGGAGAGAGAACTCAGGAGGTGGTGTTGAAGGGCTGGGATTACAAAGACTCGGATATGTCCTAGAAGAGATGAGT

CGCATACCAGGAGGAAGGATGTATGCAGATGACACTGCTGGCTGGGACACCCGCATCAGCAGGTTTGATCTGGAGAATGAAG

CTCTAATCACCAACCAAATGGAGAAAGGGCACAGGGCCTTGGCATTGGCCATAATCAAGTACACATACCAAAACAAAGTGGTA

AAGGTCCTTAGACCAGCTGAAAAAGGGAAAACAGTTATGGACATTATTTCGAGACAAGACCAAAGGGGGAGCGGACAAGTT

GTCACTTACGCTCTTAACACATTTACCAACCTAGTGGTGCAACTCATTCGGAATATGGAGGCTGAGGAAGTTCTAGAGATGCAA

GACTTGTGGCTGCTGCGGAGGTCAGAGAAAGTGACCAACTGGTTGCAGAGCAACGGATGGGATAGGCTCAAACGAATGGCA

GTCAGTGGAGATGATTGCGTTGTGAAGCCAATTGATGATAGGTTTGCACATGCCCTCAGGTTCTTGAATGATATGGGAAAAGT

TAGGAAGGACACACAAGAGTGGAAACCCTCAACTGGATGGGACAACTGGGAAGAAGTTCCGTTTTGCTCCCACCACTTCAACA

AGCTCCATCTCAAGGACGGGAGGTCCATTGTGGTTCCCTGCCGCCACCAAGATGAACTGATTGGCCGGGCCCGCGTCTCTCCA

GGGGCGGGATGGAGCATCCGGGAGACTGCTTGCCTAGCAAAATCATATGCGCAAATGTGGCAGCTCCTTTATTTCCACAGAA

GGGACCTCCGACTGATGGCCAATGCCATTTGTTCATCTGTGCCAGTTGACTGGGTTCCAACTGGGAGAACTACCTGGTCAATCC

ATGGAAAGGGAGAATGGATGACCACTGAAGACATGCTTGTGGTGTGGAACAGAGTGTGGATTGAGGAGAACGACCACATGG

AAGACAAGACCCCAGTTACGAAATGGACAGACATTCCCTATTTGGGAAAAAGGGAAGACTTGTGGTGTGGATCTCTCATAGG

GCACAGACCGCGCACCACCTGGGCTGAGAACATTAAAAATACAGTCAACATGGTGCGCAGGATCATAGGTGATGAAGAAAAG

TACATGGACTACCTATCCACCCAAGTTCGCTACTTGGGTGAAGAAGGGTCTACACCTGGAGTGCTGTGAGCACCAATCTTAATG

TTGTCAGGCCTGCTAGTCAGCCACAGCTTGGGGAAAGCTGTGCAGCCTGTGACCCCTCAGGAGAAGCTGGGTAACCAAGCCT

ATAGTCAGGCCGAGAACGCCATGGCACGGAAGAAGCCATGCTGCCTGTGAGCCCCTCAGAGGACACTGAGTCAAAAAACCCC

ACGCGCTTGGAGGCGCAGGATGGGAAAAGAAGGTGGCGACCTTCCCCACCCTTCAATCTGGGGCCTGAACTGGAGATCAGCT

GTGGATCTCCAGAAGAGGGACTAGTGGTTAGAGGAGACCCCCCGGAAAACGCAAAACAGCATATTGACGCTGGGAAAGACC

AGAGACTCCATGAGTTTCCACCACGCTGGCCGCCAGGCACAGATCGCCGAATAGCGGCGGCCGGTGTGGGGAAATCCA
```

KU501215.1 Zika virus strain PRVABC59, Puerto Rico, complete genome

SEQ ID NO: 4

```
GTTGTTGATCTGTGTGAATCAGACTGCGACAGTTCGAGTTTGAAGCGAAAGCTAGCAACAGTATCAACAGGTTTTATTTTGGAT

TTGGAAACGAGAGTTTCTGGTCATGAAAAACCCAAAAAAGAAATCCGGAGGATTCCGGATTGTCAATATGCTAAAACGCGGA

GTAGCCCGTGTGAGCCCCTTTGGGGGCTTGAAGAGGCTGCCAGCCGGACTTCTGCTGGGTCATGGGCCCATCAGGATGGTCTT

GGCGATTCTAGCCTTTTTGAGATTCACGGCAATCAAGCCATCACTGGGTCTCATCAATAGATGGGGTTCAGTGGGGAAAAAG

AGGCTATGGAAACAATAAAGAAGTTCAAGAAAGATCTGGCTGCCATGCTGAGAATAATCAATGCTAGGAAGGAGAAGAAGA

GACGAGGCGCAGATACTAGTGTCGGAATTGTTGGCCTCCTGCTGACCACAGCTATGGCAGCGGAGGTCACTAGACGTGGGAG

TGCATACTATATGTACTTGGACAGAAACGATGCTGGGGAGGCCATATCTTTTCCAACCACATTGGGGATGAATAAGTGTTATAT

ACAGATCATGGATCTTGGACACATGTGTGATGCCACCATGAGCTATGAATGCCCTATGCTGGATGAGGGGGTGGAACCAGAT
```

-continued

```
GACGTCGATTGTTGGTGCAACACGACGTCAACTTGGGTTGTGTACGGAACCTGCCATCACAAAAAAGGTGAAGCACGGAGAT
CTAGAAGAGCTGTGACGCTCCCCTCCCATTCCACCAGGAAGCTGCAAACGCGGTCGCAAACCTGGTTGGAATCAAGAGAATAC
ACAAAGCACTTGATTAGAGTCGAAAATTGGATATTCAGGAACCCTGGCTTCGCGTTAGCAGCAGCTGCCATCGCTTGGCTTTTG
GGAAGCTCAACGAGCCAAAAAGTCATATACTTGGTCATGATACTGCTGATTGCCCCGGCATACAGCATCAGGTGCATAGGAGT
CAGCAATAGGGACTTTGTGGAAGGTATGTCAGGTGGGACTTGGGTTGATGTTGTCTTGGAACATGGAGGTTGTGTCACCGTA
ATGGCACAGGACAAACCGACTGTCGACATAGAGCTGGTTACAACAACAGTCAGCAACATGGCGGAGGTAAGATCCTACTGCT
ATGAGGCATCAATATCAGACATGGCTTCTGACAGCCGCTGCCCAACACAAGGTGAAGCCTACCTTGACAAGCAATCAGACACT
CAATATGTCTGCAAAAGAACGTTAGTGGACAGAGGCTGGGGAAATGGATGTGGACTTTTTGGCAAAGGGAGCCTGGTGACAT
GCGCTAAGTTTGCATGCTCCAAGAAAATGACCGGGAAGAGCATCCAGCCAGAGAATCTGGAGTACCGGATAATGCTGTCAGT
TCATGGCTCCCAGCACAGTGGGATGATCGTTAATGACACAGGACATGAAACTGATGAGAATAGAGCGAAAGTTGAGATAACG
CCCAATTCACCGAGAGCCGAAGCCACCCTGGGGGGTTTTGGAAGCCTAGGACTTGATTGTGAACCGAGGACAGGCCTTGACTT
TTCAGATTTGTATTACTTGACTATGAATAACAAGCACTGGTTGGTTCACAAGGAGTGGTTCCACGACATTCCATTACCTTGGCAC
GCTGGGCAGACACCGGAACTCCACACTGGAACAACAAAGAAGCACTGGTAGAGTTCAAGGACGCACATGCCAAAAGGCAA
ACTGTCGTGGTTCTAGGGAGTCAAGAAGGAGCAGTTCACACGGCCCTTGCTGGAGCTCTGGAGGCTGAGATGGATGGTGCAA
AGGGAAGGCTGTCCTCTGGCCACTTGAAATGTCGCCTGAAATGGATAAACTTAGATTGAAGGGCGTGTCATACTCCTTGTGT
ACTGCAGCGTTCACATTCACCAAGATCCCGGCTGAAACACTGCACGGGACAGTCACAGTGGAGGTACAGTACGCAGGGACAG
ATGGACCTTGCAAGGTTCCAGCTCAGATGGCGGTGGACATGCAAACTCTGACCCCAGTTGGGAGGTTGATAACCGCTAACCCC
GTAATCACTGAAAGCACTGAGAACTCTAAGATGATGCTGGAACTTGATCCACCATTTGGGGACTCTTACATTGTCATAGGAGTC
GGGGAGAAGAAGATCACCCACCACTGGCACAGGAGTGGCAGCACCATTGGAAAAGCATTTGAAGCCACTGTGAGAGGTGCC
AAGAGAATGGCAGTCTTGGGAGACACAGCCTGGGACTTTGGATCAGTTGGAGGCGCTCTCAACTCATTGGGCAAGGGCATCC
ATCAAATTTTTGGAGCAGCTTTCAAATCATTGTTTGGAGGAATGTCCTGGTTCTCACAAATTCTCATTGGAACGTTGCTGATGTG
GTTGGGTCTGAACACAAAGAATGGATCTATTTCCCTTATGTGCTTGGCCTTAGGGGAGTGTTGATCTTCTTATCCACAGCCGT
CTCTGCTGATGTGGGGTGCTCGGTGGACTTCTCAAAGAAGGAGACGAGATGCGGTACAGGGGTGTTCGTCTATAACGACGTT
GAAGCCTGGAGGGACAGGTACAAGTACCATCCTGACTCCCCCCGTAGATTGGCAGCAGCAGTCAAGCAAGCCTGGGAAGATG
GTATCTGCGGGATCTCCTCTGTTTCAAGAATGGAAAACATCATGTGGAGATCAGTAGAAGGGAGCTCAACGCAATCCTGGAA
GAGAATGGAGTTCAACTGACGGTCGTTGTGGGATCTGTAAAAAACCCCATGTGGAGAGGTCCACAGAGATTGCCCGTGCCTG
TGAACGAGCTGCCCCACGGCTGGAAGGCTTGGGGGAAATCGTATTTCGTCAGAGCAGCAAAGACAAATAACAGCTTTGTCGT
GGATGGTGACACACTGAAGGAATGCCCACTCAAACATAGAGCATGGAACAGCTTTCTTGTGGAGGATCATGGGTTCGGGGTA
TTTCACACTAGTGTCTGGCTCAAGGTTAGAGAAGATTATTCATTAGAGTGTGATCCAGCCGTTATTGGAACAGCTGTTAAGGGA
AAGGAGGCTGTACACAGTGATCTAGGCTACTGGATTGAGAGTGAGAAGAATGACACATGGAGGCTGAAGAGGGCCCATCTG
ATCGAGATGAAAACATGTGAATGGCCAAAGTCCCACACATTGTGGACAGATGGAATAGAAGAGAGTGATCTGATCATACCCA
AGTCTTTAGCTGGGCCACTCAGCCATCACAATACCAGAGAGGGCTACAGGACCCAAATGAAAGGGCCATGGCACAGTGAAGA
GCTTGAAATTCGGTTTGAGGAATGCCCAGGCACTAAGGTCCACGTGGAGGAAACATGTGGAACAAGAGGACCATCTCTGAGA
TCAACCACTGCAAGCGGAAGGGTGATCGAGGAATGGTGCTGCAGGGAGTGCACAATGCCCCACTGTCGTTCCGGGCTAAAG
ATGGCTGTTGGTATGGAATGGAGATAAGGCCCAGGAAAGAACCAGAAAGCAACTTAGTAAGGTCAATGGTGACTGCAGGATC
AACTGATCACATGGACCACTTCTCCCTTGGAGTGCTTGTGATCCTGCTCATGGTGCAGGAAGGGCTGAAGAAGAGAATGACCA
CAAAGATCATCATAAGCACATCAATGGCAGTGCTGGTAGCTATGATCCTGGGAGGATTTTCAATGAGTGACCTGGCTAAGCTT
GCAATTTTGATGGGTGCCACCTTCGCGGAAATGAACACTGGAGGAGATGTAGCTCATCTGGCGCTGATAGCGGCATTCAAAGT
CAGACCAGCGTTGCTGGTATCTTTCATCTTCAGAGCTAATTGGACACCCCGTGAAAGCATGCTGCTGGCCTTGGCCTCGTGTCT
TTTGCAAACTGCGATCTCCGCCTTGGAAGGCGACCTGATGGTTCTCATCAATGGTTTTGCTTTGGCCTGGTTGGCAATACGAGC
GATGGTTGTTCCACGCACTGATAACATCACCTTGGCAATCCTGGCTGCTCTGACACCACTGGCCCGGGGCACACTGCTTGTGGC
```

-continued

```
GTGGAGAGCAGGCCTTGCTACTTGCGGGGGGTTTATGCTCCTCTCTCTGAAGGGAAAAGGCAGTGTGAAGAAGAACTTACCA
TTTGTCATGGCCCTGGGACTAACCGCTGTGAGGCTGGTCGACCCCATCAACGTGGTGGGACTGCTGTTGCTCACAAGGAGTGG
GAAGCGGAGCTGGCCCCCTAGCGAAGTACTCACAGCTGTTGGCCTGATATGCGCATTGGCTGGAGGGTTCGCCAAGGCAGAT
ATAGAGATGGCTGGGCCCATGCCGCGGTCGGTCTGCTAATTGTCAGTTACGTGGTCTCAGGAAAGAGTGTGGACATGTACA
TTGAAAGAGCAGGTGACATCACATGGGAAAAGATGCGGAAGTCACTGGAAACAGTCCCCGGCTCGATGTGGCGCTAGATGA
GAGTGGTGATTTCTCCCTGGTGGAGGATGACGGTCCCCCCATGAGAGAGATCATACTCAAGGTGGTCCTGATGACCATCTGTG
GCATGAACCCAATAGCCATACCCTTTGCAGCTGGAGCGTGGTACGTATACGTGAAGACTGGAAAAAGGAGTGGTGCTCTATG
GGATGTGCCTGCTCCCAAGGAAGTAAAAAAGGGGGAGACCACAGATGGAGTGTACAGAGTAATGACTCGTAGACTGCTAGG
TTCAACACAAGTTGGAGTGGGAGTTATGCAAGAGGGGGTCTTTCACACTATGTGGCACGTCACAAAAGGATCCGCGCTGAGA
AGCGGTGAAGGGAGACTTGATCCATACTGGGGAGATGTCAAGCAGGATCTGGTGTCATACTGTGGTCCATGGAAGCTAGATG
CCGCCTGGGATGGGCACAGCGAGGTGCAGCTCTTGGCCGTGCCCCCCGGAGAGAGAGCGAGGAACATCCAGACTCTGCCCG
GAATATTTAAGACAAAGGATGGGGACATTGGAGCGGTTGCGCTGGATTACCCAGCAGGAACTTCAGGATCTCCAATCCTAGA
CAAGTGTGGGAGAGTGATAGGACTTTATGGCAATGGGGTCGTGATCAAAAACGGGAGTTATGTTAGTGCCATCACCCAAGGG
AGGAGGGAGGAAGAGACTCCTGTTGAGTGCTTCGAGCCCTCGATGCTGAAGAAGAAGCAGCTAACTGTCTTAGACTTGCATC
CTGGAGCTGGGAAAACCAGGAGAGTTCTTCCTGAAATAGTCCGTGAAGCCATAAAAACAAGACTCCGTACTGTGATCTTAGCT
CCAACCAGGGTTGTCGCTGCTGAAATGGAGGAGGCCCTTAGAGGGCTTCCAGTGCGTTATATGACAACAGCAGTCAATGTCAC
CCACTCTGGAACAGAAATCGTCGACTTAATGTGCCATGCCACCTTCACTTCACGTCTACTACAGCCAATCAGAGTCCCCAACTAT
AATCTGTATATTATGGATGAGGCCCACTTCACAGATCCCTCAAGTATAGCAGCAAGAGGATACATTTCAACAAGGGTTGAGAT
GGGCGAGGCGGCTGCCATCTTCATGACCGCCACGCCACCAGGAACCCGTGACGCATTTCCGGACTCCAACTCACCAATTATGG
ACACCGAAGTGGAAGTCCCAGAGAGAGCCTGGAGCTCAGGCTTTGATTGGGTGACGGATCATTCTGGAAAAACAGTTTGGTT
TGTTCCAAGCGTGAGGAACGGCAATGAGATCGCAGCTTGTCTGACAAAGGCTGGAAAACGGGTCATACAGCTCAGCAGAAAG
ACTTTTGAGACAGAGTTCCAGAAAACAAAACATCAAGAGTGGGACTTTGTCGTGACAACTGACATTTCAGAGATGGGCGCCAA
CTTTAAAGCTGACCGTGTCATAGATTCCAGGAGATGCCTAAAGCCGGTCATACTTGATGGCGAGAGAGTCATTCGGCTGGAC
CCATGCCTGTCACACATGCCAGCGCTGCCCAGAGGAGGGGCGCATAGGCAGGAATCCCAACAAACCTGGAGATGAGTATCT
GTATGGAGGTGGGTGCGCAGAGACTGACGAAGACCATGCACACTGGCTTGAAGCAAGAATGCTCCTTGACAATATTTACCTCC
AAGATGGCCTCATAGCCTCGCTCTATCGACCTGAGGCCGACAAAGTAGCAGCCATTGAGGGAGAGTTCAAGCTTAGGACGGA
GCAAAGGAAGACCTTTGTGGAACTCATGAAAAGAGGAGATCTTCCTGTTTGGCTGGCCTATCAGGTTGCATCTGCCGGAATAA
CCTACACAGATAGAAGATGGTGCTTTGATGGCACGACCAACAACACCATAATGGAAGACAGTGTGCCGGCAGAGGTGTGGAC
CAGACACGGAGAGAAAGAGTGCTCAAACCGAGGTGGATGGACGCCAGAGTTTGTTCAGATCATGCGGCCCTGAAGTCATTC
AAGGAGTTTGCCGCTGGGAAAAGAGGAGCGGCTTTTGGAGTGATGGAAGCCCTGGGAACACTGCCAGGACACATGACAGAG
AGATTCCAGGAAGCCATTGACAACCTCGCTGTGCTCATGCGGGCAGAGACTGGAAGCAGGCCTTACAAAGCCGCGGCGGCCC
AATTGCCGGAGACCCTAGAGACCATAATGCTTTTGGGGTTGCTGGGAACAGTCTCGCTGGGAATCTTCTTCGTCTTGATGAGG
AACAAGGGCATAGGGAAGATGGGCTTTGGAATGGTGACTCTTGGGGCCAGCGCATGGCTCATGTGGCTCTCGGAAATTGAGC
CAGCCAGAATTGCATGTGTCCTCATTGTTGTGTTCCTATTGCTGGTGGTGCTCATACCTGAGCCAGAAAAGCAAAGATCTCCCC
AGGACAACCAAATGGCAATCATCATCATGGTAGCAGTAGGTCTTCTGGGCTTGATTACCGCCAATGAACTCGGATGGTTGGAG
AGAACAAAGAGTGACCTAAGCCATCTAATGGGAAGGAGAGAGGAGGGGGCAACCATAGGATTCTCAATGGACATTGACCTG
CGGCCAGCCTCAGCTTGGGCCATCTATGCTGCCTTGACAACTTTCATTACCCCAGCCGTCCAACATGCAGTGACCACCTCATACA
ACAACTACTCCTTAATGGCGATGGCCACGCAAGCTGGAGTGTTGTTTGGCATGGGCAAAGGGATGCCATTCTACGCATGGGAC
TTTGGAGTCCCGCTGCTAATGATAGGTTGCTACTCACAATTAACACCCCTGACCCTAATAGTGGCCATCATTTTGCTCGTGGCGC
ACTACATGTACTTGATCCCAGGGCTGCAGGCAGCAGCTGCGCGTGCTGCCCAGAAGAGAACGGCAGCTGGCATCATGAAGAA
CCCTGTTGTGGATGGAATAGTGGTGACTGACATTGACACAATGACAATTGACCCCCAAGTGGAGAAAAAGATGGGACAGGTG
```

-continued

```
CTACTCATAGCAGTAGCCGTCTCCAGCGCCATACTGTCGCGGACCGCCTGGGGGTGGGGGAGGCTGGGGCTCTGATCACAG
CCGCAACTTCCACTTTGTGGGAAGGCTCTCCGAACAAGTACTGGAACTCCTCTACAGCCACTTCACTGTGTAACATTTTAGGG
GAAGTTACTTGGCTGGAGCTTCTCTAATCTACACAGTAACAAGAAACGCTGGCTTGGTCAAGAGACGTGGGGGTGGAACAGG
AGAGACCCTGGGAGAGAAATGGAAGGCCCGCTTGAACCAGATGTCGGCCCTGGAGTTCTACTCCTACAAAAAGTCAGGCATC
ACCGAGGTGTGCAGAGAAGAGGCCCGCCGCGCCCTCAAGGACGGTGTGGCAACGGGAGGCCATGCTGTGTCCCGAGGAAGT
GCAAAGCTGAGATGGTTGGTGGAGCGGGGATACCTGCAGCCCTATGGAAAGGTCATTGATCTTGGATGTGGCAGAGGGGGC
TGGAGTTACTACGTCGCCACCATCCGCAAAGTTCAAGAAGTGAAAGGATACACAAAAGGAGGCCCTGGTCATGAAGAACCCG
TGTTGGTGCAAAGCTATGGGTGGAACATAGTCCGTCTTAAGAGTGGGGTGGACGTCTTTCATATGGCGGCTGAGCCGTGTGA
CACGTTGCTGTGTGACATAGGTGAGTCATCATCTAGTCCTGAAGTGGAAGAAGCACGGACGCTCAGAGTCCTCTCCATGGTGG
GGGATTGGCTTGAAAAAAGACCAGGAGCCTTTTGTATAAAAGTGTTGTGCCCATACACCAGCACTATGATGGAAACCCTGGAG
CGACTGCAGCGTAGGTATGGGGAGGACTGGTCAGAGTGCCACTCTCCCGCAACTCTACACATGAGATGTACTGGGTCTCTG
GAGCGAAAAGCAACACCATAAAAAGTGTGTCCACCACGAGCCAGCTCCTCTTGGGGCGCATGGACGGGCCTAGGAGGCCAGT
GAAATATGAGGAGGATGTGAATCTCGGCTCTGGCACGCGGGCTGTGGTAAGCTGCGCTGAAGCTCCCAACATGAAGATCATT
GGTAACCGCATTGAAAGGATCCGCAGTGAGCACGCGGAAACGTGGTTCTTTGACGAGAACCACCCATATAGGACATGGGCTT
ACCATGGAAGCTATGAGGCCCCCACACAAGGGTCAGCGTCCTCTCTAATAAACGGGGTTGTCAGGCTCCTGTCAAAACCCTGG
GATGTGGTGACTGGAGTCACAGGAATAGCCATGACCGACACCACACCGTATGGTCAGCAAAGAGTTTTCAAGGAAAAAGTGG
ACACTAGGGTGCCAGACCCCCAAGAAGGCACTCGTCAGGTTATGAGCATGGTCTCTTCCTGGTTGTGGAAAGAGCTAGGCAA
ACACAAACGGCCACGAGTCTGCACCAAAGAAGAGTTCATCAACAAGGTTCGTAGCAATGCAGCATTAGGGGCAATATTTGAA
GAGGAAAAAGAGTGGAAGACTGCAGTGGAAGCTGTGAACGATCCAAGGTTCTGGGCTCTAGTGGACAAGGAAAGAGAGCAC
CACCTGAGAGGAGAGTGCCAGAGCTGTGTGTACAACATGATGGGAAAAAGAGAAAAGAAACAAGGGGAATTTGGAAAGGCC
AAGGGCAGCCGCGCCATCTGGTATATGTGGCTAGGGGCTAGATTTCTAGAGTTCGAAGCCCTTGGATTCTTGAACGAGGATCA
CTGGATGGGAGAGAGAACTCAGGAGGTGGTGTTGAAGGGCTGGGATTACAAAGACTCGGATATGTCCTAGAAGAGATGAG
TCGTATACCAGGAGGAAGGATGTATGCAGATGACACTGCTGGCTGGGACACCCGCATTAGCAGGTTTGATCTGGAGAATGAA
GCTCTAATCACCAACCAAATGGAGAAAGGGCACAGGGCCTTGGCATTGGCCATAATCAAGTACACATACCAAAACAAAGTGGT
AAAGGTCCTTAGACCAGCTGAAAAAGGGAAAACAGTTATGGACATTATTTCGAGACAAGACCAAAGGGGGAGCGGACAAGTT
GTCACTTACGCTCTTAACACATTTACCAACCTAGTGGTGCAACTCATTCGGAATATGGAGGCTGAGGAAGTTCTAGAGATGCAA
GACTTGTGGCTGCTGCGGAGGTCAGAGAAAGTGACCAACTGGTTGCAGAGCAACGGATGGGATAGGCTCAAACGAATGGCA
GTCAGTGGAGATGATTGCGTTGTGAAGCCAATTGATGATAGGTTTGCACATGCCCTCAGGTTCTTGAATGATATGGGAAAAGT
TAGGAAGGACACACAAGAGTGGAAACCCTCAACTGGATGGGACAACTGGGAAGAAGTTCCGTTTTGCTCCCACCACTTCAACA
AGCTCCATCTCAAGGACGGGAGGTCCATTGTGGTTCCCTGCCGCCACCAAGATGAACTGATTGGCCGGGCCCGCGTCTCTCCA
GGGGCGGGATGGAGCATCCGGGAGACTGCTTGCCTAGCAAAATCATATGCGCAAATGTGGCAGCTCCTTTATTTCCACAGAA
GGGACCTCCGACTGATGGCCAATGCCATTTGTTCATCTGTGCCAGTTGACTGGGTTCCAACTGGGAGAACTACCTGGTCAATCC
ATGGAAAGGGAGAATGGATGACCACTGAAGACATGCTTGTGGTGTGGAACAGAGTGTGGATTGAGGAGAACGACCACATGG
AAGACAAGACCCCAGTTACGAAATGGACAGACATTCCCTATTTGGGAAAAAGGGAAGACTTGTGGTGTGGATCTCTCATAGG
GCACAGACCGCGCACCACCTGGGCTGAGAACATTAAAAACACAGTCAACATGGTGCGCAGGATCATAGGTGATGAAGAAAG
TACATGGACTACCTATCCACCCAAGTTCGCTACTTGGGTGAAGAAGGGTCTACACCTGGAGTGCTGTAAGCACCAATCTTAATG
TTGTCAGGCCTGCTAGTCAGCCACAGCTTGGGGAAAGCTGTGCAGCCTGTGACCCCCCAGGAGAAGCTGGGAAACCAAGCC
TATAGTCAGGCCGAGAACGCCATGGCACGGAAGAAGCCATGCTGCCTGTGAGCCCCTCAGAGGACACTGAGTCAAAAACCC
CACGCGCTTGGAGGCGCAGGATGGGAAAAGAAGGTGGCGACCTTCCCCACCCTTCAATCTGGGGCCTGAACTGGAGATCAGC
TGTGGATCTCCAGAAGAGGGACTAGTGGTTAGAGGA
```

-continued

KU509998.1 Zika virus strain Haiti/1225/2014, Haiti, complete genome

SEQ ID NO: 5

GTTGTTACTGTTGCTGACTCAGACTGCGACAGTTCGAGTTTGAAGCGAAAGCTAGCAACAGTATCAACAGGTTTTATTTGGATT

TGGAAACGAGAGTTTCTGGTCATGAAAAACCCAAAAAAGAAATCCGGAGGATTCCGGATTGTCAATATGCTAAAACGCGGAG

TAGCCCGTGTGAGCCCCTTTGGGGGCTTGAAGAGGCTGCCAGCCGGACTTCTGCTGGGTCATGGGCCCATCAGGATGGTCTTG

GCAATTCTAGCCTTTTTGAGATTCACGGCAATCAAGCCATCACTGGGTCTCATCAATAGATGGGGTTCAGTGGGAAAAAAGA

GGCTATGGAAATAATAAAGAAGTTCAAGAAAGATCTGGCTGCCATGCTGAGAATAATCAATGCTAGGAAGGAGAAGAAGAG

ACGAGGCGCAGATACTAGTGTCGGAATTGTTGGCCTCCTGCTGACCACAGCTATGGCAGCGGAGGTCACTAGACGTGGGAGT

GCATACTATATGTACTTGGACAGAAACGATGCTGGGGAGGCCATATCTTTTCCAACCACATTGGGGATGAATAAGTGTTATAT

ACAGATCATGGATCTTGGACACATGTGTGATGCCACCATGAGCTATGAATGCCCTATGCTGGATGAGGGGGTGGAACCAGAT

GACGTCGATTGTTGGTGCAACACGACGTCAACTTGGGTTGTGTACGGAACCTGCCATCACAAAAAAGGTGAAGCACGGAGAT

CTAGAAGAGCTGTGACGCTCCCCTCCCATTCCACTAGGAAGCTGCAAACGCGGTCGCAAACCTGGTTGGAATCAAGAGAATAC

ACAAAGCACTTGATTAGAGTCGAAAATTGGATATTCAGGAACCCTGGCTTCGCGTTAGCAGCAGCTGCCATCGCTTGGCTTTTG

GGAAGCTCAACGAGCCAAAAAGTCATATACTTGGTCATGATACTGCTGATTGCCCCGGCATACAGCATCAGGTGCATAGGAGT

CAGCAATAGGGACTTTGTGGAAGGTATGTCAGGTGGGACTTGGGTTGATGTTGTCTTGGAACATGGAGGTTGTGTCACCGTA

ATGGCACAGGACAAACCGACTGTCGACATAGAGCTGGTTACAACAACAGTCAGCAACATGGCGGAGGTAAGATCCTACTGCT

ATGAGGCATCAATATCAGACATGGCTTCGGACAGCCGCTGCCCAACACAAGGTGAAGCCTACCTTGACAAGCAATCAGACACT

CAATATGTCTGCAAAAGAACGTTAGTGGACAGAGGCTGGGGAAATGGATGTGGACTTTTTGGCAAAGGGAGTCTGGTGACAT

GCGCTAAGTTTGCATGCTCCAAGAAAATGACCGGGAAGAGCATCCAGCCAGAGAATCTGGAGTACCGGATAATGCTGTCAGT

TCATGGCTCCCAGCACAGTGGGATGATCGTTAATGACACAGGACATGAAACTGATGAGAATAGAGCGAAGGTTGAGATAACG

CCCAATTCACCAAGAGCCGAAGCCACCCTGGGGGGTTTTGGAAGCCTAGGACTTGATTGTGAACCGAGGACAGGCCTTGACTT

TTCAGATTTGTATTACTTGACTATGAATAACAAGCACTGGTTGGTTCACAAGGAGTGGTTCCACGACATTCCATTACCTTGGCAC

GCTGGGGCAGACACCGGAACTCCACACTGGAACAACAAAGAAGCACTGGTAGAGTTCAAGGACGCACATGCCAAAAGGCAA

ACTGTCGTGGTTCTAGGGAGTCAAGAAGGAGCAGTTCACACGGCCCTTGCTGGAGCTCTGGAGGCTGAGATGGATGGTGCAA

AGGGAAGGCTGTCCTCTGGCCACTTGAAATGTCGCCTGAAAATGGATAAACTTAGATTGAAGGGCGTGTCATACTCCTTGTGT

ACCGCAGCGTTCACATTCACCAAGATCCCGGCTGAAACACTGCACGGGACAGTCACAGTGGAGGTACAGTACGCAGGGACAG

ATGGACCTTGCAAGGTTCCAGCTCAGATGGCGGTGGACATGCAAACTCTGACCCCAGTTGGGAGGTTGATAACCGCTAACCCC

GTAATCACTGAAAGCACTGAGAACTCTAAGATGATGCTGGAACTTGATCCACCATTTGGGGACTCTTACATTGTCATAGGAGTC

GGGGAGAAGAAGATCACCCACCACTGGCACAGGAGTGGCAGCACCATTGGAAAAGCATTTGAAGCCACTGTGAGAGGTGCC

AAGAGAATGGCAGTCTTGGGAGACACAGCCTGGGACTTTGGATCAGTTGGAGGCGCTCTCAACTCATTGGGCAAGGGCATCC

ATCAAATTTTTGGAGCAGCTTTCAAATCATTGTTTGGAGGAATGTCCTGGTTCTCACAAATTCTCATTGGAACGTTGCTGATGTG

GTTGGGTCTGAACACAAAGAATGGATCTATTTCCCTTATGTGCTTGGCCTTAGGGGGAGTGTTGATCTTCTTATCCACAGCCGT

CTCTGCTGATGTGGGGTGCTCGGTGGACTTCTCAAAGAAGGAGACGAGATGCGGTACAGGGGTGTTCGTCTATAACGACGTT

GAAGCCTGGAGGGACAGGTACAAGTACCATCCTGACTCCCCCCGTAGATTGGCAGCAGCAGTCAAGCAAGCCTGGGAAGATG

GTATCTGCGGGATCTCCTCTGTTTCAAGAATGGAAAACATCATGTGGAGATCAGTAGAAGGGGAGCTCAACGCAATCCTGGAA

GAGAATGGAGTTCAACTGACGGTCGTTGTGGGATCTGTAAAAAACCCCATGTGGAGAGGTCCACAGAGATTGCCCGTGCCTG

TGAACGAGCTGCCCCACGGCTGGAAGGCTTGGGGGAAATCGCACTTCGTCAGAGCAGCAAAGACAAATAACAGCTTTGTCGT

GGATGGTGACACACTGAAGGAATGCCCACTCAAACATAGAGCATGGAACAGCTTTCTTGTGGAGGATCATGGGTTCGGGGTA

TTTCACACTAGTGTCTGGCTCAAGGTTAGAGAAGATTATTCATTAGAGTGTGATCCAGCCGTTATTGGAACAGCTGTTAAGGGA

AAGGAGGCTGTACACAGTGATCTAGGCTACTGGATTGAGAGTGAGAAGAATGACACATGGAGGCTGAAGAGGGCCCATCTG

ATCGAGATGAAAACATGTGAATGGCCAAAGTCCCACACATTGTGGACAGATGGAATAGAAGAGAGTGATCTGATCATACCCA

AGTCTTTAGCTGGGCCACTCAGCCATCACAATACCAGAGAGGGCTACAGGACCCAAATGAAAGGGCCATGGCACAGTGAAGA

-continued
```
GCTTGAAATTCGGTTTGAGGAATGCCCAGGCACTAAGGTCCACGTGGAGGAAACATGTGGAACAAGAGGACCATCTCTGAGA TCAACCACTGCAAGCGGAAGGGTGATCGAGGAATGGTGCTGCAGGGAGTGCACAATGCCCCCACTGTCGTTCCGGGCTAAAG ATGGCTGTTGGTATGGAATGGAGATAAGGCCCAGGAAAGAACCAGAAAGCAACTTAGTAAGGTCAATGGTGACTGCAGGATC AACTGATCACATGGATCACTTCTCCCTTGGAGTGCTTGTGATTCTGCTCATGGTGCAGGAAGGGCTGAAGAAGAGAATGACCA CAAAGATCATCATAAGCACATCAATGGCAGTGCTGGTAGCTATGATCCTGGGAGGATTTTCAATGAGTGACCTGGCTAAGCTT GCAATTTTGATGGGTGCCACCTTCGCGGAAATGAACACTGGAGGAGATGTAGCTCATCTGGCGCTGATAGCGGCATTCAAAGT CAGACCAGCGTTGCTGGTATCTTTCATCTTCAGAGCTAATTGGACACCCCGTGAAAGCATGCTGCTGGCCTTGGCCTCGTGTCT TTTGCAAACTGCGATCTCCGCCTTGGAAGGCGACCTGATGGTTCTCATCAATGGTTTTGCTTTGGCCTGGTTGGCAATACGAGC GATGGTTGTTCCACGCACTGATAACATCACCTTGGCAATCCTGGCTGCTCTGACACCACTGGCCCGGGGCACACTGCTTGTGGC GTGGAGAGCAGGCCTTGCTACTTGCGGGGGGTTTATGCTCCTCTCTCTGAAGGGAAAAGGCAGTGTGAAGAAGAACTTACCA TTTGTCATGGCCCTGGGACTAACCGCTGTGAGGCTGGTCGACCCCATCAACGTGGTGGGGCTGCTGTTGCTCACAAGGAGTGG GAAGCGGAGCTGGCCCCCTAGCGAAGTACTCACAGCTGTTGGCCTGATATGCGCATTGGCTGGAGGGTTCGCCAAGGCAGAT ATAGAGATGGCTGGGCCCATGGCCGCGGTCGGTCTGCTAATTGTCAGTTACGTGGTCTCAGGAAAGAGTGTGGACATGTACA TTGAAAGAGCAGGTGACATCACATGGGAAAAAGATGCGGAAGTCACTGGAAACAGTCCCCGGCTCGATGTGGCGCTAGATGA GAGTGGTGATTTCTCCCTGGTGGAGGATGACGGTCCCCCCATGAGAGAGATCATACTCAAGGTGGTCCTGATGACCATCTGTG GCATGAACCCAATAGCCATACCCTTTGCAGCTGGAGCGTGGTACGTATACGTGAAGACTGGAAAAAGGAGTGGTGCTCTATG GGATGTGCCTGCTCCCAAGGAAGTAAAAAAGGGGGAGACCACAGATGGAGTGTACAGAGTAATGACTCGTAGACTGCTAGG TTCAACACAAGTTGGAGTGGGAGTTATGCAAGAGGGGGTCTTTCACACTATGTGGCACGTCACAAAAGGATCCGCGCTGAGA AGCGGTGAAGGGAGACTTGATCCATACTGGGGAGATGTCAAGCAGGATCTGGTGTCATACTGTGGTCCATGGAAGCTAGATG CCGCCTGGGACGGGCACAGCGAGGTGCAGCTCTTGGCCGTGCCCCCCGGAGAGAGAGCGAGGAACATCCAGACTCTGCCCG GAATATTTAAGACAAAGGATGGGGACATTGGAGCGGTTGCGCTGGATTACCCAGCAGGAACTTCAGGATCTCCAATCCTAGA CAAGTGTGGGAGAGTGATAGGACTTTATGGCAATGGGGTCGTGATCAAAAATGGGAGTTATGTTAGTGCCATCACCCAAGGG AGGAGGGAGGAAGAGACTCCTGTTGAGTGCTTCGAGCCTTCGATGCTGAAGAAGAAGCAGCTAACTGTCTTAGACTTGCATC CTGGAGCTGGGAAAACCAGGAGAGTTCTTCCTGAAATAGTCCGTGAAGCCATAAAAACAAGACTCCGTACTGTGATCTTAGCT CCAACCAGGGTTGTCGCTGCTGAAATGGAGGAAGCCCTTAGAGGGCTTCCAGTGCGTTATATGCAACAGCAGTCAATGTCAC CCACTCTGGAACAGAAATCGTCGACTTAATGTGCCATGCCACCTTCACTTCACGTCTACTACAGCCAATCAGAGTCCCCAACTAT AATCTGTATATTATGGATGAGGCCCACTTCACAGATCCCTCAAGTATAGCAGCAAGAGGATACATTTCAACAAGGGTTGAGAT GGGCGAGGCGGCTGCCATCTTCATGACCGCCACGCCACCAGGAACCCGTGACGCATTTCCGGACTCCAACTCACCAATTATGG ACACCGAAGTGGAAGTCCCAGAGAGAGCCTGGAGCTCAGGCTTTGATTGGGTGACGGATTATTCTGGAAAAACAGTTTGGTT TGTTCCAAGCGTGAGGAACGGCAATGAGATCGCAGCTTGTCTGACAAAGGCTGGAAAACGGGTCATACAGCTCAGCAGAAAG ACTTTTGAGACAGAGTTCCAGAAAACAAAACATCAAGAGTGGGACTTTGTCGTGACAACTGACATTTCAGAGATGGGCGCCAA CTTTAAAGCTGACCGTGTCATAGATTCCAGGAGATGCCTAAAGCCGGTCATACTTGATGGCGAGAGAGTCATTCTGGCTGGAC

CCATGCCTGTCACACATGCCAGCGCTGCCCAGAGGAGGGGCGCATAGGCAGGAATCCAACAAACCTGGAGATGAGTATCT

GTATGGAGGTGGGTGCGCAGAGACTGACGAAGACCATGCACACTGGCTTGAAGCAAGAATGCTCCTTGACAATATTTACCTCC

AAGATGGCCTCATAGCCTCGCTCTATCGACCTGAGGCCGACAAAGTAGCAGCCATTGAGGGAGAGTTCAAGCTTAGGACGGA

GCAAAGGAAGACCTTTGTGGAACTCATGAAAAGAGGAGATCTTCCTGTTTGGCTGGCCTATCAGGTTGCATCTGCCGGAATAA

CCTACACAGATAGAAGATGGTGCTTTGATGGCACGACCAACAACACCATAATGGAAGACAGTGTGCCGGCAGAGGTGTGGAC

CAGACACGGAGAGAAAAGAGTGCTCAAACCGAGGTGGATGGACGCCAGAGTTTGTTCAGATCATGCGGCCCTGAAGTCATTC

AAGGAGTTTGCCGCTGGGAAAAGAGGAGCGGCTTTTGGAGTGATGGAAGCCCTGGGAACACTGCCAGGACACATGACAGAG

AGATTCCAGGAAGCCATTGACAACCTCGCTGTGCTCATGCGGGCAGAGACTGGAAGCAGGCCTTACAAAGCCGCGGCGGCCC

AATTGCCGGAGACCCTAGAGACCATTATGCTTTTGGGGTTGCTGGGAACAGTCTCGCTGGGAATCTTTTTCGTCTTGATGAGG
```

-continued

```
AACAAGGGCATAGGGAAGATGGGCTTTGGAATGGTGACTCTTGGGGCAGCGCATGGCTCATGTGGCTCTCGGAAATTGAGC
CAGCCAGAATTGCATGTGTCCTCATTGTTGTGTTCCTATTGCTGGTGGTGCTCATACCTGAGCCAGAAAAGCAAAGATCTCCCC
AGGACAACCAAATGGCAATCATCATCATGGTAGCAGTAGGTCTTCTGGGCTTGATTACCGCCAATGAACTCGGATGGTTGGAG
AGAACAAAGAGTGACCTAAGCCATCTAATGGGAAGGAGAGAGGAGGGGGCAACCATGGGATTCTCAATGGACATTGACCTG
CGGCCAGCCTCAGCTTGGGCCATCTATGCTGCCTTGACAACTTTCATTACCCCAGCCGTCCAACATGCAGTGACCACTTCATACA
ACAACTACTCCTTAATGGCGATGGCCACGCAAGCTGGAGTGTTGTTTGGTATGGGCAAAGGGATGCCATTCTACGCATGGGAC
TTTGGAGTCCCGCTGCTAATGATAGGTTGCTACTCACAATTAACGCCCCTGACCCTAATAGTGGCCATCATTTTGCTCGTGGCG
CACTACATGTACTTGATCCCAGGGCTGCAGGCAGCAGCTGCGCGTGCTGCCCAGAAGAGAACGGCAGCTGGCATCATGAAGA
ACCCTGTTGTGGATGGAATAGTGGTGACTGACATTGACACAATGACAATTGACCCCCAAGTGGAGAAAAAGATGGGACAGGT
GCTACTCATGGCAGTAGCCGTCTCCAGCGCCATACTGTCGCGGACCGCCTGGGGGTGGGGGGAGGCTGGGGCCCTGATCACA
GCCGCAACTTCCACTTTGTGGGAAGGCTCTCCGAACAAGTACTGGAACTCCTCTACAGCCACTTCACTGTGTAACATTTTTAGG
GGAAGTTACTTGGCTGGAGCTTCTCTAATCTACACAGTAACAAGAAACGCTGGCTTGGTCAAGAGACGTGGGGGTGGAACAG
GAGAGACCCTGGGAGAGAAATGGAAGGCCCGCTTGAACCAGATGTCGGCCCTGGAGTTCTACTCCTACAAAAAGTCAGGCAT
CACCGAGGTGTGCAGAGAAGAGGCCCGCCGCGCCCTCAAGGACGGTGTGGCAACGGGAGGCCATGCTGTGTCCCGAGGAAG
TGCAAAGCTGAGATGGTTGGTGGAGCGGGGATACCTGCAGCCCTATGGAAAGGTCATTGATCTTGGATGTGGCAGAGGGGG
CTGGAGTTACTACGCCGCCACCATCCGCAAAGTTCAAGAAGTGAAAGGATACACAAAAGGAGGCCCTGGTCATGAAGAACCC
GTGTTGGTGCAAAGCTATGGGTGGAACATAGTCCGTCTTAAGAGTGGGGTGGACGTCTTTCATATGGCGGCTGAGCCGTGTG
ACACGTTGCTGTGTGACATAGGTGAGTCATCATCTAGTCCTGAAGTGGAAGAAGCACGGACGCTCAGAGTCCTCTCCATGGTG
GGGGATTGGCTTGAAAAAAGACCAGGAGCCTTTTGTATAAAAGTGTTGTGCCCATACACCAGCACTATGATGGAAACCCTGGA
GCGACTGCAGCGTAGGTATGGGGAGGACTGGTCAGAGTGCCACTCTCCCGCAACTCTACACATGAGATGTACTGGGTCTCT
GGAGCGAAAAGCAACACCATAAAAAGTGTGTCCACCACGAGCCAGCTCCTCTTGGGGCGCATGGACGGGCCTAGGAGGCCA
GTGAAATATGAGGAGGATGTGAATCTCGGCTCTGGCACGCGGGCTGTGGTAAGCTGCGCTGAAGCTCCCAACATGAAGATCA
TTGGTAACCGCATTGAAAGGATCCGCAGTGAGCACGCGGAAACGTGGTTCTTTGACGAGAACCACCCATATAGGACATGGGC
TTACCATGGAAGCTATGAGGCCCCCACACAAGGGTCAGCGTCCTCTCTAATAAACGGGGTTGTCAGGCTCCTGTCAAACCCT
GGGATGTGGTGACTGGAGTCACAGGAATAGCCATGACCGACACCACACCGTATGGTCAGCAAAGAGTTTTCAAGGAAAAAGT
GGACACTAGGGTGCCAGACCCCCAAGAAGGCACTCGTCAGGTTATGAGCATGGTCTCTTCCTGGTTGTGGAAAGAGCTAGGC
AAACACAAACGGCCACGAGTCTGTACCAAAGAAGAGTTCATCAACAAGGTTCGTAGCAATGCAGCATTAGGGGCAATATTTGA
AGAGGAAAAGAGTGGAAGACTGCAGTGGAAGCTGTGAACGATCCAAGGTTCTGGGCTCTAGTGGACAAGGAAAGAGAGCA
CCACCTGAGAGGAGAGTGCCAGAGTTGTGTGTACAACATGATGGGAAAAAGAGAAAAGAAACAAGGGGAATTTGGAAAGGC
CAAGGGCAGCCGCGCCATCTGGTATATGTGGCTAGGGGCTAGATTTCTAGAGTTCGAAGCCCTTGGATTCTTGAACGAGGATC
ACTGGATGGGGAGAGAGAACTCAGGAGGTGGTGTTGAAGGGCTGGGATTACAAAGACTCGGATATGTCCTAGAAGAGATGA
GTCGCATACCAGGAGGAAGGATGTATGCAGATGACACTGCTGGCTGGGACACCCGCATCAGCAGGTTTGATCTGGAGAATGA
AGCTCTAATCACCAACCAAATGGAGAAAGGGCACAGGGCCTTGGCATTGGCCATAATCAAGTACACATACCAAAACAAAGTG
GTAAAGGTCCTTAGACCAGCTGAAAAAGGGAAGACAGTTATGGACATTATTTCGAGACAAGACCAAAGGGGGAGCGGACAA
GTTGTCACTTACGCTCTTAACACATTTACCAACCTAGTGGTGCAACTCATTCGGAATATGGAGGCTGAGGAAGTTCTAGAGATG
CAAGACTTGTGGCTGCTGCGGAGGTCAGAGAAAGTGACCAACTGGTTGCAGAGCAACGGATGGGATAGGCTCAAACGAATG
GCAGTCAGTGGAGATGATTGCGTTGTGAAGCCAATTGATGATAGGTTTGCACATGCCCTCAGGTTCTTGAATGATATGGGAAA
AGTTAGGAAGGACACACAAGAGTGGAAACCCTCAACTGGATGGGACAACTGGGAAGAAGTTCCGTTTTGCTCCCACCACTTCA
ACAAGCTCCATCTCAAGGACGGGAGGTCCATTGTGGTTCCCTGCCGCCACCAAGATGAACTGATTGGCCGGGCCCGCGTCTCT
CCAGGGGCGGGATGGAGCATCCGGGAGACTGCTTGCCTAGCAAAATCATATGCGCAAATGTGGCAGCTCCTTTATTTCCACAG
AAGGGACCTCCGACTGATGGCCAATGCCATTTGTTCATCTGTGCCAGTTGACTGGGTTCCAACTGGGAGAACTACCTGGTCAAT
```

-continued

```
CCATGGAAAGGGAGAATGGATGACCACTGAAGACATGCTTGTGGTGTGGAACAGAGTGTGGATTGAGGAGAACGACCACAT

GGAAGACAAGACCCCAGTTACGAAATGGACAGACATTCCCTATTTGGGAAAAAGGGAAGACTTGTGGTGTGGATCTCTCATA

GGGCACAGACCGCGCACCACCTGGGCTGAGAACATTAAAAACACAGTCAACATGGTGCGCAGGATCATAGGTGATGAAGAAA

AGTACATGGACTACCTATCCACCCAAGTTCGCTACTTGGGTGAAGAAGGGTCTACACCTGGAGTGCTGTAAGCACCAATCTTA

ATGTTGTCAGGCCTGCTAGTCAGCCACAGCTTGGGGAAAGCTGTGCAGCCTGTGACCCCCCCAGGAGAAGCTGGGAAACCAA

GCCTATAGTCAGGCCGAGAACGCCATGGCACGGAAGAAGCCATGCTGCCTGTGAGCCCCTCAGAGGACACTGAGTCAAAAAA

CCCCACGCGCTTGGAGGCGCAGGATGGGAAAAGAAGGTGGCGACCTTCCCCACCCTTCAATCTGGGGCCTGAACTGGAGATC

AGCTGTGGATCTCCAGAAGAGGGACTAGTGGTTAGAGGAGA
```

KU527068.1 Zika virus strain Natal RGN, Brazil: Rio Grande do
Norte, Natal, complete genome

SEQ ID NO: 6

```
AGTTGTTGATCTGTGTGAATCAGACTGCGACAGTTCGAGTTTGAAGCGAAAGCTAGCAACAGTATCAACAGGTTTTATTTTGG

ATTTGGAAACGAGAGTTTCTGGTCATGAAAAACCCAAAAAAGAAATCCGGAGGATTCCGGATTGTCAATATGCTAAAACGCGG

AGTAGCCCGTGTGAGCCCCTTTGGGGGCTTGAAGAGGCTGCCAGCCGGACTTCTGCTGGGTCATGGGCCCATCAGGATGGTC

TTGGCAATTCTAGCCTTTTTGAGATTCACGGCAATCAAGCCATCACTGGGTCTCATCAATAGATGGGGTTCAGTGGGGAAAAA

AGAGGCTATGGAAATAATAAAGAAGTTCAAGAAAGATCTGGCTGCCATGCTGAGAATAATCAATGCTAGGAAGGAGAAGAA

GAGACGAGGCGCAGATACTAGTGTCGGAATTGTTGGCCTCCTGCTGACCACAGCTATGGCAGCGGAGGTCACTAGACGTGGG

AGTGCATACTATATGTACTTGGACAGAAACGATGCTGGGGAGGCCATATCTTTTCCAACCACATTGGGGATGAATAAGTGTTA

TATACAGATCATGGATCTTGGACACATGTGTGATGCCACCATGAGCTATGAATGCCCTATGCTGGATGAGGGGGTGGAACCAG

ATGACGTCGATTGTTGGTGCAACACGACGTCAACTTGGGTTGTGTACGGAACCTGCCATCACAAAAAAGGTGAAGCACGGAG

ATCTAGAAGAGCTGTGACGCTCCCCTCCCATTCCACTAGGAAGCTGCAAACGCGGTCGCAAACCTGGTTGGAATCAAGAGAAT

ACACAAAGCACTTGATTAGAGTCGAAAATTGGATATTCAGGAACCCTGGCTTCGCGTTAGCAGCAGCTGCCATCGCTTGGCTTT

TGGGAAGCTCAACGAGCCAAAAAGTCATATACTTGGTCATGATACTGCTGATTGCCCCGGCATACAGCATCAGGTGCATAGGA

GTCAGCAATAGGGACTTTGTGGAAGGTATGTCAGGTGGGACTTGGGTTGATGTTGTCTTGGAACATGGAGGTTGTGTCACCG

TAATGGCACAGGACAAACCGACTGTCGACATAGAGCTGGTTACAACAACAGTCAGCAACATGGCGGAGGTAAGATCCTACTG

CTATGAGGCATCAATATCAGACATGGCTTCGGACAGCCGCTGCCCAACACAAGGTGAAGCCTACCTTGACAAGCAATCAGACA

CTCAATATGTCTGCAAAAGAACGTTAGTGGACAGAGGCTGGGGAAATGGATGTGGACTTTTTGGCAAAGGGAGCCTGGTGAC

ATGCGCTAAGTTTGCATGCTCCAAGAAAATGACCGGGAAGAGCATCCAGCCAGAGAATCTGGAGTACCGGATAATGCTGTCA

GTTCATGGCTCCCAGCACAGTGGGATGATCGTTAATGACACAGGACATGAAACTGATGAGAATAGAGCGAAGGTTGAGATAA

CGCCCAATTCACCAAGAGCCGAAGCCACCCTGGGGGGTTTTGGAAGCCTAGGACTTGATTGTGAACCGAGGACAGGCCTTGA

CTTTTCAGATTTGTATTACTTGACTATGAATAACAAGCACTGGTTGGTCCACAAGGAGTGGTTCCACGACATTCCATTACCTTGG

CACGCTGGGGCAGACACCGGAACTCCACACTGGAACAACAAAGAAGCACTGGTAGAGTTCAAGGACGCACATGCCAAAAGG

CAAACTGTCGTGGTTCTAGGGAGTCAAGAAGGAGCAGTTCACACGGCCCTTGCTGGAGCTCTGGAGGCTGAGATGGATGGTG

CAAAGGGAAGGCTGTCCTCTGGCCACTTGAAATGTCGCCTGAAAATGGATAAACTTAGATTGAAGGGCGTGTCATACTCCTTG

TGTACCGCAGCGTTCACATTCACCAAGATCCCGGCTGAAACACTGCACGGGACAGTCACAGTGGAGGTACAGTACGCAGGGA

CAGATGGACCTTGCAAGGTTCCAGCTCAGATGGCGGTGGACATGCAAACTCTGACCCCAGTTGGGAGGTTGATAACCGCTAAC

CCCGTAATCACTGAAAGCACTGAGAACTCTAAGATGATGCTGGAACTTGATCCACCATTTGGGGACTCTTACATTGTCATAGGA

GTCGGGGAGAAGAAGATCACCCACCACTGGCACAGGAGTGGCAGCACCATTGGAAAAGCATTTGAAGCCACTGTGAGAGGT

GCCAAGAGAATGGCAGTCTTGGGAGACACAGCCTGGGACTTTGGATCAGTTGGAGGCGCTCTCAACTCATTGGGCAAGGGCA

TCCATCAAATTTTTGGAGCAGCTTTCAAATCATTGTTTGGAGGAATGTCCTGGTTCTCACAAATCCTCATTGGAACGTTGCTGAT

GTGGTTGGGTCTGAACACAAAGAATGGATCTATTTCCCTTATGTGCTTGGCCTTAGGGGAGTGTTGATCTTCTTATCCACAGC

CGTCTCTGCTGATGTGGGGTGCTCGGTGGACTTCTCAAAGAAGGAGACGAGATGCGGTACAGGGGTGTTCGTCTATAACGAC
```

-continued

```
GTTGAAGCCTGGAGGGACAGGTACAAGTACCATCCTGACTCCCCCCGTAGATTGGCAGCAGCAGTCAAGCAAGCCTGGGAAG
ATGGTATCTGCGGGATCTCCTCTGTTTCAAGAATGGAGAACATCATGTGGAGATCAGTAGAAGGGGAGCTCAACGCAATCTTG
GAAGAGAATGGAGTTCAACTGACGGTCGTTGTGGGATCTGTAAAAAACCCCATGTGGAGAGGTCCACAGAGATTGCCCGTGC
CTGTGAACGAGCTGCCCCACGGCTGGAAGGCTTGGGGGAAATCGTACTTCGTCAGAGCAGCAAAGACAAATAACAGCTTTGT
CGTGGATGGTGACACACTGAAGGAATGCCCACTCGAACATAGAGCATGGAACAGCTTTCTTGTGGAGGATCATGGGTTCGGG
GTATTTCACACTAGTGTCTGGCTCAAGGTTAGAGAAGATTATTCATTAGAGTGTGATCCAGCCGTTATTGGAACAGCTGTTAAG
GGGAAGGAGGCTGTACACAGTGATCTAGGCTACTGGATTGAGAGTGAGAAGAATGACACATGGAGGCTGAAGAGGGCCCAT
CTAATCGAGATGAAAACATGTGAATGGCCAAAGTCCCACACATTGTGGGCAGATGGAATAGAAGAGAGTGATCTGATCATTCC
CAAGTCTTTAGCTGGGCCACTCAGCCATCACAATACCAGAGAGGGCTACAGGACCCAAATGAAAGGGCCATGGCACAGTGAA
GAGCTTGAAATTCGGTTTGAGGAATGCCCGGGCACTAAGGTCCACGTGGAGGAAACATGTGGAACAAGAGGACCATCTCTGA
GATCAACCACTGCAAGCGGAAGGGTGATCGAGGAATGGTGCTGCAGGGAGTGCACAATGCCCCCACTGTCGTTCCGGGCTAA
AGATGGCTGTTGGTATGGAATGGAGATAAGGCCCAGGAAAGAACCAGAAAGCAACTTAGTAAGGTCAGTGGTGACTGCAGG
ATCAACTGATCACATGGATCACTTCTCCCTTGGAGTGCTTGTGATTCTGCTCATGGTGCAGGAAGGGCTGAAGAAGAGAATGA
CCACAAAGATCATCATAAGCACATCAATGGCAGTGCTGGTAGCTATGATCCTGGGAGGATTTTCAATGAGTGACCTGGCTAAG
CTTGCAATTTTGATGGGCGCCACCTTCGCGGAAATGAACACTGGAGGAGATGTAGCTCATCTGGCGCTGATAGCGGCATTCAA
AGTCAGACCAGCGTTGCTGGTATCTTTCATCTTCAGAGCTAATTGGACACCCCGTGAAAGCATGCTGCTGGCCTTGGCCTCGTG
TCTTTTGCAAACTGCGATCTCCGCCTTGGAAGGCGACCTGATGGTTCTCATCAATGGTTTTGCTTTGGCCTGGTTGGCAATACG
AGCGATGGTTGTTCCACGCACTGATAACATCACCTTGGCAATCCTGGCTGCTCTGACACCACTGGCCCGGGGCACACTGCTTGT
GGCGTGGAGAGCAGGCCTTGCTACTTGCGGGGGGTTTATGCTCCTCTCTCTGAAGGGAAAAGGCAGTGTGAAGAAGAACTTA
CCATTTGTCATGGCCCTGGGACTAACCGCTGTGAGGCTGGTCGACCCCATCAACGTGGTGGGACTGCTGTTGCTCACAAGGAG
TGGGAAGCGGAGCTGGCCCCCTAGCGAAGTACTCACAGCTGTTGGCCTGATATGCGCATTGGCTGGAGGGTTCGCCAAGGCA
GATATAGAGATGGCTGGGCCCATGGCCGCGGTCGGTCTGCTAATTGTCAGTTACGTGGTCTCAGGAAAGAGTGTGGACATGT
ACATTGAAAGAGCAGGTGACATCACATGGGAAAAAGATGCGGAAGTCACTGGAAACAGTCCCCGGCTCGATGTGGCGCTAGA
TGAGAGTGGTGATTTCTCCCTGGTGGAGGATGACGGTCCCCCCATGAGAGAGATCATACTCAAGGTGGTCCTGATGACCATCT
GTGGCATGAACCCAATAGCCATACCCTTTGCAGCTGGAGCGTGGTACGTATACGTGAAGACTGGAAAAAGGAGTGGTGCTCT
ATGGGATGTGCCTGCTCCCAAGGAAGTAAAAAAGGGGGAGACCACAGATGGAGTGTACAGAGTAATGACTCGTAGACTGCTA
GGTTCAACACAAGTTGGAGTGGGAGTTATGCAAGAGGGGGTCTTTCACACTATGTGGCACGTCACAAAAGGATCCGCGCTGA
GAAGCGGTGAAGGGAGACTTGATCCATACTGGGGAGATGTCAAGCAGGATCTGGTGTCATACTGTGGTCCATGGAAGCTAGA
TGCCGCCTGGGACGGGCACAGCGAGGTGCAGCTCTTGGCCGTGCCCCCCGGAGAGAGAGCGAGGAACATCCAGACTCTGCCC
GGAATATTTAAGACAAAGGATGGGGACATTGGAGCGGTTGCGCTGGATTACCCAGCAGGAACTTCAGGATCTCCAATCCTAG
ACAAGTGTGGGAGAGTGATAGGACTTTATGGCAATGGGGTCGTGATCAAAAATGGGAGTTATGTTAGTGCCATCACCCAAGG
GAGGAGGGAGGAAGAGACTCCTGTTGAGTGCTTCGAGCCTTCGATGCTGAAGAAGAAGCAGCTAACTGTCTTAGACTTGCAT
CCTGGAGCTGGGAAAACCAGGAGAGTTCTTCCTGAAATAGTCCGTGAAGCCATAAAAACAAGACTCCGTACTGTGATCTTAGC
TCCAACCAGGGTTGTCGCTGCTGAAATGGAGGAAGCCCTTAGAGGGCTTCCAGTGCGTTATATGACAACAGCAGTCAATGTCA
CCCACTCTGGAACAGAAATCGTCGACTTAATGTGCCATGCCACCTTCACTTCACGTCTACTACAGCCAATCAGAGTCCCCAACTA
TAATCTGTATATTATGGATGAGGCCCACTTCACAGATCCCTCAAGTATAGCAGCAAGAGGATACATTTCAACAAGGGTTGAGA
TGGGCGAGGCGGCTGCCATCTTCATGACCGCCACGCCACCAGGAACCCGTGACGCATTTCCGGACTCCAACTCACCAATTATG
GACACCGAAGTGGAAGTCCCAGAGAGAGCCTGGAGCTCAGGCTTTGATTGGGTGACGGATCATTCTGGAAAAACAGTTTGGT
TTGTTCCAAGCGTGAGGAACGGCAATGAGATCGCAGCTTGTCTGACAAAGGCTGGAAAACGGGTCATACAGCTCAGCAGAAA
GACTTTTGAGACAGAGTTCCAGAAAACAAAACATCAAGAGTGGGACTTTGTCGTGACAACTGACATTTCAGAGATGGGCGCCA
ACTTTAAAGCTGACCGTGTCATAGATTCCAGGAGATGCCTAAAGCCGGTCATACTTGATGGCGAGAGAGTCATTTTGGCTGGA
```

```
CCCATGCCTGTCACACATGCCAGCGCTGCCCAGAGGAGGGGGCGCATAGGCAGGAATCCCAACAAACCTGGAGATGAGTATC
TGTATGGAGGTGGGTGCGCAGAGACTGACGAAGACCATGCACACTGGCTTGAAGCAAGAATGCTCCTTGACAATATTTACCTC
CAAGATGGCCTCATAGCCTCGCTCTATCGACCTGAGGCCGACAAAGTAGCAGCCATTGAGGGAGAGTTCAAGCTTAGGACGG
AGCAAAGGAAGACCTTTGTGGAACTCATGAAAAGAGGAGATCTTCCTGTTTGGCTGGCCTATCAGGTTGCATCTGCCGGAATA
ACCTACACAGATAGAAGATGGTGCTTTGATGGCACGACCAACAACACCATAATGGAAGACAGTGTGCCGGCAGAGGTGTGGA
CCAGACACGGAGAGAAAAGAGTGCTCAAACCGAGGTGGATGGACGCCAGAGTTTGTTCAGATCATGCGGCCCTGAAGTCATT
CAAGGAGTTTGCCGCTGGGAAAAGAGGAGCGGCTTTTGGAGTGATGGAAGCCCTGGGAACACTGCCAGGACACATGACAGA
GAGATTCCAGGAAGCCATTGACAACCTCGCTGTGCTCATGCGGGCAGAGACTGGAAGCAGGCCTTACAAAGCCGCGGCGGCC
CAATTGCCGGAGACCCTAGAGACCATTATGCTTTTGGGGTTGCTGGGAACAGTCTCGCTGGGAATCTTTTTCGTCTTGATGAGG
AACAAGGGCATAGGGAAGATGGGCTTTGGAATGGTGACTCTTGGGGCCAGCGCATGGCTCATGTGGCTCTCGGAAATTGAGC
CAGCCAGAATTGCATGTGTCCTCATTGTTGTGTTCCTATTGCTGGTGGTGCTCATACCTGAGCCAGAAAAGCAAAGATCTCCCC
AGGACAACCAAATGGCAATCATCATCATGGTAGCAGTAGGTCTTCTGGGCTTGATTACCGCCAATGAACTCGGATGGTTGGAG
AGAACAAAGAGTGACCTAAGCCATCTAATGGGAAGGAGAGAGGAGGGAGCAACCATAGGATTCTCAATGGACATTGACCTG
CGGCCAGCCTCAGCTTGGGCCATCTATGCTGCCTTGACAACTTTCATTACCCCAGCCGTCCAACATGCAGTGACCACTTCATACA
ACAACTACTCCTTAATGGCGATGGCCACGCAAGCTGGAGTGTTGTTTGGTATGGGCAAAGGGATGCCATTCTACGCATGGGAC
TTTGGAGTCCCGCTGCTAATGATAGGTTGCTACTCACAATTAACACCCCTGACCCTAATAGTGGCCATCATTTTGCTCGTGGCGC
ACTACATGTACTTGATCCCAGGGCTGCAGGCAGCAGCTGCGCGTGCTGCCCAGAAGAGAACGGCAGCTGGCATCATGAAGAA
CCCTGTTGTGGATGGAATAGTGGTGACTGACATTGACACAATGACAATTGACCCCCAAGTGGAGAAAAAGATGGGACAGGTG
CTACTCATAGCAGTAGCAGTCTCCAGCGCCATACTGTCGCGGACCGCCTGGGGGTGGGGGAGGCTGGGGCCCTGATCACAG
CCGCAACTTCCACTTTGTGGGAAGGCTCTCCGAACAAGTACTGGAACTCCTCTACAGCCACTTCACTGTGTAACATTTTTAGGG
GAAGTTACTTGGCTGGAGCTTCTCTAATCTACATAGTAACAAGAAACGCTGGCTTGGTCAAGAGACGTGGGGGTGGAACAGG
AGAGACCCTGGGAGAGAAATGGAAGGCCCGCTTGAACCAGATGTCGGCCCTGGAGTTCTACTCCTACAAAAAGTCAGGCATC
ACCGAGGTGTGCAGAGAAGAGGCCCGCCGCGCCCTCAAGGATGGTGTGGCAACGGGAGGCCATGCTGTGTCCCGAGGAAGT
GCAAAGCTGAGATGGTTGGTGGAGCGGGGATACCTGCAGCCCTATGGAAAGGTCATTGATCTTGGATGTGGCAGAGGGGGC
TGGAGTTACTACGCCGCCACCATCCGCAAAGTTCAAGAAGTGAAAGGATACACAAAAGGAGGCCCTGGTCATGAAGAACCCG
TGTTGGTGCAAAGCTATGGGTGGAACATAGTCCGTCTTAAGAGTGGGGTGGACGTCTTTCATATGGCGGCTGAGCCGTGTGA
CACGTTGCTGTGTGACATAGGTGAGTCATCATCTAGTCCTGAAGTGGAAGAAGCACGGACGCTCAGAGTCCTCTCCATGGTGG
GGGATTGGCTTGAAAAAAGACCAGGAGCCTTTTGTATAAAAGTGTTGTGCCCATACACCAGCACTATGATGGAAACCCTGGAG
CGACTGCAGCGTAGGTATGGGGAGGACTGGTCAGAGTGCCACTCTCCCGCAACTCTACACATGAGATGTACTGGGTCTCTG
GAGCGAAAAGCAACACCATAAAAAGTGTGTCCACCACGAGCCAGCTCCTCTTGGGCGCATGGACGGGCCTAGGAGGCCAGT
GAAATATGAGGAGGATGTGAATCTCGGCTCTGGCACGCGGGCTGTGGTAAGCTGCGCTGAAGCTCCCAACATGAAGATCATT
GGTAACCGCATTGAAAGGATCCGCAGTGAGCACGCGGAAACGTGGTTCTTTGACGAGAACCACCCATATAGGACATGGGCTT
ACCATGGAAGCTATGAGGCCCCCACACAAGGGTCAGCGTCCTCTCTAATAAACGGGGTTGTCAGGCTCCTGTCAAAACCCTGG
GATGTGGTGACTGGAGTCACAGGAATAGCCATGACCGACACCACACCGTATGGTCAGCAAAGAGTTTTCAAGGAAAAAGTGG
ACACTAGGGTGCCAGACCCCCAAGAAGGCACTCGTCAGGTTATGAGCATGGTCTCTTCCTGGTTGTGGAAAGAGCTAGGCAA
ACACAAACGGCCACGAGTCTGTACCAAAGAAGAGTTCATCAACAAGGTTCGTAGCAATGCAGCATTAGGGGCAATATTTGAA
GAGGAAAAAGAGTGGAAGACTGCAGTGGAAGCTGTGAACGATCCAAGGTTCTGGGCTCTAGTGGACAAGGAAAGAGAGCAC
CACCTGAGAGGAGAGTGCCAGAGTTGTGTGTACAACATGATGGGAAAAAGAGAAAAGAAACAAGGGGAATTTGGAAAGGCC
AAGGGCAGCCGCGCCCATCTGGTATATGTGGCTAGGGGCTAGATTTCTAGAGTTCGAAGCCCTTGGATTCTTGAACGAGGATCA
CTGGATGGGAGAGAGAACTCAGGAGGTGGTGTTGAAGGGCTGGATTACAAAGACTCGGATATGTCCTAGAAGAGATGAG
TCGCATACCAGGAGGAAGGATGTATGCAGATGACACTGCTGGCTGGGACACCCGCATCAGCAGGTTCGATCTGGAGAATGAA
```

-continued

```
GCTCTAATCACCAACCAAATGGAGAAAGGGCATAGGGCCTTGGCATTGGCCATAATCAAGTACACATACCAAAACAAAGTGGT

AAAGGTCCTTAGACCAGCTGAAAAAGGGAAAACAGTTATGGACATTATTTCGAGACAAGACCAAAGGGGGAGCGGACAAGTT

GTCACTTACGCTCTTAACACATTTACCAACCTAGTGGTGCAACTCATTCGGAATATGGAGGCTGAGGAAGTTCTAGAGATGCAA

GACTTGTGGCTGCTGCGGAGGTCAGAGAAAGTGACCAACTGGTTGCAGAGCAACGGATGGGATAGGCTCAAACGAATGGCA

GTCAGTGGAGATGATTGCGTTGTGAAGCCAATTGATGATAGGTTTGCACATGCCCTCAGGTTCTTGAATGATATGGGAAAGT

TAGGAAGGACACACAAGAGTGGAAACCCTCAACTGGATGGGACAACTGGGAAGAAGTTCCGTTTTGCTCCCACCACTTCAACA

AGCTCCATCTCAAGGACGGGAGGTCCATTGTGGTTCCCTGCCGCCACCAAGATGAACTGATTGGCCGGGCCCGCGTCTCTCCA

GGGGCGGGATGGAGCATCCGGGAGACTGCTTGCCTAGCAAAATCATATGCGCAAATGTGGCAGCTCCTTTATTTCCACAGAA

GGGACCTCCGACTGATGGCCAATGCCATTTGTTCATCTGTGCCAGTTGACTGGGTTCCAACTGGGAGAACTACCTGGTCAATCC

ATGGAAAGGGAGAATGGATGACCACTGAAGACATGCTTGTGGTGTGAACAGAGTGTGGATTGAGGAGAACGACCACATGG

AAGACAAGACCCCAGTTACGAAATGGACAGACATTCCCTATTTGGGAAAAAGGGAAGACTTGTGGTGTGGATCTCTCATAGG

GCACAGACCGCGCACCACCTGGGCTGAGAACATTAAAAACACAGTCAACATGGTGCGCAGGATCATAGGTGATGAAGAAAAG

TACATGGACTACCTATCCACCCAAGTTCGCTACTTGGGTGAAGAAGGGTCTACACCTGGAGTGCTGTAAGCACCAATCTTAATG

TTGTCAGGCCTGCTAGTCAGCCACAGCTTGGGGAAAGCTGTGCAGCCTGTGACCCCCCCAGGAGAAGCTGGGAAACCAAGCC

TATAGTCAGGCCGAGAACGCCATGGCACGGAAGAAGCCATGCTGCCTGTGAGCCCCTCAGAGGACACTGAGTCAAAAAACCC

CATGCGCTTGGAGGCGCAGGATGGGAAAAGAAGGTGGCGACCTTCCCCACCCTTCAATCTGGGGCCTGAACTGGAGATCAGC

TGTGGATCTCCAGAAGAGGGACTAGTGGTTAGAGGAGACCCCCCGGAAAACGCAAAACAGCATATTGACGCTGGGAAAGAC

CAGAGACTCCATGAGTTTCCACCACGCTGGCCGCCAGGCACAGATCGCCGAATAGCGGCGGCCGGTGTGGGGAAATCCATGG

GTCTT
```

KU681081.3 Zika virus isolate Zika virus/*H. sapiens*-tc/THA/2014/SV0127-14,
Thailand, complete genome

SEQ ID NO: 7

```
AGTTGTTGATCTGTGTGAATCAGACTGCGACAGTTCGAGTTTGAAGCGAAAGCTAGCAACAGTATCAACAGGTTTTATTTTGG

ATTTGGAAACGAGAGTTTCTGGTCATGAAAAACCCAAAAAAGAAATCCGGAGGATTCCGGATTGTCAATATGCTAAAACGCGG

AGTAGCCCGTGTGAGCCCCTTTGGGGGCTTGAAGAGGCTGCCAGCCGGACTTCTGCTGGGTCATGGGCCCATCAGGATGGTC

TTGGCGATTCTAGCCTTTTTGAGATTCACGGCAATCAAGCCATCACTGGGTCTCATCAATAGATGGGGTTCAGTGGGAAAAA

AGAGGCTATGGAAATAATAAAGAAGTTCAAGAAAGATCTGGCTGCCATGCTGAGAATAATCAATGCTAGGAAGGAGAAGAA

GAGACGAGGCACAGATACTAGTGTCGGAATTGTTGGCCTCCTGCTGACCACAGCTATGGCAGCGGAGGTCACTAGACGTGGG

AGTGCATACTATATGTACTTGGACAGAAGCGATGCTGGGGAGGCCATATCTTTTCCAACCACACTGGGGATGAATAAGTGTTA

TATACAGATCATGGATCTTGGACACATGTGTGATGCCACCATGAGCTATGAATGCCCTATGCTGGATGAGGGGGTAGAACCAG

ATGACGTCGATTGTTGGTGCAACACGACGTCAACTTGGGTTGTGTACGGAACCTGCCATCACAAAAAAGGTGAAGCACGGAG

ATCCAGAAGAGCTGTGACGCTCCCCTCCCATTCCACTAGGAAGCTGCAAACGCGGTCGCAGACCTGGTTGGAATCAAGAGAAT

ACACAAAGCACTTGATTAGAGTCGAAAATTGGATATTCAGGAACCCTGGCTTCGCGTTAGCAGCAGCTGCCATCGCTTGGCTTT

TGGGAAGCTCAACGAGCCAAAAAGTCATATACTTGGTCATGATACTGCTGATTGCCCCGGCATACAGCATCAGGTGCATAGGA

GTCAGTAATAGGGACTTTGTGGAAGGTATGTCAGGTGGGACTTGGGTTGATGTTGTCTTGGAACATGGAGGTTGTGTCACCGT

AATGGCACAGGACAAACCGACTGTCGACATAGAGCTGGTTACAACAACAGTCAGCAACATGGCGGAGGTAAGATCCTACTGC

TATGAGGCATCAATATCGGACATGGCTTCGGACAGCCGCTGCCCAACACAAGGTGAAGCCTACCTTGACAAGCAATCAGACAC

TCAATATGTCTGCAAAAGAACGTTAGTGGACAGAGGCTGGGGAAATGGATGTGGACTTTTTGGCAAAGGGAGCCTGGTGACA

TGCGCTAAGTTTGCATGCTCCAAGAAAATGACCGGGAAGAGCATCCAGCCAGAGAATCTGGAGTACCGGATAATGCTGTCAG

TTCATGGCTCCCAGCACAGTGGGATGATCGTTAATGACACAGGACATGAAACTGATGAGAATAGAGCGAAGGTTGAGATAAC

GCCCAATTCACCAAGAGCCGAAGCCACCCTGGGGGGTTTTGGAAGCCTAGGACTTGATTGTGAACCGAGGACAGGCCTTGAC

TTTTCAGATTTGTATTACTTGACTATGAACAACAAGCACTGGTTGGTTCACAAGGAGTGGTTCCACGACATTCCATTACCTTGGC
```

```
ACACTGGGGCAGACACCGGAACTCCACACTGGAACAACAAAGAAGCACTGGTAGAGTTCAAGGACGCACATGCCAAAAGGC
AAACTGTCGTGGTTCTAGGGAGTCAAGAAGGAGCAGTTCACACGGCCCTTGCTGGAGCTCTGGAGGCTGAGATGGATGGTGC
AAAGGGAAGGCTGTCCTCTGGCCACTTGAAATGTCGCCTGAAAATGGATAAACTTAGATTGAAGGGCGTGTCATACTCCTTGT
GTACCGCAGCGTTCACATTCACCAAGATCCCGGCTGAAACACTGCACGGGACAGTCACAGTGGAGGTACAGTACGCAGGGAC
AGATGGACCTTGCAAGGTTCCAGCTCAGATGGCGGTGGACATGCAAACTCTGACCCCAGTTGGGAGGTTGATAACCGCTAACC
CCGTAATCACTGAAGGCACTGAGAACTCTAAGATGATGCTGGAACTTGATCCACCATTTGGGGACTCTTACATTGTCATAGGA
GTCGGGGAGAAGAAGATCACCCACCACTGGCACAGGAGTGGCAGCACCATTGGAAAAGCATTTGAAGCCACTGTGAGAGGT
GCCAAGAGAATGGCAGTCTTGGGAGACACAGCCTGGGACTTTGGATCAGTTGGAGGCGTTCTTAACTCATTGGGCAAGGGCA
TCCATCAAATTTTTGGAGCAGCTTTCAAATCATTGTTTGGAGGAATGTCCTGGTTCTCACAAATTCTCATTGGAACGTTGCTGAT
GTGGTTGGGTCTGAATACAAAGAATGGATCTATTTCCCTTATGTGCTTGGCCTTAGGGGAGTGTTGATCTTCTTATCCACAGC
CGTCTCCGCTGATGTGGGGTGCTCGGTGGACTTCTCAAAGAAGGAAACGAGATGCGGTACAGGGGTGTTCGTCTATAACGAC
GTTGAAGCCTGGAGGGACAGGTACAAGTACCATCCTGACTCCCCTCGTAGATTGGCAGCAGTAGTCAAGCAAGCCTGGGAAG
ATGGTATCTGTGGGATCTCCTCTGTTTCAAGAATGGAAAACATCATGTGGAGATCAGTAGAAGGGGAGCTCAACGCAATCCTG
GAAGAGAATGGAGTTCAACTGACGGTCGTTGTGGGATCTGTAAAAAACCCCATGTGGAGAGGTCCACAGAGATTGCCCGTGC
CTGTGAACGAGCTGCCCCACGGCTGGAAGGCTTGGGGGAAATCGTACTTCGTCAGAGCAGCAAAGACAAATAACAGCTTTGT
CGTGGATGGTGACACACTGAAGGAATGCCCACTCAAACATAGAGCATGGAACAGCTTTCTTGTGGAGGATCATGGGTTCGGG
GTATTTCACACTAGTGTCTGGCTCAAGGTTAGAGAAGATTATTCACTAGAGTGTGATCCAGCCGTCATTGGAACAGCTGTTAAG
GGAAAGGAGGCTGTACACAGTGATCTAGGCTACTGGATTGAGAGTGAGAAGAACGACACATGGAGGCTGAGGAGGGCCCAC
CTGATCGAGATGAAAACATGTGAATGGCCAAAGTCCCACACATTGTGGACAGATGGAATAGAAGAGAGTGATCTGATCATAC
CCAAGTCTTTAGCTGGGCCACTCAGCCATCACAACACCAGAGAGGGCTACAGGACCCAAATGAAAGGGCCATGGCACAGTGA
AGAGCTTGAAATTCGGTTTGAGGAATGCCCAGGCACTAAGGTCCACGTGGAGGAAACATGTGGAACAAGAGGACCATCTCTG
AGATCAACCACTGCAAGCGGAAGGGTGATCGAGGAATGGTGCTGCAGGGAGTGCACAATGCCCCACTGTCGTTCCGGGCTA
AAGATGGCTGTTGGTATGGAATGGAGATAAGGCCCAGGAAAGAACCAGAAAGTAACTTAGTAAGGTCAATGGTGACTGCAG
GATCAACTGATCACATGGATCACTTTTCCCTTGGAGTGCTTGTGATTCTGCTCATGGTGCAGGAAGGGCTGAAGAAGAGAATG
ACCACAAAGATCATCATAAGCACATCAATGGCAGTGCTGGTAGCTATGATCCTGGGAGGATTTTCAATGAGTGATCTGGCTAA
GCTTGCAATTTTGATGGGTGCCACCTTTGCGGAAATGAACACTGGAGGAGATGTAGCTCATCTGGCGCTGGTAGCGGCATTCA
AAGTCAGACCAGCGTTGCTGGTATCTTTCATCTTCAGAGCTAATTGGACACCCCGTGAAAGCATGCTGCTGGCCTTGGCCTCGT
GTCTTTTGCAAACTGCGATCTCCGCCTTGGAAGGCGACCTGATGGTTCTCATCAATGGTTTTGCTTTGGCCTGGTTGGCAATAC
GAGCGATGGTTGTTCCACGCACTGACAATATCACCTTGGCAATCCTGGCTGCTCTGACACCACTGGCCCGGGGCACACTGCTTG
TGGCGTGGAGAGCAGGCCTTGCTACTTGCGGGGGGTTCATGCTCCTCTCTCTGAAGGGGAAAGGCAGTGTGAAGAAGAACTT
ACCATTTGTCATGGCCCTGGGACTAACCGCTGTGAGGCTGGTCGACCCCATCAACGTGGTGGGACTGCTGTTGCTCACAAGGA
GTGGGAAGCGGAGCTGGCCCCCTAGCGAAGTACTCACAGCTGTTGGCCTGATATGCGCATTGGCTGGAGGGTTCGCCAAGGC
AGATATAGAGATGGCTGGGCCCATGGCCGCGGTCGGTCTGCTAATTGTCAGTTACGTGGTCTCAGGAAAGAGTGTGGACATG
TACATTGAAAGAGCAGGTGACATCACATGGGAAAAAGATGCGGAAGTTACTGGAAACAGTCCCCGGCTCGATGTGGCACTAG
ATGAGAGTGGTGATTTCTCCCTGGTGGAGGATGACGGTCCCCCCATGAGAGAGATCATACTCAAAGTGGTCCTGATGACCATC
TGTGGCATGAACCCAATAGCCATACCCTTTGCAGCTGGAGCGTGGTACGTATACGTGAAAACTGGAAAAAGGAGTGGTGCTCT
ATGGGATGTGCCTGCTCCCAAGGAAGTAAAAAAGGGGGAGACCACAGATGGAGTGTACAGAGTAATGACTCGTAGACTGCTA
GGTTCAACACAAGTTGGAGTGGGAGTTATGCAAGAGGGGGTCTTTCACACTATGTGGCATGTCACAAAAGGATCCGCGCTGA
GAAGCGGTGAAGGGAGACTTGATCCATACTGGGGAGATGTCAAGCAGGATCTGGTGTCATACTGTGGTCCATGGAAGCTAGA
TGCCGCCTGGGACGGGCACAGCGAGGTGCAGCTCTTGGCCGTGCCCCCCGGAGAGAGAGCGAGGAACATCCAGACTCTGCCC
GGAATATTTAAGACAAAGGATGGGGACATTGGAGCGGTTGCGCTGGACTATCCAGCAGGAACTTCAGGATCTCCAATCCTAG
```

-continued

```
ACAAGTGTGGGAGAGTGATAGGACTCTATGGCAATGGGGTCGTGATCAAGAATGGGAGTTATGTCAGTGCCATCACCCAAGG
GAGGAGGGAGGAAGAGACTCCTGTTGAGTGCTTCGAGCCTTCGATGCTGAAGAAGAAGCAGCTAACTGTCTTAGACTTGCAT
CCTGGAGCTGGGAAAACCAGGAGAGTTCTTCCTGAAATAGTCCGTGAAGCCATAAAAACGAGACTCCGTACTGTGATCTTAGC
TCCAACCAGGGTTGTCGCTGCTGAAATGGAGGAAGCCCTTAGAGGGCTTCCAGTGCGTTATATGACAACAGCAGTCAATGTCA
CCCATTCTGGGACAGAAATCGTTGACTTAATGTGCCATGCCACCTTCACTTCACGTCTACTACAGCCAATCAGAGTCCCCAACTA
TAATCTGTATATTATGGATGAGGCCCACTTCACAGATCCCTCAAGTATAGCAGCAAGAGGATACATTTCAACAAGGGTTGAGA
TGGGCGAGGCAGCTGCCATCTTCATGACCGCCACGCCACCAGGAACCCGTGACGCATTCCCGGACTCCAACTCACCAATTATG
GACACCGAAGTGGAAGTCCCAGAGAGAGCCTGGAGCTCAGGCTTTGATTGGGTGACGGATCATTCTGGAAAAACAGTTTGGT
TTGTCCCAAGCGTGAGGAACGGCAATGAGATCGCAGCTTGTCTGACAAAGGCTGGAAAACGGGTCATACAGCTCAGCAGAAA
GACTTTTGAGACAGAGTTCCAGAAAACAAAACATCAAGAGTGGGACTTCGTCGTGACAACTGACATTTCAGAGATGGGCGCCA
ACTTTAAAGCTGACCGTGTCATAGATTCCAGGAGATGCCTAAAGCCGGTCATACTTGATGGCGAGAGAGTCATTCTGGCTGGA
CCCATGCCTGTCACACATGCCAGCGCTGCCCAGAGGAGGGGGCGCATAGGCAGGAATCCCAACAAACCTGGAGATGAGTATC
TGTATGGAGGTGGGTGCGCAGAGACTGATGAAGACCATGCACACTGGCTTGAAGCAAGAATGCTCCTTGACAATATTTACCTC
CAAGATGGCCTCATAGCCTCGCTCTATCGACCTGAGGCCGACAAAGTAGCAGCCATTGAGGGAGAGTTCAAGCTTAGGACGG
AGCAAAGGAAGACCTTTGTGGAACTCATGAAAAGAGGAGATCTTCCTGTTTGGCTGGCCTATCAGGTTGCATCTGCCGGAATA
ACCTACACAGATAGAAGATGGTGCTTTGATGGCATGACCAACAACACCATAATGGAAGACAGTGTGCCGGCAGAGGTGTGGA
CCAGACACGGAGAGAAAAGAGTGCTCAAACCGAGGTGGATGGACGCCAGAGTTTGTTCAGATCATGCGGCCCTGAAGTCATT
CAAGGAGTTTGCCGCTGGGAAAAGAGGAGCGGCTTTTGGAGTGATGGAAGCCCTGGGAACACTGCCAGGACACATGACGGA
GAGATTCCAGGAAGCCATTGACAACCTCGCTGTGCTCATGCGGGCAGAGACTGGAAGCAGGCCTTACAAAGCCGCGGCGGCC
CAATTGCCGGAGACCCTAGAGACCATTATGCTTTTGGGGTTGCTGGGAACAGTCTCGCTGGGAATCTTTTTCGTCTTGATGCGG
AACAAGGGCATAGGGAAGATGGGCTTTGGAATGGTGACTCTTGGGGCCAGCGCATGGCTCATGTGGCTCTCGGAAATTGAGC
CAGCCAGAATTGCATGCGTCCTCATTGTTGTGTTCCTATTGCTGGTGGTGCTCATACCTGAGCCAGAAAAGCAAAGATCCCCCC
AGGACAACCAAATGGCAATCATCATCATGGTAGCAGTAGGTCTTCTGGGCTTGATTACCGCCAATGAACTCGGATGGTTGGAG
AGAACAAAGAGTGACCTAAGCCATCTAATGGGAAGGAGAGAGGAGGGGGCAACCATAGGATTCTCAATGGACATTGACCTG
CGGCCAGCCTCGGCCTGGGCCATCTATGCTGCCCTGACAACTTTCATTACCCCAGCCGTCCAACATGCAGTGACCACTTCATAC
AACAACTACTCCTTAATGGCGATGGCCACGCAAGCTGGAGTGTTGTTTGGTATGGGCAAAGGGATGCCATTCTACGCATGGGA
CTTTGGAGTCCCGCTGCTAATGATAGGTTGCTACTCACAATTAACACCCCTGACCCTAATAGTGGCTATCATTTTGCTCGTGGCG
CACTACATGTACTTGATCCCAGGGCTGCAGGCAGCAGCTGCGCGTGCTGCCCAGAAGAGAACGGCAGCTGGCATCATGAAGA
ACCCTGTTGTGGATGGAATAGTGGTGACTGACATTGACACAATGACTATTGACCCCCAAGTGGAGAAAAAGATGGGACAGGT
GCTACTCATAGCAGTAGCCGTCTCCAGCGCCATACTGTCGCGGACCGCCTGGGGGTGGGGGGAAGCTGGGCCCTGATCACA
GCTGCAACTTCCACTTTGTGGGAAGGCTCTCCGAACAAGTACTGGAACTCCTCTACAGCCACTTCACTGTGCAACATTTTTAGG
GGAAGTTACTTGGCTGGAGCTTCTCTAATCTACACAGTAACAAGAAACGCTGGCTTGGTCAAGAGACGTGGGGGTGGAACAG
GAGAGACCCTGGGAGAGAAATGGAAGGCCCGCTTGAACCAGATGTCGGCCCTGGAGTTCTACTCCTACAAAAAGTCAGGCAT
CACCGAGGTGTGCAGAGAAGAGGCCCGCCGCGCCCTCAAGGACGGTGTGGCAACGGGAGGCCATGCTGTGTCCCGAGGAAG
TGCAAAGCTGAGATGGTTGGTGGAGCGGGGATACCTGCAGCCCTATGGAAAGGTCATTGATCTTGGATGTGGCAGAGGGGG
CTGGAGTTACTACGCCGCCACCATCCGCAAAGTTCAAGAAGTGAAAGGATACACAAAAGGAGGCCCTGGTCATGAAGAACCC
ATGTTGGTGCAAAGCTATGGGTGGAACATAGTCCGTCTTAAGAGTGGGGTGGACGTCTTTCATATGGCGGCTGAGCCGTGTG
ACACGTTGCTGTGTGACATAGGTGAGTCATCATCTAGTCCTGAAGTGGAAGAAGCACGGACGCTCAGAGTCCTCTCCATGGTG
GGGGATTGGCTTGAAAAAAGACCAGGAGCCTTTTGTGTAAAAGTGTTGTGCCCATACACCAGCACTATGATGGAAACCCTGGA
GCGACTGCAGCGTAGGTATGGGGAGGACTGGTCAGAGTGCCACTCTCCCGCAACTCTACACATGAGATGTACTGGGTCTCT
GGAGCGAAAAGCAACACCATAAAAAGTGTGTCCACCACGAGCCAGCTCCTCTTGGGGCGCATGGACGGGCCCAGGAGGCCA
```

-continued

```
GTGAAATATGAGGAGGATGTGAATCTCGGCTCTGGCACGCGGGCTGTGGTAAGCTGCGCTGAAGCTCCCAACATGAAGATCA

TTGGTAACCGCATTGAAAGGATCCGCAGTGAGCACGCGGAAACGTGGTTCTTTGACGAGAACCACCCATATAGGACATGGGC

TTACCATGGAAGCTATGAGGCCCCTACACAAGGGTCAGCGTCCTCTCTAATAAACGGGGTTGTCAGGCTCCTGTCAAACCCT

GGGATGTGGTGACTGGAGTCACAGGAATAGCCATGACCGACACCACACCGTATGGTCAGCAAAGAGTTTTCAAGGAAAAAGT

GGACACCAGGGTGCCAGACCCCCAAGAAGGCACTCGTCAGGTTATGAGCATGGTCTCTTCCTGGTTGTGGAAAGAGCTAGGC

AAACACAAACGGCCACGAGTCTGTACCAAAGAAGAGTTCATCAACAAGGTTCGTAGCAATGCAGCATTAGGGGCAATATTTGA

AGAGGAAAAGAGTGGAAGACCGCAGTGGAAGCTGTGAACGATCCAAGGTTCTGGGCTCTAGTGGACAAGGAAAGAGAGC

ACCACCTGAGAGGAGAGTGCCAGAGCTGTGTGTACAACATGATGGGAAAAGAGAAAAGAAACAAGGGGAATTTGGAAAG

GCCAAGGGCAGCCGCGCCATCTGGTATATGTGGCTAGGGGCTAGATTTCTAGAGTTCGAAGCCCTTGGATTCTTAAATGAGGA

TCACTGGATGGGGAGAGAGAACTCAGGAGGTGGTGTTGAAGGGCTGGGATTACAAAGACTCGGATATGTCCTAGAAGAGAT

GAGTCGCATACCAGGAGGAAGGATGTATGCAGATGACACTGCTGGCTGGGACACCCGCATCAGCAGGTTTGATCTGGAGAAT

GAAGCTTTAATCACCAACCAAATGGAGAAAGGGCACAGGGCCTTAGCATTGGCCATAATCAAGTACACATACCAAAACAAAGT

GGTAAAGGTCCTTAGACCAGCTGAAAAAGGGAAGACAGTTATGGACATTATTTCAAGACAAGACCAAAGGGGGAGCGGACA

AGTTGTCACTTACGCTCTTAACACATTTACCAACCTAGTGGTGCAACTCATTCGGAATATGGAGGCTGAGGAAGTTCTAGAGAT

GCAAGACTTGTGGCTGCTGCGGAGGTCAGAGAAAGTGACCAACTGGTTGCAGAGCAACGGATGGGATAGGCTCAAACGAAT

GGCAGTCAGTGGAGATGATTGCGTTGTGAAGCCAATTGATGATAGGTTTGCACATGCCCTCAGGTTCTTGAATGATATGGGAA

AAGTTAGGAAGGACACACAAGAGTGGAAACCCTCAACTGGATGGGACAACTGGGAAGAAGTTCCGTTTTGTTCCCACCACTTC

AACAAGCTCCATCTCAAGGACGGGAGGTCCATTGTGGTTCCCTGCCGCCACCAAGATGAACTGATTGGCCGGGCCCGTGTCTC

TCCAGGGGCGGGATGGAGCATCCGGGAGACTGCTTGCCTAGCAAAGTCATATGCGCAAATGTGGCAGCTCCTTTATTTCCACA

GAAGGGACCTCCGACTGATGGCCAATGCCATCTGTTCATCTGTGCCAGTTGACTGGGTTCCAACTGGGAGAACTACCTGGTCA

ATCCATGGAAAGGGAGAATGGATGACCACTGAAGACATGCTTGTGGTGTGGAACAGAGTGTGGATTGAGGAGAACGACCAC

ATGGAAGACAAGACCCCAGTTACGAAATGGACAGACATTCCCTATCTGGGAAAAAGGGAAGACTTGTGGTGTGGATCTCTCA

TAGGGCACAGACCGCGCACCACCTGGGCTGAGAACATTAAAAACACAGTCAACATGGTGCGCAGGATCATAGGTGATGAAGA

AAAGTACATGGACTACCTATCCACCCAAGTTCGCTACTTGGGTGAAGAAGGGTCTACACCTGGAGTGCTATAAGCACCAATCTT

AGTGTTGTCAGGCCTGCTAGTCAGCCACAGCTTGGGGAAAGCTGTGCAGCCTGTGACCCCCCCAGGAGAGGCTGGGAAACCA

AGCCCATAGTCAGGCCGAGAACGCCATGGCACGGAAGAAGCCATGCTGCCTGTGAGCCCCTCAGAGGACACTGAGTCAAAAA

ACCCCACGCGCTTGGAGGCGCAGGATGGGAAAAGAAGGTGGCGACCTTCCCCACCCTTCAATCTGGGGCCTGAACTGGAGAT

CAGCTGTGGATCTCCAGAAGAGGGACTAGTGGTTAGAGGAGACCCCCCGGAAAACGCAAAACAGCATATTGACGCTGGGAA

AGACCAGAGACTCCATGAGTTTCCACCACGCTGGCCGCCAGGCACAGATCGCCGAATAGCGGCGGCCGGTGTGGGGAAATCC

ATGGGTCT
```

KU681082.3 Zika virus isolate Zika virus/H. sapiens-tc

-continued
```
ATCTAGAAGAGCTGTGACGCTCCCCTCCCATTCCACTAGGAAGCTGCAAACGCGGTCGCAGACCTGGTTGGAATCAAGAGAAT
ACACAAAGCACCTGATTAGAGTTGAAAATTGGATATTCAGGAACCCTGGCTTCGCGTTAGCAGCAGCTGTCATCGCTTGGCTTT
TGGGAAGTTCAACGAGCCAAAAAGTCATATATCTGGTCATGATACTGCTGATTGCCCCGGCATACAGCATCAGGTGCATAGGA
GTCAGCAATAGGGACTTTGTGGAAGGTATGTCAGGTGGGACTTGGGTTGATGTTGTCTTGGAACATGGAGGTTGTGTTACCGT
AATGGCACAGGACAAACCGACTGTCGACATAGAGCTGGTTACAACAACAGTCAGCAACATGGCGGAGGTAAGATCCTACTGC
TATGAGGCATCAATATCGGATATGGCTTCGGACAGCCGCTGCCCAACACAAGGTGAGGCCTACCTTGACAAGCAGTCAGACAC
TCAATATGTCTGCAAAAGAACGTTAGTGGACAGAGGCTGGGGAAATGGATGTGGACTTTTTGGCAAAGGGAGCCTGGTGACA
TGCGCTAAGTTTGCATGCTCCAAGAAAATGACCGGGAAGAGCATCCAGCCAGAGAATCTGGAGTACCGGATAATGCTGTCAG
TTCATGGCTCCCAGCACAGTGGGATGATCGTTAATGACACAGGACATGAAACTGATGAGAATAGAGCGAAGGTTGAGATAAC
GCCCAATTCACCAAGAGCCGAAGCCACCCTGGGGGGTTTTGGGAGCCTAGGACTTGATTGTGAACCGAGGACAGGCCTTGAC
TTTTCAGATTTGTATTACCTGACTATGAATAACAAGCACTGGTTGGTTCACAAGGAGTGGTTCCACGACATTCCATTACCTTGGC
ATGCTGGGGCAGACACTGGAACTCCACATTGGAACAACAAAGAAGCACTGGTAGAGTTCAAGGACGCACATGCAAAAAGGCA
AACTGTCGTGGTTCTAGGGAGTCAAGAAGGAGCAGTTCACACGGCCCTTGCTGGAGCTCTGGAGGCTGAGATGGATGGAGCC
AAGGGAAGGCTGTCCTCTGGCCACTTGAAATGTCGCCTGAAAATGGATAAACTTAGATTGAAGGGCGTGTCATACTCCTTGTG
CACTGCAGCGTTCACATTCACCAAGATCCCGGCTGAAACACTGCACGGGACAGTCACAGTGGAGGTACAGTACGCAGGGACA
GATGGACCTTGCAAGGTTCCAGCTCAGATGGCGGTGGATATGCAAACTCTGACCCCAGTTGGGAGGTTGATAACCGCTAACCC
TGTAATCACTGAAAGCACCGAGAACTCTAAGATGATGCTGGAACTTGATCCACCATTTGGGGACTCTTACATTGTCATAGGAGT
CGGGGAGAAGAAGATCACCCATCACTGGCACAGGAGTGGCAGCACCATTGGAAAAGCATTTGAAGCCACTGTGAGAGGTGC
CAAGAGAATGGCAGTCTTGGGAGACACAGCCTGGACTTTGGATCAGTTGGGGGTGCTCTCAACTCATTGGGCAAGGGCATC
CATCAAATTTTTGGAGCAGCTTTCAAATCATTGTTCGGAGGAATGTCCTGGTTCTCACAAATTCTCATTGGAACGTTGCTGGTGT
GGTTGGGTCTGAATACAAAGAATGGATCTATTTCCCTTACGTGCTTGGCCTTAGGGGAGTGTTGATCTTCTTATCCACAGCCG
TTTCTGCTGATGTGGGGTGCTCGGTGGACTTCTCAAAGAAGGAAACGAGATGCGGTACAGGGGTGTTCGTCTATAACGACGTT
GAAGCCTGGAGGGACAGGTACAAGTACCATCCTGACTCCCCTCGTAGATTGGCAGCAGCAGTCAAGCAAGCCTGGGAAGATG
GGATCTGTGGGATCTCCTCTGTCTCAAGAATGGAAAACATCATGTGGAGATCAGTAGAAGGGGAGCTCAACGCAATCCTGGA
AGAGAATGGAGTTCAACTGACGGTCGTTGTGGGATCTGTAAAAAACCCCATGTGGAGAGGTCCACAGAGATTGCCCGTGCCT
GTGAACGAGCTGCCCCACGGCTGGAAGGCTTGGGGGAAATCGTACTTCGTCAGAGCAGCAAAGACAAATAACAGCTTTGTCG
TGGATGGTGACACACTGAAGGAATGCCCCACTCAAACATAGAGCATGGAACAGCTTTCTTGTGGAGGATCATGGGTTTGGGT
ATTTCACACTAGTGTCTGGCTCAAGGTTAGAGAAGATTATTCATTAGAGTGTGATCCAGCCGTCATTGGAACAGCTGCTAAGG
GAAAGGAGGCTGTGCACAGCGATCTAGGCTACTGGATTGAGAGTGAGAAGAACGACACATGGAGGCTGAAGAGGGCCCACC
TGATCGAGATGAAAACATGTGAATGGCCAAAGTCCCACACATTGTGGACAGATGGAGTAGAAGAAAGTGATCTGATCATACC
CAAGTCTTTAGCTGGGCCACTCAGCCATCACAACACCAGAGAGGGCTACAGGACTCAAATGAAAGGGCCATGGCACAGTGAA
GAGCTTGAAATTCGGTTTGAGGAATGCCCAGGCACTAAGGTCCACGTGGAGGAAACATGTGGGACAAGAGGACCATCCCTGA
GATCAACCACTGCAAGCGGAAGGGTGATCGAGGAATGGTGCTGCAGGGAATGCACAATGCCCCACTGTCGTTCCGAGCTAA
AGATGGCTGTTGGTATGGAATGGAGATAAGGCCCAGGAAAGAACCAGAAAGTAACTTAGTAAGGTCAATGGTGACTGCAGG
ATCAACTGATCACATGGATCACTTCTCTCTTGGAGTGCTTGTGATTTTGCTCATGGTGCAGGAAGGGCTGAAGAAGAGAATGA
CCACAAAGATCATCATAAGCACATCAATGGCAGTGCTGGTAGCCATGATCCTGGGAGGATTTTCAATGAGTGACCTGGCTAAG
CTTGCAATTTTGATGGGTGCCACCTTCGCGGAAATGAACACTGGAGGAGATGTAGCTCATTTGGCGCTGATAGCGGCATTCAA
AGTCAGACCTGCGTTGCTGGTATCTTTCATCTTCAGAGCTAATTGGACACCCCGTGAGAGCATGCTGCTGGCCTTGGCCTCGTG
TCTTCTGCAAACTGCGATCTCCGCCTTGGAAGGCGACCTGATGGTTCTCATCAATGGTTTTGCTTTGGCCTGGTTGGCAATACG
AGCGATGGTTGTTCCACGCACTGACAACATCACCTTGGCAATCCTGGCTGCTCTGACACCACTGGCCCGGGGCACACTGCTTGT
GGCGTGGAGAGCAGGCCTTGCTACTTGCGGGGGGTTCATGCTCCTCTCTCTGAAGGGGAAAGGCAGTGTGAAGAAGAACCTA
```

-continued

```
CCATTTGTCATGGCCTTGGGACTAACTGCTGTGAGGCTGGTCGACCCCATCAACGTGGTGGGACTGCTGTTGCTCACAAGGAG

TGGGAAGCGGAGCTGGCCCCCTAGTGAAGTACTCACAGCTGTTGGCCTGATATGCGCATTGGCTGGAGGGTTCGCCAAGGCG

GATATAGAGATGGCTGGGCCCATGGCCGCGGTCGGTCTGCTAATTGTCAGTTACGTGGTCTCAGGAAAGAGTGTGGACATGT

ACATTGAAAGAGCAGGTGACATCACATGGGAAAAAGATGCGGAAATCACTGGAAACAGTCCCCGGCTCGATGTGGCACTAGA

TGAGAGTGGTGATTTCTCCCTAGTGGAGGATGATGGTCCACCCATGAGAGAGATCATACTCAAAGTGGTCCTGATGACCATCT

GCGGCATGAACCCAATAGCCATACCCTTTGCAGCTGGAGCGTGGTACGTGTATGTGAAGACTGGAAAAAGGAGTGGTGCTCT

ATGGGATGTGCCTGCTCCCAAGGAAGTAAAAAAGGGGGAGACCACAGATGGAGTGTACAGAGTAATGACTCGTAGACTGCTT

GGTTCAACACAAGTTGGAGTGGGAGTCATGCAAGAGGGGGTCTTCCACACTATGTGGCACGTCACAAAAGGATCCGCGCTGA

GAAGCGGTGAAGGGAGACTTGATCCATACTGGGGAGATGTCAAGCAGGATCTGGTGTCATACTGTGGTCCGTGGAAGCTAGA

CGCCGCCTGGGACGGGCACAGCGAGGTGCAGCTCTTGGCCGTGCCCCCCGGAGAGAGAGCGAGGAACATCCAGACTCTGCC

CGGAACATTTAAGACAAAGGATGGGGACATTGGAGCAGTTGCGCTGGACTACCCAGCAGGAACTTCAGGATCTCCAATCCTA

GACAAGTGTGGGAGAGTGATAGGACTCTATGGTAATGGGGTCGTGATAAAAAATGGGAGTTATGTTAGTGCCATCACCCAAG

GGAGGAGGGAGGAAGAGACTCCTGTTGAGTGCTTCGAGCCTTCGATGCTGAAGAAGAAGCAGCTAACTGTCTTAGACCTGCA

TCCTGGAGCCGGGAAAACCAGGAGAGTTCTTCCTGAAATAGTCCGTGAAGCCATAAAAACAAGACTCCGTACTGTGATCTTAG

CTCCAACCAGGGTCGTCGCTGCTGAAATGGAGGAAGCCCTTAGAGGGCTTCCAGTTCGTTATATGACAACAGCAGTCAATGTC

ACCCATTCTGGGACAGAAATCGTTGACTTAATGTGCCATGCTACCTTCACTTCACGCCTACTACAACCAATCAGAGTCCCCAACT

ATAATTTGTATATTATGGATGAGGCCCACTTCACAGATCCCTCAAGTATAGCAGCAAGAGGATACATTTCAACAAGGGTTGAG

ATGGGCGAGGCGGCTGCCATCTTCATGACCGCCACGCCACCAGGAACCCGTGACGCATTCCCGGACTCCAACTCACCAATTAT

GGACACCGAGGTGGAAGTCCCAGAGAGAGCCTGGAGCACAGGCTTTGATTGGGTGACGGATCATTCTGGGAAAACAGTCTG

GTTTGTTCCAAGCGTGAGGAACGGCAATGAGATCGCAGCTTGTCTGACAAAGGCTGGAAAACGGGTCATACAGCTCAGCAGA

AAGACTTTTGAGACAGAGTTCCAGAAAACGAAAAATCAAGAGTGGGACTTCGTCGTGACAACCGACATTTCAGAGATGGGCG

CCAACTTTAAAGCTGACCGTGTCATAGATTCCAGGAGATGCTTAAAGCCGGTCATACTTGATGGCGAGAGAGTCATTTTGGCT

GGACCCATGCCTGTCACACATGCCAGCGCTGCTCAGAGGAGGGGCGCATAGGCAGGAATCCCAACAAACCTGGAGATGAGT

ATCTGTATGGAGGTGGGTGCGCAGAGACTGATGAAGATCACGCACACTGGCTTGAAGCAAGAATGCTTCTTGACAACATTTAC

CTCCAAGATGGCCTCATAGCTTCGCTCTATCGACCTGAGGCCGACAAAGTAGCAGCTATTGAGGGAGAGTTCAAGCTTAGGAC

GGAGCAAAGGAAGACCTTTGTGGAACTCATGAAAAGAGGAGATCTTCCGGTTTGGTTGGCCTATCAGGTTGCATCTGCCGGA

ATAACCTACACAGATAGAAGATGGTGCTTTGATGGCATGACCAACAACACCATAATGGAAGACAGTGTGCCGGCAGAGGTGT

GGACCAGATACGGAGAGAAAGAGTGCTCAAACCGAGGTGGATGGACGCCAGAGTTTGTTCAGATCATGCGGCCCTGAAGT

CATTCAAAGAGTTTGCCGCTGGGAAAAGAGGAGCGGCCTTTGGAGTGATAGAAGCCCTGGGAACACTGCCAGGACACATGAC

AGAGAGATTCCAGGAAGCCATTGACAACCTCGCTGTGCTCATGCGGGCAGAGACTGGAAGCAGGCCTTACAAAGCCGCGGCG

GCCCAATTGCCGGAGACCCTAGAGACCATTATGCTTTTGGGGTTGCTGGGAACAGTCTCGCTGGGAATCTTTTTCGTCTTGATG

CGGAACAAGGGCATGGGAAGATGGCTTTGGAATGGTGACTCTTGGGGCCAGCGCATGGCTTATGTGGCTCTCGGAAATTG

AGCCAGCCAGAATTGCATGTGTCCTCATTGTCGTGTTCCTATTGCTGGTGGTGCTCATACCTGAGCCAGAAAAGCAAAGATCTC

CTCAGGACAACCAAATGGCAATCATCATCATGGTAGCAGTGGGTCTTCTGGGCTTGATTACCGCCAATGAACTCGGATGGTTG

GAGAGAACAAAAAGTGACCTAAGCCATCTAATGGGAAGGAGAGAGGAGGGGGCAACCACAGGATTCTCAATGGACATTGAC

CTGCGGCCAGCCTCAGCTTGGGCTATCTATGCTGCTCTGACAACTTTCATCACCCCAGCCGTCCAACATGCGGTGACCACTTCAT

ACAACAACTACTCCTTAATGGCGATGGCCACGCAAGCTGGGGTGTTGTTTGGTATGGGCAAAGGGATGCCATTCTACGCATGG

GACTTTGGAGTCCCGCTGCTAATGATGGGTTGCTACTCACAATTAACACCTCTGACCCTAATAGTGGCCATCATTTTGCTCGTG

GCGCACTACATGTACTTGATCCCAGGGCTGCAGGCAGCAGCTGCGCGGGCTGCCCAGAAGAGAACGGCAGCTGGCATCATGA

AGAACCCTGTTGTGGATGGAATAGTGGTGACTGACATTGACACAATGACAATTGACCCCCAAGTGGAAAAAAAGATGGGGCA

GGTGCTACTCATAGCAGTAGCCGTCTCCAGCGCCATACTGTCGCGGACCGCCTGGGGGTGGGGGGAGGCTGGGGCCCTGATC
```

-continued

```
ACAGCTGCAACTTCCACCTTGTGGGAAGGCTCTCCGAACAAGTACTGGAACTCCTCCACAGCCACTTCACTGTGTAACATTTTTA
GGGGAAGTTACTTGGCTGGAGCTTCTCTAATCTACACAGTAACAAGAAACGCTGGCTTGGTCAAGAGACGTGGGGGTGGAAC
GGGAGAGACCCTGGGAGAGAAATGGAAGGCCCGCCTGAACCAGATGTCGGCCCTGGAGTTCTACTCCTACAAAAAGTCAGGC
ATCACCGAGGTGTGCAGAGAAGAGGCCCGCCGTGCCCTCAAGGACGGTGTGGCAACAGGAGGCCATGCTGTGTCCCGAGGA
AGTGCAAAGCTTAGATGGCTGGTGGAGAGAGGATACCTGCAGCCCTATGGAAAGGTCATTGATCTTGGATGTGGCAGAGGG
GGCTGGAGTTACTATGCCGCCACCATCCGCAAAGTTCAGGAAGTGAAAGGATACACAAAAGGAGGCCCTGGTCATGAAGAAC
CCATGTTGGTGCAAAGCTATGGGTGGAACATAGTCCGTCTTAAGAGTGGGGTGGACGTCTTTCACATGGCGGCTGAGCCGTG
TGACACTTTGCTGTGTGATATAGGTGAGTCATCATCTAGTCCTGAAGTGGAAGAAGCACGGACGCTCAGAGTCCTCTCCATGG
TGGGGGATTGGCTTGAAAAAAGACCAGGAGCCTTTTGTATAAAAGTGTTGTGCCCATACACCAGCACTATGATGGAAACCCTG
GAGCGACTGCAGCGTAGGTATGGGGGAGGACTGGTCAGGGTGCCACTCTCCCGCAACTCTACACATGAGATGTACTGGGTCT
CTGGAGCGAAAAGCAACACCATAAAAAGTGTGTCCACCACGAGCCAGCTCCTCTTGGGGCGCATGGACGGGCCCAGGAGGCC
AGTGAAATATGAGGAGGATGTGAATCTCGGCTCTGGCACGCGGGCTGTGGTAAGCTGCGCTGAAGCTCCCAACATGAAGATC
ATTGGTAACCGCATTGAGAGGATCCGCAGTGAGCACGCGGAAACGTGGTTCTTTGACGAGAACCACCCATATAGGACATGGG
CTTACCATGGAAGCTATGAGGCCCCTACACAAGGGTCAGCGTCCTCTCTAATAAACGGGGTTGTCAGGCTCCTGTCAAAACCCT
GGGATGTGGTGACTGGAGTCACAGGAATAGCCATGACTGACACCACACCGTATGGTCAGCAAAGAGTTTTCAAGGAAAAAGT
GGACACTAGGGTGCCAGACCCCCAAGAAGGCACTCGTCAGGTTATGAGCATGGTCTCTTCCTGGTTATGGAAGGAGCTAGGC
AAACACAAACGGCCACGAGTCTGTACCAAAGAAGAGTTCATCAACAAGGTTCGTAGCAATGCAGCATTAGGGGCAATATTTGA
AGAGGAAAAAGAGTGGAAGACTGCAGTGGAAGCTGTGAATGATCCAAGGTTCTGGGCTCTAGTGGACAAGGAAAGAGAGCA
TCACCTGAGAGGAGAGTGTCAGAGCTGTGTGTACAACATGATGGGAAAAAGAGAAAAGAAACAAGGGGAATTTGGAAAGGC
CAAGGGCAGCCGCGCCATCTGGTATATGTGGCTAGGGGCTAGATTCCTAGAGTTCGAAGCCCTTGGATTCTTGAATGAGGATC
ATTGGATGGGGAGAGAGAATTCAGGAGGTGGTGTTGAAGGACTGGGATTACAAAGACTCGGATATGTCCTAGAAGAGATGA
GTCGCATACCAGGAGGAAGGATGTATGCAGATGATACTGCTGGCTGGGACACCCGCATCAGCAGGTTTGATCTGGAGAATGA
AGCTCTAATCACCAACCAAATGGAGAAAGGGCACAGGGCCTTGGCATTGGCCATAATCAAGTACACATACCAAACAAAGTG
GTAAAGGTCCTTAGACCAGCTGAAAAAGGGAAGACAGTTATGGACATTATTTCAAGACAAGACCAAAGGGGGAGCGGACAA
GTTGTCACTTACGCTCTTAATACATTCACCAACCTGGTGGTGCAGCTCATTCGGAATATGGAGGCTGAGGAAGTTCTAGAGATG
CAAGACTTGTGGCTGCTGCGGAGGCCAGAGAAAGTGACCAACTGGTTGCAAAGCAACGGATGGGATAGGCTCAAAAGAATG
GCAGTCAGTGGAGATGATTGCGTTGTGAAACCAATTGATGATAGGTTTGCACATGCCCTCAGGTTCTTGAATGATATGGGAAA
AGTTAGGAAGGACACACAAGAGTGGAAACCCTCAACTGGATGGGACAACTGGGAAGAAGTTCCGTTTTGCTCCCACCACTTCA
ACAAACTCCATCTTAAGGACGGGAGGTCCATTGTGGTTCCCTGCCGCCACCAAGATGAACTGATTGGCCGAGCCCGCGTATCA
CCAGGGGCGGGATGGAGCATCCGGGAGACTGCTTGCCTAGCAAAATCATATGCGCAAATGTGGCAGCTCCTTTATTTCCACAG
AAGGGACCTCCGACTGATGGCCAATGCCATTTGTTCATCTGTGCCAGTTGATTGGGTTCCAACTGGGAGAACTACCTGGTCAAT
CCATGGAAAGGGAGAATGGATGACCACTGAAGACATGCTTGTGGTATGGAACAGAGTGTGGATTGAGGAAAACGACCACAT
GGAAGACAAGACCCCAGTTACAAAATGGACAGACATTCCCTATTTGGGAAAAAGAGAAGACTTGTGGTGTGGATCTCTCATAG
GGCACAGACCGCGTACTACCTGGGCTGAGAACATCAAAAATACAGTCAACATGATGCGCAGGATCATAGGTGATGAAGAAA
GTACATGGACTACCTATCCACCCAGGTTCGCTACTTGGGTGAAGAAGGGTCCACACCTGGAGTGCTGTAAGCACCAATCTTAG
TGTTGTCAGGCCTGCTAGTCAGCCACAGCTTGGGGAAAGCTGTGCAGCCTGTGACCCCCCAGGAGAAGCTGGGAAACCAAG
CCTATAGTCAGGCCGAGAACGCCATGGCACGGAAGAAGCCATGCTGCCTGTGAGCCCCTCAGAGGACACTGAGTCAAAAAC
CCCACGCGCTTGGAGGCGCAGGATGGGAAAAGAAGGTGGCGACCTTCCCCACCCTTCAATCTGGGGCCTGAACTGGAGATCA
GCTGTGGATCTCCAGAAGAGGGACTAGTGGTTAGAGGAGACCCCCCGGAAAACGCAAAACAGCATATTGACGCTGGGAAAG
ACCAGAGACTCCATGAGTTTCCACCACGCTGGCCGCCAGGCACAGATCGCCGAATAGCGGCGGCCGGTGTGGGGAAATCCAT
GGGTCT
```

KU707826.1 Zika virus isolate SSABR1, Brazil, complete genome

SEQ ID NO: 9

GACAGTTCGAGTTTGAAGCGAAAGCTAGCAACAGTATCAACAGGTTTTATTTGGATTTGGAAACGAGAGTTTCTGGTCATGAA

AAACCCAAAAAGAAATCCGGAGGATTCCGGATTGTCAATATGCTAAAACGCGGAGTAGCCCGTGTGAGCCCCTTTGGGGGC

TTGAAGAGGCTGCCAGCCGGACTTCTGCTGGGTCATGGGCCCATCAGGATGGTCTTGGCGATTCTAGCCTTTTTGAGATTCAC

GGCAATCAAGCCATCACTGGGTCTCATCAATAGATGGGGTTCAGTGGGGAAAAAGAGGCTATGGAAATAATAAAGAAGTTC

AAGAAAGATCTGGCTGCCATGCTGAGAATAATCAATGCTAGGAAGGAGAAGAAGAGACGAGGCGCAGATACTAGTGTCGGA

ATTGTTGGCCTCCTGCTGACCACAGCTATGGCAGCGGAGGTCACTAGACGTGGGAGTGCATACTATATGTACTTGGACAGAAA

CGATGCTGGGGAGGCCATATCTTTTCCAACCACATTGGGATGAATAAGTGTTATATACAGATCATGGATCTTGGACACATGT

GTGATGCCACCATGAGCTATGAATGCCCTATGCTGGATGAGGGGGTGGAACCAGATGACGTCGATTGTTGGTGCAACACGAC

GTCAACTTGGGTTGTGTACGGAACCTGCCATCACAAAAAGGTGAAGCACGGAGATCTAGAAGAGCTGTGACGCTCCCCTCCC

ATTCCACTAGGAAGCTGCAAACGCGGTCGCAAACCTGGTTGGAATCAAGAGAATACACAAAGCACTTGATTAGAGTCGAAAAT

TGGATATTCAGGAACCCTGGCTTCGCGTTAGCAGCAGCTGCCATCGCTTGGCTTTTGGGAAGCTCAACGAGCCAAAAAGTCAT

ATACTTGGTCATGATACTGCTGATTGCCCCGGCATACAGCATCAGGTGCATAGGAGTCAGCAATAGGGACTTTGTGGAAGGTA

TGTCAGGTGGGACCTGGGTTGATGTTGTCTTGGAACATGGAGGTTGTGTCACCGTAATGGCACAGGACAAACCGACTGTCGA

CATAGAGCTGGTTACAACAACAGTCAGCAACATGGCGGAGGTAAGATCCTACTGCTATGAGGCATCAATATCAGACATGGCTT

CGGACAGCCGCTGCCCAACACAAGGTGAAGCCTACCTTGACAAGCAATCAGACACTCAATATGTCTGCAAAAGAACGTTAGTG

GACAGAGGCTGGGGAAATGGATGTGGACTTTTTGGCAAAGGGAGCCTGGTGACATGCGCTAAGTTTGCATGCTCCAAGAAAA

TGACCGGGAAGAGCATCCAGCCAGAGAATCTGGAGTACCGGATAATGCTGTCAGTTCATGGCTCCCAGCACAGTGGGATGAT

TGTTAATGACACAGGACATGAAACTGATGAGAATAGAGCGAAAGTTGAGATAACGCCCAATTCACCAAGAGCCGAAGCCACC

CTGGGGGGTTTTGGAAGCCTAGGACTTGATTGTGAACCGAGGACAGGCCTTGACTTTTCAGATTTGTATTACTTGACTATGAAT

AACAAGCACTGGTTGGTTCACAAGGAGTGGTTCCACGACATTCCATTACCTTGGCACGCTGGGGCAGACACCGGAACTCCACA

CTGGAACAACAAAGAAGCACTGGTAGAGTTCAAGGACGCACATGCCAAAAGGCAAACTGTCGTGGTTCTAGGGAGTCAAGAA

GGAGCAGTTCACACGGCCCTTGCTGGAGCTCTGGAGGCTGAGATGGATGGTGCAAAGGGAAGGCTGTCCTCTGGCCACTTGA

AATGTCGCCTGAAAATGGATAAACTTAGATTGAAGGGCGTGTCATACTCCTTGTGTACTGCAGCGTTCACATTCACCAAGATCC

CGGCTGAAACACTGCACGGGACAGTCACAGTGGAGGTACAGTACGCAGGGACAGATGGACCTTGCAAGGTTCCAGCTCAGAT

GGCGGTGGACATGCAAACTCTGACCCCAGTTGGGAGGTTGATAACCGCTAACCCCGTAATCACTGAAAGCACTGAGAACTCTA

AGATGATGCTGGAACTTGATCCACCATTTGGGGACTCTTACATTGTCATAGGAGTCGGGGAGAAGAAGATCACCCACCACTGG

CACAGGAGTGGCAGCACCATTGGAAAAGCATTTGAAGCCACTGTGAGAGGTGCCAAGAGAATGGCAGTCTTGGGAGACACA

GCCTGGGACTTTGGATCAGTTGGAGGCGCTCTCAACTCATTGGGCAAGGGCATCCATCAAATTTTTGGAGCAGCTTTCAAATCA

TTGTTTGGAGGAATGTCCTGGTTCTCACAAATTCTCATTGGAACGTTGCTGATGTGGTTGGGTCTGAACACAAAGAATGGATCT

ATTTCCCTTATGTGCTTGGCCTTAGGGGGAGTGTTGATCTTCTTATCCACAGCCGTCTCTGCTGATGTGGGGTGCTCGGTGGAC

TTCTCAAAGAAGGAGACGAGATGCGGTACAGGGGTGTTCGTCTATAACGACGTTGAAGCCTGGAGGGACAGGTACAAGTACC

ATCCTGACTCCCCCCGTAGATTGGCAGCAGCAGTCAAGCAAGCCTGGGAAGATGGTATCTGCGGGATCTCCTCTGTTTCAAGA

ATGGAAAACATCATGTGGAGATCAGTAGAAGGGGAGCTCAACGCAATCCTGGAAGAGAATGGAGTTCAACTGACGGTCGTTG

TGGGATCTGTAAAAAACCCCATGTGGAGAGGTCCACAGAGATTGCCCGTGCCTGTGAACGAGCTGCCCCACGGCTGGAAGGC

TTGGGGGAAATCGTACTTCGTCAGAGCAGCAAAGACAAATAACAGCTTTGTCGTGGATGGTGACACACTGAAGGAATGCCCA

CTCAAACATAGAGCATGGAACAGCTTTCTTGTGGAGGATCATGGGTTCGGGGTATTTCACACTAGTGTCTGGCTCAAGGTTAG

AGAAGATTATTCATTAGAGTGTGATCCAGCCGTTATTGGAACAGCTGTTAAGGGAAAGGAGGCTGTACACAGTGATCTAGGCT

ACTGGATTGAGAGTGAGAAGAATGACACATGGAGGCTGAAGAGGGCCCATCTGATCGAGATGAAAACATGTGAATGGCCAA

AGTCCCACACATTGTGGACAGATGGAATAGAAGAGAGTGATCTGATCATACCCAAGTCTTTAGCTGGGCCACTCAGCCATCAC

AATACCAGAGAGGGCTACAGGACCCAAATGAAAGGGCCATGGCACAGTGAAGAGCTTGAAATTCGGTTTGAGGAATGCCCA

-continued
```
GGCACTAAGGTCCACGTGGAGGAAACATGTGGAACAAGAGGACCATCTCTGAGATCAACCACTGCAAGCGGAAGGGTGATC
GAGGAATGGTGCTGCAGGGAGTGCACAATGCCCCCACTGTCGTTCCGGGCTAAAGATGGCTGTTGGTATGGAATGGAGATAA
GGCCCAGGAAAGAACCAGAAAGCAACTTAGTAAGGTCAATGGTGACTGCAGGATCAACTGATCACATGGACCACTTCTCCCTT
GGAGTGCTTGTGATTCTGCTCATGGTGCAGGAAGGGCTGAAGAAGAGAATGACCACAAAGATCATCATAAGCACATCAATGG
CAGTGCTGGTAGCTATGATCCTGGGAGGATTTTCAATGAGTGACCTGGCTAAGCTTGCAATTTTGATGGGTGCCACCTTCGCG
GAAATGAACACTGGAGGAGATGTAGCTCATCTGGCGCTGATAGCGGCATTCAAAGTCAGACCAGCGTTGCTGGTATCTTTCAT
CTTCAGAGCTAATTGGACACCCCGTGAAAGCATGCTGCTGGCCTTGGCCTCGTGTCTTTTGCAAACTGCGATCTCCGCCTTGGA
AGGCGACCTGATGGTTCTCATCAATGGTTTTGCTTTGGCCTGGTTGGCAATACGAGCGATGGTTGTTCCACGCACTGATAACAT
CACCTTGGCAATCCTGGCTGCTCTGACACCACTGGCCCGGGGCACACTGCTTGTGGCGTGGAGAGCAGGCCTTGCTACTTGCG
GGGGGTTTATGCTCCTCTCTCTGAAGGGAAAAGGCAGTGTGAAGAAGAACTTACCATTTGTCATGGCCCTGGGACTAACCGCT
GTGAGGCTGGTCGACCCCATCAACGTGGTGGGACTGCTGTTGCTCACAAGGAGTGGGAAGCGGAGCTGGCCCCCTAGCGAA
GTACTCACAGCTGTTGGCCTGATATGCGCATTGGCTGGAGGGTTCGCCAAGGCAGATATAGAGATGGCTGGGCCCATGGCCG
CGGTCGGTCTGCTAATTGTCAGTTACGTGGTCTCAGGAAAGAGTGTGGACATGTACATTGAAAGAGCAGGTGACATCACATG
GGAAAAAGATGCGGAAGTCACTGGAAACAGTCCCCGGCTCGATGTGGCGCTAGATGAGAGTGGTGATTTCTCCCTGGTGGAG
GATGACGGTCCCCCCATGAGAGAGATCATACTCAAGGTGGTCCTGATGACCATCTGTGGCATGAACCCAATAGCCATACCCTTT
GCAGCTGGAGCGTGGTACGTATACGTGAAGACTGGAAAAAGGAGTGGTGCTCTATGGGATGTGCCTGCTCCCAAGGAAGTAA
AAAAGGGGGAGACCACAGATGGAGTGTACAGAGTAATGACTCGTAGACTGCTAGGTTCAACACAAGTTGGAGTGGGAGTTA
TGCAAGAGGGGGTCTTTCACACTATGTGGCACGTCACAAAAGGATCCGCGCTGAGAAGCGGTGAAGGGAGACTTGATCCATA
CTGGGGAGATGTCAAGCAGGATCTGGTGTCATACTGTGGTCCATGGAAGCTAGATGCCGCCTGGGACGGGCACAGCGAGGT
GCAGCTCTTGGCCGTGCCCCCCGGAGAGAGAGCGAGGAACATCCAGACTCTGCCCGGAATATTTAAGACAAAGGATGGGGAC
ATTGGAGCGGTTGCGCTGGATTACCCAGCAGGAACTTCAGGATCTCCAATCCTAGACAAGTGTGGGAGAGTGATAGGACTTTA
TGGCAATGGGGTCGTGATCAAAAATGGGAGTTATGTTAGTGCCATCACCCAAGGGAGGAGGGAGGAAGAGACTCCTGTTGA
GTGCTTCGAGCCTTCGATGCTGAAGAAGAAGCAGCTAACTGTCTTAGACTTGCATCCTGGAGCTGGGAAAACCAGGAGAGTTC
TTCCTGAAATAGTCCGTGAAGCCATAAAAACAAGACTCCGTACTGTGATCTTAGCTCCAACCAGGGTTGTCGCTGCTGAAATGG
AGGAGGCCCTTAGAGGGCTTCCAGTGCGTTATATGACAACAGCAGTCAATGTCACCCACTCTGGAACAGAAATCGTCGACTTA
ATGTGCCATGCCACCTTCACTTCACGTCTACTACAGCCAATCAGAGTCCCCAACTATAATCTGTATATTATGGATGAGGCCCACT
TCACAGATCCCTCAAGTATAGCAGCAAGAGGATACATTTCAACAAGGGTTGAGATGGGCGAGGCGGCTGCCATCTTCATGACC
GCCACGCCACCAGGAACCCGTGACGCATTTCCGGACTCCAACTCACCAATTATGGACACCGAAGTGGAAGTCCCAGAGAGC
CTGGAGCTCAGGCTTTGATTGGGTGACGGATCATTCTGGAAAAACAGTTTGGTTTGTTCCAAGCGTGAGGAACGGCAATGAG
ATCGCAGCTTGTCTGACAAAGGCTGGAAAACGGGTCATACAGCTCAGCAGAAAGACTTTTGAGACAGAGTTCCAGAAAACAA
AACATCAAGAGTGGGACTTTGTCGTGACAACTGACATTTCAGAGATGGGCGCCAACTTTAAAGCTGACCGTGTCATAGATTCC
AGGAGATGCCTAAAGCCGGTCATACTTGATGGCGAGAGAGTCATTCTGGCTGGACCCATGCCTGTCACACATGCCAGCGCTGC
CCAGAGGAGGGGCGCATAGGCAGGAATCCCAACAAACCTGGAGATGAGTATCTGTATGGAGGTGGGTGCGCAGAGACTGA
CGAAGACCATGCACACTGGCTTGAAGCAAGAATGCTCCTTGACAATATTTACCTCCAAGATGGCCTCATAGCCTCGCTCTATCG
ACCTGAGGCCGACAAAGTAGCAGCCATTGAGGGAGAGTTCAAGCTTAGGACGGAGCAAAGGAAGACCTTTGTGGAACTCATG
AAAAGAGGAGATCTTCCTGTTTGGCTGGCCTATCAGGTTGCATCTGCCGGAATAACCTACACAGATAGAAGATGGTGCTTTGA
TGGCACGACCAACAACACCATAATGGAAGACAGTGTGCCGGCAGAGGTGTGGACCAGACACGGAGAGAAAAGAGTGCTCAA
ACCGAGGTGGATGGACGCCAGAGTTTGTTCAGATCATGCGGCCCTGAAGTCATTCAAGGAGTTTGCCGCTGGGAAAAGAGGA
GCGGCTTTTGGAGTGATGGAAGCCCTGGGAACACTGCCAGGACACATGACAGAGAGATTCCAGGAAGCCATTGACAACCTCG
CTGTGCTCATGCGGGCAGAGACTGGAAGCAGGCCTTACAAAGCCGCGGCGGCCCAATTGCCGGAGACCCTAGAGACCATTAT
GCTTTTGGGGTTGCTGGGAACAGTCTCGCTGGGAATCTTCTTCGTCTTGATGAGGAACAAGGGCATAGGGAAGATGGGCTTT
```

-continued

```
GGAATGGTGACTCTTGGGGCCAGCGCATGGCTCATGTGGCTCTCGGAAATTGAGCCAGCCAGAATTGCATGTGTCCTCATTGT

TGTGTTTCTATTGCTGGTGGTGCTCATACCTGAGCCAGAAAAGCAAAGATCTCCCCAGGACAACCAAATGGCAATCATCATCAT

GGTAGCAGTAGGTCTTCTGGGCTTGATTACCGCCAATGAACTCGGATGGTTGGAGAGAACAAAGAGTGACCTAAGCCATCTA

ATGGGAAGGAGAGAGGAGGGGGCAACCATAGGATTCTCAATGGACATTGACCTGCGGCCAGCCTCAGCTTGGGCCATCTATG

CTGCCTTGACAACTTTCATTACCCCAGCCGTCCAACATGCAGTGACCACTTCATACAACAACTACTCCTTAATGGCGATGGCCAC

GCAAGCTGGAGTGTTGTTTGGTATGGGCAAAGGGATGCCATTCTACGCATGGGACTTTGGAGTCCCGCTGCTAATGATAGGTT

GCTACTCACAATTAACACCCCTGACCCTAATAGTGGCCATCATTTTGCTCGTGGCGCACTACATGTACTTGATCCCAGGGCTGCA

GGCAGCAGCTGCGCGTGCTGCCCAGAAGAGAACGGCAGCTGGCATCATGAAGAACCCTGTTGTGGATGGAATAGTGGTGACT

GACATTGACACAATGACAATTGACCCCCAAGTGGAGAAAAAGATGGGACAGGTGCTACTCATAGCAGTAGCCGTCTCCAGCG

CCATACTGTCGCGGACCGCCTGGGGGTGGGGGGAGGCTGGGGCCCTGATCACAGCCGCAACTTCCACTTTGTGGGAAGGCTC

TCCGAACAAGTACTGGAACTCCTCTACAGCCACTTCACTGTGTAACATTTTTAGGGGAAGTTACTTGGCTGGAGCTTCTCTAATC

TACACAGTAACAAGAAACGCTGGCTTGGTCAAGAGACGTGGGGGTGGAACAGGAGAGACCCTGGGAGAGAAATGGAAGGC

CCGCTTGAACCAGATGTCGGCCCTGGAGTTCTACTCCTACAAAAAGTCAGGCATCACCGAGGTGTGCAGAGAAGAGGCCCGC

CGCGCCCTCAAGGACGGTGTGGCAACGGGAGGCCATGCTGTGTCCCGAGGAAGTGCAAAGCTGAGATGGTTGGTGGAGCGG

GGATACCTGCAGCCCTATGGAAAGGTCATTGATCTTGGATGTGGCAGAGGGGCTGGAGTTACTACGCCGCCACCATCCGCA

AAGTTCAAGAAGTGAAAGGATACACAAAAGGAGGCCCTGGTCATGAAGAACCCGTGTTGGTGCAAAGCTATGGGTGGAACAT

AGTCCGTCTTAAGAGTGGGGTGGACGTCTTTCATATGGCGGCTGAGCCGTGTGACACGTTGCTGTGTGACATAGGTGAGTCAT

CATCTAGTCCTGAAGTGGAAGAAGCACGGACGCTCAGAGTCCTCTCCATGGTGGGGATTGGCTTGAAAAAGACCAGGAGC

CTTTTGTATAAAGGTGTTGTGCCCATACACCAGCACTATGATGGAAACCCTGGAGCGACTGCAGCGTAGGTATGGGGAGGA

CTGGTCAGAGTGCCACTCTCCCGCAACTCTACACATGAGATGTATTGGGTCTCTGGAGCGAAAAGCAACACCATAAAAAGTGT

GTCCACCACGAGCCAGCTCCTCTTGGGGCGCATGGACGGGCCTAGGAGGCCAGTGAAATATGAGGAGGATGTGAATCTCGGC

TCTGGCACGCGGGCTGTGGTAAGCTGCGCTGAAGCTCCCAACATGAAGATCATTGGTAACCGCATTGAAAGGATCCGCAGTG

AGCACGCGGAAACGTGGTTCTTTGACGAGAACCACCCATATAGGACATGGGCTTACCATGGAAGCTATGAGGCCCCCACACAA

GGGTCAGCGTCCTCTCTAATAAACGGGGTTGTCAGGCTCCTGTCAAAACCCTGGGATGTGGTGACTGGAGTCACAGGAATAGC

CATGACCGACACCACACCGTATGGTCAGCAAAGAGTTTTCAAGGAAAAAGTGGACACTAGGGTGCCAGACCCCCAAGAAGGC

ACTCGTCAGGTTATGAGCATGGTCTCTTCCTGGTTGTGGAAAGAGCTAGGCAAACACAAACGGCCACGAGTCTGTACCAAAGA

AGAGTTCATCAACAAGGTTCGTAGCAATGCAGCATTAGGGGCAATATTTGAAGAGGAAAAAGAGTGGAAGACTGCAGTGGAA

AGCTGTGAACGATCCAAGGTTCTGGGCTCTAGTGGATAAGGAAAGAGAGCACCACCTGAGAGGAGAGTGCCAGAGTTGTGT

GTACAACATGATGGGAAAAAGAGAAAAGAAACAAGGGGAATTTGGAAAGGCCAAGGGCAGCCGCGCCATCTGGTATATGTG

GCTAGGGGCTAGATTTCTAGAGTTCGAAGCCCTTGGATTCTTGAACGAGGATCACTGGATGGGGAGAGAGAACTCAGGAGGT

GGTGTTGAAGGGCTGGGATTACAAAGACTCGGATATGTCCTAGAAGAGATGAGTCGTATACCAGGAGGAAGGATGTATGCA

GATGACACTGCTGGCTGGGACACCCGCATCAGCAGGTTTGATCTGGAGAATGAAGCTCTAATCACCAACCAAATGGAAAAAG

GGCACAGGGCCTTGGCATTGGCCATAATCAAGTACACATACCAAAACAAAGTGGTAAAGGTCCTTAGACCAGCTGAAAAAGG

GAAAACAGTTATGGACATTATTTCGAGACAAGACCAAAGGGGAGCGGACAAGTTGTCACTTACGCTCTTAACACATTTACCA

ACCTAGTGGTGCAACTCATTCGGAATATGGAGGCTGAGGAAGTTCTAGAGATGCAAGACTTGTGGCTGCTGCGGAGGTCAGA

GAAAGTGACCAACTGGTTGCAGAGCAACGGATGGGATAGGCTCAAACGAATGGCAGTCAGTGGAGATGATTGCGTTGTGAA

GCCAATTGATGATAGGTTTGCACATGCCCTCAGGTTCTTGAATGATATGGGAAAAGTTAGGAAGGACACACAAGAGTGGAAA

CCCTCAACTGGATGGGACAACTGGGAAGAAGTTCCGTTTTGCTCCCACCACTTCAACAAGCTCCATCTCAAGGACGGGAGGTC

CATTGTGGTTCCCTGCCGCCACCAAGATGAACTGATTGGCCGGGCCCGCGTCTCTCCAGGGGCGGGATGGAGCATCCGGGAG

ACTGCTTGCCTAGCAAAATCATATGCGCAAATGTGGCAGCTCCTTTATTTCCACAGAAGGGACCTCCGACTGATGGCCAATGCC

ATTTGTTCATCTGTGCCAGTTGACTGGGTTCCAACTGGGAGAACTACCTGGTCAATCCATGGAAAGGGAGAATGGATGACCAC
```

-continued

TGAAGACATGCTTGTGGTGTGGAACAGAGTGTGGATTGAGGAGAACGACCACATGGAAGACAAGACCCCAGTTACGAAATG

GACAGACATCCCCTATTTGGGAAAAAGGGAAGACTTGTGGTGTGGATCTCTCATAGGGCACAGACCGCGCACCACCTGGGCT

GAGAACATTAAAAACACAGTCAACATGGTGCGCAGGATCATAGGTGATGAAGAAAAGTACATGGACTACCTATCCACCCAAG

TTCGCTACTTGGGTGAAGAAGGGTCTACACCTGGAGTGCTGTAAGCACCAGTCTTAATGTTGTCAGGCCTGCTAGTCAGCCAC

AGCTTGGGGAAAGCTGTGCAGCCTGTGACCCCCCCAGGAGAAGCTGGGAAACCAAGCCTATAGTCAGGCCGAGAACGCCATG

GCACGGAAGAAGCCATGCTGCCTGTGAGCCCCTCAGAGGACACTGAGTCAAAAAACCCCACGCGCTTGGAGGCGCAGGATG

GGAAAAGAAGGTGGCGACCTTCCCCACCCTTCAATCTGGGGCCTGAACTGGAGATCAGCTGTGGATCTCCAGAAGAGGGACT

AGTGGTTAGAGGAG

KU744693.1 Zika virus isolate VE_Ganxian, China, complete genome

SEQ ID NO: 10

GTTGTTACTGTTGCTGACTCAGACTGCGACAGTTCGAGTTTGAAGCGAAAGCTAGCAACAGTATCAACAGGTTTTATTTGGATT

TGGAAACGAGAGTTTCTGGTCATGAAAAACCCAAAAAAGAAATCCGGAGGATTCCGGATTGTCAATATGCTAAAACGCGGAG

TAGCCCGTGTGAGCCCCTTTGGGGGCTTGAAGAGGCTGCCAGCCGGACTTCTGCTGGGTCATGGGCCCATCAGGATGGTCTTG

GCAATTCTAGCCTTTTTGAGATTCACGGCAATCAAGCCATCACTGGGTCTCATCAATAGATGGGGTTCAGTGGGGAAAAAGA

TGCTATGGAAATAATAAAGAAGTTCAAGAAAGATCTGGCTGCCATGCTGAGAATAATCAATGCTAGGAAGGAGAAGAAGAGA

CGAGGCGCAGATACTAGTGTCGGAATTGTTGGCCTCCTGCTGACCACAGCTATGGCAGCGGAGGTCACTAGACGTGGGAGTG

CATACTATATGTACTTGGACAGAAACGATGCTGGGGAGGCCATATCTTTTCCAACCACATTGGGGATGAATAAGTGTTATATAC

AGATCATGGATCTTGGACACATGTGTGATGCCACCATGAGCTATGAATGCCCTATGCTGGATGAGGGGGTGGAACCAGATGA

CGTCGATTGTTGGTGCAACACGACGTCAACTTGGGTTGTGTACGGAACCTGCCATCACAAAAAAGGTGAAGCACGGAGATCTA

GAAGAGCTGTGACGCTCCCTTCCCATTCCACTAGGAAGCTGCAAACGCGGTCGCAAACCTGGTTGGAATCAAGAGAATACACA

AAGCACTTGATTAGAGTCGAAAATTGGATATTCAGGAACCCTGGCTTCGCGTTAGCAGCAGCTGCCATCGCTTGGCTTTTGGG

AAGCTCAACGAGCCAAAAAGTCATATACTTGGTCATGATACTGCTGATTGCCCCGGCATACAGCATCAGGTGCATAGGAGTCA

GCAATAGGGACTTTGTGGAAGGTATGTCAGGTGGGACTTGGGTTGATGTTGTCTTGGAACATGGAGGTTGTGTCACCGCAAT

GGCACAGGACAAACCGACTGTCGACATAGAGCTGGTTACAACAACAGTCAGCAACATGGCGGAGGTAAGATCCTACTGCTAT

GAGGCATCAATATCAGACATGGCTTCGGACAGCCGCTGCCCAACACAAGGTGAAGCCTACCTTGACAAGCAATCAGACACTCA

ATATGTTTGCAAAAGAACGTTAGTGGACAGAGGCTGGGGAAATGGATGTGGACTTTTTGGCAAAGGGAGTCTGGTGACATGC

GCTAAGTTTGCATGCTCCAAGAAAATGACCGGGAAGAGCATCCAGCCAGAGAATCTGGAGTACCGGATAATGCTGTCAGTTC

ATGGCTCCCAGCACAGTGGGATGCTCGTTAATGACACAGGACATGAAACTGATGAGAATAGAGCGAAGGTTGAGATAACGCC

CAATTCACCAAGAGCCGAAGCCACCCTGGGGGGTTTTGGAAGCCTAGGACTTGATTGTGAACCGAGGACAGGCCTTGACTTTT

CAGATTTGTATTACTTGACTATGAATAACAAGCACTGGTTGGCTCACAAGGAGTGGTTCCACGACATTCCATTACCTTGGCACG

CTGGGGCAGCCACCGGAACTCCACACTGGAACAACAAAGAAGCACTGGTAGAGTTCAAGGACGCACATGCCAAAAGGCAAAC

TGTCGTGGTTCTAGGGAGTCAAGAAGGAGCAGTTCACACGGCCCTTGCTGGAGCTCTGGAGGCTGAGATGGATGGTGCAAAG

GGAAGGCTGTCCTCTGGCCACTTGAAATGTCGCCTGAAAATGGATAAACTTAGATTGAAGGGCGTGTCATACTCCTTGTGTAC

CGCAGCGTTCACATTCACCAAGATCCCGGCTGAAACAGTGGACGGGACAGTCACAGTGGAGGGACAGTACGGAGGGACAGA

TGGACCTTGCAAGGTTCCAGCTCAGATGGCGGTGGACATGCAGACTCTGACCCCAGTTGGGAGGTTGATAACCGCTAACCCCG

TAATCACTGAAAGCACTGAGAACTCTAAGATGATGCTGGAACTTGATCCACCATTTGGGGACTCTTACATTGTCATAGGAGTCG

GGGAGAAGAAGATCACCCACCACTGGCACAGGAGTGGCAGCACCATTGGAAAAGCATTTGAAGCCACTGTGAGAGGTGCCA

AGAGAATGGCAGTCTTGGGAGACACAGCCTGGGACTTTGGATCAGTTGGAGGCGCTCTCAACTCATTGGGCAAGGGCATCCA

TCAAATTATTGGAGCAGCTTTCAAATCATTGTTTGGAGGAATGTCCTGGTTCTCACAAATTCTCATTGGGACGTTGCTGATGTG

GTTGGGTCTGAACACAAAGAATGGATCTATTTCCCTTATGTGCTTGGCCTTAGGGGGAGTGTTGATCTTCTTATCCACAGCCGT

CTCAGGTGGTGTGGGGTGCTCGGTGGACTTCTCAAAGAAGGAGACGAGATGCGGTACAGGGGTGTTCGTCTATAACGATGTT

GAAGCCTGGAGGGACAGGTACAAGTACCATCCTGACTCCCCCCGTAGATTGGCAGCAGCAGTCAAGCAAGCCTGGGAAGATG

-continued
```
GTATCTGCGGGATCTCCTCTGTTTCAAGAATGGAAAACATCATGTGGAGATCAGTAGAAGGGGAGCTCAACGCAATCCTGGAA GAGAATGGAGTTCAACTGACGGTCGTTGTGGGATCTGTAAAAAACCCCATGTGGAGAGGTCCACAGAGATTGCCCGTGCCTG TGAACGAGCTGCCCCACGGCTGGAAGGCTTGGGGGAAATCGTACTTCGTCAGAGCAGCAAAGACAAATAACAGCTTTGTCGT GGATGGTGACACACTGAAGGAATGCCCACTCAAACATAGAGCATGGAACAGCTTTCTTGTGGAGGATCATGGGTTCGGGGTA TTTCACACTAGTGTCTGGCTCAAGGTTAGAGAAGACTATTGGTTAGAGTGTGATCCAGCCGTTATTGGAACAGCTGTTAAGGG AAAGGAGGCTGTACACAGTGATCTAGGCTACTGGATTGAGAGTGAGAAGAATGACACATGGTGGCTGAAGAGGGCCCATCT GATCGAGATGAAAACATGTGAATGGCCAAAGTCCCACACATTGTGGACAGATGGAATAGAAGAGAGTGATCTGATCATACCC AAGTCTTTAGCTGGGCCACTCAGCCATCACAATGCCAGAGAGGGCTACAGGACCCAAATGAAAGGGCCATGGCACAGTGAAG AGCTTGAAATTCGGTTTGAGGAATGCCCAGGCACTAAGGTCCACGTGGAGGAAACATGTGGAACAAGAGGACCATCTCTGAG ATCAACCACTGCAAGCGGAAGGGTGATCGAGGAATGGTGCTCCAGGGAGTGCACAATGCCCCCACTGTCCTTCCAGGCTAAA GATGGCTGTTGGTATGGAATGGAGATAAGGCCCAGGAAAGAACCAGAAAGCAACTTAGTAAGGTCAATGGTGACTGCAGGA TCAACTGATCACATGGATCACTTCTCCCTTGGAGTGCTTGTGATTCTGCTCATGGTGCAGGAAGGGCTGAAGAAGAGAATGAC CACAAAGATCATCATAAGCACATCAATGGCAGTGCTGGTAGCTATGATCCTGGGAGGATTTTCAATGAGTGACCTGGCTAAGC TTGCAATTTTGATGGGTGCCACCTTCGCGGAAATGAACACTGGAGGAGATGTAGCTCATCTGGCGCTGATAGCGGCATTCAAA GTCAGACCAGCGTTGCTGGTATCTTTCATCTTCAGAGCTAATTGGACACCCCGTGAAAGCATGCTGCTGGCCTTGGCCTCGTGT CTTTTGCAAACTGCGATCTCCGCCTTGGAAGGCGACCTGATGGTTCTCATCAATGGTTTTGCTTTGGCCTGGTTGGCAATACGA GCGATGGTTGTTCCACGCACTGATAACATCACCTTAGCAATCCTGGCTGCTCTGACACCACTGGCCCGGGGCACACTGCTTGTG GCGTGGAGAGCAGGCCTTGCTACTTGCGGGGGGTTTATGCTCCTCTCTCTGAAGGGAAAAGGCAGTGTGAAGAAGAACTTAC CATTTGTCATGGCCCTGGGACTAACCGCTGTGAGGCTGGTCGACCCCATCAACGTGGTGGGACTGCTGTTGCTCACAAGGAGT GGGAAGCGGAGCTGGCCCCCTAGCGAAGTACTCACAGCTGTTGGCCTGATATGCGCATTGGCTGGAGGGTTCGCCAAGGCAG ATATAGAGATGGCTGGGCCCATGGCCGCGGTCGGTCTGCTAATTGTCAGTTACGTGGTCTCAGGAAAGAGTGTGGACATGTA CATTGAAAGAGCAGGTGACATCACATGGGAAAAAGATGCGGAAGTCACTGGAAACAGTCCCCGGCTCGATGTGGCGCTAGAT GAGAGTGGTGATTTCTCCCTGGTGGAGGATGACGGTCCCCCCATGAGAGAGATCATACTCAAGGTGGTCCTGATGACCATCTG TGGCATGAACCCAATAGCCATACCCTTTGCAGCTGGAGCGTGGTACGTATACGTGAAGACTGGAAAAAGGAGTGGTGCTCTAT GGGATGTGCCTGCTCCCAAGGAAGTAAAAAAGGGGGAGACCACAGATGGAGTGTACAGAGTAATGACTCGCAGACTGCTAG GTTCAACACAAGTTGGAGTGGGAGTTATGCAAGAGGGGGTCTTTCACACTATGTGGCACGTCACAAAAGGATCCGCGCTGAG AAGCGGTGAAGGGAGACTTGATCCATACTGGGGAGATGTCAAGCAGGATCTGGTGTCATACTGTGGTCCATGGAAGCTAGAT GCCGCCTGGGACGGGCACAGCGAGGTGCAGCTCTTGGCCGTGCCCCCCGGAGAGAGAGCGAGGAACATCCAGACTCTGCCC GGAATATTTAAGACAAAGGATGGGGACATTGGAGCGGTTGCACTGGATTACCCAGCAGGAACTTCAGGATCTCCAATCCTAG ACAAGTGTGGGAGAGTGATAGGACTTTATGGCAATGGGGTCGTGATCAAAAATGGGAGTTATGTTAGTGCCATCACCCAAGG GAGGAGGGAGGAAGAGACTCCTGTTGAGTGCTTCGAGCCTTCGATGCTGAAGAAGAAGCAGCTAACTGTCTTAGACTTGCAT CCTGGAGCTGGGAAAACCAGGAGAGTTCTTCCTGAAATAGTCCGTGAAGCCATAAAAACAAGACTCCGTACTGTGATCTTGGC TCCAACCAGGGTTGTCGCTGCTGAAATGGAGGAGGCCCTTAGAGGGCTTCCAGTGCGTTATATGACAACAGCAGTCAATGTCA CCCACTCTGGAACAGAAATCGTCGACTTAATGTGCCATGCCACCTTCACTTCACGTCTACTACAGCCAATTAGAGTCCCCAACTA TAATCTGTATATTATGGATGAGGCCCACTTCACAGATCCCTCAAGTATAGCAGCAAGAGGATACATTTCAACAAGGGTTGAGA TGGGCGAGGCGGCTGCCATCTTCATGACCGCCACGCCACCAGGAACCCGTGACGCATTTCCGGACTCCAACTCACCAATTATG GACACCGAAGTGGAAGTCCCAGAGAGAGCCTGGAGCTCAGGCTTTGATTGGGTGACGGAGTATTCTGGAAAAACAGTTTGGT TTGTTCCACGCGTGAGGAACGGCAATGAGATCGCAGCTTGTCTGACAAAGGCTGGAAAACGGGTCATACAGCTCAGCAGAAA GACTTTTGAGACAGAGTTCCAGAAAACAAAACATCAAGAGTGGGACTTTGTCGTGACAACTGACATTTCAGAGATGGGCGCCA ACTTTAAAGCTGACCGTGTCATAGATTCCAGGAGATGCCTAAAGCCGGTCATACTTGGTGGCGAGAGAGTCATTCTGGCTGGA CCCATGCCTGTCACACATGCCAGCGCTGCCCAGAGGAGGGGGCGCATAGGCAGGAATCCCAACAAACCTGGAGATGAGTATC
```

-continued

```
TGTATGGAGGTGGGTGCGCAGAGACTGACGAAGACCATGCACACTGGCTTGAAGCAAGAATGCTCCTTGACAATATTTACCTC
CAAGATGGCCTCATAGCCTCGCTCTATCGACCTGAGGCCGACAAAGTAGCAGCCATTGAGGGAGAGTTCAAGCTTAGGACGG
AGCAAAGGAAGACCTTTGTGGAACTCATGAAAAGAGGAGATCTTCCTGTTTGGCTGGCCTATCAGGTTGCATCTGCCGGAATA
ACCTACACAGATAGAAGATGGTGCTTTGATGGCACGACCAACAACACCATAATGGAAGACAGTGTGCCGGCAGAGGTGTGGA
CCAGACACGGAGAGAAAAGAGTGCTCAAACCGAGGTGGATGGACGCCAGAGTTTGTTCAGATCATGCGGCCCTGAAGTCATT
CAAGGAGTTTGCCGCTGGGAAAAGAGGAGCGGCTTTTGGAGTGATGGAAGCCCTGGGAACACTGCCAGGACACATGACAGA
GAGATTCCAGGAAGCCATTGACAACCTCGCTGTGCTCATGCGGGCAGAGACTGGAAGCAGGCCTTACAAAGCCGCGGCGGCC
CAATTGCCGGAGACCCTAGAGACCATTATGCTTTTGGGGTTGCTGGGAACAGTCTCGCTGGGAATCTTTTTCGTCTTGATGAGG
AACAAGGGCATAGGGAAGATGGGCTTTGGAATGGTGACTCTTGGGGCCAGCGCATGGCTCATGTGGCTCTCGGAAATTGAGC
CAGCCAGAATTGCATGTGTCCTCATTGTTGTGTTCCTATTGCTGGTGGTGCTCATACCTGAGCCAGAAAAGCAAAGATCTCCCC
AGGACAACCAAATGGCCATCATCATCATGGTAGCAGTAGGTCTTCTGGGCTTGATTACCGCCAATGAACTCGGATGGTTGGAG
AGAACAAAGAGTGACCTAAGCCATCTAATGGGAAGGAGAGAGGAGGGGGCAACCATGGGATTCTCAATGGACATTGACCTG
CGGCCAGCCTCAGCTTGGGCCATCTATCCTGCCTTGACATCTTTCATTACCCCAGCCGTCCAACATGCAGTGACCACTTCATACA
ACAACTACTCCTTAATGGCGATGGCCACGCAAGCTGGAGTGTTGTTTGGTATGGGCAAAGGGATGCCATTCTACGCATGGGAC
TTTGGAGTCCCGCTGCTAATGATAGGTTGCTACTCACAATTAACGCCCCTGACCCTAATAGTGGCCATCATTTTGCTCGTGGCG
CACTACATGTACTTGATCCCAGGGCTGCAGGCAGCAGCTGCGCGTGCTGCCCAGAAGAGAACGGCAGCTGGCATCATGAAGA
ACCCTGTTGTGGAGGGAATAGTGGTGACTGACATTGACACAATGACAATTGACCCCCAAGTGGAGAAAAAGATGGGACAGGT
GCTACTCATGGCAGTAGCCGTCTCCAGCGCCATACTGTCGAGGACCGCCTGGGGGTGGGGGAGGCTGGGGCCCTGATCACA
GCCGCAACTTCCACTTTGTGGGAAGGCTCTCCGAACAAGTACTGGAACTCCTCTACAGCCACCTCACTGTGTAACATTTTTAGG
GGAAGTTACTTGGCTGGAGCTTCTCTAATCTACACAGTAACAAGAAACGCTGGCTTGGTCAAGAGACGTGGGGGTGGAACAG
GAGAGACCCTGGGAGAGAAATGGAAGGCCCGCTTGAACCAGATGTCGGCCCTGGAGTTCTACTCCTACAAAAAGTCAGGCAT
CACCGAGGTGTGCAGAGAAGAGGCCCGCCGCGCCCTCAAGGACGGTGTGGCAACGGGAGGCCATGCTGTGTCCCGAGGAAG
TGCAAAGCTGAGATGGTTGGTGGAGCGGGATACCTGCAGCCCTATGGAAAGGTCATTGATCTTGGATGTGGCAGAGGGGG
CTGGAGTTACTACGCCGCCACCATCCGCAAAGTTCAAGAAGTGAAAGGATACACAAAAGGAGGCCCTGGTCATGAAGAACCC
GTGTTGGTGCAAAGCTATGGGTGGAACATAGTCCGTCTTAAGAGTGGGGTGGACGTCTTTCATATGGCGGCTGAGCCGTGTG
ACACGTTGCTGTGTGACATAGGTGAGTCATCATCTAGTCCTGAAGTGGAAGAAGCACGGACGCTCAGAGTCCTCTCCATGGTG
GGGGATTGGCTTGAAAAAAGACCAGGAGCCTTTTGTATAAAAGTGTTGTGCCCATACACCAGCACTATGATGGAAACCCTGGA
GCGACTGCAGCGTAGGTATGGGGGAGGACTGGTCAGAGTGCCACTCTCCCGCAACTCTACACATGAGATGTACTGGGTCTCT
GGAGCGAAAAGCAACACCATAAAAAGTGTGTCCACCACGAGCCAGCTCCTCTTGGGGCGCATGGACGGGCCTAGGAGGCCA
GTGAAATATGAGGAGGATGTGAATCTCGGCTCTGGCACGCGGGCTGTGGTAAGCTGCGCTGAAGCTCCCAACATGAAGATCA
TTGGTAACCGCATTGAAAGGATCCGCGCTGAGAAAGCGGAAACGTGGTTCTTTGACGAGAACCACCCATATAGGACATGGGC
TTACCATGGAAGCTATGATGCCGCCACACAAGGGTCAGCGTCCTCTCTAATAAACGGGGTTGTCAGGCTCCTGTCAAACCCT
GGGATGTGGTGACTGGAGTCACAGGAATAGCCATGACCGACACCACACCGTATGGTCAGCAAAGAGTTTTCAAGGAAAAAGT
GGACACTAGGGTGCCAGACCCCCAAGAAGGCACTCGTCAGGTTATGAGCATGGTCTCTTCCTGGTTGTGGAAAGAGCTAGGC
AAACACAAACGGCCACGAGTCTGTACCAAAGAAGAGTTCATCAACAAGGTTCGTAGCAATGCAGCATTAGGGGCAATATTTGA
AGAGGAAAAAGAGTGGAAGACTGCAGTGGAAGCTGTGAACGATCCAAGGTTCTGGGCTCTAGTGGACAAGGAAAGAGAGCA
CCACCTGAGAGGAGAGTGCCAGAGTTGTGTGTACATCACAATGGGAAAAAGAGAAAAGAAACAAGGGGAATTTGGAAAGGC
CAAGGGCAGCCGCGCCATCTGGTATATGTGGCTAGGGGCTAGATTTCTAGAGTTCGAAGCCCTTGGATTCTTGAACGAGGATC
ACTGGATGGGGAGAGAACTCAGGAGGTGGTGTTGAAGGGCTGGGATTACAAAGACTCGGATATGTCCTAGAAGAGATGA
GTCGCATACCAGGAGGAAGGATGTATGCAGATGACACTGCTGGCTGGGACACCCGCATCAGCAGGTTTGATCTGGAGAATGA
AGCTCTAATCACCAACCAAATGGAGAAAGGGCACAGGGCCTTGGCATTGGCCATAATCAAGTACACATACCAAAACAAAGTG
```

-continued

GTAAAGGTCCTTAGACCAGCTGAAAAAGGGAAGACAGTTATGGACATTATTTCGAGACAAGACCAAAGGGGGAGCGGACAA

GTTGTCACTTACGCTCTCAACACATTTACCAACCTAGTGGTGCAACTCATTCGGAATATGGAGGCTGAGGAAGTTCTAGAGATG

CAAGACTTGTGGCTGCTGCGGAGGTCAGAGAAAGTGACCAACTGGTTGCAGAGCAACGGATGGGATAGGCTCAAACGAATG

GCGGTCAGTGGAGATGATTGCGTTGTGAAACCAATTGATGATAGGTTTGCACATGCCCTCAGGTTCTTGAATGATATGGGAAA

AGTTAGGAAGGACACACAAGAGTGGAAACCCTCAACTGGATGGGACAACTGGGAAGAAGTTCCCTTCTGCTCCCACCACTTCA

ACAAGCTCCATCTCAAGGACGGGAGGTCCATTGTGGTTCCCTGCCGCCACCAAGATGAACTGATTGGCCGGGCCCGCGTCTCT

CCAGGGGCGGGATGGAGCATCCGGGAGACTGCTTGCCTAGCAAAATCATATGCGCAAATGTGGCAGCTCCTTTATTTCCACAG

AAGGGACCTCCGACTGATGGCCAATGCCATTTGTTCATCTGTGCCAGTTGACTGGGTTCCAACTGGGAGAACTACCTGGTCAAT

CCATGGAAAGGGAGAATGGATGACCACTGAAGACATGCTTGTGGCGTGGAACAGAGTGTGGATTGAGGAGAACGACCACAT

GGAAGACAAGACCCCAGTCACGAAATGGACAGACATTCCCTATTTGGGAAAAAGGGAAGACTTGTGGTGTGGATCTCTCATA

GGGCACAGACCGCGCACCACCTGGGCTGAGAACATTAAAAACACAGTCAACATGGTGCGCAGGATCATAGGTGATGAAGAAA

AGTACATGGACTACCTATCCACCCAAGTTCGCTACTTGGGTGAAGAAGGGTCTACACCTGGAGTGCTGTAAGCACCAATCTTA

ATGTTGTCAGGCCTGCTAGTCAGCCACAGCTTGGGGAAAGCTGTGCAGCCTGTGACCCCCCCAGGAGAAGCTGGGAAACCAA

GCCTATAGTCAGGCCGAGAACGCCATGGCACGGAAGAAGCCATGCTGCCTGTGAGCCCCTCAGAGGACACTGAGTCAAAAAA

CCCCACGCGCTTGGAGGCGCAGGATGGGAAAAGAAGGTGGCGACCTTCCCCACCCTTCAATCTGGGGCCTGAACTGGAGATC

AGCTGTGGATCTCCAGAAGAGGGACTAGTGGTTAGAGGAGA

LC002520.1 Zika virus genomic RNA, strain: MR766-NIID, Uganda, complete genome

SEQ ID NO: 11

AGTTGTTGATCTGTGTGAGTCAGACTGCGACAGTTCGAGTCTGAAGCGAGAGCTAACAACAGTATCAACAGGTTTAATTTGGA

TTTGGAAACGAGAGTTTCTGGTCATGAAAAACCCAAAGAAGAAATCCGGAGGATTCCGGATTGTCAATATGCTAAAACGCGG

AGTAGCCCGTGTAAACCCCTTGGGAGGTTTGAAGAGGTTGCCAGCCGGACTTCTGCTGGGTCATGGACCCATCAGAATGGTTT

TGGCGATACTAGCCTTTTTGAGATTTACAGCAATCAAGCCATCACTGGGCCTTATCAACAGATGGGGTTCCGTGGGGAAAAAA

GAGGCTATGGAAATAATAAAGAAGTTCAAGAAAGATCTTGCTGCCATGTTGAGAATAATCAATGCTAGGAAAGAGAGGAAGA

GACGTGGCGCAGACACCAGCATCGGAATCATTGGCCTCCTGCTGACTACAGCCATGGCAGCAGAGATCACTAGACGCGGGAG

TGCATACTACATGTACTTGGATAGGAGCGATGCCGGGAAGGCCATTTCGTTTGCTACCACATTGGGAGTGAACAAGTGCCACG

TACAGATCATGGACCTCGGGCACATGTGTGACGCCACCATGAGTTATGAGTGCCCTATGCTGGATGAGGGAGTGGAACCAGA

TGATGTCGATTGCTGGTGCAACACGACATCAACTTGGGTTGTGTACGGAACCTGTCATCACAAAAAAGGTGAGGCACGGCGAT

CTAGAAGAGCCGTGACGCTCCCTTCTCACTCTACAAGGAAGTTGCAAACGCGGTCGCAGACCTGGTTAGAATCAAGAGAATAC

ACGAAGCACTTGATCAAGGTTGAAAACTGGATATTCAGGAACCCCGGGTTTGCGCTAGTGGCCGTTGCCATTGCCTGGCTTTT

GGGAAGCTCGACGAGCCAAAAAGTCATATACTTGGTCATGATACTGCTGATTGCCCCGGCATACAGTATCAGGTGCATTGGAG

TCAGCAATAGAGACTTCGTGGAGGGCATGTCAGGTGGGACCTGGGTTGATGTTGTCTTGGAACATGGAGGCTGCGTTACCGT

GATGGCACAGGACAAGCCAACAGTTGACATAGAGTTGGTCACGACGACGGTTAGTAACATGGCCGAGGTAAGATCCTATTGC

TACGAGGCATCGATATCGGACATGGCTTCGGACAGTCGTTGCCCAACACAAGGTGAAGCCTACCTTGACAAGCAATCAGACAC

TCAATATGTCTGCAAAAGAACATTAGTGGACAGAGGTTGGGGAAACGGTTGTGGACTTTTTGGCAAAGGGAGCTTGGTGACA

TGTGCCAAGTTTACGTGTTCTAAGAAGATGACCGGGAAGAGCATTCAACCGGAAAATCTGGAGTATCGGATAATGCTATCAGT

GCATGGCTCCCAGCATAGCGGGATGACTGTCAATGATATAGGATATGAAACTGACGAAAATAGAGCGAAAGTCGAGGTTACG

CCTAATTCACCAAGAGCGGAAGCAACCTTGGGAGGCTTTGGAAGCTTAGGACTTGACTGTGAACCAAGGACAGGCCTTGACTT

TTCAGATCTGTATTACCTGACCATGAACAATAAGCATTGGTTGGTGCACAAAGAGTGGTTTCATGACATCCCATTGCCTTGGCA

TGCTGGGGCAGACACTGGAACTCCACACTGGAACAACAAAGAGGCATTGGTAGAATTCAAGGATGCCCACGCCAAGAGGCAA

ACCGTCGTCGTTCTGGGGAGCCAGGAAGGAGCCGTTCACACGGCTCTCGCTGGAGCTCTAGAGGCTGAGATGGATGGTGCAA

AGGGAAAGCTGTTCTCTGGCCATTTGAAATGCCGCCTAAAAATGGACAAGCTTAGATTGAAGGGCGTGTCATATTCCTTGTGC

ACTGCGGCATTCACATTCACCAAGGTCCCAGCTGAAACACTGCATGGAACAGTCACAGTGGAGGTGCAGTATGCAGGGACAG

-continued

```
ATGGACCCTGCAAGATCCCAGTCCAGATGGCGGTGGACATGCAGACCCTGACCCCAGTTGGAAGGCTGATAACCGCCAACCC
CGTGATTACTGAAAGCACTGAGAACTCAAAGATGATGTTGGAGCTTGACCCACCATTTGGGGATTCTTACATTGTCATAGGAG
TTGGGGACAAGAAAATCACCCACCACTGGCATAGGAGTGGTAGCACCATCGGAAAGGCATTTGAGGCCACTGTGAGAGGCGC
CAAGAGAATGGCAGTCCTGGGGGATACAGCCTGGGACTTCGGATCAGTCGGGGGTGTGTTCAACTCACTGGGTAAGGGCATT
CACCAGATTTTTGGAGCAGCCTTCAAATCACTGTTTGGAGGAATGTCCTGGTTCTCACAGATCCTCATAGGCACGCTGCTAGTG
TGGTTAGGTTTGAACACAAAGAATGGATCTATCTCCCTCACATGCTTGGCCCTGGGGGGAGTGATGATCTTCCTCTCCACGGCT
GTTTCTGCTGACGTGGGGTGCTCAGTGGACTTCTCAAAAAAGGAAACGAGATGTGGCACGGGGGTATTCATCTATAATGATGT
TGAAGCCTGGAGGGACCGGTACAAGTACCATCCTGACTCCCCCCGCAGATTGGCAGCAGCAGTCAAGCAGGCCTGGGAAGAG
GGGATCTGTGGGATCTCATCCGTTTCAAGAATGGAAAACATCATGTGGAAATCAGTAGAAGGGGAGCTCAATGCTATCCTAGA
GGAGAATGGAGTTCAACTGACAGTTGTTGTGGGATCTGTAAAAAACCCCATGTGGAGAGGTCCACAAAGATTGCCAGTGCCT
GTGAATGAGCTGCCCCATGGCTGGAAAGCCTGGGGGAAATCGTATTTTGTTAGGGCGGCAAAGACCAACAACAGTTTTGTTGT
CGACGGTGACACACTGAAGGAATGTCCGCTTGAGCACAGAGCATGGAATAGTTTTCTTGTGGAGGATCACGGGTTTGGAGTC
TTCCACACCAGTGTCTGGCTTAAGGTCAGAGAAGATTACTCATTAGAATGTGACCCAGCCGTCATAGGAACAGCTGTTAAGGG
AAGGGAGGCCGCGCACAGTGATCTGGGCTATTGGATTGAAAGTGAAAAGAATGACACATGGAGGCTGAAGAGGGCCCACCT
GATTGAGATGAAAACATGTGAATGGCCAAAGTCTCACACATTGTGGACAGATGGAGTAGAAGAAAGTGATCTTATCATACCCA
AGTCTTTAGCTGGTCCACTCAGCCACCACAACACCAGAGAGGGTTACAGAACCCAAGTGAAAGGGCCATGGCACAGTGAAGA
GCTTGAAATCCGGTTTGAGGAATGTCCAGGCACCAAGGTTTACGTGGAGGAGACATGCGAACTAGAGGACCATCTCTGAGA
TCAACTACTGCAAGTGGAAGGGTCATTGAGGAATGGTGCTGTAGGGAATGCACAATGCCCCCACTATCGTTTCGAGCAAAAG
ACGGCTGCTGGTATGGAATGGAGATAAGGCCCAGGAAAGAACCAGAGAGCAACTTAGTGAGGTCAATGGTGACAGCGGGGT
CAACCGATCATATGGACCACTTCTCTCTTGGAGTGCTTGTGATTCTACTCATGGTGCAGGAGGGGTTGAAGAAGAGAATGACC
ACAAAGATCATCATGAGCACATCAATGGCAGTGCTGGTAGTCATGATCTTGGGAGGATTTTCAATGAGTGACCTGGCCAAGCT
TGTGATCCTGATGGGTGCTACTTTCGCAGAAATGAACACTGGAGGAGATGTAGCTCACTTGGCATTGGTAGCGGCATTTAAAG
TCAGACCAGCCTTGCTGGTCTCCTTCATTTTCAGAGCCAATTGGACACCCCGTGAGAGCATGCTGCTAGCCCTGGCTTCGTGTC
TTCTGCAAACTGCGATCTCTGCTCTTGAAGGTGACTTGATGGTCCTCATTAATGGATTTGCTTTGGCCTGGTTGGCAATTCGAGC
AATGGCCGTGCCACGCACTGACAACATCGCTCTACCAATCTTGGCTGCTCTAACACCACTAGCTCGAGGCACACTGCTCGTGGC
ATGGAGAGCGGGCCTGGCTACTTGTGGAGGGATCATGCTCCTCTCCCTGAAAGGGAAAGGTAGTGTGAAGAAGAACCTGCCA
TTTGTCATGGCCCTGGGATTGACAGCTGTGAGGGTAGTAGACCCTATTAATGTGGTAGGACTACTGTTACTCACAAGGAGTGG
GAAGCGGAGCTGGCCCCCTAGTGAAGTTCTCACAGCCGTTGGCCTGATATGTGCACTGGCCGGAGGGTTTGCCAAGGCAGAC
ATTGAGATGGCTGGACCCATGGCTGCAGTAGGCTTGCTAATTGTCAGCTATGTGGTCTCGGGAAAGAGTGTGGACATGTACAT
TGAAAGAGCAGGTGACATCACATGGGAAAAGGACGCGGAAGTCACTGGAAACAGTCCTCGGCTTGACGTGGCACTGGATGA
GAGTGGTGATTTCTCCTTGGTAGAGGAAGATGGTCCACCCATGAGAGAGATCATACTTAAGGTGGTCCTGATGGCCATCTGTG
GCATGAACCCAATAGCTATACCTTTTGCTGCAGGAGCGTGGTATGTGTATGTGAAGACTGGGAAAAGGAGTGGCGCCCTCTG
GGACGTGCCTGCTCCCAAAGAAGTGAAGAAAGGAGAGACCACAGATGGAGTGTACAGAGTGATGACTCGCAGACTGCTAGG
TTCAACACAGGTTGGAGTGGGAGTCATGCAAGAGGGAGTCTTCCACACCATGTGGCACGTTACAAAAGGAGCCGCACTGAGG
AGCGGTGAGGGAAGACTTGATCCATACTGGGGGGATGTCAAGCAGGACTTGGTGTCATACTGTGGGCCTTGGAAGTTGGATG
CAGCTTGGGATGGACTCAGCGAGGTACAGCTTTTGGCCGTACCTCCCGGAGAGAGGGCCAGAAACATTCAGACCCTGCCTGG
AATATTCAAGACAAAGGACGGGGACATCGGAGCAGTTGCTCTGGACTACCCTGCAGGGACCTCAGGATCTCCGATCCTAGAC
AAATGTGGAAGAGTGATAGGACTCTATGGCAATGGGGTTGTGATCAAGAATGGAAGCTATGTTAGTGCTATAACCCAGGGAA
AGAGGGAGGAGGAGACTCCGGTTGAATGTTTCGAACCCTCGATGCTGAAGAAGAAGCAGCTAACTGTCTTGGATCTGCATCC
AGGAGCCGGAAAAACCAGGAGAGTTCTTCCTGAAATAGTCCGTGAAGCCATAAAAAAGAGACTCCGGACAGTGATCTTGGCA
CCAACTAGGGTTGTCGCTGCTGAGATGGAGGAGGCCTTGAGAGGACTTCCGGTGCGTTACATGACAACAGCAGTCAACGTCA
```

```
CCCATTCTGGGACAGAAATCGTTGATTTGATGTGCCATGCCACTTTCACTTCACGCTTACTACAACCCATCAGAGTCCCTAATTA
CAATCTCTACATCATGGATGAAGCCCACTTCACAGACCCCTCAAGTATAGCTGCAAGAGGATATATATCAACAAGGGTTGAAAT
GGGCGAGGCGGCTGCCATTTTTATGACTGCCACACCACCAGGAACCCGTGATGCGTTTCCTGACTCTAACTCACCAATCATGGA
CACAGAAGTGGAAGTCCCAGAGAGAGCCTGGAGCTCAGGCTTTGATTGGGTGACAGACCATTCTGGGAAAACAGTTTGGTTC
GTTCCAAGCGTGAGAAACGGAAATGAAATCGCAGCCTGTCTGACAAAGGCTGGAAAGCGGGTCATACAGCTCAGCAGGAAG
ACTTTTGAGACAGAATTTCAGAAAACAAAAATCAAGAGTGGGACTTTGTCATAACAACTGACATCTCAGAGATGGGCGCCAA
CTTCAAGGCTGACCGGGTCATAGACTCTAGGAGATGCCTAAAACCAGTCATACTTGATGGTGAGAGAGTCATCTTGGCTGGGC
CCATGCCTGTCACGCATGCTAGTGCTGCTCAGAGGAGAGGACGTATAGGCAGGAACCCTAACAAACCTGGAGATGAGTACAT
GTATGGAGGTGGGTGTGCAGAGACTGATGAAGGCCATGCACACTGGCTTGAAGCAAGAATGCTTCTTGACAACATCTACCTCC
AGGATGGCCTCATAGCCTCGCTCTATCGGCCTGAGGCCGATAAGGTAGCCGCCATTGAGGGAGAGTTTAAGCTGAGGACAGA
GCAAAGGAAGACCTTCGTGGAACTCATGAAGAGAGGAGACCTTCCCGTCTGGCTAGCCTATCAGGTTGCATCTGCCGGAATAA
CTTACACAGACAGAAGATGGTGCTTTGATGGCACAACCAACAACACCATAATGGAAGACAGCGTACCAGCAGAGGTGTGGAC
AAAGTATGGAGAGAAGAGAGTGCTCAAACCGAGATGGATGGATGCTAGGGTCTGTTCAGACCATGCGGCCCTGAAGTCGTTC
AAAGAATTCGCCGCTGGAAAAAGAGGAGCGGCTTTGGGAGTAATGGAGGCCCTGGGAACACTGCCAGGACACATGACAGAG
AGGTTTCAGGAAGCCATTGACAACCTCGCCGTGCTCATGCGAGCAGAGACTGGAAGCAGGCCTTATAAGGCAGCGGCAGCCC
AACTGCCGGAGACCCTAGAGACCATTATGCTCTTAGGTTTGCTGGGAACAGTTTCACTGGGGATCTTCTTCGTCTTGATGCGGA
ATAAGGGCATCGGGAAGATGGGCTTTGGAATGGTAACCCTTGGGGCCAGTGCATGGCTCATGTGGCTTTCGGAAATTGAACC
AGCCAGAATTGCATGTGTCCTCATTGTTGTGTTTTTATTACTGGTGGTGCTCATACCCGAGCCAGAGAAGCAAAGATCTCCCCA
AGATAACCAGATGGCAATTATCATCATGGTGGCAGTGGGCCTTCTAGGTTTGATAACTGCAAACGAACTTGGATGGCTGGAAA
GAACAAAAAATGACATAGCTCATCTAATGGGAAGGAGAGAAGAAGGAGCAACCATGGGATTCTCAATGGACATTGATCTGCG
GCCAGCCTCCGCCTGGGCTATCTATGCCGCATTGACAACTCTCATCACCCCAGCTGTCCAACATGCGGTAACCACTTCATACAAC
AACTACTCCTTAATGGCGATGGCCACACAAGCTGGAGTGCTGTTTGGCATGGGCAAAGGGATGCCATTTTATGCATGGGACCT
TGGAGTCCCGCTGCTAATGATGGGTTGCTATTCACAATTAACACCCCTGACTCTGATAGTAGCTATCATTCTGCTTGTGGCGCA
CTACATGTACTTGATCCCAGGCCTACAAGCGGCAGCAGCGCGTGCTGCCCAGAAAAGGACAGCAGCTGGCATCATGAAGAAT
CCCGTTGTGGATGGAATAGTGGTAACTGACATTGACACAATGACAATAGACCCCCAGGTGGAGAAGAAGATGGGACAAGTGT
TACTCATAGCAGTAGCCATCTCCAGTGCTGTGCTGCTGCGGACCGCCTGGGGATGGGGGAGGCTGGAGCTCTGATCACAGC
AGCGACCTCCACCTTGTGGGAAGGCTCTCCAAACAAATACTGGAACTCCTCTACAGCCACCTCACTGTGCAACATCTTCAGAGG
AAGCTATCTGGCAGGAGCTTCCCTTATCTATACAGTGACGAGAAACGCTGGCCTGGTTAAGAGACGTGGAGGTGGGACGGGA
GAGACTCTGGGAGAGAAGTGGAAAGCTCGTCTGAATCAGATGTCGGCCCTGGAGTTCTACTCTTATAAAAAGTCAGGTATCAC
TGAAGTGTGTAGAGAGGAGGCTCGCCGTGCCCTCAAGGATGGAGTGGCCACAGGAGGACATGCCGTATCCCGGGGAAGTGC
AAAGCTCAGATGGTTGGTGGAGAGAGGATATCTGCAGCCCTATGGGAAGGTTGTTGACCTCGGATGTGGCAGAGGGGCTG
GAGCTATTATGCCGCCACCATCCGCAAAGTGCAGGAGGTGAGAGGATACACAAAGGGAGGTCCCGGTCATGAAGAACCCATG
CTGGTGCAAAGCTATGGGTGGAACATAGTTCGTCTCAAGAGTGGAGTGGACGTCTTCCACATGGCGGCTGAGCCGTGTGACA
CTCTGCTGTGTGACATAGGTGAGTCATCATCTAGTCCTGAAGTGGAAGAGACACGAACACTCAGAGTGCTCTCTATGGTGGGG
GACTGGCTTGAAAAAAAGACCAGGGGCCTTCTGTATAAAGGTGCTGTGCCCATACACCAGCACTATGATGGAAACCATGGAGC
GACTGCAACGTAGGCATGGGGAGGATTAGTCAGAGTGCCATTGTCTCGCAACTCCACACATGAGATGTACTGGGTCTCTGG
GGCAAAGAGCAACATCATAAAAAGTGTGTCCACCACAAGTCAGCTCCTCCTGGGACGCATGGATGGCCCCAGGAGGCCAGTG
AAATATGAGGAGGATGTGAACCTCGGCTCGGGTACACGAGCTGTGGCAAGCTGTGCTGAGGCTCCTAACATGAAAATCATCG
GCAGGCGCATTGAGAGAATCCGCAATGAACATGCAGAAACATGGTTTCTTGATGAAAACCACCCATACAGGACATGGGCCTAC
CATGGGAGCTACGAAGCCCCACGCAAGGATCAGCGTCTTCCCTCGTGAACGGGTTGTTAGACTCCTGTCAAAGCCTTGGGA
CGTGGTGACTGGAGTTACAGGAATAGCCATGACTGACACCACACCATACGGCCAACAAAGAGTCTTCAAAGAAAAAGTGGAC
```

```
ACCAGGGTGCCAGATCCCCAAGAAGGCACTCGCCAGGTAATGAACATAGTCTCTTCCTGGCTGTGGAAGGAGCTGGGAAAC
GCAAGCGGCCACGCGTCTGCACCAAAGAAGAGTTTATCAACAAGGTGCGCAGCAATGCAGCACTGGGAGCAATATTTGAAGA
GGAAAAAGAATGGAAGACGGCTGTGGAAGCTGTGAATGATCCAAGGTTTTGGGCCCTAGTGGATAGGGAGAGAGAACACCA
CCTGAGAGGAGAGTGTCACAGCTGTGTGTACAACATGATGGGAAAAAGAGAAAAGAAGCAAGGAGAGTTCGGGAAAGCAA
AAGGTAGCCGCGCCATCTGGTACATGTGGTTGGGAGCCAGATTCTTGGAGTTTGAAGCCCTTGGATTCTTGAACGAGGACCAT
TGGATGGGAAGAGAAAACTCAGGAGGTGGAGTCGAAGGGTTAGGATTGCAAAGACTTGGATACATTCTAGAAGAAATGAAT
CGGGCACCAGGAGGAAAGATGTACGCAGATGACACTGCTGGCTGGGACACCCGCATTAGTAAGTTTGATCTGGAGAATGAAG
CTCTGATTACCAACCAAATGGAGGAAGGGCACAGAACTCTGGCGTTGGCCGTGATTAAATACACATACCAAAACAAAGTGGTG
AAGGTTCTCAGACCAGCTGAAGGAGGAAAAACAGTTATGGACATCATTTCAAGACAAGACCAGAGAGGGAGTGGACAAGTT
GTCACTTATGCTCTCAACACATTCACCAACTTGGTGGTGCAGCTTATCCGGAACATGGAAGCTGAGGAAGTGTTAGAGATGCA
AGACTTATGGTTGTTGAGGAAGCCAGAGAAAGTGACCAGATGGTTGCAGAGCAATGGATGGGATAGACTCAAACGAATGGC
GGTCAGTGGAGATGACTGCGTTGTGAAGCCAATCGATGATAGGTTTGCACATGCCCTCAGGTTCTTGAATGACATGGGAAAA
GTTAGGAAAGACACACAGGAGTGGAAACCCTCGACTGGATGGAGCAATTGGGAAGAAGTCCCGTTCTGCTCCCACCACTTCA
ACAAGCTGTACCTCAAGGATGGGAGATCCATTGTGGTCCCTTGCCGCCACCAAGATGAACTGATTGGCCGAGCTCGCGTCTCA
CCAGGGGCAGGATGGAGCATCCGGGAGACTGCCTGTCTTGCAAAATCATATGCGCAGATGTGGCAGCTCCTTTATTTCCACAG
AAGAGACCTTCGACTGATGGCTAATGCCATTTGCTCGGCTGTGCCAGTTGACTGGGTACCAACTGGGAGAACCACCTGGTCAA
TCCATGGAAAGGGAGAATGGATGACCACTGAGGACATGCTCATGGTGTGAATAGAGTGTGGATTGAGGAGAACGACCATA
TGGAGGACAAGACTCCTGTAACAAAATGGACAGACATTCCCTATCTAGGAAAAAGGGAGGACTTATGGTGTGGATCCCTTATA
GGGCACAGACCCCGCACCACTTGGGCTGAAAACATCAAAGACACAGTCAACATGGTGCGCAGGATCATAGGTGATGAAGAA
AGTACATGGACTATCTATCCACCCAAGTCCGCTACTTGGGTGAGGAAGGGTCCACACCCGGAGTGTTGTAAGCACCAATTTTA
GTGTTGTCAGGCCTGCTAGTCAGCCACAGTTTGGGGAAAGCTGTGCAGCCTGTAACCCCCCCAGGAGAAGCTGGGAAACCAA
GCTCATAGTCAGGCCGAGAACGCCATGGCACGGAAGAAGCCATGCTGCCTGTGAGCCCCTCAGAGGACACTGAGTCAAAAAA
CCCCACGCGCTTGGAAGCGCAGGATGGGAAAAGAAGGTGGCGACCTTCCCCACCCTTCAATCTGGGGCCTGAACTGGAGACT
AGCTGTGAATCTCCAGCAGAGGGACTAGTGGTTAGAGGAGACCCCCCGGAAAACGCAAAACAGCATATTGACGCTGGGAAA
GACCAGAGACTCCATGAGTTTCCACCACGCTGGCCGCCAGGCACAGATCGCCGAACAGCGGCGGCCGGTGTGGGAAATCCA
TGGTTTCT

AY632535.2 NC_012532.1 Zika virus strain MR 766, Uganda,
complete genome
                                                                                 SEQ ID NO: 12
AGTTGTTGATCTGTGTGAGTCAGACTGCGACAGTTCGAGTCTGAAGCGAGAGCTAACAACAGTATCAACAGGTTTAATTTGGA
TTTGGAAACGAGAGTTTCTGGTCATGAAAAACCCCAAAGAAGAAATCCGGAGGATCCGGATTGTCAATATGCTAAAACGCGG
AGTAGCCCGTGTAAACCCCTTGGGAGGTTTGAAGAGGTTGCCAGCCGGACTTCTGCTGGGTCATGGACCCATCAGAATGGTTT
TGGCGATACTAGCCTTTTTGAGATTTACAGCAATCAAGCCATCACTGGGCCTTATCAACAGATGGGGTTCCGTGGGAAAAAA
GAGGCTATGGAAATAATAAAGAAGTTCAAGAAAGATCTTGCTGCCATGTTGAGAATAATCAATGCTAGGAAAGAGAGGAAGA
GACGTGGCGCAGACACCAGCATCGGAATCATTGGCCTCCTGCTGACTACAGCCATGGCAGCAGAGATCACTAGACGCGGGAG
TGCATACTACATGTACTTGGATAGGAGCGATGCCGGGAAGGCCATTTCGTTTGCTACCACATTGGGAGTGAACAAGTGCCACG
TACAGATCATGGACCTCGGGCACATGTGTGACGCCACCATGAGTTATGAGTGCCCTATGCTGGATGAGGGAGTGGAACCAGA
TGATGTCGATTGCTGGTGCAACACGACATCAACTTGGGTTGTGTACGGAACCTGTCATCACAAAAAGGTGAGGCACGGCGAT
CTAGAAGAGCCGTGACGCTCCCTTCTCACTCTACAAGGAAGTTGCAAACGCGGTCGCAGACCTGGTTAGAATCAAGAGAATAC
ACGAAGCACTTGATCAAGGTTGAAAACTGGATATTCAGGAACCCCGGGTTTGCGCTAGTGGCCGTTGCCATTGCCTGGCTTTT
GGGAAGCTCGACGAGCCAAAAAGTCATATACTTGGTCATGATACTGCTGATTGCCCCGGCATACAGTATCAGGTGCATTGGAG
TCAGCAATAGAGACTTCGTGGAGGGCATGTCAGGTGGGACCTGGGTTGATGTTGTCTTGGAACATGGAGGCTGCGTTACCGT
```

```
GATGGCACAGGACAAGCCAACAGTCGACATAGAGTTGGTCACGACGACGGTTAGTAACATGGCCGAGGTAAGATCCTATTGC
TACGAGGCATCGATATCGGACATGGCTTCGGACAGTCGTTGCCCAACACAAGGTGAAGCCTACCTTGACAAGCAATCAGACAC
TCAATATGTCTGCAAAAGAACATTAGTGGACAGAGGTTGGGGAAACGGTTGTGGACTTTTTGGCAAAGGGAGCTTGGTGACA
TGTGCCAAGTTTACGTGTTCTAAGAAGATGACCGGGAAGAGCATTCAACCGGAAAATCTGGAGTATCGGATAATGCTATCAGT
GCATGGCTCCCAGCATAGCGGGATGATTGGATATGAAACTGACGAAGATAGAGCGAAAGTCGAGGTTACGCCTAATTCACCA
AGAGCGGAAGCAACCTTGGGAGGCTTTGGAAGCTTAGGACTTGACTGTGAACCAAGGACAGGCCTTGACTTTTCAGATCTGTA
TTACCTGACCATGAACAATAAGCATTGGTTGGTGCACAAAGAGTGGTTTCATGACATCCCATTGCCTTGGCATGCTGGGGCAG
ACACCGGAACTCCACACTGGAACAACAAAGAGGCATTGGTAGAATTCAAGGATGCCCACGCCAAGAGGCAAACCGTCGTCGT
TCTGGGGAGCCAGGAAGGAGCCGTTCACACGGCTCTCGCTGGAGCTCTAGAGGCTGAGATGGATGGTGCAAAGGGAAGGCT
GTTCTCTGGCCATTTGAAATGCCGCCTAAAAATGGACAAGCTTAGATTGAAGGGCGTGTCATATTCCTTGTGCACTGCGGCATT
CACATTCACCAAGGTCCCAGCTGAAACACTGCATGGAACAGTCACAGTGGAGGTGCAGTATGCAGGGACAGATGGACCCTGC
AAGATCCCAGTCCAGATGGCGGTGGACATGCAGACCCTGACCCCAGTTGGAAGGCTGATAACCGCCAACCCCGTGATTACTGA
AAGCACTGAGAACTCAAAGATGATGTTGGAGCTTGACCCACCATTTGGGGATTCTTACATTGTCATAGGAGTTGGGGACAAGA
AAATCACCCACCACTGGCATAGGAGTGGTAGCACCATCGGAAAGGCATTTGAGGCCACTGTGAGAGGCGCCAAGAGAATGGC
AGTCCTGGGGGATACAGCCTGGGACTTCGGATCAGTCGGGGTGTGTTCAACTCACTGGGTAAGGGCATTCACCAGATTTTTG
GAGCAGCCTTCAAATCACTGTTTGGAGGAATGTCCTGGTTCTCACAGATCCTCATAGGCACGCTGCTAGTGTGGTTAGGTTTGA
ACACAAAGAATGGATCTATCTCCCTCACATGCTTGGCCCTGGGGGGAGTGATGATCTTCCTCTCCACGGCTGTTTCTGCTGACG
TGGGGTGCTCAGTGGACTTCTCAAAAAAGGAAACGAGATGTGGCACGGGGGTATTCATCTATAATGATGTTGAAGCCTGGAG
GGACCGGTACAAGTACCATCCTGACTCCCCCCGCAGATTGGCAGCAGCAGTCAAGCAGGCCTGGGAAGAGGGGATCTGTGGG
ATCTCATCCGTTTCAAGAATGGAAAACATCATGTGGAAATCAGTAGAAGGGGAGCTCAATGCTATCCTAGAGGAGAATGGAG
TTCAACTGACAGTTGTTGTGGGATCTGTAAAAAACCCCATGTGGAGAGGTCCACAAAGATTGCCAGTGCCTGTGAATGAGCTG
CCCCATGGCTGGAAAGCCTGGGGGAAATCGTATTTTGTTAGGGCGGCAAAGACCAACAACAGTTTTGTTGTCGACGGTGACAC
ACTGAAGGAATGTCCGCTTGAGCACAGAGCATGGAATAGTTTTCTTGTGGAGGATCACGGGTTTGGAGTCTTCCACACCAGTG
TCTGGCTTAAGGTCAGAGAAGATTACTCATTAGAATGTGACCCAGCCGTCATAGGAACAGCTGTTAAGGGAAGGGAGGCCGC
GCACAGTGATCTGGGCTATTGGATTGAAAGTGAAAAGAATGACACATGGAGGCTGAAGAGGGCCCACCTGATTGAGATGAAA
ACATGTGAATGGCCAAAGTCTCACACATTGTGGACAGATGGAGTAGAAGAAAGTGATCTTATCATACCCAAGTCTTTAGCTGG
TCCACTCAGCCACCACAACACCAGAGAGGGTTACAGAACCCAAGTGAAAGGGCCATGGCACAGTGAAGAGCTTGAAATCCGG
TTTGAGGAATGTCCAGGCACCAAGGTTTACGTGGAGGAGACATGCGGAACTAGAGGACCATCTCTGAGATCAACTACTGCAA
GTGGAAGGGTCATTGAGGAATGGTGCTGTAGGGAATGCACAATGCCCCCACTATCGTTTCGAGCAAAAGACGGCTGCTGGTA
TGGAATGGAGATAAGGCCCAGGAAAGAACCAGAGAGCAACTTAGTGAGGTCAATGGTGACAGCGGGGTCAACCGATCATAT
GGACCACTTCTCTCTTGGAGTGCTTGTGATTCTACTCATGGTGCAGGAGGGGTTGAAGAAGAGAATGACCACAAAGATCATCA
TGAGCACATCAATGGCAGTGCTGGTAGTCATGATCTTGGGAGGATTTTCAATGAGTGACCTGGCCAAGCTTGTGATCCTGATG
GGTGCTACTTTCGCAGAAATGAACACTGGAGGAGATGTAGCTCACTTGGCATTGGTAGCGGCATTTAAAGTCAGACCAGCCTT
GCTGGTCTCCTTCATTTTCAGAGCCAATTGGACACCCCGTGAGAGCATGCTGCTAGCCCTGGCTTCGTGTCTTCTGCAAACTGC
GATCTCTGCTCTTGAAGGTGACTTGATGGTCCTCATTAATGGATTTGCTTTGGCCTGGTTGGCAATTCGAGCAATGGCCGTGCC
ACGCACTGACAACATCGCTCTACCAATCTTGGCTGCTCTAACACCACTAGCTCGAGGCACACTGCTCGTGGCATGGAGAGCGG
GCCTGGCTACTTGTGGAGGGATCATGCTCCTCTCCCTGAAAGGGAAAGGTAGTGTGAAGAAGAACCTGCCATTTGTCATGGCC
CTGGGATTGACAGCTGTGAGGGTAGTAGACCCTATTAATGTGGTAGGACTACTGTTACTCACAAGGAGTGGGAAGCGGAGCT
GGCCCCCTAGTGAAGTTCTCACAGCCGTTGGCCTGATATGTGCACTGGCCGGAGGGTTTGCCAAGGCAGACATTGAGATGGCT
GGACCCATGGCTGCAGTAGGCTTGCTAATTGTCAGCTATGTGGTCTCGGGAAAGAGTGTGGACATGTACATTGAAAGAGCAG
GTGACATCACATGGGAAAAGGACGCGGAAGTCACTGGAAACAGTCCTCGGCTTGACGTGGCACTGGATGAGAGTGGTGACTT
```

-continued

```
CTCCTTGGTAGAGGAAGATGGTCCACCCATGAGAGAGATCATACTCAAGGTGGTCCTGATGGCCATCTGTGGCATGAACCCAA
TAGCTATACCTTTTGCTGCAGGAGCGTGGTATGTGTATGTGAAGACTGGGAAAAGGAGTGGCGCCCTCTGGGACGTGCCTGC
TCCCAAAGAAGTGAAGAAAGGAGAGACCACAGATGGAGTGTACAGAGTGATGACTCGCAGACTGCTAGGTTCAACACAGGTT
GGAGTGGGAGTCATGCAAGAGGGAGTCTTCCACACCATGTGGCACGTTACAAAAGGAGCCGCACTGAGGAGCGGTGAGGGA
AGACTTGATCCATACTGGGGGGATGTCAAGCAGGACTTGGTGTCATACTGTGGGCCTTGGAAGTTGGATGCAGCTTGGGATG
GACTCAGCGAGGTACAGCTTTTGGCCGTACCTCCCGGAGAGAGGGCCAGAAACATTCAGACCCTGCCTGGAATATTCAAGACA
AAGGACGGGACATCGGAGCAGTTGCTCTGGACTACCCTGCAGGGACCTCAGGATCTCCGATCCTAGACAAATGTGGAAGAG
TGATAGGACTCTATGGCAATGGGGTTGTGATCAAGAATGGAAGCTATGTTAGTGCTATAACCCAGGGAAAGAGGGAGGAGG
AGACTCCGGTTGAATGTTTCGAACCCTCGATGCTGAAGAAGAAGCAGCTAACTGTCTTGGATCTGCATCCAGGAGCCGGAAAA
ACCAGGAGAGTTCTTCCTGAAATAGTCCGTGAAGCCATAAAAAAGAGACTCCGGACAGTGATCTTGGCACCAACTAGGGTTGT
CGCTGCTGAGATGGAGGAGGCCTTGAGAGGACTTCCGGTGCGTTACATGACAACAGCAGTCAACGTCACCCATTCTGGGACA
GAAATCGTTGATTTGATGTGCCATGCCACTTTCACTTCACGCTTACTACAACCCATCAGAGTCCCTAATTACAATCTCAACATCAT
GGATGAAGCCCACTTCACAGACCCCTCAAGTATAGCTGCAAGAGGATACATATCAACAAGGGTTGAAATGGGCGAGGCGGCT
GCCATTTTTATGACTGCCACACCACCAGGAACCCGTGATGCGTTTCCTGACTCTAACTCACCAATCATGGACACAGAAGTGGAA
GTCCCAGAGAGAGCCTGGAGCTCAGGCTTTGATTGGGTGACAGACCATTCTGGGAAAACAGTTTGGTTCGTTCCAAGCGTGA
GAAACGGAAATGAAATCGCAGCCTGTCTGACAAAGGCTGGAAAGCGGGTCATACAGCTCAGCAGGAAGACTTTTGAGACAGA
ATTTCAGAAAACAAAAATCAAGAGTGGGACTTTGTCATAACAACTGACATCTCAGAGATGGGCGCCAACTTCAAGGCTGACC
GGGTCATAGACTCTAGGAGATGCCTAAAACCAGTCATACTTGATGGTGAGAGAGTCATCTTGGCTGGGCCCATGCCTGTCACG
CATGCTAGTGCTGCTCAGAGGAGAGGACGTATAGGCAGGAACCCTAACAAACCTGGAGATGAGTACATGTATGGAGGTGGG
TGTGCAGAGACTGATGAAGGCCATGCACACTGGCTTGAAGCAAGAATGCTTCTTGACAACATCTACCTCCAGGATGGCCTCAT
AGCCTCGCTCTATCGGCCTGAGGCCGATAAGGTAGCCGCCATTGAGGGAGAGTTTAAGCTGAGGACAGAGCAAAGGAAGAC
CTTCGTGGAACTCATGAAGAGAGGAGACCTTCCCGTCTGGCTAGCCTATCAGGTTGCATCTGCCGGAATAACTTACACAGACA
GAAGATGGTGCTTTGATGGCACAACCAACAACACCATAATGGAAGACAGTGTACCAGCAGAGGTTTGGACAAAGTATGGAGA
GAAGAGAGTGCTCAAACCGAGATGGATGGATGCTAGGGTCTGTTCAGACCATGCGGCCCTGAAGTCGTTCAAAGAATTCGCC
GCTGGAAAAAGAGGAGCGGCTTTGGGAGTAATGGAGGCCCTGGGAACACTGCCAGGACACATGACAGAGAGGTTTCAGGAA
GCCATTGACAACCTCGCCGTGCTCATGCGAGCAGAGACTGGAAGCAGGCCTTATAAGGCAGCGGCAGCCCAACTGCCGGAGA
CCCTAGAGACCATTATGCTCTTAGGTTTGCTGGGAACAGTTTCACTGGGGATCTTCTTCGTCTTGATGCGGAATAAGGGCATCG
GGAAGATGGGCTTTGGAATGGTAACCCTTGGGGCCAGTGCATGGCTCATGTGGCTTTCGGAAATTGAACCAGCCAGAATTGC
ATGTGTCCTCATTGTTGTGTTTTTATTACTGGTGGTGCTCATACCCGAGCCAGAGAAGCAAAGATCTCCCCAAGATAACCAGAT
GGCAATTATCATCATGGTGGCAGTGGGCCTTCTAGGTTTGATAACTGCAAACGAACTTGGATGGCTGGAAAGAACAAAAAAT
GACATAGCTCATCTAATGGGAAGGAGAGAAGAAGGAGCAACCATGGGATTCTCAATGGACATTGATCTGCGGCCAGCCTCCG
CCTGGGCTATCTATGCCGCATTGACAACTCTCATCACCCCAGCTGTCCAACATGCGGTAACCACTTCATACAACAACTACTCCTT
AATGGCGATGGCCACACAAGCTGGAGTGCTGTTTGGCATGGGCAAAGGGATGCCATTTATGCATGGGGACCTTGGAGTCCCG
CTGCTAATGATGGGTTGCTATTCACAATTAACACCCCTGACTCTGATAGTAGCTATCATTCTGCTTGTGGCGCACTACATGTACT
TGATCCCAGGCCTACAAGCGGCAGCAGCGCGTGCTGCCCAGAAAAGGACAGCAGCTGGCATCATGAAGAATCCCGTTGTGGA
TGGAATAGTGGTAACTGACATTGACACAATGACAATAGACCCCCAGGTGGAGAAGAAGATGGGACAAGTGTTACTCATAGCA
GTAGCCATCTCCAGTGCTGTGCTGCTGCGGACCGCCTGGGGATGGGGGGAGGCTGGAGCTCTGATCACAGCAGCGACCTCCA
CCTTGTGGGAAGGCTCTCCAAACAAATACTGGAACTCCTCTACAGCCACCTCACTGTGCAACATCTTCAGAGGAAGCTATCTGG
CAGGAGCTTCCCTTATCTATACAGTGACGAGAAACGCTGGCCTGGTTAAGAGACGTGGAGGTGGGACGGGAGAGACTCTGG
GAGAGAAGTGGAAAGCTCGTCTGAATCAGATGTCGGCCCTGGAGTTCTACTCTTATAAAAAGTCAGGTATCACTGAAGTGTGT
AGAGAGGAGGCTCGCCGTGCCCTCAAGGATGGAGTGGCCACAGGAGGACATGCCGTATCCCGGGGAAGTGCAAAGATCAGA
```

```
TGGTTGGAGGAGAGAGGATATCTGCAGCCCTATGGGAAGGTTGTTGACCTCGGATGTGGCAGAGGGGCTGGAGCTATTAT

GCCGCCACCATCCGCAAAGTGCAGGAGGTGAGAGGATACACAAAGGGAGGTCCCGGTCATGAAGAACCCATGCTGGTGCAA

AGCTATGGGTGGAACATAGTTCGTCTCAAGAGTGGAGTGGACGTCTTCCACATGGCGGCTGAGCCGTGTGACACTCTGCTGTG

TGACATAGGTGAGTCATCATCTAGTCCTGAAGTGGAAGAGACACGAACACTCAGAGTGCTCTCTATGGTGGGGGACTGGCTT

GAAAAAGACCAGGGGCCTTCTGTATAAAGGTGCTGTGCCCATACACCAGCACTATGATGGAAACCATGGAGCGACTGCAAC

GTAGGCATGGGGGAGGATTAGTCAGAGTGCCATTGTGTCGCAACTCCACACATGAGATGTACTGGGTCTCTGGGCAAAGAG

CAACATCATAAAAAGTGTGTCCACCACAAGTCAGCTCCTCCTGGGACGCATGGATGGCCCCAGGAGGCCAGTGAAATATGAG

GAGGATGTGAACCTCGGCTCGGGTACACGAGCTGTGGCAAGCTGTGCTGAGGCTCCTAACATGAAAATCATCGGCAGGCGCA

TTGAGAGAATCCGCAATGAACATGCAGAAACATGGTTTCTTGATGAAAACCACCCATACAGGACATGGGCCTACCATGGGAGC

TACGAAGCCCCCACGCAAGGATCAGCGTCTTCCCTCGTGAACGGGGTTGTTAGACTCCTGTCAAAGCCTTGGGACGTGGTGAC

TGGAGTTACAGGAATAGCCATGACTGACACCACACCATACGGCCAACAAAGAGTCTTCAAAGAAAAAGTGGACACCAGGGTG

CCAGATCCCCAAGAAGGCACTCGCCAGGTAATGAACATAGTCTCTTCCTGGCTGTGGAAGGAGCTGGGGAAACGCAAGCGGC

CACGCGTCTGCACCAAAGAAGAGTTTATCAACAAGGTGCGCAGCAATGCAGCACTGGGAGCAATATTTGAAGAGGAAAAAGA

ATGGAAGACGGCTGTGGAAGCTGTGAATGATCCAAGGTTTTGGGCCCTAGTGGATAGGGAGAGAGAACACCACCTGAGAGG

AGAGTGTCACAGCTGTGTGTACAACATGATGGGAAAAAGAGAAAAGAAGCAAGGAGAGTTCGGGAAAGCAAAAGGTAGCC

GCGCCATCTGGTACATGTGGTTGGGAGCCAGATTCTTGGAGTTTGAAGCCCTTGGATTCTTGAACGAGGACCATTGGATGGGA

AGAGAAAACTCAGGAGGTGGAGTCGAAGGGTTAGGATTGCAAAGACTTGGATACATTCTAGAAGAAATGAATCGGGCACCA

GGAGGAAAGATGTACGCAGATGACACTGCTGGCTGGGACACCCGCATTAGTAAGTTTGATCTGGAGAATGAAGCTCTGATTA

CCAACCCAAATGGAGGAAGGGCACAGAACTCTGGCGTTGGCCGTGATTAAATACACATACCAAACAAAGTGGTGAAGGTTCT

CAGACCAGCTGAAGGAGGAAAAACAGTTATGGACATCATTTCAAGACAAGACCAGAGAGGGAGTGGACAAGTTGTCACTTAT

GCTCTCAACACATTCACCAACTTGGTGGTGCAGCTTATCCGGAACATGGAAGCTGAGGAAGTGTTAGAGATGCAAGACTTATG

GTTGTTGAGGAAGCCAGAGAAAGTGACCAGATGGTTGCAGAGCAATGGATGGATAGACTCAAACGAATGGCGGTCAGTGG

AGATGACTGCGTTGTGAAGCCAATCGATGATAGGTTTGCACATGCCCTCAGGTTCTTGAATGACATGGGAAAAGTTAGGAAAG

ACACACAGGAGTGGAAACCCTCGACTGGATGGAGCAATTGGGAAGAAGTCCCGTTCTGCTCCCACCACTTCAACAAGCTGTAC

CTCAAGGATGGGAGATCCATTGTGGTCCCTTGCCGCCACCAAGATGAACTGATTGGCCGAGCTCGCGTCTCACCAGGGGCAG

GATGGAGCATCCGGGAGACTGCCTGTCTTGCAAAATCATATGCGCAGATGTGGCAGCTCCTTTATTTCCACAGAAGAGACCTT

CGACTGATGGCTAATGCCATTTGCTCGGCTGTGCCAGTTGACTGGGTACCAACTGGGAGAACCACCTGGTCAATCCATGGAAA

GGGAGAATGGATGACCACTGAGGACATGCTCATGGTGTGGAATAGAGTGTGGATTGAGGAGAACGACCATATGGAGGACAA

GACTCCTGTAACAAAATGGACAGACATTCCCTATCTAGGAAAAAGGGAGGACTTATGGTGTGGATCCCTTATAGGGCACAGAC

CCCGCACCACTTGGGCTGAAAACATCAAAGACACAGTCAACATGGTGCGCAGGATCATAGGTGATGAAGAAAAGTACATGGA

CTATCTATCCACCCAAGTCCGCTACTTGGGTGAGGAAGGGTCCACACCCGGAGTGTTGTAAGCACCAATTTTAGTGTTGTCAGG

CCTGCTAGTCAGCCACAGTTTGGGGAAAGCTGTGCAGCCTGTAACCCCCCAGGAGAAGCTGGGAAACCAAGCTCATAGTCA

GGCCGAGAACGCCATGGCACGGAAGAAGCCATGCTGCCTGTGAGCCCCTCAGGAGGACACTGAGTCAAAAAACCCCACGCGCT

TGGAAGCGCAGGATGGGAAAAGAAGGTGGCGACCTTCCCCACCCTTCAATCTGGGGCCTGAACTGGAGACTAGCTGTGAATC

TCCAGCAGAGGGACTAGTGGTTAGAGGAGACCCCCCGGAAAACGCAAACAGCATATTGACGTGGGAAAGACCAGAGACTC

CATGAGTTTCCACCACGCTGGCCGCCAGGCACAGATCGCCGAACTTCGCGGCCGGTGTGGGGAAATCCATGGTTTCT
```

KJ776791.1, Zika virus strain H/PF/2013 polyprotein gene, complete cds

SEQ ID NO: 13
```
AGTATCAACAGGTTTTATTTTGGATTTGGAAACGAGAGTTTCTGGTCATGAAAAACCCAAAAAAGAAATCCGGAGGATTCCGG

ATTGTCAATATGCTAAAACGCGGAGTAGCCCGTGTGAGCCCCTTTGGGGGCTTGAAGAGGCTGCCAGCCGGACTTCTGCTGG

GTCATGGGCCCATCAGGATGGTCTTGGCGATTCTAGCCTTTTTGAGATTCACGGCAATCAAGCCATCACTGGGTCTCATCAATA

GATGGGGTTCAGTGGGGAAAAAAGAGGCTATGGAAATAATAAAGAAGTTCAAGAAAGATCTGGCTGCCATGCTGAGAATAA
```

-continued
```
TCAATGCTAGGAAGGAGAAGAAGAGACGAGGCGCAGATACTAGTGTCGGAATTGTTGGCCTCCTGCTGACCACAGCTATGGC
AGCGGAGGTCACTAGACGTGGGAGTGCATACTATATGTACTTGGACAGAAACGACGCTGGGGAGGCCATATCTTTTCCAACC
ACATTGGGGATGAATAAGTGTTATATACAGATCATGGATCTTGGACACATGTGTGATGCCACCATGAGCTATGAATGCCCTAT
GCTGGATGAGGGGGTGGAACCAGATGACGTCGATTGTTGGTGCAACACGACGTCAACTTGGGTTGTGTACGGAACCTGCCAT
CACAAAAAAGGTGAAGCACGGAGATCTAGAAGAGCTGTGACGCTCCCCTCCCATTCCACTAGGAAGCTGCAAACGCGGTCGC
AAACCTGGTTGGAATCAAGAGAATACACAAAGCACTTGATTAGAGTCGAAAATTGGATATTCAGGAACCCTGGCTTCGCGTTA
GCAGCAGCTGCCATCGCTTGGCTTTTGGGAAGCTCAACGAGCCAAAAAGTCATATACTTGGTCATGATACTGCTGATTGCCCCG
GCATACAGCATCAGGTGCATAGGAGTCAGCAATAGGGACTTTGTGGAAGGTATGTCAGGTGGGACTTGGGTTGATGTTGTCT
TGGAACATGGAGGTTGTGTCACCGTAATGGCACAGGACAAACCGACTGTCGACATAGAGCTGGTTACAACAACAGTCAGCAA
CATGGCGGAGGTAAGATCCTACTGCTATGAGGCATCAATATCGGACATGGCTTCGGACAGCCGCTGCCCAACACAAGGTGAA
GCCTACCTTGACAAGCAATCAGACACTCAATATGTCTGCAAAAGAACGTTAGTGGACAGAGGCTGGGGAAATGGATGTGGAC
TTTTTGGCAAAGGGAGCCTGGTGACATGCGCTAAGTTTGCATGCTCCAAGAAAATGACCGGGAAGAGCATCCAGCCAGAGAA
TCTGGAGTACCGGATAATGCTGTCAGTTCATGGCTCCCAGCACAGTGGGATGATCGTTAATGACACAGGACATGAAACTGATG
AGAATAGAGCGAAGGTTGAGATAACGCCCAATTCACCAAGAGCCGAAGCCACCCTGGGGGGTTTTGGAAGCCTAGGACTTGA
TTGTGAACCGAGGACAGGCCTTGACTTTTCAGATTTGTATTACTTGACTATGAATAACAAGCACTGGTTGGTTCACAAGGAGTG
GTTCCACGACATTCCATTACCTTGGCACGCTGGGGCAGACACCGGAACTCCACACTGGAACAACAAAGAAGCACTGGTAGAGT
TCAAGGACGCACATGCCAAAAGGCAAACTGTCGTGGTTCTAGGGAGTCAAGAAGGAGCAGTTCACACGGCCCTTGCTGGAGC
TCTGGAGGCTGAGATGGATGGTGCAAAGGGAAGGCTGTCCTCTGGCCACTTGAAATGTCGCCTGAAAATGGATAAACTTAGA
TTGAAGGGCGTGTCATACTCCTTGTGTACCGCAGCGTTCACATTCACCAAGATCCCGGCTGAAACACTGCACGGGACAGTCAC
AGTGGAGGTACAGTACGCAGGGACAGATGGACCTTGCAAGGTTCCAGCTCAGATGGCGGTGGACATGCAAACTCTGACCCCA
GTTGGGAGGTTGATAACCGCTAACCCCGTAATCACTGAAAGCACTGAGAACTCTAAGATGATGCTGGAACTTGATCCACCATT
TGGGGACTCTTACATTGTCATAGGAGTCGGGGAGAAGAAGATCACCCACCACTGGCACAGGAGTGGCAGCACCATTGGAAAA
GCATTTGAAGCCACTGTGAGAGGTGCCAAGAGAATGGCAGTCTTGGGAGACACAGCCTGGGACTTTGGATCAGTTGGAGGCG
CTCTCAACTCATTGGGCAAGGGCATCCATCAAATTTTTGGAGCAGCTTTCAAATCATTGTTTGGAGGAATGTCCTGGTTCTCACA
AATTCTCATTGGAACGTTGCTGATGTGGTTGGGTCTGAACACAAAGAATGGATCTATTTCCCTTATGTGCTTGGCCTTAGGGGG
AGTGTTGATCTTCTTATCCACAGCTGTCTCTGCTGATGTGGGGTGCTCGGTGGACTTCTCAAAGAAGGAGACGAGATGCGGTA
CAGGGGTGTTCGTCTATAACGACGTTGAAGCCTGGAGGGACAGGTACAAGTACCATCCTGACTCCCCCCGTAGATTGGCAGCA
GCAGTCAAGCAAGCCTGGGAAGATGGTATCTGTGGGATCTCCTCTGTTTCAAGAATGGAAAACATCATGTGGAGATCAGTAG
AAGGGGAGCTCAACGCAATCCTGGAAGAGAATGGAGTTCAACTGACGGTCGTTGTGGGATCTGTAAAAAACCCCATGTGGAG
AGGTCCACAGAGATTGCCCGTGCCTGTGAACGAGCTGCCCCACGGCTGGAAGGCTTGGGGGAAATCGTACTTCGTCAGAGCA
GCAAAGACAAATAACAGCTTTGTCGTGGATGGTGACACACTGAAGGAATGCCCACTCAAACATAGAGCATGGAACAGCTTTCT
TGTGGAGGATCATGGGTTCGGGGTATTTCACACTAGTGTCTGGCTCAAGGTTAGAGAAGATTATTCATTAGAGTGTGATCCAG
CCGTTATTGGAACAGCTGTTAAGGGAAAGGAGGCTGTACACAGTGATCTAGGCTACTGGATTGAGAGTGAGAAGAATGACAC
ATGGAGGCTGAAGAGGGCCCATCTGATCGAGATGAAAACATGTGAATGGCCAAAGTCCCACACATTGTGGACAGATGGAATA
GAAGAGAGTGATCTGATCATACCCAAGTCTTTAGCTGGGCCACTCAGCCATCACAATACCAGAGAGGGCTACAGGACCCAAAT
GAAAGGGCCATGGCACAGTGAAGAGCTTGAAATTCGGTTTGAGGAATGCCCAGGCACTAAGGTCCACGTGGAGGAAACATG
TGGAACAAGAGGACCATCTCTGAGATCAACCACTGCAAGCGGAAGGGTGATCGAGGAATGGTGCTGCAGGGAGTGCACAAT
GCCCCCACTGTCGTTCCGGGCTAAAGATGGCTGTTGGTATGGAATGGAGATAAGGCCCAGGAAAGAACCAGAAAGTAACTTA
GTAAGGTCAATGGTGACTGCAGGATCAACTGATCACATGGATCACTTCTCCCTTGGAGTGCTTGTGATTCTGCTCATGGTGCAG
GAAGGGCTGAAGAAGAGAATGACCACAAAGATCATCATAAGCACATCGATGGCAGTGCTGGTAGCTATGATCCTGGGAGGAT
TTTCAATGAGTGACCTGGCTAAGCTTGCAATTTTGATGGGTGCCACCTTCGCGGAAATGAACACTGGAGGAGATGTAGCTCAT
```

-continued
```
CTGGCGCTGATAGCGGCATTCAAAGTCAGACCAGCGTTGCTGGTATCTTTCATCTTCAGAGCTAATTGGACACCCCGTGAAAGC
ATGCTGCTGGCCTTGGCCTCGTGTCTTTTGCAAACTGCGATCTCCGCCTTGGAAGGCGACCTGATGGTTCTCATCAATGGTTTT
GCTTTGGCCTGGTTGGCAATACGAGCGATGGTTGTTCCACGCACTGATAACATCACCTTGGCAATCCTGGCTGCTCTGACACCA
CTGGCCCGGGGCACACTGCTTGTGGCGTGGAGAGCAGGCCTTGCTACTTGCGGGGGGTTTATGCTCCTCTCTCTGAAGGGAA
AAGGCAGTGTGAAGAAGAACTTACCATTTGTCATGGCCCTGGGACTAACCGCTGTGAGGCTGGTCGACCCCATCAACGTGGTG
GGACTGCTGTTGCTCACAAGGAGTGGGAAGCGGAGCTGGCCCCCTAGCGAAGTACTCACAGCTGTTGGCCTGATATGCGCAT
TGGCTGGAGGGTTCGCCAAGGCAGATATAGAGATGGCTGGGCCCATGGCCGCGGTCGGTCTGCTAATTGTCAGTTACGTGGT
CTCAGGAAAGAGTGTGGACATGTACATTGAAAGAGCAGGTGACATCACATGGGAAAAAGATGCGGAAGTCACTGGAAACAG
TCCCCGGCTCGATGTGGCGCTAGATGAGAGTGGTGATTTCTCCCTGGTGGAGGATGACGGTCCCCCCATGAGAGAGATCATAC
TCAAGGTGGTCCTGATGACCATCTGTGGCATGAACCCAATAGCCATACCCTTTGCAGCTGGAGCGTGGTACGTATACGTGAAG
ACTGGAAAAAGGAGTGGTGCTCTATGGGATGTGCCTGCTCCCAAGGAAGTAAAAAAGGGGGAGACCACAGATGGAGTGTAC
AGAGTAATGACTCGTAGACTGCTAGGTTCAACACAAGTTGGAGTGGGAGTTATGCAAGAGGGGGTCTTTCACACTATGTGGC
ACGTCACAAAAGGATCCGCGCTGAGAAGCGGTGAAGGGAGACTTGATCCATACTGGGGAGATGTCAAGCAGGATCTGGTGT
CATACTGTGGTCCATGGAAGCTAGATGCCGCCTGGGACGGGCACAGCGAGGTGCAGCTCTTGGCCGTGCCCCCCGGAGAGAG
AGCGAGGAACATCCAGACTCTGCCCGGAATATTTAAGACAAAGGATGGGGACATTGGAGCGGTTGCGCTGGATTACCCAGCA
GGAACTTCAGGATCTCCAATCCTAGACAAGTGTGGGAGAGTGATAGGACTTTATGGCAATGGGTCGTGATCAAAAATGGGA
GTTATGTTAGTGCCATCACCCAAGGGAGGAGGGAGGAAGAGACTCCTGTTGAGTGCTTCGAGCCTTCGATGCTGAAGAAGAA
GCAGCTAACTGTCTTAGACTTGCATCCTGGAGCTGGGAAAACCAGGAGAGTTCTTCCTGAAATAGTCCGTGAAGCCATAAAAA
CAAGACTCCGTACTGTGATCTTAGCTCCAACCAGGGTTGTCGCTGCTGAAATGGAGGAAGCCCTTAGAGGGCTTCCAGTGCGT
TATATGACAACAGCAGTCAATGTCACCCACTCTGGAACAGAAATCGTCGACTTAATGTGCCATGCCACCTTCACTTCACGTCTAC
TACAGCCAATCAGAGTCCCCAACTATAATCTGTATATTATGGATGAGGCCCACTTCACAGATCCCTCAAGTATAGCAGCAAGAG
GATACATTTCAACAAGGGTTGAGATGGGCGAGGCGGCTGCCATCTTCATGACCGCCACGCCACCAGGAACCCGTGACGCATTT
CCGGACTCCAACTCACCAATTATGGACACCGAAGTGGAAGTCCCAGAGAGAGCCTGGAGCTCAGGCTTTGATTGGGTGACGG
ATCATTCTGGAAAAACAGTTTGGTTTGTTCCAAGCGTGAGGAACGGCAATGAGATCGCAGCTTGTCTGACAAAGGCTGGAAAA
CGGGTCATACAGCTCAGCAGAAAGACTTTTGAGACAGAGTTCCAGAAAACAAAACATCAAGAGTGGGACTTTGTCGTGACAA
CTGACATTTCAGAGATGGGCGCCAACTTTAAAGCTGACCGTGTCATAGATTCCAGGAGATGCCTAAAGCCGGTCATACTTGAT
GGCGAGAGAGTCATTCTGGCTGGACCCATGCCTGTCACACATGCCAGCGCTGCCCAGAGGAGGGGGCGCATAGGCAGGAAT
CCCAACAAACCTGGAGATGAGTATCTGTATGGAGGTGGGTGCGCAGAGACTGACGAAGACCATGCACACTGGCTTGAAGCAA
GAATGCTCCTTGACAATATTTACCTCCAAGATGGCCTCATAGCCTCGCTCTATCGACCTGAGGCCGACAAAGTAGCAGCCATTG
AGGGAGAGTTCAAGCTTAGGACGGAGCAAAGGAAGACCTTTGTGGAACTCATGAAAAGAGGAGATCTTCCTGTTTGGCTGGC
CTATCAGGTTGCATCTGCCGGAATAACCTACACAGATAGAAGATGGTGCTTTGATGGCACGACCAACAACACCATAATGGAAG
ACAGTGTGCCGGCAGAGGTGTGGACCAGACACGGAGAGAAAAGAGTGCTCAAACCGAGGTGGATGGACGCCAGAGTTTGTT
CAGATCATGCGGCCCTGAAGTCATTCAAGGAGTTTGCCGCTGGGAAAAGAGGAGCGGCTTTTGGAGTGATGAAGCCCTGGG
AACACTGCCAGGACACATGACAGAGAGATTCCAGGAAGCCATTGACAACCTCGCTGTGCTCATGCGGGCAGAGACTGGAAGC
AGGCCTTACAAAGCCGCGGCGGCCCAATTGCCGGAGACCCTAGAGACCATTATGCTTTTGGGGTTGCTGGGAACAGTCTCGCT
GGGAATCTTTTTCGTCTTGATGAGGAACAAGGGCATAGGGAAGATGGGCTTTGGAATGGTGACTCTTGGGGCCAGCGCATGG
CTCATGTGGCTCTCGGAAATTGAGCCAGCCAGAATTGCATGTGTCCTCATTGTTGTGTTCCTATTGCTGGTGGTGCTCATACCTG
AGCCAGAAAAGCAAAGATCTCCCCAGGACAACCAAATGGCAATCATCATCATGGTAGCAGTAGGTCTTCTGGGCTTGATTACC
GCCAATGAACTCGGATGGTTGGAGAGAACAAAGAGTGACCTAAGCCATCTAATGGGAAGGAGAGAGGAGGGGGCAACCATA
GGATTCTCAATGGACATTGACCTGCGCCAGCCTCAGCTTGGGCCATCTATGCTGCCTTGACAACTTTCATTACCCCAGCCGTCC
AACATGCAGTGACCACTTCATACAACAACTACTCCTTAATGGCGATGGCCACGCAAGCTGGAGTGTTGTTTGGTATGGGCAAA
```

-continued
GGGATGCCATTCTACGCATGGGACTTTGGAGTCCCGCTGCTAATGATAGGTTGCTACTCACAATTAACACCCCTGACCCTAATA
GTGGCCATCATTTTGCTCGTGGCGCACTACATGTACTTGATCCCAGGGCTGCAGGCAGCAGCTGCGCGTGCTGCCCAGAAGAG
AACGGCAGCTGGCATCATGAAGAACCCTGTTGTGGATGGAATAGTGGTGACTGACATTGACACAATGACAATTGACCCCCAA
GTGGAGAAAAAGATGGGACAGGTGCTACTCATAGCAGTAGCCGTCTCCAGCGCCATACTGTCGCGGACCGCCTGGGGGTGG
GGGGAGGCTGGGGCCCTGATCACAGCGGCAACTTCCACTTTGTGGGAAGGCTCTCCGAACAAGTACTGGAACTCCTCTACAGC
CACTTCACTGTGTAACATTTTTAGGGGAAGTTACTTGGCTGGAGCTTCTCTAATCTACACAGTAACAAGAAACGCTGGCTTGGT
CAAGAGACGTGGGGGTGGAACAGGAGAGACCCTGGGAGAGAAATGGAAGGCCCGCTTGAACCAGATGTCGGCCCTGGAGT
TCTACTCCTACAAAAGTCAGGCATCACCGAGGTGTGCAGAGAAGAGGCCCGCCGCGCCCTCAAGGACGGTGTGGCAACGGG
AGGCCATGCTGTGTCCCGAGGAAGTGCAAAGCTGAGATGGTTGGTGGAGCGGGGATACCTGCAGCCCTATGGAAAGGTCATT
GATCTTGGATGTGGCAGAGGGGGCTGGAGTTACTACGCCGCCACCATCCGCAAAGTTCAAGAAGTGAAAGGATACACAAAAG
GAGGCCCTGGTCATGAAGAACCCATGTTGGTGCAAAGCTATGGGTGGAACATAGTCCGTCTTAAGAGTGGGGTGGACGTCTT
TCATATGGCGGCTGAGCCGTGTGACACGTTGCTGTGTGACATAGGTGAGTCATCATCTAGTCCTGAAGTGGAAGAAGCACGG
ACGCTCAGAGTCCTCTCCATGGTGGGGATTGGCTTGAAAAAAGACCAGGAGCCTTTTGTATAAAAGTGTTGTGCCCATACAC
CAGCACTATGATGGAAACCCTGGAGCGACTGCAGCGTAGGTATGGGGAGGACTGGTCAGAGTGCCACTCTCCCGCAACTCT
ACACATGAGATGTACTGGGTCTCTGGAGCGAAAAGCAACACCATAAAAAGTGTGTCCACCACGAGCCAGCTCCTCTTGGGGC
GCATGGACGGGCCCAGGAGGCCAGTGAAATATGAGGAGGATGTGAATCTCGGCTCTGGCACGCGGGCTGTGGTAAGCTGCG
CTGAAGCTCCCAACATGAAGATCATTGGTAACCGCATTGAAAGGATCCGCAGTGAGCACGCGGAAACGTGGTTCTTTGACGA
GAACCACCCATATAGGACATGGGCTTACCATGGAAGCTATGAGGCCCCCACACAAGGGTCAGCGTCCTCTCTAATAAACGGGG
TTGTCAGGCTCCTGTCAAAACCCTGGGATGTGGTGACTGGAGTCACAGGAATAGCCATGACCGACACCACACCGTATGGTCAG
CAAAGAGTTTTCAAGGAAAAAGTGGACACTAGGGTGCCAGACCCCCAAGAAGGCACTCGTCAGGTTATGAGCATGGTCTCTTC
CTGGTTGTGGAAAGAGCTAGGCAAACACAAACGGCCACGAGTCTGTACCAAAGAAGAGTTCATCAACAAGGTTCGTAGCAAT
GCAGCATTAGGGGCAATATTTGAAGAGGAAAAAGAGTGGAAGACTGCAGTGGAAGCTGTGAACGATCCAAGGTTCTGGGCT
CTAGTGGACAAGGAAAGAGAGCACCACCTGAGAGGAGAGTGCCAGAGTTGTGTGTACAACATGATGGGAAAAAGAGAAAAG
AAACAAGGGGAATTTGGAAAGGCCAAGGGCAGCCGCGCCATCTGGTATATGTGGCTAGGGGCTAGATTTCTAGAGTTCGAAG
CCCTTGGATTCTTGAACGAGGATCACTGGATGGGAGAGAGAACTCAGGAGGTGGTGTTGAAGGGCTGGGATTACAAAGAC
TCGGATATGTCCTAGAAGAGATGAGTCGCATACCAGGAGGAAGGATGTATGCAGATGACACTGCTGGCTGGGACACCCGCAT
CAGCAGGTTTGATCTGGAGAATGAAGCTCTAATCACCAACCAAATGGAGAAAGGGCACAGGGCCTTGGCATTGGCCATAATC
AAGTACACATACCAAAACAAAGTGGTAAAGGTCCTTAGACCAGCTGAAAAAGGGAAGACAGTTATGGACATTATTTCGAGAC
AAGACCAAAGGGGGAGCGGACAAGTTGTCACTTACGCTCTTAACACATTTACCAACCTAGTGGTGCAACTCATTCGGAATATG
GAGGCTGAGGAAGTTCTAGAGATGCAAGACTTGTGGCTGCTGCGGAGGTCAGAGAAAGTGACCAACTGGTTGCAGAGCAAC
GGATGGGATAGGCTCAAACGAATGGCAGTCAGTGGAGATGATTGCGTTGTGAAGCCAATTGATGATAGGTTTGCACATGCCC
TCAGGTTCTTGAATGATATGGGAAAAGTTAGGAAGGACACACAAGAGTGGAAACCCTCAACTGGATGGGACAACTGGGAAG
AAGTTCCGTTTTGCTCCCACCACTTCAACAAGCTCCATCTCAAGGACGGGAGGTCCATTGTGGTTCCCTGCCGCCACCAAGATG
AACTGATTGGCCGGGCCCGCGTCTCTCCAGGGGCGGGATGGAGCATCCGGGAGACTGCTTGCCTAGCAAAATCATATGCGCA
AATGTGGCAGCTCCTTTATTTCCACAGAAGGGACCTCCGACTGATGGCCAATGCCATTTGTTCATCTGTGCCAGTTGACTGGGT
TCCAACTGGGAGAACTACCTGGTCAATCCATGGAAAGGGAGAATGGATGACCACTGAAGACATGCTTGTGGTGTGGAACAGA
GTGTGGATTGAGGAGAACGACCACATGGAAGACAAGACCCCAGTTACGAAATGGACAGACATTCCCTATTTGGGAAAAAGGG
AAGACTTGTGGTGTGGATCTCTCATAGGGCACAGACCGCGCACCACCTGGGCTGAGAACATTAAAAACACAGTCAACATGGT
GCGCAGGATCATAGGTGATGAAGAAAGTACATGGACTACCTATCCACCCAAGTTCGCTACTTGGGTGAAGAAGGGTCTACA
CCTGGAGTGCTGTAAGCACCAATCTTAGTGTTGTCAGGCCTGCTAGTCAGCCACAGCTTGGGGAAAGCTGTGCAGCCTGTGAC
CCCCCCAGGAGAAGCTGGGAAACCAAGCCTATAGTCAGGCCGAGAACGCCATGGCACGGAAGAAGCCATGCTGCCTGTGAGC -continued

```
CCCTCAGAGGACACTGAGTCAAAAAACCCCACGCGCTTGGAGGCGCAGGATGGGAAAAGAAGGTGGCGACCTTCCCCACCCT

TCAATCTGGGGCCTGAACTGGAGATCAGCTGTGGATCTCCAGAAGAGGGACTAGTGGTTAGAGGAG
```

In some embodiments, the Zika virus has a RNA genome corresponding to the DNA sequence provided by the nucleic acid sequence of any one of SEQ ID NOs: 2-13 or 73. In some embodiments, the Zika virus has a variant genome that is at least 80%, 81%, 82%, 83%, 84%, 85%, 86%, 87%, 88%, 89%, 90%, 91%, 92%. 93%, 94%, 95%, 96%, 97%, 98%, 99%, 99.5%, 99.6%, 99.7%, 99.8% or 99.9% identical to any one of SEQ ID NOs: 2-13 or 78.

Provided below are amino acid sequences of the E-proteins of Zika strains that may be used in the methods, compositions, and/or vaccines described herein.

```
isol-ARB15076.AHF49784.1.Central_African_Republic/291-788
Flavivirus envelope glycoprotein E.
                                                                   SEQ ID NO: 14
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMIVNDENRAKVEVTPNSPRA EATLGGFGSLGLDCEPRTGLDFSDLYYLTMNNKHWLVHKEWFHDIPLPWHAGADTGTPHWNNKEALVEFKDAHAKRQTVVVLGS QEGAVHTALAGALEAEMDGAKGRLFSGHLKCRLKMDKLRLKGVSYSLCTAAFTFTKVPAETLHGTVTVEVQYAGTDGPCKVPAQM AVDMQTLTPVGRLITANPVITESTENSKMMLELDPPFGDSYIVIGVGDKKITHHWHRSGSTIGKAFEATVRGAKRMAVLGDTAWDF

GSVGGVFNSLGKGIHQIFGAAFKSLFGGMSWFSQILIGTLLVWLGLNTKNGSISLTCLALGGVMIFLSTAVSA isol-IbH_30656.AEN75265.1.Nigeria/291-788 Flavivirus envelope
glycoprotein E.
                                                                   SEQ ID NO: 15
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMIVNDENRAKVEVTPNSPRA EATLGGFGSLGLDCEPRTGLDFSDLYYLTMNNKHWLVHKEWFHDIPLPWHSGADTETPHWNNKEALVEFKDAHAKRQTVVVLGS QEGAVHTALAGALEAEMDGAKGRLSSGHLKCRLKMDKLRLKGVSYSLCTAAFTFTKVPAETLHGTVTVEVQYAGRDGPCKVPAQM AVDMQTLTPVGRLITANPVITESTENSKMMLELDPPFGDSYIVIGVGDKKITHHWHRSGSIIGKAFEATVRGAKRMAVLGDTAWDF

GSVGGVFNSLGKGIHQIFGAAFKSLFGGMSWFSQILIGTLLVWLGLNTKNGSISLTCLALGGVMIFLSTAVSA

ArB1362.AHL43500.1.-/291-794 Flavivirus envelope glycoprotein E.
                                                                   SEQ ID NO: 16
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMIVNDXXXXXXXNRAEVEVT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLFSGHLKCRLKMDKLRLKGVSYSLCTAAFTFTKVPAETLHGTVTVEVQYAGTDGPCK VPAQMAVDMQTLTPVGRLITANPVITESTENSKMMLELDPPFGDSYIVIGVGDKKITHHWHRSGSTIGKAFEATVRGAKRMAVLG

DTAWDFGSVGGVFNSLGKGIHQIFGAAFKSLFGGMSWFSQILIGTLLVWLGLNTKNGSISLTCLALGGVMIFLSTAVSA

ArD128000.AHL43502.1.-/291-794 Flavivirus envelope glycoprotein E.
                                                                   SEQ ID NO: 17
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMXXXXXGHETDENRAKVEVT PNSPRAEATLGGFGSLGLDCEPRTGLDFSDLYYLTMNNKHRLVRKEWFHDIPLPWHAGADTGTPHWNNKEALVEFKDAHAKRQT VVVLGSQEGAVHTALAGALEAEMDGAKGRLFSGHLKCRLKMDKLRLKGVSYSLCTAAFTFTKVPAETLHGTVTVEVQYAGTDGPCK VPAQMAVDMQTLTPVGRLITANPVITESTENSKMMLELDPPFGDSYIVIGVGDKKITHHWLKKGSSIGKAFEATVRGAKRMAVLGD

TAWDFGSVGGVFNSLGKGVHQIFGAAFKSLFGGMSWFSQILIGTLLVWLGLNTKNGSISLTCLALGGVMIFLSTAVSA

ArD158095.AHL43505.1.-/291-794 Flavivirus envelope glycoprotein E.
                                                                   SEQ ID NO: 18
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMIVNDIGHETDENRAKVEVT PNSPRAEATLGGFGSLGLDCEPRTGLDFSDLYYLTMNNKHWLVHKEWFHDIPLPWHAGADTGTPHWNNKEALVEFKDAHAKRQT
```

-continued

VVVLGSQEGAVHTALAGALEAEMDGAKGRLFSGHLKCRLKMDKLRLKGVSYSLCTAAFTFTKVPAETLHGTVTVEVQYAGTDGPCK

VPAQMAVDMQTLTPVGRLITANPVITESTENSKMMLELDPPFGDSYIVIGVGDKKITHHWHRSGSTIGKAFEATVRGAKRMAVLG

DTAWDFGSVGGVFNSLGKGIHQIFGAAFKSLFGGMSWFSQILIGTLLVWLGLNTKNGSISLTCLALGGVMIFLSTAVSA

ArD158084.AHL43504.1.-/291-794 Flavivirus envelope glycoprotein E.
SEQ ID NO: 19

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIVNDIGHETDENRAKVEVT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLFSGHLKCRLKMDKLRLKGVSYSLCTAAFTFTKVPAETLHGTVTVEVQYAGTDGPCK

VPAQMAVDMQTLTPVGRLITANPVITESTENSKMMLELDPPFGDSYIVIGVGDKKITHHWHRSGSTIGKAFEATVRGAKRMAVLG

DTAWDFGSVGGVFNSLGKGIHQIFGAAFKSLFGGMSWFSQILIGTLLVWLGLNTKNGSISLTCLALGGVMIFLSTAVSA isol-ARB13565.AHF49783.1.Central_African_Republic/291-794
Flavivirus envelope glycoprotein E.
SEQ ID NO: 20

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIVNDIGHETDENRAKVEVT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLFSGHLKCRLKMDKLRLKGVSYSLCTAAFTFTKVPAETLHGTVTVEVQYAGTDGPCK

VPAQMAVDMQTLTPVGRLITANPVITESTENSKMMLELDPPFGDSYIVIGVGDKKITHHWHRSGSTIGKAFEATVRGAKRMAVLG

DTAWDFGSVGGVFNSLGKGVHQIFGAAFKSLFGGMSWFSQILIGTLLVWLGLNTKNGSISLTCLALGGVMIFLSTAVSA isol-ARB7701.AHF49785.1.Central_African_Republic/291-794
Flavivirus envelope glycoprotein E.
SEQ ID NO: 21

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIVNDIGHETDENRAKVEVT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLFSGHLKCRLKMDKLRLKGVSYSLCTAAFTFTKVPAETLHGTVTVEVQYAGTDGPCK

VPAQMAVDMQTLTPVGRLITANPVITESTENSKMMLELDPPFGDSYIVIGVGDKKITHHWHRSGSTIGKAFEATVRGAKRMAVLG

DTAWDFGSVGGVFNSLGKGVHQIFGAAFKSLFGGMSWFSQILIGTLLVWLGLNTKNGSISLTCLALGGVMIFLSTAVSA isol-ArD_41519.AEN75266.1.Senegal/291-794 Flavivirus envelope
glycoprotein E.
SEQ ID NO: 22

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIVNDTGHETDENRAKVEVT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLFSGHLKCRLKMDKLRLKGVSYSLCTAAFTFTKVPAETLHGTVTVEVQYAGTDGPCK

VPAQMAVDMQTLTPVGRLITANPVITESTENSKMMLELDPPFGDSYIVIGVGDKKITHHWHRSGSTIGKAFEATVRGAKRMAVLG

DTAWDFGSVGGVFNSLGKGIHQIFGAAFKSLFGGMSWFSQILIGTLLVWLGLNTKNGSISLTCLALGGVMIFLSTAVSA

MR766-NIID.BAP47441.1.Uganda/291-794 Flavivirus envelope glycoprotein E.
SEQ ID NO: 23

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMTVNDIGYETDENRAKVEVT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGKLFSGHLKCRLKMDKLRLKGVSYSLCTAAFTFTKVPAETLHGTVTVEVQYAGTDGPCK

IPVQMAVDMQTLTPVGRLITANPVITESTENSKMMLELDPPFGDSYIVIGVGDKKITHHWHRSGSTIGKAFEATVRGAKRMAVLGD

TAWDFGSVGGVFNSLGKGIHQIFGAAFKSLFGGMSWFSQILIGTLLVWLGLNTKNGSISLTCLALGGVMIFLSTAVSA

-continued

LC002520.1/326-829 Zika virus genomic RNA, strain: MR766-NIID, Uganda,
Flavivirus envelope glycoprotein E.
SEQ ID NO: 24
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMTVNDIGYETDENRAKVEVT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGKLFSGHLKCRLKMDKLRLKGVSYSLCTAAFTFTKVPAETLHGTVTVEVQYAGTDGPCK IPVQMAVDMQTLTPVGRLITANPVITESTENSKMMLELDPPFGDSYIVIGVGDKKITHHWHRSGSTIGKAFEATVRGAKRMAVLGD

TAWDFGSVGGVFNSLGKGIHQIFGAAFKSLFGGMSWFSQILIGTLLVWLGLNTKNGSISLTCLALGGVMIFLSTAVSA isol-MR_766.AEN75263.1.Uganda/291-794 Flavivirus envelope glycoprotein E.
SEQ ID NO: 25
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMIVNDTGYETDENRAKVEVT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGKLFSGHLKCRLKMDKLRLKGVSYSLCTAAFTFTKVPAETLHGTVTVEVQYAGTDGPCK IPVQMAVDMQTLTPVGRLITANPVITESTENSKMMLELDPPFGDSYIVIGVGDKKITHHWHRSGSTIGKAFEATVRGAKRMAVLGD

TAWDFGSVGGVFNSLGKGIHQIFGAAFKSLFGGMSWFSQILIGTLLVWLGLNTKNGSISLTCLALGGVMIFLSTAVSA

ArD7117.AHL43501.1.-/291-794 Flavivirus envelope glycoprotein E.
SEQ ID NO: 26
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMIVNDIGHETDENRAKVEVT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLFSGHLKCRLKMDKLRLKGVSYSLCTAVCTAAKVPAETLHGTVTVEVQYAGTDGPC KVPAQMAVDMQTLTPVGRLITANPVITESTENSKMMLELDPPFGDSYIVIGVGDKKITHHWHRSGSTIGKAFEATVRGAKRMAVL

GDTAWDFGSVGGVFNSLGKGIHQIFGAAFKSLFGGMSWFSQILIGTLLVWLGLNTKNGSISLTCLALGGVMIFLSTAVSA

AY632535.2/326-825 NC_012532.1 Zika virus strain MR 766, Uganda,
Flavivirus envelope glycoprotein E.
SEQ ID NO: 27
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMIGYETDEDRAKVEVTPNSPR AEATLGGFGSLGLDCEPRTGLDFSDLYYLTMNNKHWLVHKEWFHDIPLPWHAGADTGTPHWNNKEALVEFKDAHAKRQTVVVL GSQEGAVHTALAGALEAEMDGAKGRLFSGHLKCRLKMDKLRLKGVSYSLCTAAFTFTKVPAETLHGTVTVEVQYAGTDGPCKIPVQ MAVDMQTLTPVGRLITANPVITESTENSKMMLELDPPFGDSYIVIGVGDKKITHHWHRSGSTIGKAFEATVRGAKRMAVLGDTAW

DFGSVGGVFNSLGKGIHQIFGAAFKSLFGGMSWFSQILIGTLLVWLGLNTKNGSISLTCLALGGVMIFLSTAVSA

MR_766.AAV34151.1.Uganda/291-790 Flavivirus envelope glycoprotein E.
|Q32ZE1|Q32ZE1_9FL
SEQ ID NO: 28
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMIGYETDEDRAKVEVTPNSPR AEATLGGFGSLGLDCEPRTGLDFSDLYYLTMNNKHWLVHKEWFHDIPLPWHAGADTGTPHWNNKEALVEFKDAHAKRQTVVVL GSQEGAVHTALAGALEAEMDGAKGRLFSGHLKCRLKMDKLRLKGVSYSLCTAAFTFTKVPAETLHGTVTVEVQYAGTDGPCKIPVQ MAVDMQTLTPVGRLITANPVITESTENSKMMLELDPPFGDSYIVIGVGDKKITHHWHRSGSTIGKAFEATVRGAKRMAVLGDTAW

DFGSVGGVFNSLGKGIHQIFGAAFKSLFGGMSWFSQILIGTLLVWLGLNTKNGSISLTCLALGGVMIFLSTAVSA

MR_766.YP_009227198.1.Uganda/1-500 envelope protein E
[Zika virus]
SEQ ID NO: 29
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMIGYETDEDRAKVEVTPNSPR AEATLGGFGSLGLDCEPRTGLDFSDLYYLTMNNKHWLVHKEWFHDIPLPWHAGADTGTPHWNNKEALVEFKDAHAKRQTVVVL

```
GSQEGAVHTALAGALEAEMDGAKGRLFSGHLKCRLKMDKLRLKGVSYSLCTAAFTFTKVPAETLHGTVTVEVQYAGTDGPCKIPVQ

MAVDMQTLTPVGRLITANPVITESTENSKMMLELDPPFGDSYIVIGVGDKKITHHWHRSGSTIGKAFEATVRGAKRMAVLGDTAW

DFGSVGGVFNSLGKGIHQIFGAAFKSLFGGMSWFSQILIGTLLVWLGLNTKNGSISLTCLALGGVMIFLSTAVSA

KU681081.3/308-811 Zika virus isolate Zika virus/H. sapiens-tc/THA/2014/
SV0127-14, Thailand, Flavivirus envelope glycoprotein E.
                                                             SEQ ID NO: 30
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFACSKKMTGKSIQPENLEYRIMLSVHGSQHSGMIVNDTGHETDENRAKVEIT PNSPRAEATLGGFGSLGLDCEPRTGLDFSDLYYLTMNNKHWLVHKEWFHDIPLPWHTGADTGTPHWNNKEALVEFKDAHAKRQT VVVLGSQEGAVHTALAGALEAEMDGAKGRLSSGHLKCRLKMDKLRLKGVSYSLCTAAFTFTKIPAETLHGTVTVEVQYAGTDGPCK VPAQMAVDMQTLTPVGRLITANPVITEGTENSKMMLELDPPFGDSYIVIGVGEKKITHHWHRSGSTIGKAFEATVRGAKRMAVLG

DTAWDFGSVGGVLNSLGKGIHQIFGAAFKSLFGGMSWFSQILIGTLLMWLGLNTKNGSISLMCLALGGVLIFLSTAVSA isol-Zika_virus % H. sapiens-tc % THA % 2014 %
SV0127-_14.AMD61710.1.Thailand/291-794 Flavivirus envelope glycoprotein E.
                                                             SEQ ID NO: 31
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFACSKKMTGKSIQPENLEYRIMLSVHGSQHSGMIVNDTGHETDENRAKVEIT PNSPRAEATLGGFGSLGLDCEPRTGLDFSDLYYLTMNNKHWLVHKEWFHDIPLPWHTGADTGTPHWNNKEALVEFKDAHAKRQT VVVLGSQEGAVHTALAGALEAEMDGAKGRLSSGHLKCRLKMDKLRLKGVSYSLCTAAFTFTKIPAETLHGTVTVEVQYAGTDGPCK VPAQMAVDMQTLTPVGRLITANPVITEGTENSKMMLELDPPFGDSYIVIGVGEKKITHHWHRSGSTIGKAFEATVRGAKRMAVLG

DTAWDFGSVGGVLNSLGKGIHQIFGAAFKSLFGGMSWFSQILIGTLLMWLGLNTKNGSISLMCLALGGVLIFLSTAVSA

CK-ISL_2014.AIC06934.1.Cook_Islands/1-504 Flavivirus
envelope glycoprotein E. (Fragment) OS = Zika virus GN = E
PE = 4 SV = 1
                                                             SEQ ID NO: 32
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFACSKKMTGKSIQPENLEYRIMLSVHGSQHSGMIVNDTGHETDENRAKVEIT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLSSGHLKCRLKMDKLRLKGVSYSLCTAAFTFTKIPAETLHGTVTVEVQYAGTDGPCK VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

Natal_RGN.AMB18850.1.Brazil:_Rio_Grande_do_Norte,_Natal/291-794
Flavivirus envelope glycoprotein E.]
                                                             SEQ ID NO: 33
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFACSKKMTGKSIQPENLEYRIMLSVHGSQHSGMIVNDTGHETDENRAKVEIT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLSSGHLKCRLKMDKLRLKGVSYSLCTAAFTFTKIPAETLHGTVTVEVQYAGTDGPCK VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-Si323.AMC37200.1.Colombia/1-504 Flavivirus envelope glycoprotein E.
                                                             SEQ ID NO: 34
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFACSKKMTGKSIQPENLEYRIMLSVHGSQHSGMIVNDTGHETDENRAKVEIT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLSSGHLKCRLKMDKLRLKGVSYSLCTAAFTFTKIPAETLHGTVTVEVQYAGTDGPCK VPAQMAVDMQTLTPVGRLITANPVITESTENSKMMLELDPPFGDSYIVIGVGEKKITHHWHRSGSTIGKAFEATVRGAKRMAVLGD TAWDFGSVGGALNSLGKGIHQIFGAAFKSLFGGMSWFSQILIGTLLMWLGLNTKNGSISLMCLALGGVLIFLSTAVSA
```

KU707826.1/317-820 Zika virus isolate SSABR1, Brazil, Flavivirus envelope
glycoprotein E.

SEQ ID NO: 35

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

KU509998.1/326-829 Zika virus strain Haiti/1225/2014, Haiti, Flavivirus
envelope glycoprotein E.

SEQ ID NO: 36

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-GDZ16001.AML82110.1.China/291-794 Flavivirus envelope glycoprotein E.

SEQ ID NO: 37

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

BeH819015.AMA12085.1.Brazil/291-794 Flavivirus envelope glycoprotein E.]

SEQ ID NO: 38

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

MRS_OPY_Martinique_PaRi_2015.AMC33116.1.Martinique/291-794
Flavivirus envelope glycoprotein E.

SEQ ID NO: 39

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

KU501215.1/308-811 Zika virus strain PRVABC59, Puerto Rico, Flavivirus
envelope glycoprotein E.

SEQ ID NO: 40

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

```
VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

Haiti_%_1225%2014.AMB37295.1.Haiti/291-794 Flavivirus envelope glycoprotein E.
                                                                         SEQ ID NO: 41
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFACSKKMTGKSIQPENLEYRIMLSVHGSQHSGMIVNDTGHETDENRAKVEIT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLSSGHLKCRLKMDKLRLKGVSYSLCTAAFTFTKIPAETLHGTVTVEVQYAGTDGPCK VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

KU527068.1/308-811 Zika virus strain Natal RGN, Brazil: Rio Grande do Norte,
Natal, Flavivirus envelope glycoprotein E.
                                                                         SEQ ID NO: 42
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFACSKKMTGKSIQPENLEYRIMLSVHGSQHSGMIVNDTGHETDENRAKVEIT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLSSGHLKCRLKMDKLRLKGVSYSLCTAAFTFTKIPAETLHGTVTVEVQYAGTDGPCK VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-Z1106027.ALX35662.1.Suriname/5-508 Flavivirus envelope glycoprotein E.
                                                                         SEQ ID NO: 43
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFACSKKMTGKSIQPENLEYRIMLSVHGSQHSGMIVNDTGHETDENRAKVEIT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLSSGHLKCRLKMDKLRLKGVSYSLCTAAFTFTKIPAETLHGTVTVEVQYAGTDGPCK VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-FLR.AMM39804.1.Colombia:_Barranquilla/291-794 Flavivirus envelope
glycoprotein E.
                                                                         SEQ ID NO: 44
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFACSKKMTGKSIQPENLEYRIMLSVHGSQHSGMIVNDTGHETDENRAKVEIT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLSSGHLKCRLKMDKLRLKGVSYSLCTAAFTFTKIPAETLHGTVTVEVQYAGTDGPCK VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

PLCal_ZV_isol-From_Vero_E6_cells.AHL37808.1.Canada/254-757
Flavivirus envelope glycoprotein E.
                                                                         SEQ ID NO: 45
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFACSKKMTGKSIQPENLEYRIMLSVHGSQHSGMIVNDTGHETDENRAKVEIT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLSSGHLKCRLKMDKLRLKGVSYSLCTAAFTFTKIPAETLHGTVTVEVQYAGTDGPCK VPAQMAVDMQTLTPVGRLITANPVITESTENSKMMLELDPPFGDSYIVIGVGEKKITHHWHRSGSTIGKAFEATVRGAKRMAVLGD TAWDFGSVGGALNSLGKGIHQIFGAAFKSLFGGMSWFSQILIGTLLMWLGLNTKNGSISLMCLALGGVLIFLSTAVSA
```

-continued

BeH818995.AMA12084.1.Brazil/291-794 Flavivirus envelope glycoprotein E.
[Zika virus].
SEQ ID NO: 46
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIFGAAFKSLFGGMSWFSQILIGTLLMWLGLNTKNGSISLMCLALGGVLIFLSTAVSA H/PF/2013.AHZ13508.1.French_Polynesia/291-794 Flavivirus envelope glycoprotein E.
SEQ ID NO: 47
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIFGAAFKSLFGGMSWFSQILIGTLLMWLGLNTKNGSISLMCLALGGVLIFLSTAVSA PRVABC59.AMC13911.1.Puerto_Rico/291-794 Flavivirus envelope glycoprotein E.
SEQ ID NO: 48
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIFGAAFKSLFGGMSWFSQILIGTLLMWLGLNTKNGSISLMCLALGGVLIFLSTAVSA KU321639.1/326-829 Zika virus strain ZikaSPH2015, Brazil, Flavivirus
envelope glycoprotein E.
SEQ ID NO: 49
IRCIGVSNRDFVEGMSGGTWVDIVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIFGAAFKSLFGGMSWFSQILIGTLLMWLGLNTKNGSISLMCLALGGVLIFLSTAVSA ZikaSPH2015.ALU33341.1.Brazil/291-794 Flavivirus envelope glycoprotein E.
SEQ ID NO: 50
IRCIGVSNRDFVEGMSGGTWVDIVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIFGAAFKSLFGGMSWFSQILIGTLLMWLGLNTKNGSISLMCLALGGVLIFLSTAVSA 103344.AMC13912.1.Guatemala/291-794 polyprotein [Zika virus].
103344.AMC13912.1.Guatemala Flavivirus envelope glycoprotein E.
SEQ ID NO: 51
IRCIGVSNRDFVEGMSGGTWVDVVLEHGGCVTVMAQDKPTVDIELVTTTVSNMAEIRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT -continued VVVLGSQEGAVHTALAGALEAEMDGAKGRLSSGHLKCRLKMDKLRLKGVSYSLCTAAFTFTKIPAETLHGTVTVEVQYAGTDGPCK VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-Brazil-ZKV2015.AMD16557.1.Brazil/291-794 Flavivirus envelope glycoprotein E.
SEQ ID NO: 52

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGTQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

KU497555.1/308-811 Zika virus isolate Brazil-ZKV2015, Flavivirus envelope
glycoprotein E.
SEQ ID NO: 53

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGTQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-ZJ03.AMM39806.1.China/291-794 Flavivirus envelope glycoprotein E.
SEQ ID NO: 54

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGARRMAVLG

DTAWDFGSVGGALNSLGKGIHQIFGAAFKSLFGGMSWFSQILIGTLLMWLGLNTKNGSISLMCLALGGVLIFLSTAVSA isol-FSS13025.AFD30972.1.Cambodia/291-794 Flavivirus envelope glycoprotein E.
SEQ ID NO: 55

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLVWLGLNTKNGSISLMCLALGGVLIFLSTAVSA isol-Z1106032.ALX35660.1.Suriname/291-794 Flavivirus envelope glycoprotein E.
[Zika virus]
SEQ ID NO: 56

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNAKNGSISLMCLALGGVLIFLSTAVSA

-continued isol-Z1106033.ALX35659.1.Suriname/291-794 Flavivirus envelope glycoprotein E.
[Zika virus]

SEQ ID NO: 57

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNAKNGSISLMCLALGGVLIFLSTAVSA isol-BeH828305.AMK49165.1.Brazil/291-794 Flavivirus envelope glycoprotein E.

SEQ ID NO: 58

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDTQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-GD01.AMK79468.1.China/291-794 Flavivirus envelope glycoprotein E.

SEQ ID NO: 59

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNGTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-Z1106031.ALX35661.1.Suriname/291-794 Flavivirus envelope glycoprotein E.

SEQ ID NO: 60

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VLAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

ACD75819.1.Micronesia/291-794 Flavivirus envelope glycoprotein E.

SEQ ID NO: 61

IRCIGVSNRDFVEGMSGGTWVDVVLEHGGCVTVMAQDKPAVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLVWLGLNTKNGSISLTCLALGGVLIFLSTAVSA

KU681082.3/308-811 Zika virus isolate Zika virus/*H. sapiens*-tc/PHL/2012/CPC-0740,
Philippines, Flavivirus envelope glycoprotein E.

SEQ ID NO: 62

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

-continued

```
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIFGAAFKSLFGGMSWFSQILIGTLLVWLGLNTKNGSISLTCLALGGVLIFLSTAVSA isol-Zika_virus % H. sapiens-tc % PHL % 2012 % CPC-0740.AMD61711.1.Philippines/
291-794 Flavivirus envelope glycoprotein E.
                                                                    SEQ ID NO: 63
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIFGAAFKSLFGGMSWFSQILIGTLLVWLGLNTKNGSISLTCLALGGVLIFLSTAVSA isol-BeH823339.AMK49164.2.Brazil/291-794 Flavivirus envelope glycoprotein E.
                                                                    SEQ ID NO: 64
IRCIGVSNRDFVEGMSGGTWVDVVLEHGGCVTVMAQDKPTVDIELVSTTTVSNMAEVRSYCYEATISDIASDSRCPTQGEAYLDKQS
DTQYVCKRTLVDRGWGNGCGLFGKGSLVTCAKFACSKKMTGKSIQPENLEYRIMLSVHGSQHSGMIVNDTGHETDENRAKVEITP
NSPRAEATLGGFGSLGLDCEPRTGLDFSDLYYLTMNNKHWLVHKEWFHDIPLPWHAGADTGTPHWNNKEALVEFKDAHAKRQT
AVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIFGAAFKSLFGGMSWFSQILIGTLLMWLGLNTKNGSISLMCLALGGVLIFLSTAVSA isol-P6-740.AEN75264.1.Malaysia/291-794 Flavivirus envelope glycoprotein E.
                                                                    SEQ ID NO: 65
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDXGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDMQTLTPVGRLITANPVITESTENSKMMLELDPPFGDSYIVIGVGDKKITHHWXRSGSTIGKAFEATVRGAKRMAVLG
DTAWDFGSVGGALNSLGKGIHQIFGAAFKSLFGGMSWFSQILIGTLLVWLGLNTKNGSISLTCLALGGVLIFLSTAVSA KU744693.1/326-829 Zika virus isolate VE_Ganxian, China, Flavivirus envelope
glycoprotein E.
                                                                    SEQ ID NO: 66
IRCIGVSNRDFVEGMSGGTWVDVVLEHGGCVTAMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMLVNDTGHETDENRAKVEIT
PNSPRAEATLGGFGSLGLDCEPRTGLDFSDLYYLTMNNKHWLAHKEWFHDIPLPWHAGAATGTPHWNNKEALVEFKDAHAKRQT
VVVLGSQEGAVHTALAGALEAEMDGAKGRLSSGHLKCRLKMDKLRLKGVSYSLCTAAFTFTKIPAETVDGTVTVEGQYGGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIIGAAFKSLFGGMSWFSQILIGTLLMWLGLNTKNGSISLMCLALGGVLIFLSTAVSG isol-VE_Ganxian.AMK79469.1.China/291-794 Flavivirus envelope glycoprotein E.
                                                                    SEQ ID NO: 67
IRCIGVSNRDFVEGMSGGTWVDVVLEHGGCVTAMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMLVNDTGHETDENRAKVEIT
PNSPRAEATLGGFGSLGLDCEPRTGLDFSDLYYLTMNNKHWLAHKEWFHDIPLPWHAGAATGTPHWNNKEALVEFKDAHAKRQT
VVVLGSQEGAVHTALAGALEAEMDGAKGRLSSGHLKCRLKMDKLRLKGVSYSLCTAAFTFTKIPAETVDGTVTVEGQYGGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIIGAAFKSLFGGMSWFSQILIGTLLMWLGLNTKNGSISLMCLALGGVLIFLSTAVSG ArD157995.AHL43503.1.-/291-794 Flavivirus envelope glycoprotein E.
                                                                    SEQ ID NO: 68
ISCIGVSNRDLVEGMSGGTWVDVVLEHGGCVTEMAQDKPTVDIELVTMTVSNMAEVRSYCYEASLSDMASASRCPTQGEPSLDK
QSDTQSVCKRTLGDRGWGNGCGIFGKGSLVTCSKFTCCKKMPGKSIQPENLEYRIMLPVHGSQHSGMIVNDIGHETDENRAKVEV
```

-continued

```
TPNSPRAEATLGGFGSLGLDCEPRTGLDFSDLYYLTMNNKHWLVHKEWFHDIPLPWHAGADTGTPHWNNKEALVEFKDAHAKRQ

TVVVLGSQEGAVHTALAGALEAEMDGAKGRLFSGHLKCRLKMDKLRLKGVSYSLCTAAFTFTKVPAETLHGTVTVEVQSAGTDGPC

KVPAQMAVDMQTLTPVGRLITANPVITESTENSKMMLELDPPFGDSYIVIGVGDKKITHHWHRSGSTIGKAFEATVRGAKRMAVL

GDTAWDFGSVGGVFNSLGKGIHQIFGAAFKSLFGGMSWFSQILIGTLLVWLGLNTKNGSISLTCLALGGVMIFLSTAVSA

MR_766.ABI54475.1.Uganda/291-788 Flavivirus envelope glycoprotein E.
                                                                         SEQ ID NO: 69
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMIVNDENRAKVEVTPNSPRA EATLGGFGSLGLDCEPRTGLDFSDLYYLTMNNKHWLVHKEWFHDIPLPWHAGADTGTPHWNNKEALVEFKDAHAKRQTVVVLGS QEGAVHTALAGALEAEMDGAKGRLFSGHLKCRLKMDKLRLKGVSYSLCTAAFTFTKVPAETLHGTVTVEVQYAGTDGPCKVPAQM AVDMQTLTPVGRLITANPVITESTENSKMMLELDPPFGDSYIVIGVGDKKITHHWHRSGSTIGKAFEATVRGAKRMAVLGDTAWDF

GSVGGVFNSLGKGIHQIFGAAFKSLFGGMSWFSQILIGTLLVWLGLNTKNGSISLTCLALGGVMIFLSTAVSA

5'-(dldC)₁₃-3'
                                                                         SEQ ID NO: 70
dldC dldC dldC dldC dldC dldC dldC dldC dldC dldC dldC dldC dldC KLK peptide
                                                                         SEQ ID NO: 71
KLKLLLLLKLK
```

Provided below are examples of nucleic acid sequences of the genomes of Chikungunya, Japanese Encephalitis and yellow fever viruses that may be used in the methods, compositions, and/or vaccines described herein.

```
Chikungunya virus strain LR2006_OPY1, complete genome ACCESSION: DQ443544
                                                                         SEQ ID NO: 72
ATGGCTGCGTGAGACACACGTAGCCTACCAGTTTCTTACTGCTCTACTCTGCAAAGCAAGAGATTAATAACCCATCATGGATC CTGTGTACGTGGACATAGACGCTGACAGCGCCTTTTTGAAGGCCCTGCAACGTGCGTACCCCATGTTTGAGGTGGAACCAA GGCAGGTCACACCGAATGACCATGCTAATGCTAGAGCGTTCTCGCATCTAGCTATAAAACTAATAGAGCAGGAAATTGACCC CGACTCAACCATCCTGGATATCGGCAGTGCGCCAGCAAGGAGGATGATGTCGGACAGGAAGTACCACTGCGTCTGCCCGAT

GCGCAGTGCGGAAGATCCCGAGAGACTCGCCAATTATGCGAGAAAGCTAGCATCTGCCGCAGGAAAAGTCCTGGACAGAA

ACATCTCTGGAAAGATCGGGGACTTACAAGCAGTAATGGCCGTGCCAGACACGGAGACGCCAACATTCTGCTTACACACAG

ACGTCTCATGTAGACAGAGAGCAGACGTCGCTATATACCAAGACGTCTATGCTGTACACGCACCCACGTCGCTATACCACCA

GGCGATTAAAGGGGTCCGAGTGGCGTACTGGGTTGGGTTCGACACAACCCCGTTCATGTACAATGCCATGGCGGGTGCCTA

CCCCTCATACTCGACAAACTGGGCAGATGAGCAGGTACTGAAGGCTAAGAACATAGGATTATGTTCAACAGACCTGACGGA

AGGTAGACGAGGCAAGTTGTCTATTATGAGAGGGAAAAAGCTAAAACCGTGCGACCGTGTGCTGTTCTCAGTAGGGTCAAC

GCTCTACCCGGAAAGCCGCAAGCTACTTAAGAGCTGGCACCTGCCATCGGTGTTCCATTTAAAGGGCAAACTCAGCTTCACA

TGCCGCTGTGATACAGTGGTTTCGTGTGAGGGCTACGTCGTTAAGAGAATAACGATGAGCCCAGGCCTTTATGGAAAAACC

ACAGGGTATGCGGTAACCCACCACGCAGACGGATTCCTGATGTGCAAGACTACCGACACGGTTGACGGCGAAAGARTGTCA

TTCTCGGTGTGCACATACGTGCCGGCGACCATTTGTGATCAAATGACCGGCATCCTTGCTACAGAAGTCACGCCGGAGGATG

CACAGAAGCTGTTGGTGGGCTGAACCAGAGAATAGTGGTTAACGGCAGAACGCAACGGAATACGAACACCATGAAAAAT

TATCTGCTTCCCGTGGTCGCCCAAGCCTTCAGTAAGTGGGCAAAGGAGTGCCGGAAAGACATGGAAGATGAAAAACTCCTG

GGGGTCAGAGAAAGAACACTGACCTGCTGCTGTCTATGGGCATTCAAGAAGCAGAAAACACACACGGTCTACAAGAGGCCT

GATACCCAGTCAATTCAGAAGGTTCAGGCCGAGTTTGACAGCTTTGTGGTACCGAGTCTGTGGTCGTCCGGGTTGTCAATCC

CTTTGAGGACTAGAATCAAATGGTTGTTAAGCAAGGTGCCAAAAACCGACCTGATCCCATACAGCGGAGACGCCCGAGAAG

CCCGGGACGCAGAAAAGAAGCAGAGGAAGAACGAGAAGCAGAACTGACTCGCGAAGCCCTACCACCTCTACAGGCAGCA

CAGGAAGATGTTCAGGTCGAAATCGACGTGGAACAGCTTGAGGACAGAGCGGGCGCAGGAATAATAGAGACTCCGAGAG

GAGCTATCAAAGTTACTGCCCAACCAACAGACCACGTCGTGGGAGAGTACCTGGTACTCTCCCCGCAGACCGTACTACGTAG
```

-continued

```
CCAGAAGCTCAGTCTGATTCACGCTTTGGCGGAGCAAGTGAAGACGTGCACGCACAACGGACGAGCAGGGAGGTATGCGG
TCGAAGCGTACGACGGCCGAGTCCTAGTGCCCTCAGGCTATGCAATCTCGCCTGAAGACTTCCAGAGTCTAAGCGAAAGCG
CAACGATGGTGTATAACGAAAGAGAGTTCGTAAACAGAAAGCTACACCATATTGCGATGCACGGACCAGCCCTGAACACCG
ACGAAGAGTCGTATGAGCTGGTGAGGGCAGAGAGGACAGAACACGAGTACGTCTACGACGTGGATCAGAGAAGATGCTG
TAAGAAGGAAGAAGCCGCAGGACTGGTACTGGTGGGCGACTTGACTAATCCGCCCTACCACGAATTCGCATATGAAGGGCT
AAAAATCCGCCCTGCCTGCCCATACAAAATTGCAGTCATAGGAGTCTTCGGAGTACCGGGATCTGGCAAGTCAGCTATTATC
AAGAACCTAGTTACCAGGCAGGACCTGGTGACTAGCGGAAAGAAAGAAAACTGCCAAGAAATCACCACCGACGTGATGAG
ACAGAGAGGTCTAGAGATATCTGCACGTACGGTTGACTCGCTGCTCTTGAATGGATGCAACAGACCAGTCGACGTGTTGTA
CGTAGACGAGGCGTTTGCGTGCCACTCTGGAACGCTACTTGCTTTGATCGCCTTGGTGAGACCAAGGCAGAAAGTTGTACTT
TGTGGTGACCCGAAGCAGTGCGGCTTCTTCAATATGATGCAGATGAAAGTCAACTATAATCACAACATCTGCACCCAAGTGT
ACCACAAAAGTATCTCCAGGCGGTGTACACTGCCTGTGACCGCCATTGTGTCATCGTTGCATTACGAAGGCAAAATGCGCAC
TACGAATGAGTACAACAAGCCGATTGTAGTGGACACTACAGGCTCAACAAAACCTGACCCTGGAGACCTCGTGTTAACGTG
CTTCAGAGGGTGGGTTAAACAACTGCAAATTGACTATCGTGGATACGAGGTCATGACAGCAGCCGCATCCCAAGGGTTAAC
CAGAAAAGGAGTTTACGCAGTTAGACAAAAAGTTAATGAAAACCCGCTCTATGCATCAACGTCAGAGCACGTCAACGTACTC
CTAACGCGTACGGAAGGTAAACTGGTATGGAAGACACTTTCCGGCGACCCGTGGATAAAGACGCTGCAGAACCCACCGAAA
GGAAACTTCAAAGCAACTATTAAGGAGTGGGAGGTGGAGCATGCATCAATAATGGCGGGCATCTGCAGTCACCAAATGAC
CTTCGATACATTCCAAAATAAAGCCAACGTTTGTTGGGCTAAGAGCTTGGTCCCTATCCTCGAAACAGCGGGGATAAAACTA
AATGATAGGCAGTGGTCTCAGATAATTCAAGCCTTCAAAGAAGACAAAGCATACTCACCTGAAGTAGCCCTGAATGAAATAT
GTACGCGCATGTATGGGGTGGATCTAGACAGCGGGCTATTTTCTAAACCGTTGGTGTCTGTGTATTACGCGGATAACCACTG
GGATAATAGGCCTGGAGGGAAAATGTTCGGATTTAACCCCGAGGCAGCATCCATTCTAGAAAGAAAGTATCCATTCACAAA
AGGGAAGTGGAACATCAACAAGCAGATCTGCGTGACTACCAGGAGGATAGAAGACTTTAACCCTACCACCAACATCATACC
GGCCAACAGGAGACTACCACACTCATTAGTGGCCGAACACCGCCCAGTAAAAGGGGAAAGAATGGAATGGCTGGTTAACA
AGATAAACGGCCACCACGTGCTCCTGGTCAGTGGCTATAACCTTGCACTGCCTACTAAGAGAGTCACTTGGGTAGCGCCGTT
AGGTGTCCGCGGAGCGGACTACACATACAACCTAGAGTTGGGTCTGCCAGCAACGCTTGGTAGGTATGACCTAGTGGTCAT
AAACATCCACACACCTTTTCGCATACACCATTACCAACAGTGCGTCGACCACGCAATGAAACTGCAAATGCTCGGGGGTGAC
TCATTGAGACTGCTCAAACCGGGCGGCTCTCTATTGATCAGAGCATATGGTTACGCAGATAGAACCAGTGAACGAGTCATCT
GCGTATTGGACGCAAGTTTAGATCGTCTAGAGCGTTGAAACCACCATGTGTCACCAGCAACACTGAGATGTTTTTCCTATTC
AGCAACTTTGACAATGGCAGAAGGAATTTCACAACTCATGTCATGAACAATCAACTGAATGCAGCCTTCGTAGGACAGGTCA
CCCGAGCAGGATGTGCACCGTCGTACCGGGTAAAACGCATGGACATCGCGAAGAACGATGAAGAGTGCGTAGTCAACGCC
GCTAACCCTCGCGGGTTACCGGGTGRCGGTGTTTGCAAGGCAGTATACAAAAAATGGCCGGAGTCCTTTAAGAACAGTGCA
ACACCAGTGGGAACCGCAAAAACAGTTATGTGCGGTACGTATCCAGTAATCCACGCTGTTGGACCAAACTTCTCTAATTATT
CGGAGTCTGAAGGGGACCGGGAATTGGCAGCTGCCTATCGAGAAGTCGCAAAGGAAGTAACTAGGCTGGGAGTAAATAGT
GTAGCTATACCTCTCCTCTCCACAGGTGTATACTCAGGAGGGAAAGACAGGCTGACCCAGTCACTGAACCACCTCTTTACAG
CCATGGACTCGACGGATGCAGACGTGGTCATCTACTGCCGCGACAAAGAATGGGAGAAGAAAATATCTGAGGCCATACAG
ATGCGGACCCAAGTAGAGCTGCTGGATGAGCACATCTCCATAGACTGCGATATTGTTCGCGTGCACCCTGACAGCAGCTTG
GCAGGCAGAAAAGGATACAGCACCACGGAAGGCGCACTGTACTCATATCTAGAAGGGACCCGTTTTCATCAGACGGCTGTG
GATATGGCGGAGATACATACTATGTGGCCAAAGCAAACAGAGGCCAATGAGCAAGTCTGCCTATATGCCCTGGGGGAAAG
TATTGAATCGATCAGGCAGAAATGCCCGGTGGATGATGCAGACGCATCATCTCCCCCCAAAACTGTCCCGTGCCTTTGCCGT
TACGCTATGACTCCAGAACGCGTCACCCGGCTTCGCATGAACCACGTCACAAGCATAATTGTGTGTTCTTCGTTTCCCCTCCC
AAAGTACAAAATAGAAGGAGTGCAAAAAGTCAAATGCTCTAAGGTAATGCTATTTGACCACAACGTGCCATCGCGCGTAAG
TCCAAGGGAATATAKATCTTCCCAGGAGTCTGCACAGGAGGCGAGTACAATCACGTCACTGACGCATAGTCAATTCGACCTA
```

-continued

```
AGCGTTGATGGCGAGATACTGCCCGTCCCGTCAGACCTGGATGCTGACGCCCCAGCCCTAGAACCAGCACTAGACGACGGG
GCGACACACACGCTGCCATCCACAACCGGAAACCTTGCGGCCGTGTCTGATTGGGTAATGAGCACCGTACCTGTCGCGCCG
CCCAGAAGAAGGCGAGGGAGAAACCTGACTGTGACATGTGACGAGAGAGAAGGGAATATAACACCCATGGCTAGCGTCCG
ATTCTTTAGGGCAGAGCTGTGTCCGGTCGTACAAGAAACAGCGGAGACGCGTGACACAGCAATGTCTCTTCAGGCACCACC
GAGTACCGCCACGGAACCGAATCATCCGCCGATCTCCTTCGGAGCATCAAGCGAGACGTTCCCCATTACATTTGGGGACTTC
AACGAAGGAGAAATCGAAAGCTTGTCTTCTGAGCTACTAACTTTCGGAGACTTCTTACCAGGAGAAGTGGATGACTTGACA
GACAGCGACTGGTCCACGTGCTCAGACACGGACGACGAGTTATGACTAGACAGGGCAGGTGGGTATATATTCTCGTCGGAC
ACCGGTCCAGGTCATTTACAACAGAAGTCAGTACGCCAGTCAGTGCTGCCGGTGAACACCCTGGAGGAAGTCCACGAGGAG
AAGTGTTACCCACCTAAGCTGGATGAAGCAAAGGAGCAACTATTACTTAAGAAACTCCAGGAGAGTGCATCCATGCCAAC
AGAAGCAGGTATCAGTCGCGCAAAGTAGAAAACATGAAAGCAGCAATCATCCAGAGACTAAAGAGAGGCTGTAGACTATA
CTTAATGTCAGAGACCCCAAAAGTCCCTACTTACCGGACTACATATCCGGCGCCTGTGTACTCGCCTCCGATCAACGTCCGAT
TGTCCAATCCCGAGTCCGCAGTGGCAGCATGCAATGAGTTCTTAGCTAGAAACTATCCAACTGTCTCATCATACCAAATTACC
GACGAGTATGATGCATATCTAGACATGGTGGACGGGTCGGAGAGTTGCCTGGACCGAGCGACATTCAATCCGTCAAAACTC
AGGAGCTACCCGAAACAGCACGCTTACCACGCGCCCTCCATCAGAAGCGCTGTACCGTCCCCATTCCAGAACACACTACAGA
ATGTACTGGCAGCAGCCACGAAAAGAAACTGCAACGTCACACAGATGAGGGAATTACCCACTTTGGACTCAGCAGTATTCA
ACGTGGAGTGTTTCAAAAAATTCGCATGCAACCAAGAATACTGGGAAGAATTTGCTGCCAGCCCTATTAGGATAACAACTGA
GAATTTAGCAACCTATGTTACTAAACTAAAAGGGCCAAAAGCAGCAGCGCTATTCGCAAAAACCCATAATCTACTGCCACTA
CAGGAAGTACCAATGGATAGGTTCACAGTAGATATGAAAAGGGACGTAAAGGTGACTCCTGGTACAAAGCATACAGAGGA
AAGACCTAAGGTGCAGGTTATACAGGCGGCTGAACCCTTGGCGACAGCATACCTATGTGGGATTCACAGAGAGCTGGTTAG
GAGGCTGAACGCCGTCCTCCTACCCAATGTACATACACTATTTGACATGTCTGCCGAGGATTTCGATGCCATCATAGCCGCAC
ACTTTAAGCCAGGAGACACTGTTTTGGAAACGGACATAGCCTCCTTTGATAAGAGCCAAGATGATTCACTTGCGCTTACTGC
TTTGATGCTGTTAGAGGATTTAGGGGTGGATCACTCCCTGCTGGACTTGATAGAGGCTGCTTTCGGAGAGATTTCCAGCTGT
CACCTACCGACAGGTACGCGCTTCAAGTTCGGCGCCATGATGAAATCAGGTATGTTCCTAACTCTGTTCGTCAACACATTGTT
AAACATCACCATCGCCAGCCGAGTGCTGGAAGATCGTCTGACAAAATCCGCGTGCGCGGCCTTCATCGGCGACGACAACAT
AATACATGGAGTCGTCTCCGATGAATTGATGGCAGCCAGATGTGCCACTTGGATGAACATGGAAGTGAAGATCATAGATGC
AGTTGTATCCTTGAAAGCCCCTTACTTTTGTGGAGGGTTTATACTGCACGATACTGTGACAGGAACAGCTTGCAGAGTGGCA
GACCCGCTAAAAAGGCTTTTTAAACTGGGCAAACCGCTAGCGGCAGGTGACGAACAAGATGAAGATAGAAGACGAGCGCT
GGCTGACGAAGTGATCAGATGGCAACGAACAGGGCTAATTGATGAGCTGGAGAAAGCGGTATACTCTAGGTACGAAGTGC
AGGGTATATCAGTTGTGGTAATGTCCATGGCCACCTTTGCAAGCTCCAGATCCAACTTCGAGAAGCTCAGAGGACCCGTCAT
AACTTTGTACGGCGGTCCTAAATAGGTACGCACTACAGCTACCTATTTTGCAGAAGCCGACAGCAAGTATCTAAACACTAAT
CAGCTACAATGGAGTTCATCCCAACCCAAACTTTTTACAATAGGAGGTACCAGCCTCGACCCTGGACTCCGCGCCCTACTATC
CAAGTCATCAGGCCCAGACCGCGCCCTCAGAGGCAAGCTGGGCAACTTGCCCAGCTGATCTCAGCAGTTAATAAACTGACA
ATGCGCGCGGTACCCCAACAGAAGCCACGCAGGAATCGGAAGAATAAGAAGCAAAAGCAAAAACAACAGGCGCCACAAAA
CAACACAAATCAAAGAAGCAGCCACCTAAAAAGAAACCGGCTCAAAAGAAAAGAAGCCGGGCCGCAGAGAGAGGATG
TGCATGAAAATCGAAAATGATTGTATTTTCGAAGTCAAGCACGAAGGTAAGGTAACAGGTTACGCGTGCCTGGTGGGGAC
AAAGTAATGAAACCAGCACACGTAAAGGGGACCATCGATAACGCGGACCTGGCCAAACTGGCCTTTAAGCGGTCATCTAAG
TATGACCTTGAATGCGCGCAGATACCCGTGCACATGAAGTCCGACGCTTCGAAGTTCACCCATGAGAAACCGGAGGGGTAC
TACAACTGGCACCACGGAGCAGTACAGTACTCAGGAGGCCGGTTCACCATCCCTACAGGTGCTGGCAAACCAGGGGACAGC
GGCAGACCGATCTTCGACAACAAGGGACGCGTGGTGGCCATAGTCTTAGGAGGAGCTAATGAAGGAGCCCGTACAGCCCT
CTCGGTGGTGACCTGGAATAAAGACATTGTCACTAAAATCACCCCCGAGGGGGCCGAAGAGTGGAGTCTTGCCATCCCAGT
TATGTGCCTGTTGGCAAACACCACGTTCCCCTGCTCCCAGCCCCCTTGCACGCCCTGCTGCTACGAAAAGGAACCGGAGGAA
```

-continued

ACCCTACGCATGCTTGAGGACAACGTCATGAGACCTGGGTACTATCAGCTGCTACAAGCATCCTTAACATGTTCTCCCCACCG
CCAGCGACGCAGCACCAAGGACAACTTCAATGTCTATAAAGCCACAAGACCATACTTAGCTCACTGTCCCGACTGTGGAGAA
GGGCACTCGTGCCATAGTCCCGTAGCACTAGAACGCATCAGAAATGAAGCGACAGACGGGACGCTGAAAATCCAGGTCTCC
TTGCAAATCGGAATAAAGACGGATGACAGCCACGATTGGACCAAGCTGCGTTATATGGACAACCACATGCCAGCAGACGCA
GAGAGGGCGGGGCTATTTGTAAGAACATCAGCACCGTGTACGATTACTGGAACAATGGGACACTTCATCCTGGCCCGATGT
CCAAAAGGGGAAACTCTGACGGTGGGATTCACTGACAGTAGGAAGATTAGTCACTCATGTACGCACCCATTTCACCACGAC
CCTCCTGTGATAGGTCGGGAAAAATTCCATTCCCGACCGCAGCACGGTAAAGAGCTACCTTGCAGCACGTACGTGCAGAGC
ACCGCCGCAACTACCGAGGAGATAGAGGTACACATGCCCCCAGACACCCCTGATCGCACATTAATGTCACAACAGTCCGGC
AACGTAAAGATCACAGTCAATGGCCAGACGGTGCGGTACAAGTGTAATTGCGGTGGCTCAAATGAAGGACTAACAACTACA
GACAAAGTGATTAATAACTGCAAGGTTGATCAATGTCATGCCGCGGTCACCAATCACAAAAAGTGGCAGTATAACTCCCCTC
TGGTCCCGCGTAATGCTGAACTTGGGGACCGAAAAGGAAAAATTCACATCCCGTTTCCGCTGGCAAATGTAACATGCAGGG
TGCCTAAAGCAAGGAACCCCACCGTGACGTACGGGAAAAACCAAGTCATCATGCTACTGTATCCTGACCACCCAACACTCCT
GTCCTACCGGAATATGGGAGAAGAACCAAACTATCAAGAAGAGTGGGTGATGCATAAGAAGGAAGTCGTGCTAACCGTGC
CGACTGAAGGGCTCGAGGTCACGTGGGGCAACAACGAGCCGTATAAGTATTGGCCGCAGTTATCTACAAACGGTACAGCCC
ATGGCCACCCGCATGAGATAATTCTGTATTATTATGAGCTGTACCCCACTATGACTGTAGTAGTTGTGTCAGTGGCCACGTTC
ATACTCCTGTCGATGGTGGGTATGGCAGCGGGATGTGCATGTGTGCACGACGCAGATGCATCACACCGTATGAACTGACA
CCAGGAGCTACCGTCCCTTTCCTGCTTAGCCTAATATGCTGCATCAGAACAGCTAAAGCGGCCACATACCAAGAGGCTGCGA
TATACCTGTGGAACGAGCAGCAACCTTTGTTTTGGCTACAAGCCCTTATTCCGCTGGCAGCCCTGATTGTTCTATGCAACTGT
CTGAGACTCTTACCATGCTGCTGTAAAACGTTGGCTTTTTTAGCCGTAATGAGCGTCGGTGCCCACACTGTGAGCGCGTACG
AACACGTAACAGTGATCCCGAACACGGTGGGAGTACCGTATAAGACTCTAGTCAATAGACCTGGCTACAGCCCCATGGTATT
GGAGATGGAACTACTGTCAGTCACTTTGGAGCCAACACTATCGCTTGATTACATCACGTGCGAGTACAAAACCGTCATCCCG
TCTCCGTACGTGAAGTGCTGCGGTACAGCAGAGTGCAAGGACAAAAACCTACCTGACTACAGCTGTAAGGTCTTCACCGGC
GTCTACCCATTTATGTGGGCGGCGCCTACTGCTTCTGCGACGCTGAAAACACGCAGTTGAGCGAAGCACACGTGGAGAAG
TCCGAATCATGCAAAACAGAATTTGCATCAGCATACAGGGCTCATACCGCATCTGCATCAGCTAAGCTCCGCGTCCTTTACCA
AGGAAATAACATCACTGTAACTGCCTATGCAAACGGCGACCATGCCGTCACAGTTAAGGACGCCAAATTCATTGTGGGGCC
AATGTCTTCAGCCTGGACACCTTTCGACAACAAAATTGTGGTGTACAAAGGTGACGTCTATAACATGGACTACCCGCCCTTTG
GCGCAGGAAGACCAGGACAATTTGGCGATATCCAAAGTCGCACACCTGAGAGTAAAGACGTCTATGCTAATACACAACTGG
TACTGCAGAGACCGGCTGTGGGTACGGTACACGTGCCATACTCTCAGGCACCATCTGGCTTTAAGTATTGGCTAAAAGAACG
CGGGGCGTCGCTGCAGCACACAGCACCATTTGGCTGCCAAATAGCAACAAACCCGGTAAGAGCGGTGAACTGCGCCGTAG
GGAACATGCCCATCTCCATCGACATACCGGAAGCGGCCTTCACTAGGGTCGTCGACGCGCCCTCTTTAACGGACATGTCGTG
CGAGGTACCAGCCTGCACCCATTCCTCAGACTTTGGGGGCGTCGCCATTATTAAATATGCAGCCAGCAAGAAAGGCAAGTG
TGCGGTGCATTCGATGACTAACGCCGTCACTATTCGGGAAGCTGAGATAGAAGTTGAAGGGAATTCTCAGCTGCAAATCTCT
TTCTCGACGGCCTTAGCCAGCGCCGAATTCCGCGTACAAGTCTGTTCTACACAAGTACACTGTGCAGCCGAGTGCCACCCCC
CGAAGGACCACATAGTCAACTACCCGGCGTCACATACCACCCTCGGGGTCCAGGACATCTCCGCTACGGCGATGTCATGGG
TGCAGAAGATCACGGGAGGTGTGGGACTGGTTGTTGCTGTTGCCGCACTGATTCTAATCGTGGTGCTATGCGTGTCGTTCA
GCAGGCACTAACTTGACAATTAAGTATGAAGGTATATGTGTCCCCTAAGAGACACACTGTACATAGCAAATAATCTATAGAT
CAAAGGGCTACGCAACCCCTGAATAGTAACAAAATACAAAATCACTAAAAATTATAAAAACAGAAAAATACATAAATAGGT
ATACGTGTCCCCTAAGAGACACATTGTATGTAGGTGATAAGTATAGATCAAAGGGCCGAATAACCCCTGAATAGTAACAAA
ATATGAAAATCAATAAAAATCATAAAATAGAAAAACCATAAACAGAAGTAGTTCAAAGGGCTATAAAACCCCTGAATAGTA
ACAAAACATAAAATTAATAAAAATCAAATGAATACCATAATTGGCAAACGGAAGAGATGTAGGTACTTAAGCTTCCTAAAAG

-continued

CAGCCGAACTCACTTTGAGAAGTAGGCATAGCATACCGAACTCTTCCACGATTCTCCGAACCCACAGGGACGTAGGAGATGT

TATTTTGTTTTTAATATTTCAAAAAAAAAAAAAAAAAAAAAAAAAAAAAA

Japanese encephalitis virus strain SA14-14-2, complete genome, ACCESSION: KC517497

SEQ ID NO: 73

TTTAAACAGTTTTTTAGAACGGAAGATAACCATGACTAAAAAACCAGGAGGGCCCGGTAAAAACCGGGCTATCAATATGCT

GAAACGCGGCCTACCCCGCGTATTCCCACTAGTGGGAGTGAAGAGGGTAGTAATGAGCTTGTTGGACGGCAGAGGGCCAG

TACGTTTCGTGCTGGCTCTTATCACGTTCTTCAAGTTTACAGCATTAGCCCCGACCAAGGCGCTTTTAGGCCGATGGAAAGCA

GTGGAAAAGAGTGTGGCAATGAAACATCTTACTAGTTTCAAACGAGAACTTGGAACACTCATTGACGCCGTGAACAAGCGG

GGCAGAAAGCAAAACAAAAGAGGAGGAAATGAAGGCTCAATCATGTGGCTCGCGAGCTTGGCAGTTGTCATAGCTTGTGC

AGGAGCCATGAAGTTGTCGAATTTCCAGGGGAAGCTTTTGATGACCATCAACAACACGGACATTGCAGACGTTATCGTGATT

CCCACCTCAAAAGGAGAGAACAGATGCTGGGTCCGGGCAATCGACGTCGGCTACATGTGTGAGGACACTATCACGTACGAA

TGTCCTAAGCTTACCATGGGCAATGATCCAGAGGATGTGGATTGCTGGTGTGACAACCAAGAAGTCTACGTCCAATATGGA

CGGTGCACGCGGACCAGGCATTCCAAGCGAAGCAGGAGATCCGTGTCGGTCCAAACACATGGGGAGAGTTCACTAGTGAA

TAAAAAAGAGGCTTGGCTGGATTCAACGAAAGCCACACGATATCTCATGAAAACTGAGAACTGGATCATAAGGAATCCTGG

CTATGCTTTCCTGGCGGCGGTACTTGGCTGGATGCTTGGCAGTAACAACGGTCAACGCGTGGTATTTACCATCCTCCTGCTGT

TGGTCGCTCCGGCTTACAGTTTTAATTGTCTGGGAATGGGCAATCGTGACTTCATAGAAGGAGCCAGTGGAGCCACTTGGG

TGGACTTGGTGCTAGAAGGAGATAGCTGCTTGACAATCATGGCAAACGACAAACCAACATTGGACGTCCGCATGATTAACA

TCGAAGCTAGCCAACTTGCTGAGGTCAGAAGTTACTGCTATCATGCTTCAGTCACTGACATCTCGACGGTGGCTCGGTGCCC

CACGACTGGAGAAGCCCACAACGAGAAGCGAGCTGATAGTAGCTATGTGTGCAAACAAGGCTTCACTGACCGTGGGTGGG

GCAACGGATGTGGACTTTTCGGGAAGGGAAGCATTGACACATGTGCAAAATTCTCCTGCACCAGTAAAGCGATTGGGAGAA

CAATCCAGCCAGAAAACATCAAATACGAAGTTGGCATTTTTGTGCATGGAACCACCACTTCGGAAAACCATGGGAATTATTC

AGCGCAAGTTGGGGCGTCCCAGGCGGCAAAGTTTACAGTAACACCCAATGCTCCTTCGATAACCCTCAAACTTGGTGACTAC

GGAGAAGTCACACTGGACTGTGAGCCAAGGAGTGGACTGAACACTGAAGCGTTTTACGTCATGACCGTGGGGTCAAAGTC

ATTTCTGGTCCATAGGGAGTGGTTTCATGACCTCGCTCTCCCCTGGACGTCCCCTTCGAGCACAGCGTGGAGAAACAGAGAA

CTCCTCATGGAATTTGAAGGGCGCACGCCACAAAACAGTCCGTTGTTGCTCTTGGGTCACAGGAAGGAGGCCTCCATCAG

GCGTTGGCAGGAGCCATCGTGGTGGAGTACTCAAGCTCAGTGAAGTTAACATCAGGCCACCTGAAATGTAGGCTGAAAATG

GACAAACTGGCTCTGAAAGGCACAACCTATGGCATGTGTACAGAAAAATTCTCGTTCGCGAAAAATCCGGCGGACACTGGT

CACGGAACAGTTGTCATTGAACTCTCCTACTCTGGGAGTGATGGCCCCTGCAAAATTCCGATTGTTTCCGTTGCGAGCCTCAA

TGACATGACCCCCGTTGGGCGGCTGGTGACAGTGAACCCCTTCGTCGCGACTTCCAGTGCCAACTCAAAGGTGCTGGTCGA

GATGGAACCCCCCTTCGGAGACTCCTACATCGTAGTTGGAAGGGGAGACAAGCAGATCAACCACCATTGGCACAAAGCTGG

AAGCACGCTGGGCAAGGCCTTTTCAACAACTTTGAAGGGAGCTCAAAGACTGGCAGCGTTGGGCGACACAGCCTGGGACTT

TGGCTCTATTGGAGGGGTCTTCAACTCCATAGGAAAAGCCGTTCACCAAGTGTTTGGTGGTGCCTTCAGAACACTCTTTGGG

GGAATGTCTTGGATCACACAAGGGCTAATGGGTGCCCTACTGCTCTGGATGGGCGTCAACGCACGAGACCGATCAATTGCT

TTGGCCTTCTTAGCCACAGGGGGTGTGCTCGTGTTCTTAGCGACCAATGTGCATGCTGACACTGGATGTGCCATTGACATCA

CAAGAAAAGAGATGAGATGTGGAAGTGGCATCTTCGTGCACAACGACGTGGAAGCCTGGGTGGATAGGTATAAATATTTG

CCAGAAACGCCCAGATCCCTAGCGAAGATCGTCCACAAAGCGCACAAGGAAGGCGTGTGCGGAGTCAGATCTGTCACTAGA

CTGGAGCACCAAATGTGGGAAGCCGTACGGGACGAATTGAACGTCCTGCTCAAAGAGAATGCAGTGGACCTCAGTGTGGT

TGTGAACAAGCCCGTGGGAAGATATCGCTCAGCCCCTAAACGCCTATCCATGACGCAAGAGAAGTTTGAAATGGGCTGGAA

AGCATGGGAAAAAGCATTCTCTTTGCCCCGGAATTGGCTAACTCCACATTTGTCGTAGATGGACCTGAGACAAAGGAATG

CCCTGATGAGCACAGAGCTTGGAACAGCATGCAAATCGAAGACTTCGGCTTTGGCATCACATCAACCCGTGTGTGGCTGAA

AATTAGAGAGGAGAGCACTGACGAGTGTGATGGAGCGATCATAGGCACGGCTGTCAAAGGACATGTGGCAGTCCATAGTG

ACTTGTCGTACTGGATTGAGAGTCGCTACAACGACACATGGAAACTTGAGAGGGCAGTCTTTGGAGAGGTCAAATCTTGCA

-continued

```
CTTGGCCAGAGACACACACCCTTTGGGGAGATGATGTTGAGGAAAGTGAACTCATCATTCCGCACACCATAGCCGGACCAA
AAAGCAAGCACAATCGGAGGGAAGGGTATAAGACACAAAACCAGGGACCTTGGGATGAGAATGGCATAGTCTTGGACTTT
GATTATTGCCCAGGGACAAAAGTCACCATTACAGAGGATTGTGGCAAGAGAGGCCCTTCGGTCAGAACCACTACTGACAGT
GGAAAGTTGATCACTGACTGGTGCTGTCGCAGTTGCTCCCTTCCGCCCCTACGATTCCGGACAGAAAATGGCTGCTGGTACG
GAATGGAAATCAGACCTGTTAGGCATGATGAAACAACACTCGTCAGATCACAGGTTGATGCTTTCAATGGTGAAATGGTTG
ACCCTTTTCAGCTGGGCCTTCTGGTGATGTTTCTGGCCACCCAGGAGGTCCTTCGCAAGAGGTGGACGGCCAGATTGACCAT
TCCTGCGGTTTTGGGGGCCCTACTTGTGCTGATGCTTGGGGGCATCACTTACACTGATTTGGCGAGGTATGTGGTGCTAGTC
GCTGCTGCTTTCGCAGAGGCCAACAGTGGAGGAGACGTCCTGCACCTTGCTTTGATTGCCGTTTTTAAGATCCAACCAGCAT
TTCTAGTGATGAACATGCTTAGCACGAGATGGACGAACCAAGAAAACGTGGTTCTGGTCCTAGGGGCTGCCTTTTTCCAATT
GGCCTCAGTAGATCTGCAAATAGGAGTCCACGGAATCCTGAATGCCGCCGCTATAGCATGGATGATTGTCCGAGCGATCAC
CTTCCCCACAACCTCCTCCGTCACCATGCCAGTCTTAGCGCTTCTAACTCCGGGGATGAGGGCTCTATACCTAGACACTTACA
GAATCATCCTCCTCGTCATAGGGATTTGCTCCCTGCTGCACGAGAGGAAAAAGACCATGGCAAAAAAGAAAGGAGCTGTAC
TCTTGGGCTTAGCGCTCACATCCACTGGATGGTTCTCGCCCACCACTATAGCTGCCGGACTAATGGTCTGCAACCCAAACAA
GAAGAGAGGGTGGCCAGCTACTGAGTTTTTGTCGGCAGTTGGATTGATGTTTGCCATCGTAGGTGGTTTGGCCGAGTTGGA
TATTGAATCCATGTCAATACCCTTCATGCTGGCAGGTCTCATGGCAGTGTCCTACGTGGTGTCAGGAAAAGCAACAGATATG
TGGCTTGAACGGGCCGCCGACATCAGCTGGGAGATGGATGCTGCAATCACAGGAAGCAGTCGGAGGCTGGATGTGAAACT
GGATGATGACGGAGATTTTCACTTGATTGATGATCCCGGTGTTCCATGGAAGGTCTGGGTCCTGCGCATGTCTTGCATTGGC
TTAGCCGCCCTCACGCCTTGGGCCATCGTTCCCGCCGCTTTCGGTTATTGGCTCACTTTAAAAACAACAAAAGAGGGGGCG
TGTTTTGGGACACGCCATCCCCAAAACCTTGCTCAAAAGGAGACACCACTACAGGAGTCTACCGAATTATGGCTAGAGGGAT
TCTTGGCACTTACCAGGCCGGCGTCGGAGTCATGTACGAGAATGTTTTCCACACACTATGGCACACAACTAGAGGAGCAGCC
ATTATGAGTGGAGAAGGAAAATTGACGCCATACTGGGGTAGTGTGAGAGAAGACCGCATAGCTTACGGAGGCCCATGGAG
GTTTGACCGAAAATGGAATGAACAGATGACGTGCAAGTGATCGTGGTAGAACCGGGGAAGGCTGCAGTAAACATCCAGA
CAAAACCAGGAGTGTTTCGGACTCCCTTCGGGGAGGTTGGGGCTGTTAGTCTGGATTACCCGCGAGGAACATCCGGCTCAC
CCATTCTGGATTCCAATGGAGACATTATAGGCCTATACGGCAATGGAGTTGAGCTTGGCGATGGCTCATACGTCAGCGCCAT
CGTGCAGGGTGACCGTCAGGAGGAACCAGTCCCAGAAGCTTACACCCCAAACATGTTGAGAAAGAGACAGATGACTGTGC
TAGATTTGCACCCTGGTTCAGGGAAAACCAGGAAAATTCTGCCACAAATAATTAAGGACGCTATCCAGCAGCGCCTAAGAAC
AGCTGTGTTGGCACCGACGCGGGTGGTAGCAGCAGAAATGGCAGAAGCTTTGAGAGGGCTCCCAGTACGATATCAAACTTC
AGCAGTGCAGAGAGAGCACCAAGGGAATGAAATAGTGGATGTGATGTGCCACGCCACTCTGACCCATAGACTGATGTCACC
GAACAGAGTGCCCAACTACAACCTATTTGTCATGGATGAAGCTCATTTCACCGACCCAGCCAGTATAGCCGCACGAGGATAC
ATTGCTACCAAGGTGGAATTAGGGGAGGCAGCAGCCATCTTTATGACAGCGACCCCGCCTGGAACCACGGATCCTTTTCCTG
ACTCAAATGCCCCAATCCATGATTTGCAAGATGAGATACCAGACAGGGCATGGAGCAGTGGATACGAATGGATCACAGAAT
ATGCGGGTAAAACCGTGTGGTTTGTGGCGAGCGTAAAAATGGGGAATGAGATTGCAATGTGCCTCCAAAGAGCGGGGAAA
AAGGTCATCCAACTCAACCGCAAGTCCTATGACACAGAATACCCAAAATGTAAGAATGGAGACTGGGATTTTGTCATTACCA
CCGACATCTCTGAAATGGGGGCCAACTTCGGTGCGAGCAGGGTCATCGACTGTAGAAAGAGCGTGAAACCCACCATCTTAG
AAGAGGGAGAAGGCAGAGTCATCCTCGGAAACCCATCTCCCATAACCAGTGCAAGCGCAGCTCAACGGAGGGGCAGAGTA
GGCAGAAACCCCAACCAAGTTGGAGATGAATACCACTATGGGGGGCTACCAGTGAAGATGACAGTAACCTAGCCCATTG
GACAGAGGCAAAGATCATGTTAGACAACATACACATGCCCAATGGACTGGTGGCCCAGCTCTATGGACCAGAGAGGGAAA
AGGCTTTCACAATGGATGGCGAATACCGTCTCAGAGGTGAAGAAAAGAAAAACTTCTTAGAGCTGCTTAGGACGGCTGACC
TCCCGGTGTGGCTGGCCTACAAGGTGGCGTCCAATGGCATTCAGTACACCGACAGAAAGTGGTGTTTTGATGGGCCGCGTA
CGAATGCCATACTGGAGGACAACACCGAGGTAGAGATAGTCACCCGGATGGGTGAGAGGAAAATCCTCAAGCCGAGATGG
CTTGATGCAAGAGTTTATGCAGATCACCAAGCCCTCAAGTGGTTCAAAGACTTTGCAGCAGGGAAGAGATCAGCCGTTAGC
```

-continued
```
TTCATAGAGGTGCTCGGTCGCATGCCTGAGCATTTCATGGGAAAGACGCGGGAAGCTTTAGACACCATGTACTTGGTTGCA
ACGGCTGAGAAAGGTGGGAAAGCACACCGAATGGCTCTCGAAGAGCTGCCAGATGCACTGGAAACCATCACACTTATTGTC
GCCATTACTGTGATGACAGGAGGATTCTTCCTACTAATGATGCAGCGAAAGGGTATAGGGAAGATGGGTCTTGGAGCTCTA
GTGCTCACGCTAGCTACCTTCTTCCTGTGGGCGGCAGAGGTTCCTGGAACCAAAATAGCAGGGACCCTGCTGATCGCCCTGC
TGCTGATGGTGGTTCTCATCCCAGAACCGGAAAAACAGAGGTCACAGACAGATAACCAACTGGCGGTGTTTCTCATCTGTGT
CTTGACCGTGGTTGGAGTGGTGGCAGCAAACGAGTACGGGATGCTAGAAAAAACCAAAGCAGATCTCAAGAGCATGTTTG
GCGGAAAGACGCAGGCATCAGGACTGACTGGATTGCCAAGCATGGCACTGGACCTGCGTCCAGCCACAGCCTGGGCACTG
TATGGGGGGAGCACAGTCGTGCTAACCCCTCTTCTGAAGCACCTGATCACGTCGGAATACGTCACCACATCGCTAGCCTCAA
TTAACTCACAAGCTGGCTCATTATTCGTCTTGCCACGAGGCGTGCCTTTTACCGACCTAGACTTGACCGTTGGCCTCGTCTTCC
TTGGCTGTTGGGGTCAAATCACCCTCACAACGTTTCTGACAGCCATGGTTCTGGCGACACTTCACTATGGGTACATGCTCCCT
GGATGGCAAGCAGAAGCACTCAGGGCTGCCCAGAGAAGGACAGCGGCTGGAATAATGAAGAATGCCGTTGTTGACGGAA
TGGTCGCCACTGATGTGCCTGAACTGGAAAGGACTACTCCTCTGATGCAAAAGAAAGTCGGACAGGTGCTCCTCATAGGGG
TAAGCGTGGCAGCGTTCCTCGTCAACCCTAATGTCACCACTGTGAGAGAAGCAGGGGTGTTGGTGACGGCGGCTACGCTTA
CTTTGTGGGACAATGGAGCCAGTGCCGTTTGGAATTCCACCACAGCCACGGGACTCTGCCATGTCATGCGAGGTAGCTACCT
GGCTGGAGGCTCCATTGCTTGGACTCTCATCAAGAACGCTGATAAGCCCTCCTTGAAAAGGGGAAGGCCTGGGGCAGGA
CGCTAGGGGAGCAGTGGAAGGAAAAACTAAATGCCATGAGCAGAGAAGAGTTTTTTAAATACCGGAGAGAGGCCATAATC
GAGGTGGACCGCACTGAAGCACGCAGGGCCAGACGTGAAAATAACATAGTGGGAGGACATCCGGTTTCGCGAGGCTCAGC
AAAACTCCGTTGGCTCGTGGAGAAAGGATTTGTCTCGCCAATAGGAAAAGTCATTGATCTAGGGTGTGGGCGTGGAGGATG
GAGCTACTACGCAGCAACCCTGAAGAAGGTCCAGGAAGTCAGAGGATACACGAAAGGTGGGGCGGGACATGAAGAACCG
ATGCTCATGCAGAGCTACGGCTGGAACCTGGTCTCCCTGAAGAGTGGAGTGGACGTGTTTTACAAACCTTCAGAGCCCAGT
GACACCCTGTTCTGTGACATAGGGGAATCCTCCCCAAGTCCAGAAGTAGAAGAACAACGCACACTACGCGTCCTAGAGATG
ACATCTGACTGGTTGCACCGAGGACCTAGAGAGTTCTGCATTAAAGTTCTCTGCCCTTACATGCCCAAGGTTATAGAAAAAA
TGGAAGTTCTGCAGCGCCGCTTCGGAGGTGGGCTAGTGCGTCTCCCCCTGTCCCGAAACTCCAATCACGAGATGTATTGGGT
TAGTGGAGCCGCTGGCAATGTGGTGCACGCTGTGAACATGACCAGCCAGGTACTACTGGGGCGAATGGATCGCACAGTGT
GGAGAGGGCCAAAGTATGAGGAAGATGTCAACCTAGGGAGCGGAACAAGAGCCGTGGGAAAGGGAGAAGTCCATAGCA
ATCAGGAGAAAATCAAGAAGAGAATCCAGAAGCTTAAAGAAGAATTCGCCACAACGTGGCACAAAGACCCTGAGCATCCAT
ACCGCACTTGGACATACCACGGAAGCTATGAAGTGAAGGCTACTGGCTCAGCCAGCTCTCTCGTCAACGGAGTGGTGAAGC
TCATGAGCAAACCTTGGGACGCCATTGCCAACGTCACCACCATGGCCATGACTGACACCACCCCTTTTGGACAGCAAAGAGT
TTTCAAGGAGAAAGTTGACACGAAGGCTCCTGAGCCACCAGCTGGAGCCAAGGAAGTGCTCAACGAGACCACCAACTGGCT
GTGGGCCCACTTGTCACGGGAAAAAGACCCCGCTTGTGCACCAAGGAAGAATTCATAAAGAAAGTCAACAGCAACGCGG
CTCTTGGAGCAGTGTTCGCTGAACAGAATCAATGGAGCACGGCGCGTGAGGCTGTGGATGACCCGCGGTTTTGGGAGATG
GTTGATGAAGAGGGGAAAACCATCTGCGAGGAGAGTGTCACACATGTATCTACAACATGATGGGAAAAAGAGAGAAGAA
GCCTGGAGAGTTTGGAAAAGCTAAAGGAAGCAGGGCCATTTGGTTCATGTGGCTTGGAGCACGGTATCTAGAGTTTGAAGC
TTTGGGGTTCCTGAATGAAGACCATTGGCTGAGCCGAGAGAATTCAGGAGGTGGAGTGGAAGGCTCAGGCGTCCAAAAGC
TGGGATACATCCTCCGTGACATAGCAGGAAAGCAAGGAGGGAAAATGTACGCTGATGATACCGCCGGGTGGGACACTAGA
ATTACCAGAACTGATTTAGAAAATGAAGCTAAGGTACTGGAGCTCCTAGACGGTGAACACCGCATGCTCGCCCCGAGCCATA
ATTGAACTGACTTACAGGCACAAAGTGGTCAAGGTCATGAGACCTGCAGCAGAAGGAAAGACCGTGATGGACGTGATATC
AAGAGAAGATCAAAGGGGGAGTGGACAGGTGGTCACTTATGCTCTTAACACTTTCACGAACATCGCTGTCCAGCTCGTCAG
GCTGATGGAGGCTGAGGGGGTCATTGGACCACAACACTTGGAACAGCTACCTAGGAAAAACAAGATAGCTGTCAGGACCT
GGCTCTTTGAGAATGGAGAGGAGAGTGACCAGGATGGCGATCAGCGGAGACGACTGTGTCGTCAAGCCGCTGGACGA
CAGATTCGCCACAGCCCTCCACTTCCTCAACGCAATGTCAAAGGTCAGAAAAGACATCCAGGAATGGAAGCCTTCGCATGGC
```

-continued

TGGCACGATTGGCAGCAAGTTCCCTTCTGCTCTAACCATTTTCAGGAGATTGTGATGAAAGATGGAAGGAGTATAGTTGTCC

CGTGCAGAGGACAGGATGAGCTGATAGGCAGGGCTCGCATCTCTCCAGGAGCTGGATGGAATGTGAAGGACACAGCTTGC

CTGGCCAAAGCATATGCACAGATGTGGCTACTCCTATACTTCCATCGCAGGGACTTGCGTCTCATGGCAAATGCGATTTGCTC

AGCAGTGCCAGTGGATTGGGTGCCCACAGGCAGGACATCCTGGTCAATACACTCGAAAGGAGAGTGGATGACCACGGAAG

ACATGCTGCAGGTCTGGAACAGAGTCTGGATTGAAGAAAATGAATGGATGATGGACAAGACTCCAATCACAAGCTGGACA

GACGTTCCGTATGTGGGAAAGCGTGAGGACATCTGGTGTGGCAGCCTCATCGGAACGCGATCCAGAGCAACCTGGGCTGA

GAACATCTATGCGGCGATAAACCAGGTTAGAGCTGTCATTGGGAAGAAAATTATGTTGACTACATGACCTCACTCAGGAG

ATACGAAGACGTCTTGATCCAGGAAGACAGGGTCATCTAGTGTGATTTAAGGTAGAAAAGTAGACTATGTAAATAATGTAA

ATGAGAAAATGCATGCATATGGAGTCAGGCCAGCAAAAGCTGCCACCGGATACTGGGTAGACGGTGCTGCCTGCGTCTCAG

TCCCAGGAGGACTGGGTTAACAAATCTGACAACAGAAAGTGAGAAAGCCCTCAGAACCGTCTCGGAAGTAGGTCCCTGCTC

ACTGGAAGTTGAAAGACCAACGTCAGGCCACAAATTTGTGCCACTCCGCTAGGGAGTGCGGCCTGCGCAGCCCCAGGAGG

ACTGGGTTACCAAAGCCGTTGAGGCCCCCACGGCCCAAGCCTCGTCTAGGATGCAATAGACGAGGTGTAAGGACTAGAGGT

TAGAGGAGACCCCGTGGAAACAACAACATGCGGCCCAAGCCCCCTCGAAGCTGTAGAGGAGGTGGAAGGACTAGAGGTTA

GAGGAGACCCCGCATTTGCATCAAACAGCATATTGACACCTGGGAATAGACTGGGAGATCTTCTGCTCTATCTCAACATCAG

CTACTAG

Japanese encephalitis virus strain SA14-14-2, complete genome, ACCESSION: JN604986

SEQ ID NO: 74

AGAAGTTTATCTGTGTGAACTTCTTGGCTTAGTATCGTAGAGAAGAATCGAGAGATTAGTGCAGTTTAAACAGTTTTTTAGA

ACGGAAGATAACCATGACTAAAAAACCAGGAGGGCCCGGTAAAAACCGGGCTATCAATATGCTGAAACGCGGCCTACCCC

GCGTATTCCCACTAGTGGGAGTGAAGAGGGTAGTAATGAGCTTGTTGGACGGCAGAGGGCCAGTACGTTTCGTGCTGGCTC

TTATCACGTTCTTCAAGTTTACAGCATTAGCCCCGACCAAGGCGCTTTCAGGCCGATGGAAAGCAGTGGAAAGAGTGTGG

CAATGAAACATCTTACTAGTTTCAAACGAGAACTTGGAACACTCATTGACGCCGTGAACAAGCGGGGCAGAAAGCAAAACA

AAAGAGGAGGAAATGAAGGCTCAATCATGTGGCTCGCGAGCTTGGCAGTTGTCATAGCTTGTGCAGGAGCCATGAAGTTGT

CGAATTTCCAGGGGAAGCTTTTGATGACCATCAACAACACGGACATTGCAGACGTTATCGTGATTCCCACCTCAAAAGGAGA

GAACAGATGCTGGGTCCGGGCAATCGACGTCGGCTACATGTGTGAGGACACTATCACGTACGAATGTCCTAAGCTTACCAT

GGGCAATGATCCAGAGGATGTGGATTGCTGGTGTGACAACCAAGAAGTCTACGTCCAATATGGACGGTGCACGCGGACCA

GGCATTCCAAGCGAAGCAGGAGATCCGTGTCGGTCCAAACACATGGGAGAGTTCACTAGTGAATAAAAAAGAGGCTTGG

CTGGATTCAACGAAAGCCACACGATATCTCATGAAAACTGAGAACTGGATCATAAGGAATCCTGGCTATGCTTTCCTGGCGG

CGGTACTTGGCTGGATGCTTGGCAGTAACAACGGTCAACGCGTGGTATTTACCATCCTCCTGCTGTTGGTCGCTCCGGCTTA

CAGTTTTAATTGTCTGGGAATGGGCAATCGTGACTTCATAGAAGGAGCCAGTGGAGCCACTTGGGTGGACTTGGTGCTAGA

AGGAGACAGCTGCTTGACAATCATGGCAAACGACAAACCAACATTGGACGTCCGCATGATTAACATCGAAGCTAGCCAACT

TGCTGAGGTCAGAAGTTACTGCTATCATGCTTCAGTCACTGACATCTCGACGGTGGCTCGGTGCCCCACGACTGGAGAAGCC

CACAACGAGAAGCGAGCTGATAGTAGCTATGTGTGCAAACAAGGCTTCACTGACCGTGGGTGGGCAACGGATGTGGATT

TTTCGGGAAGGGAAGCATTGACACATGTGCAAAATTCTCCTGCACCAGTAAAGCGATTGGGAGAACAATCCAGCCAGAAAA

CATCAAATACAAAGTTGGCATTTTTGTGCATGGAACCACCACTTCGGAAAACCATGGGAATTATTCAGCGCAAGTTGGGGCG

TCCCAGGCGGCAAAGTTTACAGTAACACCCAATGCTCCTTCGGTAGCCCTCAAACTTGGTGACTACGGAGAAGTCACACTGG

ACTGTGAGCCAAGGAGTGGACTGAACACTGAAGCGTTTTACGTCATGACCGTGGGGTCAAAGTCATTTCTGGTCCATAGGG

AGTGGTTTCATGACCTCGCTCTCCCCTGGACGTCCCCTTCGAGCACAGCGTGGAGAAACAGAGAACTCCTCATGGAATTTGA

AGGGGCGCACGCCACAAAACAGTCCGTTGTTGCTCTTGGGTCACAGGAAGGAGGCCTCCATCATGCGTTGGCAGGAGCCAT

CGTGGTGGAGTACTCAAGCTCAGTGATGTTAACATCAGGCCACCTGAAATGTAGGCTGAAAATGGACAAACTGGCTCTGAA

AGGCACAACCTATGGCATGTGTACAGAAAAATTCTCGTTCGCGAAAAATCCGGTGGACACTGGTCACGGAACAGTTGTCATT

GAACTCTCCTACTCTGGGAGTGATGGCCCCTGCAAAATTCCGATTGTTTCCGTTGCGAGCCTCAATGACATGACCCCCGTTGG

-continued

GCGGCTGGTGACAGTGAACCCCTTCGTCGCGACTTCCAGTGCCAACTCAAAGGTGCTGGTCGAGATGGAACCCCCCTTCGG

AGACTCCTACATCGTAGTTGGAAGGGGAGACAAGCAGATCAACCACCATTGGCACAAAGCTGGAAGCACGCTGGGCAAGG

CCTTTTCAACAACTTTGAAGGGAGCTCAAAGACTGGCAGCGTTGGGCGACACAGCCTGGGACTTTGGCTCTATTGGAGGGG

TCTTCAACTCCATAGGAAGAGCCGTTCACCAAGTGTTTGGTGGTGCCTTCAGAACACTCTTTGGGGGAATGTCTTGGATCAC

ACAAGGGCTAATGGGTGCCCTACTGCTCTGGATGGGCGTCAACGCACGAGACCGATCAATTGCTTTGGCCTTCTTAGCCACA

GGAGGTGTGCTCGTGTTCTTAGCGACCAATGTGCATGCTGACACTGGATGTGCCATTGACATCACAAGAAAAGAGATGAGA

TGTGGAAGTGGCATCTTCGTGCACAACGACGTGGAAGCCTGGGTGGATAGGTATAAATATTTGCCAGAAACGCCCAGATCC

CTAGCGAAGATCGTCCACAAAGCGCACAAGGAAGGCGTGTGCGGAGTCAGATCTGTCACTAGACTGGAGCACCAAATGTG

GGAAGCCGTAAGGGACGAATTGAACGTCCTGCTCAAAGAGAATGCAGTGGACCTCAGTGTGGTTGTGAACAAGCCCGTGG

GAAGATATCGCTCAGCCCCTAAACGCCTATCCATGACGAAGAGAAGTTTGAAATGGGCTGGAAAGCATGGGGAAAAAGC

ATCCTCTTTGCCCCGGAATTGGCTAACTCCACATTTGTCGTAGATGGACCTGAGACAAAGGAATGCCCTGATGAGCACAGAG

CTTGGAACAGCATGCAAATCGAAGACTTCGGCTTTGGCATCACATCAACCCGTGTGTGGCTGAAAATTAGAGAGGAGAGCA

CTGACGAGTGTGATGGAGCGATCATAGGCACGGCTGTCAAAGGACATGTGGCAGTCCATAGTGACTTGTCGTACTGGATTG

AGAGTCGCTACAACGACACATGGAAACTTGAGAGGGCAGTCTTTGGAGAGGTCAAATCTTGCACTTGGCCAGAGACACACA

CCCTTTGGGGAGATGATGTTGAGGAAAGTGAACTCATCATTCCGCACACCATAGCCGGACCAAAAAGCAAGCACAATCGGA

GGGAAGGGTATAAGACACAAAACCAGGGACCTTGGGATGAGAATGGCATAGTCTTGGACTTTGATTATTGCCCAGGGACA

AAAGTCACCATTACAGAGGATTGTAGCAAGAGAGGCCCTTCGGTCAGAACCACTACTGACAGTGGAAAGTTGATCACTGAC

TGGTGCTGTCGCAGTTGCTCCCTTCCGCCCCTACGATTCCGGACAGAAAATGGCTGCTGGTACGGAATGGAAATCAGACCTG

TTATGCATGATGAAACAACACTCGTCAGATCACAGGTTCATGCTTTCAAAGGTGAAATGGTTGACCCTTTTCAGCTGGGCCTT

CTGGTGATGTTTCTGGCCACCCAGGAAGTCCTTCGCAAGAGGTGGACGGCCAGATTGACCATTCCTGCGGTTTTGGGGGTC

CTACTTGTGCTGATGCTTGGGGGTATCACTTACACTGATTTGGCGAGGTATGTGGTGCTAGTCGCTGCTGCTTTCGCAGAGG

CCAACAGTGGAGGAGACGTCCTGCACCTTGCTTTGATTGCTGTTTTTAAGATCCAACCAGCATTTTTAGTGATGAACATGCTT

AGCACGAGATGGACGAACCAAGAAAACGTGGTTCTGGTCCTAGGGGCTGCCTTTTTCCAATTGGCCTCAGTAGATCTGCAA

ATAGGAGTCCACGGAATCCTGAATGCCGCCGCTATAGCATGGATGATTGTCCGAGCGATCACCTTCCCCACAACCTCCTCCG

TCACCATGCCAGTCTTAGCGCTTCTAACTCCGGGGATGAGGGCTCTATACCTAGACACTTACAGAATCATCCTCCTCGTCATA

GGGATTTGCTCCCTGCTGCACGAGAGGAAAAAGACCATGGCGAAAAAGAAAGGAGCTGTACTCTTGGGCTTAGCGCTCACA

TCCACTGGATGGTTCTCGCCCACCACTATAGCTGCCGGACTAATGGTCTGCAACCCAAACAAGAAGAGAGGGTGGCCAGCT

ACTGAGTTTTTGTCGGCAGTTGGATTGATGTTTGCCATCGTAGGTGGTTTGGCCGAGTTGGATATTGAATCCATGTCAATACC

CTTCATGCTGGCAGGTCTCATGGCAGTGTCCTACGTGGTGTCAGGAAAAGCAACAGATATGTGGCTTGAACGGGCCGCCGA

CATCAGCTGGGATATGGGTGCTGCAATCACAGGAAGCAGTCGGAGGCTGGATGTGAAACTGGATGATGACGGAGATTTTC

ACTTGATTGATGATCCCGGTGTTCCATGGAAGGTCTGGGTCCTGCGCATGTCTTGCATTGGCTTAGCCGCCCTCACGCCTTGG

GCCATCGTTCCCGCCGCTTTCGGTTATTGGCTCACTTTAAAAACAACAAAAAGAGGGGGCGTGTTTTGGGACACGCCATCCC

CAAAACCTTGCTCAAAAGGAGACACCACTACAGGAGTCTACCGAATTATGGCTAGAGGGATTCTTGGCACTTACCAGGCCG

GCGTCGGAGTCATGTACGAGAATGTTTTCCACACACTATGGCACACAACTAGAGGAGCAGCCATTGTGAGTGGAGAAGGAA

AATTGACGCCATACTGGGGTAGTGTGAAAGAAGACCGCATAGCTTACGGAGGCCCATGGAGGTTTGACCGAAAATGGAAT

GGAACAGATGACGTGCAAGTGATCGTGGTAGAACCGGGGAAGGGCGCAGTAAACATCCAGACAAAACCAGGAGTGTTTCG

GACTCCCTTCGGGGAGGTTGGGGCTGTTAGTCTGGATTACCCGCGAGGAACATCCGGCTCACCCATTCTGGATTCCAATGGA

GACATTATAGGCCTATACGGCAATGGAGTTGAGCTTGGCGATGGCTCATACGTCAGCGCCATCGTGCAGGGTGACCGTCAG

GAGGAACCAGTCCCAGAAGCTTACACCCCAAACATGTTGAGAAAGAGACAGATGACTGTGCTAGATTTGCACCCTGGTTCA

GGGAAAACCAGGAAAATTCTGCCACAAATAATTAAGGACGCTATCCAGCAGCGCCTAAGAACAGCTGTGTTGGCACCGACG

CGGGTGGTAGCAGCAGAAATGGCAGAAGCTTTGAGAGGGCTCCCAGTACGATATCAAACTTCAGCAGTGCAGAGAGAGCA

```
CCAAGGGAATGAAATAGTGGATGTGATGTGCCACGCCACTCTGACCCATAGACTGATGTCACCGAACAGAGTGCCCAACTA
CAACCTATTTGTCATGGATGAAGCTCATTTCACCGACCCAGCCAGTATAGCCGCACGAGGATACATTGCTACCAAGGTGGAA
TTAGGGGAGGCAGCAGCCATCTTTATGACAGCGACCCCGCCTGGAACCACGGATCCTTTTCCTGACTCAAATGCCCCAATCC
ATGATTTGCAAGATGAGATACCAGACAGGGCATGGAGCAGTGGATACGAATGGATCACAGAATATGCGGGTAAAACCGTG
TGGTTTGTGGCGAGCGTAAAAATGGGGAATGAGATTGCAATGTGCCTCCAAAGAGCGGGGAAAAAGGTCATCCAACTCAA
CCGCAAGTCCTATGACACAGAATACCCAAAATGTAAGAATGGAGACTGGGATTTTGTCATTACCACCGACATCTCTGAAATG
GGGGCCAACTTCGGTGCGAGCAGGGTCATCGACTGTAGAAAGAGCGTGAAACCCACCATCTTAGAAGAGGGAGAAGGCA
GAGTCATCCTCGGAAACCCATCTCCCATAACCAGTGCAAGCGCAGCTCAACGGAGGGGCAGAGTAGGCAGAAACCCCAATC
AAGTTGGAGATGAATACCACTATGGGGGGCTACCAGTGAAGATGACAGTAACCTAGCCCATTGGACAGAGGCAAAGATC
ATGTTAGACAACATACACATGCCCAATGGACTGGTGGCCCAGCTCTATGGACCAGAGAGGGAAAAGGCTTTCACAATGGAT
GGCGAATACCGTCTCAGAGGTGAAGAAAGAAAAACTTCTTAGAGCTGCTTAGGACGGCTGACCTCCCGGTGTGGCTGGCC
TACAAGGTGGCGTCCAATGGCATTCAGTACACCGACAGAAAGTGGTGTTTTGATGGGCCGCGTACGAATGCCATACTGGAG
GACAACACCGAGGTAGAGATAGTCACCCGGATGGGTGAGAGGAAAATCCTCAAGCCGAGATGGCTTGATGCAAGAGTTTA
TGCAGATCACCAGGCCCTCAAGTGGTTCAAAGACTTTGCAGCAGGGAAGAGATCAGCCGTTAGCTTCATAGAGGTGCTCGG
TCGCATGCCTGAGCATTTCATGGGAAAGACGCGGGAAGCTTTAGACACCATGTACTTGGTTGCAACGGCTGAGAAAGGTGG
GAAAGCACACCGAATGGCTCTCGAAGAGCTGCCAGATGCACTGGAAACCATCACACTTATTGTCGCCATTACTGTGATGACA
GGAGGATTCTTCCTACTAATGATGCAGCGAAAGGGTATAGGGAAGATGGGTCTTGGAGCTCTAGTGCTCACACTAGCTACC
TTCTTCCTGTGGGCGGCAGAGGTTCCTGGAACCAAAATAGCAGGGACCCTGCTGATCGCCCTGCTGCTGATGGTGGTTCTCA
TCCCAGAACCGGAAAAACAGAGGTCACAGACAGATAACCAACTGGCGGTGTTTCTCATCTGTGTCTTGACCGTGGTTGGAG
TGGTGGCAGCAAACGAGTACGGGATGCTAGAAAAAACCAAAGCGGATCTCAAGAGCATGTTTGGCGGAAAGACGCAGGCA
TCAGGACTGACTGGATTGCCAAGCATGGCACTGGACCTGCGTCCAGCCACAGCCTGGGCACTGTATGGGGGAGCACAGTC
GTGCTAACCCCTCTTCTGAAGCACCTGATCACGTCGGAATACGTCACCACATCGCTAGCTTCAATTAACTCACAAGCTGGCTC
ATTATTCGTCTTGCCACGAGGCGTGCCTTTTACCGACCTAGACTTGACTGTTGGCCTCGTCTTCCTTGGCTGTTGGGGTCAAG
TCACCCTCACAACGTTTCTGACAGCCATGGTTCTGGCGACACTTCACTATGGGTACATGCTCCCTGGATGGCAAGCAGAAGC
ACTCAGGGCTGCCCAGAGAAGGACAGCGGCTGGAATAATGAAGAATGCCGTTGTTGACGGAATGGTCGCCACTGATGTGC
CTGAACTGGAAAGGACTACTCCTCTGATGCAAAAGAAAGTCGGACAGGTGCTCCTCATAGGGGTAAGCGTGGCAGCGTTCC
TCGTCAACCCTAATGTCACCACTGTGAGAGAAGCAGGGGTGTTGGTGACGGCGGCTACGCTTACTTTGTGGGACAATGGAG
CCAGTGCCGTTTGGAATTCCACCACAGCCACGGGACTCTGCCATGTCATGCGAGGTAGCTACCTGGCTGGAGGCTCCATTGC
TTGGACTCTCATCAAGAACGCTGATAAGCCCTCCTTGAAAAGGGGAAGGCCTGGGGCAGGACGCTAGGGGAGCAGTGGA
AGGAAAAACTAAATGCCATGAGTAGAGAAGAGTTTTTTAAATACCGGAGAGAGGCCATAATCGAGGTGGACCGCACTGAA
GCACGCAGGGCCAGACGTGAAAATAACATAGTGGGAGGACATCCGGTTTCGCGAGGCTCAGCAAAACTCCGTTGGCTCGT
GGAGAAAGGATTTGTCTCGCCAATAGGAAAAGTCATTGATCTAGGGTGTGGGCGTGGAGGATGGAGCTACTACGCAGCAA
CCCTGAAGAAGGTCCAGGAAGTCAGAGGATACACGAAAGGTGGGGCGGGACATGAAGAACCGATGCTCATGCAGAGCTA
CGGCTGGAACCTGGTCTCCCTGAAGAGTGGAGTGGACGTGTTTTACAAACCTTCAGAGCCCAGTGATACCCTGTTCTGTGAC
ATAGGGGAATCCTCCCCAAGTCCAGAAGTAGAAGAACAACGCACACTACGCGTCCTAGAGATGACATCTGACTGGTTGCAC
CGAGGACCTAGAGAGTTCTGCATTAAAGTTCTCTGCCCTTACATGCCCAAGGTTATAGAAAAAATGGAAGTTCTGCAGCGTC
GCTTCGGAGGTGGGCTAGTGCGTCTCCCCCTGTCCCGAAACTCCAATCACGAGATGTATTGGGTTAGTGGAGCCGCTGGCA
ATGTGGTGCACGCTGTGAACATGACCAGCCAGGTATTACTGGGGCGAATGGATCGCACAGTGTGGAGAGGGCCAAAGTAT
GAGGAAGATGTCAACCTAGGGAGCGGAACAAGAGCCGTGGGAAAGGGAGAAGTCCATAGCAATCAGGAGAAAATCAAGA
AGAGAATCCAGAAGCTTAAAGAAGAATTCGCCACAACGTGGCACAAAGACCCTGAGCATCCATACCGCACTTGGACATACC
ACGGAAGCTATGAAGTGAAGGCTACTGGCTCAGCCAGCTCTCTCGTCAACGGAGTGGTGAAGCTCATGAGCAAACCTTGGG
```

-continued

```
ACGCCATTGCCAACGTCACCACCATGGCCATGACTGACACCACCCCTTTTGGACAGCAAAGAGTTTTCAAGGAGAAAGTTGA
CACGAAGGCTCCTGAGCCACCAGCTGGAGCCAAGGAAGTGCTCAACGAGACCACCAACTGGCTGTGGGCCTACTTGTCACG
GGAAAAAAGACCCCGCTTGTGCACCAAGGAAGAATTCATTAAGAAAGTTAACAGCAACGCGGCTCTTGGAGCAGTGTTCGC
TGAACAGAATCAATGGAGCACGGCGCGTGAGGCTGTGGATGACCCGCGGTTTTGGGAGATGGTTGATGAAGAGAGGGAA
AACCATCTGCGAGGAGAGTGTCACACATGTATCTACAACATGATGGGAAAAAGAGAGAAGAAGCCTGGAGAGTTTGGAAA
AGCTAAAGGAAGCAGGGCCATTTGGTTCATGTGGCTTGGAGCACGGTATCTAGAGTTTGAAGCTTTGGGGTTCCTGAATGA
AGACCATTGGCTGAGCCGAGAGAATTCAGGAGGTGGAGTGGAAGGCTCAGGCGTCCAAAAGCTGGGATACATCCTCCGTG
ACATAGCAGGAAAGCAAGGAGGGAAAATGTACGCTGATGATACCGCCGGGTGGGACACTAGAATTACCAGAACTGATTTA
GAAAATGAAGCTAAGGTACTGGAGCTCCTAGACGGTGAACACCGCATGCTCGCCCGAGCCATAATTGAACTGACTTACAGG
CACAAAGTGGTCAAGGTCATGAGACCTGCAGCAGAAGGAAAGACCGTGATGGACGTGATATCAAGAGAAGATCAAAGGG
GGAGTGGACAGGTGGTCACTTATGCTCTTAACACTTTCACGAACATCGCTGTCCAGCTCGTCAGGCTGATGGAGGCTGAGG
GGGTCATTGGACCACAACACTTGGAACATCTACCTAGGAAAAACAAGATAGCTGTCAGGACCTGGCTCTTTGAGAATGGAG
AGGAGAGAGTGACCAGGATGGCGATCAGCGGAGACGACTGTGCCGTCAAACCGCTGGACGACAGATTCGCCACAGCCCTC
CACTTCCTCAACGCAATGTCAAAGGTCAGAAAAGACATCCAGGAATGGAAGCCTTCGCATGGCTGGCACGATTGGCAGCAA
GTTCCCTTCTGTTCTAACCATTTTCAGGAGATTGTGATGAAAGATGGAAGGAGTATAGTTGTCCCGTGCAGAGGACAGGATG
AGCTGATAGGCAGGGCTCGCATCTCTCCTGGAGCTGGATGGAATGTGAAGGACACAGCTTGCCTGGCCAAAGCATATGCAC
AGATGTGGCTACTCCTATACTTCCATCGCAGGGACTTGCGTCTCATGGCAAATGCGATTTGCTCAGCAGTGCCAGTAGATTG
GGTGCCCACAGGCAGGACATCCTGGTCAATACACTCGAAAGGAGAGTGGATGACCACGGAAGACATGCTGCAGGTCTGGA
ACAGAGTTTGGATTGAAGAAAATGAATGGATGATGGACAAGACTCCAATCACAAGCTGGACAGACGTTCCGTATGTGGGA
AAGCGCGAGGACATCTGGTGTGGCAGCCTCATCGGAACGCGATCCAGAGCAACCTGGGCTGAGAACATCTATGCGGCGAT
AAAACCAGGTTAGAGCTGTCATTGGGAAAGAAAATTATGTTGACTACATGACCTCACTCAGGAGATACGAAGACGTCTTGATC
CAGGAAGACAGGGTCATCTAGTGTGATTTAAGGTAGAAAAGTAGACTATGTAAACAATGTAAATGAGAAATGCATGCATA
TGGAGTCAGGCCAGCAAAAGCTGCCACCGGATACTGGGTAGACGGTGCTGCCTGCGTCTCAGTCCCAGGAGGACTGGGTT
AACAAATCTGACAACAGAAAGTGAGAAAGCCCTCAGAACCGTCTCGGAAGTAGGTCCCTGCTCACTGGAAGTTGAAAGACC
AACGTCAGGCCACAAATTTGTGCCACTCCGCTAGGGAGTGCGGCCTGCGCAGCCCCAGGAGGACTGGGTTACCAAAGCCGT
TGAGGCCCCCACGGCCCAAGCCTCGTCTAGGATGCAATAGACGAGGTGTAAGGACTAGAGGTTAGAGGAGACCCCGTGGA
AACAACAACATGCGGCCCAAGCCCCCTCGAAGCTGTAGAGGAGGTGGAAGGACTAGAGGTTAGAGGAGACCCCGCATTTG
CATCAAACAGCATATTGACACCTGGGAATAGACTGGGAGATCTTCTGCTCTATCTCAACATCAGCTACTAGGCACAGAGCGC
CGAAGTATGTAGCTGGTGGTGAGGAAGAACACAGGATCT
```

Japanese encephalitis virus strain SA14-14-2, complete genome, ACCESSION: AF315119

SEQ ID NO: 75

```
AGAAGTTTATCTGTGTGAACTTCTTGGCTTAGTATCGTAGAGAAGAATCGAGAGATTAGTGCAGTTTAAACAGTTTTTTAGA
ACGGAAGATAACCATGACTAAAAAACCAGGAGGGCCCGGTAAAAACCGGGCTATCAATATGCTGAAACGCGGCCTACCCC
GCGTATTCCCACTAGTGGGAGTGAAGAGGGTAGTAATGAGCTTGTTGGACGGCAGAGGGCCAGTACGTTTCGTGCTGGCTC
TTATCACGTTCTTCAAGTTTACAGCATTAGCCCCGACCAAGGCGCTTTCAGGCCGATGGAAAGCAGTGGAAAAGAGTGTGG
CAATGAAACATCTTACTAGTTTCAAACGAGAACTTGGAACACTCATTGACGCCGTGAACAAGCGGGGCAGAAAGCAAAACA
AAAGAGGAGGAAATGAAGGCTCAATCATGTGGCTCGCGAGCTTGGCAGTTGTCATAGCTTGTGCAGGAGCCATGAAGTTGT
CGAATTTCCAGGGGAAGCTTTTGATGACCATCAACAACACGGACATTGCAGACGTTATCGTGATTCCCACCTCAAAAGGAGA
GAACAGATGCTGGGTCCGGGCAATCGACGTCGGCTACATGTGTGAGGACACTATCACGTACGAATGTCCTAAGCTTACCAT
GGGCAATGATCCAGAGGATGTGGATTGCTGGTGTGACAACCAAGAAGTCTACGTCCAATATGGACGGTGCACGCGGACCA
GGCATTCCAAGCGAAGCAGGAGATCCGTGTCGGTCCAAACACATGGGAGAGTTCACTAGTGAATAAAAAGAGGCTTGG
CTGGATTCAACGAAAGCCACACGATATCTCATGAAAACTGAGAACTGGATCATAAGGAATCCTGGCTATGCTTTCCTGGCGG
```

-continued

```
CGGTACTTGGCTGGATGCTTGGCAGTAACAACGGTCAACGCGTGGTATTTACCATCCTCCTGCTGTTGGTCGCTCCGGCTTA
CAGTTTTAATTGTCTGGGAATGGGCAATCGTGACTTCATAGAAGGAGCCAGTGGAGCCACTTGGGTGGACTTGGTGCTAGA
AGGAGACAGCTGCTTGACAATCATGGCAAACGACAAACCAACATTGGACGTCCGCATGATTAACATCGAAGCTAGCCAACT
TGCTGAGGTCAGAAGTTACTGCTATCATGCTTCAGTCACTGACATCTCGACGGTGGCTCGGTGCCCCACGACTGGAGAAGCC
CACAACGAGAAGCGAGCTGATAGTAGCTATGTGTGCAAACAAGGCTTCACTGACCGTGGGTGGGGCAACGGATGTGGATT
TTTCGGGAAGGGAAGCATTGACACATGTGCAAAATTCTCCTGCACCAGTAAAGCGATTGGGAGAACAATCCAGCCAGAAAA
CATCAAATACAAAGTTGGCATTTTTGTGCATGGAACCACCACTTCGGAAAACCATGGGAATTATTCAGCGCAAGTTGGGGCG
TCCCAGGCGGCAAAGTTTACAGTAACACCCAATGCTCCTTCGGTAGCCCTCAAACTTGGTGACTACGGAGAAGTCACACTGG
ACTGTGAGCCAAGGAGTGGACTGAACACTGAAGCGTTTTACGTCATGACCGTGGGGTCAAAGTCATTTCTGGTCCATAGGG
AGTGGTTTCATGACCTCGCTCTCCCCTGGACGTCCCCTTCGAGCACAGCGTGGAGAAACAGAGAACTCCTCATGGAATTTGA
AGGGGCGCACGCCACAAAACAGTCCGTTGTTGCTCTTGGGTCACAGGAAGGAGGCCTCCATCATGCGTTGGCAGGAGCCAT
CGTGGTGGAGTACTCAAGCTCAGTGATGTTAACATCAGGCCACCTGAAATGTAGGCTGAAAATGGACAAACTGGCTCTGAA
AGGCACAACCTATGGCATGTGTACAGAAAAATTCTCGTTCGCGAAAAATCCGGTGGACACTGGTCACGGAACAGTTGTCATT
GAACTCTCCTACTCTGGGAGTGATGGCCCCTGCAAAATTCCGATTGTTTCCGTTGCGAGCCTCAATGACATGACCCCCGTTGG
GCGGCTGGTGACAGTGAACCCCTTCGTCGCGACTTCCAGTGCCAACTCAAAGGTGCTGGTCGAGATGGAACCCCCCTTCGG
AGACTCCTACATCGTAGTTGGAAGGGGAGACAAGCAGATCAACCACCATTGGCACAAAGCTGGAAGCACGCTGGGCAAGG
CCTTTTCAACAACTTTGAAGGGAGCTCAAAGACTGGCAGCGTTGGGCGACACAGCCTGGACTTTGGCTCTATTGGAGGGG
TCTTCAACTCCATAGGAAGAGCCGTTCACCAAGTGTTTGGTGATGCCTTCAGAACACTCTTTGGGGGAATGTCTTGGATCAC
ACAAGGGCTAATGGGTGCCCTACTGCTCTGGATGGGCGTCAACGCACGAGACCGATCAATTGCTTTGGCCTTCTTAGCCACA
GGAGGTGTGCTCGTGTTCTTAGCGACCAATGTGCATGCTGACACTGGATGTGCCATTGACATCACAAGAAAAGAGATGAGA
TGTGGAAGTGGCATCTTCGTGCACAACGACGTGGAAGCCTGGGTGGATAGGTATAAATATTTGCCAGAAACGCCCAGATCC
CTAGCGAAGATCGTCCACAAAGCGCACAAGGAAGGCGTGTGCGGAGTCAGATCTGTCACTAGACTGGAGCACCAAATGTG
GGAAGCCGTAAGGGACGAATTGAACGTCCTGCTCAAAGAGAATGCAGTGGACCTCAGTGTGGTTGTGAACAAGCCCGTGG
GAAGATATCGCTCAGCCCCTAAACGCCTATCCATGACGCAAGAGAAGTTTGAAATGGGCTGGAAAGCATGGGGAAAAAGC
ATCCTCTTTGCCCCGGAATTGGCTAACTCCACATTTGTCGTAGATGGACCTGAGACAAAGGAATGCCCTGATGAGCACAGAG
CTTGGAACAGCATGCAAATCGAAGACTTCGGCTTTGGCATCACATCAACCCGTGTGTGGCTGAAAATTAGAGAGGAGAGCA
CTGACGAGTGTGATGGAGCGATCATAGGCACGGCTGTCAAAGGACATGTGGCAGTCCATAGTGACTTGTCGTACTGGATTG
AGAGTCGCTACAACGACACATGGAAACTTGAGAGGGCAGTCTTTGGAGAGGTCAAATCTTGCACTTGGCCAGAGACACACA
CCCTTTGGGGAGATGATGTTGAGGAAAGTGAACTCATCATTCCGCACACCATAGCCGGACCAAAAAGCAAGCACAATCGGA
GGGAAGGGTATAAGACACAAAACCAGGGACCTTGGGATGAGAATGGCATAGTCTTGGACTTTGATTATTGCCCAGGGACA
AAAGTCACCATTACAGAGGATTGTAGCAAGAGAGGCCCTTCGGTCAGAACCACTACTGACAGTGGAAAGTTGATCACTGAC
TGGTGCTGTCGCAGTTGCTCCCTTCCGCCCCTACGATTCCGGACAGAAAATGGCTGCTGGTACGGAATGGAAATCAGACCTG
TTATGCATGATGAAACAACACTCGTCAGATCACAGGTTCATGCTTTCAAAGGTGAAATGGTTGACCCTTTTCAGCTGGGCCTT
CTGGTGATGTTTCTGGCCACCCAGGAAGTCCTTCGCAAGAGGTGGACGGCCAGATTGACCATTCCTGCGGTTTTGGGGGTC
CTACTTGTGCTGATGCTTGGGGGTATCACTTACACTGATTTGGCGAGGTATGTGGTGCTAGTCGCTGCTGCTTTCGCAGAGG
CCAACAGTGGAGGAGACGTCCTGCACCTTGCTTTGATTGCTGTTTTTAAGATCCAACCAGCATTTTTAGTGATGAACATGCTT
AGCACGAGATGGACGAACCAAGAAAACGTGGTTCTGGTCCTAGGGGCTGCCTTTTTCCAATTGGCCTCAGTAGATCTGCAA
ATAGGAGTCCACGGAATCCTGAATGCCGCCGCTATAGCATGGATGATTGTCCGAGCGATCACCTTCCCCACAACCTCCTCCG
TCACCATGCCAGTCTTAGCGCTTCTAACTCCGGGGATGAGGGCTCTATACCTAGACACTTACAGAATCATCCTCCTCGTCATA
GGGATTTGCTCCCTGCTGCACGAGAGGAAAAAGACCATGGCGAAAAGAAAGGAGCTGTACTCTTGGGCTTAGCGCTCACA
TCCACTGGATGGTTCTCGCCCACCACTATAGCTGCCGGACTAATGGTCTGCAACCCAAACAAGAAGAGAGGGTGGCCAGCT
```

-continued

```
ACTGAGTTTTTGTCGGCAGTTGGATTGATGTTTGCCATCGTAGGTGGTTTGGCCGAGTTGGATATTGAATCCATGTCAATACC
CTTCATGCTGGCAGGTCTCATGGCAGTGTCCTACGTGGTGTCAGGAAAAGCAACAGATATGTGGCTTGAACGGGCCGCCGA
CATCAGCTGGGATATGGGTGCTGCAATCACAGGAAGCAGTCGGAGGCTGGATGTGAAACTGGATGATGACGGAGATTTTC
ACTTCATTGATGATCCCGGTGTTCCATGGAAGGTCTGGGTCCTGCGCATGTCTTGCATTGGCTTAGCCGCCCTCACGCCTTGG
GCCATCGTTCCCGCCGCTTTCGGTTATTGGCTCACTTTAAAAACAACAAAAAGAGGGGGCGTGTTTTGGGACACGCCATCCC
CAAAACCTTGCTCAAAAGGAGACACCACTACAGGAGTCTACCGAATTATGGCTAGAGGGATTCTTGGCACTTACCAGGCCG
GCGTCGGAGTCATGTACGAGAATGTTTTCCACACACTATGGCACACAACTAGAGGAGCAGCCATTGTGAGTGGAGAAGGAA
AATTGACGCCATACTGGGGTAGTGTGAAAGAAGACCGCATAGCTTACGGAGGCCCATGGAGGTTTGACCGAAAATGGAAT
GGAACAGATGACGTGCAAGTGATCGTGGTAGAACCGGGGAAGGGCGCAGTAAACATCCAGACAAAACCAGGAGTGTTTCG
GACTCCCTTCGGGGAGGTTGGGGCTGTTAGTCTGGATTACCCGCGAGGAACATCCGGCTCACCCATTCTGGATTCCAATGGA
GACATTATAGGCCTATACGGCAATGGAGTTGAGCTTGGCGATGGCTCATACGTCAGCGCCATCGTGCAGGGTGACCGTCAG
GAGGAACCAGTCCCAGAAGCTTACACCCCAAACATGTTGAGAAAGAGACAGATGACTGTGCTAGATTTGCACCCTGGTTCA
GGGAAAACCAGGAAAATTCTGCCACAAATAATTAAGGACGCTATCCAGCAGCGCCTAAGAACAGCTGTGTTGGCACCGACG
CGGGTGGTAGCAGCAGAAATGGCAGAAGTTTTGAGAGGGCTCCCAGTACGATATCAAACTTCAGCAGTGCAGAGAGAGCA
CCAAGGGAATGAAATAGTGGATGTGATGTGCCACGCCACTCTGACCCATAGACTGATGTCACCGAACAGAGTGCCCAACTA
CAACCTATTTGTCATGGATGAAGCTCATTTCACCGACCCAGCCAGTATAGCCGCACGAGGATACATTGCTACCAAGGTGGAA
TTAGGGGAGGCAGCAGCCATCTTTATGACAGCGACCCCGCCTGGAACCACGGATCCTTTTCCTGACTCAAATGCCCCAATCC
ATGATTTGCAAGATGAGATACCAGACAGGGCATGGAGCAGTGGATACGAATGGATCACAGAATATGCGGGTAAAACCGTG
TGGTTTGTGGCGAGCGTAAAAATGGGGAATGAGATTGCAATGTGCCTCCAAAGAGCGGGGAAAAAGGTCATCCAACTCAA
CCGCAAGTCCTATGACACAGAATACCCAAAATGTAAGAATGGAGACTGGGATTTTGTCATTACCACCGACATCTCTGAAATG
GGGGCCAACTTCGGTGCGAGCAGGGTCATCGACTGTAGAAAGAGCGTGAAACCCACCATCTTAGAAGAGGGAGAAGGCA
GAGTCATCCTCGGAAACCCATCTCCCATAACCAGTGCAAGCGCAGCTCAACGGAGGGGCAGAGTAGGCAGAAACCCCAATC
AAGTTGGAGATGAATACCACTATGGGGGGCTACCAGTGAAGATGACAGTAACCTAGCCCATTGGACAGAGGCAAAGATC
ATGTTAGACAACATACACATGCCCAATGGACTGGTGGCCCAGCTCTATGGACCAGAGAGGGAAAAGGCTTTCACAATGGAT
GGCGAATACCGTCTCAGAGGTGAAGAAAAGAAAAACTTCTTAGAGCTGCTTAGGACGGCTGACCTCCCGGTGTGGCTGGCC
TACAAGGTGGCGTCCAATGGCATTCAGTACACCGACAGAAAGTGGTGTTTTGATGGGCCGCGTACGAATGCCATACTGGAG
GACAACACCGAGGTAGAGATAGTCACCCGGATGGGTGAGAGGAAAATCCTCAAGCCGAGATGGCTTGATGCAAGAGTTTA
TGCAGATCACCAGGCCCTCAAGTGGTTCAAAGACTTTGCAGCAGGGAAGAGATCAGCCGTTAGCTTCATAGAGGTGCTCGG
TCGCATGCCTGAGCATTTCATGGGAAAGACGCGGGAAGCTTTAGACACCATGTACTTGGTTGCAACGGCTGAGAAAGGTGG
GAAAGCACACCGAATGGCTCTCGAAGAGCTGCCAGATGCACTGGAAACCATCACACTTATTGTCGCCATTACTGTGATGACA
GGAGGATTCTTCCTACTAATGATGCAGCGAAAGGGTATAGGGAAGATGGGTCTTGGAGCTCTAGTGCTCACACTAGCTACC
TTCTTCCTGTGGGCGGCAGAGGTTCCTGGAACCAAAATAGCAGGGACCCTGCTGATCGCCCTGCTGCTGATGGTGGTTCTCA
TCCCAGAACCGGAAAAACAGAGGTCACAGACAGATAACCAACTGGCGGTGTTTCTCATCTGTGTCTTGACCGTGGTTGGAG
TGGTGGCAGCAAACGAGTACGGGATGCTAGAAAAAACCAAAGCGGATCTCAAGAGCATGTTTGGCGGAAAGACGCAGGCA
TCAGGACTGACTGGATTGCCAAGCATGGCACTGGACCTGCGTCCAGCCACAGCCTGGGCACTGTATGGGGGAGCACAGTC
GTGCTAACCCCTCTTCTGAAGCACCTGATCACGTCGGAATACGTCACCACATCGCTAGCTTCAATTAACTCACAAGCTGGCTC
ATTATTCGTCTTGCCACGAGGCGTGCCTTTTACCGACCTAGACTTGACTGTTGGCCTCGTCTTCCTTGGCTGTTGGGGTCAAG
TCACCCTCACAACGTTTCTGACAGCCATGGTTCTGGCGACACTTCACTATGGGTACATGCTCCCTGGATGGCAAGCAGAAGC
ACTCAGGGCTGCCCAGAGAAGGACAGCGGCTGGAATAATGAAGAATGCCGTTGTTGACGGAATGGTCGCCACTGATGTGC
CTGAACTGGAAAGGACTACTCCTCTGATGCAAAAGAAAGTCGGACAGGTGCTCCTCATAGGGGTAAGCGTGGCAGCGTTCC
TCGTCAACCCTAATGTCACCACTGTGAGAGAAGCAGGGGTGTTGGTGACGGCGGCTACGCTTACTTTGTGGGACAATGGAG
```

-continued

```
CCAGTGCCGTTTGGAATTCCACCACAGCCACGGGACTCTGCCATGTCATGCGAGGTAGCTACCTGGCTGGAGGCTCCATTGC
TTGGACTCTCATCAAGAACGCTGATAAGCCCTCCTTGAAAAGGGGAAGGCCTGGGGCAGGACGCTAGGGGAGCAGTGGA
AGGAAAAACTAAATGCCATGAGTAGAGAAGAGTTTTTTAAATACCGGAGAGAGGGCATAATCGAGGTGGACCGCACTGAA
GCACGCAGGGCCAGAAGTGAAAATAACATAGTGGGAGGACATCCGGTTTCGCGAGGCTCAGCAAAACTCCGTTGGCTTGT
GGAGAAAGGATTTGTCTCGCCAATAGGAAAAGTCATTGATCTAGGGTGTGGGCGTGGAGGATGGAGCTACTACGCAGCAA
CCCTGAAGAAGGTCCAGGAAGTCAGAGGATACACGAAAGGTGGGGCGGGACATGAAGAACCGATGCTCATGCAGAGCTA
CGGCTGGAACCTGGTCTCCCTGAAGAGTGGAGTGGACGTGTTTTACAAACCTTCAGAGCCCAGTGATACCCTGTTCTGTGAC
ATAGGGGAATCCTCCCCAAGTCCAGAAGTAGAAGAACAACGCACACTACGCGTCCTAGAGATGACATCTGACTGGTTGCAC
CGAGGACCTAGAGAGTTCTGCATTAAAGTTCTCTGCCCTTACATGCCCAAGGTTATAGAAAAAATTGAAGTTCTGCAGCGCC
GCTTCGGAGGTGGGCTAGTGCGTCTCCCCCTGTCCCGAAACTCCAATCACGAGATGTATTGGGTTAGTGGAGCCGCTGGCA
ATGTGGTGCACGCTGTGAACATGACCAGCCAGGTATTACTGGGGCGAATGGATCGCACAGTGTGGAGAGGGCCAAAGTAT
GAGGAAGATGTCAACCTAGGGAGCGGAACAAGAGCCGTGGGAAAGGGAGAAGTCCATAGCAATCAGGAGAAAATCAAGA
AGAGAATCCAGAAGCTTAAAGAAGAATTCGCCACAACGTGGCACAAAGACCCTGAGCATCCATACCGCACTTGGACATACC
ACGGAAGCTATGAAGTGAAGGCTACTGGCTCAGCCAGCTCTCTCGTCAACGGAGTGGTGAAGCTCATGAGCAAACCTTGGG
ACGCCATTGCCAACGTCACCACCATGGCCATGACTGACACCACCCCTTTTGGACAGCAAAGAGTTTTCAAGGAGAAAGTTGA
CACGAAGGCTCCTGAGCCACCAGCTGGAGCCAAGGAAGTGCTCAACGAGACCACCAACTGGCTGTGGGCCTACTTGTCACG
GGAAAAAAGACCCCGCTTGTGCACCAAGGAAGAATTCATTAAGAAAGTTAACAGCAACGCGGCTCTTGGAGCAGTGTTCGC
TGAACAGAATCAATGGAGCACGGCGCGTGAGGCTGTGGATGACCCGCGGTTTTGGGAGATGGTTGATGAAGAGAGGGAA
AACCATCTGCGAGGAGAGTGTCACACATGTATCTACAACATGATGGGAAAAAGAGAGAAGAAGCCTGGAGAGTTTGGAAA
AGCTAAAGGAAGCAGGGCCATTTGGTTCATGTGGCTTGGAGCACGGTATCTAGAGTTTGAAGCTTTGGGGTTCCTGAATGA
AGACCATTGGCTGAGCCGAGAGAATTCAGGAGGTGGAGTGGAAGGCTCAGGCGTCCAAAAGCTGGGATACATCCTCCGTG
ACATAGCAGGAAAGCAAGGAGGGAAAATGTACGCTGATGATACCGCCGGGTGGGACACTAGAATTACCAGAACTGATTTA
GAAAATGAAGCTAAGGTACTGGAGCTCCTAGACGGTGAACACCGCATGCTCGCCCGAGCCATAATTGAACTGACTTACAGG
CACAAAGTGGTCAAGGTCATGAGACCTGCAGCAGAAGGAAAGACCGTGATGGACGTGATATCAAGAGAAGATCAAAGGG
GGAGTGGACAGGTGGTCACTTATGCTCTTAACACTTTCACGAACATCGCTGTCCAGCTCGTCAGGCTGATGGAGGCTGAGG
GGGTCATTGGACCACAACACTTGGAACATCTACCTAGGAAAAACAAGATAGCTGTCAGGACCTGGCTCTTTGAGAATGGAG
AGGAGAGAGTGACCAGGATGGCGATCAGCGGAGACGACTGTGCCGTCAAACCGCTGGACGACAGATTCGCCACAGCCCTC
CACTTCCTCAACGCAATGTCAAAGGTCAGAAAAGACATCCAGGAATGGAAGCCTTCGCATGGCTGGCACGATTGGCAGCAA
GTTCCCTTCTGTTCTAACCATTTTCAGGAGATTGTGATGAAAGATGGAAGGAGTATAGTTGTCCCGTGCAGAGGACAGGATG
AGCTGATAGGCAGGGCTCGCATCTCTCCAGGAGCTGGATGGAATGTGAAGGACACAGCTTGCCTGCCCAAAGCATATGCAC
AAATGTGGGTACTCCTATACTTCCACCGCAGGGACTTGCGTCTCATGGCAAATGCGATTTGCTCAGCAGTGCCAGTAGATTG
GGTGCCCACAGGCAGGACATCCTGGTCAATACACTCGAAAGGAGAGTGGATGACCACGGAAGACATGCTGCAGGTCTGGA
ACAGAGTTTGGATTGAAGAAAATGAATGGATGATGGACAAGACTCCAATCACAAGCTGGACAGACGTTCCGTATGTGGGA
AAGCGCGAGGACATCTGGTGTGGCAGCCTCATCGGAACGCGATCCAGAGCAACCTGGGCTGAGAACATCTATGCGGCGAT
AAACCAGGTTAGAGCTGTCATTGGGAAAGAAAATTATGTTGACTACATGACCTCACTCAGGAGATACGAAGACGTCTTGATC
CAGGAAGACAGGGTCATCTAGTGTGATTTAAGGTAGAAAAGTAGACTATGTAAACAATGTAAATGAGAAATGCATGCATA
TGGAGTCAGGCCAGCAAAAGCTGCCACCGGATACTGGGTAGACGGTGCTGCCTGCGTCTCAGTCCCAGGAGGACTGGGTT
AACAAATCTGACAACAGAAAGTGAGAAAGCCCTCAGAACTGTCTCGGAAGTAGGTCCCTGCTCACTGGAAGTTGAAAGACC
AACGTCAGGCCACAAATTTGTGCCACTCCGCTAGGGAGTGCGGCCTGCGCAGCCCCAGGAGGACTGGGTTACCAAAGCCGT
TGAGCCCCCACGGCCCAAGCCTCGTCTAGGATGCAATAGACGAGGTGTAAGGACTAGAGGTTAGAGGAGACCCCGTGGAA
ACAACAACATGCGGCCCAAGCCCCCTCGAAGCTGTAGAGGAGGTGGAAGGACTAGAGGTTAGAGGAGACCCCGCATTTGC
```

-continued

ATCAAACAGCATATTGACACCTGGGAATAGACTGGGAGATCTTCTGCTCTATCTCAACATCAGCTACTAGGCACAGAGCGCC

GAAGTATGTACGTGGTGGTGAGGAAGAACACAGGATCT

>gi|564014614|gb|KF769015.1| Yellow fever virus strain 17D-204, complete genome

SEQ ID NO: 76

GTGCTAATTGAGGTGCATTGGTCTGCAAATCGAGTTGCTAGGCAATAAACACATTTGGATTAATTTTAATCGTTCGTTGAGCGA

TTAGCAGAGAACTGACCAGAACATGTCTGGTCGTAAAGCTCAGGGAAAAACCCTGGGCGTCAATATGGTACGACGAGGAGTT

CGCTCCTTGTCAAACAAAATAAAACAAAAAACAAAACAAATTGGAAACAGACCTGGACCTTCAAGAGGTGTTCAAGGATTTAT

CTTTTTCTTTTTGTTCAACATTTTGACTGGAAAAAAGATCACAGCCCACCTAAAGAGGTTGTGGAAAATGCTGGACCCAAGACA

AGGCTTGGCTGTTCTAAGGAAAGTCAAGAGAGTGGTGGCCAGTTTGATGAGAGGATTGTCCTCAAGGAAACGCCGTTCCCAT

GATGTTCTGACTGTGCAATTCCTAATTTTGGGAATGCTGTTGATGACGGGTGGAGTGACCTTGGTGCGGAAAAACAGATGGTT

GCTCCTAAATGTGACATCTGAGGACCTCGGGAAAACATTCTCTGTGGGCACAGGCAACTGCACAACAAACATTTTGGAAGCCA

AGTACTGGTGCCCAGACTCAATGGAATACAACTGTCCCAATCTCAGTCCAAGAGAGGAGCCAGATGACATTGATTGCTGGTGC

TATGGGGTGGAAAACGTTAGAGTCGCATATGGTAAGTGTGACTCAGCAGGCAGGTCTAGGAGGTCAAGAAGGGCCATTGACT

TGCCTACGCATGAAAACCATGGTTTGAAGACCCGGCAAGAAAATGGATGACTGGAAGAATGGGTGAAAGGCAACTCCAAAA

GATTGAGAGATGGTTCGTGAGGAACCCCTTTTTTGCAGTGACGGCTCTGACCATTGCCTACCTTGTGGGAAGCAACATGACGC

AACGAGTCGTGATTGCCCTACTGGTCTTGGCTGTTGGTCCGGCCTACTCAGCTCACTGCATTGGAATTACTGACAGGGATTTCA

TTGAGGGGGTGCATGGAGGAACTTGGGTTTCAGCTACCCTGGAGCAAGACAAGTGTGTCACTGTTATGGCCCCTGACAAGCCT

TCATTGGACATCTCACTAGAGACAGTAGCCATTGATAGACCTGCTGAGGTGAGGAAAGTGTGTTACAATGCAGTTCTCACTCAT

GTGAAGATTAATGACAAGTGCCCCAGCACTGGAGAGGCCCACCTAGCTGAAGAGAACGAAGGGGACAATGCGTGCAAGCGC

ACTTATTCTGATAGAGGCTGGGGCAATGGCTGTGGCCTATTTGGGAAAGGGAGCATTGTGGCATGCGCCAAATTCACTTGTGC

CAAATCCATGAGTTTGTTTGAGGTTGATCAGACCAAAATTCAGTATGTCATCAGAGCACAATTGCATGTAGGGGCCAAGCAGG

AAAATTGGACTACCGACATTAAGACTCTCAAGTTTGATGCCCTGTCAGGCTCCCAGGAAGTCGAGTTCATTGGGTATGGAAAA

GCTACACTGGAATGCCAGGTGCAAACTGCGGTGGACTTTGGTAACAGTTACATCGCTGAGATGGAAACAGAGAGCTGGATAG

TGGACAGACAGTGGGCCCAGGACTTGACCCTGCCATGGCAGAGTGGAAGTGGCGGGGTGTGGAGAGAGATGCATCATCTTG

TCGAATTTGAACCTCCGCATGCCGCCACTATCAGAGTACTGGCCCTGGGAAACCAGGAAGGCTCCTTGAAAACAGCTCTTACT

GGCGCAATGAGGGTTACAAAGGACACAAATGACAACAACCTTTACAAACTACATGGTGGACATGTTTCTTGCAGAGTGAAATT

GTCAGCTTTGACACTCAAGGGGACATCCTACAAAATATGCACTGACAAAATGTTTTTTGTCAAGAACCCAACTGACACTGGCCA

TGGCACTGTTGTGATGCAGGTGAAAGTGTCAAAAGGAGCCCCCTGCAGGATTCCAGTGATAGTAGCTGATGATCTTACAGCG

GCAATCAATAAAGGCATTTTGGTTACAGTTAACCCCATCGCCTCAACCAATGATGATGAAGTGCTGATTGAGGTGAACCCACCT

TTTGGAGACAGCTACATTATCGTTGGGAGAGGAGATTCACGTCTCACTTACCAGTGGCACAAAGAGGGAAGCTCAATAGGAA

AGTTGTTCACTCAGACCATGAAAGGCGTGGAACGCCTGGCCGTCATGGGAGACACCGCCTGGGATTTCAGCTCCGCTGGAGG

GTTCTTCACTTCGGTTGGGAAAGGAATTCATACGGTGTTTGGCTCTGCCTTTCAGGGGCTATTTGGCGGCTTGAACTGGATAAC

AAAGGTCATCATGGGGGCGGTACTTATATGGGTTGGCATCAACACAAGAAACATGACAATGTCCATGAGCATGATCTTGGTAG

GAGTGATCATGATGTTTTTGTCTCTAGGAGTTGGGGCGGATCAAGGATGCGCCATCAACTTTGGCAAGAGAGAGCTCAAGTGC

GGAGATGGTATCTTCATATTTAGAGACTCTGATGACTGGCTGAACAAGTACTCATACTATCCAGAAGATCCTGTGAAGCTTGCA

TCAATAGTGAAAGCCTCTTTTGAAGAAGGGAAGTGTGGCCTAAATTCAGTTGACTCCCTTGAGCATGAGATGTGGAGAAGCAG

GGCAGATGAGATCAATGCCATTTTTGAGGAAAACGAGGTGGACATTTCTGTTGTCGTGCAGGATCCAAAGAATGTTTACCAGA

GAGGAACTCATCCATTTTCCAGAATTCGGGATGGTCTGCAGTATGGTTGGAAGACTTGGGGTAAGAACCTTGTGTTCTCCCCA

GGGAGGAAGAATGGAAGCTTCATCATAGATGGAAAGTCCAGGAAGAATGCCCGTTTTCAAACCGGGTCTGGAATTCTTTCC

AGATAGAGGAGTTTGGGACGGGAGTGTTCACCACACGCGTGTACATGGACGCAGTCTTTGAATACACCATAGACTGCGATGG

ATCTATCTTGGGTGCAGCGGTGAACGGAAAAAAGAGTGCCCATGGCTCTCCAACATTTTGGATGGGAAGTCATGAAGTAAAT

GGGACATGGATGATCCACACCTTGGAGGCATTAGATTACAAGGAGTGTGAGTGGCCACTGACACATACGATTGGAACATCAG

-continued

```
TTGAAGAGAGTGAAATGTTCATGCCGAGATCAATCGGAGGCCCAGTTAGCTCTCACAATCATATCCCTGGATACAAGGTTCAG
ACGAACGGACCTTGGATGCAGGTACCACTAGAAGTGAAGAGAGAAGCTTGCCCAGGGACTAGCGTGATCATTGATGGCAACT
GTGATGGACGGGAAAATCAACCAGATCCACCACGGATAGCGGGAAAGTTATTCCTGAATGGTGTTGCCGCTCCTGCACAAT
GCCGCCTGTGAGCTTCCATGGTAGTGATGGGTGTTGGTATCCCATGGAAATTAGGCCAAGGAAAACGCATGAAAGCCATCTG
GTGCGCTCCTGGGTTACAGCTGGAGAAATACATGCTGTCCCTTTTGGTTTGGTGAGCATGATGATAGCAATGGAAGTGGTCCT
AAGGAAAAGACAGGGACCAAAGCAAATGTTGGTTGGAGGAGTAGTGCTCTTGGGAGCAATGCTGGTCGGGCAAGTAACTCT
CCTTGATTTGCTGAAACTCACAGTGGCTGTGGGATTGCATTTCCATGAGATGAACAATGGAGGAGACGCCATGTATATGGCGT
TGATTGCTGCCTTTTCAATCAGACCAGGGCTGCTCATCGGCTTTGGGCTCAGGACCCTATGGAGCCCTCGGGAACGCCTTGTGC
TGACCCTAGGAGCAGCCATGGTGGAGATTGCCTTGGGTGGCGTGATGGGCGGCCTGTGGAAGTATCTAAATGCAGTTTCTCTC
TGCATCCTGACAATAAATGCTGTTGCTTCTAGGAAAGCATCAAATACCATCTTGCCCCTCATGGCTCTGTTGACACCTGTCACTA
TGGCTGAGGTGAGACTTGCCGCAATGTTCTTTTGTGCCGTGGTTATCATAGGGGTCCTTCACCAGAATTTCAAGGACACCTCCA
TGCAGAAGACTATACCTCTGGTGGCCCTCACACTCACATCTTACCTGGGCTTGACACAACCTTTTTTGGGCCTGTGTGCATTTCT
GGCAACCCGCATATTTGGGCGAAGGAGTATCCCAGTGAATGAGGCACTCGCAGCAGCTGGTCTAGTGGGAGTGCTGGCAGG
ACTGGCTTTTCAGGAGATGGAGAACTTCCTTGGTCCGATTGCAGTTGGAGGACTCCTGATGATGCTGGTTAGCGTGGCTGGGA
GGGTGGATGGGCTAGAGCTCAAGAAGCTTGGTGAAGTTTCATGGGAAGAGGAGGCGGAGATCAGCGGGAGTTCCGCCCGCT
ATGATGTGGCACTCAGTGAACAAGGGGAGTTCAAGCTGCTTTCTGAAGAGAAAGTGCCATGGGACCAGGTTGTGATGACCTC
GCTGGCCTTGGTTGGGGCTGCCCTCCATCCATTTGCTCTTCTGCTGGTCCTTGCTGGGTGGCTGTTTCATGTCAGGGGAGCTAG
GAGAAGTGGGGATGTCTTGTGGGATATTCCCACTCCTAAGATCATCGAGGAATGTGAACATCTGGAGGATGGGATTTATGGC
ATATTCCAGTCAACCTTCTTGGGGGCCTCCCAGCGAGGAGTGTGGGAGTGGCACAGGGAGGGGTGTTCCACACAATGTGGCATG
TCACAAGAGGAGCTTTCCTTGTCAGGAATGGCAAGAAGTTGATTCCATCTTGGGCTTCAGTAAAGGAAGACCTTGTCGCCTAT
GGTGGCTCATGGAAGTTGGAAGGCAGATGGGATGGAGAGGAAGAGGTCCAGTTGATCGCGGCTGTTCCAGGAAAGAACGTG
GTCAACGTCCAGACAAAACCGAGCTTGTTCAAAGTGAGGAATGGGGGAGAAATCGGGGCTGTCGCTCTTGACTATCCGAGTG
GCACTTCAGGATCTCCTATTGTTAACAGGAACGGAGAGGTGATTGGGCTGTACGGCAATGGCATCCTTGTCGGTGACAACTCC
TTCGTGTCCGCCATATCCCAGACTGAGGTGAAGGAAGAAGGAAAGGAGGAGCTCCAAGAGATCCCGACAATGCTAAAGAAA
GGAATGACAACTGTCCTTGATTTTCATCCTGGAGCTGGGAAGACAAGACGTTTCCTCCCACAGATCTTGGCCGAGTGCGCACG
GAGACGCTTGCGCACTCTTGTGTTGGCCCCCACCAGGGTTGTTCTTTCTGAAATGAAGGAGGCTTTTCACGGCCTGGACGTGA
AATTCCACACACAGGCTTTTTCCGCTCACGGCAGCGGGAGAGAAGTCATTGATGCTATGTGCCATGCCACCCTAACTTACAGGA
TGTTGGAACCAACTAGGGTTGTTAACTGGGAAGTGATCATTATGGATGAAGCCCATTTTTTGGATCCAGCTAGCATAGCCGCTA
GAGGTTGGGCAGCGCACAGAGCTAGGGCAAATGAAAGTGCAACAATCTTGATGACAGCCACACCGCCTGGGACTAGTGATG
AATTTCCACATTCAAATGGTGAAATAGAAGATGTTCAAACGGACATACCCAGTGAGCCCTGGAACACAGGGCATGACTGGATC
CTGGCTGACAAAAGGCCCACGGCATGGTTCCTTCCATCCATCAGAGCTGCAAATGTCATGGCTGCCTCTTTGCGTAAGGCTGG
AAAGAGTGTGGTGGTCCTGAACAGGAAAACCTTTGAGAGAGAATACCCCACGATAAAGCAGAAGAAACCTGACTTTATATTG
GCCACTGACATAGCTGAAATGGGAGCCAACCTTTGCGTGGAGCGAGTGCTGGATTGCAGGACGGCTTTTAAGCCTGTGCTTGT
GGATGAAGGGAGGAAGGTGGCAATAAAAGGGCCACTTCGTATCTCCGCATCCTCTGCTGCTCAAAGGAGGGGCGCATTGG
GAGAAATCCCAACAGAGATGGAGACTCATACTACTATTCTGAGCCTACAAGTGAAAATAATGCCCACCACGTCTGCTGGTTGG
AGGCCTCAATGCTCTTGGACAACATGGAGGTGAGGGGTGGAATGGTCGCCCCACTCTATGGCGTTGAAGGAACTAAAACACC
AGTTTCCCCTGGTGAAATGAGACTGAGGGATGACCAGAGGAAAGTCTTCAGAGAACTAGTGAGGAATTGTGACCTGCCCGTT
TGGCTTTCGTGGCAAGTGGCCAAGGCTGGTTTGAAGACGAATGATCGTAAGTGGTGTTTTGAAGGCCCTGAGGAACATGAGA
TCTTGAATGACAGCGGTGAAACAGTGAAGTGCAGGGCTCCTGGAGGAGCAAAGAAGCCTCTGCGCCCAAGGTGGTGTGATG
AAAGGGTGTCATCTGACCAGAGTGCGCTGTCTGAATTTATTAAGTTTGCTGAAGGTAGGAGGGGAGCTGCTGAAGTGCTAGTT
GTGCTGAGTGAACTCCCTGATTTCCTGGCTAAAAAAGGTGGAGAGGCAATGGATACCATCAGTGTGTTTCTCCACTCTGAGGA
```

-continued
AGGCTCTAGGGCTTACCGCAATGCACTATCAATGATGCCTGAGGCAATGACAATAGTCATGCTGTTTATACTGGCTGGACTACT
GACATCGGGAATGGTCATCTTTTTCATGTCTCCCAAAGGCATCAGTAGAATGTCTATGGCGATGGGCACAATGGCCGGCTGTG
GATATCTCATGTTCCTTGGAGGCGTCAAACCCACTCACATCTCCTATATCATGCTCATATTCTTTGTCCTGATGGTGGTTGTGATC
CCCGAGCCAGGGCAACAAAGGTCCATCCAAGACAACCAAGTGGCATACCTCATTATTGGCATCCTGACGCTGGTTTCAGCGGT
GGCAGCCAACGAGCTAGGCATGCTGGAGAAAACCAAAGAGGACCTCTTTGGGAAGAAGAACTTAATTCCATCTAGTGCTTCAC
CCTGGAGTTGGCCGGATCTTGACCTGAAGCCAGGAGCTGCCTGGACAGTGTACGTTGGCATTGTTACAATGCTCTCTCCAATG
TTGCACCACTGGATCAAAGTCGAATATGGCAACCTGTCTCTGTCTGGAATAGCCCAGTCAGCCTCAGTCCTTTCTTTCATGGACA
AGGGGATACCATTCATGAAGATGAATATCTCGGTCATAATGCTGCTGGTCAGTGGCTGGAATTCAATAACAGTGATGCCTCTG
CTCTGTGGCATAGGGTGCGCCATGCTCCACTGGTCTCTCATTTTACCTGGAATCAAAGCGCAGCAGTCAAAGCTTGCACAGAG
AAGGGTGTTCCATGGCGTTGCCAAGAACCCTGTGGTTGATGGGAATCCAACAGTTGACATTGAGGAAGCTCCTGAAATGCCTG
CCCTTTATGAGAAGAAACTGGCTCTATATCTCCTTCTTGCTCTCAGCCTAGCTTCTGTTGCCATGTGCAGAACGCCCTTTTCATTG
GCTGAAGGCATTGTCCTAGCATCAGCTGCCCTAGGGCCGCTCATAGAGGGAAACACCAGCCTTCTTTGGAATGGACCCATGGC
TGTCTCCATGACAGGAGTCATGAGGGGGAATCACTATGCTTTTGTGGGAGTCATGTACAATCTATGGAAGATGAAAACTGGAC
GCCGGGGAGCGCGAATGGAAAAACTTTGGGTGAAGTCTGGAAGAGGGAACTGAATCTGTTGGACAAGCGACAGTTTGAGT
TGTATAAAAGGACCGACATTGTGGAGGTGGATCGTGATACGGCACGCAGGCATTTGGCCGAAGGGAAGGTGGACACCGGGG
TGGCGGTCTCCAGGGGGACCGCAAAGTTAAGGTGGTTCCATGAGCGTGGCTATGTCAAGCTGGAAGGTAGGGTGATTGACCT
GGGGTGTGGCCGCGGAGGCTGGTGTTACTACGCTGCTGCGCAAAAGGAAGTGAGTGGGGTCAAAGGATTTACTCTTGGAAG
AGACGGCCATGAGAAACCCATGAATGTGCAAAGTCTGGGATGGAACATCATCACCTTCAAGGACAAAACTGATATCCACCGCC
TAGAACCAGTGAAATGTGACACCCTTTTGTGTGACATTGGAGAGTCATCATCGTCATCGGTCACAGAGGGGGAAAGGACCGT
GAGAGTTCTTGATACTGTAGAAAAATGGCTGGCTTGTGGGGTTGACAACTTCTGTGTGAAGGTGTTAGCTCCATACATGCCAG
ATGTTCTCGAGAAACTGGAATTGCTCCAAAGGAGGTTTGGCGGAACAGTGATCAGGAACCCTCTCTCCAGGAATTCCACTCAT
GAAATGTACTACGTGTCTGGAGCCCGCAGCAATGTCACATTTACTGTGAACCAAACATCCCGCCTCCTGATGAGGAGAATGAG
GCGTCCAACTGGAAAAGTGACCCTGGAGGCTGACGTCATCCTCCCAATTGGGACACGCAGTGTTGAGACAGACAAGGGACCC
CTGGACAAAGAGGCCATAGAAGAAAGGGTTGAGAGGATAAAATCTGAGTACATGACCTCTTGGTTTTATGACAATGACAACC
CCTACAGGACCTGGCACTACTGTGGCTCCTATGTCACAAAAACCTCAGGAAGTGCGGCGAGCATGGTAAATGGTGTTATTAAA
ATTCTGACATATCCATGGGACAGGATAGAGGAGGTCACAAGAATGGCAATGACTGACACAACCCCTTTTGGACAGCAAAGAG
TGTTTAAAGAAAAAGTTGACACCAGAGCAAAGGATCCACCAGCGGGAACTAGGAAGATCATGAAAGTTGTCAACAGGTGGCT
GTTCCGCCACCTGGCCAGAGAAAAGAACCCCAGACTGTGCACAAAGGAAGAATTTATTGCAAAAGTCCGAAGTCATGCAGCC
ATTGGAGCTTACCTGGAAGAACAAGAACAGTGGAAGACTGCCAATGAGGCTGTCCAAGACCCAAAGTTCTGGGAACTGGTGG
ATGAAGAAAGGAAGCTGCACCAACAAGGCAGGTGTCGGACTTGTGTGTACAACATGATGGGAAAAGAGAGAAGAAGCTGT
CAGAGTTTGGGAAAGCAAAGGGAAGCCGTGCCATATGGTATATGTGGCTGGGAGCGCGGTATCTTGAGTTTGAGGCCCTGGG
ATTCCTGAATGAGGACCATTGGGCTTCCAGGGAAAACTCAGGAGGAGGAGTGGAAGGCATTGGCTTACAATACCTAGGATAT
GTGATCAGAGACCTGGCTGCAATGGATGGTGGTGGATTCTACGCGGATGACACCGCTGGATGGGACACGCGCATCACAGAG
GCAGACCTTGATGATGAACAGGAGATCTTGAACTACATGAGCCCACATCACAAAAAACTGGCACAAGCAGTGATGGAAATGA
CATACAAGAACAAAGTGGTGAAAGTGTTGAGACCAGCCCCAGGAGGGAAAGCCTACATGGATGTCATAAGTCGACGAGACCA
GAGAGGATCCGGGCAGGTAGTGACTTATGCTCTGAACACCATCACCAACTTGAAAGTCCAATTGATCAGAATGGCAGAAGCA
GAGATGGTGATACATCACCAACATGTTCAAGATTGTGATGAATCAGTTCTGACCAGGCTGGAGGCATGGCTCACTGAGCACGG
ATGTAACAGACTGAAGAGGATGGCGGTGAGTGGAGACGACTGTGTGGTCCGGCCCATCGATGACAGGTTCGGCCTGGCCCTG
TCCCATCTCAACGCCATGTCCAAGGTTAGAAAGGACATATCTGAATGGCAGCCATCAAAAGGGTGGAATGATTGGGAGAATG
TGCCCTTCTGTTCCCACCACTTCCATGAACTACAGCTGAAGGATGGCAGGAGGATTGTGGTGCCTTGCCGAGAACAGGACGAG
CTCATTGGGAGAGGAAGGGTGTCTCCAGGAAACGGCTGGATGATCAAGGAAACAGCTTGCCTCAGCAAAGCCTATGCCAACA -continued TGTGGTCACTGATGTATTTTCACAAAAGGGACATGAGGCTACTGTCATTGGCTGTTTCCTCAGCTGTTCCCACCTCATGGGTTCC ACAAGGACGCACAACATGGTCGATTCATGGGAAAGGGGAGTGGATGACCACGGAAGACATGCTTGAGGTGTGGAACAGAGT ATGGATAACCAACAACCCACACATGCAGGACAAGACAATGGTGAAAAAATGGAGAGATGTCCCTTATCTAACCAAGAGACAA GACAAGCTGTGCGGATCACTGATTGGAATGACCAATAGGGCCACCTGGGCCTCCCACATCCATTTGGTCATCCATCGTATCCGA ACGCTGATTGGACAGGAGAAATACACTGACTACCTAACAGTCATGGACAGGTATTCTGTGGATGCTGACCTGCAACTGGGTGA GCTTATCTGAAACACCATCTAACAGGAATAACCGGGATACAAACCACGGGTGGAGAACCGGACTCCCCACAACCTGAAACCG GGATATAAACCACGGCTGGAGAACCGGACTCCGCACTTAAAATGAAACAGAAACCGGGATAAAAACTACGGATGGAGAACC GGACTCCACACATTGAGACAGAAGAAGTTGTCAGCCCAGAACCCCACACGAGTTTTGCCACTGCTAAGCTGTGAGGCAGTGCA GGCTGGGACAGCCGACCTCCAGGTTGCGAAAAACCTGGTTTCTGGGACCTCCCACCCCAGAGTAAAAAGAACGGAGCCTCCG CTACCACCCTCCCACGTGGTGGTAGAAAGACGGGGTCTAGAGGTTAGAGGAGACCCTCCAGGGAACAAATAGTGGGACCATA TTGACGCCAGGGAAAGACCGGAGTGGTTCTCTGCTTTTCCTCCAGAGGTCTGTGAGCACAGTTTGCTCAAGAATAAGCAGACC

TTTGGATGACAAA

Attenuated Chikungunya "Delta5nsP3" sequence

SEQ ID NO: 77

GATGGCTGCGTGAGACACACGTAGCCTACCAGTTTCTTACTGCTCTACTCTGCAAAGCAAGAGATTAATAACCCATCATGGATC

CTGTGTACGTGGACATAGACGCTGACAGCGCCTTTTTGAAGGCCCTGCAACGTGCGTACCCCATGTTTGAGGTGGAACCAAGG

CAGGTCACACCGAATGACCATGCTAATGCTAGAGCGTTCTCGCATCTAGCTATAAAACTAATAGAGCAGGAAATTGACCCCGA

CTCAACCATCCTGGATATCGGCAGTGCGCCAGCAAGGAGGATGATGTCGGACAGGAAGTACCACTGCGTCTGCCCGATGCGC

AGTGCGGAAGATCCCGAGAGACTCGCCAATTATGCGAGAAAGCTAGCATCTGCCGCAGGAAAAGTCCTGGACAGAAACATCT

CTGGAAAGATCGGGGACTTACAAGCAGTAATGGCCGTGCCAGACACGGAGACGCCAACATTCTGCTTACACACAGACGTCTCA

TGTAGACAGAGAGCAGACGTCGCTATATACCAAGACGTCTATGCTGTACACGCACCCACGTCGCTATACCACCAGGCGATTAA

AGGGGTCCGAGTGGCGTACTGGGTTGGGTTCGACACAACCCCGTTCATGTACAATGCCATGGCGGGTGCCTACCCCTCATACT

CGACAAACTGGGCAGATGAGCAGGTACTGAAGGCTAAGAACATAGGATTATGTTCAACAGACCTGACGGAAGGTAGACGAG

GCAAGTTGTCTATTATGAGAGGGAAAAAGCTAAACCGTGCGACCGTGTGCTGTTCTCAGTAGGGTCAACGCTCTACCCGGAA

AGCCGCAAGCTACTTAAGAGCTGGCACCTGCCATCGGTGTTCCATTTAAAGGGCAAACTCAGCTTCACATGCCGCTGTGATACA

GTGGTTTCGTGTGAGGGCTACGTCGTTAAGAGAATAACGATGAGCCCAGGCCTTTATGGAAAAACCACAGGGTATGCGGTAA

CCCACCACGCAGACGGATTCCTGATGTGCAAGACTACCGACACGGTTGACGGCGAAAGAATGTCATTCTCGGTGTGCACATAC

GTGCCGGCGACCATTTGTGATCAAATGACCGGCATCCTTGCTACAGAAGTCACGCCGGAGGATGCACAGAAGCTGTTGGTGG

GGCTGAACCAGAGAATAGTGGTTAACGGCAGAACGCAACGGAATACGAACACCATGAAAAATTATCTGCTTCCCGTGGTCGC

CCAAGCCTTCAGTAAGTGGGCAAAGGAGTGCCGGAAAGACATGGAAGATGAAAAACTCCTGGGGGTCAGAGAAAGAACACT

GACCTGCTGCTGTCTATGGGCATTCAAGAAGCAGAAAACACACACGGTCTACAAGAGGCCTGATACCCAGTCAATTCAGAAGG

TTCAGGCCGAGTTTGACAGCTTTGTGGTACCGAGTCTGTGGTCGTCCGGGTTGTCAATCCCTTTGAGGACTAGAATCAAATGGT

TGTTAAGCAAGGTGCCAAAAACCGACCTGATCCCATACAGCGGAGACGCCCGAGAAGCCCGGGACGCAGAAAAGAAGCAG

AGGAAGAACGAGAAGCAGAACTGACTCGCGAAGCCCTACCACCTCTACAGGCAGCACAGGAAGATGTTCAGGTCGAAATCGA

CGTGGAACAGCTTGAGGACAGAGCGGGCGCAGGAATAATAGAGACTCCGAGAGGAGCTATCAAAGTTACTGCCCAACCAAC

AGACCACGTCGTGGGAGAGTACCTGGTACTCTCCCCGCAGACCGTACTACGTAGCCAGAAGCTCAGTCTGATTCACGCTTTGG

CGGAGCAAGTGAAGACGTGCACGCACAACGGACGAGCAGGGAGGTATGCGGTCGAAGCGTACGACGGCCGAGTCCTAGTGC

CCTCAGGCTATGCAATCTCGCCTGAAGACTTCCAGAGTCTAAGCGAAAGCGCAACGATGGTGTATAACGAAAGAGAGTTCGTA

AACAGAAAGCTACACCATATTGCGATGCACGGACCAGCCCTGAACACCGACGAAGAGTCGTATGAGCTGGTGAGGGCAGAGA

GGACAGAACACGAGTACGTCTACGACGTGGATCAGAGAAGATGCTGTAAGAAGGAAGAAGCCGCAGGACTGGTACTGGTGG

GCGACTTGACTAATCCGCCCTACCACGAATTCGCATATGAAGGGCTAAAAATCCGCCCTGCCTGCCCATACAAAATTGCAGTCA

TAGGAGTCTTCGGAGTACCGGGATCTGGCAAGTCAGCTATTATCAAGAACCTAGTTACCAGGCAGGACCTGGTGACTAGCGG

-continued

```
AAAGAAAGAAAACTGCCAAGAAATCACCACCGACGTGATGAGACAGAGAGGTCTAGAGATATCTGCACGTACGGTTGACTCG
CTGCTCTTGAATGGATGCAACAGACCAGTCGACGTGTTGTACGTAGACGAGGCGTTTGCGTGCCACTCTGGAACGCTACTTGC
TTTGATCGCCTTGGTGAGACCAAGGCAGAAAGTTGTACTTTGTGGTGACCCGAAGCAGTGCGGCTTCTTCAATATGATGCAGA
TGAAAGTCAACTATAATCACAACATCTGCACCCAAGTGTACCACAAAAGTATCTCCAGGCGGTGTACACTGCCTGTGACCGCCA
TTGTGTCATCGTTGCATTACGAAGGCAAAATGCGCACTACGAATGAGTACAACAAGCCGATTGTAGTGGACACTACAGGCTCA
ACAAAACCTGACCCTGGAGACCTCGTGTTAACGTGCTTCAGAGGGTGGGTTAAACAACTGCAAATTGACTATCGTGGATACGA
GGTCATGACAGCAGCCGCATCCCAAGGGTTAACCAGAAAAGGAGTTTACGCAGTTAGACAAAAAGTTAATGAAAACCCGCTCT
ATGCATCAACGTCAGAGCACGTCAACGTACTCCTAACGCGTACGGAAGGTAAACTGGTATGGAAGACACTTTCCGGCGACCCG
TGGATAAAGACGCTGCAGAACCCACCGAAAGGAAACTTCAAAGCAACTATTAAGGAGTGGGAGGTGGAGCATGCATCAATAA
TGGCGGGCATCTGCAGTCACCAAATGACCTTCGATACATTCCAAAATAAAGCCAACGTTTGTTGGGCTAAGAGCTTGGTCCCTA
TCCTCGAAACAGCGGGGATAAAACTAAATGATAGGCAGTGGTCTCAGATAATTCAAGCCTTCAAAGAAGACAAAGCATACTCA
CCTGAAGTAGCCCTGAATGAAATATGTACGCGCATGTATGGGGTGGATCTAGACAGCGGGCTATTTTCTAAACCGTTGGTGTC
TGTGTATTACGCGGATAACCACTGGGATAATAGGCCTGGAGGGAAAATGTTCGGATTTAACCCCGAGGCAGCATCCATTCTAG
AAAGAAAGTATCCATTCACAAAAGGGAAGTGGAACATCAACAAGCAGATCTGCGTGACTACCAGGAGGATAGAAGACTTTAA
CCCTACCACCAACATCATACCGGCCAACAGGAGACTACCACACTCATTAGTGGCCGAACACCGCCCAGTAAAAGGGGAAAGAA
TGGAATGGCTGGTTAACAAGATAAACGGCCACCACGTGCTCCTGGTCAGTGGCTATAACCTTGCACTGCCTACTAAGAGAGTC
ACTTGGGTAGCGCCGTTAGGTGTCCGCGGAGCGGACTACACATACAACCTAGAGTTGGGTCTGCCAGCAACGCTTGGTAGGT
ATGACCTAGTGGTCATAAACATCCACACACCTTTTCGCATACACCATTACCAACAGTGCGTCGACCACGCAATGAAACTGCAAA
TGCTCGGGGGTGACTCATTGAGACTGCTCAAACCGGGCGGCTCTCTATTGATCAGAGCATATGGTTACGCAGATAGAACCAGT
GAACGAGTCATCTGCGTATTGGGACGCAAGTTTAGATCGTCTAGAGCGTTGAAACCACCATGTGTCACCAGCAACACTGAGAT
GTTTTTCCTATTCAGCAACTTTGACAATGGCAGAAGGAATTTCACAACTCATGTCATGAACAATCAACTGAATGCAGCCTTCGTA
GGACAGGTCACCCGAGCAGGATGTGCACCGTCGTACCGGGTAAAACGCATGGACATCGCGAAGAACGATGAAGAGTGCGTA
GTCAACGCCGCTAACCCTCGCGGGTTACCGGGTGGCGGTGTTTGCAAGGCAGTATACAAAAAATGGCCGGAGTCCTTTAAGA
ACAGTGCAACACCAGTGGGAACCGCAAAAACAGTTATGTGCGGTACGTATCCAGTAATCCACGCTGTTGGACCAAACTTCTCT
AATTATTCGGAGTCTGAAGGGGACCGGGAATTGGCAGCTGCCTATCGAGAAGTCGCAAAGGAAGTAACTAGGCTGGGAGTA
AATAGTGTAGCTATACCTCTCCTCTCCACAGGTGTATACTCAGGAGGGAAAGACAGGCTGACCCAGTCACTGAACCACCTCTTT
ACAGCCATGGACTCGACGGATGCAGACGTGGTCATCTACTGCCGCGACAAAGAATGGGAGAAGAAAATATCTGAGGCCATAC
AGATGCGGACCCAAGTAGAGCTGCTGGATGAGCACATCTCCATAGACTGCGATATTGTTCGCGTGCACCCTGACAGCAGCTTG
GCAGGCAGAAAAGGATACAGCACCACGGAAGGCGCACTGTACTCATATCTAGAAGGGACCCGTTTTCATCAGACGGCTGTGG
ATATGGCGGAGATACATACTATGTGGCCAAAGCAAACAGAGGCCAATGAGCAAGTCTGCCTATATGCCCTGGGGGAAAGTAT
TGAATCGATCAGGCAGAAATGCCCGGTGGATGATGCAGACGCATCATCTCCCCCCAAAACTGTCCCGTGCCTTTGCCGTTACGC
TATGACTCCAGAACGCGTCACCCGGCTTCGCATGAACCACGTCACAAGCATAATTGTGTGTTCTTCGTTTCCCCTCCCAAAGTAC
AAAATAGAAGGAGTGCAAAAAGTCAAATGCTCTAAGGTAATGCTATTTGACCACAACGTGCCATCGCGCGTAAGTCCAAGGG
CTTATAGAGGTGCCGCTGCCGGTAACCTTGCGGCCGTGTCTGATTGGGTAATGAGCACCGTACCTGTCGCGCCGCCCAGAAGA
AGGCGAGGGAGAAACCTGACTGTGACATGTGACGAGAGAGAAGGGAATATAACACCCATGGCTAGCGTCCGATTCTTTAGG
GCAGAGCTGTGTCCGGTCGTACAAGAAACAGCGGAGACGCGTGACACAGCAATGTCTCTTCAGGCACCACCGAGTACCGCCA
CGGAACCGAATCATCCGCCGATCTCCTTCGGAGCATCAAGCGAGACGTTCCCCATTACATTTGGGGACTTCAACGAAGGAGAA
ATCGAAAGCTTGTCTTCTGAGCTACTAACTTTCGGAGACTTCTTACCAGGAGAAGTGGATGACTTGACAGACAGCGACTGGTC
CACGTGCTCAGACACGGACGACGAGTTAAGACTAGACAGGGCAGGTGGGTATATATTCTCGTCGGACACCGGTCCAGGTCAT
TTACAACAGAAGTCAGTACGCCAGTCAGTGCTGCCGGTGAACACCCTGGAGGAAGTCCACGAGGAGAAGTGTTACCCACCTA
AGCTGGATGAAGCAAAGGAGCAACTATTACTTAAGAAACTCCAGGAGAGTGCATCCATGGCCAACAGAAGCAGGTATCAGTC
```

-continued

```
GCGCAAAGTAGAAAACATGAAAGCAGCAATCATCCAGAGACTAAAGAGAGGCTGTAGACTATACTTAATGTCAGAGACCCCA
AAAGTCCCTACTTACCGGACTACATATCCGGCGCCTGTGTACTCGCCTCCGATCAACGTCCGATTGTCCAATCCCGAGTCCGCA
GTGGCAGCATGCAATGAGTTCTTAGCTAGAAACTATCCAACTGTCTCATCATACCAAATTACCGACGAGTATGATGCATATCTA
GACATGGTGGACGGGTCGGAGAGTTGCCTGGACCGAGCGACATTCAATCCGTCAAAACTCAGGAGCTACCCGAAACAGCACG
CTTACCACGCGCCCTCCATCAGAAGCGCTGTACCGTCCCCATTCCAGAACACACTACAGAATGTACTGGCAGCAGCCACGAAAA
GAAACTGCAACGTCACACAGATGAGGGAATTACCCACTTTGGACTCAGCAGTATTCAACGTGGAGTGTTTCAAAAAATTCGCA
TGCAACCAAGAATACTGGGAAGAATTTGCTGCCAGCCCTATTAGGATAACAACTGAGAATTTAGCAACCTATGTTACTAAACTA
AAAGGGCCAAAAGCAGCAGCGCTATTCGCAAAAACCCATAATCTACTGCCACTACAGGAAGTACCAATGGATAGGTTCACAGT
AGATATGAAAAGGGACGTAAAGGTGACTCCTGGTACAAAGCATACAGAGGAAAGACCTAAGGTGCAGGTTATACAGGCGGC
TGAACCCTTGGCGACAGCATACCTATGTGGGATTCACAGAGAGCTGGTTAGGAGGCTGAACGCCGTCCTCCTACCCAATGTAC
ATACACTATTTGACATGTCTGCCGAGGATTTCGATGCCATCATAGCCGCACACTTTAAGCCAGGAGACACTGTTTTGGAAACGG
ACATAGCCTCCTTTGATAAGAGCCAAGATGATTCACTTGCGCTTACTGCTTTGATGCTGTTAGAGGATTTAGGGGTGGATCACT
CCCTGCTGGACTTGATAGAGGCTGCTTTCGGAGAGATTTCCAGCTGTCACCTACCGACAGGTACGCGCTTCAAGTTCGGCGCC
ATGATGAAATCAGGTATGTTCCTAACTCTGTTCGTCAACACATTGTTAAACATCACCATCGCCAGCCGAGTGCTGGAAGATCGT
CTGACAAAATCCGCGTGCGCGGCCTTCATCGGCGACGACAACATAATACATGGAGTCGTCTCCGATGAATTGATGGCAGCCAG
ATGTGCCACTTGGATGAACATGGAAGTGAAGATCATAGATGCAGTTGTATCCTTGAAAGCCCCTTACTTTTGTGGAGGGTTTAT
ACTGCACGATACTGTGACAGGAACAGCTTGCAGAGTGGCAGACCCGCTAAAAAGGCTTTTTAAACTGGGCAAACCGCTAGCG
GCAGGTGACGAACAAGATGAAGATAGAAGACGAGCGCTGGCTGACGAAGTGATCAGATGGCAACGAACAGGGCTAATTGAT
GAGCTGGAGAAAGCGGTATACTCTAGGTACGAAGTGCAGGGTATATCAGTTGTGGTAATGTCCATGGCCACCTTTGCAAGCTC
CAGATCCAACTTCGAGAAGCTCAGAGGACCCGTCATAACTTTGTACGGCGGTCCTAAATAGGTACGCACTACAGCTACCTATTT
TGCAGAAGCCGACAGCAAGTATCTAAACACTAATCAGCTACAATGGAGTTCATCCCAACCCAAACTTTTTACAATAGGAGGTAC
CAGCCTCGACCCTGGACTCCGCGCCCTACTATCCAAGTCATCAGGCCCAGACCGCGCCCTCAGAGGCAAGCTGGGCAACTTGC
CCAGCTGATCTCAGCAGTTAATAAACTGACAATGCGCGCGGTACCACAACAGAAGCCACGCAGGAATCGGAAGAATAAGAAG
CAAAAGCAAAAACAACAGGCGCCACAAAACAACACAAATCAAAAGAAGCAGCCACCTAAAAAGAAACCGGCTCAAAAGAAAA
AGAAGCCGGCCGCAGAGAGAGGATGTGCATGAAAATCGAAAATGATTGTATTTTCGAAGTCAAGCACGAAGGTAAGGTAA
CAGGTTACGCGTGCCTGGTGGGGACAAAGTAATGAAACCAGCACACGTAAAGGGGACCATCGATAACGCGGACCTGGCCA
AACTGGCCTTTAAGCGGTCATCTAAGTATGACCTTGAATGCGCGCAGATACCCGTGCACATGAAGTCCGACGCTTCGAAGTTC
ACCCATGAGAAACCGGAGGGGTACTACAACTGGCACCACGGAGCAGTACAGTACTCAGGAGGCCGGTTCACCATCCCTACAG
GTGCTGGCAAACCAGGGGACAGCGGCAGACCGATCTTCGACAACAAGGGACGCGTGGTGGCCATAGTCTTAGGAGGAGCTA
ATGAAGGAGCCCGTACAGCCCTCTCGGTGGTGACCTGGAATAAAGACATTGTCACTAAAATCACCCCCGAGGGGCCGAAGA
GTGGAGTCTTGCCATCCCAGTTATGTGCCTGTTGGCAAACACCACGTTCCCTGCTCCCAGCCCCCTTGCACGCCCTGCTGCTAC
GAAAAGGAACCGGAGGAAACCCTACGCATGCTTGAGGACAACGTCATGAGACCTGGGTACTATCAGCTGCTACAAGCATCCTT
AACATGTTCTCCCCACCGCCAGCGACGCAGCACCAAGGACAACTTCAATGTCTATAAAGCCACAAGACCATACTTAGCTCACTG
TCCCGACTGTGGAGAAGGGCACTCGTGCCATAGTCCCGTAGCACTAGAACGCATCAGAAATGAAGCGACAGACGGGACGCTG
AAAATCCAGGTCTCCTTGCAAATCGGAATAAAGACGGATGACAGCCACGATTGGACCAAGCTGCGTTATATGGACAACCACAT
GCCAGCAGACGCAGAGAGGGCGGGGCTATTTGTAAGAACATCAGCACCGTGTACGATTACTGGAACAATGGGACACTTCATC
CTGGCCCGATGTCCAAAAGGGGAAACTCTGACGGTGGGATTCACTGACAGTAGGAAGATTAGTCACTCATGTACGCACCCATT
TCACCACGACCCTCCTGTGATAGGTCGGGAAAAATTCCATTCCCGACCGCAGCACGGTAAAGAGCTACCTTGCAGCACGTACG
TGCAGAGCACCGCCGCAACTACCGAGGAGATAGAGGTACACATGCCCCCAGACACCCCTGATCGCACATTAATGTCACAACAG
TCCGGCAACGTAAAGATCACAGTCAATGGCCAGACGGTGCGGTACAAGTGTAATTGCGGTGGCTCAAATGAAGGACTAACAA
CTACAGACAAAGTGATTAATAACTGCAAGGTTGATCAATGTCATGCCGCGGTCACCAATCACAAAAAGTGGCAGTATAACTCC
```

-continued

CCTCTGGTCCCGCGTAATGCTGAACTTGGGGACCGAAAAGGAAAAATTCACATCCCGTTTCCGCTGGCAAATGTAACATGCAG

GGTGCCTAAAGCAAGGAACCCCACCGTGACGTACGGGAAAAACCAAGTCATCATGCTACTGTATCCTGACCACCCAACACTCC

TGTCCTACCGGAATATGGGAGAAGAACCAAACTATCAAGAAGAGTGGGTGATGCATAAGAAGGAAGTCGTGCTAACCGTGCC

GACTGAAGGGCTCGAGGTCACGTGGGGCAACAACGAGCCGTATAAGTATTGGCCGCAGTTATCTACAAACGGTACAGCCCAT

GGCCACCCGCATGAGATAATTCTGTATTATTATGAGCTGTACCCCACTATGACTGTAGTAGTTGTGTCAGTGGCCACGTTCATA

CTCCTGTCGATGGTGGGTATGGCAGCGGGGATGTGCATGTGTGCACGACGCAGATGCATCACACCGTATGAACTGACACCAG

GAGCTACCGTCCCTTTCCTGCTTAGCCTAATATGCTGCATCAGAACAGCTAAAGCGGCCACATACCAAGAGGCTGCGATATACC

TGTGGAACGAGCAGCAACCTTTGTTTTGGCTACAAGCCCTTATTCCGCTGGCAGCCCTGATTGTTCTATGCAACTGTCTGAGAC

TCTTACCATGCTGCTGTAAAACGTTGGCTTTTTTAGCCGTAATGAGCGTCGGTGCCCACACTGTGAGCGCGTACGAACACGTAA

CAGTGATCCCGAACACGGTGGGAGTACCGTATAAGACTCTAGTCAATAGACCTGGCTACAGCCCCATGGTATTGGAGATGGA

ACTACTGTCAGTCACTTTGGAGCCAACACTATCGCTTGATTACATCACGTGCGAGTACAAAACCGTCATCCCGTCTCCGTACGT

GAAGTGCTGCGGTACAGCAGAGTGCAAGGACAAAAACCTACCTGACTACAGCTGTAAGGTCTTCACCGGCGTCTACCCATTTA

TGTGGGCGGCGCCTACTGCTTCTGCGACGCTGAAAACACGCAGTTGAGCGAAGCACACGTGGAGAAGTCCGAATCATGCAA

AACAGAATTTGCATCAGCATACAGGGCTCATACCGCATCTGCATCAGCTAAGCTCCGCGTCCTTTACCAAGGAAATAACATCAC

TGTAACTGCCTATGCAAACGGCGACCATGCCGTCACAGTTAAGGACGCCAAATTCATTGTGGGGCCAATGTCTTCAGCCTGGA

CACCTTTCGACAACAAAATTGTGGTGTACAAAGGTGACGTCTATAACATGGACTACCCGCCCTTTGGCGCAGGAAGACCAGGA

CAATTTGGCGATATCCAAAGTCGCACACCTGAGAGTAAAGACGTCTATGCTAATACACAACTGGTACTGCAGAGACCGGCTGT

GGGTACGGTACACGTGCCATACTCTCAGGCACCATCTGGCTTTAAGTATTGGCTAAAAGAACGCGGGGCGTCGCTGCAGCACA

CAGCACCATTTGGCTGCCAAATAGCAACAAACCCGGTAAGAGCGGTGAACTGCGCCGTAGGGAACATGCCCATCTCCATCGAC

ATACCGGAAGCGGCCTTCACTAGGGTCGTCGACGCGCCCTCTTTAACGGACATGTCGTGCGAGGTACCAGCCTGCACCCATTC

CTCAGACTTTGGGGGCGTCGCCATTATTAAATATGCAGCCAGCAAGAAAGGCAAGTGTGCGGTGCATTCGATGACTAACGCCG

TCACTATTCGGGAAGCTGAGATAGAAGTTGAAGGGAATTCTCAGCTGCAAATCTCTTTCTCGACGGCCTTAGCCAGCGCCGAA

TTCCGCGTACAAGTCTGTTCTACACAAGTACACTGTGCAGCCGAGTGCCACCCCCCGAAGGACCACATAGTCAACTACCCGGC

GTCACATACCACCCTCGGGGTCCAGGACATCTCCGCTACGGCGATGTCATGGGTGCAGAAGATCACGGGAGGTGTGGGACTG

GTTGTTGCTGTTGCCGCACTGATTCTAATCGTGGTGCTATGCGTGTCGTTCAGCAGGCACTAACTTGACAATTAAGTATGAAGG

TATATGTGTCCCCTAAGAGACACACTGTACATAGCAAATAATCTATAGATCAAAGGGCTACGCAACCCCTGAATAGTAACAAAA

TACAAAATCACTAAAAATTATAAAAACAGAAAAATACATAAATAGGTATACGTGTCCCCTAAGAGACACATTGTATGTAGGTG

ATAAGTATAGATCAAAGGGCCGAATAACCCCTGAATAGTAACAAAATATGAAAATCAATAAAAATCATAAAATAGAAAAACCA

TAAACAGAAGTAGTTCAAAGGGCTATAAAACCCCTGAATAGTAACAAAACATAAAATTAATAAAAATCAAATGAATACCATAA

TTGGCAAACGGAAGAGATGTAGGTACTTAAGCTTCCTAAAAGCAGCCGAACTCACTTTGAGAAGTAGGCATAGCATACCGAAC

TCTTCCACGATTCTCCGAACCCACAGGGACGTAGGAGATGTTATTTTGTTTTTAATATTTCAAAAAAAAAAAAAAAAAAAAAAA

ZIKV Sequence H/PF/2013 as sequenced

SEQ ID NO: 78

CAGACTGCGACAGTTCGAGTTTGAAGCGAAAGCTAGCAACAGTATCAACAGGTTTTATTTTGGATTTGGAAACGAGAGTTTCT

GGTCATGAAAAACCCAAAAAAGAAATCCGGAGGATTCCGGATTGTCAATATGCTAAAACGCGGAGTAGCCCGTGTGAGCCCC

TTTGGGGGCTTGAAGAGGCTGCCAGCCGGACTTCTGCTGGGTCATGGGCCCATCAGGATGGTCTTGGCGATTCTAGCCTTTTT

GAGATTCACGGCAATCAAGCCATCACTGGGTCTCATCAATAGATGGGGTTCAGTGGGAAAAAGAGGCTATGGAAATAATA

AAGAAGTTCAAGAAAGATCTGGCTGCCATGCTGAGAATAATCAATGCTAGGAAGGAGAAGAAGACGAGGCGCAGATACT

AGTGTCGGAATTGTTGGCCTCCTGCTGACCACAGCTATGGCAGCGGAGGTCACTAGACGTGGGAGTGCATACTATATGTACTT

GGACAGAAACGACGCTGGGGAGGCCATATCTTTTCCAACCACATTGGGGATGAATAAGTGTTATATACAGATCATGGATCTTG

GACACATGTGTGATGCCACCATGAGCTATGAATGCCCTATGCTGGATGAGGGGGTGGAACCAGATGACGTCGATTGTTGGTG

CAACACGACGTCAACTTGGGTTGTGTACGGAACCTGCCATCACAAAAAAGGTGAAGCACGGAGATCTAGAAGAGCTGTGACG

-continued

```
CTCCCCTCCCATTCCACTAGGAAGCTGCAAACGCGGTCGCAAACCTGGTTGGAATCAAGAGAATACACAAAGCACTTGATTAG
AGTCGAAAATTGGATATTCAGGAACCCTGGCTTCGCGTTAGCAGCAGCTGCCATCGCTTGGCTTTTGGGAAGCTCAACGAGCC
AAAAAGTCATATACTTGGTCATGATACTGCTGATTGCCCCGGCATACAGCATCAGGTGCATAGGAGTCAGCAATAGGGACTTT
GTGGAAGGTATGTCAGGTGGGACTTGGGTTGATGTTGTCTTGGAACATGGAGGTTGTGTCACCGTAATGGCACAGGACAAAC
CGACTGTCGACATAGAGCTGGTTACAACAACAGTCAGCAACATGGCGGAGGTAAGATCCTACTGCTATGAGGCATCAATATCG
GACATGGCTTCGGACAGCCGCTGCCCAACACAAGGTGAAGCCTACCTTGACAAGCAATCAGACACTCAATATGTCTGCAAAAG
AACGTTAGTGGACAGAGGCTGGGGAAATGGATGTGGACTTTTTGGCAAAGGGAGCCTGGTGACATGCGCTAAGTTTGCATGC
TCCAAGAAAATGACCGGGAAGAGCATCCAGCCAGAGAATCTGGAGTACCGGATAATGCTGTCAGTTCATGGCTCCCAGCACA
GTGGGATGATCGTTAATGACACAGGACATGAAACTGATGAGAATAGAGCGAAGGTTGAGATAACGCCCAATTCACCAAGAGC
CGAAGCCACCCTGGGGGGTTTTGGAAGCCTAGGACTTGATTGTGAACCGAGGACAGGCCTTGACTTTTCAGATTTGTATTACT
TGACTATGAATAACAAGCACTGGTTGGTTCACAAGGAGTGGTTCCACGACATTCCATTACCTTGGCACGCTGGGGCAGACACC
GGAACTCCACACTGGAACAACAAAGAAGCACTGGTAGAGTTCAAGGACGCACATGCCAAAAGGCAAACTGTCGTGGTTCTAG
GGAGTCAAGAAGGAGCAGTTCACACGGCCCTTGCTGGAGCTCTGGAGGCTGAGATGGATGGTGCAAAGGGAAGGCTGTCCT
CTGGCCACTTGAAATGTCGCCTGAAAATGGATAAACTTAGATTGAAGGGCGTGTCATACTCCTTGTGTACCGCAGCGTTCACAT
TCACCAAGATCCCGGCTGAAACACTGCACGGGACAGTCACAGTGGAGGTACAGTACGCAGGGACAGATGGACCTTGCAAGGT
TCCAGCTCAGATGGCGGTGGACATGCAAACTCTGACCCCAGTTGGGAGGTTGATAACCGCTAACCCCGTAATCACTGAAAGCA
CTGAGAACTCTAAGATGATGCTGGAACTTGATCCACCATTTGGGGACTCTTACATTGTCATAGGAGTCGGGGAGAAGAAGATC
ACCCACCACTGGCACAGGAGTGGCAGCACCATTGGAAAAGCATTTGAAGCCACTGTGAGAGGTGCCAAGAGAATGGCAGTCT
TGGGAGACACAGCCTGGGACTTTGGATCAGTTGGAGGCGCTCTCAACTCATTGGGCAAGGGCATCCATCAAATTTTTGGAGCA
GCTTTCAAATCATTGTTTGGAGGAATGTCCTGGTTCTCACAAATTCTCATTGGAACGTTGCTGATGTGGTTGGGTCTGAACACA
AAGAATGGATCTATTTCCCTTATGTGCTTGGCCTTAGGGGGAGTGTTGATCTTCTTATCCACAGCTGTCTCTGCTGATGTGGGG
TGCTCGGTGGACTTCTCAAAGAAGGAGACGAGATGCGGTACAGGGGTGTTCGTCTATAACGACGTTGAAGCCTGGAGGGACA
GGTACAAGTACCATCCTGACTCCCCCCGTAGATTGGCAGCAGCAGTCAAGCAAGCCTGGAAGATGGTATCTGTGGGATCTCC
TCTGTTTCAAGAATGGAAAACATCATGTGGAGATCAGTAGAAGGGGAGCTCAACGCAATCCTGGAAGAGAATGGAGTTCAAC
TGACGGTCGTTGTGGGATCTGTAAAAAAACCCCATGTGGAGAGGTCCACAGAGATTGCCCGTGCCTGTGAACGAGCTGCCCCAC
GGCTGGAAGGCTTGGGGGAAATCGTACTTCGTCAGAGCAGCAAAGACAAATAACAGCTTTGTCGTGGATGGTGACACACTGA
AGGAATGCCCACTCAAACATAGAGCATGGAACAGCTTTCTTGTGGAGGATCATGGGTTCGGGGTATTTCACACTAGTGTCTGG
CTCAAGGTTAGAGAAGATTATTCATTAGAGTGTGATCCAGCCGTTATTGGAACAGCTGTTAAGGGAAAGGAGGCTGTACACA
GTGATCTAGGCTACTGGATTGAGAGTGAGAAGAATGACACATGGAGGCTGAAGAGGGCCCATCTGATCGAGATGAAAACAT
GTGAATGGCCAAAGTCCCACACATTGTGGACAGATGGAATAGAAGAGAGTGATCTGATCATACCCAAGTCTTTAGCTGGGCCA
CTCAGCCATCACAATACCAGAGAGGGCTACAGGACCCAAATGAAAGGGCCATGGCACAGTGAAGAGCTTGAAATTCGGTTTG
AGGAATGCCCAGGCACTAAGGTCCACGTGGAGGAAACATGTGGAACAAGAGGACCATCTCTGAGATCAACCACTGCAAGCGG
AAGGGTGATCGAGGAATGGTGCTGCAGGGAGTGCACAATGCCCCACTGTCGTTCCGGGCTAAAGATGGCTGTTGGTATGGA
ATGGAGATAAGGCCCAGGAAAGAACCAGAAAGTAACTTAGTAAGGTCAATGGTGACTGCAGGATCAACTGATCACATGGATC
ACTTCTCCCTTGGAGTGCTTGTGATTCTGCTCATGGTGCAGGAAGGGCTGAAGAAGAGAATGACCACAAAGATCATCATAAGC
ACATCGATGGCAGTGCTGGTAGCTATGATCCTGGGAGGATTTTCAATGAGTGACCTGGCTAAGCTTGCAATTTTGATGGGTGC
CACCTTCGCGGAAATGAACACTGGAGGAGATGTAGCTCATCGGCGCTGATAGCGGCATTCAAAGTCAGACCAGCGTTGCTG
GTATCTTTCATCTTCAGAGCTAATTGGACACCCCGTGAAAGCATGCTGCTGGCCTTGGCCTCGTGTCTTTTGCAAACTGCGATCT
CCGCCTTGGAAGGCGACCTGATGGTTCTCATCAATGGTTTTGCTTTGGCCTGGTTGGCAATACGAGCGATGGTTGTTCCACGCA
CTGATAACATCACCTTGGCAATCCTGGCTGCTCTGACACCACTGGCCCGGGGCACACTGCTTGTGGCGTGGAGAGCAGGCCTT
GCTACTTGCGGGGGGTTTATGCTCCTCTCTCTGAAGGGAAAAGGCAGTGTGAAGAAGAACTTACCATTTGTCATGGCCCTGGG
```

-continued

```
ACTAACCGCTGTGAGGCTGGTCGACCCCATCAACGTGGTGGGACTGCTGTTGCTCACAAGGAGTGGGAAGCGGAGCTGGCCC
CCTAGCGAAGTACTCACAGCTGTTGGCCTGATATGCGCATTGGCTGGAGGGTTCGCCAAGGCAGATATAGAGATGGCTGGGC
CCATGGCCGCGGTCGGTCTGCTAATTGTCAGTTACGTGGTCTCAGGAAAGAGTGTGGACATGTACATTGAAAGAGCAGGTGA
CATCACATGGGAAAAAGATGCGGAAGTCACTGGAAACAGTCCCCGGCTCGATGTGGCGCTAGATGAGAGTGGTGATTTCTCC
CTGGTGGAGGATGACGGTCCCCCCATGAGAGAGATCATACTCAAGGTGGTCCTGATGACCATCTGTGGCATGAACCCAATAGC
CATACCCTTTGCAGCTGGAGCGTGGTACGTATACGTGAAGACTGGAAAAAGGAGTGGTGCTCTATGGGATGTGCCTGCTCCCA
AGGAAGTAAAAAAGGGGGAGACCACAGATGGAGTGTACAGAGTAATGACTCGTAGACTGCTAGGTTCAACACAAGTTGGAG
TGGGAGTTATGCAAGAGGGGGTCTTTCACACTATGTGGCACGTCACAAAAGGATCCGCGCTGAGAAGCGGTGAAGGGAGAC
TTGATCCATACTGGGGAGATGTCAAGCAGGATCTGGTGTCATACTGTGGTCCATGGAAGCTAGATGCCGCCTGGGACGGGCA
CAGCGAGGTGCAGCTCTTGGCCGTGCCCCCCGGAGAGAGAGCGAGGAACATCCAGACTCTGCCCGGAATATTTAAGACAAAG
GATGGGACATTGGAGCGGTTGCGCTGGATTACCCAGCAGGAACTTCAGGATCTCCAATCCTAGACAAGTGTGGGAGAGTGA
TAGGACTTTATGGCAATGGGGTCGTGATCAAAAATGGGAGTTATGTTAGTGCCATCACCCAAGGGAGGAGGGAGGAAGAGA
CTCCTGTTGAGTGCTTCGAGCCTTCGATGCTGAAGAAGAAGCAGCTAACTGTCTTAGACTTGCATCCTGGAGCTGGGAAAACC
AGGAGAGTTCTTCCTGAAATAGTCCGTGAAGCCATAAAAACAAGACTCCGTACTGTGATCTTAGCTCCAACCAGGGTTGTCGCT
GCTGAAATGGAGGAAGCCCTTAGAGGGCTTCCAGTGCGTTATATGACAACAGCAGTCAATGTCACCCACTCTGGAACAGAAAT
CGTCGACTTAATGTGCCATGCCACCTTCACTTCACGTCTACTACAGCCAATCAGAGTCCCCAACTATAATCTGTATATTATGGAT
GAGGCCCACTTCACAGATCCCTCAAGTATAGCAGCAAGAGGATACATTTCAACAAGGGTTGAGATGGGCGAGGCGGCTGCCA
TCTTCATGACCGCCACGCCACCAGGAACCCGTGACGCATTTCCGGACTCCAACTCACCAATTATGGACACCGAAGTGGAAGTCC
CAGAGAGAGCCTGGAGCTCAGGCTTTGATTGGGTGACGGATCATTCTGGAAAAACAGTTTGGTTTGTTCCAAGCGTGAGGAA
CGGCAATGAGATCGCAGCTTGTCTGACAAAGGCTGGAAAACGGGTCATACAGCTCAGCAGAAAGACTTTTGAGACAGAGTTC
CAGAAAACAAAACATCAAGAGTGGGACTTTGTCGTGACAACTGACATTTCAGAGATGGGCGCCAACTTTAAAGCTGACCGTGT
CATAGATTCCAGGAGATGCCTAAAGCCGGTCATACTTGATGGCGAGAGAGTCATTCTGGCTGGACCCATGCCTGTCACACATG
CCAGCGCTGCCCAGAGGAGGGGCGCATAGGCAGGAATCCCAACAAACCTGGAGATGAGTATCTGTATGGAGGTGGGTGCG
CAGAGACTGACGAAGACCATGCACACTGGCTTGAAGCAAGAATGCTCCTTGACAATATTTACCTCCAAGATGGCCTCATAGCC
TCGCTCTATCGACCTGAGGCCGACAAAGTAGCAGCCATTGAGGGAGAGTTCAAGCTTAGGACGGAGCAAAGGAAGACCTTTG
TGGAACTCATGAAAAGAGGAGATCTTCCTGTTTGGCTGGCCTATCAGGTTGCATCTGCCGGAATAACCTACACAGATAGAAGA
TGGTGCTTTGATGGCACGACCAACAACACCATAATGGAAGACAGTGTGCCGGCAGAGGTGTGGACCAGACACGGAGAGAAA
AGAGTGCTCAAACCGAGGTGGATGGACGCCAGAGTTTGTTCAGATCATGCGGCCCTGAAGTCATTCAAGGAGTTTGCCGCTG
GGAAAAGAGGAGCGGCTTTTGGAGTGATGGAAGCCCTGGGAACACTGCCAGGACACATGACAGAGAGATTCCAGGAAGCCA
TTGACAACCTCGCTGTGCTCATGCGGGCAGAGACTGGAAGCAGGCCTTACAAAGCCGCGGCGGCCCAATTGCCGGAGACCCT
AGAGACCATTATGCTTTTGGGGTTGCTGGGAACAGTCTCGCTGGGAATCTTTTTCGTCTTGATGAGGAACAAGGGCATAGGGA
AGATGGGCTTTGGAATGGTGACTCTTGGGGCCAGCGCATGGCTCATGTGGCTCTCGGAAATTGAGCCAGCCAGAATTGCATGT
GTCCTCATTGTTGTGTTCCTATTGCTGGTGGTGCTCATACCTGAGCCAGAAAAGCAAAGATCTCCCCAGGACAACCAAATGGCA
ATCATCATCATGGTAGCAGTAGGTCTTCTGGGCTTGATTACCGCCAATGAACTCGGATGGTTGGAGAGAACAAAGAGTGACCT
AAGCCATCTAATGGAAGGAGAGAGGAGGGGGCAACCATAGGATTCTCAATGGACATTGACCTGCGGCCAGCCTCAGCTTGG
GCCATCTATGCTGCCTTGACAACTTTCATTACCCCAGCCGTCCAACATGCAGTGACCACTTCATACAACAACTACTCCTTAATGG
CGATGGCCACGCAAGCTGGAGTGTTGTTTGGTATGGGCAAAGGGATGCCATTCTACGCATGGGACTTTGGAGTCCCGCTGCTA
ATGATAGGTTGCTACTCACAATTAACACCCCTGACCCTAATAGTGGCCATCATTTTGCTCGTGGCGCACTACATGTACTTGATCC
CAGGGCTGCAGGCAGCAGCTGCGCGTGCTGCCCAGAAGAGAACGGCAGCTGGCATCATGAAGAACCCTGTTGTGGATGGAA
TAGTGGTGACTGACATTGACACAATGACAATTGACCCCCAAGTGGAGAAAAAGATGGGACAGGTGCTACTCATAGCAGTAGC
CGTCTCCAGCGCCATACTGTCGCGGACCGCCTGGGGGTGGGGGGAGGCTGGGCCCTGATCACAGCGGCAACTTCCACTTTG
```

-continued

```
TGGGAAGGCTCTCCGAACAAGTACTGGAACTCCTCTACAGCCACTTCACTGTGTAACATTTTTAGGGGAAGTTACTTGGCTGGA
GCTTCTCTAATCTACACAGTAACAAGAAACGCTGGCTTGGTCAAGAGACGTGGGGGTGGAACAGGAGAGACCCTGGGAGAG
AAATGGAAGGCCCGCTTGAACCAGATGTCGGCCCTGGAGTTCTACTCCTACAAAAAGTCAGGCATCACCGAGGTGTGCAGAG
AAGAGGCCCGCCGCGCCCTCAAGGACGGTGTGGCAACGGGAGGCCATGCTGTGTCCCGAGGAAGTGCAAAGCTGAGATGGT
TGGTGGAGCGGGATACCTGCAGCCCTATGGAAAGGTCATTGATCTTGGATGTGGCAGAGGGGCTGGAGTTACTACGCCGC
CACCATCCGCAAAGTTCAAGAAGTGAAAGGATACACAAAAGGAGGCCCTGGTCATGAAGAACCCATGTTGGTGCAAAGCTAT
GGGTGGAACATAGTCCGTCTTAAGAGTGGGGTGGACGTCTTTCATATGGCGGCTGAGCCGTGTGACACGTTGCTGTGTGACA
TAGGTGAGTCATCATCTAGTCCTGAAGTGGAAGAAGCACGGACGCTCAGAGTCCTCTCCATGGTGGGGGATTGGCTTGAAAA
AAGACCAGGAGCCTTTTGTATAAAAGTGTTGTGCCCATACACCAGCACTATGATGGAAACCCTGGAGCGACTGCAGCGTAGGT
ATGGGGGAGGACTGGTCAGAGTGCCACTCTCCCGCAACTCTACACATGAGATGTACTGGGTCTCTGGAGCGAAAAGCAACAC
CATAAAAGTGTGTCCACCACGAGCCAGCTCCTCTTGGGGCGCATGGACGGGCCCAGGAGGCCAGTGAAATATGAGGAGGAT
GTGAATCTCGGCTCTGGCACGCGGGCTGTGGTAAGCTGCGCTGAAGCTCCCAACATGAAGATCATTGGTAACCGCATTGAAAG
GATCCGCAGTGAGCACGCGGAAACGTGGTTCTTTGACGAGAACCACCCATATAGGACATGGGCTTACCATGGAAGCTATGAG
GCCCCCACACAAGGGTCAGCGTCCTCTCTAATAAACGGGGTTGTCAGGCTCCTGTCAAAACCCTGGGATGTGGTGACTGGAGT
CACAGGAATAGCCATGACCGACACCACACCGTATGGTCAGCAAAGAGTTTTCAAGGAAAAAGTGGACACTAGGGTGCCAGAC
CCCCAAGAAGGCACTCGTCAGGTTATGAGCATGGTCTCTTCCTGGTTGTGGAAAGAGCTAGGCAAACACAAACGGCCACGAG
TCTGTACCAAAGAAGAGTTCATCAACAAGGTTCGTAGCAATGCAGCATTAGGGGCAATATTTGAAGAGGAAAAAGAGTGGAA
GACTGCAGTGGAAGCTGTGAACGATCCAAGGTTCTGGGCTCTAGTGGACAAGGAAAGAGAGCACCACCTGAGAGGAGAGTG
CCAGAGTTGTGTGTACAACATGATGGGAAAAAGAGAAAAGAAACAAGGGGAATTTGGAAAGGCCAAGGGCAGCCGCGCCAT
CTGGTATATGTGGCTAGGGGCTAGATTTCTAGAGTTCGAAGCCCTTGGATTCTTGAACGAGGATCACTGGATGGGGAGAGAG
AACTCAGGAGGTGGTGTTGAAGGGCTGGGATTACAAAGACTCGGATATGTCCTAGAAGAGATGAGTCGCATACCAGGAGGA
AGGATGTATGCAGATGACACTGCTGGCTGGGACACCCGCATCAGCAGGTTTGATCTGGAGAATGAAGCTCTAATCACCAACCA
AATGGAGAAAGGGCACAGGGCCTTGGCATTGGCCATAATCAAGTACACATACCAAAACAAAGTGGTAAAGGTCCTTAGACCA
GCTGAAAAAGGGAAGACAGTTATGGACATTATTTCGAGACAAGACCAAAGGGGAGCGGACAAGTTGTCACTTACGCTCTTA
ACACATTTACCAACCTAGTGGTGCAACTCATTCGGAATATGGAGGCTGAGGAAGTTCTAGAGATGCAAGACTTGTGGCTGCTG
CGGAGGTCAGAGAAAGTGACCAACTGGTTGCAGAGCAACGGATGGGATAGGCTCAAACGAATGGCAGTCAGTGGAGATGAT
TGCGTTGTGAAGCCAATTGATGATAGGTTTGCACATGCCCTCAGGTTCTTGAATGATATGGGAAAAGTTAGGAAGGACACACA
AGAGTGGAAACCCTCAACTGGATGGGACAACTGGGAAGAAGTTCCGTTTTGCTCCCACCACTTCAACAAGCTCCATCTCAAGG
ACGGGAGGTCCATTGTGGTTCCCTGCCGCCACCAAGATGAACTGATTGGCCGGGCCCGCGTCTCTCCAGGGGCGGGATGGAG
CATCCGGGAGACTGCTTGCCTAGCAAAATCATATGCGCAAATGTGGCAGCTCCTTTATTTCCACAGAAGGGACCTCCGACTGAT
GGCCAATGCCATTTGTTCATCTGTGCCAGTTGACTGGGTTCCAACTGGGAGAACTACCTGGTCAATCCATGGAAAGGGAGAAT
GGATGACCACTGAAGACATGCTTGTGGTGTGGAACAGAGTGTGGATTGAGGAGAACGACCACATGGAAGACAAGACCCCAG
TTACGAAATGGACAGACATTCCCTATTTGGGAAAAAGGGAAGACTTGTGGTGTGGATCTCTCATAGGGCACAGACCGCGCACC
ACCTGGGCTGAGAACATTAAAAACACAGTCAACATGGTGCGCAGGATCATAGGTGATGAAGAAAGTACATGGACTACCTAT
CCACCCAAGTTCGCTACTTGGGTGAAGAAGGGTCTACACCTGGAGTGCTGTAAGCACCAATCTTAGTGTTGTCAGGCCTGCTA
GTCAGCCACAGCTTGGGGAAAGCTGTGCAGCCTGTGACCCCCCAGGAGAAGCTGGGAAACCAAGCCTATAGTCAGGCCGAG
AACGCCATGGCACGGAAGAAGCCATGCTGCCTGTGAGCCCCTCAGAGGACACTGAGTCAAAAAACCCCACGCGCTTGGAGGC
GCAGGATGGGAAAAGAAGGTGGCGACCTTCCCCACCCTTCAATCTGGGGCCTGAACTGGAGATCAGCTGTGGATCTCCAGAA
GAGGGACTAGTGGTTAGAGGAGACCCCCCGGAAAACGCAAAACAGCATATTGACGCTGGGAAAGACCAGAGACTCCATGAG
TTTCCACCACGCTGGCCGCCAGGCACAGATCGCCGAATAGCGGCGGCCGGTGTGGGG
```

AHZ13508.1, Zika virus polyprotein from Polynesian outbreak (H/PF/2013)

SEQ ID NO: 79

MKNPKKKSGGFRIVNMLKRGVARVSPFGGLKRLPAGLLLGHGPIRMVLAILAFLRFTAIKPSLGLINRWGSVGKKEAMEIIKKFKKDL

AAMLRIINARKEKKRRGADTSVGIVGLLLTTAMAAEVTRRGSAYYMYLDRNDAGEAISFPTTLGMNKCYIQIMDLGHMCDATMSYE

CPMLDEGVEPDDVDCWCNTTSTWVVYGTCHHKKGEARRSRRAVTLPSHSTRKLQTRSQTWLESREYTKHLIRVENWIFRNPGFAL

AAAAIAWLLGSSTSQKVIYLVMILLIAPAYSIRCIGVSNRDFVEGMSGGTWVDVVLEHGGCVTVMAQDKPTVDIELVTTTVSNMAE

VRSYCYEASISDMASDSRCPTQGEAYLDKQSDTQYVCKRTLVDRGWGNGCGLFGKGSLVTCAKFACSKKMTGKSIQPENLEYRIML

SVHGSQHSGMIVNDTGHETDENRAKVEITPNSPRAEATLGGFGSLGLDCEPRTGLDFSDLYYLTMNNKHWLVHKEWFHDIPLPWH

AGADTGTPHWNNKEALVEFKDAHAKRQTVVVLGSQEGAVHTALAGALEAEMDGAKGRLSSGHLKCRLKMDKLRLKGVSYSLCTA

AFTFTKIPAETLHGTVTVEVQYAGTDGPCKVPAQMAVDMQTLTPVGRLITANPVITESTENSKMMLELDPPFGDSYIVIGVGEKKIT

HHWHRSGSTIGKAFEATVRGAKRMAVLGDTAWDFGSVGGALNSLGKGIHQIFGAAFKSLFGGMSWFSQILIGTLLMWLGLNTKN

GSISLMCLALGGVLIFLSTAVSADVGCSVDFSKKETRCGTGVFVYNDVEAWRDRYKYHPDSPRRLAAAVKQAWEDGICGISSVSRME

NIMWRSVEGELNAILEENGVQLTVVVGSVKNPMWRGPQRLPVPVNELPHGWKAWGKSYFVRAAKTNNSFVVDGDTLKECPLKH

RAWNSFLVEDHGFGVFHTSVWLKVREDYSLECDPAVIGTAVKGKEAVHSDLGYWIESEKNDTWRLKRAHLIEMKTCEWPKSHTLW

TDGIEESDLIIPKSLAGPLSHHNTREGYRTQMKGPWHSEELEIRFEECPGTKVHVEETCGTRGPSLRSTTASGRVIEEWCCRECTMPPL

SFRAKDGCWYGMEIRPRKEPESNLVRSMVTAGSTDHMDHFSLGVLVILLMVQEGLKKRMTTKIIISTSMAVLVAMILGGFSMSDLA

KLAILMGATFAEMNTGGDVAHLALIAAFKVRPALLVSFIFRANWTPRESMLLALASCLLQTAISALEGDLMVLINGFALAWLAIRAM

VVPRTDNITLAILAALTPLARGTLLVAWRAGLATCGGFMLLSLKGKGSVKKNLPFVMALGLTAVRLVDPINVVGLLLLTRSGKRSWPP

SEVLTAVGLICALAGGFAKADIEMAGPMAAVGLLIVSYVVSGKSVDMYIERAGDITWEKDAEVTGNSPRLDVALDESGDFSLVEDD

GPPMREIILKVVLMTICGMNPIAIPFAAGAWYVYVKTGKRSGALWDVPAPKEVKKGETTDGVYRVMTRRLLGSTQVGVGVMQEG

VFHTMWHVTKGSALRSGEGRLDPYWGDVKQDLVSYCGPWKLDAAWDGHSEVQLLAVPPGERARNIQTLPGIFKTKDGDIGAVAL

DYPAGTSGSPILDKCGRVIGLYGNGVVIKNGSYVSAITQGRREEETPVECFEPSMLKKKQLTVLDLHPGAGKTRRVLPEIVREAIKTRLR

TVILAPTRVVAAEMEEALRGLPVRYMTTAVNVTHSGTEIVDLMCHATFTSRLLQPIRVPNYNLYIMDEAHFTDPSSIAARGYISTRVE

MGEAAAIFMTATPPGTRDAFPDSNSPIMDTEVEVPERAWSSGFDWVTDHSGKTVWFVPSVRNGNEIAACLTKAGKRVIQLSRKTF

ETEFQKTKHQEWDFVVTTDISEMGANFKADRVIDSRRCLKPVILDGERVILAGPMPVTHASAAQRRGRIGRNPNKPGDEYLYGGGC

AETDEDHAHWLEARMLLDNIYLQDGLIASLYRPEADKVAAIEGEFKLRTEQRKTFVELMKRGDLPVWLAYQVASAGITYTDRRWCF

DGTTNNTIMEDSVPAEVWTRHGEKRVLKPRWMDARVCSDHAALKSFKEFAAGKRGAAFGVMEALGTLPGHMTERFQEAIDNLA

VLMRAETGSRPYKAAAAQLPETLETIMLLGLLGTVSLGIFFVLMRNKGIGKMGFGMVTLGASAWLMWLSEIEPARIACVLIVVFLLLV

VLIPEPEKQRSPQDNQMAIIIMVAVGLLGLITANELGWLERTKSDLSHLMGRREEGATIGFSMDIDLRPASAWAIYAALTTFITPAVQ

HAVTTSYNNYSLMAMATQAGVLFGMGKGMPFYAWDFGVPLLMIGCYSQLTPLTLIVAIILLVAHYMYLIPGLQAAAARAAQKRTA

AGIMKNPVVDGIVVTDIDTMTIDPQVEKKMGQVLLIAVAVSSAILSRTAWGWGEAGALITAATSTLWEGSPNKYWNSSTATSLCNI

FRGSYLAGASLIYTVTRNAGLVKRRGGGTGETLGEKWKARLNQMSALEFYSYKKSGITEVCREEARRALKDGVATGGHAVSRGSAKL

RWLVERGYLQPYGKVIDLGCGRGGWSYYAATIRKVQEVKGYTKGGPGHEEPMLVQSYGWNIVRLKSGVDVFHMAAEPCDTLLCDI

GESSSSPEVEEARTLRVLSMVGDWLEKRPGAFCIKVLCPYTSTMMETLERLQRRYGGGLVRVPLSRNSTHEMYWVSGAKSNTIKSVS

TTSQLLLGRMDGPRRPVKYEEDVNLGSGTRAVVSCAEAPNMKIIGNRIERIRSEHAETWFFDENHPYRTWAYHGSYEAPTQGSASS

LINGVVRLLSKPWDVVTGVTGIAMTDTTPYGQQRVFKEKVDTRVPDPQEGTRQVMSMVSSWLWKELGKHKRPRVCTKEEFINKV

RSNAALGAIFEEEKEWKTAVEAVNDPRFWALVDKEREHHLRGECQSCVYNMMGKREKKQGEFGKAKGSRAIWYMWLGARFLEF

EALGFLNEDHWMGRENSGGGVEGLGLQRLGYVLEEMSRIPGGRMYADDTAGWDTRISRFDLENEALITNQMEKGHRALALAIIKY

TYQNKVVKVLRPAEKGKTVMDIISRQDQRGSGQVVTYALNTFTNLVVQLIRNMEAEEVLEMQDLWLLRRSEKVTNWLQSNGWDR

LKRMAVSGDDCVVKPIDDRFAHALRFLNDMGKVRKDTQEWKPSTGWDNWEEVPFCSHHFNKLHLKDGRSIVVPCRHQDELIGRA

RVSPGAGWSIRETACLAKSYAQMWQLLYFHRRDLRLMANAICSSVPVDWVPTGRTTWSIHGKGEWMTTEDMLVVWNRVWIEE

NDHMEDKTPVTKWTDIPYLGKREDLWCGSLIGHRPRTTWAENIKNTVNMVRRIIGDEEKYMDYLSTQVRYLGEEGSTPGVL

-continued

| | |
|---|---|
| 9320_Zika_PF_1F<br>ttaggatccGTTGTTGATCTGTGTGAAT | SEQ ID NO: 80 |
| 9321_Zika_PF_1R<br>taactcgagCGTACACAACCCAAGTT | SEQ ID NO: 81 |
| 9322_Zika_PF_2F<br>ttaggatccTCACTAGACGTGGGAGTG | SEQ ID NO: 82 |
| 9323_Zika_PF_2R<br>taactcgagAAGCCATGTCYGATATTGAT | SEQ ID NO: 83 |
| 9324_Zika_PF_3F<br>ttaggatccGCATACAGCATCAGGTG | SEQ ID NO: 84 |
| 9325_Zika_PF_3R<br>taactcgagTGTGGAGTTCCGGTGTCT | SEQ ID NO: 85 |
| 9326_Zika_PF_4F<br>ttaggatccGAATAGAGCGAARGTTGAGATA | SEQ ID NO: 86 |
| 9327_Zika_PF_4R<br>taactcgAGTGGTGGGTGATCTTCTTCT | SEQ ID NO: 87 |
| 9328_Zika_PF_5F<br>ttaggatccCAGTCACAGTGGAGGTACAGTAC | SEQ ID NO: 88 |
| 9329_Zika_PF_5R<br>taactcgagCRCAGATACCATCTTCCC | SEQ ID NO: 89 |
| 9330_Zika_PF_6F<br>ttaggatCCCTTATGTGCTTGGCCTTAG | SEQ ID NO: 90 |
| 9331_Zika_PF_6R<br>taactcgagTCTTCAGCCTCCATGTG | SEQ ID NO: 91 |
| 9332_Zika_PF_7F<br>ttaggatccAATGCCCACTCAAACATAGA | SEQ ID NO: 92 |
| 9333_Zika_PF_7R<br>taactcgagTCATTCTCTTCTTCAGCCCTT | SEQ ID NO: 93 |
| 9334_Zika_PF_8F<br>ttaggatccAAGGGTGATCGAGGAAT | SEQ ID NO: 94 |
| 9335_Zika_PF_8R<br>taactcgagTTCCCTTCAGAGAGAGGAGC | SEQ ID NO: 95 |
| 9336_Zika_PF_9F<br>ttaggatccTCTTTTGCAAACTGCGATC | SEQ ID NO: 96 |
| 9337_Zika_PF_9R<br>taactcgagTCCAGCTGCAAAGGGTAT | SEQ ID NO: 97 |
| 9338_Zika_PF_10F<br>ttaggatccGTGTGGACATGTACATTGA | SEQ ID NO: 98 |
| 9339_Zika_PF_10R<br>taactcgagCCCATTGCCATAAAGTC | SEQ ID NO: 99 |

-continued

| | |
|---|---|
| 9340_Zika_PF_11F<br>ttaggatccTCATACTGTGGTCCATGGA | SEQ ID NO: 100 |
| 9341_Zika_PF_11R<br>taactcgagGCCCATCTCAACCCTTG | SEQ ID NO: 101 |
| 9342_Zika_PF_12F<br>ttaggatccTAGAGGGCTTCCAGTGC | SEQ ID NO: 102 |
| 9343_Zika_PF_12R<br>taactcgAGATACTCATCTCCAGGTTTGTTG | SEQ ID NO: 103 |
| 9344_Zika_PF_13F<br>ttaggatccGAAAACAAAACATCAAGAGTG | SEQ ID NO: 104 |
| 9345_Zika_PF_13R<br>taactcgagGAATCTCTCTGTCATGTGTCCT | SEQ ID NO: 105 |
| 9346_Zika_PF_14F<br>ttaggatccTTGATGGCACGACCAAC | SEQ ID NO: 106 |
| 9347_Zika_PF_14R<br>ttaggatccGTTGTTGATCTGTGTGAAT | SEQ ID NO: 107 |
| 9348_Zika_PF_15F<br>taactcgagCAGGTCAATGTCCATTG | SEQ ID NO: 108 |
| 9349_Zika_PF_15R<br>ttaggatccTGTTGTGTTCCTATTGCTGGT | SEQ ID NO: 109 |
| 9350_Zika_PF_16F<br>taactcgaGTGATCAGRGCCCCAGC | SEQ ID NO: 110 |
| 9351_Zika_PF_16R<br>ttaggatccTGCTGCCCAGAAGAGAA | SEQ ID NO: 111 |
| 9352_Zika_PF_17F<br>taactcgaGCACCAACAYGGGTTCTT | SEQ ID NO: 112 |
| 9353_Zika_PF_17R<br>ttaggatcCTCAAGGACGGTGTGGC | SEQ ID NO: 113 |
| 9354_Zika_PF_18F<br>taactcgagCAATGATCTTCATGTTGGG | SEQ ID NO: 114 |
| 9355_Zika_PF_18R<br>ttaggatccTATGGGGAGGACTGGT | SEQ ID NO: 115 |
| 9356_Zika_PF_19F<br>taactcGAGCCCAGAACCTTGGATC | SEQ ID NO: 116 |
| 9357_Zika_PF_19R<br>ttaggatccAGACCCCCAAGAAGGC | SEQ ID NO: 117 |
| 9358_Zika_PF_20F<br>taactcgagCCCCTTTGGTCTTGTCT | SEQ ID NO: 118 |
| 9359_Zika_PF_20R<br>ttaggatccAGGAAGGATGTATGCAGATG | SEQ ID NO: 119 |

```
9360_Zika_PF_21F
                                                          SEQ ID NO: 120
taactcgagACATTTGCGCATATGATTTTG 9361_Zika_PF_21R
                                                          SEQ ID NO: 121
ttaggatccAGGAAGGACACACAAGAGT 9362_Zika_PF_22F
                                                          SEQ ID NO: 122
taactcgagACAGGCTGCACAGCTTT 9363_Zika_PF_22R
                                                          SEQ ID NO: 123
ttaggatccTCTCTCATAGGGCACAGAC
```

In some embodiments, the Zika virus has a polyprotein, including an envelope (E) protein, with an amino acid sequence provided by any one of SEQ ID NO: 14-69 or 78. In some embodiments, the polyprotein or E protein sequence is at least 80%, 81%, 82%, 83%, 84%, 85%, 86%, 87%, 88%, 89%, 90%, 91%, 92%. 93%, 94%, 95%, 96%, 97%, 98%, 99%, 99.5%, 99.6%, 99.7%, 99.8% or 99.9% identical to any one of SEQ ID NOs: 2-69 or 78.

The terms "identical" or percent "identity" in the context of two or more nucleic acids or amino acid sequences refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, or 99% identity) over a specified region or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length. In some embodiments, the identity exists over the length of a protein, such as the E protein.

For sequence comparison, typically one sequence acts as a reference sequence, to which test sequences are compared. Methods of alignment of sequences for comparison are well known in the art. See, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman. Proc. Natl. Acad. Sci. USA 85:2444, 1988, by computerized implementations of these algorithms (GAP, BESTFIT, FASTA, Jalview and TFASTA in the Wisconsin Genetics Software Package, Genetics Computer Group. 575 Science Dr., Madison. Wis.), by multi sequence alignment implementation using e.g. CLUSTALW (Larkin et al., (2007). Bioinformatics, 23, 2947-2948.) or MAFFT (Katoh & Toh 2008 Briefings in Bioinformatics 9:286-298), or by manual alignment and visual inspection (see. e.g., Brent et al., Current Protocols in Molecular Biology, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977 and Altschul et al., J. Mol. Biol. 215:403-410, 1990, respectively.

EXAMPLES

Example 1: Development of a Purification Process for Live Attenuated Chikungunya Virus Vaccine Produced in Vero Cells A downstream process was developed for the purification of infectious Chikungunya virus particles whereby non-infectious virus particles and aggregates are removed by the addition of protamine sulphate. The unexpected and novel purification properties of protamine sulphate (PS) were evaluated in purification processes for Chikungunya Virus (ChikV) as follows:

A downstream purification process for the attenuated Chikungunya virus mutant "Δ5nsP3" (as described by Hallengird et al., 2014, supra and provided by SEQ ID NO: 77) produced under standard cell culture conditions in Vero cells was developed. The attenuated Δ5nsP3 Chikungunya virus was derived from the strain LR2006-OPY1, the complete genome of which is provided herein as SEQ ID NO: 72. Briefly, the downstream process consists of crude harvest filtration followed by concentration and diafiltration on a tangential flow filtration (TFF) system. Host cell DNA and host cell proteins were reduced by precipitation with protamine sulphate and by batch adsorption, respectively. Sucrose density gradient centrifugation was done as a final polishing step. Out of 16 roller bottles $1\times10^{12}$ total PFU were purified with an overall DSP process yield of 10-15% (~1 log 10 TCID50 loss). Sucrose gradient pool samples were characterized with regard to product-related impurities, such as hcDNA, HCP and endotoxins and met safety criteria.

Harvest of Vero Cell Culture Medium Containing ChikV Δ5nsP3

ChikV Δ5nsP3 was grown on Vero cells in roller bottles. A first harvest was performed after 24 hours post infection (hpi; day 1 harvest) and stored at 2-8° C. until further processing. After the first harvest, fresh medium was added and the roller bottles were returned to the incubator. A second harvest was done after 48 hours post infection (day 2 harvest) and stored at 2-8° C.

Filtration of Crude Cell Culture Harvest

At both harvest timepoints, the crude harvest was immediately filtered using a 0.2 μm filter capsule (GE ULTA™ CG, 2 inch). The filtered harvest after 48 hpi was pooled together with the 24 hpi harvest and the pooled filtered harvest material was immediately further processed by ultrafiltration.

Purification of ChikV Δ5nsP3 by Tangential Flow Filtration (TFF)

The pooled filtered harvest material was further processed by tangential flow filtration (TFF) in order to concentrate the harvest, reduce host cell proteins and replace the depleted cell culture medium with a defined buffer system (buffer exchange). A Millipore TFF system (Millipore Pellicon II mini membrane holder) equipped with a 100 kDa cutoff PES membrane module (Pellicon2 Biomax, 1000 cm$^2$) was used for concentration and buffer exchange. A Pellicon2 Biomax membrane module was mounted on the Pellicon II mini filter holder and the device was connected to a peristaltic pump. The system was first rinsed with ultra-pure water and then sanitized by recirculation of 0.1 M NaOH for 60 min. In case the system was not used immediately, it was stored in 0.1 M NaOH until use. Prior to use the system was rinsed with 1 L of RO-water followed by buffer A until the permeate pH value was constant at pH 7.4±0.2.

Adjustment of the ChikV Δ5nsP3 Harvest (pH, Salt)

The pooled filtered harvest material was adjusted to a final concentration of 25 mM Tris and 150 mM NaCl using stock solutions of both components (see Table 1). This adjustment was done to increase buffering capacity and to reduce unspecific adsorption to the membrane. The necessary volumes of stock solutions D (1 M Tris, pH 7.4) and E (4.5 M NaCl) were calculated as follows:

Volume of stock solution $D$ (1 M Tris, pH 7.4) added to pooled harvest=Volume of pooled filtered harvest/40

Volume of stock solution $E$ (4.5 M NaCl) added to pooled harvest=Volume of pooled filtered harvest/30

Example: 4 L harvest obtained from 20 RB (850 cm$^2$) would require addition of 100 mL stock solution D (1 M Tris, pH 7.4) and 133 mL stock solution E (4.5 M NaCl).

The calculated volumes of stock solution D and Buffer E were added to the pooled filtered harvest under gentle stirring. The adjusted harvest was then stirred using a magnetic stirrer for 5 minutes at room temperature.

Concentration and Diafiltration of the ChikV Δ5nsP3 Harvest by TFF

In a first step, the adjusted harvest material was concentrated approximately 10 fold. The feed flowrate was approximately 220 mL/min. The transmembrane flux at a transmembrane pressure of approximately 0.6 bar was in the range of 90±5 mL/min per 1000 cm$^2$ membrane. After concentration, the cell culture medium was exchanged against 25 mM Tris, 150 mM NaCl, pH 7.5, by continuous diafiltration with 6 volume exchanges. The diafiltration buffer was supplied to the feed vessel from a measuring cylinder by a second peristaltic pump set to a flowrate of approximately 90 mL/min. Minor flowrate adjustments of the second peristaltic pump in the range of +10 mL/min were done manually to ensure a constant volume of harvest in the feed vessel. After 6 volume exchanges, diafiltration was stopped. The liquid remaining in the membrane module was recovered by pumping the module empty with air.

Sucrose Addition to Diafiltrated ChikV Δ5nsP3 Material

After diafiltration, sucrose stock solution H (50% (w/w) sucrose solution) was added to the diafiltrated material to achieve a final sucrose concentration of 10% (w/w). The volume of buffer H was calculated as follows:

Volume of stock solution $H$ added (mL)=Volume (mL) of diafiltrated ChikV material×0.25

(dilution factor=1:4) (i.e., final sucrose concentration is 10%)

Example: 400 mL diafiltrated ChikV solution would require addition of 100 mL stock solution H (50% sucrose).

The calculated volume of solution H was added to the diafiltrated ChikV Δ5nsP3 material under gentle stirring and the solution was then stirred using a magnetic stirrer for a further 5 minutes at room temperature. (At this stage of the process the material can be either immediately further processed or stored frozen (<−65° C., hold step).)

DNA Reduction by Protamine Sulphate Precipitation

A DNA precipitation step using protamine sulphate (PS) was performed to reduce hcDNA. Protamine sulphate stock solution L (50 mg/mL PS in PBS) was added to the diafiltrated ChikV Δ5nsP3 material to a final nominal concentration of ~1.6 mg/mL. The necessary volume of stock solution L was calculated as follows:

Volume of stock solution $L$ (50 mg/mL PS) added=Volume of diafiltrated ChikV Δ5nsP3 material in 10% sucrose/31

Example: 500 mL diafiltrated ChikV Δ5nsP3 solution in 10% sucrose would require addition of 16 mL stock solution L (50 mg/mL PS in PBS).

The protamine sulphate stock solution was added while stirring the ChikV Δ5nsP3 material using a magnetic stirrer followed by incubation at 2-8° C. for 30 minutes. After incubation, the precipitate was not removed. The material was immediately further processed by batch adsorption with Capto™ Core 700 chromatography media.

Batch Adsorption with Capto™ Core 700

To reduce HCPs, a batch adsorption step with Capto™ Core 700 (CC700) chromatography medium was performed after DNA precipitation. CC700 slurry (50% slurry in buffer A) was added directly to the protamine sulphate treated material. The required slurry volume was determined based on the volume of Δ5nsP3 ChikV harvest material (d1+d2) and was calculated as follows:

Volume of CC700 slurry added to PS-treated concentrated harvest (mL)=Volume of Δ5nsP3 ChikV harvest material (mL)×0.02 (dilution factor=1:50) (i.e., final concentration of CC700 is 1%)

After slurry addition, the material was incubated at 4° C. for 15 minutes under constant agitation using a magnetic stirrer. After incubation, the CC700 solid matter was allowed to settle by gravity for 10 minutes. The Δ5nsP3 ChikV material was then removed from the top of the solution in order to avoid blocking of the filter by the CaptoCore particles. The remaining CaptoCore particles and the DNA precipitate were then removed from the solution by filtration using a 0.2 μm Mini Kleenpak EKV filter capsule (Pall). The resulting filtrate was further processed by sucrose density gradient centrifugation.

Sucrose Density Gradient Centrifugation

Sucrose density gradient centrifugation (SGC) was used for final concentration and polishing of the Δ5nsP3 ChikV material. The Δ5nsP3 ChikV material was loaded on top of a solution consisting of three layers of sucrose with different densities. The three sucrose layers were selected based on a preliminary study which showed the formation of a linear sucrose gradient and good separation of the virus particles from residual contaminants. The optimal volumes of the sucrose solutions were determined empirically. The volumes of individual layers for a centrifugation at 500 mL scale are shown in Table 3.

TABLE 3

Sucrose concentrations and volumes (500 mL scale).

| Solution | Volume (mL) |
| --- | --- |
| Harvest with 10% sucrose | 360 |
| 15% sucrose | 40 |
| 35% sucrose | 40 |
| 50% sucrose | 60 |
| Total volume | 500 |

Preparation of the Sucrose Gradient

Figure 14:
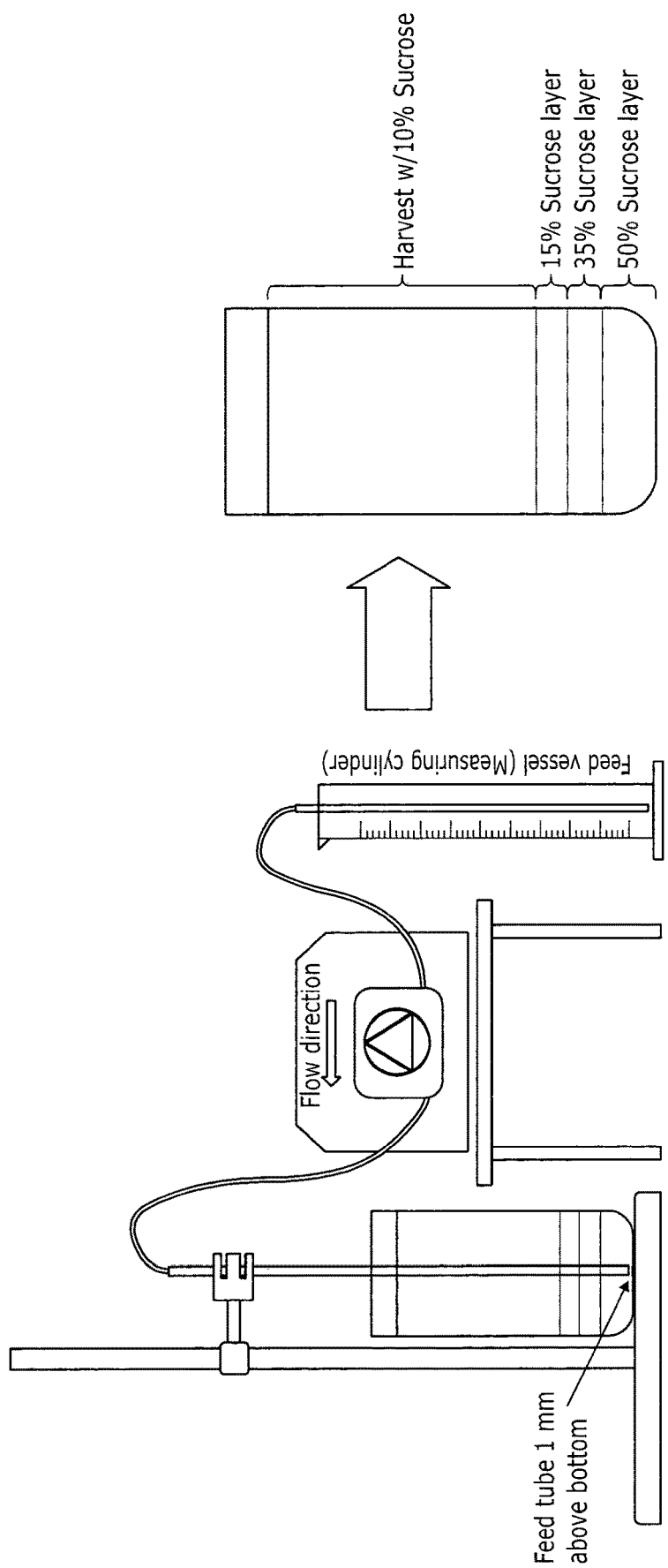
FIG. 14: Preparation of the sucrose gradient.

The sucrose gradient bottles (500 mL) were prepared by underlaying the individual sucrose layers. A 3.5 mm ID plastic tube was attached to 60 cm of peristaltic pump tubing. The plastic tube was mounted on a laboratory stand using a clamp and placed into the centrifuge bottle. The nozzle of the plastic tube was placed at the bottom of the bottle. Using a peristaltic pump set to a flow rate of 25 mL per minute, the Δ5nsP3 ChikV material and the sucrose solutions were pumped into the cylinder. A measuring cylinder was used as a feed vessel. The first solution pumped was the Δ5nsP3 ChikV material as it had the lowest density (10% sucrose (w/w)). Following the addition of the Δ5nsP3 ChikV material, the sucrose solutions were pumped in ascending order starting with the lowest (15%), followed by the 35% sucrose solution and finishing with the highest density sucrose solution (50%). After all sucrose solutions were transferred, the plastic tubing was carefully removed in order not to disturb the layers. An illustration of a completed gradient is shown in FIG. 14.

Centrifugation

Prior to centrifugation a Beckman Avanti JXN-26 centrifuge equipped with rotor Beckman 10.500 was pre-cooled to 4° C. The prepared SG bottles were carefully transferred into the pre-cooled (4° C.) rotor so as to not to disturb the sucrose layers. The bottles were centrifuged at 10,000 rpm (~18,500 rcf) at 4° C. for 17-20 hours. (In case a different centrifuge system with a different rotor would be used, the necessary speed and centrifugation times would need to be calculated based on the k-factor in order to achieve comparable centrifugation efficiency.)

Sucrose Gradient Harvest Harvesting of the sucrose gradient following centrifugation was done manually using a peristaltic pump.

A 3.5 mm ID plastic tube attached to 60 cm of peristaltic pump tubing was used for harvesting the sucrose gradient. The 500 mL bottle containing the centrifuged gradient was mounted onto a laboratory stand in a tilted position (~12°) using a clamp. The plastic tubing was then placed into the bottle touching the bottom edge of the bottle and was fastened in position using a clamp. This resulted in a small gap of 1-2 mm between the tubing inlet and the bottom of the bottle (see FIG. 14). Using a peristaltic pump set to a flow rate of 60 mL per minute, the gradient was harvested and manually split into 5 mL fractions. A third of the bottle volume was harvested and the rest was discarded. The fractions were immediately tested by measuring UV absorbance in a plate reader as described below.

Analysis of fractions by UV absorbance and SEC-HPLC

Figure 11A:
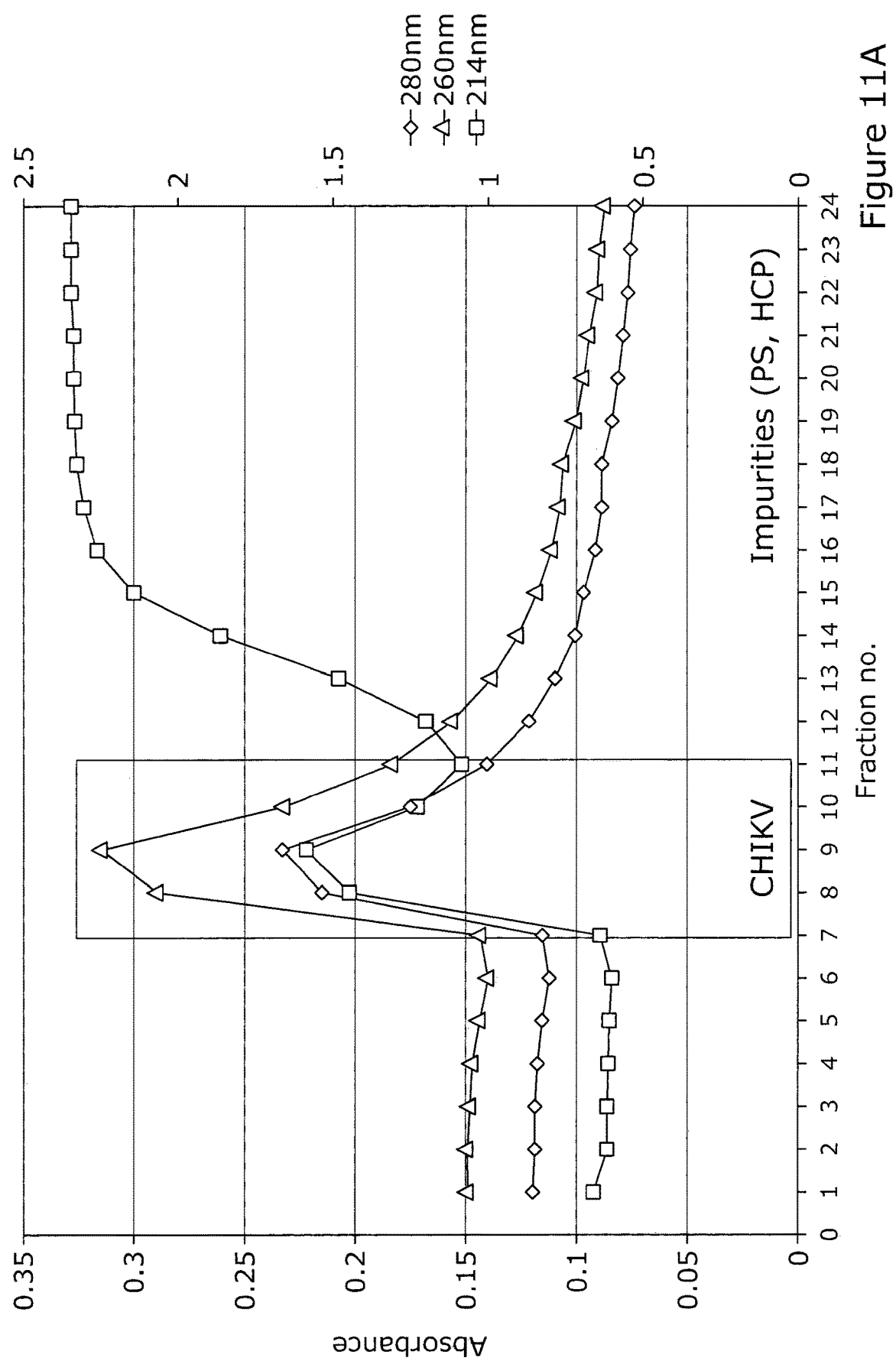
FIG. 11: Absorbance at 214 nm, 260 nm and 280 nm of individual sucrose gradient centrifugation (SGC) fractions of a representative purification run of the process of the invention (A); the SEC-HPLC analysis of the final pooled fractions containing purified infectious attenuated Δ5nsP3 ChikV virus particles (B); and a silver-stained SDS-PAGE gel showing the protein content of the virus preparation following different steps of the process of the invention (defined in the table below the figure) (C). The SGC purified pool consisting of SGC fractions F7-F11 is shown in lane 12.

UV absorbance measurement was used as primary method for analysis of the sucrose gradient fractions. Absorbance at 214, 280 and 260 nm was tested immediately after fractionation was completed. Briefly, a 100 µL sample of each fraction was transferred into a 96 well plate and absorbance at 214, 260 and 280 nm was measured using a plate reader. The absorbance values were plotted against the fraction number. A representative profile is shown in FIG. 11A. The Δ5nsP3 ChikV containing fractions were indicated by a peak in all three measured wavelengths (FIG. 11A, grey shaded area). The presence of impurities was indicated by an increase of the UV214 signal after the main peak. The fractions comprising the main peak were pooled from the peak start to the valley of the 214 nm curve. This method can be used as single method for pooling Δ5nsP3 ChikV fractions.

After identification of the virus containing fractions, the respective fractions were pooled. Pooling criteria for SGC fractions were based on UV 260 nm data, e.g. start of pooling at ~10% of peak maximum, end of pooling at ~30% of peak maximum. (Final pooling criteria at a manufacturing scale may need to be determined empirically.) The sucrose gradient pool was either stored at <−65° C. or immediately further formulated to drug substance (DS).

Size Exclusion Chromatography

The final pooled SGC fractions containing purified infectious Δ5nsP3 ChikV particles were analyzed for purity by SEC-HPLC. In brief, SEC was performed as follows: a Superose 6 10/300 Increase column (GE Healthcare) equilibrated with PBS+250 mM NaCl, pH 7.4 at 1 ml/min and 25° C., was used to detect ChikV particles at 214 nm detection wavelength in the pooled samples. SEC-HPLC is a semi-quantitative (relative yield) and qualitative (purity) method that separates intact virus particles from virus aggregates and host cell proteins (HCPs). The method cannot distinguish between infectious and non-infectious virus particles due to their identical retention time.

Figure 11B:
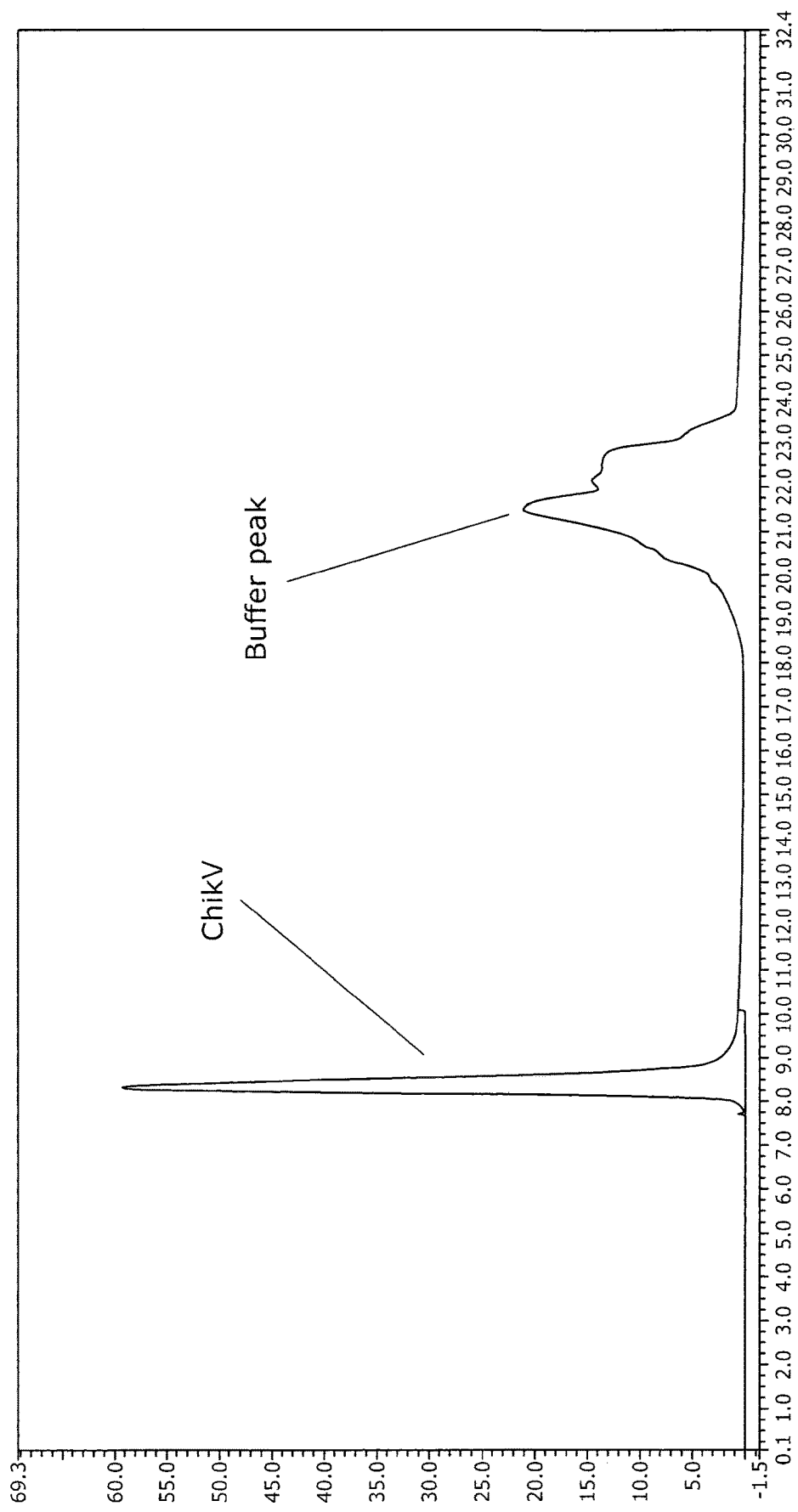

As shown in FIG. 11B, there were two defined peaks identified by SEC: the Δ5nsP3 ChikV peak and a peak corresponding to buffer components. The SGC step yield based on SEC-HPLC data for pooled fractions F6-F11 was estimated at ~70%. The final purity of the Δ5nsP3 ChikV SGC pool, based on SEC-HPLC analysis, was estimated at >95%.

SDS-PAGE and Silver Stain

SDS-PAGE silver stain was performed in order to qualitatively assess sample purity throughout the purification process from the first crude harvest through SGC. Briefly, ChikV process samples analyzed by SDS-PAGE/silver stain were diluted 1:1.33 with LDS buffer and were heated to 70° C. for 5 minutes. The samples were loaded onto 4-12% Bis-Tris Gels (NuPAGE). Silver staining was done using the Silver Express staining kit (Invitrogen).

A silver-stained gel of a representative ChikV Δ5nsP3 purification is shown in FIG. 11C. The viral proteins E1, E2 and C are marked on the right-hand side of the gel. The final SGC pool (fraction 7-fraction 11) is shown in lane 12. Note that a defined HCP band migrating between ChikV protein E2 and C still appears after CaptoCore700 treatment that has been identified as a single band in SDS-PAGE. This impurity is removed by sucrose gradient centrifugation, but can still be seen in fractions 13 and 14 (corresponding to lanes 14 and 15 of FIG. 11C).

Enrichment of Infectious Δ5nsP3 ChikV particles by PS Treatment

Although generally used as a method of removing contaminating hcDNA, it was observed in the course of the present invention that PS treatment also removes virus aggregates and HCPs. Size exclusion chromatography (SEC-HPLC, as described above) was used throughout the purification process to determine the purity of the ChikV virus relative to impurities which also generate UV absorption.

Figure 12A:
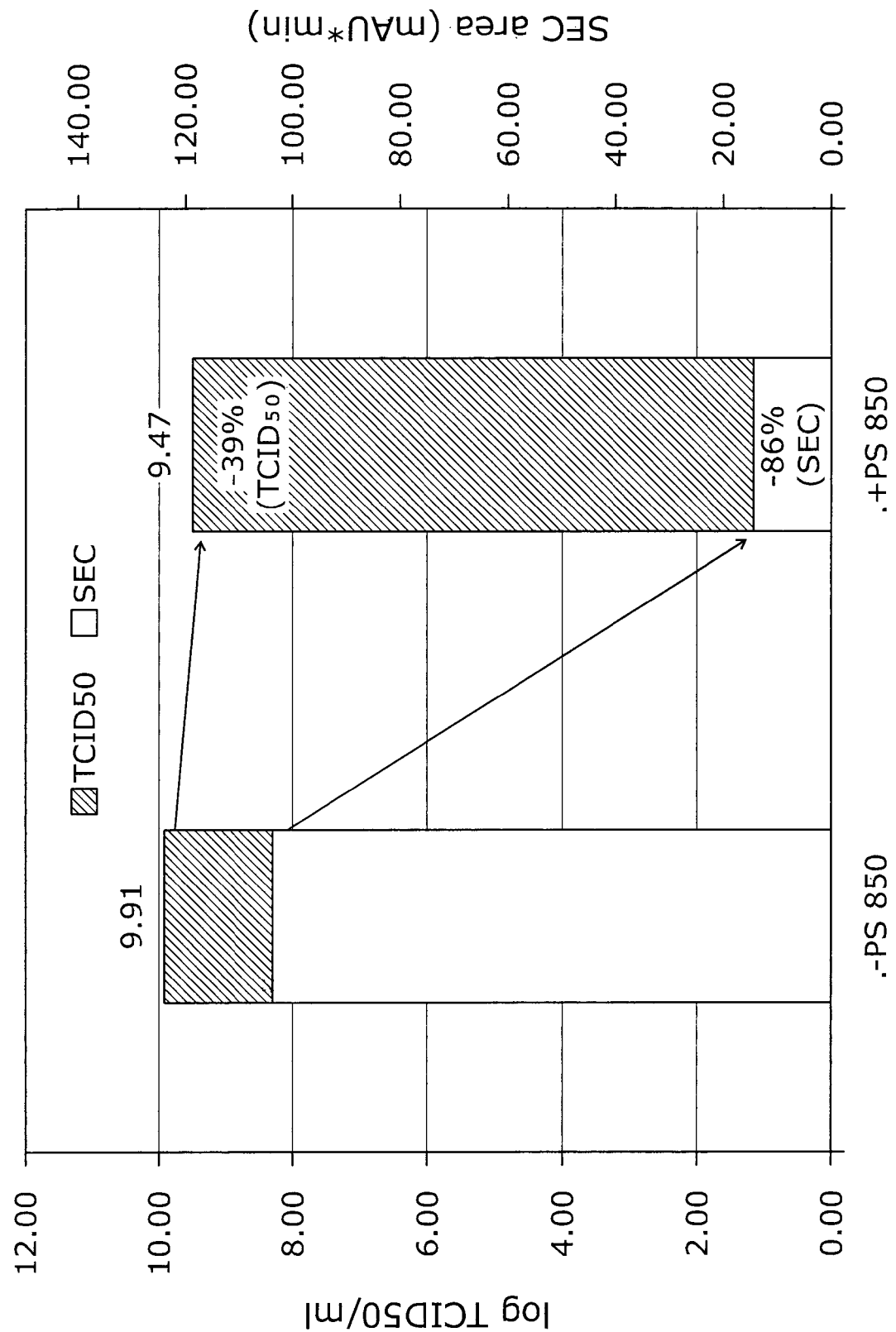
FIG. 12: SEC area (mAU*min; right axis) and $TCID_{50}$ results (log TCID50/mL; left axis) of attenuated Δ5nsP3 ChikV production harvests before and after PS treatment. The grey portions of the bars indicate large losses in SEC area following PS treatment, but no corresponding change in the total number of infectious particles (indicated by black portions of the bars) (A); SEC profile of virus preparation before and after PS addition, showing a complete removal of large size virus aggregates by PS treatment as well as a reduction in host cell proteins (HCP) and LMW impurities (B).
Figure 12B:
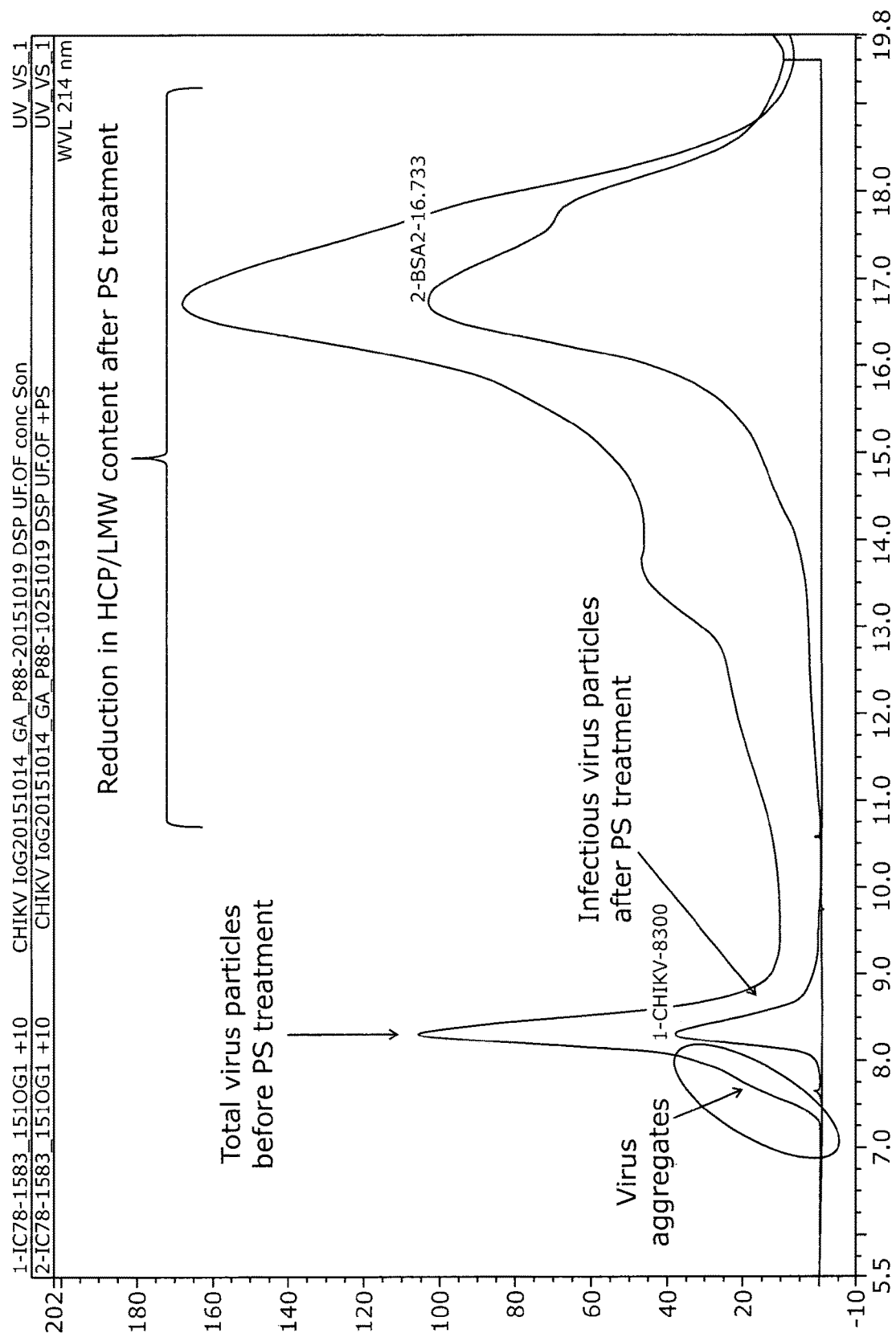

As can be seen in FIG. 12B, treatment with PS reduces not only host cell proteins and low molecular weight contaminants of the Δ5nsP3 ChikV preparation, but also reduces the SEC area corresponding to virus products, including aggregates as indicated. A surprising finding, however, was that even a reduction of the total SEC area by 86% (in a representative experiment shown in FIG. 12A, grey portion of bars) did not result in a concomitant reduction in infectious virus particles as measured by TCID50 (FIG. 12A, left axis). Instead, even though a large percentage of virus particles were removed by PS treatment, the majority of infectious particles remained. This observation indicates that PS treatment selectively enriches infectious virus particles from a larger pool of total virus particles present in the crude harvest.

TCID50 was performed to quantify infectious virus particles during the course of the purification process and to assign an active virus titer to final drug substance and drug product samples. Briefly, Vero cells were seeded at $2\times10^4$ cells per well in 100 µL medium (EMEM with 2 mM L-Glutamine+5% FBS+1% antibiotic/antimycotic) in 96-well TC-treated flat-bottom plates and incubated overnight at 35° C./5% $CO_2$. On day two, Vero cell monolayers were infected by adding 100 µL of 1:10 serial dilutions of test samples to each of quintuplicate wells seeded with Vero cells and incubated at 35° C./5% $CO_2$. On day seven, plaques were counted by visualization under a microscope. The TCID50 was calculated according to the Reed & Münch endpoint calculation method (Reed, L. J.; Muench, H. (1938) A simple method of estimating fifty percent endpoints, The American Journal of Hygiene 27: 493-497).

Figure 13:
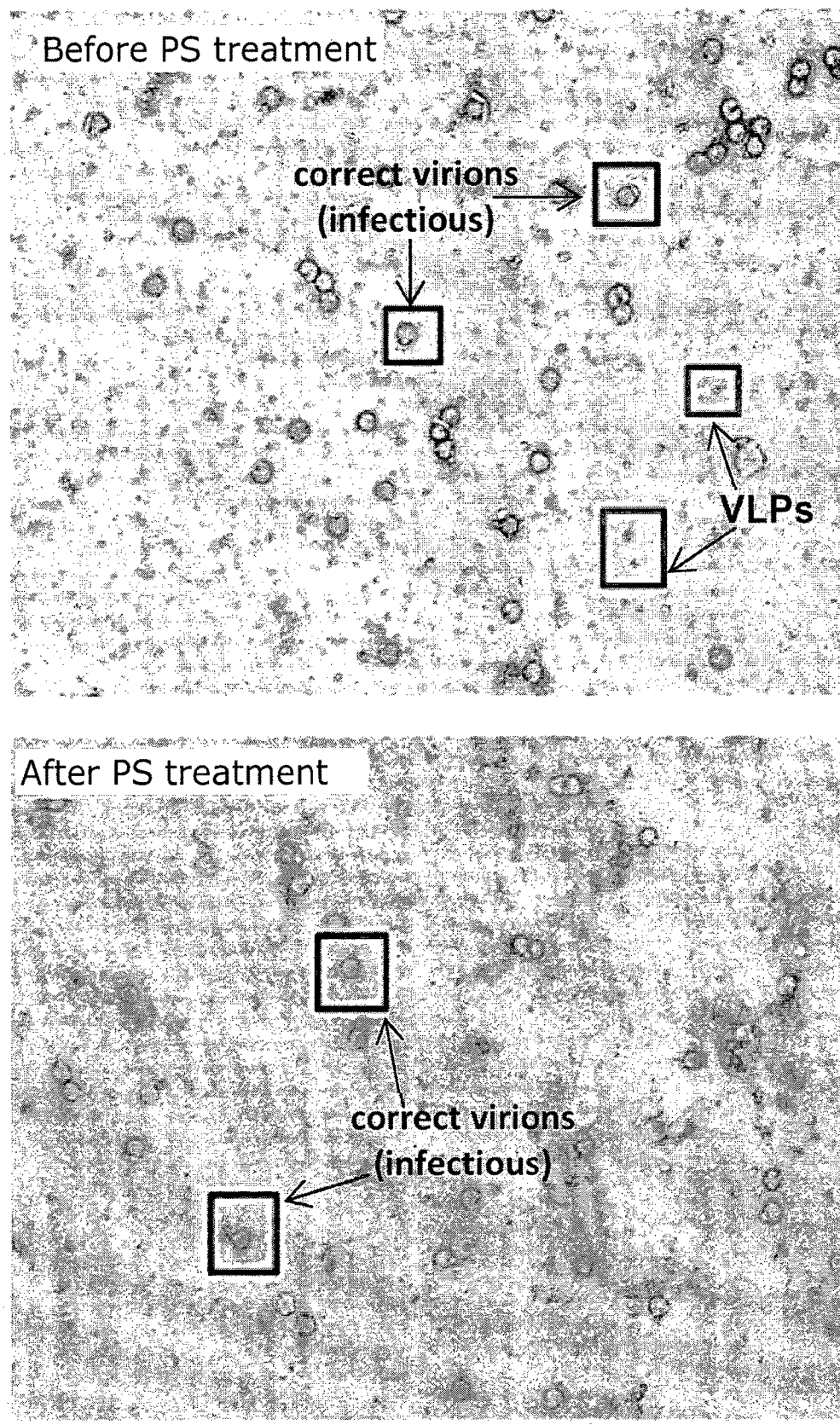
FIG. 13: Electron micrographs of attenuated Δ5nsP3 ChikV harvest before and after PS treatment.

Furthermore, electron microscopy of Δ5nsP3 ChikV samples before and after PS treatment showed that not only large aggregates but also smaller non-infectious virus-like particles (essentially not fully assembled particles lacking the RNA genome) were effectively removed by PS (FIG. 13).

This enrichment of infectious virus particles was also observed when analyzing day one and day two crude harvests separately. As presented in Table 4, the SEC area (total virus particles) of the day 1 harvest remains roughly the same after PS treatment; whereas a large decrease in virus peak area is seen for the day 2 harvest after PS treatment. This observation was confirmed by MALLS analysis of the virus preparation, wherein it was seen that a higher percentage of virus particles were of the correct size following PS treatment. Similarly to the results shown in FIG. 12, day 1 and day 2 harvests showed no reduction in infectious particles as measured by TCID50 following PS treatment, indicating that mainly non-infectious, immature and/or aggregated virus particles are removed during the PS treatment and infectious particles are enriched in the preparation.

Figure 15A:
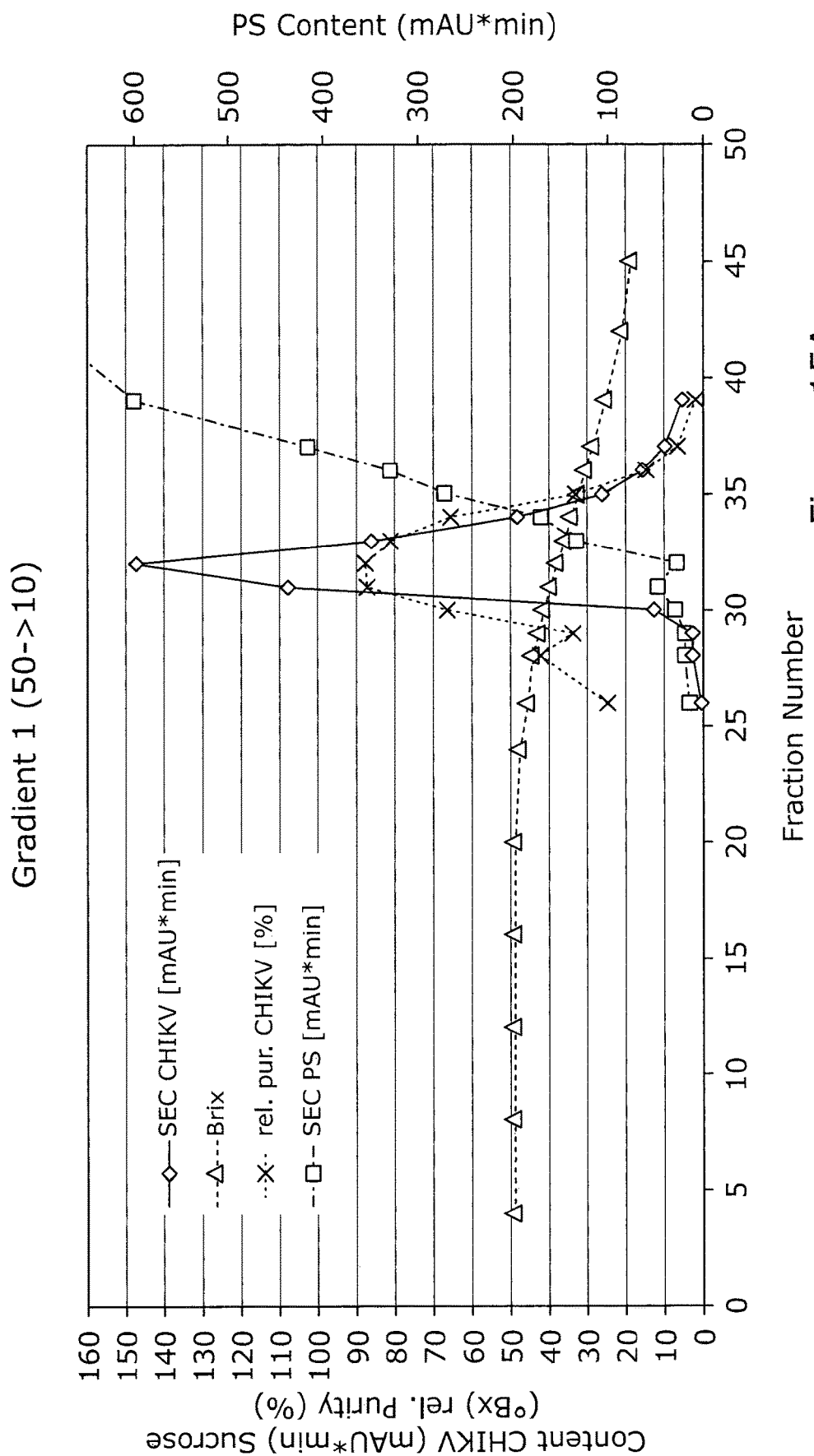
FIG. 15: Comparison of four different sucrose gradient centrifugation experiments performed to empirically determine the optimal combination of sucrose layers for CHIKV purification. The CHIKV content in the gradient fractions was determined by SEC. The sucrose content in the gradient fractions was determined by refractometry (comparing the value of the refractive index of the sucrose solution to that of sucrose standard curve the concentration of sucrose solution can be determined with good accuracy, this is also referred to as "Brix" scale that is calibrated to give the percentage (w/w) of sucrose dissolved in water, i.e. "° Bx"). Protamine sulphate (PS) was determined by SEC. PS is separated within the sucrose gradient alongside host cell derived residual contaminants and was therefore used to assess the quality of CHIKV separation from residual contaminants in the tested gradients. A: CHIKV load material containing 10% sucrose was loaded on top of one 50% (w/w) sucrose layer. Determination of sucrose content in the fractions showed the formation of a linear gradient. SEC showed concentration of CHIKV within a sucrose concentration range from 40-30% (w/w) sucrose. PS SEC showed insufficient separation of PS from CHIKV. B: CHIKV load material containing 10% sucrose was loaded on top of a two layer system consisting of a 50% (w/w) sucrose bottom layer and a second 35% (w/w) sucrose layer. Determination of sucrose content in the fractions showed the formation of a linear gradient. SEC showed concentration of CHIKV within a sucrose concentration range from 40-30% (w/w)
Figure 15B:
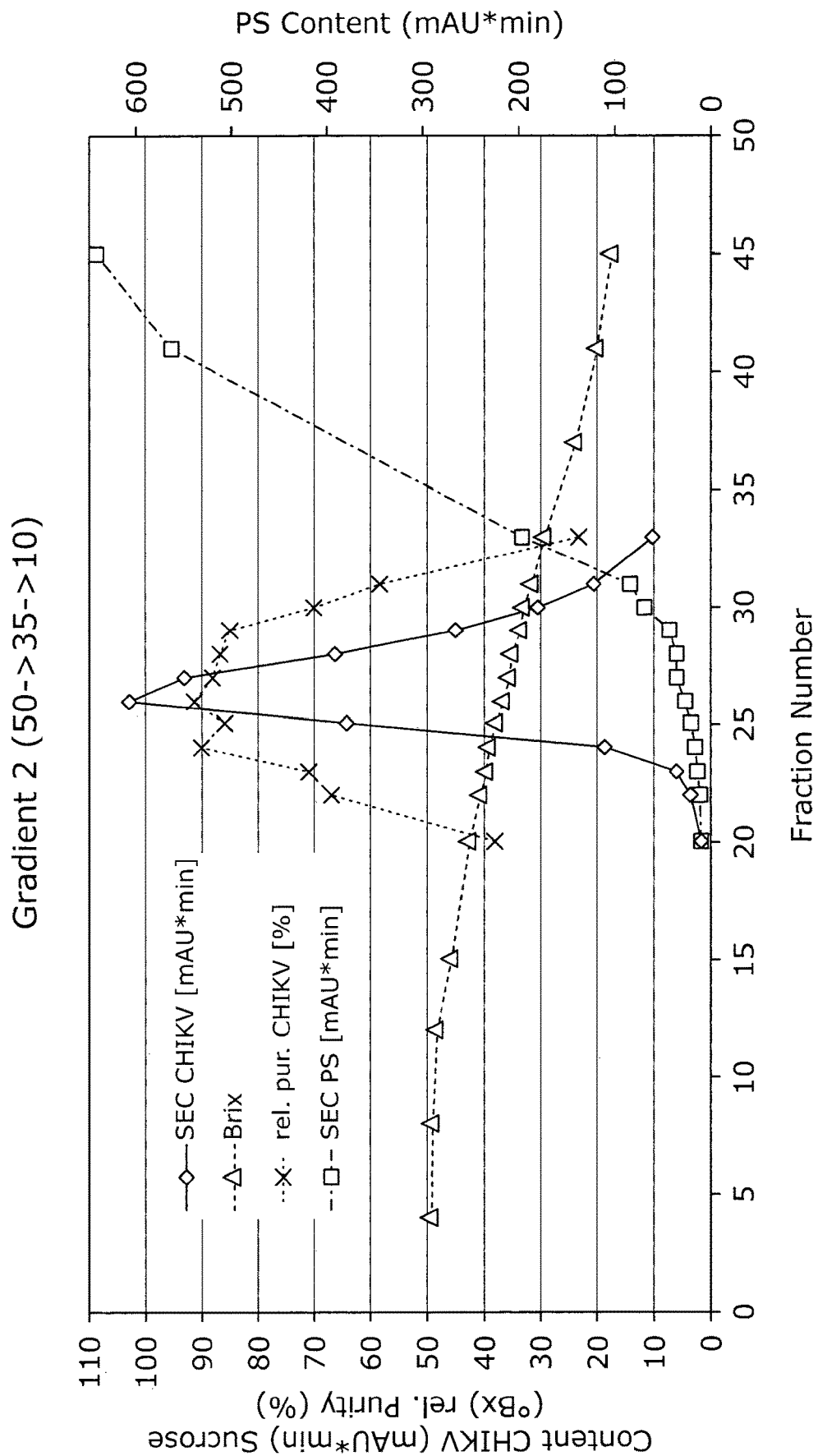
Figure 15C:
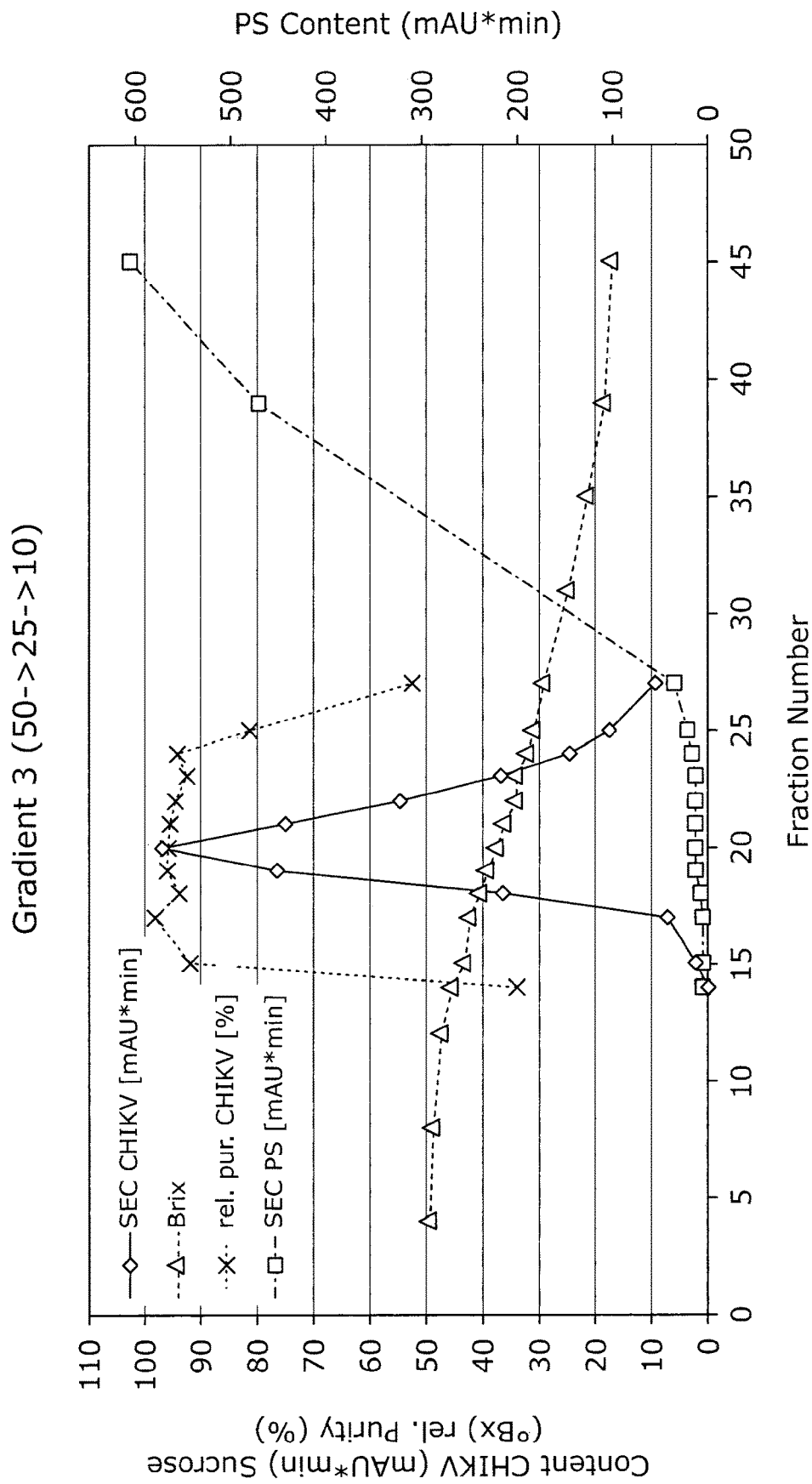
Figure 15D:
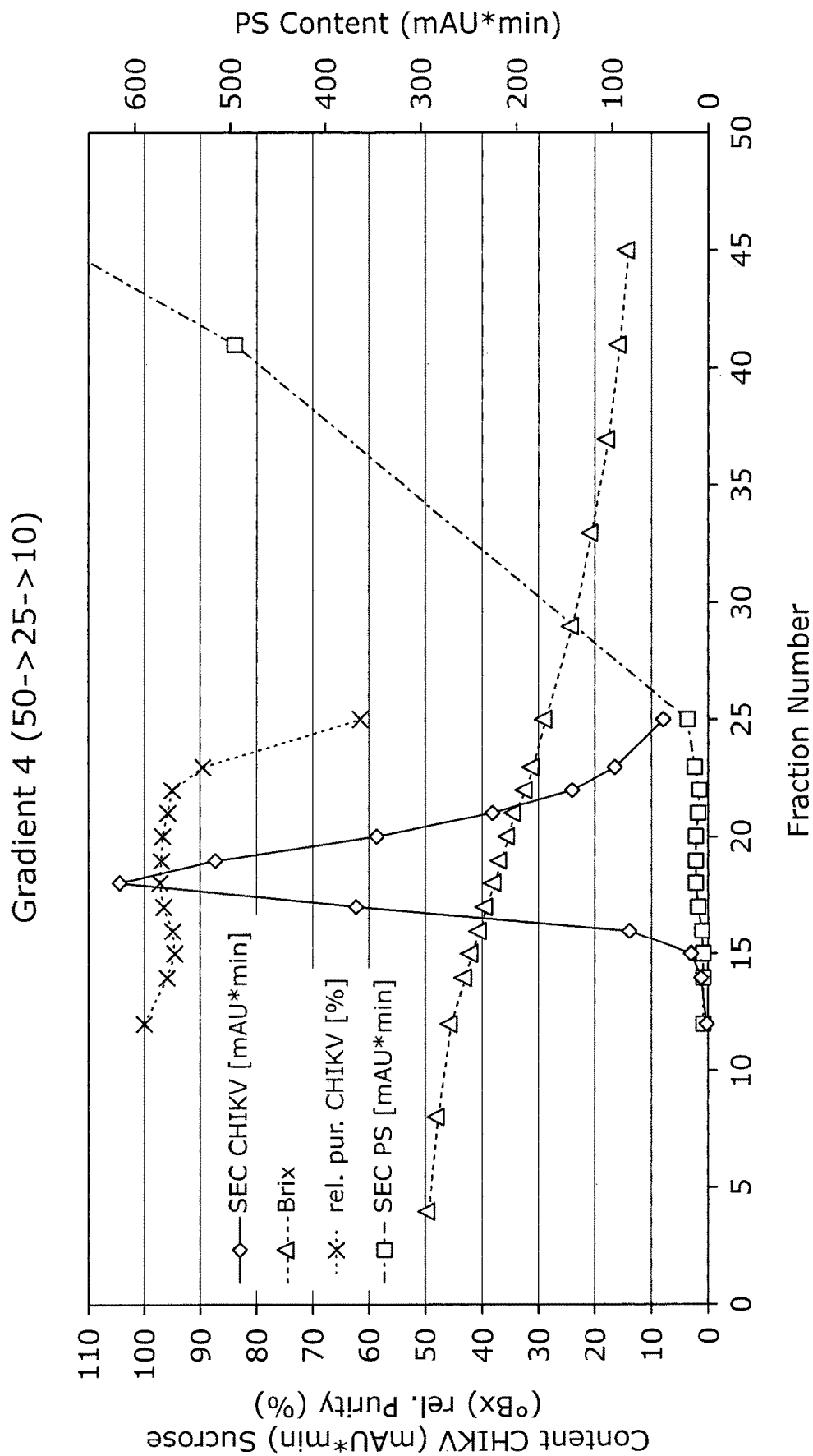

The PS-treated samples were further purified by sucrose gradient centrifugation (see FIG. 14 for a schematic preparation of an optimized sucrose gradient). An optimal sucrose gradient was determined experimentally as shown in FIG. 15. Results of the further purification of PS-treated ChikV on the optimized sucrose gradient of the invention are shown in FIG. 15D.

TABLE 4

Overview of the process of Δ5nsP3 ChikV purification as described in Example 1. SEC-MALLS analysis of harvests before and after PS treatment shows the removal of larger virus particles (aggregates), an effect that is particularly pronounced for day 2 harvests.

| | SEC Area [mAU*min] | MALLS | | Infectious particles TCID50 log 10 |
|---|---|---|---|---|
| | | Total particles/mL | % correct size (20-40 nm) | |
| Harvest 1 (H1) | 57 | 1.17E+11 | 49% | 10.2 |
| H1 + protamine sulphate | 53 | 1.33E+11 | 81% | 10.0 |
| Harvest 2 (H2) | 36 | 4.60E+09 | 3% | 7.9 |
| H2 + protamine sulphate | 2 | 8.80E+09 | 59% | 7.9 |
| Combined Harvests (C) | 67 | 2.60E+10 | 14% | 9.9 |
| C + protamine sulphate | 24 | 8.00E+10 | 72% | 10.1 |

Finally, an overview of the relative amounts of Δ5nsP3 ChikV particles and other components as measured by SEC-HPLC at various steps throughout the entire virus purification process from crude harvest (a) to the final SGC purified pool is presented in FIG. 16. In sum, not only are the vast majority of contaminants and undesired products removed by the process, infectious ChikV particles are highly purified. As shown by the previously presented data, the final preparation is a highly enriched preparation of infectious ChikV particles.

Drug Substance (DS) Formulation

The pooled SGC fractions are diluted with DS formulation buffer M (10 mM Tris, 5% Sucrose (w/w), 1% (10 mg/mL) rHSA, pH 7.4±0.2). The final target volume of DS should be in the range of approximately 2 L. Based on current data the estimated range of the dilution factor might be 1:20 to 1:50.

Final DS Sterile Filtration

The final DS was filtered under aseptic conditions in a laminar flow hood using a sterility grade 0.2 µm syringe filter (e.g. 0.2 µm Mini Kleenpak EKV filter capsule with 220 $cm^2$ filter surface, Pall).

Quantification of Host Cell DNA (hcDNA) Host Cell Protein (HCP) and Endotoxin

The residual host cell DNA content of the sucrose gradient pool samples was determined by using the qPCR based assay. The DNA content in SGC pool was determined to be <0.002 ng/mL. The presence of residual host cell protein (HCP) from Vero cells was determined by ELISA. Residual host cell proteins present in the sucrose gradient pool samples were quantified using the Vero Cell HCP ELISA kit (Cygnus, F500). The residual host cell protein content in SGC pool was determined to be <200 ng/mL.

Endotoxin content of the SGC pool and DS was measured by Endosafe®-PTS™ system (Charles River). The system uses Limulus Amembocyte Lysate (LAL) reagents by a kinetic chromogenic methodology to measure color intensity directly related to the endotoxin content in a sample. Each cartridge contains precise amounts of a licensed LAL reagent, chromogenic substrate and an endotoxin control standard. Samples were diluted 1:100 in WFI. The SGC Pool F7-F11 was determined to be <5.00 EU/mL; likewise, the Drug Substance was also determined to have <5.00 EU/mL.

The following specifications for impurities in final Drug product were proposed: hcDNA <10 ng/dose; Endotoxins <50 EU/dose; HCP <200 ng/dose. These residual specifications would already be met in the highly concentrated SGC pool (~10 log TCID50/mL), which provides a high margin of safety considering the high dilution factor of SGC pool to final DP of >1:1000.

Example 2: Production of a Zika Drug Substance Suitable for Application as a Vaccine in Humans and Animals Materials and Methods:

For the production of ZikaV the JEV process platform (Srivastava et al., Vaccine 19 (2001) 4557-4565; U.S. Pat. No. 6,309,650B1) was used as a basis. Small changes of certain process steps were adapted to ZikaV properties and to improve purity. A short summary of the process steps is outlined below (see also FIGS. 17A and B). Briefly, the unexpected and novel purification properties of protamine sulphate (PS) were evaluated in purification processes for Zika Virus similarly as found above. Again non-infectious virus particle aggregates, HCP and other LMW impurities were removed by PS precipitation as shown by removal of aggregate shoulder in SEC-HPLC and no loss of infectious virus titer by PS treatment (FIG. 18). Further optimization of the Zika purification protocol is provided below.

Upstream:
  Roller Bottle based Vero cell expansion (25×850 cm2 CellBind):
  5% $CO_2$, 35° C., MEM+2 mM L-Glutamine+10% FBS
  Infection with ZikaV research Master Seed Bank (rMSB) at MOI 0.01
  Virus Production without serum
  5% $CO_2$, 35° C., MEM+2 mM L-Glutamine
  Multiple harvests (days 2, 3, 5 and 7) with re-feed
  Sterile filtration of harvests and storage at 2-8° C. until further processing Downstream:
  Pooling of harvests and concentration by ultrafiltration (100 kDa)
  Stabilization of concentrated harvest (Tris/10% sucrose) for storage if required (−80° C.)
  Removal of hcDNA by Protamine Sulphate (2 mg/mL)
  Sucrose Gradient Purification (optimized three layered gradient)
  Formaldehyde Inactivation (0.02%, 22° C., 10 days), neutralization with Na-metabisulfite
  Dilution to DS antigen target content and formulation with Aluminium hydroxide (0.5 mg Al/mL)

Zika Virus Strain H/PF/2013 was originally isolated from a 51-year-old woman (accession number KJ776791.1, also SEQ ID NO: 13 herein) from French Polynesia. A sample was obtained from the European Virus Archive (EVAg; Ref-SKU: 001v-EVA1545). Based on this material, a research master seed bank (rMSB) was prepared on Vero cells as the cell substrate and the genomic sequence was checked by sequencing. Because the genomic sequence at the 5' and 3' flanking sequences of Zika virus strain H/PF/2013 was unknown, primers for sequencing were designed in those regions based on other Zika virus strains whereas the internal primers were designed from the published sequence (SEQ ID NOs: 80 to 123, see also Table A). The sequence obtained from the rMSB by use of these primers is provided by SEQ ID NO: 78. There was 100% overlap of the sequence with the published sequence of Zika Virus Strain H/PF/2013 (SEQ ID NO: 13). However, we sequenced additional regions 5' (an additional 40 bp) and 3 (an additional 160 bp) represented in SEQ ID NO: 78. In a preferred embodiment, the Zika virus of the invention comprises SEQ ID NO: 78. The genomic RNA is somewhat longer than the sequence according to SEQ ID NO: 78 (perhaps an additional 200 bp). Additionally, a Zika virus adapted to a host cell such as e.g. Vero cells may be expected to contain one or more mutations. For these reasons, the Zika virus of the current invention comprises the sequence of SEQ ID NO: 78 or, preferably, a sequence with at least 95%, 96%, 97%, 98%, or at least 99% sequence identity to the sequence provided by SEQ ID NO: 78. Furthermore, because the viral genome is likely to contain even further flanking regions to SEQ ID NO: 78; in one embodiment, the Zika virus of the invention contains the sequence of SEQ ID NO: 78 and optionally further comprises extensions at the 5' and/or 3' ends of at least 10, at least 20, at least 30, at least 40, at least 50, at least 60, at least 70, at least 80, at least 90, at least 100, at least 110, at least 120 or at least 130 nucleotides. In a preferred embodiment, the Zika virus comprises at least the coding sequence for the entire polyprotein of Zika Virus Strain H/PF/2013 of the invention i.e. the amino acid sequence of SEQ ID NO: 79 or a polyprotein with at least 95%, 96%, 97%, 98%, or at least 99% sequence identity to the sequence provided by SEQ ID NO: 79. Furthermore, the Zika virus comprises at least the coding sequence for the E-protein of Zika Virus Strain H/PF/2013 of the invention SEQ ID NO: 47 or an E-protein thereof with at least 95%, 96%, 97%, 98%, or at least 99% sequence identity to the sequence provided by SEQ ID NO: 47.

Virus Growth on Vero Cells

Vero cells were grown in Eagle's minimal essential medium (EMEM) containing 10% fetal bovine serum (FBS). Roller bottle cultures of Vero cell monolayers were infected with Zika Virus Strain H/PF/2013 at a multiplicity of infection (moi) of 0.01 plaque forming units (pfu) per cell. After 2 hours of virus adsorption, the cultures were washed 3 times with PBS and fed with EMEM without FBS and incubated at +35° C. with 5% $CO_2$. Infected Vero cell cultures were incubated until the virus titer reaches a desired level.

The culture medium was harvested at days 2, 3, 5 and 7 and were pooled from those harvest days and then centrifuged in a standard centrifuge. The supernatants were then filtered. Virus culture supernatants were concentrated by TFF ultrafiltration to remove cell culture media components and to reduce batch volume.

Evaluation of Harvest Procedure

The current JEV harvest process has scheduled harvests on days 3, 5, 7 and 9 post infection. To mimic the JEV process roller bottles were infected with ZIKV bank P4-FBS at an MOI of 0.01 in infection medium (MEM with 2% FBS+2 mM L-glutamine) for 2 hours. After removing the inoculum the cells were washed twice with PBS and 200 mL production medium (MEM+2 mM L-glutamine) was added.

After taking a sample on day 2 the first virus harvest was conducted on day 3 after infection. At this point significantly higher CPE could be observed compared to cells where virus was removed on day 2. Plaque assay analysis showed that the viral titers on day 2 were in the same range as for the standard harvesting schedule. However, starting with the day 3 harvest, the observed titers were significantly lower correlating with the increased CPE observed compared to the standard harvest schedule. On day 5 post infection no more living cells could be observed at all and the experiment was terminated with a final day 5 harvest.

TABLE 5

The calculated titers per plaque assay
are summarized in the list below.

| | Log 10 PFU/mL |
|---|---|
| sample day 2 | 7.02 |
| harvest day 3 | 6.66 |
| harvest day 5 | 6.26 |

This finding led to an optimized harvest schedule to better control of CPE and allow additional harvest day 5 and 7, see FIG. 23. For both harvest days the optimized ZikaV protocol yield significant higher virus titers compared to the modified protocol showing that the time of the first harvest is crucial for production yields. Additionally first harvesting at day 3 results in maximum 2 harvest points whereas first harvesting at day 2 allows for 4 harvest points further increasing the yield gain.

Downstream Purification of Zika virus

The purification process was carried out at room temperature (18-22° C.) unless stated otherwise. Virus purification started with concentration of filtered combined harvest using 100 kDa cut-off TFF ultrafiltration modules to remove cell culture media components and reduce batch volume. After concentration, the pooled filtered harvest material was adjusted to a final concentration of 25 mM Tris pH 7.5 and 10% sucrose (w/w) using stock solution of both components (see FIG. 19 for SEC-HPLC of different harvests prior to PS treatment). This allowed for freezing the concentrated harvest at <−65° C. if required.

Host cell DNA and protein reduction as well reduction of non-infectious virus aggregates in the concentrated material was achieved by precipitation with protamine sulphate (2 mg/mL) followed by sucrose density centrifugation (2-8° C.) as final polishing step (see FIG. 20 for SEC-HPLC of different harvests post PS treatment). The purification process was designed to be completed within 2 working days with SGC starting on end of day 1 followed by fractionation and SDS-PAGE analysis on day 2. The sucrose gradient fractions were stored at 2-8° C. during the SDS-PAGE analysis (Silver staining) to identify the pure fractions containing ZikaV (see FIG. 21). After pooling the relevant fractions, the pool was diluted and inactivated by Formalin. After pooling the relevant fractions of sucrose gradient centrifugation, the pool was diluted 1:3 in PBS and inactivated by Formalin (0.02% v/v, 200 ppm). Fractions were subjected to analysis by SDS-PAGE.

Effect of PS Treatment on Virus Recovery

Samples of individual 30× concentrated harvests days 2, 3, 5 and 7 were analysed before (FIG. 19) and after PS (FIG. 20) treatment by SEC-HPLC and plaque assay. SEC-HPLC was used for determination of relative total ZikaV content (active+inactive) expressed as peak area, whereas the rel. ZikaV peak purity is given as relative content of virus monomer population to total virus peak. Plaque assay states the content of total active virus particles in each sample. Experimental results are summarized in Table 1. The virus peak recovery by SEC-HPLC was only between 12 to 36% with peak purity after PS treatment in the range of >90% (no virus aggregates detected). The recovery of active virus particles by plaque assay was all >100% (130-700%, range within the variability of the assay) showing that no active virus particles were lost during PS treatment. These results show that during PS treatment only non-infective (immature and/or aggregated virus) particles were removed.

TABLE 6

ZikaV recovery by SEC-HPLC and plaque
assay before and after PS treatment.

SEC-HPLC

| | Peak area mAU*min | | | |
|---|---|---|---|---|
| Harvest day | 30x conc | 30x + PS | SEC Recovery (%) | rel. virus monomer content after PS (%) |
| Day 2 | 101.36 | 18.63 | 18 | 89% |
| Day 3 | 144.51 | 17.48 | 12 | 90% |
| Day 5 | 19.97 | 5.92 | 30 | 96% |
| Day 7 | 68.80 | 24.43 | 36 | 99% |

Plaque Assay

| | PFU/mL | | Plaque |
|---|---|---|---|
| Harvest day | 30x conc | 30x + PS | Recovery (%) |
| Day 2 | 3E+08 | 5E+08 | 179 |
| Day 3 | 2E+08 | 4E+08 | 193 |
| Day 5 | 1E+08 | 9E+08 | 700 |
| Day 7 | 3E+08 | 4E+08 | 132 |

Sucrose Gradient Centrifugation

The PS treated harvest was split in two parts and loaded on two centrifuge bottles.

Sucrose density gradient centrifugation (SGC) was used for final concentration and polishing of the ZikaV material. The ZikaV PS treated concentrated harvest was loaded on top of a solution consisting of three layers of sucrose with different densities. The three sucrose layers were selected based on a preliminary study which showed the formation of a linear sucrose gradient and complete separation of the virus particles from residual contaminants as demonstrated for ChikV (FIG. 15D). The optimal volumes of the sucrose solutions were determined empirically. The volumes of individual layers for a centrifugation in 100 mL bottle scale are shown in Table 2.

TABLE 7

Individual layers/volumes for a centrifugation in bottle.

| Solution | Volume (mL) |
|---|---|
| PS treated harvest in 10% sucrose (L) | 40 |
| 15% sucrose (J) | 15 |
| 35% sucrose (I) | 15 |
| 50% sucrose (H) | 20 |
| Total volume | 90 |

The sucrose gradient bottles were prepared by stratifying the individual sucrose layers. A plastic tube was attached to peristaltic pump tubing. The plastic tube was mounted on a laboratory stand using a clamp and placed into the centrifuge bottle. The nozzle of the plastic tube was touching the bottom of the bottle. Using a peristaltic pump the ZikaV material and the sucrose solutions were pumped into the cylinder. A measuring cylinder was used as feed vessel. The first solution pumped was the ZikaV material as it represented the solution of lowest density (10% sucrose (w/w)). After the ZikaV material the sucrose solutions were pumped in ascending order starting with the 15% (w/w) solution J, followed by 35% sucrose solution I and finishing with the highest density sucrose solution H (50% (w/w)). The described setup is shown in FIG. 14. After all sucrose solutions were transferred the plastic tubing was carefully removed in order not to disturb the layers.

Prior to centrifugation the centrifuge was pre-cooled to 4° C. The prepared SG bottles were carefully transferred into the pre-cooled rotor. (Note: Sudden movement of the bottles during transfer to the rotor must be avoided in order not to disturb the sucrose layers.) The bottles were centrifuged at ~11.000 RCF max at 4° C. for at least 20 hours, no brake/deceleration activated. In case a different centrifuge system with a different rotor is used the necessary speed and centrifugation times need to be calculated based on the k-factor in order to achieve comparable centrifugation efficiency.

Harvesting of the sucrose gradient was done manually using a peristaltic pump. A plastic tube attached to peristaltic pump tubing was used for harvesting the sucrose gradient. The bottle containing the gradient was mounted onto a laboratory stand in a tilted position (~12°) using a clamp. The plastic tubing was then placed into the bottle touching the bottom edge of the bottle and was fastened in position using a clamp.

This resulted in a small gap of 1-2 mm between the tubing inlet and the bottom of the bottle (see FIG. 14).

Using a peristaltic pump set to a flow rate of 30 mL per minute the gradient was harvested and manually split into 2 mL fractions. A total number of 32 fractions per bottle were harvested (~64 mL) and the remaining volume was discarded. The fractions were immediately tested by SDS-PAGE/silver stain to identify the virus containing fractions with sufficient high purity. Representative SDS-PAGE is shown in FIG. 21. Fraction 10-14 were pooled and further processed.

The purified viral solution was inactivated by incubation with 0.02% formaldehyde over a period of ten days in a 22° C. controlled-temperature incubator. The formaldehyde is neutralized by addition of sodium metabisulphite on the tenth day.

The sucrose gradient pool (~17 mL after sampling) was further diluted 3-fold with PBS to a final volume of 51 mL in a PETG container. A volume of 1% formaldehyde (10,000 ppm) solution equivalent to 1/50 of the final volume of the pre-formaldehyde pool was added to this pool resulting in an effective concentration of 200 ppm. The formaldehyde-treated solution was mixed on a magnetic stirrer for 10 minutes. After sampling, the formaldehyde-treated viral solution was placed within a cooled incubator at 22° C.±2° C. On Day 5 post addition of formaldehyde, the formaldehyde-treated viral solution was filtered through a 0.2 m filter and then placed in the incubator at 22° C.±2° C. again. On Day 10, after removing the 10-Day inactivation final sample, a volume of 1% (of the weight of the final formaldehyde-treated viral solution) of 200 mM-sodium metabisulphite solution (2 mM final concentration) was aseptically transferred into the PETG container containing the formaldehyde-treated viral solution. After mixing for 5 minutes on a magnetic stirrer, the neutralized inactivated viral solution is held at room temperature (20 to 25° C.) for a minimum of 30 minutes. After sampling, the neutralized inactivated viral solution is stored at 5° C.±3° C. until further processing.

Inactivation by Formaldehyde

Critical parameters for this step are final formalin concentration, temperature, mixing and transfer into a new container. A preliminary acceptance criterion for maximum pfu/mL (determined by plaque assay) has been set on the diluted pool pre formaldehyde treatment.

The quality of the neutralized inactivated viral solution was monitored by the following parameters: Plaque assay on Day 10, SEC-HPLC, SDS-PAGE/Western Blot.

Interestingly, SEC-HPLC analysis of samples taken during the inactivation period followed by neutralization with bisulfite showed more or less constant peak area throughout the inactivation period. This is in contrast to JEV where losses of viral particles up to 60% are observed using the process disclosed by Srivastava et al. Vaccine 19 (2001) 4557-4565. In a scale-down model the viral losses were even much higher due to surface/area ratio at smaller scale and high losses due to unspecific adsorption. Differences of the ZikaV inactivation experiment and JEV inactivation were noticed as follows:

A) Much higher purity of ZikaV SGP pool with regard to residual PS (<2 µg/mL) compared to JEV. The 3-fold ZikaV inactivated sample contained therefore <<1 µg/mL of residual PS. Commercial JEV SGP pool contains on average ~120 g/mL (up to 152 μg/mL possible). The average dilution to inactivation solution of ~14-fold results in a residual PS content up to ~11 μg/mL. It may be that higher amount of residual PS could cause virus precipitation due to cross-linking/reaction with formalin.

B) ZikaV inactivation sample contained ~10% sucrose (3-fold dilution of SGP pool containing ~30-35% sucrose). Sucrose might have stabilizing effect of viral ZikaV particles during treatment with formalin.

Dilution to DS and Formulation with Aluminium Hydroxide (DP)

For preparation of ZikaV drug substance used in mouse potency assay an antigen content (expressed as total viral particles or SEC peak area) of 5 times higher compared to Ixiaro was targeted. The basis for determination of antigen content was SEC-HPLC. Briefly, a Superose 6 10/300 Increase column (GE Healthcare) equilibrated with PBS+ 250 mM NaCl, pH 7.4 at 1 ml/min and 25° C., was used to detect ZikaV at 214 nm detection wavelength in harvest samples and throughout the downstream process. In the current JEV process the antigen content in NIV is determined by a specific ELISA. A good correlation was observed between antigen content determined by ELISA and SEC-HPLC. On average, the antigen content in commercial NIV samples is in the range of 33 AU/mL corresponding to ~5.2 mAU JEV peak area, see FIG. 22.

ZikaV NIV day 10 (Zika peak ~36 mAU, analysed on Waters HPLC/Superose6 Increase column) was diluted with PBS to a target of 6.3 (~5.7× dilution). Aluminium hydroxide was added to a final concentration of 0.5 mg/mL Aluminium (1/20 v/v Alum 2% stock solution added) to prepare ZikaV Drug Product (DP). The DP was gently mixed for 5 min. An aliquot of the DP was removed, Alum sedimented by centrifugation and the clear supernatant analysed by SEC-HPLC. No ZikaV peak was detected in the supernatant indicating complete adsorption (estimated as >95%) of viral particles on the mineral adjuvant. Formulated ZikaV DP was stored at 2-8° C.

The impurity profile of the inactivated Zika virus DS is comparable to the profile of JEV DS with the exception of a lower PS content (Table 8).

TABLE 8

Determination of impurity profile in Zika and JEV DS samples:

| | Specification (JEV DS) | JEV | Zika |
|---|---|---|---|
| HCP (ng/mL) | <100<br>LOQ 12 ng/mL | <LOQ | <LOQ |

TABLE 8-continued

Determination of impurity profile in Zika and JEV DS samples:

| | Specification (JEV DS) | JEV | Zika |
|---|---|---|---|
| DNA (pg/mL) | <200 LOQ 40 pg/mL | <40 | <40 |
| Aggregates by SEC-MALLS (%) | Not specified, part of characterization LOQ 5% | <LOQ | <LOQ |
| PS (µg/mL) | Specification only at SGP pool to demonstrate consistent process performance (19-152 µg/mL), *PS content in DS calculated based on PS content in SGP pool (~100 µg/mL) and average dilution factor (~28×) to DS; LOQ 2 µg/mL | ~4* | <<LOQ |

*Typical PS impurity in a JEV sample produced in accordance with protocol disclosed in Srivastava et al. Vaccine 19 (2001) 4557-4565.

SEC-MALLS Results

A representative SEC-HPLC elution profile of ZikaV NIV at 214 nm detection wave length is shown in FIG. 24. Note that BSA (50 g/mL) was added to the sample to minimize losses in HPLC glass vial due to unspecific surface adsorption. ZikaV monomer content was estimated as ~98% with a multimer content of ~2%.

SEC-MALLS analysis (FIG. 25) of the sample confirmed the radius Rz of the monomer ZikaV population peak 1 as 21.6 nm and ~49 nm for the multimer peak 2. Cumulative particle size distribution showed that 89% of all viral particles are within a radius range between 18 to 25 nm (FIG. 26).

Results confirm purity and homogeneity of ZikaV NIV.

Viral Titer by Plaque Assay

TABLE 9

Active ZikaV pfus were quantified by plaque assay throughout the process.

| Sample | Pfu/mL |
|---|---|
| Harvest day 2 (filtered) | $6.4 \times 10^7$ |
| Harvest day 3 (filtered) | $1.0 \times 10^8$ |
| Harvest day 5 (filtered) | $1.5 \times 10^8$ |
| Harvest day 7 (filtered) | $1.1 \times 10^8$ |
| PS treated harvest 300× concentrate (=SGP load) | $9.0 \times 10^8$ |
| SGP pool | $8.9 \times 10^8$ |
| Inactivation start (SGP pool 1:3 diluted) | $3.4 \times 10^8$ |
| Inactivation day 5 | <LOD |
| Inactivation day 10 | <LOD |

Comparison of PS and Benzonase on Process Performance

A direct comparison of DNA removal method of concentrated ZikaV harvest pool was done. One aliquot was treated with PS (2 mg/mL, 15 min at room temperature), the other aliquot was treated with Benzonase (50 U/mL, 2 mM MgCl2, 4 h RT, 48 h 2-8° C.). Both samples were further purified by sucrose gradient as described in this report. Interestingly, the Benzonase treated samples did not yield any pure fractions after sucrose gradient centrifugation of the treated ZikaV harvest. In those fractions where the specific virus bands were detected, a high amount of host cell protein was detected throughout the collected fractions. The PS treated material resulted in pure ZikaV containing fractions as expected. This finding may suggest that PS is not only effective for DNA removal by precipitation; in addition it improves the recovery of virus particles in the gradient by disrupting interaction of DNA (fragments) and virus particles. Benzonase treatment does not remove DNA, it only results in its fragmentation. Residual DNA fragments might still interact with virus particles and residual HCPs resulting in cross-contamination and co-purification in the sucrose gradient. Pooled SGP fractions were also analysed by SEC-HPLC. Although a large peak was detected, SDS-PAGE confirmed that this sample was highly contaminated with HCPs. A large peak might be detected at UV214 and 280 nm after SEC-HPLC analysis due to possible interaction of HCPs with large virus particles, changing the UV absorbance.

Immunogenicity of Vero Grown Zika Virus

Immunization of Mice

Prior to immunization, groups of ten 6-week-old female CD1 mice were bled via vena facialis and pre-immune sera were prepared. One intraperitoneal immunizations of 200 µL were administered. A dose titration (12 µg, 3 µg, 1 µg, 0.33 µg, 0.11 µg, 0.037 µg and 0.012 µg, equivalent to the protein amount in IXIARO) of inactivated Zika virus formulated with aluminium hydroxide (Al(OH)3) at a final concentration of 0.7%. Three weeks after immunization, blood was collected and immune sera were prepared. All animal experiments were conducted in accordance with Austrian law (BGB1 Nr. 501/1989) and approved by "Magistratsabteilung 58".

Plaque Reduction Neutralization Test (PRNT)

Twelve well plates were used for PRNT. Each well was seeded with 1 mL medium containing $4 \times 10^5$ Vero cells and incubated 35° C. with 5% CO2 overnight. Pools of heat inactivated sera from each dose group were tested in triplicate. The target viruses (H/PF/2013 (SEQ ID NO: 13) or MR766 (SEQ ID NO: 11)) were diluted to 100 pfu/165 µL. Equal volumes of target virus and serum dilution were incubated at 35° C. with 5% $CO_2$ for 1 hour. The cell culture medium was aspirated from the Vero cells and 330 µL of the mixture target virus/serum dilution were added to each well and the plates were rocked back and forth 5 times before incubating for 2 hours at 35° C. with 5% $CO_2$. To each well 1 mL of a 2% methylcellulose solution containing EMEM and nutrients was added, the plates were then incubated for 5 days at 35° C. with 5% $CO_2$ before staining the cells for 1 hour with crystal violet/5% formaldehyde and subsequently washed 3 times with deionized water. The plates were air dried and the numbers of plaques in each well were manually counted.

Results

Neutralization was observed with serum pools from mice immunized with inactivated Zika virus vaccine (H/PF/2013) down to 37 ng (dosing equivalent to the amount protein in IXIARO®) against Zika viruses of both the Asian (H/PF/2013) and African (MR766) lineages (FIGS. 27 and 28, respectively). Complete inhibition was seen at the 1:20 serum dilution with an immunization dose down to 110 ng (dosing equivalent to the amount protein in IXIARO®). The neutralization of both the Asian (H/PF/2013) and African (MR766) lineages of the Zika virus was equivalent, which indicates high cross-neutralization between different Zika virus strains of the inactivated Zika virus vaccine (H/PF/2013).

Another neutralization assay was performed using the microneutralization assay as described by Larocca, et al. (2016, Nature doi:10.1038/nature18952). It was found that the inactivated Zika virus of the current invention had an MN50 (microneutralization) titer of 90 at 1 µg of inactivated purified virus.

Further methods: The immunogenicity of inactivated Zika virus preparations is assessed using a mouse model of Zika infection. Groups of adult mice are immunized subcutaneously (s.c.) with 500, 50, or 5 ng of inactivated Zika virus with adjuvant (e.g. aluminium hydroxide with or without IC31®), or without adjuvant. An additional group of mice receive PBS as a negative control. Each group is administered the indicated inoculum at t=0 and in some cases also at three to four weeks later (t=3/4). Beginning approximately three weeks after administration of the last immunization, serum samples are obtained from each of the mice at regular intervals. The serum samples are tested for the presence of neutralizing antibodies using PRNT.

The in vivo protective efficacy of the inactivated Zika virus preparations is also assessed using a mouse model of Zika infection, i.e. IFN-alpha/beta receptor knock-out mice (A129) (see e.g. Dowall et al., 4. Mar. 2016, http://dx.doi.org/10.1101/042358) or blocking of the IFN-alpha/beta receptor by administration of anti-IFN-alpha/beta receptor monoclonal antibodies to C57BL/6 or BALB/c mice (see e.g. Pinto et al., 7. Dec. 2011, DOI: 10.1371/journal.ppat.1002407). For protection assays, groups of 10 three- to eight-weeks-old A129, C57BL/6 of BALB/c mice are inoculated subcutaneously in the hindquarters with inactivated Zika virus with adjuvant (aluminium hydroxide) or without adjuvant at t=0. Age-matched controls are inoculated with PBS or non-specific antigens in alum. Mice are optionally boosted with a second administration of the indicated inoculation three to four weeks later. The mice are then challenged subcutaneously at three to eight weeks post immunization by inoculation with a deadly dose of live Zika virus. One day prior to challenge of C57BL/6 and BALB/c mice, they are passively administered (intraperitoneally) anti-IFN-alpha/beta receptor monoclonal antibodies. Challenged mice are monitored daily for morbidity and mortality for up to twenty-one days. Another alternative is to challenge intracranially adult vaccinated/non-vaccinated adult mice and observe protection.

It is expected that the Zika virus produced by the process of the invention will provide very similar functional readouts in in vitro, in vivo and finally human trials as the currently licensed JEV vaccine in the EU and US and elsewhere, IXIARO®. The dosage may alter but due to the very similar impurity profile and almost identical manufacture, a very similar efficacy and safety result will be expected as was determined for the currently licensed JEV vaccine (licensed in the EU and US and elsewhere).

Discussion & Conclusion

The existing manufacturing platform for production of inactivated JEV vaccine IXIARO® was used as a basis for a manufacturing feasibility study of inactivated ZikaV vaccine candidate (Asian strain H/PF/2013). The virus was produced on Vero cells cultivated in roller bottles. The virus was purified by PS treatment followed by an optimized sucrose gradient. Inactivation was done by formalin treat (0.02%, 10 days at 22° C.). For exploratory immunization studies in mice, a DP formulated with Alum was prepared with an estimated 5-fold higher virus particle content compared to IXIARO®, the commercial JEV Vaccine. The impurity profile of the DS met all criteria as defined in the specification for IXIARO®, the commercial JEV vaccine. The neutralization of both the Asian (H/PF/2013) and African (MR766) lineages of the Zika virus was equivalent, which indicates high cross-neutralization between different Zika virus strains of the inactivated Zika virus vaccine (H/PF/2013).

The in vivo data regarding immunogenicity of the inactivated Zika virus vaccine of the current invention indicates that the virus is surprisingly potently immunogenic and also highly cross-protective (very similar immunogenicity in African and Asian strains). Data indicate that immunogenicity was higher than the recently reported inactivated Zika virus vaccine candidate (Larocca, et. al, 2016, supra.). Inactivated viruses are among the safest vaccines and especially preferred for deliver to populations where safety is especially concerning, such as pregnant women, children and immunocompromised individuals, which makes the herein disclosed inactivated Zika virus particularly suitable. Obtaining a high titer of inactivated virus is a challenge in the field. The herein disclosed process for purifying inactivated Zika virus results in not only a high yield, but also a very pure drug substance.

Example 3: Development of a Purification Process for Yellow Fever Virus Vaccine Produced in Vero Cells A downstream process was developed for the purification of infectious yellow fever virus particles whereby host cell nucleic acids, non-infectious virus particles and aggregates are removed by the addition of protamine sulphate as described in Examples 1 and 2. The unexpected and novel purification properties of protamine sulphate (PS) were evaluated in purification processes for yellow fever (YF) as follows:

As before the treatment of YF-harvest with PS significantly reduces the amount of aggregates as seen with SEC for two vaccine strains currently in development (FIG. 29).

Further more detailed aspects of the invention:

A1. A process of purification of infectious alphavirus particles, preferably Chikungunya virus particles, comprising the steps of:
  a) providing a crude harvest (a) comprising virus particles and impurities, wherein the impurities are generated from growing said virus particles on a cell substrate;
  b) reducing impurities from the crude harvest (a) by precipitation with an agent comprising a protamine salt, preferably a protamine sulphate, even more preferably a recombinant protamine sulphate, to obtain a virus preparation (b);
  c) contacting the virus preparation (b) with (i) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cut-off of the pores can enter the ligand-activated core and collecting the virus particles to obtain a virus preparation (d), or (ii) a solid-phase matrix comprising a ligand-activated core and an inactive shell comprising pores, wherein the molecular weight cut off of the pores excludes the virus particles from entering the ligand-activated core, and wherein a molecule smaller than the molecular weight cut-off of the pores can enter the ligand-activated core and separating the solid-phase matrix from the virus particles by filtration to produce a virus preparation (c); and
  d) further purifying the virus preparation (c) by sucrose density gradient centrifugation to obtain a virus preparation (d) comprising the infectious virus particles, wherein the residual host cell DNA of the virus preparation (d) is less than 100 ng/mL and the residual host cell protein of the final virus preparation (d) is less than 1 μg/mL.

A2. The process of A1, wherein the residual host cell DNA of the virus preparation (d) is less than 10 ng/mL and the residual host cell protein of the final virus preparation (d) is less than 100 ng/mL.

A3. The process of A1 or A2, wherein the crude harvest (a) comprising virus particles and impurities is subjected to one or more pre-purification step(s) prior to step (b).

A4. The process of any one of A1 to A3, wherein the one or more pre-purification step(s) comprises
  a) filtration using a filter having a pore size equal to or less than 0.2 µm; and/or
  b) digestion of host cell genomic DNA by enzymatic treatment; and/or
  c) ultra/diafiltration using a hollow fiber membrane having a pore size equal to or greater than 300 kDa, preferably equal to or greater than 100 kDa.

A5. The process of any one of A1 to A4, wherein the concentration of protamine sulphate is 1 to 2 mg/ml, more preferably 1.2 to 1.8 mg/ml, more preferably 1.4 to 1.6 mg/ml, most preferably 1.6 mg/ml.

A6. The process of any one of A1 to A5, wherein the molecule entering the core of the solid-phase matrix has a molecular weight less than 700 kDa.

A7. The process of any one of A1 to A6, wherein the ligand of the ligand-activated core of the solid-phase matrix is capable of binding the molecule that enters the ligand-activated core via cationic-, anionic-, hydrophobic- or mixed interactions.

A8. The process of any one of A1 to A7, wherein the ligand of the ligand-activated core of the solid-phase matrix is octylamine.

A9. The process of any one of A1 to A8, wherein the solid-phase matrix is used as a slurry and at a final concentration between 0.5% (v/v) and 10% (v/v), preferably 0.6%, 0.7%, 0.9%, 1%, 2%, 3%, 4%, 5%, 6%, 7%, 8%, 9%, 10%, most preferably 1%.

A10. The process of any one of A1 to A9, wherein the solid-phase matrix is incubated with the protamine-treated virus preparation (b) at refrigerated temperatures (2° C. to 8° C.) with a stirring for at least 10 minutes, preferably 15 minutes, 30 minutes or 1 hour, most preferably 15 minutes.

A11. The process of any one of A1 to A10, wherein the enrichment of infectious virus particles in the final virus preparation relative to total virus products in the crude harvest (a) is in the range from at least 50% to 95%, preferably at least 80%.

A12. The process of any one A1 to A11, wherein the filtration of step (c) of preferred aspect 1 is performed using a filter having a pore size equal to or less than 1 µm, preferably 0.2 µm.

A13. The process of any one of A1 to A12, wherein the residual impurity of the final virus preparation is less than 10%.

A14. The process of any one of A1 to A13, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

A15. The process of A14, wherein said cell line is a Vero cell line.

A16. The process of any one of A1 to A15, wherein the Chikungunya virus is a live virus, an attenuated live virus, a chimeric virus, a modified live virus, or a recombinant live virus.

A17. The process of any one of A1 to A16, wherein the Chikungunya virus is the Δ5nsP3 attenuated mutant or an immunogenic variant thereof.

A18. The process of any one of A1 to A17, wherein said process resulting in final virus preparation (d) is followed by an inactivation step, wherein the virus is inactivated preferably by formaldehyde.

A19. Use of the process according to any one of A1 to A18 for manufacturing a composition for immunization against a Chikungunya virus infection.

A20. The use according to A19, wherein the composition for immunization against a Chikungunya virus infection is a vaccine.

A21. A composition comprising the virus particles obtainable by the process of any one of A1 to A18 for treating and/or preventing a Chikungunya virus infection.

N1. A process of purification of infectious alphavirus particles, preferably Chikungunya virus particles, comprising the steps of:
  (a) providing a crude harvest (a) comprising virus particles and impurities, wherein the impurities are generated from growing said virus particles on a cell substrate;
  (b) reducing impurities from the crude harvest (a) by precipitation with an agent comprising a protamine salt, preferably a protamine sulphate, even more preferably a recombinant protamine sulphate, to obtain a virus preparation (b);
  (c) contacting the virus preparation (b) with (i) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cut-off of the pores can enter the ligand-activated core and collecting the virus particles to obtain a virus preparation (d), or (ii) a solid-phase matrix comprising a ligand-activated core and an inactive shell comprising pores, wherein the molecular weight cut off of the pores excludes the virus particles from entering the ligand-activated core, and wherein a molecule smaller than the molecular weight cut-off of the pores can enter the ligand-activated core and separating the solid-phase matrix from the virus particles by filtration to produce a virus preparation (c); and
  (d) further purifying the virus preparation (c) by sucrose density gradient centrifugation to obtain a virus preparation (d) comprising the infectious virus particles, wherein the residual host cell DNA of the virus preparation (d) is less than 100 ng/mL and the residual host cell protein of the final virus preparation (d) is less than 1 µg/mL.

N2. The process of N1, wherein the residual host cell DNA of the virus preparation (d) is less than 10 ng/mL and the residual host cell protein of the final virus preparation (d) is less than 100 ng/mL.

N3. The process of N1 or 2, wherein the crude harvest (a) comprising virus particles and impurities is subjected to one or more pre-purification step(s) prior to step (b).

N4. The process of any one of N1 to 3, wherein the one or more pre-purification step(s) comprises
  (a) filtration using a filter having a pore size equal to or less than 0.2 µm; and/or
  (b) digestion of host cell genomic DNA by enzymatic treatment; and/or (c) ultra/diafiltration using a hollow fiber membrane having a pore size equal to or greater than 300 kDa, preferably equal to or greater than 100 kDa.

N5. The process of any one of N1 to 4, wherein the concentration of protamine sulphate is 1 to 2 mg/ml, more preferably 1.2 to 1.8 mg/ml, more preferably 1.4 to 1.6 mg/ml, most preferably 1.6 mg/ml.

N6. The process of any one of N1 to 5, wherein the molecule entering the core of the solid-phase matrix has a molecular weight less than 700 kDa.

N7. The process of any one of N1 to 6, wherein the ligand of the ligand-activated core of the solid-phase matrix is capable of binding the molecule that enters the ligand-activated core via cationic-, anionic-, hydrophobic- or mixed interactions.

N8. The process of any one of N1 to 7, wherein the ligand of the ligand-activated core of the solid-phase matrix is octylamine.

N9. The process of any one of N1 to 8, wherein the solid-phase matrix is used as a slurry and at a final concentration between 0.5% (v/v) and 10% (v/v), preferably 0.6%, 0.7%, 0.9%, 1%, 2%, 3%, 4%, 5%, 6%, 7%, 8%, 9%, 10%, most preferably 1%.

N10. The process of any one of N1 to 9, wherein the solid-phase matrix is incubated with the protamine-treated virus preparation (b) at refrigerated temperatures (2° C. to 8° C.) with a stirring for at least 10 minutes, preferably 15 minutes, 30 minutes or 1 hour, most preferably 15 minutes.

N11. The process of any one of N1 to 10, wherein the enrichment of infectious virus particles in the final virus preparation relative to total virus products in the crude harvest (a) is in the range from at least 50% to 95%, preferably at least 80%.

N12. The process of any one of N1 to 11, wherein the filtration of step (c) of N1 is performed using a filter having a pore size equal to or less than 1 μm, preferably 0.2 μm.

N13. The process of any one of N1 to 12, wherein the residual impurity of the final virus preparation is less than 10%.

N14. The process of any one of N1 to 13, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

N15. The process of N14, wherein said cell line is a Vero cell line.

N16. The process of any one of N1 to 15, wherein the Chikungunya virus is a live virus, an attenuated live virus, a chimeric virus, a modified live virus, or a recombinant live virus.

N17. The process of any one of N1 to 16, wherein the Chikungunya virus is the Δ5nsP3 attenuated mutant or an immunogenic variant thereof.

N18. The process of any one of N1 to 17, wherein said process resulting in final virus preparation (d) is followed by an inactivation step, wherein the virus is inactivated preferably by formaldehyde.

N19. Use of the process according to any one of N1 to 18 for manufacturing a composition for immunization against a Chikungunya virus infection.

N20. The use according to N19, wherein the composition for immunization against a Chikungunya virus infection is a vaccine.

N21. A composition comprising the virus particles obtainable by the process of any one of N1 to 18 for treating and/or preventing a Chikungunya virus infection.

P1. A Zika virus vaccine comprising an optimally inactivated Zika virus particle, wherein the Zika virus particle is able to seroconvert a subject that is administered the Zika virus vaccine with at least a 70% probability.

P2. The Zika virus vaccine of P1, wherein the Zika virus particle is able to seroconvert the subject that is administered the Zika virus vaccine with at least a 80%, 85%, 90%, or 95% probability, preferably a 80% probability.

P3. The vaccine of P1 or 2, wherein the Zika virus particle has a RNA genome corresponding to the DNA sequence provided by any one of the nucleic acid sequences of SEQ ID NOs: 2-13, or a variant nucleic acid sequence that is at least 88% identical to any one of SEQ ID NOs: 2-13 and able to pack a virulent Zika virus.

P4. The vaccine of any one of P1-3, wherein the Zika virus particle has an E protein selected from the amino acid sequences provided by any one of SEQ ID NOs: 14-69, or a variant amino acid sequence that is at least 95% identical to any one of SEQ ID NOs: 14-69 and able to pack a virulent Zika virus.

P5. The vaccine of any one of P1-4, wherein the Zika virus is inactivated by chemical inactivation, thermal inactivation, pH inactivation, or UV inactivation.

P6. The vaccine of P5, wherein the chemical inactivation comprises contacting the Zika virus with a chemical inactivation agent for longer than is required to completely inactivate the Zika virus as measured by plaque assay.

P7. The vaccine of P6, wherein the chemical inactivation comprises contacting the Zika virus with formaldehyde.

P8. The vaccine of P7, wherein the formaldehyde inactivation comprises contacting the Zika virus with formaldehyde for between 2-10 days.

P9. The vaccine of any one of P5-8, wherein the chemical activation is performed at about +4° C. or about +22° C.

P10. The vaccine of any one of P1-9, further comprising an adjuvant.

P11. The vaccine of P10, wherein the adjuvant is an aluminum salt adjuvant.

P12. The vaccine of P11, wherein the aluminum salt adjuvant is aluminium hydroxide or aluminium phosphate salt.

P13. The vaccine of any one of P10-12, wherein the vaccine comprises or further comprises an adjuvant comprising a peptide and a deoxyinosine-containing immunostimulatory oligodeoxynucleic acid molecule (I-ODN).

P14. The vaccine of P13, wherein the peptide comprises the sequence KLKL5KLK (SEQ ID NO: 71) and the I-ODN comprises oligo-d(IC)13 (SEQ ID NO: 70).

P15. The vaccine of any one of P1-14, further comprising one or more pharmaceutically acceptable excipient.

Q1. A process of purification of infectious virus particles, comprising the steps of:

(a) providing a crude harvest (a) comprising virus particles and impurities, wherein the impurities are generated from growing said virus particles on a cell substrate;

(b) reducing impurities from the crude harvest (a) by precipitation with an agent comprising protamine, preferably a protamine salt, more preferably a protamine sulphate, even more preferably a recombinant protamine sulphate, to obtain a virus preparation (b);

(c) further purifying the virus preparation (b) by an optimized sucrose density gradient centrifugation, wherein the optimized sucrose gradient is provided such that the protamine can be completely or almost completely separated from the virus fraction; and wherein the protamine concentration is reduced by this step to the extent that the protamine concentration in the final drug substance is below 1 µg/ml, preferably below 0.5 µg/mL, more preferably below 0.1 µg/mL, most preferably below 0.05 µg/mL.

Q2. The process of Q2, wherein the virus particles are selected from the group consisting of flaviviruses, e.g. yellow fever virus or Zika virus and alphaviruses, e.g. Chikungunya.

Q3. The process of Q1 or Q2, additionally comprising the step of:

(d) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles.

Q4. The process of any of Q1 to 3, wherein the residual host cell DNA of the virus preparation (c) is less than 10 ng/mL and the residual host cell protein of the final virus preparation (c) is less than 100 ng/mL.

Q5. The process of any of Q1 to 4, wherein the crude harvest (a) comprising virus particles and impurities is subjected to one or more pre-purification step(s) prior to step (b).

Q6. The process of Q5, wherein the one or more pre-purification step(s) comprises (a) filtration using a filter having a pore size equal to or less than 0.2 µm; and/or (b) digestion of host cell genomic DNA by enzymatic treatment; and/or (c) ultra/diafiltration using a hollow fiber membrane having a pore size equal to or greater than 300 kDa, preferably equal to or greater than 100 kDa.

Q7. The process of any one of Q1 to 6, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml or 2 mg/ml.

Q8. The process of any one of Q1 to 7, wherein the enrichment of infectious virus particles in the virus preparation (c) or any final virus preparation relative to total virus products in the crude harvest (a) is in the range from at least 50% to 95%, preferably at least 80%.

Q9. The process of any one of Q5 to 8, wherein the one or more pre-purification step(s) prior to step (b) of any of Q5 to 8 is performed using a filter having a pore size equal to or less than 1 µm, preferably 0.2 µm.

Q10. The process of any one of Q1 to 9, wherein the residual impurity of the virus preparation (c) is less than 10%.

Q11. The process of any one of Q1 to 10, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

Q12. The process of Q11, wherein said cell line is a Vero cell line.

Q13. The process of any one of Q1 to 12, wherein the infectious virus particles is an infectious Zika virus particle that is a live virus, an attenuated live virus, a chimeric virus, a modified live virus, or a recombinant live virus.

Q14. The process of any one of Q1 to 13, wherein the Zika virus is a Zika virus strain of the Asian lineage or an immunogenic variant thereof.

Q15. The process of any one of Q1 to 14, wherein said process resulting in final virus preparation (c) or (d) is followed by an inactivation step, wherein the virus is inactivated preferably by formaldehyde.

Q16. Use of the process according to any one of Q1 to 15 for manufacturing a composition for immunization against a virus infection.

Q17. The use according to Q16, wherein the composition for immunization against a virus infection is an infection caused by a group of viruses consisting of yellow fever virus, Chikungunya virus and Zika virus.

Q18. A composition comprising the virus particles obtainable or obtained by the process of any one of Q1 to 17 for treating and/or preventing an infection, such as e.g. a Zika virus infection.

Q19. A Zika virus vaccine comprising an inactivated Zika virus particle grown on vero cells, wherein the Zika virus particle is able to seroconvert a subject that is administered the Zika virus vaccine with at least a 70% probability and comprises minor amounts of protamine sulphate, preferably below the detection limit.

Q20. The Zika virus vaccine of Q19, wherein the Zika virus particle is able to seroconvert the subject that is administered the Zika virus vaccine with at least a 80%, 85%, 90%, or 95% probability, preferably a 80% probability.

Q21. The vaccine of Q19 or 20, wherein the Zika virus particle has a RNA genome corresponding to the DNA sequence provided by any one of the nucleic acid sequences of SEQ ID NOs: 2-13, or a variant nucleic acid sequence that is at least 88% identical to any one of SEQ ID NOs: 2-13 and able to pack a virulent Zika virus.

Q22. The vaccine of any one of Q19, 20 and 21, wherein the Zika virus particle has an E protein selected from the amino acid sequences provided by any one of SEQ ID NOs: 14-69, or a variant amino acid sequence that is at least 95% identical to any one of SEQ ID NOs: 14-69 and able to pack a virulent Zika virus.

Q23. The vaccine of any one of Q19, 20 to 22, wherein the Zika virus obtained by culturing on Vero cells is purified by protamine sulfate precipitation and sucrose gradient centrifugation.

Q24. The vaccine of Q23, wherein the sucrose gradient centrifugation is an optimized sucrose gradient centrifugation.

Q25. The vaccine of Q24, wherein the optimized sucrose gradient centrifugation comprises a virus comprising fraction in a 10% (w/w) sucrose solution and three layers of sucrose with different densities, i.e. a first sucrose solution with 15% (w/w) sucrose solution, a second sucrose solution with 35% (w/w) sucrose solution, and a third sucrose solution with a 50% (w/w) sucrose solution.

Q26. The vaccine of any one of Q19, 20 to 25, wherein the Zika virus is inactivated by chemical inactivation, thermal inactivation, pH inactivation, or UV inactivation.

Q27. The vaccine of Q26, wherein the chemical inactivation comprises contacting the Zika virus with a chemical inactivation agent for longer than is required to completely inactivate the Zika virus as measured by plaque assay.

Q28. The vaccine of Q27, wherein the chemical inactivation comprises contacting the Zika virus with formaldehyde.

Q29. The vaccine of Q28, wherein the formaldehyde inactivation comprises contacting the Zika virus with formaldehyde for between 2-10 days.

Q30. The vaccine of any one of Q27-29, wherein the chemical activation is performed at about +4° C. or about +22° C.

Q31. The vaccine of any one of Q19 to 30, further comprising an adjuvant.

Q32. The vaccine of Q31, wherein the adjuvant is an aluminum salt adjuvant.

Q33. The vaccine of Q32, wherein the aluminum salt adjuvant is aluminium hydroxide or aluminium phosphate salt.

Q34. The vaccine of Q32, wherein the aluminum salt adjuvant is aluminium hydroxide with less than 1.25 ppb Cu based on the final pharmaceutical composition comprising the Zika virus, preferably the inactivated Zika virus.

Q35. The vaccine of any one of Q19 to 34, further comprising one or more pharmaceutically acceptable excipient.

R1. Use of protamine, preferably a protamine salt, to separate infectious and non-infectious virus particles, host cell proteins and/or undefined low molecular weight materials.

R2. A process of purification of infectious virus particles, comprising the steps of:
(a) providing a crude harvest (a) comprising virus particles and impurities, wherein the impurities are generated from growing said virus particles on a cell substrate;
(b) reducing impurities from the crude harvest (a) by precipitation with an agent comprising protamine, preferably a protamine salt, more preferably a protamine sulphate, even more preferably a recombinant protamine sulphate, to obtain a virus preparation (b), wherein the enrichment of infectious virus particles in the virus preparation (b) relative to total virus products in the crude harvest (a) is in the range from at least 50% to 95%, preferably at least 80%.

R3. The use of R1 or the process of R2, wherein the virus particles are selected from the group consisting of flaviviruses, e.g. yellow fever virus or Zika virus and alphaviruses, e.g.
Chikungunya.

R4. A process of purification of infectious virus particles, comprising the steps of:
(a) providing a crude harvest (a) comprising virus particles and impurities, wherein the impurities are generated from growing said virus particles on a cell substrate;
(b) reducing impurities from the crude harvest (a) by precipitation with an agent comprising protamine, preferably a protamine salt, more preferably a protamine sulphate, even more preferably a recombinant protamine sulphate, to obtain a virus preparation (b);
(c) further purifying the virus preparation (b) by one or more size exclusion methods such as (i) a sucrose density gradient centrifugation, (ii) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles, and/or (iii) size exclusion chromatography to obtain a virus preparation (c) comprising the infectious virus particles, wherein the residual host cell DNA of the virus preparation (c) is less than 100 ng/mL and the residual host cell protein and the residual aggregates of infectious virus particles of the final virus preparation (c) is less than 1 µg/mL.

R5. The process of R4, wherein the residual host cell DNA of the virus preparation (c) is less than 10 ng/mL and the residual host cell protein of the final virus preparation (c) is less than 100 ng/mL.

R6. The process of any of R2 to 5, wherein the crude harvest (a) comprising virus particles and impurities is subjected to one or more pre-purification step(s) prior to step (b).

R7. The process of R6, wherein the one or more pre-purification step(s) comprises
(a) filtration using a filter having a pore size equal to or less than 0.2 µm; and/or
(b) digestion of host cell genomic DNA by enzymatic treatment; and/or
(c) ultra/diafiltration using a hollow fiber membrane having a pore size equal to or greater than 300 kDa, preferably equal to or greater than 100 kDa.

R8. The process of any one of R2 to 7, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml.

R9. The process of any one of R2 to 8, wherein the enrichment of infectious virus particles in the virus preparation (c) or any final virus preparation relative to total virus products in the crude harvest (a) is in the range from at least 50% to 95%, preferably at least 80%.

R10. The process of any one of R6 to 9, wherein the one or more pre-purification step(s) prior to step (b) of any of R6 to 9 is performed using a filter having a pore size equal to or less than 1 µm, preferably 0.2 µm.

R11. The process of any one of R2 to 10, wherein the residual impurity of the virus preparation (c) is less than 10%.

R12. The process of any one of R2 to 11, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

R13. The process of R12, wherein said cell line is a Vero cell line.

R14. The process of any one of R2 to 13, wherein the Zika virus is a live virus, an attenuated live virus, a chimeric virus, a modified live virus, or a recombinant live virus.

R15. The process of any one of R2 to 14, wherein the Zika virus is a Zika virus strain of the Asian lineage or an immunogenic variant thereof.

R16. The process of any one of R2 to 15, wherein said process resulting in final virus preparation (c) is followed by an inactivation step, wherein the virus is inactivated preferably by formaldehyde.

R17. Use of the process according to any one of R1 to 16 for manufacturing a composition for immunization against a virus infection.

R18. The use according to R17, wherein the composition for immunization against a virus infection is an infection caused by a group of viruses consisting of yellow fever virus, Chikungunya virus and Zika virus.

R19. A composition comprising the virus particles obtainable or obtained by the process of any one of R2 to 16 for treating and/or preventing an infection.

What is claimed is:

1. A method for purifying infectious virus particles, comprising the steps of
   - (A) providing a crude harvest (a) comprising infectious virus particles, non-infectious virus particles, and impurities, wherein the impurities are generated from growing said virus particles on a cell substrate;
   - (B) contacting said crude harvest (a) with an agent comprising protamine to obtain a virus preparation (b) comprising infectious virus particles; and
   - (C) further purifying said virus preparation (b) by one or more size exclusion methods wherein said one or more size exclusion methods comprise
     - (i) sucrose density gradient centrifugation, and/or
     - (ii) a solid-phase matrix packed in a column comprising a ligand-activated core and an inactive shell comprising pores, wherein the pores comprise a molecular weight cut-off that excludes the virus particles from entering the ligand-activated core, and wherein a molecule smaller than the molecular weight cut-off of the pores can enter the ligand-activated core, and/or
     - (iii) size exclusion chromatography;
   - to obtain a final virus preparation (c) comprising the infectious virus particles, less than 100 ng/mL residual host cell DNA, less than 1 μg/mL residual host cell protein, and less than 1 μg/mL residual aggregates of virus particles are selected from the group consisting of filovirus particles of a flavivirus or alphavirus particles of a alphavirus but;

wherein the virus particles are not of a Japanese encephalitis virus.

2. The method according to claim 1, wherein the final virus preparation (c) comprises less than 10 ng/mL residual host cell DNA and less than 100 ng/mL residual host cell protein.

3. The method according to claim 1, wherein said crude harvest (a) is subjected to one or more pre-purification step(s) prior to step (B), wherein the one or more pre-purification step(s) comprise a) filtration using a filter having a pore size equal to or less than 0.2 μm; and/or b) digestion of host cell genomic DNA by enzymatic treatment; and/or c) ultra/diafiltration using a hollow fiber membrane having a pore size equal to or greater than 100 kDa.

4. The method according to claim 1, wherein the concentration of protamine is between 0.5 mg/ml and 3 mg/ml.

5. The method according to claim 1, wherein the infectious virus particles in said final virus preparation (c) are enriched by at least 50% to 95% relative to total virus particles in said crude harvest (a).

6. The method according to claim 1, wherein said virus preparation (c) comprises less than 10% impurities.

7. The method according to claim 1, wherein said infectious virus particles are propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, an MDSK cell line, a chicken embryonic fibroblast cell line, a duck cell line, and a diploid avian cell line.

8. The method according to claim 1, wherein said infectious virus particles are selected from the group consisting of a live virus, an attenuated live virus, a chimeric virus, a modified live virus and a recombinant live virus.

9. The method according to claim 8, wherein said infectious virus particles are selected from the group of viruses consisting of Zika virus, Chikungunya virus, yellow fever virus, and Dengue virus.

10. The method according to claim 1, further comprising a step (D) comprising inactivating the final virus preparation (c).

11. The method according to claim 9, wherein said Chikungunya virus is an attenuated Chikungunya virus comprising a deletion mutation in the non-structural protein 3 provided by SEQ ID NO: 77 or an immunogenic variant thereof, wherein said immunogenic variant is defined as having at least 80% sequence identity to SEQ ID NO: 77.

12. The method according to claim 1, wherein said protamine is selected from the group comprising a protamine salt, a protamine sulphate and a recombinant protamine sulphate.

13. The method according to claim 10, wherein said inactivating step (D) is performed using formaldehyde.

14. The method according to claim 1, wherein said infectious virus particles are selected from the group consisting of flaviviruses and flaviviruses but not Japanese encephalitis virus.

* * * * *

UNITED STATES PATENT AND TRADEMARK OFFICE
CERTIFICATE OF CORRECTION

PATENT NO. : 10,660,950 B2
APPLICATION NO. : 15/781959
DATED : May 26, 2020
INVENTOR(S) : Jana Barbero Calzado et al.

It is certified that error appears in the above-identified patent and that said Letters Patent is hereby corrected as shown below:

In the Claims

At Column 551, Line 14, Claim 1 should read:
1. A method for purifying infectious virus particles, comprising the steps of
(A) providing a crude harvest (a) comprising infectious virus particles, non-infectious virus particles, and impurities, wherein the impurities are generated from growing said virus particles on a cell substrate;
(B) contacting said crude harvest (a) with an agent comprising protamine to obtain a virus preparation (b) comprising infectious virus particles; and
(C) further purifying said virus preparation (b) by one or more size exclusion methods wherein said one or more size exclusion methods comprise
(i) sucrose density gradient centrifugation, and/or
(ii) a solid-phase matrix packed in a column comprising a ligand-activated core and an inactive shell comprising pores, wherein the pores comprise a molecular weight cut-off that excludes the virus particles from entering the ligand-activated core, and wherein a molecule smaller than the molecular weight cut-off of the pores can enter the ligand-activated core, and/or
(iii) size exclusion chromatography;
to obtain a final virus preparation (c) comprising the infectious virus particles, less than 100 ng/mL residual host cell DNA, less than 1 μg/mL residual host cell protein, and less than 1 μg/mL residual aggregates of virus particles are selected from the group consisting of particles of a flavivirus or particles of an alphavirus but;
wherein the virus particles are not of a Japanese encephalitis virus.

At Column 552, Line 53, Claim 14 should read:
14. The method according to claim 1, wherein said infectious virus particles are selected from the group consisting of alphaviruses and flaviviruses but not Japanese encephalitis virus.

Signed and Sealed this
Twentieth Day of September, 2022

*Katherine Kelly Vidal*
Katherine Kelly Vidal
*Director of the United States Patent and Trademark Office*

SEQUENCE LISTING

<160> NUMBER OF SEQ ID NOS: 123

<210> SEQ ID NO 1
<211> LENGTH: 32
<212> TYPE: PRT
<213> ORGANISM: Artificial Sequence
<220> FEATURE:
<223> OTHER INFORMATION: synthetic peptide

<400> SEQUENCE: 1

```
Pro Arg Arg Arg Arg Ser Ser Ser Arg Pro Val Arg Arg Arg Arg Arg
1               5                   10                  15

Pro Arg Val Ser Arg Arg Arg Arg Arg Arg Gly Gly Arg Arg Arg Arg
            20                  25                  30
```

<210> SEQ ID NO 2
<211> LENGTH: 10676
<212> TYPE: DNA
<213> ORGANISM: Zika virus

<400> SEQUENCE: 2

```
gttgttactg ttgctgactc agactgcgac agttcgagtt tgaagcgaaa gctagcaaca      60
gtatcaacag gttttatttg gatttggaaa cgagagtttc tggtcatgaa aaacccaaaa     120
aagaaatccg gaggattccg gattgtcaat atgctaaaac gcggagtagc ccgtgtgagc     180
ccctttgggg gcttgaagag gctgccagcc ggacttctgc tgggtcatgg gcccatcagg     240
atggtcttgg caattctagc ctttttgaga ttcacggcaa tcaagccatc actgggtctc     300
atcaatagat ggggttcagt ggggaaaaaa gaggctatgg aaataataaa gaagttcaag     360
aaagatctgg ctgccatgct gagaataatc aatgctagga aggagaagaa gagacggggc     420
gcagatacta gtgtcggaat tgttggcctc ctgctgacca cagctatggc agcggaggtc     480
actagacgtg ggagtgcata ctatatgtac ttggacagaa acgatgctgg ggaggccata     540
tcttttccaa ccacattggg gatgaataag tgttatatac agatcatgga tcttggacac     600
atgtgtgatg ccaccatgag ctatgaatgc cctatgctgg atgagggggt ggaaccagat     660
gacgtcgatt gttggtgcaa cacgacgtca acttgggttg tgtacggaac ctgccatcac     720
aaaaaaggtg aagcacggag atctagaaga gctgtgacgc tcccctccca ttccactagg     780
aagctgcaaa cgcggtcgca aacctggttg gaatcaagag aatacacaaa gcacttgatt     840
agagtcgaaa attggatatt caggaaccct ggcttcgcgt tagcagcagc tgccatcgct     900
tggcttttgg gaagctcaac gagccaaaaa gtcatatact tggtcatgat actgctgatt     960
gccccggcat acagcatcag gtgcatagga gtcagcaata gggactttgt ggaaggtatg    1020
tcaggtggga cttgggttga tattgtcttg gaacatggag gttgtgtcac cgtaatggca    1080
caggacaaac cgactgtcga catagagctg gttacaacaa cagtcagcaa catggcggag    1140
gtaagatcct actgctatga ggcatcaata tcagacatgg cttcggacag ccgctgccca    1200
acacaaggtg aagcctacct tgacaagcaa tcagacactc aatatgtctg caaaagaacg    1260
ttagtggaca gaggctgggg aaatggatgt ggactttttg gcaaagggag tctggtgaca    1320
tgcgctaagt ttgcatgctc caagaaaatg accgggaaga gcatccagcc agagaatctg    1380
gagtaccgga taatgctgtc agttcatggc tcccagcaca gtgggatgat cgttaatgac    1440
acaggacatg aaactgatga gaatagagcg aaggttgaga taacgcccaa ttcaccaaga    1500
gccgaagcca ccctgggggg ttttggaagc ctaggacttg attgtgaacc gaggacaggc    1560
cttgactttt cagatttgta ttacttgact atgaataaca agcactggtt ggttcacaag    1620
```

```
gagtggttcc acgacattcc attaccttgg cacgctgggg cagacaccgg aactccacac    1680
tggaacaaca aagaagcact ggtagagttc aaggacgcac atgccaaaag gcaaactgtc    1740
gtggttctag ggagtcaaga aggagcagtt cacacggccc ttgctggagc tctggaggct    1800
gagatggatg gtgcaaaggg aaggctgtcc tctggccact tgaaatgtcg cctgaaaatg    1860
gataaactta gattgaaggg cgtgtcatac tccttgtgta ccgcagcgtt cacattcacc    1920
aagatcccgg ctgaaacact gcacgggaca gtcacagtgg aggtacagta cgcagggaca    1980
gatggacctt gcaaggttcc agctcagatg gcggtggaca tgcaaactct gaccccagtt    2040
gggaggttga taaccgctaa ccccgtaatc actgaaagca ctgagaactc taagatgatg    2100
ctggaacttg atccaccatt tggggactct tacattgtca taggagtcgg ggagaagaag    2160
atcacccacc actggcacag gagtggcagc accattggaa aagcatttga agccactgtg    2220
agaggtgcca agagaatggc agtcttggga gacacagcct gggactttgg atcagttgga    2280
ggcgctctca actcattggg caagggcatc catcaaattt ttggagcagc tttcaaatca    2340
ttgtttggag gaatgtcctg gttctcacaa attctcattg gaacgttgct gatgtggttg    2400
ggtctgaaca caaagaatgg atctatttcc cttatgtgct tggccttagg gggagtgttg    2460
atcttcttat ccacagccgt ctctgctgat gtggggtgct cggtggactt ctcaaagaag    2520
gagacgagat gcgtacagg ggtgttcgtc tataacgacg ttgaagcctg gagggacagg    2580
tacaagtacc atcctgactc ccccgtaga ttggcagcag cagtcaagca agcctgggaa    2640
gatggtatct gcgggatctc ctctgtttca agaatggaaa acatcatgtg gagatcagta    2700
gaagggagc tcaacgcaat cctggaagag aatggagttc aactgacggt cgttgtggga    2760
tctgtaaaaa accccatgtg gagaggtcca cagagattgc ccgtgcctgt gaacgagctg    2820
ccccacggct ggaaggcttg ggggaaatcg cacttcgtca gagcagcaaa gacaaataac    2880
agctttgtcg tggatggtga cacactgaag gaatgcccac tcaaacatag agcatggaac    2940
agctttcttg tggaggatca tgggttcggg gtatttcaca ctagtgtctg gctcaaggtt    3000
agagaagatt attcattaga gtgtgatcca gccgttattg gaacagctgt taagggaaag    3060
gaggctgtac acagtgatct aggctactgg attgagagtg agaagaatga cacatggagg    3120
ctgaagaggg cccatctgat cgagatgaaa acatgtgaat ggccaaagtc ccacacattg    3180
tggacagatg gaatagaaga gagtgatctg atcataccca gtctttagc tgggccactc    3240
agccatcaca ataccagaga gggctacagg acccaaatga aagggccatg gcacagtgaa    3300
gagcttgaaa ttcggtttga ggaatgccca ggcactaagg tccacgtgga ggaaacatgt    3360
ggaacaagag gaccatctct gagatcaacc actgcaagcg gaagggtgat cgaggaatgg    3420
tgctgcaggg agtgcacaat gccccactg tcgttccggg ctaaagatgg ctgttggtat    3480
ggaatggaga taaggcccag gaaagaacca gaaagcaact tagtaaggtc aatggtgact    3540
gcaggatcaa ctgatcacat ggatcacttc tcccttggag tgcttgtgat tctgctcatg    3600
gtgcaggaag ggctgaagaa gagaatgacc acaaagatca tcataagcac atcaatggca    3660
gtgctggtag ctatgatcct gggaggattt tcaatgagtg acctggctaa gcttgcaatt    3720
ttgatgggtg ccaccttcgc ggaaatgaac actggaggag atgtagctca tctgcgctct    3780
atagcggcat tcaaagtcag accagcgttg ctggtatctt tcatcttcag agctaattgg    3840
acaccccgtg aaagcatgct gctggccttg gcctcgtgtc ttttgcaaac tgcgatctcc    3900
gccttggaag gcgacctgat ggttctcatc aatggttttg ctttggcctg gttggcaata    3960
```

```
cgagcgatgg ttgttccacg cactgataac atcaccttgg caatcctggc tgctctgaca      4020
ccactggccc ggggcacact gcttgtggcg tggagagcag gccttgctac ttgcggggggg     4080 tttatgctcc tctctctgaa gggaaaaggc agtgtgaaga agaacttacc atttgtcatg      4140
gccctgggac taaccgctgt gaggctggtc gacccccatca acgtggtggg gctgctgttg    4200
ctcacaagga gtgggaagcg gagctggccc cctagcgaag tactcacagc tgttggcctg     4260
atatgcgcat tggctggagg gttcgccaag gcagatatag agatggctgg gcccatggcc     4320
gcggtcggtc tgctaattgt cagttacgtg gtctcaggaa agagtgtgga catgtacatt     4380
gaaagagcag gtgacatcac atgggaaaaa gatgcggaag tcactggaaa cagtccccgg    4440
ctcgatgtgg cgctagatga gagtggtgat ttctccctgg tggaggatga cggtcccccc    4500
atgagagaga tcatactcaa ggtggtcctg atgaccatct gtggcatgaa cccaatagcc    4560
ataccctttg cagctggagc gtggtacgta tacgtgaaga ctggaaaaag gagtggtgct    4620
ctatgggatg tgcctgctcc caaggaagta aaaaaggggg agaccacaga tggagtgtac    4680
agagtaatga ctcgtagact gctaggttca acacaagttg gagtgggagt tatgcaagag    4740
ggggtctttc acactatgtg gcacgtcaca aaaggatccg cgctgagaag cggtgaaggg    4800
agacttgatc catactgggg agatgtcaag caggatctgg tgtcatactg tggtccatgg    4860
aagctagatg ccgcctggga cgggcacagc gaggtgcagc tcttggccgt gccccccgga    4920
gagagagcga ggaacatcca gactctgccc ggaatattta agacaaagga tggggacatt    4980
ggagcggttg cgctggatta cccagcagga acttcaggat ctccaatcct agacaagtgt    5040
gggagagtga taggacttta tggcaatggg gtcgtgatca aaaatgggag ttatgttagt    5100
gccatcaccc aagggaggag ggaggaagag actcctgttg agtgcttcga gccttcgatg    5160
ctgaagaaga agcagctaac tgtcttagac ttgcatcctg gagctgggaa aaccaggaga    5220
gttcttcctg aaatagtccg tgaagccata aaaacaagac tccgtactgt gatcttagct    5280
ccaaccaggg ttgtcgctgc tgaaatggag gaagccctta gagggcttcc agtgcgttat    5340
atgacaacag cagtcaatgt caccccactct ggaacagaaa tcgtcgactt aatgtgccat   5400
gccaccttca cttcacgtct actacagcca atcagagtcc ccaactataa tctgtatatt    5460
atggatgagg cccacttcac agatccctca gtatagcag caagaggata catttcaaca    5520
agggttgaga tggcgaggc ggctgccatc ttcatgaccg ccacgccacc aggaaccccgt    5580 gacgcatttc cggactccaa ctcaccaatt atggacaccg aagtggaagt cccagagaga    5640
gcctggagct caggctttga ttgggtgacg gattattctg gaaaaacagt ttggtttgtt    5700
ccaagcgtga ggaacggcaa tgagatcgca gcttgtctga caaaggctgg aaaacgggtc    5760
atacagctca gcagaaagac ttttgagaca gagttccaga aaacaaaaca tcaagagtgg   5820
gactttgtcg tgacaactga catttcagag atgggcgcca actttaaagc tgaccgtgtc    5880
atagattcca ggagatgcct aaagccggtc atacttgatg cgagagagt cattctggct    5940 ggacccatgc ctgtcacaca tgccagcgct gcccagagga gggggcgcat aggcaggaat    6000
cccaacaaac ctggagatga gtatctgtat ggaggtgggt gcgcagagac tgacgaagac    6060
catgcacact ggcttgaagc aagaatgctc cttgacaata tttacctcca agatggcctc    6120
atagcctcgc tctatcgacc tgaggccgac aaagtagcag ccattgaggg agagttcaag    6180
cttaggacgg agcaaaggaa gacctttgtg gaactcatga aaagaggaga tcttcctgtt    6240
tggctggcct atcaggttgc atctgccgga ataacctaca cagatagaag atggtgcttt    6300
gatggcacga ccaacaacac cataatggaa gacagtgtgc cggcagaggt gtggaccaga    6360
```

```
cacggagaga aaagagtgct caaaccgagg tggatggacg ccagagtttg ttcagatcat    6420
gcggccctga agtcattcaa ggagtttgcc gctgggaaaa gaggagcggc ttttggagtg    6480
atggaagccc tgggaacact gccaggacac atgacagaga gattccagga agccattgac    6540
aacctcgctg tgctcatgcg ggcagagact ggaagcaggc cttacaaagc cgcggcggcc    6600
caattgccgg agaccctaga gaccattatg cttttggggt tgctgggaac agtctcgctg    6660
ggaatctttt tcgtcttgat gaggaacaag ggcataggga agatgggctt tggaatggtg    6720
actcttgggg ccagcgcatg gctcatgtgg ctctcggaaa ttgagccagc cagaattgca    6780
tgtgtcctca ttgttgtgtt cctattgctg gtggtgctca tacctgagcc agaaaagcaa    6840
agatctcccc aggacaacca aatggcaatc atcatcatgg tagcagtagg tcttctgggc    6900
ttgattaccg ccaatgaact cggatggttg agagaacaa agagtgacct aagccatcta    6960
atgggaagga gagaggaggg ggcaaccatg ggattctcaa tggacattga cctgcggcca    7020
gcctcagctt gggccatcta tgctgccttg acaactttca ttaccccagc cgtccaacat    7080
gcagtgacca cttcatacaa caactactcc ttaatggcga tggccacgca agctggagtg    7140
ttgtttggta tgggcaaagg gatgccattc tacgcatggg actttggagt cccgctgcta    7200
atgataggtt gctactcaca attaacgccc ctgaccctaa tagtggccat cattttgctc    7260
gtggcgcact acatgtactt gatcccaggg ctgcaggcag cagctgcgcg tgctgcccag    7320
aagagaacgg cagctggcat catgaagaac cctgttgtgg atggaatagt ggtgactgac    7380
attgacacaa tgacaattga cccccaagtg gagaaaaaga tgggacaggt gctactcatg    7440
gcagtagccg tctccagcgc catactgtcg cggaccgcct gggggtgggg ggaggctggg    7500
gccctgatca cagccgcaac ttccactttg tgggaaggct ctccgaacaa gtactggaac    7560
tcctctacag ccacttcact gtgtaacatt tttagggga gttacttggc tggagcttct    7620
ctaatctaca cagtaacaag aaacgctggc ttggtcaaga cgtgggggg tggaacagga    7680
gagaccctgg gagagaaatg gaaggcccgc ttgaaccaga tgtcggccct ggagttctac    7740
tcctacaaaa agtcaggcat caccgaggtg tgcagagaag aggcccgccg cgccctcaag    7800
gacggtgtgg caacgggagg ccatgctgtg tcccgaggaa gtgcaaagct gagatggttg    7860
gtggagcggg gatacctgca gcccatggga aaggtcattg atcttggatg tggcagaggg    7920
ggctggagtt actacgccgc caccatccgc aaagttcaag aagtgaaagg atacacaaaa    7980
ggaggccctg gtcatgaaga acccgtgttg gtgcaaagct atgggtggaa catagtccgt    8040
cttaagagtg gggtggacgt ctttcatatg gcggctgagc gtgtgacac gttgctgtgt    8100
gacataggtg agtcatcatc tagtcctgaa gtggaagaag cacggacgct cagagtcctc    8160
tccatggtgg gggattggct tgaaaaaaga ccaggagcct tttgtataaa agtgttgtgc    8220
ccatacacca gcactatgat ggaaaccctg agcgactgc agcgtaggta tggggagga    8280
ctggtcagag tgccactctc ccgcaactct acacatgaga tgtactgggt ctctggagcg    8340
aaaagcaaca ccataaaaag tgtgtccacc acgagccagc tcctcttggg gcgcatggac    8400
gggcctagga ggccagtgaa atatgaggag gatgtgaatc tcggctctgg cacgcgggct    8460
gtggtaagct gcgctgaagc tcccaacatg aagatcattg gtaaccgcat tgaaaggatc    8520
cgcagtgagc acgcggaaac gtggttcttt gacgagaacc acccatatag gacatgggct    8580
taccatggaa gctatgaggc ccccacacaa gggtcagcgt cctctctaat aaacgggggtt    8640
gtcaggctcc tgtcaaaacc ctgggatgtg gtgactggag tcacaggaat agccatgacc    8700
```

| | |
|---|---|
| gacaccacac cgtatggtca gcaaagagtt ttcaaggaaa agtggacac tagggtgcca | 8760 |
| gacccccaag aaggtactcg tcaggttatg agcatggtct cttcctggtt gtggaaagag | 8820 |
| ctaggcaaac acaaacggcc acgagtctgt accaaagaag agttcatcaa caaggttcgt | 8880 |
| agcaatgcag cattagggc aatatttgaa gaggaaaaag agtggaagac tgcagtggaa | 8940 |
| gctgtgaacg atccaaggtt ctgggctcta gtggacaagg aaagagagca ccacctgaga | 9000 |
| ggagagtgcc agagttgtgt gtacaacatg atggggaaaa gagaaaagaa acaaggggaa | 9060 |
| tttggaaagg ccaagggcag ccgcgccatc tggtatatgt ggctaggggc tagatttcta | 9120 |
| gagttcgaag cccttggatt cttgaacgag atcactgga tggggagaga gaactcagga | 9180 |
| ggtggtgttg aagggctggg attacaaaga ctcggatatg tcctagaaga gatgagtcgc | 9240 |
| ataccaggag aaggatgta tgcagatgac actgctggct gggacacccg catcagcagg | 9300 |
| tttgatctgg agaatgaagc tctaatcacc aaccaaatgg agaaagggca cagggccttg | 9360 |
| gcattggcca taatcaagta cacataccaa aacaaagtgg taaaggtcct tagaccagct | 9420 |
| gaaaaaggga aaacagttat ggacattatt tcgagacaag accaaggggg agcggacaa | 9480 |
| gttgtcactt acgctcttaa cacatttacc aacctagtgg tgcaactcat tcggaatatg | 9540 |
| gaggctgagg aagtcctaga gatgcaagac ttgtggctgc tgcggaggtc agagaaagtg | 9600 |
| accaactggt tgcagagcaa cggatgggat aggctcaaac gaatggcagt cagtggagat | 9660 |
| gattgcgttg tgaagccaat tgatgatagg tttgcacatg ccctcaggtt cttgaatgat | 9720 |
| atgggaaaag ttaggaagga cacacaagag tggaaaccct caactggatg ggacaactgg | 9780 |
| gaagaagttc cgttttgctc ccaccacttc aacaagctcc atctcaagga cgggaggtcc | 9840 |
| attgtggttc cctgccgcca ccaagatgaa ctgattggcc gggcccgcgt ctctccaggg | 9900 |
| gcgggatgga gcatccggga gactgcttgc ctagcaaaat catatgcgca aatgtggcag | 9960 |
| ctcctttatt tccacagaag ggacctccga ctgatggcca atgccatttg ttcatctgtg | 10020 |
| ccagttgact gggttccaac tgggagaact acctggtcaa tccatggaaa gggagaatgg | 10080 |
| atgaccactg aagacatgct tgtggtgtgg aacagagtgt ggattgagga gaacgaccac | 10140 |
| atggaagaca gaccccagt tacgaaatgg acagacattc cctatttggg aaaaagggaa | 10200 |
| gacttgtggt gtggatctct catagggcac agaccgcgca ccacctgggc tgagaacatt | 10260 |
| aaaaacacag tcaacatggt gcgcaggatc ataggtgatg aagaaaagta catgactac | 10320 |
| ctatccaccc aagttcgcta cttgggtgaa gaagggtcta cacctggagt gctgtaagca | 10380 |
| ccaatcttaa tgttgtcagg cctgctagtc agccacagct tggggaaagc tgtgcagcct | 10440 |
| gtgacccccc caggagaagc tgggaaacca agcctatagt caggccgaga acgccatggc | 10500 |
| acggaagaag ccatgctgcc tgtgagcccc tcagaggaca ctgagtcaaa aaaccccacg | 10560 |
| cgcttggagg cgcaggatgg gaaaagaagg tggcgacctt ccccaccctt caatctgggg | 10620 |
| cctgaactgg agatcagctg tggatctcca gaagagggac tagtggttag aggaga | 10676 |

<210> SEQ ID NO 3
<211> LENGTH: 10793
<212> TYPE: DNA
<213> ORGANISM: Zika virus

<400> SEQUENCE: 3

| | |
|---|---|
| ccaatctgtg aatcagactg cgacagttcg agtttgaagc gaaagctagc aacagtatca | 60 |
| acaggtttta ttttggattt ggaaacgaga gtttctggtc atgaaaaacc caaaaagaa | 120 |
| atccggagga ttccggattg tcaatatgct aaaacgcgga gtagcccgtg tgagcccctt | 180 |

```
tgggggcttg aagaggctgc cagccggact tctgctgggt catgggccca tcaggatggt        240
cttggcgatt ctagccttt  tgagattcac ggcaatcaag ccatcactgg gtctcatcaa        300
tagatggggt tcagtgggga aaaagaggc  tatggaaata taaagaagt  tcaagaaaga        360 tctggctgcc atgctgagaa taatcaatgc caggaaggaa agaagagac  gaggcgcaga        420 tactagtgtc ggaatcgttg gcctcctgct gaccacagct atggcagcgg aggtcactag        480
acgtgggagt gcatactata tgtacttgga cagaaacgat gctggggagg ccatatcttt        540
tccaaccaca ttggggatga ataagtgtta tatacagatc atggatcttg gacacatgtg        600
tgatgccacc atgagctatg aatgccctat gctggatgag ggggtggaac cagatgacgt        660
cgattgttgg tgcaacacga cgtcaacttg ggttgtgtac ggaacctgcc atcacaaaaa        720
aggtgaagca cggagatcta aagagctgt  gacgctcccc tcccattcca ctaggaagct        780
gcaaacgcgg tcgcaaacct ggttggaatc aagagaatac acaaagcact tgattagagt        840
cgaaaattgg atattcagga accctggctt cgcgttagca gcagctgcca tcgcttggct        900
tttgggaagc tcaacgagcc aaaaagtcat atacttggtc atgatactgc tgattgcccc        960
ggcatacagc atcaggtgca taggagtcag caataggggac tttgtggaag gtatgtcagg       1020
tgggacttgg gttgatgttg tcttggaaca tgggggttgt gtcaccgtaa tggcacagga       1080
caaaccgact gtcgacatag agctggttac aacaacagtc agcaacatgg cggaggtaag       1140
atcctactgc tatgaggcat caatatcaga catggcttcg acagccgct  gcccaacaca       1200 aggtgaagcc taccttgaca agcaatcaga cactcaatat gtctgcaaaa gaacgttagt       1260
ggacagaggc tggggaaatg gatgtggact ttttggcaaa gggagcctgg tgacatgcgc       1320
taagtttgca tgctccaaga aaatgaccgg gaagagcatc cagccagaga tctggagta        1380 ccggataatg ctgtcagttc atggctccca gcacagtggg atgatcgtta atgacacagg       1440
acatgaaact gatgagaata gagcgaaggt tgagataacg cccaattcac caagagccga       1500
agccaccctg ggggtttttg aagcttagg  acttgattgt gaaccgagga caggccttga       1560
cttttcagat ttgtattact tgactatgaa taacaagcac tggttggttc acaaggagtg       1620
gttccacgac attccattac cttggcacgc tgggcagcac accggaactc cacactggaa       1680
caacaaagaa gcactggtag agttcaagga cgcacatgcc aaaaggcaaa ctgtcgtggt       1740
tctagggact caagaaggag cagttcacac ggcccttgct ggagctctgg aggctgagat       1800
ggatggtgca agggaaggc  tgtcctctgg ccacttgaaa tgtcgcctga aaatggataa       1860
acttagattg aagggcgtgt catactcctt gtgtaccgca gcgttcacat tcaccaagat       1920
cccggctgaa acactgcacg ggacagtcac agtggaggta cagtacgcag ggacagatgg       1980
accttgcaag gttccagctc agatggcggt ggacatgcaa actctgaccc cagttgggag       2040
gttgataacc gctaaccccg taatcactga aagcactgag aactctaaga tgatgctgga       2100
acttgatcca ccatttgggg actcttacat tgtcatagga gtcggggaga agaagatcac       2160
ccaccactgg cacaggagtg gcagcaccat tggaaaagca tttgaagcca ctgtgagagg       2220
tgccaagaga atggcagtct tgggagacac agcctgggac tttggatcag ttggaggcgc       2280
tctcaactca ttgggcaagg gcatccatca aatttttgga gcagctttca atcattgtt        2340 tggaggaatg tcctggttct cacaaattct cattggaacg ttgctgatgt ggttgggtct       2400
gaacacaaag aatggatcta tttcccttat gtgcttggcc ttaggggag  tgttgatctt       2460 cttatccaca gccgtctctg ctgatgtggg gtgctcggtg gacttctcaa agaaggagac       2520
```

-continued

```
gagatgtggt acaggggtgt tcgtctataa cgacgttgaa gcctggaggg acaggtacaa    2580
gtaccatcct gactctcccc gtagattggc agcagcagtc aagcaagcct gggaagatgg    2640
tatctgcggg atctcctctg tttcaagaat ggaaaacatc atgtggagat cagtagaagg    2700
ggagcttaac gcaatcctgg aagagaatgg agttcaactg acggtcgttg tgggatctgt    2760
aaaaaacccc atgtggagag gtccacagag attgcccgtg cctgtgaacg agctgcccca    2820
cggctggaag gcttggggga aatcgtactt cgtcagagca gcaaagacaa ataacagctt    2880
tgtcgtggat ggtgacacac tgaaggaatg cccactcaaa catagagcat ggaacagctt    2940
tcttgtggag gatcatgggt tcggggtatt tcacactagt gtctggctca aggttagaga    3000
agattattca ttagagtgtg atccagccgt tattggaaca gctgttaagg gaaaggaggc    3060
tgtacacagt gatctaggct actggattga gagtgagaag aatgacacat ggaggctgaa    3120
gagggcccat ctgatcgaga tgaaaacatg tgaatggcca aagtcccaca cattgtggac    3180
agatggaata gaagagagtg atctgatcat acccaagtct ttagctgggc cactcagcca    3240
tcacaatacc agagagggct acaggaccca aatgaaaggg ccatggcaca gtgaagagct    3300
tgaaattcgg tttgaggaat gcccaggcac taaggtccac gtggaggaaa catgtggaac    3360
aagaggacca tctctgagat caaccactgc aagcggaagg gtgatcgagg aatggtgctg    3420
cagggagtgc acaatgcccc cactgtcgtt ccgggctaaa gatggctgtt ggtatggaat    3480
ggagataagg cccaggaaag aaccagaaag caacttagta aggtcaatgg tgactgcagg    3540
atcaactgat cacatggatc acttctccct tggagtgctt gtgattctgc tcatggtgca    3600
ggaagggctg aagaagagaa tgaccacaaa gatcatcata agcacatcaa tggcagtgct    3660
ggtagctatg atcctgggag gattttcaat gagtgacctg gctaagcttg caattttgat    3720
gggtgccacc ttcgcggaaa tgaacactgg aggagatgta gctcatctgg cgctgatagc    3780
ggcattcaaa gtcagaccag cgttgctggt atctttcatc ttcagagcta attggacacc    3840
ccgtgaaagc atgctgctgg ccttggcctc gtgttttttg caaactgcga tctccgcctt    3900
ggaaggcgac ctgatggttc tcatcaatgg ttttgctttg gcctggttgg caatacgagc    3960
gatggttgtt ccacgcactg acaacatcac cttggcaatc ctggctgctc tgacaccact    4020
ggcccggggc acactgcttg tggcgtggag agcaggcctt gctacttgcg ggggtttat    4080
gctcctctct ctgaagggaa aaggcagtgt gaagaagaac ttaccatttg tcatggccct    4140
gggactaacc gctgtgaggc tggtcgaccc catcaacgtg gtgggactgc tgttgctcac    4200
aaggagtggg aagcggagct ggcccccctag cgaagtactc acagctgttg gcctgatatg    4260
cgcattggct ggagggttcg ccaaggcaga tatagagatg gctgggccca tggccgcggt    4320
cggtctgcta attgtcagtt acgtggtctc aggaaagagt gtggacatgt acattgaaag    4380
agcaggtgac atcacatggg aaaaagatgc ggaagtcact ggaaacagtc cccggctcga    4440
tgtggcgcta gatgagagtg gtgacttctc cctggtggag gatgacggtc cccccatgag    4500
agagatcata ctcaaggtgg tcctgatgac catctgtggc atgaacccaa tagccatacc    4560
ctttgcagct ggagcgtggt acgtatacgt gaagactgga aaaaggagtg gtgctctatg    4620
ggatgtgcct gctcccaagg aagtaaaaaa ggggagacc acagatggag tgtacagagt    4680
aatgactcgt agactgctag gttcaacaca agttggagtg ggagttatgc aagagggggt    4740
ctttcacact atgtggcacg tcacaaaagg atccgcgctg agaagcggtg aagggagact    4800
tgatccatac tggggagatg tcaagcagga tctggtgtca tactgtggtc catggaagct    4860
agatgccgcc tgggacgggc acagcgaggt gcagctcttg gccgtgcccc ccggagagag    4920
```

```
agcgaggaac atccagactc tgcccggaat atttaagaca aaggatgggg acattggagc   4980
ggttgcgctg gattacccag caggaacttc aggatctcca atcctagaca agtgtgggag   5040
agtgatagga cttatggca atggggtcgt gataaaaaat gggagttatg ttagtgccat    5100
cacccaaggg aggagggagg aagagactcc tgttgagtgc ttcgagcctt cgatgctgaa   5160
gaagaagcag ctaactgtct tagacttgca tcctggagct gggaaaacca ggagagttct   5220
tcctgaaata gtccgtgaag ccataaaaac aagactccgt actgtgatct tagctccaac   5280
cagggttgtc gctgctgaaa tggaggaagc ccttagaggg cttccagtgc gttatatgac   5340
aacagcagtc aatgtcaccc actctggaac agaaatcgtc gacttaatgt gccatgccac   5400
cttcacttca cgtctactac agccaatcag agtccccaac tataatctgt atattatgga   5460
tgaggcccac ttcacagatc cctcaagcat agcagcaaga ggatacattt caacaagggt   5520
tgagatgggc gaggcggctg ccatcttcat gaccgccacg ccaccaggaa cccgtgacgc   5580
atttccggac tccaactcac caattatgga caccgaagtg gaagtcccag agagagcctg   5640
gagctcaggc tttgattggg tgacggatca ttctggaaaa acagtttggt ttgttccaag   5700
cgtgaggaac ggcaatgaga tcgcagcttg tctgacaaag gctggaaaac gggtcataca   5760
gctcagcaga aagactttg acagagtt ccagaaaaca aaacatcaag agtgggactt      5820
tgtcgtgaca actgacattt cagagatggg cgccaacttt aaagctgacc gtgtcataga   5880
ttccaggaga tgcctaaagc cggtcatact tgatggcgag agagtcattc tggctggacc   5940
catgcctgtc acacatgcca gcgctgccca gaggaggggg cgcataggca ggaatcccaa   6000
caaacctgga gatgagtacc tgtatggagg tgggtgcgca gagactgacg aagaccatgc   6060
acactggctt gaagcaagaa tgctccttga caatatttac ctccaagatg gcctcatagc   6120
ctcgctctat cgacctgagg ccgacaaagt agcagccatt gagggagagt tcaagcttag   6180
gacggagcaa aggaagacct tgtggaact catgaaaaga ggagatcttc ctgtttggct    6240
ggcctatcag gttgcatctg ccggaataac ctacacagat agaagatggt gctttgatgg   6300
cacgaccaac aacaccataa tggaagacag tgtgccggca gaggtgtgga ccagacacgg   6360
agagaaaaga gtgctcaaac cgaggtggat ggacgccaga gtttgttcag atcatgcggc   6420
cctgaagtca ttcaaggagt ttgccgctgg gaaaagagga gcggcttttg gagtgatgga   6480
agccctggga acactgccag acacatgac agagagattc caggaagcca ttgacaacct   6540
cgctgtgctc atgcgggcag agactggaag caggccttac aaagccgcgg cggcccaatt   6600
gccggagacc ctagagacca ttatgctttt ggggttgctg ggaacagtct cgctgggaat   6660
ctttttcgtc ttgatgagga caagggcat agggaagatg ggctttggaa tggtgactct   6720
tggggccagc gcatggctca tgtggctctc ggaaattgag ccagccagaa ttgcatgtgt   6780
cctcattgtt gtgttcctat tgctggtggt gctcataccct gagccagaaa agcaaagatc   6840
tccccaggac aaccaaatgg caatcatcat catggtagca gtaggtcttc tgggcttgat   6900
taccgccaat gaactcggat ggttggagag aacaaagagt gacctaagcc atctaatggg   6960
aaggagagag gagggggcaa ccataggat ctcaatggac attgacctgc ggccagcctc   7020
agcttgggcc atctatgctg ccttgacaac tttcattacc ccagccgtcc aacatgcagt   7080
gaccacttca tacaacaact actccttaat ggcgatggcc acgcaagctg gagtgttgtt   7140
tggtatgggg aaagggatgc cattctacgc atgggacttt ggagtcccgc tgctaatgat   7200
aggttgctac tcacaattaa cacccctgac cctaatagtg gccatcattt tgctcgtggc   7260
```

```
gcactacatg tacttgatcc cagggctgca ggcagcagct gcgcgtgctg cccagaagag   7320
aacggcagct ggcatcatga agaaccctgt tgtggatgga atagtggtga ctgacattga   7380
cacaatgaca attgaccccc aagtggagaa aaagatggga caggtgctac tcatagcagt   7440
agccgtctcc agcgccatac tgtcgcggac cgcctggggg tgggggagg ctggggccct    7500 gatcacagcc gcaacttcca ctttgtggga aggctctccg aacaagtact ggaactcctc   7560
tacagccact tcactgtgta acattttag gggaagttac ttggctggag cttctctaat    7620
ctacacagta acaagaaacg ctggcttggt caagagacgt gggggtggaa caggagagac   7680
cctgggagag aaatggaagg cccgcttgaa ccagatgtcg gccctggagt tctactccta   7740
caaaaagtca ggcatcaccg aggtgtgcag agaagaggcc cgccgcgccc tcaaggacgg   7800
tgtggcaacg ggaggccatg ctgtgtcccg aggaagtgca aagctgagat ggttggtgga   7860
gcggggatac ctgcagccct atggaaaggt cattgatctt ggatgtggca gagggggctg   7920
gagttactac gccgccacca tccgcaaagt tcaagaagtg aaaggataca caaaaggagg   7980
ccctggtcat gaagaacccg tgttggtgca aagctatggg tggaacatag tccgtcttaa   8040 gagtgggtg gacgtctttc atatggcggc tgagccgtgt gacacgttgc tgtgtgacat    8100
aggtgagtca tcatctagtc ctgaagtgga agaagcacgg acgctcagag tcctctccat   8160
ggtgggggat tggcttgaaa aaagaccagg agccttttgc ataaaagtgt tgtgcccata   8220
caccagcact atgatggaaa ccctggagcg actgcagcgt aggtatgggg aggactggt   8280 cagagtgcca ctctcccgca actctacaca tgagatgtac tgggtctctg gagcgaaaag   8340
caacaccata aaaagtgtgt ccaccacgag ccagctcctc ttggggcgca tggacgggcc   8400
taggaggcca gtgaaatatg aggaggatgt gaatctcggc tctggcacgc gggctgtggt   8460
aagctgcgct gaagctccca acatgaagat cattggtaac cgcattgaaa ggatccgcag   8520
tgagcacgcg gaaacgtggt tctttgacga aaaccaccca tataggacat gggcttacca   8580
tggaagctat gtgccccca cacaagggtc agcgtcctct ctaataaacg gggttgtcag    8640
gctcctgtca aaaccctggg atgtggtgac tggagtcaca ggaatagcca tgaccgacac   8700
cacaccgtat ggtcagcaaa gagttttcaa ggaaaaagtg gacactaggg tgccagaccc   8760
ccaagaaggc actcgtcagg ttatgagcat ggtctcttcc tggttgtgga aagagctagg   8820
caaacacaaa cgaccacgag tctgtaccaa agaaagttc atcaacaagg ttcgtagcaa    8880
tgcagcatta ggggcaatat ttgaagagga aaaagagtgg aagactgcag tggaagctgt   8940
gaacgatcca aggttctggg ctctagtgga caaggaaaga gagcaccacc tgagaggaga   9000
gtgccagagt tgtgtgtaca acatgatggg aaaaagagaa aagaaacaag gggaatttgg   9060
aaaggccaag ggcagccgcg ccatctggta tatgtggcta ggggctagat ttctagagtt   9120
cgaagccctt ggattcttga cgaggatca ctggatgggg agagagaact caggaggtgg    9180
tgttgaaggg ctgggattac aaagactcgg atatgtccta aagagatga gtcgcatacc    9240 aggaggaagg atgtatgcag atgacactgc tggctggac acccgcatca gcaggtttga    9300
tctggagaat gaagctctaa tcaccaacca aatggagaaa gggcacaggg ccttggcatt   9360
ggccataatc aagtacacat accaaaacaa agtggtaaag gtccttagac agctgaaaa    9420 agggaaaaca gttatggaca ttatttcgag acaagaccaa aggggggagcg acaagttgt    9480 cacttacgct cttaacacat ttaccaacct agtggtgcaa ctcattcgga atatggaggc   9540
tgaggaagtt ctagagatgc aagacttgtg gctgctgcgg aggtcagaga agtgaccaa    9600 ctggttgcag agcaacggat gggataggct caaacgaatg gcagtcagtg gagatgattg   9660
```

| | | | |
|---|---|---|---|
| cgttgtgaag ccaattgatg ataggtttgc acatgccctc aggttcttga atgatatggg | 9720 |
| aaaagttagg aaggacacac aagagtggaa accctcaact ggatgggaca actgggaaga | 9780 |
| agttccgttt tgctcccacc acttcaacaa gctccatctc aaggacggga ggtccattgt | 9840 |
| ggttccctgc cgccaccaag atgaactgat tggccgggcc cgcgtctctc caggggcggg | 9900 |
| atggagcatc cgggagactg cttgcctagc aaaatcatat gcgcaaatgt ggcagctcct | 9960 |
| ttatttccac agaagggacc tccgactgat ggccaatgcc atttgttcat ctgtgccagt | 10020 |
| tgactgggtt ccaactggga gaactacctg gtcaatccat ggaaagggag aatggatgac | 10080 |
| cactgaagac atgcttgtgg tgtggaacag agtgtggatt gaggagaacg accacatgga | 10140 |
| agacaagacc ccagttacga aatggacaga cattccctat ttgggaaaaa gggaagactt | 10200 |
| gtggtgtgga tctctcatag ggcacagacc gcgcaccacc tgggctgaga acattaaaaa | 10260 |
| tacagtcaac atggtgcgca ggatcatagg tgatgaagaa aagtacatgg actacctatc | 10320 |
| cacccaagtt cgctacttgg gtgaagaagg gtctacacct ggagtgctgt gagcaccaat | 10380 |
| cttaatgttg tcaggcctgc tagtcagcca cagcttgggg aaagctgtgc agcctgtgac | 10440 |
| ccctccagga gaagctgggt aaccaagcct atagtcaggc cgagaacgcc atggcacgga | 10500 |
| agaagccatg ctgcctgtga gcccctcaga ggacactgag tcaaaaaacc ccacgcgctt | 10560 |
| ggaggcgcag gatgggaaaa gaaggtggcg accttcccca cccttcaatc tggggcctga | 10620 |
| actggagatc agctgtggat ctccagaaga gggactagtg gttagaggag accccccgga | 10680 |
| aaacgcaaaa cagcatattg acgctgggaa agaccagaga ctccatgagt ttccaccacg | 10740 |
| ctggccgcca ggcacagatc gccgaatagc ggcggccggt gtgggaaat cca | 10793 |

<210> SEQ ID NO 4
<211> LENGTH: 10675
<212> TYPE: DNA
<213> ORGANISM: Zika virus

<400> SEQUENCE: 4

| | | |
|---|---|---|
| gttgttgatc tgtgtgaatc agactgcgac agttcgagtt tgaagcgaaa gctagcaaca | 60 |
| gtatcaacag gttttatttt ggatttggaa acgagagttt ctggtcatga aaaacccaaa | 120 |
| aaagaaatcc ggaggattcc ggattgtcaa tatgctaaaa cgcggagtag cccgtgtgag | 180 |
| ccccttggg ggcttgaaga ggctgccagc cggacttctg ctgggtcatg gcccatcag | 240 |
| gatggtcttg gcgattctag ccttttttgag attcacggca atcaagccat cactgggtct | 300 |
| catcaataga tggggttcag tggggaaaaa agaggctatg gaaacaataa agaagttcaa | 360 |
| gaaagatctg gctgccatgc tgagaataat caatgctagg aaggagaaga gagacgagg | 420 |
| cgcagatact agtgtcggaa ttgttggcct cctgctgacc acagctatgg cagcggaggt | 480 |
| cactagacgt gggagtgcat actatatgta cttggacaga aacgatgctg gggaggccat | 540 |
| atcttttcca accacattgg ggatgaataa gtgttatata cagatcatgg atcttgaca | 600 |
| catgtgtgat gccaccatga gctatgaatg ccctatgctg gatgaggggg tggaaccaga | 660 |
| tgacgtcgat tgttggtgca acacgacgtc aacttgggtt gtgtacggaa cctgccatca | 720 |
| caaaaaggt gaagcacgga gatctagaag agctgtgacg ctcccctccc attccaccag | 780 |
| gaagctgcaa acgcggtcgc aaacctggtt ggaatcaaga gaatacacaa agcacttgat | 840 |
| tagagtcgaa aattggatat tcaggaaccc tggcttcgcg ttagcagcag ctgccatcgc | 900 |
| ttggcttttg ggaagctcaa cgagccaaaa agtcatatac ttggtcatga tactgctgat | 960 |

-continued

```
tgccccggca tacagcatca ggtgcatagg agtcagcaat agggactttg tggaaggtat  1020
gtcaggtggg acttgggttg atgttgtctt ggaacatgga ggttgtgtca ccgtaatggc  1080
acaggacaaa ccgactgtcg acatagagct ggttacaaca acagtcagca acatggcgga  1140
ggtaagatcc tactgctatg aggcatcaat atcagacatg gcttctgaca gccgctgccc  1200
aacacaaggt gaagcctacc ttgacaagca atcagacact caatatgtct gcaaaagaac  1260
gttagtggac agaggctggg gaaatggatg tggactttt ggcaaaggga gcctggtgac  1320
atgcgctaag tttgcatgct ccaagaaaat gaccgggaag agcatccagc cagagaatct  1380
ggagtaccgg ataatgctgt cagttcatgg ctcccagcac agtgggatga tcgttaatga  1440
cacaggacat gaaactgatg agaatagagc gaaagttgag ataacgccca attcaccgag  1500
agccgaagcc accctggggg gttttggaag cctaggactt gattgtgaac cgaggacagg  1560
ccttgacttt tcagatttgt attacttgac tatgaataac aagcactggt tggttcacaa  1620
ggagtggttc cacgacattc cattaccttg gcacgctggg gcagacaccg gaactccaca  1680
ctggaacaac aaagaagcac tggtagagtt caaggacgca catgccaaaa ggcaaactgt  1740
cgtggttcta gggagtcaag aaggagcagt tcacacggcc cttgctggag ctctggaggc  1800
tgagatggat ggtgcaaagg gaaggctgtc ctctggccac ttgaaatgtc gcctgaaaat  1860
ggataaactt agattgaagg gcgtgtcata ctccttgtgt actgcagcgt tcacattcac  1920
caagatcccg gctgaaacac tgcacgggac agtcacagtg gaggtacagt acgcagggac  1980
agatggacct tgcaaggttc cagctcagat ggcggtggac atgcaaactc tgaccccagt  2040
tgggaggttg ataaccgcta accccgtaat cactgaaagc actgagaact ctaagatgat  2100
gctggaactt gatccaccat ttgggactct ttacattgtc ataggagtcg gggagaagaa  2160
gatcacccac cactgcgcac ggagtggcag caccattgga aaagcatttg aagccactgt  2220
gagaggtgcc aagagaatgg cagtcttggg agacacagcc tgggactttg gatcagttgg  2280
aggcgctctc aactcattgg gcaagggcat ccatcaaatt tttggagcag ctttcaaatc  2340
attgtttgga ggaatgtcct ggttctcaca aattctcatt ggaacgttgc tgatgtggtt  2400
gggtctgaac acaaagaatg gatctatttc ccttatgtgc ttggccttag gggagtgtt   2460
gatcttctta tccacagccg tctctgctga tgtggggtgc tcggtggact tctcaaagaa  2520
ggagacgaga tgcggtacag gggtgttcgt ctataacgac gttgaagcct ggagggacag  2580
gtacaagtac catcctgact ccccccgtag attggcagca gcagtcaagc aagcctggga  2640
agatggtatc tgcgggatct cctctgtttc aagaatggaa acatcatgt ggagatcagt  2700
agaaggggag ctcaacgcaa tcctggaaga gaatggagtt caactgacgg tcgttgtggg  2760
atctgtaaaa aaccccatgt ggagaggtcc acagagattg cccgtgcctg tgaacgagct  2820
gccccacggc tggaaggctt gggggaaatc gtatttcgtc agagcagcaa agacaaataa  2880
cagctttgtc gtggatggtg acacactgaa ggaatgccca ctcaaacata gcatggaa   2940
cagctttctt gtggaggatc atgggttcgg ggtatttcac actagtgtct ggctcaaggt  3000
tagagaagat tattcattag agtgtgatcc agccgttatt ggaacagctg ttaagggaaa  3060
ggaggctgta cacagtgatc taggctactg gattgagagt gagaagaatg acacatggag  3120
gctgaagagg gcccatctga tcgagatgaa acatgtgaa tggccaaagt cccacacatt  3180
gtggacagat ggaatagaag agagtgatct gatcataccc aagtctttag ctgggccact  3240
cagccatcac aataccagag agggctacag gacccaaatg aaagggccat ggcacagtga  3300
agagcttgaa attcggtttg aggaatgccc aggcactaag gtccacgtgg aggaaacatg  3360
```

```
tggaacaaga ggaccatctc tgagatcaac cactgcaagc ggaagggtga tcgaggaatg   3420
gtgctgcagg gagtgcacaa tgcccccact gtcgttccgg gctaaagatg gctgttggta   3480
tggaatggag ataaggccca ggaaagaacc agaaagcaac ttagtaaggt caatggtgac   3540
tgcaggatca actgatcaca tggaccactt ctcccttgga gtgcttgtga tcctgctcat   3600
ggtgcaggaa gggctgaaga agagaatgac cacaaagatc atcataagca catcaatggc   3660
agtgctggta gctatgatcc tgggaggatt ttcaatgagt gacctggcta agcttgcaat   3720
tttgatgggt gccaccttcg cggaaatgaa cactggagga gatgtagctc atctggcgct   3780
gatagcggca ttcaaagtca gaccagcgtt gctggtatct ttcatcttca gagctaattg   3840
gacaccccgt gaaagcatgc tgctggcctt ggcctcgtgt cttttgcaaa ctgcgatctc   3900
cgccttggaa ggcgacctga tggttctcat caatggtttt gctttggcct ggttggcaat   3960
acgagcgatg gttgttccac gcactgataa catcaccttg gcaatcctgg ctgctctgac   4020
accactggcc cggggcacac tgcttgtggc gtggagagca ggccttgcta cttgcggggg   4080
gtttatgctc ctctctctga agggaaaagg cagtgtgaag aagaacttac catttgtcat   4140
ggccctggga ctaaccgctg tgaggctggt cgacccatc aacgtggtgg gactgctgtt   4200
gctcacaagg agtgggaagc ggagctggcc ccctagcgaa gtactcacag ctgttggcct   4260
gatatgcgca ttggctggag ggttcgccaa ggcagatata gagatggctg ggcccatggc   4320
cgcggtcggt ctgctaattg tcagttacgt ggtctcagga aagagtgtgg acatgtacat   4380
tgaaagagca ggtgacatca catgggaaaa agatgcggaa gtcactggaa acagtccccg   4440
gctcgatgtg gcgctagatg agagtggtga tttctccctg gtggaggatg acggtccccc   4500
catgagagag atcatactca aggtggtcct gatgaccatc tgtggcatga acccaatagc   4560
catacccttt gcagctggag cgtggtacgt atacgtgaag actggaaaaa ggagtggtgc   4620
tctatgggat gtgcctgctc ccaaggaagt aaaaaagggg gagaccacag atggagtgta   4680
cagagtaatg actcgtagac tgctaggttc aacacaagtt ggagtgggag ttatgcaaga   4740
gggggtcttt cacactatgt ggcacgtcac aaaaggatcc cgcgctgagaa gcggtgaagg   4800 gagacttgat ccatactggg gagatgtcaa gcaggatctg gtgtcatact gtggtccatg   4860
gaagctagat gccgcctggg atgggcacag cgaggtgcag ctcttggccg tgccccccgg   4920
agagagagcg aggaacatcc agactctgcc cggaatattt aagacaaagg atggggacat   4980
tggagcggtt gcgctggatt acccagcagg aacttcagga tctccaatcc tagacaagtg   5040
tgggagagtg ataggacttt atggcaatgg ggtcgtgatc aaaaacggga gttatgttag   5100
tgccatcacc caagggagga gggaggaaga gactcctgtt gagtgcttcg agccctcgat   5160
gctgaagaag aagcagctaa ctgtcttaga cttgcatcct ggagctggga aaaccaggag   5220
agttcttcct gaaatagtcc gtgaagccat aaaaacaaga ctccgtactg tgatcttagc   5280
tccaaccagg gttgtcgctg ctgaaatgga ggaggccctt agagggcttc cagtgcgtta   5340
tatgacaaca gcagtcaatg tcacccactc tggaacagaa atcgtcgact aatgtgccca   5400
tgccaccttc acttcacgtc tactacagcc aatcagagtc cccaactata atctgtatat   5460
tatggatgag gccacttca cagatccctc aagtatagca gcaagaggat acatttcaac   5520
aagggttgag atgggcgagg cggctgccat cttcatgacc gccacgccac caggaacccg   5580
tgacgcattt ccggactcca actcaccaat tatggacacc gaagtggaag tcccagagag   5640
agcctggagc tcaggctttg attgggtgac ggatcattct ggaaaaacag tttggtttgt   5700
```

```
tccaagcgtg aggaacggca atgagatcgc agcttgtctg acaaaggctg gaaaacgggt    5760
catacagctc agcagaaaga cttttgagac agagttccag aaaacaaaac atcaagagtg    5820
ggactttgtc gtgacaactg acatttcaga gatgggcgcc aactttaaag ctgaccgtgt    5880
catagattcc aggagatgcc taaagccggt catacttgat ggcgagagag tcattctggc    5940
tggacccatg cctgtcacac atgccagcgc tgcccagagg aggggcgca taggcaggaa     6000 tcccaacaaa cctggagatg agtatctgta tggaggtggg tgcgcagaga ctgacgaaga    6060
ccatgcacac tggcttgaag caagaatgct ccttgacaat atttacctcc aagatggcct    6120
catagcctcg ctctatcgac ctgaggccga caaagtagca gccattgagg gagagttcaa    6180
gcttaggacg gagcaaagga agacctttgt ggaactcatg aaaagaggag atcttcctgt    6240
ttggctggcc tatcaggttg catctgccgg aataacctac acagatagaa gatggtgctt    6300
tgatggcacg accaacaaca ccataatgga agacagtgtg ccggcagagg tgtggaccag    6360
acacggagag aaaagagtgc tcaaaccgag gtggatggac gccagagttt gttcagatca    6420
tgcggccctg aagtcattca aggagtttgc cgctgggaaa agaggagcgg cttttggagt    6480
gatggaagcc ctgggaacac tgccaggaca catgacagag agattccagg aagccattga    6540
caacctcgct gtgctcatgc gggcagagac tggaagcagg ccttacaaag ccgcggcggc    6600
ccaattgccg gagaccctag agaccataat gcttttgggg ttgctgggaa cagtctcgct    6660
gggaatcttc ttcgtcttga tgaggaacaa gggcataggg aagatgggct ttggaatggt    6720
gactcttggg gccagcgcat ggctcatgtg gctctcggaa attgagccag ccagaattgc    6780
atgtgtcctc attgttgtgt tcctattgct ggtggtgctc atacctgagc cagaaaagca    6840
aagatctccc caggacaacc aaatggcaat catcatcatg gtagcagtag gtcttctggg    6900
cttgattacc gccaatgaac tcggatggtt ggagagaaca aagagtgacc taagccatct    6960
aatgggaagg agagaggagg gggcaaccat aggattctca atggacattg acctgcggcc    7020
agcctcagct tgggccatct atgctgcctt gacaactttc attaccccag ccgtccaaca    7080
tgcagtgacc acctcataca acaactactc cttaatggcg atgccacgc aagctggagt    7140 gttgtttggc atgggcaaag gatgccatt ctacgcatgg gactttggag tcccgctgct    7200 aatgatagt tgctactcac aattaacacc cctgacccta atagtggcca tcattttgct    7260
cgtggcgcac tacatgtact tgatcccagg gctgcaggca gcagctgcgc gtgctgccca    7320
gaagagaacg gcagctggca tcatgaagaa ccctgttgtg gatggaatag tggtgactga    7380
cattgacaca atgacaattg accccaagt ggagaaaaag atgggacagg tgctactcat    7440
agcagtagcc gtctccagcg ccatactgtc gcggaccgcc tgggggtggg gggaggctgg    7500
ggctctgatc acagccgcaa cttccacttt gtgggaaggc tctccgaaca agtactggaa    7560
ctcctctaca gccacttcac tgtgtaacat ttttaggggga agttacttgg ctggagcttc    7620
tctaatctac acagtaacaa gaaacgctgg cttggtcaag agacgtgggg gtggaacagg    7680
agagaccctg ggagagaaat ggaaggcccg cttgaaccag atgtcggccc tggagttcta    7740
ctcctacaaa aagtcaggca tcaccgaggt gtgcagagaa gaggcccgcc gcgccctcaa    7800
ggacggtgtg gcaacgggag ccatgctgt gtcccgagga agtgcaaagc tgagatggtt    7860
ggtggagcgg ggatacctgc agccctatgg aaaggtcatt gatcttggat gtggcagagg    7920
gggctggagt tactacgtcg ccaccatccg caaagtcaa gaagtgaaag atacacaaa    7980 aggaggccct ggtcatgaag aacccgtgtt ggtgcaagc tatgggtgga acatagtccg    8040
tcttaagagt ggggtggacg tctttcatat ggcggctgag ccgtgtgaca cgttgctgtg    8100
```

```
tgacataggt gagtcatcat ctagtcctga agtggaagaa gcacggacgc tcagagtcct    8160
ctccatggtg ggggattggc ttgaaaaaag accaggagcc ttttgtataa aagtgttgtg    8220
cccatacacc agcactatga tggaaaccct ggagcgactg cagcgtaggt atggggagg     8280 actggtcaga gtgccactct cccgcaactc tacacatgag atgtactggg tctctgagc    8340 gaaaagcaac accataaaaa gtgtgtccac cacgagccag ctcctcttgg ggcgcatgga    8400
cgggcctagg aggccagtga aatatgagga ggatgtgaat ctcggctctg gcacgcgggc    8460
tgtggtaagc tgcgctgaag ctcccaacat gaagatcatt ggtaaccgca ttgaaaggat    8520
ccgcagtgag cacgcggaaa cgtggttctt tgacgagaac cacccatata ggacatgggc    8580
ttaccatgga agctatgagg cccccacaca agggtcagcg tcctctctaa taaacggggt    8640
tgtcaggctc ctgtcaaaac cctgggatgt ggtgactgga gtcacaggaa tagccatgac    8700
cgacaccaca ccgtatggtc agcaaagagt tttcaaggaa aaagtggaca ctagggtgcc    8760 agaccccaa gaaggcactc gtcaggttat gagcatggtc tcttcctggt tgtggaaaga    8820
gctaggcaaa cacaaacggc cacgagtctg caccaaagaa gagttcatca acaaggttcg    8880
tagcaatgca gcattagggg caatatttga agaggaaaaa gagtggaaga ctgcagtgga    8940
agctgtgaac gatccaaggt tctgggctct agtggacaag gaaagagagc accacctgag    9000
aggagagtgc cagagctgtg tgtacaacat gatgggaaaa agagaaaaga acaaggggga    9060
atttggaaag gccaagggca gccgcgccat ctggtatatg tggctagggg ctagatttct    9120
agagttcgaa gcccttggat tcttgaacga ggatcactgg atggggagag agaactcagg    9180
aggtggtgtt gaagggctgg gattacaaag actcggatat gtcctagaag atgagtcg    9240 tataccagga ggaaggatgt atgcagatga cactgctggc tgggacaccc gcattagcag    9300
gtttgatctg gagaatgaag ctctaatcac caaccaaatg gagaaagggc acaggccctt    9360
ggcattggcc ataatcaagt acacatacca aaacaaagtg gtaaaggtcc ttagaccagc    9420
tgaaaagggg aaaacagtta tggacattat ttcgagacaa gaccaagggg ggagcggaca    9480
agttgtcact tacgctctta acacatttac caacctagtg gtgcaactca ttcggaatat    9540
ggaggctgag gaagttctag agatgcaaga cttgtggctg ctgcggaggt cagagaaagt    9600
gaccaactgg ttgcagagca acggatggga taggctcaaa cgaatggcag tcagtggaga    9660
tgattgcgtt gtgaagccaa ttgatgatag gtttgcacat gccctcaggt tcttgaatga    9720
tatgggaaaa gttaggaagg acacacaaga gtggaaaccc tcaactggat gggacaactg    9780
ggaagaagtt ccgttttgct cccaccactt caacaagctc catctcaagg acgggaggtc    9840
cattgtggtt ccctgccgcc accaagatga actgattggc cgggcccgcg tctctccagg    9900
ggcgggatgg agcatccggg agactgcttg cctagcaaaa tcatatgcgc aaatgtggca    9960
gctcctttat ttccacagaa gggacctccg actgatggcc aatgccattt gttcatctgt    10020
gccagttgac tgggttccaa ctgggagaac tacctggtca atccatggaa agggagaatg    10080
gatgaccact gaagacatgc ttgtggtgtg aacagagtg tggattgagg agaacgacca    10140
catggaagac aagaccccag ttacgaaatg gacagacatt ccctatttgg gaaaaaggga    10200
agacttgtgg tgtggatctc tcataggcca cagaccgcgc accacctggg ctgagaacat    10260
taaaaacaca gtcaacatgg tgcgcaggat cataggtgat gaagaaaagt acatggacta    10320
cctatccacc caagttcgct acttgggtga agaagggtct acacctggag tgctgtaagc    10380
accaatctta atgttgtcag gcctgctagt cagccacagc ttggggaaag ctgtgcagcc    10440
```

```
tgtgacccccc ccaggagaag ctgggaaacc aagcctatag tcaggccgag aacgccatgg   10500
cacggaagaa gccatgctgc ctgtgagccc ctcagaggac actgagtcaa aaacccccac   10560
gcgcttggag gcgcaggatg ggaaaagaag gtggcgacct tccccaccct tcaatctggg   10620
gcctgaactg gagatcagct gtggatctcc agaagaggga ctagtggtta gagga         10675
```

<210> SEQ ID NO 5
<211> LENGTH: 10676
<212> TYPE: DNA
<213> ORGANISM: Zika virus

<400> SEQUENCE: 5

```
gttgttactg ttgctgactc agactgcgac agttcgagtt tgaagcgaaa gctagcaaca     60
gtatcaacag gtttatttg gatttggaaa cgagagtttc tggtcatgaa aaacccaaaa    120
aagaaatccg gaggattccg gattgtcaat atgctaaaac gcggagtagc ccgtgtgagc    180 cccttgggg gcttgaagag gctgccagcc ggacttctgc tgggtcatgg gcccatcagg    240
atggtcttgg caattctagc cttttgaga ttcacggcaa tcaagccatc actgggtctc    300
atcaatagat ggggttcagt ggggaaaaaa gaggctatgg aaataataaa gaagttcaag    360
aaagatctgg ctgccatgct gagaataatc aatgctagga aggagaagaa gagacgaggc    420
gcagatacta gtgtcggaat tgttggcctc ctgctgacca cagctatggc agcggaggtc    480
actagacgtg ggagtgcata ctatatgtac ttggacagaa cgatgctggg gaggccata    540 tcttttccaa ccacattggg gatgaataag tgttatatac agatcatgga tcttggacac    600
atgtgtgatg ccaccatgag ctatgaatgc cctatgctgg atgaggggt ggaaccagat    660 gacgtcgatt gttggtgcaa cacgacgtca acttgggttg tgtacggaac ctgccatcac    720
aaaaaaggtg aagcacggag atctagaaga gctgtgacgc tccccctccca ttccactagg    780 aagctgcaaa cgcggtcgca aacctggttg gaatcaagag aatacacaaa gcacttgatt    840
agagtcgaaa attggatatt caggaaccct ggcttcgcgt tagcagcagc tgccatcgct    900
tggcttttgg gaagctcaac gagccaaaaa gtcatatact tggtcatgat actgctgatt    960
gccccggcat acagcatcag gtgcatagga gtcagcaata gggactttgt ggaaggtatg   1020
tcaggtggga cttgggttga tgttgtcttg gaacatggag gttgtgtcac cgtaatggca   1080
caggacaaac cgactgtcga catagagctg gttacaacaa cagtcagcaa catggcggag   1140
gtaagatcct actgctatga ggcatcaata tcagacatgg cttcggacag ccgctgccca   1200
acacaaggtg aagcctacct tgacaagcaa tcagacactc aatatgtctg caaaagaacg   1260
ttagtggaca gaggctgggg aaatggatgt ggacttttg gcaaagggag tctggtgaca   1320
tgcgctaagt ttgcatgctc caagaaaatg accgggaaga gcatccagcc agagaatctg   1380
gagtaccgga taatgctgtc agttcatggc tcccagcaca gtgggatgat cgttaatgac   1440
acaggacatg aaactgatga aatagcgcg aaggttgaga taacgcccaa ttcaccaaga    1500
gccgaagcca ccctgggggg ttttggaagc ctaggacttg attgtgaacc gaggacaggc   1560
cttgactttt cagatttgta ttacttgact atgaataaca agcactggtt ggttcacaag   1620
gagtggttcc acgacattcc attaccttgg cacgctgggg cagacaccgg aactccacac   1680
tggaacaaca agaagcact ggtagagttc aaggacgcac atgccaaaag gcaaactgtc   1740
gtggttctag ggagtcaaga aggagcagtt cacacggccc ttgctggagc tctggaggct   1800
gagatggatg gtgcaaaggg aaggctgtcc tctggccact tgaaatgtcg cctgaaaatg   1860
gataaactta gattgaaggg cgtgtcatac tccttgtgta ccgcagcgtt cacattcacc   1920
```

```
aagatcccgg ctgaaacact gcacgggaca gtcacagtgg aggtacagta cgcagggaca   1980
gatggacctt gcaaggttcc agctcagatg gcggtggaca tgcaaactct gaccccagtt   2040
gggaggttga taaccgctaa ccccgtaatc actgaaagca ctgagaactc taagatgatg   2100
ctggaacttg atccaccatt tggggactct tacattgtca taggagtcgg ggagaagaag   2160
atcacccacc actggcacag gagtggcagc accattggaa aagcatttga agccactgtg   2220
agaggtgcca agagaatggc agtcttggga gacacagcct gggactttgg atcagttgga   2280
ggcgctctca actcattggg caagggcatc catcaaattt ttggagcagc tttcaaatca   2340
ttgtttggag gaatgtcctg gttctcacaa attctcattg gaacgttgct gatgtggttg   2400
ggtctgaaca caaagaatgg atctatttcc cttatgtgct tggccttagg gggagtgttg   2460
atcttcttat ccacagccgt ctctgctgat gtggggtgct cggtggactt ctcaaagaag   2520
gagacgagat gcggtacagg ggtgttcgtc tataacgacg ttgaagcctg agggacagg    2580
tacaagtacc atcctgactc ccccgtaga ttggcagcag cagtcaagca agcctgggaa    2640
gatggtatct gcgggatctc ctctgtttca agaatggaaa acatcatgtg gagatcagta   2700
gaaggggagc tcaacgcaat cctggaagag aatggagttc aactgacggt cgttgtggga   2760
tctgtaaaaa accccatgtg gagaggtcca cagagattgc ccgtgcctgt gaacgagctg   2820
ccccacggct ggaaggcttg ggggaaatcg cacttcgtca gagcagcaaa gacaaataac   2880
agctttgtcg tggatggtga cacactgaag gaatgcccac tcaaacatag agcatggaac   2940
agctttcttg tggaggatca tgggttcggg gtatttcaca ctagtgtctg gctcaaggtt   3000
agagaagatt attcattaga gtgtgatcca gccgttattg gaacagctgt taagggaaag   3060
gaggctgtac acagtgatct aggctactgg attgagagtg agaagaatga cacatggagg   3120
ctgaagaggg cccatctgat cgagatgaaa acatgtgaat ggccaaagtc ccacacattg   3180
tggacagatg gaatagaaga gagtgatctg atcataccca agtctttagc tgggccactc   3240
agccatcaca ataccagaga gggctacagg acccaaatga aagggccatg gcacagtgaa   3300
gagcttgaaa ttcggtttga ggaatgccca ggcactaagg tccacgtgga ggaaacatgt   3360
ggaacaagag gaccatctct gagatcaacc actgcaagcg gaagggtgat cgaggaatgg   3420
tgctgcaggg agtgcacaat gccccactg tcgttccggg ctaaagatgg ctgttggtat   3480
ggaatggaga taaggcccag gaaagaacca gaaagcaact tagtaaggtc aatggtgact   3540
gcaggatcaa ctgatcacat ggatcacttc tcccttggag tgcttgtgat tctgctcatg   3600
gtgcaggaag ggctgaagaa gagaatgacc acaaagatca tcataagcac atcaatggca   3660
gtgctggtag ctatgatcct gggaggattt tcaatgagtg acctggctaa gcttgcaatt   3720
ttgatgggtg ccaccttcgc ggaaatgaac actggaggag atgtagctca tctggcgctg   3780
atagcggcat tcaaagtcag accagcgttg ctggtatctt tcatcttcag agctaattgg   3840
acaccccgtg aaagcatgct gctggccttg gcctcgtgtc ttttgcaaac tgcgatctcc   3900
gccttggaag gcgacctgat ggttctcatc aatggttttg ctttggcctg gttggcaata   3960
cgagcgatgt tgttccacg cactgataac atcaccttgg caatcctggc tgctctgaca   4020
ccactggccc ggggcacact gctgtgtgcg tggagagcag gccttgctac ttgcgggggg   4080
tttatgctcc tctctctgaa gggaaaaggc agtgtgaaga agaacttacc atttgtcatg   4140
gccctgggac taaccgctgt gaggctggtc gaccccatca acgtggtggg gctgctgttg   4200
ctcacaagga gtgggaagcg gagctggccc cctagcgaag tactcacagc tgttggcctg   4260
```

```
atatgcgcat tggctggagg gttcgccaag gcagatatag agatggctgg gcccatggcc    4320
gcggtcggtc tgctaattgt cagttacgtg gtctcaggaa agagtgtgga catgtacatt    4380
gaaagagcag gtgacatcac atgggaaaaa gatgcggaag tcactggaaa cagtccccgg    4440
ctcgatgtgg cgctagatga gagtggtgat ttctccctgg tggaggatga cggtcccccc    4500
atgagagaga tcatactcaa ggtggtcctg atgaccatct gtggcatgaa cccaatagcc    4560
ataccctttg cagctggagc gtggtacgta tacgtgaaga ctggaaaaag gagtggtgct    4620
ctatgggatg tgcctgctcc caaggaagta aaaaggggg agaccacaga tggagtgtac    4680
agagtaatga ctcgtagact gctaggttca acacaagttg gagtgggagt tatgcaagag    4740
ggggtctttc acactatgtg gcacgtcaca aaaggatccg cgctgagaag cggtgaaggg    4800
agacttgatc catactgggg agatgtcaag caggatctgg tgtcatactg tggtccatgg    4860
aagctagatg ccgcctggga cgggcacagc gaggtgcagc tcttggccgt gcccccggga    4920
gagagagcga ggaacatcca gactctgccc ggaatattta agacaaagga tgggacatt    4980
ggagcggttg cgctggatta cccagcagga acttcaggat ctccaatcct agacaagtgt    5040
gggagagtga taggactta tggcaatggg gtcgtgatca aaaatgggag ttatgttagt    5100
gccatcaccc aagggaggag ggaggaagag actcctgttg agtgcttcga gccttcgatg    5160
ctgaagaaga agcagctaac tgtcttagac ttgcatcctg gagctgggaa aaccaggaga    5220
gttcttcctg aaatagtccg tgaagccata aaaacaagac tccgtactgt gatcttagct    5280
ccaaccaggg ttgtcgctgc tgaaatggag gaagccctta gagggcttcc agtgcgttat    5340
atgacaacag cagtcaatgt cacccactct ggaacagaaa tcgtcgactt aatgtgccat    5400
gccaccttca cttcacgtct actacagcca atcagagtcc ccaactataa tctgtatatt    5460
atggatgagg cccacttcac agatccctca gtatagcag caagaggata catttcaaca    5520
agggttgaga tgggcgaggc ggctgccatc ttcatgaccg ccacgccacc aggaacccgt    5580
gacgcatttc cggactccaa ctcaccaatt atggacaccg aagtggaagt cccagagaga    5640
gcctggagct caggctttga ttgggtgacg gattattctg gaaaaacagt ttggtttgtt    5700
ccaagcgtga ggaacggcaa tgagatcgca gcttgtctga caaaggctgg aaaacgggtc    5760
atacagctca gcagaaagac ttttgagaca gagttccaga aaacaaaaca tcaagagtgg    5820
gactttgtcg tgacaactga catttcagag atgggcgcca actttaaagc tgaccgtgtc    5880
atagattcca ggagatgcct aaagccggtc atacttgatg gcgagagagt cattctggct    5940
ggacccatgc ctgtcacaca tgccagcgct gcccagagga gggggcgcat aggcaggaat    6000
cccaacaaac ctgagatga gtatctgtat ggaggtgggt gcgcagagac tgacgaagac    6060
catgcacact ggcttgaagc aagaatgctc cttgacaata tttacctcca agatggcctc    6120
atagcctcgc tctatcgacc tgaggccgac aaagtagcag ccattgaggg agagttcaag    6180
cttaggacgg agcaaggaa gacctttgtg gaactcatga aaagaggaga tcttcctgtt    6240
tggctggcct atcaggttgc atctgccgga ataacctaca cagatagaag atggtgcttt    6300
gatggcacga ccaacaacac cataatggaa gacagtgtgc cggcagaggt gtggaccaga    6360
cacgagaga aaagagtgct caaaccgagg tggatgacg ccagagtttg ttcagatcat    6420
gcggccctga agtcattcaa ggagtttgcc gctgggaaaa gaggagcggc ttttggagtg    6480
atggaagccc tgggaacact gccaggacac atgacagaga gattccagga agccattgac    6540
aacctcgctg tgctcatgcg ggcagagact ggaagcaggc cttacaaagc cgcggcggcc    6600
caattgccgg agaccctaga gaccattatg ctttttgggt tgctgggaac agtctcgctg    6660
```

```
ggaatctttt tcgtcttgat gaggaacaag ggcatagggga agatgggctt tggaatggtg    6720
actcttgggg ccagcgcatg gctcatgtgg ctctcggaaa ttgagccagc cagaattgca    6780
tgtgtcctca ttgttgtgtt cctattgctg gtggtgctca tacctgagcc agaaaagcaa    6840
agatctcccc aggacaacca aatggcaatc atcatcatgg tagcagtagg tcttctgggc    6900
ttgattaccg ccaatgaact cggatggttg gagagaacaa agagtgacct aagccatcta    6960
atgggaagga gagaggaggg ggcaaccatg ggattctcaa tggacattga cctgcggcca    7020
gcctcagctt gggccatcta tgctgccttg acaactttca ttaccccagc cgtccaacat    7080
gcagtgacca cttcatacaa caactactcc ttaatggcga tggccacgca agctggagtg    7140
ttgtttggta tgggcaaagg gatgccattc tacgcatggg actttggagt cccgctgcta    7200
atgataggtt gctactcaca attaacgccc ctgacctaa tagtggccat cattttgctc    7260
gtggcgcact acatgtactt gatcccaggg ctgcaggcag cagctgcgcg tgctgcccag    7320
aagagaacgg cagctggcat catgaagaac cctgttgtgg atggaatagt ggtgactgac    7380
attgacacaa tgacaattga cccccaagtg gagaaaaaga tgggacaggt gctactcatg    7440
gcagtagccg tctccagcgc catactgtcg cggaccgcct gggggtgggg ggaggctggg    7500
gccctgatca cagccgcaac ttccactttg tgggaaggct ctccgaacaa gtactggaac    7560
tcctctacag ccacttcact gtgtaacatt tttaggggaa gttacttggc tggagcttct    7620
ctaatctaca cagtaacaag aaacgctggc ttggtcaaga acgtgggggg tggaacagga    7680
gagaccctgg gagagaaatg gaaggccgc ttgaaccaga tgtcggccct ggagttctac    7740
tcctacaaaa agtcaggcat caccgaggtg tgcagagaag aggcccgccg cgccctcaag    7800
gacggtgtgg caacgggagg ccatgctgtg tcccgaggaa gtgcaaagct gagatggttg    7860
gtggagcggg gataccctgca gccctatgga aaggtcattg atcttggatg tggcagaggg    7920
ggctggagtt actacgccgc caccatccgc aaagttcaag aagtgaaagg atacacaaaa    7980
ggaggccctg gtcatgaaga acccgtgttg gtgcaaagct atgggtggaa catagtccgt    8040
cttaagagtg gggtggacgt cttcatatg gcggctgagc cgtgtgacac gttgctgtgt    8100
gacataggtg agtcatcatc tagtcctgaa gtggaagaag cacggacgct cagagtcctc    8160
tccatggtgg gggattggct tgaaaaaaga ccaggagcct tttgtataaa agtgttgtgc    8220
ccatacacca gcactatgat ggaaaaccctg gagcgactgc agcgtaggta tggggggagga    8280 ctggtcagag tgccactctc ccgcaactct acacatgaga tgtactgggt ctctggagcg    8340
aaaagcaaca ccataaaaag tgtgtccacc acgagccagc tcctcttggg gcgcatggac    8400
gggcctagga ggccagtgaa atatgaggag gatgtgaatc tcggctctgg cacgcgggct    8460
gtggtaagct gcgctgaagc tcccaacatg aagatcattg gtaaccgcat tgaaaggatc    8520
cgcagtgagc acgcggaaac gtggttcttt gacgagaacc acccatatag gacatgggct    8580
taccatggaa gctatgaggc ccccacacaa gggtcagcgt cctctctaat aaacggggtt    8640
gtcaggctcc tgtcaaaacc ctgggatgtg gtgactggag tcacaggaat agccatgacc    8700
gacaccacac cgtatggtca gcaaagagtt ttcaaggaaa aagtggacac tagggtgcca    8760
gacccccaag aaggcactcg tcaggttatg agcatggtct cttcctggtt gtggaaagag    8820
ctaggcaaac acaaacggcc acgagtctgt accaaagaag agttcatcaa caaggttcgt    8880
agcaatgcag cattagggc aatatttgaa gaggaaaaag agtggaagac tgcagtggaa    8940
gctgtgaacg atccaaggtt ctgggctcta gtggacaagg aaagagagca ccacctgaga    9000
```
ggagagtgcc agagttgtgt gtacaacatg atgggaaaaa gagaaaagaa acaaggggaa 9060
tttggaaagg ccaagggcag ccgcgccatc tggtatatgt ggctaggggc tagatttcta 9120
gagttcgaag cccttggatt cttgaacgag gatcactgga tggggagaga gaactcagga 9180
ggtggtgttg aagggctggg attacaaaga ctcggatatg tcctagaaga gatgagtcgc 9240
ataccaggag gaaggatgta tgcagatgac actgctggct gggacacccg catcagcagg 9300
tttgatctgg agaatgaagc tctaatcacc aaccaaatgg agaaagggca cagggccttg 9360
gcattggcca taatcaagta cacataccaa aacaaagtgg taaaggtcct tagaccagct 9420
gaaaaaggga agacagttat ggacattatt tcgagacaag accaaagggg gagcggacaa 9480
gttgtcactt acgctcttaa cacatttacc aacctagtgg tgcaactcat tcggaatatg 9540
gaggctgagg aagttctaga gatgcaagac ttgtggctgc tgcggaggtc agagaaagtg 9600
accaactggt tgcagagcaa cggatgggat aggctcaaac gaatggcagt cagtggagat 9660
gattgcgttg tgaagccaat tgatgatagg tttgcacatg ccctcaggtt cttgaatgat 9720
atgggaaaag ttaggaagga cacacaagag tggaaaccct caactggatg ggacaactgg 9780
gaagaagttc cgttttgctc ccaccacttc aacaagctcc atctcaagga cgggaggtcc 9840
attgtggttc cctgccgcca ccaagatgaa ctgattggcc gggcccgcgt ctctccaggg 9900
gcgggatgga gcatccggga gactgcttgc ctagcaaaat catatgcgca aatgtggcag 9960
ctcctttatt tccacagaag ggacctccga ctgatggcca atgccatttg ttcatctgtg 10020
ccagttgact gggttccaac tgggagaact acctggtcaa tccatggaaa gggagaatgg 10080
atgaccactg aagacatgct tgtggtgtgg aacagagtgt ggattgagga gaacgaccac 10140
atggaagaca agaccccagt tacgaaatgg acagacattc cctatttggg aaaaagggaa 10200
gacttgtggt gtggatctct catagggcac agaccgcgca ccacctgggc tgagaacatt 10260
aaaaacacag tcaacatggt gcgcaggatc ataggtgatg aagaaaagta catggactac 10320
ctatccaccc aagttcgcta cttgggtgaa gaagggtcta cacctggagt gctgtaagca 10380
ccaatcttaa tgttgtcagg cctgctagtc agccacagct tggggaaagc tgtgcagcct 10440
gtgacccccc caggagaagc tgggaaacca agcctatagt caggccgaga acgccatggc 10500
acggaagaag ccatgctgcc tgtgagcccc tcagaggaca ctgagtcaaa aaaccccacg 10560
cgcttggagg cgcaggatgg gaaaagaagg tggcgacctt ccccaccctt caatctgggg 10620
cctgaactgg agatcagctg tggatctcca gaagagggac tagtggttag aggaga 10676

<210> SEQ ID NO 6
<211> LENGTH: 10808
<212> TYPE: DNA
<213> ORGANISM: Zika virus

<400> SEQUENCE: 6
agttgttgat ctgtgtgaat cagactgcga cagttcgagt ttgaagcgaa agctagcaac 60
agtatcaaca ggttttattt tggatttgga aacgagagtt tctggtcatg aaaaacccaa 120
aaaagaaatc cggaggattc cggattgtca atatgctaaa acgcggagta gcccgtgtga 180
gcccctttgg gggcttgaag aggctgccag ccggacttct gctgggtcat gggcccatca 240
ggatggtctt ggcaattcta gcctttttga gattcacggc aatcaagcca tcactgggtc 300
tcatcaatag atggggttca gtggggaaaa aagaggctat ggaaataata aagaagttca 360
agaaagatct ggctgccatg ctgagaataa tcaatgctag gaaggagaag aagagacgag 420
gcgcagatac tagtgtcgga attgttggcc tcctgctgac cacagctatg gcagcggagg 480

-continued

```
tcactagacg tgggagtgca tactatatgt acttggacag aaacgatgct ggggaggcca      540
tatcttttcc aaccacattg gggatgaata agtgttatat acagatcatg gatcttggac      600
acatgtgtga tgccaccatg agctatgaat gccctatgct ggatgagggg gtggaaccag      660
atgacgtcga ttgttggtgc aacacgacgt caacttgggt tgtgtacgga acctgccatc      720
acaaaaaagg tgaagcacgg agatctagaa gagctgtgac gctcccctcc cattccacta      780
ggaagctgca aacgcggtcg caaacctggt tggaatcaag agaatacaca aagcacttga      840
ttagagtcga aaattggata ttcaggaacc ctggcttcgc gttagcagca gctgccatcg      900
cttggctttt gggaagctca acgagccaaa aagtcatata cttggtcatg atactgctga      960
ttgccccggc atacagcatc aggtgcatag gagtcagcaa tagggacttt gtggaaggta     1020
tgtcaggtgg gacttgggtt gatgttgtct tggaacatgg aggttgtgtc accgtaatgg     1080
cacaggacaa accgactgtc gacatagagc tggttacaac aacagtcagc aacatggcgg     1140
aggtaagatc ctactgctat gaggcatcaa tatcagacat ggcttcggac agccgctgcc     1200
caacacaagg tgaagcctac cttgacaagc aatcagacac tcaatatgtc tgcaaaagaa     1260
cgttagtgga cagaggctgg ggaaatggat gtggactttt tggcaaaggg agcctggtga     1320
catgcgctaa gtttgcatgc tccaagaaaa tgaccgggaa gagcatccag ccagagaatc     1380
tggagtaccg gataatgctg tcagttcatg gctcccagca cagtgggatg atcgttaatg     1440
acacaggaca tgaaactgat gagaatagag cgaaggttga gataacgccc aattcaccaa     1500
gagccgaagc caccctgggg ggttttggaa gcctaggact tgattgtgaa ccgaggacag     1560
gccttgactt ttcagatttg tattacttga ctatgaataa caagcactgg ttggtccaca     1620
aggagtggtt ccacgacatt ccattacctt ggcacgctgg ggcagacacc ggaactccac     1680
actggaacaa caaagaagca ctggtagagt tcaaggacgc acatgccaaa aggcaaactg     1740
tcgtggttct agggagtcaa gaaggagcag ttcacacggc ccttgctgga gctctggagg     1800
ctgagatgga tggtgcaaag ggaaggctgt cctctggcca cttgaaatgt cgcctgaaaa     1860
tggataaact tagattgaag ggcgtgtcat actccttgtg taccgcagcg ttcacattca     1920
ccaagatccc ggctgaaaca ctgcacggga cagtcacagt ggaggtacag tacgcaggga     1980
cagatggacc ttgcaaggtt ccagctcaga tggcggtgga catgcaaact ctgaccccag     2040
ttgggaggtt gataaccgct aacccegtaa tcactgaaag cactgagaac tctaagatga     2100
tgctggaact tgatccacca tttggggact cttacattgt cataggagtc ggggagaaga     2160
agatcaccca ccactggcac aggagtggca gcaccattgg aaaagcattt gaagccactg     2220
tgagaggtgc caagagaatg gcagtcttgg gagacacagc ctgggacttt ggatcagttg     2280
gaggcgctct caactcattg ggcaagggca tccatcaaat ttttggagca gctttcaaat     2340
cattgtttgg aggaatgtcc tggttctcac aaatcctcat tggaacgttg ctgatgtggt     2400
tgggtctgaa cacaaagaat ggatctattt cccttatgtg cttggcctta ggggagtgt      2460 tgatcttctt atccacagcc gtctctgctg atgtggggtg ctcggtggac ttctcaaaga     2520
aggagacgag atgcggtaca ggggtgttcg tctataacga cgttgaagcc tgagggaca      2580 ggtacaagta ccatcctgac tcccccegta gattggcagc agcagtcaag caagcctggg     2640
aagatggtat ctgcgggatc tcctctgttt caagaatgga gaacatcatg tggagatcag     2700
tagaagggga gctcaacgca atcttggaag agaatggagt tcaactgacg gtcgttgtgg     2760
gatctgtaaa aaacccatg tggagaggtc cacagagatt gcccgtgcct gtgaacgagc      2820
```

-continued

```
tgccccacgg ctggaaggct tgggggaaat cgtacttcgt cagagcagca aagacaaata    2880
acagctttgt cgtggatggt gacacactga aggaatgccc actcgaacat agagcatgga    2940
acagctttct tgtggaggat catgggttcg gggtatttca cactagtgtc tggctcaagg    3000
ttagagaaga ttattcatta gagtgtgatc cagccgttat tggaacagct gttaagggga    3060
aggaggctgt acacagtgat ctaggctact ggattgagag tgagaagaat gacacatgga    3120
ggctgaagag ggcccatcta atcgagatga aaacatgtga atggccaaag tcccacacat    3180
tgtgggcaga tggaatagaa gagagtgatc tgatcattcc caagtctttt gctgggccac    3240
tcagccatca aataccaga gagggctaca ggacccaaat gaaagggcca tggcacagtg    3300
aagagcttga aattcggttt gaggaatgcc cgggcactaa ggtccacgtg gaggaaacat    3360
gtggaacaag aggaccatct ctgagatcaa ccactgcaag cggaagggtg atcgaggaat    3420
ggtgctgcag ggagtgcaca atgcccccac tgtcgttccg ggctaaagat ggctgttggt    3480
atggaatgga gataaggccc aggaaagaac cagaaagcaa cttagtaagg tcagtggtga    3540
ctgcaggatc aactgatcac atggatcact tctcccttgg agtgcttgtg attctgctca    3600
tggtgcagga agggctgaag aagagaatga ccacaaagat catcataagc acatcaatgg    3660
cagtgctggt agctatgatc ctgggaggat tttcaatgag tgacctggct aagcttgcaa    3720
ttttgatggg cgccaccttc gcggaaatga acactggagg agatgtagct catctggcgc    3780
tgatagcggc attcaaagtc agaccagcgt tgctggtatc tttcatcttc agagctaatt    3840
ggacaccccg tgaaagcatg ctgctggcct tggcctcgtg tcttttgcaa actgcgatct    3900
ccgccttgga aggcgacctg atggttctca tcaatggttt tgctttggcc tggttggcaa    3960
tacgagcgat ggttgttcca cgcactgata acatcacctt ggcaatcctg ctgctctga    4020 caccactggc ccgggcaca ctgcttgtgg cgtggagagc aggccttgct acttgcgggg    4080
ggtttatgct cctctctctg aagggaaaag gcagtgtgaa gaagaactta ccatttgtca    4140 tggcccctggg actaaccgct gtgaggctgg tcgaccccat caacgtggtg ggactgctgt    4200
tgctcacaag gagtgggaag cggagctggc cccctagcga agtactcaca gctgttggcc    4260
tgatatgcgc attggctgga gggttcgcca aggcagatat agagatggct gggcccatgg    4320
ccgcggtcgg tctgctaatt gtcagttacg tggtctcagg aaagagtgtg gacatgtaca    4380
ttgaaagagc aggtgacatc acatgggaaa aagatgcgga agtcactgga aacagtcccc    4440
ggctcgatgt ggcgctagat gagagtggtg atttctccct ggtggaggat gacggtcccc    4500
ccatgagaga gatcatactc aaggtggtcc tgatgaccat ctgtggcatg aacccaatag    4560
ccataccctt tgcagctgga gcgtggtacg tatacgtgaa gactggaaaa aggagtggtg    4620
ctctatggga tgtgcctgct cccaaggaag taaaaaaggg ggagaccaca gatgagtgt    4680 acagagtaat gactcgtaga ctgctaggtt caacacaagt tggagtggga gttatgcaag    4740
aggggtcttt tcacactatg tggcacgtca caaaaggatc cgcgctgaga agcggtgaag    4800
ggagacttga tccatactgg ggagatgtca agcaggatct ggtgtcatac tgtggtccat    4860
ggaagctaga tgccgcctgg gacgggcaca gcgaggtgca gctcttggcc gtgccccccg    4920
gagagagagc gaggaacatc cagactctgc ccggaatatt taagacaaag gatgggacca    4980
ttggagcggt tgcgctggat tacccagcag gaacttcagg atctccaatc ctagacaagt    5040
gtgggagagt gataggactt tatggcaatg gggtcgtgat caaaaatggg agttatgtta    5100
gtgccatcac ccaagggagg agggaggaag agactcctgt tgagtgcttc gagccttcga    5160
tgctgaagaa gaagcagcta actgtcttag acttgcatcc tggagctggg aaaaccagga    5220
```

```
gagttcttcc tgaaatagtc cgtgaagcca taaaaacaag actccgtact gtgatcttag    5280
ctccaaccag ggttgtcgct gctgaaatgg aggaagccct tagagggctt ccagtgcgtt    5340
atatgacaac agcagtcaat gtcacccact ctggaacaga aatcgtcgac ttaatgtgcc    5400
atgccacctt cacttcacgt ctactacagc caatcagagt ccccaactat aatctgtata    5460
ttatggatga ggcccacttc acagatccct caagtatagc agcaagagga tacatttcaa    5520
caagggttga gatgggcgag gcggctgcca tcttcatgac cgccacgcca ccaggaaccc    5580
gtgacgcatt tccggactcc aactcaccaa ttatggacac cgaagtggaa gtcccagaga    5640
gagcctggag ctcaggcttt gattgggtga cggatcattc tggaaaaaca gtttggtttg    5700
ttccaagcgt gaggaacggc aatgagatcg cagcttgtct gacaaaggct ggaaaacggg    5760
tcatacagct cagcagaaag acttttgaga cagagttcca gaaaacaaaa catcaagagt    5820
gggactttgt cgtgacaact gacatttcag agatgggcgc caactttaaa gctgaccgtg    5880
tcatagattc caggagatgc ctaaagccgg tcatacttga tggcgagaga gtcattttgg    5940
ctggacccat gcctgtcaca catgccagcg ctgcccagag gaggggcgc ataggcagga    6000 atcccaacaa acctggagat gagtatctgt atggaggtgg gtgcgcagag actgacgaag    6060
accatgcaca ctggcttgaa gcaagaatgc tccttgacaa tatttacctc caagatggcc    6120
tcatagcctc gctctatcga cctgaggccg acaaagtagc agccattgag ggagagttca    6180
agcttaggac ggagcaaagg aagacctttg tggaactcat gaaaagagga gatcttcctg    6240
tttggctggc ctatcaggtt gcatctgccg gaataaccta cacagataga agatggtgct    6300 tgatggcac gaccaacaac accataatgg aagacagtgt gccggcagag gtgtggacca    6360 gacacgaga gaaaagagtg ctcaaaccga ggtggatgga cgccagagtt tgttcagatc    6420
atgcggccct gaagtcattc aaggagtttg ccgctgggaa aagaggagcg gcttttggag    6480
tgatggaagc cctgggaaca ctgccaggac acatgacaga gagattccag gaagccattg    6540
acaacctcgc tgtgctcatg cgggcagaga ctggaagcag gccttacaaa gccgcggcgg    6600
cccaattgcc ggagacccta gagaccatta tgcttttggg gttgctggga acagtctcgc    6660
tgggaatctt tttcgtcttg atgaggaaca agggcatagg gaagatgggc tttggaatgg    6720
tgactcttgg ggccagcgca tggctcatgt ggctctcgga aattgagcca gccagaattg    6780
catgtgtcct cattgttgtg ttcctattgc tggtggtgct cataccggag ccagaaaagc    6840
aaagatctcc ccaggacaac caaatggcaa tcatcatcat ggtagcagta ggtcttctgg    6900
gcttgattac cgccaatgaa ctcggatggt tggagagaac aaaagagtga ctaagccatc    6960
taatgggaag gagagaggag ggagcaacca taggattctc aatggacatt gacctgcggc    7020
cagcctcagc ttgggccatc tatgctgcct tgacaacttt cattacccca gccgtccaac    7080
atgcagtgac cacttcatac aacaactact ccttaatggc gatggccacg caagctggag    7140
tgttgtttgg tatgggcaaa gggatgccat tctacgcatg gactttggaa gtcccgctgc    7200
taatgatagg ttgctactca caattaacac ccctgaccct aatagtggcc atcattttgc    7260
tcgtggcgca ctacatgtac ttgatcccag ggctgcaggc agcagctgcg cgtgctgccc    7320
agaagagaac ggcagctggc atcatgaaga accctgttgt ggatggaata gtggtgactg    7380
acattgacac aatgacaatt gacccccaag tggagaaaaa gatgggacag gtgctactca    7440
tagcagtagc agtctccagc gccatactgt cgcggaccgc ctgggggtgg ggggaggctg    7500 gggcctgat cacagccgca acttccactt tgtgggaagg ctctccgaac aagtactgga    7560
```

```
actcctctac agccacttca ctgtgtaaca ttttaggggg aagttacttg gctggagctt    7620
ctctaatcta catagtaaca agaaacgctg gcttggtcaa gagacgtggg ggtggaacag    7680
gagagaccct gggagagaaa tggaaggccc gcttgaacca gatgtcggcc ctggagttct    7740
actcctacaa aaagtcaggc atcaccgagg tgtgcagaga agaggcccgc cgcgccctca    7800
aggatggtgt ggcaacggga ggccatgctg tgtcccgagg aagtgcaaag ctgagatggt    7860
tggtggagcg gggatacctg cagccctatg gaaaggtcat tgatcttgga tgtggcagag    7920
ggggctggag ttactacgcc gccaccatcc gcaaagttca agaagtgaaa ggatacacaa    7980
aaggaggccc tggtcatgaa gaacccgtgt tggtgcaaag ctatgggtgg aacatagtcc    8040
gtcttaagag tggggtggac gtctttcata tggcggctga gccgtgtgac acgttgctgt    8100
gtgacatagg tgagtcatca tctagtcctg aagtggaaga agcacggacg ctcagagtcc    8160
tctccatggt gggggattgg cttgaaaaaa gaccaggagc cttttgtata aaagtgttgt    8220
gcccatacac cagcactatg atggaaaccc tggagcgact gcagcgtagg tatgggggag    8280
gactggtcag agtgccactc tcccgcaact ctacacatga gatgtactgg gtctctggag    8340
cgaaaagcaa caccataaaa agtgtgtcca ccacgagcca gctcctcttg gggcgcatgg    8400
acgggcctag gaggccagtg aaatatgagg aggatgtgaa tctcggctct ggcacgcggg    8460
ctgtggtaag ctgcgctgaa gctcccaaca tgaagatcat tggtaaccgc attgaaagga    8520
tccgcagtga gcacgcggaa acgtggttct ttgacgagaa ccacccatat aggacatggg    8580
cttaccatgg aagctatgag gcccccacac aagggtcagc gtcctctcta ataaacgggg    8640
ttgtcaggct cctgtcaaaa ccctgggatg tggtgactgg agtcacagga atagccatga    8700
ccgacaccac accgtatggt cagcaaagag ttttcaagga aaaagtggac actagggtgc    8760
cagaccccca agaaggcact cgtcaggtta tgagcatggt ctcttcctgg ttgtggaaag    8820
agctaggcaa acacaaacgg ccacgagtct gtaccaaaga agagttcatc aacaaggttc    8880
gtagcaatgc agcattaggg gcaatatttg aagaggaaaa agagtggaag actgcagtgg    8940
aagctgtgaa cgatccaagg ttctgggctc tagtggacaa ggaaagagag caccacctga    9000
gaggagagtg ccagagttgt gtgtacaaca tgatgggaaa aagagaaaag aaacaagggg    9060
aatttggaaa ggccaagggc agccgcgcca tctggtatat gtggctaggg gctagatttc    9120
tagagttcga agcccttgga ttcttgaacg aggatcactg gatggggaga gagaactcag    9180
gaggtggtgt tgaagggctg ggattacaaa gactcggata tgtcctagaa gagatgagtc    9240
gcataccagg aggaaggatg tatgcagatg acactgctgg ctgggacacc cgcatcagca    9300
ggttcgatct ggagaatgaa gctctaatca ccaaccaaat ggagaaaggg catagggcct    9360
tggcattggc cataatcaag tacacatacc aaaacaaagt ggtaaaggtc cttagaccag    9420
ctgaaaaagg gaaaacagtt atggacatta tttcgagaca agaccaaagg gggagcggac    9480
aagttgtcac ttacgctctt aacacatta ccaacctagt ggtgcaactc attcggaata    9540
tggaggctga ggaagttcta gagatgcaag acttgtggct gctgcggagg tcagagaaag    9600
tgaccaactg gttgcagagc aacggatggg ataggctcaa acgaatggca gtcagtggag    9660
atgattgcgt tgtgaagcca attgatgata ggttttgcac atgccctcag ttcttgaatg    9720
atatgggaaa agttaggaag gacacacaag agtggaaacc ctcaactgga tgggacaact    9780
gggaagaagt tccgttttgc tcccaccact caacaagct ccatctcaag gacgggaggt    9840
ccattgtggt tccctgccgc caccaagatg aactgattgg ccgggcccgc gtctctccag    9900
gggcgggatg gagcatccgg gagactgctt gcctagcaaa atcatatgcg caaatgtggc    9960
```

| | |
|---|---|
| agctccttta tttccacaga agggacctcc gactgatggc caatgccatt tgttcatctg | 10020 |
| tgccagttga ctgggttcca actgggagaa ctacctggtc aatccatgga aagggagaat | 10080 |
| ggatgaccac tgaagacatg cttgtggtgt ggaacagagt gtggattgag gagaacgacc | 10140 |
| acatggaaga caagacccca gttacgaaat ggacagacat tccctatttg ggaaaaaggg | 10200 |
| aagacttgtg gtgtggatct ctcatagggc acagaccgcg caccacctgg gctgagaaca | 10260 |
| ttaaaaacac agtcaacatg gtgcgcagga tcataggtga tgaagaaaag tacatggact | 10320 |
| acctatccac ccaagttcgc tacttgggtg aagaagggtc tacacctgga gtgctgtaag | 10380 |
| caccaatctt aatgttgtca ggcctgctag tcagccacag cttggggaaa gctgtgcagc | 10440 |
| ctgtgacccc cccaggagaa gctgggaaac caagcctata gtcaggccga gaacgccatg | 10500 |
| gcacggaaga agccatgctg cctgtgagcc cctcagagga cactgagtca aaaaacccca | 10560 |
| tgcgcttgga ggcgcaggat gggaaaagaa ggtggcgacc ttccccaccc ttcaatctgg | 10620 |
| ggcctgaact ggagatcagc tgtggatctc cagaagaggg actagtggtt agaggagacc | 10680 |
| cccggaaaa cgcaaaacag catattgacg ctgggaaaga ccagagactc catgagtttc | 10740 |
| caccacgctg gccgccaggc acagatcgcc gaatagcggc ggccggtgtg gggaaatcca | 10800 |
| tgggtctt | 10808 |

<210> SEQ ID NO 7
<211> LENGTH: 10807
<212> TYPE: DNA
<213> ORGANISM: Zika virus

<400> SEQUENCE: 7

| | |
|---|---|
| agttgttgat ctgtgtgaat cagactgcga cagttcgagt ttgaagcgaa agctagcaac | 60 |
| agtatcaaca ggttttattt tggatttgga acgagagtt tctggtcatg aaaaacccaa | 120 |
| aaaagaaatc cggaggattc cggattgtca atatgctaaa acgcggagta gcccgtgtga | 180 |
| gccccttggg gggcttgaag aggctgccag ccggacttct gctgggtcat gggcccatca | 240 |
| ggatggtctt ggcgattcta gccttttga gattcacggc aatcaagcca tcactgggtc | 300 |
| tcatcaatag atggggttca gtgggaaaaa aagaggctat ggaaataata aagaagttca | 360 |
| agaaagatct ggctgccatg ctgagaataa tcaatgctag aaggagaag aagagacgag | 420 |
| gcacagatac tagtgtcgga attgttggcc tcctgctgac cacagctatg gcagcggagg | 480 |
| tcactagacg tgggagtgca tactatatgt acttggacag aagcgatgct ggggaggcca | 540 |
| tatcttttcc aacccactg gggatgaata agtgttatat acagatcatg gatcttggac | 600 |
| acatgtgtga tgccaccatg agctatgaat gccctatgct ggatgagggg gtagaaccag | 660 |
| atgacgtcga ttgttggtgc aacacgacgt caacttgggt tgtgtacgga acctgccatc | 720 |
| acaaaaaagg tgaagcacgg agatccagaa gagctgtgac gctccccctcc cattccacta | 780 |
| ggaagctgca aacgcggtcg cagacctggt tggaatcaag agaatacaca aagcacttga | 840 |
| ttagagtcga aaattggata ttcaggaacc ctggcttcgc gttagcagca gctgccatcg | 900 |
| cttggctttt gggaagctca acgagccaaa aagtcatata cttggtcatg atactgctga | 960 |
| ttgccccggc atacagcatc aggtgcatag gagtcagtaa tagggacttt gtggaaggta | 1020 |
| tgtcaggtgg gacttgggtt gatgttgtct tggaacatgg aggttgtgtc accgtaatgg | 1080 |
| cacaggacaa accgactgtc gacatagagc tggttacaac aacagtcagc aacatggcgg | 1140 |
| aggtaagatc ctactgctat gaggcatcaa tatcggacat ggcttcggac agccgctgcc | 1200 |

-continued

```
caacacaagg tgaagcctac cttgacaagc aatcagacac tcaatatgtc tgcaaaagaa    1260
cgttagtgga cagaggctgg ggaaatggat gtggactttt tggcaaaggg agcctggtga    1320
catgcgctaa gtttgcatgc tccaagaaaa tgaccgggaa gagcatccag ccagagaatc    1380
tggagtaccg gataatgctg tcagttcatg gctcccagca cagtgggatg atcgttaatg    1440
acacaggaca tgaaactgat gagaatagag cgaaggttga gataacgccc aattcaccaa    1500
gagccgaagc caccctgggg ggttttggaa gcctaggact tgattgtgaa ccgaggacag    1560
gccttgactt ttcagatttg tattacttga ctatgaacaa caagcactgg ttggttcaca    1620
aggagtggtt ccacgacatt ccattacctt ggcacactgg ggcagacacc ggaactccac    1680
actggaacaa caaagaagca ctggtagagt tcaaggacgc acatgccaaa aggcaaactg    1740
tcgtggttct agggagtcaa gaaggagcag ttcacacggc ccttgctgga gctctggagg    1800
ctgagatgga tggtgcaaag ggaaggctgt cctctggcca cttgaaatgt cgcctgaaaa    1860
tggataaact tagattgaag ggcgtgtcat actccttgtg taccgcagcg ttcacattca    1920
ccaagatccc ggctgaaaca ctgcacggga cagtcacagt ggaggtacag tacgcaggga    1980
cagatggacc ttgcaaggtt ccagctcaga tggcggtgga catgcaaact ctgaccccag    2040
ttgggaggtt gataaccgct aacccgtaa  tcactgaagg cactgagaac tctaagatga    2100
tgctggaact tgatccacca tttggggact cttacattgt cataggagtc ggggagaaga    2160
agatcaccca ccactggcac aggagtggca gcaccattgg aaaagcattt gaagccactg    2220
tgagaggtgc caagagaatg gcagtcttgg gagacacagc ctgggacttt ggatcagttg    2280
gaggcgttct taactcattg ggcaagggca tccatcaaat ttttggagca gctttcaaat    2340
cattgtttgg aggaatgtcc tggttctcac aaattctcat tggaacgttg ctgatgtggt    2400
tgggtctgaa tacaaagaat ggatctattt cccttatgtg cttggcctta ggggagtgt    2460 tgatcttctt atccacagcc gtctccgctg atgtggggtg ctcggtggac ttctcaaaga    2520
aggaaacgag atgcggtaca ggggtgttcg tctataacga cgttgaagcc tggagggaca    2580
ggtacaagta ccatcctgac tcccctcgta gattggcagc agtagtcaag caagcctggg    2640
aagatggtat ctgtgggatc tcctctgttt caagaatgga aaacatcatg tggagatcag    2700
tagaagggga gctcaacgca atcctggaag agaatggagt tcaactgacg gtcgttgtgg    2760
gatctgtaaa aaaccccatg tggagaggtc cacagagatt gcccgtgcct gtgaacgagc    2820
tgccccacgg ctggaaggct tgggggaaat cgtacttcgt cagagcagca aagacaaata    2880
acagctttgt cgtggatggt gacacactga aggaatgccc actcaaacat agagcatgga    2940
acagctttct tgtggaggat catgggttcg gggtatttca cactagtgtc tggctcaagg    3000
ttagagaaga ttattcacta gagtgtgatc cagccgtcat tggaacagct gttaagggaa    3060
aggaggctgt acacagtgat ctaggctact ggattgagag tgagaagaac gacacatgga    3120
ggctgaggag ggcccacctg atcgagatga aaacatgtga atggccaaag tcccacacat    3180
tgtggacaga tggaatagaa gagagtgatc tgatcatacc caagtctta gctgggccac    3240 tcagccatca caacaccaga gagggctaca ggacccaaat gaaagggcca tggcacagtg    3300
aagagcttga aattcggttt gaggaatgcc caggcactaa ggtccacgtg gaggaaacat    3360
gtggaacaag aggaccatct ctgagatcaa ccactgcaag cggaagggtg atcgaggaat    3420
ggtgctgcag ggagtgcaca atgccccac tgtcgttccg ggctaaagat ggctgttggt    3480
atggaatgga gataaggccc aggaaagaac cagaaagtaa cttagtaagg tcaatggtga    3540
ctgcaggatc aactgatcac atggatcact tttcccttgg agtgcttgtg attctgctca    3600
```

```
tggtgcagga agggctgaag aagagaatga ccacaaagat catcataagc acatcaatgg   3660
cagtgctggt agctatgatc ctgggaggat tttcaatgag tgatctggct aagcttgcaa   3720
ttttgatggg tgccaccttt gcggaaatga acactggagg agatgtagct catctggcgc   3780
tggtagcgga attcaaagtc agaccagcgt tgctggtatc tttcatcttc agagctaatt   3840
ggacaccccg tgaaagcatg ctgctggcct tggcctcgtg tcttttgcaa actgcgatct   3900
ccgccttgga aggcgacctg atggttctca tcaatggttt tgctttggcc tggttggcaa   3960
tacgagcgat ggttgttcca cgcactgaca atatcacctt ggcaatcctg ctgctctga   4020 caccactggc ccggggcaca ctgcttgtgg cgtggagagc aggccttgct acttgcgggg   4080
ggttcatgct cctctctctg aaggggaaag gcagtgtgaa gaagaactta ccatttgtca   4140
tggccctggg actaaccgct gtgaggctgg tcgaccccat caacgtggtg ggactgctgt   4200
tgctcacaag gagtgggaag cggagctggc cccctagcga agtactcaca gctgttggcc   4260
tgatatgcgc attggctgga gggttcgcca aggcagatat agatgtgct gggcccatgg   4320 ccgcggtcgg tctgctaatt gtcagttacg tggtctcagg aaagagtgtg acatgtaca   4380 ttgaaagagc aggtgacatc acatgggaaa aagatgcgga agttactgga aacagtcccc   4440
ggctcgatgt ggcactagat gagagtggtg atttctccct ggtggaggat gacggtcccc   4500
ccatgagaga gatcatactc aaagtggtcc tgatgaccat ctgtggcatg aacccaatag   4560
ccataccctt tgcagctgga gcgtggtacg tatacgtgaa aactggaaaa aggagtggtg   4620
ctctatggga tgtgcctgct cccaaggaag taaaaaggg ggagaccaca gatggagtgt   4680
acagagtaat gactcgtaga ctgctaggtt caacacaagt tggagtggga gttatgcaag   4740
agggggtctt tcacactatg tggcatgtca caaaaggatc cgcgctgaga agcggtgaag   4800
ggagacttga tccatactgg ggagatgtca agcaggatct ggtgtcatac tgtggtccat   4860
ggaagctaga tgccgcctgg gacgggcaca gcgaggtgca gctcttggcc gtgccccccg   4920
gagagagagc gaggaacatc cagactctgc ccggaatatt taagacaaag gatggggaca   4980
ttggagcggt tgcgctggac tatccagcag gaacttcagg atctccaatc ctagacaagt   5040
gtgggagagt gataggactc tatggcaatg gggtcgtgat caagaatggg agttatgtca   5100
gtgccatcac ccaagggagg agggaggaag agactcctgt tgagtgcttc gagccttcga   5160
tgctgaagaa gaagcagcta actgtcttag acttgcatcc tggagctggg aaaaccagga   5220
gagttcttcc tgaaatagtc cgtgaagcca taaaaacgag actccgtact gtgatcttag   5280
ctccaaccag ggttgtcgct gctgaaatgg aggaagccct tagagggctt ccagtgcgtt   5340
atatgacaac agcagtcaat gtcacccatt ctgggacaga aatcgttgac ttaatgtgcc   5400
atgccacctt cacttcacgt ctactacagc caatcagagt ccccaactat aatctgtata   5460
ttatggatga ggcccacttc acagatccct caagtatagc agcaagagga tacatttcaa   5520
caagggttga gatgggcgag gcagctgcca tcttcatgac cgccacgcca ccaggaaccc   5580
gtgacgcatt cccggactcc aactcaccaa ttatggacac cgaagtggaa gtcccagaga   5640
gagcctggag ctcaggcttt gattgggtga cggatcattc tggaaaaaca gtttggtttg   5700
tcccaagcgt gaggaacggc aatgagatcg cagcttgtct gacaaaggct ggaaaacggg   5760
tcatacagct cagcagaaag acttttgaga cagagttcca gaaaacaaaa catcaagagt   5820
gggacttcgt cgtgacaact gacatttcag agatgggcgc caactttaaa gctgaccgtg   5880
tcatagattc caggagatgc ctaaagccgg tcatacttga tggcgagaga gtcattctgg   5940
```

```
ctggacccat gcctgtcaca catgccagcg ctgcccagag gaggggcgc ataggcagga      6000 atcccaacaa acctggagat gagtatctgt atggaggtgg gtgcgcagag actgatgaag      6060
accatgcaca ctggcttgaa gcaagaatgc tccttgacaa tatttacctc caagatggcc      6120
tcatagcctc gctctatcga cctgaggccg acaaagtagc agccattgag ggagagttca      6180
agcttaggac ggagcaaagg aagacctttg tggaactcat gaaaagagga gatcttcctg      6240
tttggctggc ctatcaggtt gcatctgccg gaataaccta cacagataga agatggtgct      6300 tgatggcat gaccaacaac accataatgg aagacagtgt gccggcagag gtgtggacca      6360
gacacggaga gaaagagtg ctcaaaccga ggtggatgga cgccagagtt tgttcagatc      6420
atgcggccct gaagtcattc aaggagtttg ccgctgggaa aagaggagcg gcttttggag      6480
tgatggaagc cctgggaaca ctgccaggac acatgacgga gagattccag gaagccattg      6540
acaacctcgc tgtgctcatg cgggcagaga ctggaagcag gccttacaaa gccgcggcgg      6600
cccaattgcc ggagacccta gagaccatta tgctttggg gttgctggga acagtctcgc      6660
tgggaatctt tttcgtcttg atgcggaaca agggcatagg gaagatgggc tttggaatgg      6720
tgactcttgg ggccagcgca tggctcatgt ggctctcgga aattgagcca gccagaattg      6780
catgcgtcct cattgttgtg ttcctattgc tggtggtgct cataccctgag ccagaaaagc      6840 aaagatcccc ccaggacaac caaatggcaa tcatcatcat ggtagcagta ggtcttctgg      6900
gcttgattac cgccaatgaa ctcggatggt tggagagaac aaagagtgac ctaagccatc      6960
taatgggaag gagagaggag ggggcaacca taggattctc aatggacatt gacctgcggc      7020
cagcctcggc ctgggccatc tatgctgccc tgacaacttt cattacccca gccgtccaac      7080
atgcagtgac cacttcatac aacaactact ccttaatggc gatggccacg caagctggag      7140
tgttgtttgg tatgggcaaa gggatgccat tctacgcatg gacttttgga gtcccgctgc      7200
taatgatagg ttgctactca caattaacac ccctgacccct aatagtggct atcattttgc      7260
tcgtggcgca ctacatgtac ttgatcccag ggctgcaggc agcagctgcg cgtgctgccc      7320
agaagagaac ggcagctggc atcatgaaga accctgttgt ggatggaata gtggtgactg      7380
acattgacac aatgactatt gaccccccaag tggagaaaaa gatgggacag gtgctactca      7440
tagcagtagc cgtctccagc gccatactgt cgcggaccgc ctggggtgg ggggaagctg      7500 gggccctgat cacagctgca acttccactt tgtgggaagg ctctccgaac aagtactgga      7560
actcctctac agccacttca ctgtgcaaca ttttttagggg aagttacttg gctggagctt      7620
ctctaatcta cacagtaaca agaaacgctg gcttggtcaa gagacgtggg ggtggaacag      7680
gagagaccct gggagagaaa tggaaggccc gcttgaacca gatgtcggcc ctggagttct      7740
actcctacaa aaagtcaggc atcaccgagg tgtgcagaga agaggcccgc cgcgccctca      7800
aggacggtgt ggcaacggga ggccatgctg tgtcccgagg aagtgcaaag ctgagatggt      7860
tggtggagcg gggataccctg cagccctatg gaaaggtcat tgatcttgga gtgtggcagag      7920 ggggctggag ttactacgcc gccaccatcc gcaaagttca agaagtgaaa ggatacacaa      7980
aaggaggccc tggtcatgaa gaacccatgt tggtgcaaag ctatgggtgg aacatagtcc      8040
gtcttaagag tggggtggac gtctttcata tggcggctga gccgtgtgac acgttgctgt      8100
gtgacatagg tgagtcatca tctagtcctg aagtggaaga agcacggacg ctcagagtcc      8160
tctccatggt gggggattgg cttgaaaaaa gaccaggagc ctttttgtgta aaagtgttgt      8220 gcccatacac cagcactatg atggaaaccc tggagcgact gcagcgtagg tatggggag      8280 gactggtcag agtgccactc tcccgcaact ctacacatga gatgtactgg gtctctggag      8340
```

```
cgaaaagcaa caccataaaa agtgtgtcca ccacgagcca gctcctcttg gggcgcatgg   8400
acgggcccag gaggccagtg aaatatgagg aggatgtgaa tctcggctct ggcacgcggg   8460
ctgtggtaag ctgcgctgaa gctcccaaca tgaagatcat tggtaaccgc attgaaagga   8520
tccgcagtga gcacgcggaa acgtggttct ttgacgagaa ccacccatat aggacatggg   8580
cttaccatgg aagctatgag gcccctacac aagggtcagc gtcctctcta ataaacgggg   8640
ttgtcaggct cctgtcaaaa ccctgggatg tggtgactgg agtcacagga atagccatga   8700
ccgacaccac accgtatggt cagcaaagag ttttcaagga aaagtggac accagggtgc    8760 cagacccca agaaggcact cgtcaggtta tgagcatggc tcttcctgg ttgtggaaag     8820 agctaggcaa acacaaacgg ccacgagtct gtaccaaaga agagttcatc aacaaggttc    8880
gtagcaatgc agcattaggg gcaatatttg aagaggaaaa agagtggaag accgcagtgg   8940
aagctgtgaa cgatccaagg ttctgggctc tagtggacaa ggaaagagag caccacctga   9000
gaggagagtg ccagagctgt gtgtacaaca tgatgggaaa aagagaaaag aaacaagggg   9060
aatttggaaa ggccaagggc agccgcgcca tctggtatat gtggctaggg gctagatttc   9120
tagagttcga agcccttgga ttcttaaatg aggatcactg gatggggaga gagaactcag   9180
gaggtggtgt tgaagggctg ggattacaaa gactcggata tgtcctagaa gagatgagtc    9240
gcataccagg aggaaggatg tatgcagatg acactgctgg ctgggacacc cgcatcagca    9300
ggtttgatct ggagaatgaa gctttaatca ccaaccaaat ggagaaaggg cacagggcct   9360
tagcattggc cataatcaag tacacatacc aaaacaaagt ggtaaaggtc cttagaccag   9420
ctgaaaaagg gaagacagtt atggacatta tttcaagaca agaccaaagg gggagcggac   9480
aagttgtcac ttacgctctt aacacattta ccaacctagt ggtgcaactc attcggaata   9540
tggaggctga ggaagttcta gagatgcaag acttgtggct gctgcggagg tcagagaaag   9600
tgaccaactg gttgcagagc aacggatggg ataggctcaa acgaatggca gtcagtggag    9660
atgattgcgt tgtgaagcca attgatgata ggtttgcaca tgccctcagg ttcttgaatg   9720
atatgggaaa agttaggaag gacacacaag agtggaaacc ctcaactgga tgggacaact    9780
gggaagaagt tccgttttgt tcccaccact tcaacaagct ccatctcaag gacgggaggt    9840
ccattgtggt tccctgccgc caccaagatg aactgattgg ccgggcccgt gtctctccag   9900
gggcgggatg gagcatccgg gagactgctt gcctagcaaa gtcatatgcg caaatgtggc   9960
agctccttta tttccacaga agggaccctcc gactgatggc caatgccatc tgttcatctg   10020
tgccagttga ctgggttcca actgggagaa ctacctggtc aatccatgga aagggagaat   10080
ggatgaccac tgaagacatg cttgtggtgt ggaacagagt gtggattgag gagaacgacc   10140
acatggaaga caagacccca gttacgaaat ggacagacat tccctatctg ggaaaaaggg   10200
aagacttgtg gtgtggatct ctcataggc acagaccgcg caccacctgg gctgagaaca   10260
ttaaaaacac agtcaacatg gtgcgcagga tcataggtga tgaagaaaag tacatggact   10320
acctatccac ccaagttcgc tacttgggtg aagaagggtc tacacctgga gtgctataag   10380
caccaatctt agtgttgtca ggcctgctag tcagccacag cttggggaaa gctgtgcagc   10440
ctgtgacccc cccaggagag gctgggaaac caagcccata gtcaggccga gaacgccatg   10500
gcacggaaga agccatgctg cctgtgagcc cctcagagga cactgagtca aaaaccccca    10560
cgcgcttgga ggcgcaggat gggaaaagaa ggtggcgacc ttccccaccc ttcaatctgg   10620
ggcctgaact ggagatcagc tgtggatctc cagaagaggg actagtggtt agaggagacc   10680
```

| | |
|---|---:|
| ccccggaaaa cgcaaaacag catattgacg ctgggaaaga ccagagactc catgagtttc | 10740 |
| caccacgctg gccgccaggc acagatcgcc gaatagcggc ggccggtgtg gggaaatcca | 10800 |
| tgggtct | 10807 |

<210> SEQ ID NO 8
<211> LENGTH: 10807
<212> TYPE: DNA
<213> ORGANISM: Zika virus

<400> SEQUENCE: 8

| | |
|---|---:|
| agttgttgat ctgtgtgaat cagactgcga cagttcgagt ttgaagcgaa agctagcaac | 60 |
| agtatcaaca ggttttattt tggatttgga acgagagtt tctggtcatg aaaaacccaa | 120 |
| aaaagaaatc cggaggattc cggattgtca atatgctaaa acgcggagta gcccgtgtga | 180 |
| gcccctttgg gggcttgaag aggctgccag ccggacttct gctgggccat gggcccatca | 240 |
| ggatggtctt ggcgatacta gccttttga gattcacggc aatcaagcca tcactgggtc | 300 |
| tcatcaatag atggggttca gtggggaaaa agaggctat ggaataata agaagttca | 360 |
| agaaagatct ggctgccatg ctgagaataa tcaatgctag gaaggagaag aagagacgag | 420 |
| gcgcagatac tagcgtcgga attgttggcc tcctcctgac cacagccatg gcagtagagg | 480 |
| tcactagacg tgggagtgca tactatatgt acttggacag aagcgatgct ggggaggcca | 540 |
| tatcttttcc aaccacactg gggatgaata agtgttacat acaaatcatg gatcttggac | 600 |
| acatgtgtga tgccaccatg agctatgaat gccctatgtt ggatgagggg gtagaaccag | 660 |
| atgacgtcga ttgctggtgc aacacgacat caacttgggt tgtgtatgga acctgccacc | 720 |
| acaaaaaagg tgaagcacgg agatctagaa gagctgtgac gctcccctcc cattccacta | 780 |
| ggaagctgca aacgcggtcg cagacctggt tggaatcaag agaatacaca aagcacctga | 840 |
| ttagagttga aaattggata ttcaggaacc ctggcttcgc gttagcagca gctgtcatcg | 900 |
| cttggctttt gggaagttca acgagccaaa aagtcatata tctggtcatg atactgctga | 960 |
| ttgccccggc atacagcatc aggtgcatag gagtcagcaa tagggacttt gtggaaggta | 1020 |
| tgtcaggtgg gacttgggtt gatgttgtct tggaacatgg aggttgtgtt accgtaatgg | 1080 |
| cacaggacaa accgactgtc gacatagagc tggttacaac aacagtcagc aacatggcgg | 1140 |
| aggtaagatc ctactgctat gaggcatcaa tatcggatat ggcttcggac agccgctgcc | 1200 |
| caacacaagg tgaggcctac cttgacaagc agtcagacac tcaatatgtc tgcaaaagaa | 1260 |
| cgttagtgga cagaggctgg ggaaatggat gtggactttt tggcaagggg agcctggtga | 1320 |
| catgcgctaa gtttgcatgc tccaagaaaa tgaccgggaa gagcatccag ccagagaatc | 1380 |
| tggagtaccg gataatgctg tcagttcatg gctcccagca cagtgggatg atcgttaatg | 1440 |
| acacaggaca tgaaactgat gagaatagag cgaaggttga gataacgccc aattcaccaa | 1500 |
| gagccgaagc caccctgggg ggttttggga gcctaggact tgattgtgaa ccgaggacag | 1560 |
| gccttgactt ttcagatttg tattacctga ctatgaataa caagcactgg ttggttcaca | 1620 |
| aggagtggtt ccacgacatt ccattacctt ggcatgctgg ggcagacact ggaactccac | 1680 |
| attggaacaa caaagaagca ctggtagagt tcaaggacgc acatgcaaaa aggcaaactg | 1740 |
| tcgtggttct agggagtcaa gaaggagcag ttcacacggc ccttgctgga gctctggagg | 1800 |
| ctgagatgga tggagccaag ggaaggctgt cctctggcca cttgaaatgt cgcctgaaaa | 1860 |
| tggataaact tagattgaag ggcgtgtcat actccttgtg cactgcagcg ttcacattca | 1920 |
| ccaagatccc ggctgaaaca ctgcacggga cagtcacagt ggaggtacag tacgcaggga | 1980 |

```
cagatggacc ttgcaaggtt ccagctcaga tggcggtgga tatgcaaact ctgaccccag    2040
ttgggaggtt gataaccgct aaccctgtaa tcactgaaag caccgagaac tctaagatga    2100
tgctggaact tgatccacca tttggggact cttacattgt cataggagtc ggggagaaga    2160
agatcaccca tcactggcac aggagtggca gcaccattgg aaaagcattt gaagccactg    2220
tgagaggtgc caagagaatg gcagtcttgg gagacacagc ctgggacttt ggatcagttg    2280
ggggtgctct caactcattg gcaagggca tccatcaaat ttttggagca gctttcaaat    2340
cattgttcgg aggaatgtcc tggttctcac aaattctcat ggaacgttg ctggtgtggt    2400 tgggtctgaa tacaaagaat ggatctattt cccttacgtg cttggcctta ggggagtgt    2460 tgatcttctt atccacagcc gtttctgctg atgtggggtg ctcggtggac ttctcaaaga    2520
aggaaacgag atgcggtaca ggggtgttcg tctataacga cgttgaagcc tggagggaca    2580
ggtacaagta ccatcctgac tcccctcgta gattggcagc agcagtcaag caagcctggg    2640
aagatgggat ctgtgggatc tcctctgtct caagaatgga aaacatcatg tggagatcag    2700
tagaagggga gctcaacgca atcctggaag agaatggagt tcaactgacg gtcgttgtgg    2760
gatctgtaaa aaaccccatg tggagaggtc cacagagatt gcccgtgcct gtgaacgagc    2820
tgccccacgg ctggaaggct tgggggaaat cgtacttcgt cagagcagca aagacaaata    2880
acagctttgt cgtggatggt gacacactga aggaatgccc actcaaacat agagcatgga    2940 acagcttct tgtggaggat catgggtttg ggtatttca cactagtgtc tggctcaagg    3000
ttagagaaga ttattcatta gagtgtgatc cagccgtcat tggaacagct gctaagggaa    3060
aggaggctgt gcacagcgat ctaggctact ggattgagag tgagaagaac gacacatgga    3120
ggctgaagag ggcccacctg atcgagatga aacatgtga atggccaaag tcccacacat    3180
tgtggacaga tggagtagaa gaaagtgatc tgatcatacc caagtcttta gctgggccac    3240
tcagccatca aacaccaga gagggctaca ggactcaaat gaaagggcca tggcacagtg    3300
aagagcttga aattcggttt gaggaatgcc caggcactaa ggtccacgtg gaggaaacat    3360 gtggacaag aggaccatcc ctgagatcaa ccactgcaag cggaagggtg atcgaggaat    3420
ggtgctgcag ggaatgcaca atgccccac tgtcgttccg agctaaagat ggctgttggt    3480
atggaatgga gataaggccc aggaaagaac cagaaagtaa cttagtaagg tcaatggtga    3540
ctgcaggatc aactgatcac atggatcact tctctcttgg agtgcttgtg attttgctca    3600
tggtgcagga agggctgaag aagagaatga ccacaaagat catcataagc acatcaatgg    3660
cagtgctggt agccatgatc ctgggaggat tttcaatgag tgacctggct aagcttgcaa    3720
ttttgatggg tgccaccttc gcggaaatga acactggagg agatgtagct catttggcgc    3780
tgatagcgga attcaaagtc agacctgcgt tgctggtatc tttcatcttc agagctaatt    3840
ggacaccccg tgagagcatg ctgctggcct tggcctcgtg tcttctgcaa actgcgatct    3900
ccgccttgga aggcgacctg atggttctca tcaatggttt tgctttggcc tggttggcaa    3960
tacgagcgat ggttgttcca cgcactgaca acatcacctt ggcaatcctg gctgctctga    4020
caccactggc ccggggcaca ctgcttgtgg cgtggagagc aggccttgct acttgcgggg    4080
ggttcatgct cctctctctg aagggaaag gcagtgtgaa gaagaaccta ccatttgtca    4140
tggccttggg actaactgct gtgaggctgg tcgaccccat caacgtggtg gactgctgt    4200 tgctcacaag gagtgggaag cggagctggc cccctagtga agtactcaca gctgttggcc    4260
tgatatgcgc attggctgga gggttcgcca aggcggatat agagatggct gggcccatgg    4320
```

```
ccgcggtcgg tctgctaatt gtcagttacg tggtctcagg aaagagtgtg gacatgtaca    4380
ttgaaagagc aggtgacatc acatgggaaa aagatgcgga aatcactgga aacagtcccc    4440
ggctcgatgt ggcactagat gagagtggtg atttctccct agtggaggat gatggtccac    4500
ccatgagaga gatcatactc aaagtggtcc tgatgaccat ctgcggcatg aacccaatag    4560
ccatacccct tgcagctgga gcgtggtacg tgtatgtgaa gactggaaaa aggagtggtg    4620
ctctatggga tgtgcctgct cccaaggaag taaaaaaggg ggagaccaca gatggagtgt    4680
acagagtaat gactcgtaga ctgcttggtt caacacaagt tggagtggga gtcatgcaag    4740 aggggggtctt ccacactatg tggcacgtca caaaaggatc cgcgctgaga agcggtgaag    4800
ggagacttga tccatactgg ggagatgtca agcaggatct ggtgtcatac tgtggtccgt    4860
ggaagctaga cgccgcctgg gacgggcaca gcgaggtgca gctcttggcc gtgcccccccg    4920 gagagagagc gaggaacatc cagactctgc ccggaacatt taagacaaag gatgggggaca    4980 ttggagcagt tgcgctggac tacccagcag gaacttcagg atctccaatc ctagacaagt    5040
gtgggagagt gataggactc tatggtaatg gggtcgtgat aaaaaatggg agttatgtta    5100
gtgccatcac ccaagggagg agggaggaag agactcctgt tgagtgcttc gagccttcga    5160
tgctgaagaa aagcagcta actgtcttag acctgcatcc tggagccggg aaaaccagga    5220
gagttcttcc tgaaatagtc cgtgaagcca taaaacaag actccgtact gtgatcttag    5280
ctccaaccag ggtcgtcgct gctgaaatgg aggaagcccct tagagggcctt ccagttcgtt    5340 atatgacaac agcagtcaat gtcacccatt ctgggacaga aatcgttgac ttaatgtgcc    5400
atgctaccct tcacttcacgc ctactacaac caatcagagt ccccaactat aatttgtata    5460
ttatggatga ggcccacttc acagatccct caagtatagc agcaagagga tacatttcaa    5520
caagggttga gatgggcgag gcggctgcca tcttcatgac cgccacgcca ccaggaaccc    5580
gtgacgcatt cccggactcc aactcaccaa ttatggacac cgaggtggaa gtcccagaga    5640
gagcctggag cacaggctt gattgggtga cggatcattc tggaaaaca gtctggtttg    5700 ttccaagcgt gaggaacggc aatgagatcg cagcttgtct gacaaaggct ggaaaacggg    5760
tcatacagct cagcagaaag actttttgaga cagagttcca gaaaacgaaa aatcaagagt    5820
gggacttcgt cgtgacaacc gacatttcag agatgggcgc caactttaaa gctgaccgtg    5880
tcatagattc caggagatgc ttaaagccgg tcatacttga tggcgagaga gtcattttgg    5940
ctggacccat gcctgtcaca catgccagcg ctgctcagag gagggggcgc ataggcagga    6000
atcccaacaa acctggagat gagtatctgt atggaggtgg gtgcgcagag actgatgaag    6060
atcacgcaca ctggcttgaa gcaagaatgc ttcttgacaa catttacctc caagatggcc    6120
tcatagcttc gctctatcga cctgaggccg acaaagtagc agctattgag ggagagttca    6180
agcttaggac ggagcaaagg aagaccttg tggaactcat gaaaagagga gatcttccgg    6240
tttggttggc ctatcaggtt gcatctgccg gaataaccta cacagataga agatggtgct    6300
ttgatggcat gaccaacaac accataatgg aagacagtgt gccggcagag gtgtggacca    6360
gatacggaga gaaagagtg ctcaaaccga ggtggatgga cgccagagtt tgttcagatc    6420
atgcggccct gaagtcattc aaagagtttg ccgctgggaa aagaggagcg gcctttggag    6480
tgatagaagc cctgggaaca ctgccaggac acatgacaga gagattccag gaagccattg    6540
acaacctcgc tgtgctcatg cgggcagaga ctggaagcag gccttacaaa gccgcggcgg    6600
cccaattgcc ggagaccta gagaccatta tgctttggg gttgctggga acagtctcgc    6660
tgggaatctt tttcgtcttg atgcggaaca agggcatggg gaagatgggc tttggaatgg    6720
```

```
tgactcttgg ggccagcgca tggcttatgt ggctctcgga aattgagcca gccagaattg    6780
catgtgtcct cattgtcgtg ttcctattgc tggtggtgct cataccctgag ccagaaaagc   6840 aaagatctcc tcaggacaac caaatggcaa tcatcatcat ggtagcagtg ggtcttctgg    6900
gcttgattac cgccaatgaa ctcggatggt tggagagaac aaaaagtgac ctaagccatc    6960
taatgggaag gagagaggag ggggcaacca caggattctc aatggacatt gacctgcggc    7020
cagcctcagc ttgggctatc tatgctgctc tgacaacttt catcacccca gccgtccaac    7080
atgcggtgac cacttcatac aacaactact ccttaatggc gatggccacg caagctgggg    7140
tgttgtttgg tatgggcaaa gggatgccat tctacgcatg ggactttgga gtcccgctgc    7200
taatgatggg ttgctactca caattaacac ctctgaccct aatagtggcc atcattttgc    7260
tcgtggcgca ctacatgtac ttgatcccag ggctgcaggc agcagctgcg cgggctgccc    7320
agaagagaac ggcagctggc atcatgaaga accctgttgt ggatggaata gtggtgactg    7380
acattgacac aatgacaatt gacccccaag tggaaaaaaa gatggggcag gtgctactca    7440
tagcagtagc cgtctccagc gccatactgt cgcggaccgc ctgggggtgg gggaggctg    7500 gggccctgat cacagctgca acttccacct tgtgggaagg ctctccgaac aagtactgga    7560
actcctccac agccacttca ctgtgtaaca ttttttagggg aagttacttg gctggagctt    7620
ctctaatcta cacagtaaca agaaacgctg gcttggtcaa gagacgtggg ggtggaacgg    7680
gagagaccct gggagagaaa tggaaggccc gcctgaacca gatgtcggcc ctggagttct    7740
actcctacaa aaagtcaggc atcaccgagg tgtgcagaga agaggcccgc cgtgccctca    7800
aggacggtgt ggcaacagga ggccatgctg tgtcccgagg aagtgcaaag cttagatggc    7860
tggtggagag aggatacctg cagccctatg gaaaggtcat tgatcttgga tgtggcagag    7920
ggggctggag ttactatgcc gccaccatcc gcaaagttca ggaagtgaaa ggatacacaa    7980
aaggaggccc tggtcatgaa gaacccatgt tggtgcaaag ctatgggtgg aacatagtcc    8040
gtcttaagag tggggtggac gtctttcaca tggcggctga gccgtgtgac actttgctgt    8100
gtgatatagg tgagtcatca tctagtcctg aagtggaaga agcacggacg ctcagagtcc    8160
tctccatggt gggggattgg cttgaaaaaa gaccaggagc cttttgtata aaagtgttgt    8220
gcccatacac cagcactatg atggaaaccc tggagcgact gcagcgtagg tatggggag    8280 gactggtcag ggtgccactc tcccgcaact ctacacatga gatgtactgg gtctctggaa    8340
cgaaaagcaa caccataaaa agtgtgtcca ccacgagcca gctcctcttg gggcgcatgg    8400
acgggcccag gaggccagtg aaatatgagg aggatgtgaa tctcggctct ggcacgcggg    8460
ctgtggtaag ctgcgctgaa gctcccaaca tgaagatcat tggtaaccgc attgagagga    8520
tccgcagtga gcacgcggaa acgtggttct ttgacgagaa ccacccatat aggacatggg    8580
cttaccatgg aagctatgag gcccctacac aagggtcagc gtcctctcta ataaacgggg    8640
ttgtcaggct cctgtcaaaa ccctgggatg tggtgactgg agtcacagga atagccatga    8700
ctgacaccac accgtatggt cagcaaagag ttttcaagga aaaagtggac actagggtgc    8760
cagaccccca agaaggcact cgtcaggtta tgagcatggt ctcttcctgg ttatggaagg    8820
agctaggcaa acacaaacgg ccacgagtct gtaccaagaa agagttcatc aacaaggttc    8880
gtagcaatgc agcattaggg gcaatatttg aagaggaaaa agagtggaag actgcagtgg    8940
aagctgtgaa tgatccaagg ttctgggctc tagtggacaa ggaaagagag catcacctga    9000
gaggagagtg tcagagctgt gtgtacaaca tgatgggaaa aagagaaaag aaacaagggg    9060
```

| | | | | | |
|---|---|---|---|---|---|
| aatttggaaa | ggccaagggc | agccgcgcca | tctggtatat | gtggctaggg | gctagattcc | 9120 |
| tagagttcga | agcccttgga | ttcttgaatg | aggatcattg | gatggggaga | gagaattcag | 9180 |
| gaggtggtgt | tgaaggactg | ggattacaaa | gactcggata | tgtcctagaa | gagatgagtc | 9240 |
| gcataccagg | aggaaggatg | tatgcagatg | atactgctgg | ctgggacacc | cgcatcagca | 9300 |
| ggtttgatct | ggagaatgaa | gctctaatca | ccaaccaaat | ggagaaaggg | cacagggcct | 9360 |
| tggcattggc | cataatcaag | tacacatacc | aaaacaaagt | ggtaaaggtc | cttagaccag | 9420 |
| ctgaaaaagg | gaagacagtt | atggacatta | tttcaagaca | agaccaaagg | gggagcggac | 9480 |
| aagttgtcac | ttacgctctt | aatacattca | ccaacctggt | ggtgcagctc | attcggaata | 9540 |
| tggaggctga | ggaagttcta | gagatgcaag | acttgtggct | gctgcggagg | ccagagaaag | 9600 |
| tgaccaactg | gttgcaaagc | aacggatggg | ataggctcaa | aagaatggca | gtcagtggag | 9660 |
| atgattgcgt | tgtgaaacca | attgatgata | ggtttgcaca | tgccctcagg | ttcttgaatg | 9720 |
| atatgggaaa | agttaggaag | gacacacaag | agtggaaacc | ctcaactgga | tgggacaact | 9780 |
| gggaagaagt | tccgttttgc | tcccaccact | tcaacaaact | ccatcttaag | gacgggaggt | 9840 |
| ccattgtggt | tccctgccgc | caccaagatg | aactgattgg | ccgagcccgc | gtatcaccag | 9900 |
| gggcgggatg | gagcatccgg | gagactgctt | gcctagcaaa | atcatatgcg | caaatgtggc | 9960 |
| agctcctttta | tttccacaga | agggacctcc | gactgatggc | caatgccatt | tgttcatctg | 10020 |
| tgccagttga | ttgggttcca | actgggagaa | ctacctggtc | aatccatgga | aagggagaat | 10080 |
| ggatgaccac | tgaagacatg | cttgtggtat | ggaacagagt | gtggattgag | gaaaacgacc | 10140 |
| acatggaaga | caagacccca | gttacaaaat | ggacagacat | tccctatttg | ggaaaaagag | 10200 |
| aagacttgtg | gtgtggatct | ctcataggg | acagaccgcg | tactacctgg | gctgagaaca | 10260 |
| tcaaaaatac | agtcaacatg | atgcgcagga | tcataggtga | tgaagaaaag | tacatggact | 10320 |
| acctatccac | ccaggttcgc | tacttgggtg | aagaagggtc | cacacctgga | gtgctgtaag | 10380 |
| caccaatctt | agtgttgtca | ggcctgctag | tcagccacag | cttggggaaa | gctgtgcagc | 10440 |
| ctgtgacccc | cccaggagaa | gctgggaaac | caagcctata | gtcaggccga | gaacgccatg | 10500 |
| gcacggaaga | agccatgctg | cctgtgagcc | cctcagagga | cactgagtca | aaaaccccca | 10560 |
| cgcgcttgga | ggcgcaggat | gggaaaagaa | ggtggcgacc | ttccccaccc | ttcaatctgg | 10620 |
| ggcctgaact | ggagatcagc | tgtggatctc | cagaagaggg | actagtggtt | agaggagacc | 10680 |
| ccccggaaaa | cgcaaaacag | catattgacg | ctgggaaaga | ccagagactc | catgagtttc | 10740 |
| caccacgctg | gccgccaggc | acagatcgcc | gaatagcggc | ggccggtgtg | gggaaatcca | 10800 |
| tgggtct | | | | | 10807 |

```
<210> SEQ ID NO 9
<211> LENGTH: 10648
<212> TYPE: DNA
<213> ORGANISM: Zika virus

<400> SEQUENCE: 9
```

| | | | | | |
|---|---|---|---|---|---|
| gacagttcga | gtttgaagcg | aaagctagca | acagtatcaa | caggttttat | ttggatttgg | 60 |
| aaacgagagt | ttctggtcat | gaaaaaccca | aaaagaaat | ccggaggatt | ccggattgtc | 120 |
| aatatgctaa | aacgcggagt | agcccgtgtg | agccccttg | ggggcttgaa | gaggctgcca | 180 |
| gccggacttc | tgctgggtca | tgggcccatc | aggatggtct | tggcgattct | agccttttg | 240 |
| agattcacgg | caatcaagcc | atcactgggt | ctcatcaata | gatggggttc | agtggggaaa | 300 |
| aaagaggcta | tggaaataat | aaagaagttc | aagaaagatc | tggctgccat | gctgagaata | 360 |

```
atcaatgcta ggaaggagaa gaagagacga ggcgcagata ctagtgtcgg aattgttggc    420
ctcctgctga ccacagctat ggcagcggag gtcactagac gtgggagtgc atactatatg    480
tacttggaca gaaacgatgc tggggaggcc atatcttttc caaccacatt ggggatgaat    540
aagtgttata tacagatcat ggatcttgga cacatgtgtg atgccaccat gagctatgaa    600
tgccctatgc tggatgaggg ggtggaacca gatgacgtcg attgttggtg caacacgacg    660
tcaacttggg ttgtgtacgg aacctgccat cacaaaaaag gtgaagcacg gagatctaga    720
agagctgtga cgctcccctc ccattccact aggaagctgc aaacgcggtc gcaaacctgg    780
ttggaatcaa gagaatacac aaagcacttg attagagtcg aaaattggat attcaggaac    840
cctggcttcg cgttagcagc agctgccatc gcttggcttt tgggaagctc aacgagccaa    900
aaagtcatat acttggtcat gatactgctg attgccccgg catacagcat caggtgcata    960
ggagtcagca atagggactt tgtggaaggt atgtcaggtg ggacctgggt tgatgttgtc   1020
ttggaacatg gaggttgtgt caccgtaatg gcacaggaca aaccgactgt cgacatagag   1080
ctggttacaa caacagtcag caacatggcg gaggtaagat cctactgcta tgaggcatca   1140
atatcagaca tggcttcgga cagccgctgc ccaacacaag gtgaagccta ccttgacaag   1200
caatcagaca ctcaatatgt ctgcaaaaga acgttagtgg acagaggctg gggaaatgga   1260
tgtggacttt ttggcaaagg gagcctggtg acatgcgcta agtttgcatg ctccaagaaa   1320
atgaccggga agagcatcca gccagagaat ctggagtacc ggataatgct gtcagttcat   1380
ggctcccagc acagtgggat gattgttaat gacacaggac atgaaactga tgagaataga   1440
gcgaaagttg agataacgcc caattcacca agagccgaag ccaccctggg gggttttgga   1500
agcctaggac ttgattgtga accgaggaca ggccttgact tttcagattt gtattacttg   1560
actatgaata caagcactg gttggttcac aaggagtggt tccacgacat tccattacct   1620
tggcacgctg gggcagacac cggaactcca cactggaaca caaagaagc actggtagag   1680 ttcaaggacg cacatgccaa aaggcaaact gtcgtggttc tagggagtca agaaggagca   1740
gttcacacgg cccttgctgg agctctggag gctgagatgg atggtgcaaa gggaaggctg   1800
tcctctggcc acttgaaatg tcgcctgaaa atggataaac ttagattgaa gggcgtgtca   1860
tactccttgt gtactgcagc gttcacattc accaagatcc cggctgaaac actgcacggg   1920
acagtcacag tggaggtaca gtacgcaggg acagatggac cttgcaaggt tccagctcag   1980
atggcggtgg acatgcaaac tctgaccccca gttgggaggt tgataaccgc taaccccgta   2040
atcactgaaa gcactgagaa ctcaagatg atgctgaac ttgatccacc atttgggac    2100 tcttacattg tcataggagt cggggagaag aagatcaccc accactggca caggagtggc   2160
agcaccattg gaaaagcatt tgaagccact gtgagaggtg ccaagagaat ggcagtcttg   2220
ggagacacag cctgggactt tggatcagtt ggaggcgctc tcaactcatt gggcaagggc   2280
atccatcaaa ttttttggagc agctttcaaa tcattgtttg gaggaatgtc ctggttctca   2340
caaattctca ttggaacgtt gctgatgtgg ttgggtctga acacaaagaa tggatctatt   2400
tcccttatgt gcttggcctt agggggagtg ttgatcttct tatccacagc cgtctctgct   2460
gatgtggggt gctcggtgga cttctcaaag aaggagacga gatgcggtac aggggtgttc   2520
gtctataacg acgttgaagc ctggagggac aggtacaagt accatcctga ctccccccgt   2580
agattggcag cagcagtcaa gcaagcctgg gaagatggta tctgcgggat ctcctctgtt   2640
tcaagaatgg aaaacatcat gtggagatca gtagaagggg agctcaacgc aatcctggaa   2700
```

```
gagaatggag ttcaactgac ggtcgttgtg ggatctgtaa aaaaccccat gtggagaggt    2760
ccacagagat tgcccgtgcc tgtgaacgag ctgccccacg gctggaaggc ttgggggaaa    2820
tcgtacttcg tcagagcagc aaagacaaat aacagctttg tcgtggatgg tgacacactg    2880
aaggaatgcc cactcaaaca tagagcatgg aacagctttc ttgtggagga tcatgggttc    2940
ggggtatttc acactagtgt ctggctcaag gttagagaag attattcatt agagtgtgat    3000
ccagccgtta ttggaacagc tgttaaggga aaggaggctg tacacagtga tctaggctac    3060
tggattgaga gtgagaagaa tgacacatgg aggctgaaga gggcccatct gatcgagatg    3120
aaaacatgtg aatggccaaa gtcccacaca ttgtggacag atggaataga agagagtgat    3180
ctgatcatac ccaagtcttt agctgggcca ctcagccatc acaataccag agagggctac    3240
aggacccaaa tgaaagggcc atggcacagt gaagagcttg aaattcggtt tgaggaatgc    3300
ccaggcacta aggtccacgt ggaggaaaca tgtggaacaa gaggaccatc tctgagatca    3360
accactgcaa gcggaagggt gatcgaggaa tggtgctgca gggagtgcac aatgccccca    3420
ctgtcgttcc gggctaaaga tggctgttgg tatggaatgg agataaggcc caggaaagaa    3480
ccagaaagca acttagtaag gtcaatggtg actgcaggat caactgatca catggaccac    3540
ttctcccttg gagtgcttgt gattctgctc atggtgcagg aagggctgaa gaagagaatg    3600
accacaaaga tcatcataag cacatcaatg gcagtgctgg tagctatgat cctgggagga    3660
ttttcaatga gtgacctggc taagcttgca attttgatgg gtgccacctt cgcggaaatg    3720
aacactggag gagatgtagc tcatctggcg ctgatagcgg cattcaaagt cagaccagcg    3780
ttgctggtat ctttcatctt cagagctaat tggacacccc gtgaaagcat gctgctggcc    3840
ttggcctcgt gtcttttgca aactgcgatc tccgccttgg aaggcgacct gatggttctc    3900
atcaatggtt ttgctttggc ctggttggca atacgagcga tggttgttcc acgcactgat    3960
aacatcacct tggcaatcct ggctgctctg acaccactgg cccggggcac actgcttgtg    4020
gcgtggagag caggccttgc tacttgcggg gggtttatgc tcctctctct gaagggaaaa    4080
ggcagtgtga agaagaactt accatttgtc atggcctgg gactaaccgc tgtgaggctg    4140
gtcgacccca tcaacgtggt gggactgctg ttgctcacaa ggagtgggaa gcggagctgg    4200 cccccctagcg aagtactcac agctgttggc ctgatatgcg cattggctgg agggttcgcc    4260
aaggcagata tagagatggc tgggcccatg gccgcggtcg gtctgctaat tgtcagttac    4320
gtggtctcag gaaagagtgt ggacatgtac attgaaagag caggtgacat cacatgggaa    4380
aaagatgcgg aagtcactgg aaacagtccc cggctcgatg tggcgctaga tgagagtggt    4440
gatttctccc tggtggagga tgacggtccc cccatgagag agatcatact caaggtggtc    4500
ctgatgacca tctgtggcat gaacccaata gccatacccc ttgcagctgg agcgtggtac    4560
gtatacgtga agactggaaa aaggagtggt gctctatggg atgtgcctgc tcccaaggaa    4620
gtaaaaaagg gggagaccac agatggagtg tacagagtaa tgactcgtag actgctaggt    4680
tcaacacaag ttggagtggg agttatgcaa gagggggtct ttcacactat gtggcacgtc    4740
acaaaaggat ccgcgctgag aagcggtgaa gggagacttg atccatactg gggagatgtc    4800
aagcaggatc tggtgtcata ctgtggtcca tggaagctag atgccgcctg gacgggcac    4860 agcgaggtgc agctcttggc cgtgccccc ggagagagag cgaggaacat ccagactctg    4920
cccggaatat ttaagacaaa ggatgggac attggagcgg ttgcgctgga ttacccagca    4980
ggaacttcag gatctccaat cctagacaag tgtgggagag tgataggact ttatggcaat    5040
ggggtcgtga tcaaaaatgg gagttatgtt agtgccatca cccaagggag gagggaggaa    5100
```

```
gagactcctg ttgagtgctt cgagccttcg atgctgaaga agaagcagct aactgtctta      5160
gacttgcatc ctggagctgg gaaaaccagg agagttcttc ctgaaatagt ccgtgaagcc      5220
ataaaaacaa gactccgtac tgtgatctta gctccaacca gggttgtcgc tgctgaaatg      5280
gaggaggccc ttagagggct tccagtgcgt tatatgacaa cagcagtcaa tgtcacccac      5340
tctggaacag aaatcgtcga cttaatgtgc catgccacct tcacttcacg tctactacag      5400
ccaatcagag tccccaacta taatctgtat attatggatg aggcccactt cacagatccc      5460
tcaagtatag cagcaagagg atacatttca acaaggggttg agatgggcga ggcggctgcc      5520
atcttcatga ccgccacgcc accaggaacc cgtgacgcat ttccggactc caactcacca      5580
attatggaca ccgaagtgga agtcccagag agagcctgga gctcaggctt tgattgggtg      5640
acggatcatt ctggaaaaac agtttggttt gttccaagcg tgaggaacgg caatgagatc      5700
gcagcttgtc tgacaaaggc tggaaaacgg gtcatacagc tcagcagaaa gacttttgag      5760
acagagttcc agaaaacaaa acatcaagag tgggactttg tcgtgacaac tgacatttca      5820
gagatgggcg ccaactttaa agctgaccgt gtcatagatt ccaggagatg cctaaagccg      5880
gtcatacttg atgcgagag agtcattctg gctggaccca tgcctgtcac acatgccagc      5940
gctgcccaga ggaggggcg cataggcagg aatcccaaca aacctggaga tgagtatctg      6000 tatgaggtg ggtgcgcaga gactgacgaa gaccatgcac actggcttga agcaagaatg      6060
ctccttgaca atatttacct ccaagatggc ctcatagcct cgctctatcg acctgaggcc      6120
gacaaagtag cagccattga gggagagttc aagcttagga cggagcaaag gaagaccttt      6180
gtggaactca tgaaaagagg agatcttcct gtttggctgg cctatcaggt tgcatctgcc      6240 ggaataaacct acacagatag aagatggtgc tttgatggca cgaccaacaa caccataatg      6300
gaagacagtg tgccggcaga ggtgtggacc agacacggag agaaaagagt gctcaaaccg      6360
aggtggatgg acgccagagt ttgttcagat catgcggccc tgaagtcatt caaggagttt      6420
gccgctggga aaagaggagc ggcttttgga gtgatggaag ccctgggaac actgccagga      6480
cacatgacag agagattcca ggaagccatt gacaacctcg ctgtgctcat gcgggcagag      6540
actggaagca ggccttacaa agccgcggcg gcccaattgc cggagaccct agagaccatt      6600
atgctttggg ggttgctggg aacagtctcg ctgggaatct tcttcgtctt gatgaggaac      6660
aagggcatag gaagatggg ctttggaatg gtgactcttg gggccagcgc atggctcatg      6720
tggctctcgg aaattgagcc agccagaatt gcatgtgtcc tcattgttgt gtttctattg      6780
ctggtggtgc tcatacctga gccagaaaag caaagatctc cccaggacaa ccaaatggca      6840
atcatcatca tggtagcagt aggtcttctg gcttgattta ccgccaatga actcggatgg      6900
ttggagagaa caaagagtga cctaagccat ctaatgggaa ggagagagga ggggcaacc      6960 ataggattct caatggacat tgacctgcgg ccagcctcag cttgggccat ctatgctgcc      7020
ttgacaactt tcattacccc agccgtccaa catgcagtga ccacttcata caacaactac      7080
tccttaatgg cgatggccac gcaagctgga gtgttgtttg gtatgggcaa agggatgcca      7140
ttctacgcat gggacttttgg agtcccgctg ctaatgatag gttgctactc acaattaaca      7200
cccctgaccc taatagtggc catcattttg ctcgtggcgc actacatgta cttgatccca      7260
gggctgcagg cagcagctgc gcgtgctgcc cagaagagaa cggcagctgg catcatgaag      7320
aaccctgttg tggatggaat agtggtgact gacattgaca caatgacaat tgaccccaa      7380 gtggagaaaa agatgggaca ggtgctactc atagcagtag ccgtctccag cgccatactg      7440
```

```
tcgcggaccg cctgggggtg gggggaggct ggggccctga tcacagccgc aacttccact   7500
ttgtgggaag gctctccgaa caagtactgg aactcctcta cagccacttc actgtgtaac   7560 attttaggg gaagttactt ggctggagct tctctaatct acacagtaac aagaaacgct     7620
ggcttggtca agagacgtgg gggtggaaca ggagagaccc tgggagagaa atggaaggcc   7680
cgcttgaacc agatgtcggc cctggagttc tactcctaca aaagtcagg catcaccgag    7740 gtgtgcagag aagaggcccg ccgcgccctc aaggacggtg tggcaacggg aggccatgct   7800
gtgtcccgag gaagtgcaaa gctgagatgg ttggtggagc ggggatacct gcagccctat   7860
ggaaaggtca ttgatcttgg atgtggcaga ggggctgga gttactacgc cgccaccatc     7920
cgcaaagttc aagaagtgaa aggatacaca aaaggaggcc ctggtcatga agaacccgtg   7980
ttggtgcaaa gctatgggtg gaacatagtc cgtcttaaga gtggggtgga cgtctttcat   8040
atggcggctg agccgtgtga cacgttgctg tgtgacatag gtgagtcatc atctagtcct   8100
gaagtggaag aagcacggac gctcagagtc ctctccatgg tgggggattg gcttgaaaaa   8160
agaccaggag ccttttgtat aaaggtgttg tgcccataca ccagcactat gatggaaacc   8220
ctggagcgac tgcagcgtag gtatggggga ggactggtca gagtgccact ctcccgcaac   8280
tctacacatg agatgtattg ggtctctgga gcgaaaagca acaccataaa aagtgtgtcc   8340
accacgagcc agctcctctt ggggcgcatg gacgggccta ggaggccagt gaaatatgag   8400
gaggatgtga atctcggctc tggcacgcgg gctgtggtaa gctgcgctga agctcccaac   8460
atgaagatca ttggtaaccg cattgaaagg atccgcagtg agcacgcgga acgtggttc    8520 tttgacgaga accacccata taggacatgg gcttaccatg gaagctatga gccccccaca   8580
caagggtcag cgtcctctct aataaacggg gttgtcaggc tcctgtcaaa accctgggat   8640
gtggtgactg gagtcacagg aatagccatg accgacacca caccgtatgg tcagcaaaga   8700
gttttcaagg aaaaagtgga cactagggtg ccagaccccc aagaaggcac tcgtcaggtt   8760
atgagcatgt tctcttcctg gttgtggaaa gagctaggca acacaaacg gccacgagtc    8820 tgtaccaaag aagagttcat caacaaggtt cgtagcaatg cagcattagg ggcaatattt   8880
gaagaggaaa aagagtggaa gactgcagtg gaagctgtga acgatccaag gttctgggct   8940
ctagtggata aggaaagaga gcaccacctg agaggagagt gccagagttg tgtgtacaac   9000
atgatgggaa aaagagaaaa gaaacaaggg gaatttggaa aggccaaggg cagccgcgcc   9060
atctggtata tgtggctagg gctagatt ctagagttcg aagcccttgg attcttgaac    9120
gaggatcact ggatggggag agagaactca ggaggtggtg ttgaagggct gggattacaa   9180
agactcggat atgtcctaga agagatgagt cgtataccag aggaaggat gtatgcagat    9240 gacactgctg gctgggacac ccgcatcagc aggtttgatc tggagaatga agctctaatc   9300
accaaccaaa tggaaaaagg gcacagggcc ttggcattgg ccataatcaa gtacacatac   9360
caaaacaaag tggtaaaggt ccttagacca gctgaaaaag ggaaaacagt tatggacatt   9420
atttcgagac aagaccaaag ggggagcgga caagttgtca cttacgctct taacacatt    9480 accaacctag tggtgcaact cattcggaat atggaggctg aggaagttct agagatgcaa   9540
gacttgtggc tgctgcggag gtcagagaaa gtgaccaact ggttcagag caacggatgg   9600 gataggctca aacgaatggc agtcagtgga gatgattgcg ttgtgaagcc aattgatgat   9660
aggtttgcac atgccctcag gttcttgaat gatatgggaa agttaggaa ggacacacaa    9720 gagtggaaac cctcaactgg atgggacaac tgggaagaag ttccgttttg ctcccaccac   9780
ttcaacaagc tccatctcaa ggacgggagg tccattgtgg ttccctgccg ccaccaagat   9840
```

```
gaactgattg gccgggcccg cgtctctcca ggggcgggat ggagcatccg ggagactgct    9900
tgcctagcaa aatcatatgc gcaaatgtgg cagctccttt atttccacag aagggacctc    9960
cgactgatgg ccaatgccat ttgttcatct gtgccagttg actgggttcc aactgggaga   10020
actacctggt caatccatgg aaagggagaa tggatgacca ctgaagacat gcttgtggtg   10080
tggaacagag tgtggattga ggagaacgac cacatggaag acaagacccc agttacgaaa   10140
tggacagaca tccctatt ttggaaaagg gaagacttgt ggtgtggatc tctcataggg      10200
cacagaccgc gcaccacctg ggctgagaac attaaaaaca cagtcaacat ggtgcgcagg   10260
atcataggtg atgaagaaaa gtacatggac tacctatcca cccaagttcg ctacttgggt   10320
gaagaagggt ctacacctgg agtgctgtaa gcaccagtct taatgttgtc aggcctgcta   10380
gtcagccaca gcttggggaa agctgtgcag cctgtgaccc ccccaggaga agctgggaaa   10440
ccaagcctat agtcaggccg agaacgccat ggcacggaag aagccatgct gcctgtgagc   10500
ccctcagagg acactgagtc aaaaaacccc acgcgcttgg aggcgcagga tgggaaaaga   10560
aggtggcgac cttccccacc cttcaatctg gggcctgaac tggagatcag ctgtggatct   10620
ccagaagagg gactagtggt tagaggag                                       10648
```

<210> SEQ ID NO 10
<211> LENGTH: 10676
<212> TYPE: DNA
<213> ORGANISM: Zika virus

<400> SEQUENCE: 10

```
gttgttactg ttgctgactc agactgcgac agttcgagtt tgaagcgaaa gctagcaaca      60
gtatcaacag ttttatttg gatttggaaa cgagagtttc tggtcatgaa aacccaaaa     120 aagaaatccg gaggattccg gattgtcaat atgctaaaac gcggagtagc ccgtgtgagc    180 cccctttgggg gcttgaagag gctgccagcc ggacttctgc tgggtcatgg gcccatcagg    240
atggtcttgg caattctagc ctttttgaga ttcacggcaa tcaagccatc actgggtctc    300
atcaatagat ggggttcagt ggggaaaaaa gatgctatgg aaataataaa gaagttcaag    360
aaagatctgg ctgccatgct gagaataatc aatgctagga aggagaagaa gagacgaggc    420
gcagatacta gtgtcggaat tgttggcctc ctgctgacca cagctatggc agcggaggtc    480
actagacgtg ggagtgcata ctatatgtac ttggacagaa cgatgctggg gaggccata    540 tcttttccaa ccacattggg gatgaataag tgttatatac agatcatgga tcttggacac    600
atgtgtgatg ccaccatgag ctatgaatgc cctatgctgg atgaggggt ggaaccagat    660 gacgtcgatt gttggtgcaa cacgacgtca acttgggttg tgtacggaac ctgccatcac    720
aaaaaaggtg aagcacggag atctagaaga gctgtgacgc tcccttccca ttccactagg    780
aagctgcaaa cgcggtcgca aacctggttg gaatcaagag aatacacaaa gcacttgatt    840
agagtcgaaa attggatatt caggaaccct ggcttcgcgt tagcagcagc tgccatcgct    900
tggcttttgg gaagctcaac gagccaaaaa gtcatatact tggtcatgat actgctgatt    960
gccccggcat acagcatcag gtgcatagga gtcagcaata gggactttgt ggaaggtatg   1020
tcaggtggga cttgggttga tgttgtcttg gaacatggag gttgtgtcac cgcaatggca   1080
caggacaaac cgactgtcga catagagctg gttacaacaa cagtcagcaa catggcggag   1140
gtaagatcct actgctatga ggcatcaata tcagacatgg cttcggacag ccgctgccca   1200
acacaaggtg aagcctacct tgacaagcaa tcagacactc aatatgtttg caaaagaacg   1260
```

```
ttagtggaca gaggctgggg aaatggatgt ggacttttg gcaaagggag tctggtgaca      1320
tgcgctaagt ttgcatgctc caagaaaatg accgggaaga gcatccagcc agagaatctg      1380
gagtaccgga taatgctgtc agttcatggc tcccagcaca gtgggatgct cgttaatgac      1440
acaggacatg aaactgatga gaatagagcg aaggttgaga taacgcccaa ttcaccaaga      1500
gccgaagcca ccctgggggg ttttggaagc ctaggacttg attgtgaacc gaggacaggc      1560
cttgactttt cagatttgta ttacttgact atgaataaca agcactggtt ggctcacaag      1620
gagtggttcc acgacattcc attaccttgg cacgctgggg cagccaccgg aactccacac      1680
tggaacaaca aagaagcact ggtagagttc aaggacgcac atgccaaaag gcaaactgtc      1740
gtggttctag ggagtcaaga aggagcagtt cacacggccc ttgctggagc tctggaggct      1800
gagatggatg tgcaaaggg aaggctgtcc tctggccact tgaaatgtcg cctgaaaatg      1860
gataaactta gattgaaggg cgtgtcatac tccttgtgta ccgcagcgtt cacattcacc      1920
aagatcccgg ctgaaacagt ggacgggaca gtcacagtgg agggacagta cggagggaca      1980
gatgggacctt gcaaggttcc agctcagatg gcggtggaca tgcagactct gaccccagtt      2040
gggaggttga taaccgctaa ccccgtaatc actgaaagca ctgagaactc taagatgatg      2100
ctggaacttg atccaccatt tggggactct tacattgtca taggagtcgg ggagaagaag      2160
atcacccacc actggcacag gagtggcagc accattggaa aagcatttga agccactgtg      2220
agaggtgcca agagaatggc agtcttggga gacacagcct gggactttgg atcagttgga      2280
ggcgctctca actcattggg caagggcatc catcaaatta ttggagcagc tttcaaatca      2340
ttgtttggag aatgtcctg ttctcacaa attctcattg gacgttgct gatgtggttg      2400
ggtctgaaca caaagaatgg atctatttcc cttatgtgct tggccttagg gggagtgttg      2460
atcttcttat ccacagccgt ctcaggtggt gtggggtgct cggtggactt ctcaaagaag      2520
gagacgagat gcggtacagg ggtgttcgtc tataacgatg ttgaagcctg agggacagg      2580
tacaagtacc atcctgactc ccccgtaga ttggcagcag cagtcaagca agcctgggaa      2640
gatggtatct gcgggatctc ctctgtttca agaatggaaa acatcatgtg gagatcagta      2700
gaagggagc tcaacgcaat cctggaagag aatggagttc aactgacggt cgttgtggga      2760
tctgtaaaaa accccatgtg gagaggtcca cagagattgc ccgtgcctgt gaacgagctg      2820
ccccacgggct ggaaggcttg ggggaaatcg tacttcgtca gagcagcaaa gacaaataac      2880
agctttgtcg tggatggtga cacactgaag gaatgcccac tcaaacatag agcatggaac      2940
agctttcttg tggaggatca tgggttcggg gtatttcaca ctagtgtctg gctcaaggtt      3000
agagaagact attggttaga gtgtgatcca gccgttattg gaacagctgt taagggaaag      3060
gaggctgtac acagtgatct aggctactgg attgagagtg agaagaatga cacatggtgg      3120
ctgaagaggg cccatctgat cgagatgaaa acatgtgaat ggccaaagtc ccacacattg      3180
tggacagatg gaatagaaga gagtgatctg atcataccca gtctttagc tgggccactc      3240
agccatcaca atgccagaga gggctacagg acccaaatga aagggccatg gcacagtgaa      3300
gagcttgaaa ttcggtttga ggaatgccca ggcactaagg tccacgtgga ggaaacatgt      3360
ggaacaagag gaccatctct gagatcaacc actgcaagcg gaagggtgat cgaggaatgg      3420
tgctccaggg agtgcacaat gccccactg tccttccagg ctaaagatgg ctgttggtat      3480
ggaatggaga taaggcccag gaaagaacca gaaagcaact tagtaaggtc aatggtgact      3540
gcaggatcaa ctgatcacat ggatcacttc tcccttggag tgcttgtgat tctgctcatg      3600
gtgcaggaag ggctgaagaa gagaatgacc acaaagatca tcataagcac atcaatggca      3660
```

-continued

```
gtgctggtag ctatgatcct gggaggattt tcaatgagtg acctggctaa gcttgcaatt    3720
ttgatgggtg ccaccttcgc ggaaatgaac actggaggag atgtagctca tctggcgctg    3780
atagcggcat tcaaagtcag accagcgttg ctggtatctt tcatcttcag agctaattgg    3840
acaccccgtg aaagcatgct gctggccttg gcctcgtgtc ttttgcaaac tgcgatctcc    3900
gccttggaag gcgacctgat ggttctcatc aatggttttg ctttggcctg gttggcaata    3960
cgagcgatgg ttgttccacg cactgataac atcaccttag caatcctggc tgctctgaca    4020
ccactggccc ggggcacact gcttgtggcg tggagagcag gccttgctac ttgcgggggg    4080
tttatgctcc tctctctgaa gggaaaaggc agtgtgaaga agaacttacc atttgtcatg    4140
gccctgggac taaccgctgt gaggctggtc gaccccatca acgtggtggg actgctgttg    4200
ctcacaagga gtgggaagcg gagctggccc cctagcgaag tactcacagc tgttggcctg    4260
atatgcgcat tggctggagg gttcgccaag gcagatatag agatggctgg gcccatggcc    4320
gcggtcggtc tgctaattgt cagttacgtg gtctcaggaa agagtgtgga catgtacatt    4380
gaaagagcag gtgacatcac atgggaaaaa gatgcggaag tcactggaaa cagtccccgg    4440
ctcgatgtgg cgctagatga gagtggtgat ttctccctgg tggaggatga cggtccccc    4500
atgagagaga tcatactcaa ggtggtcctg atgaccatct gtggcatgaa cccaatagcc    4560
atacccttg cagctggagc gtggtacgta tacgtgaaga ctggaaaaag gagtggtgct    4620
ctatgggatg tgcctgctcc caaggaagta aaaaggggg agaccacaga tggagtgtac    4680
agagtaatga ctcgcagact gctaggttca acacaagttg gagtgggagt tatgcaagag    4740
ggggtctttc acactatgtg gcacgtcaca aaaggatccg cgctgagaag cggtgaaggg    4800
agacttgatc catactgggg agatgtcaag caggatctgg tgtcatactg tggtccatgg    4860
aagctagatg ccgcctggga cgggcacagc gaggtgcagc tcttggccgt gccccccgga    4920
gagagagcga ggaacatcca gactctgccc ggaatattta agacaaagga tgggacatt    4980
ggagcggttg cactggatta cccagcagga acttcaggat ctccaatcct agacaagtgt    5040
gggagagtga taggactta tggcaatggg gtcgtgatca aaaatgggag ttatgttagt    5100
gccatcaccc aagggaggag ggaggaagag actcctgttg agtgcttcga gccttcgatg    5160
ctgaagaaga agcagctaac tgtcttagac ttgcatcctg gagctgggaa accaggaga    5220
gttcttcctg aaatagtccg tgaagccata aaaacaagac tccgtactgt gatcttggct    5280
ccaaccaggg ttgtcgctgc tgaaatggag gaggccctta gggcttcc agtgcgttat    5340
atgacaacag cagtcaatgt cacccactct ggaacagaaa tcgtcgactt aatgtgccat    5400
gccaccttca cttcacgtct actacagcca attagagtcc ccaactataa tctgtatatt    5460
atggatgagg cccacttcac agatccctca agtatagcag caagaggata catttcaaca    5520
agggttgaga tgggcgaggc ggctgccatc ttcatgaccg ccacgccacc aggaaccegt    5580
gacgcatttc cggactccaa ctcaccaatt atggacaccg aagtggaagt cccagagaga    5640
gcctggagct caggctttga ttgggtgacg gagtattctg gaaaaacagt ttggtttgtt    5700
ccacgcgtga ggaacggcaa tgagatcgcc gcttgtctga caaaggctgg aaaacgggtc    5760
atacagctca gcagaaagac ttttgagaca gagttccaga aacaaaaaca tcaagagtgg    5820
gactttgtcg tgacaactga catttcagag atgggcgcca actttaaagc tgaccgtgtc    5880
atagattcca ggagatgcct aaagccggtc atacttggtg gcgagagagt cattctggct    5940
ggacccatgc ctgtcacaca tgccagcgct gcccagagga gggggcgcat aggcaggaat    6000
```

```
cccaacaaac ctggagatga gtatctgtat ggaggtgggt gcgcagagac tgacgaagac    6060
catgcacact ggcttgaagc aagaatgctc cttgacaata tttacctcca agatggcctc    6120
atagcctcgc tctatcgacc tgaggccgac aaagtagcag ccattgaggg agagttcaag    6180
cttaggacga agcaaaggaa gacctttgtg gaactcatga aaagaggaga tcttcctgtt    6240
tggctggcct atcaggttgc atctgccgga ataacctaca cagatagaag atggtgcttt    6300
gatggcacga ccaacaacac cataatggaa gacagtgtgc cggcagaggt gtggaccaga    6360
cacggagaga aaagagtgct caaaccgagg tggatggacg ccagagtttg ttcagatcat    6420
gcggccctga agtcattcaa ggagtttgcc gctgggaaaa gaggagcggc ttttggagtg    6480
atggaagccc tgggaacact gccaggacac atgacagaga gattccagga agccattgac    6540
aacctcgctg tgctcatgcg ggcagagact ggaagcaggc cttacaaagc cgcggcggcc    6600
caattgccgg agaccctaga gaccattatg cttttggggt tgctgggaac agtctcgctg    6660
ggaatctttt tcgtcttgat gaggaacaag ggcataggga agatgggctt tggaatggtg    6720
actcttgggg ccagcgcatg gctcatgtgg ctctcggaaa ttgagccagc cagaattgca    6780
tgtgtcctca ttgttgtgtt cctattgctg gtggtgctca tacctgagcc agaaaagcaa    6840
agatctcccc aggacaacca aatggccatc atcatcatgg tagcagtagg tcttctgggc    6900
ttgattaccg ccaatgaact cggatggttg gagagaacaa agagtgacct aagccatcta    6960
atgggaagga gagaggaggg ggcaaccatg ggattctcaa tggacattga cctgcggcca    7020
gcctcagctt gggccatcta tcctgccttg acatctttca ttaccccagc cgtccaacat    7080
gcagtgacca cttcatacaa caactactcc ttaatggcga tggccacgca agctggagtg    7140
ttgtttggta tgggcaaagg gatgccattc tacgcatggg actttggagt cccgctgcta    7200
atgatagctt gctactcaca attaacgccc ctgaccctaa tagtggccat cattttgctc    7260
gtggcgcact acatgtactt gatcccaggg ctgcaggcag cagctgcgcg tgctgcccag    7320
aagagaacgg cagctggcat catgaagaac cctgttgtgg agggaatagt ggtgactgac    7380
attgacacaa tgacaattga cccccaagtg gagaaaaaga tgggacaggt gctactcatg    7440
gcagtagccg tctccagcgc catactgtcg aggaccgcct gggggtgggg ggaggctggg    7500
gccctgatca cagccgcaac ttccactttg tgggaaggct ctccgaacaa gtactggaac    7560
tcctctacag ccacctcact gtgtaacatt tttagggga gttacttggc tggagcttct    7620
ctaatctaca cagtaacaag aaacgctggc ttggtcaaga cgtgggggg tggaacagga    7680 gagaccctgg gagagaaatg gaaggcccgc ttgaaccaga tgtcggccct ggagttctac    7740
tcctacaaaa agtcaggcat caccgaggtg tgcagagaag aggcccgccg cgccctcaag    7800
gacggtgtgg caacgggagg ccatgctgtg tcccgaggaa gtgcaaagct gagatggttg    7860
gtggagcggg ataccctgca gccctatgga aaggtcattg atcttggatg tggcagaggg    7920
ggctggagtt actacgccgc caccatccgc aaagttcaag aagtgaaagg atacacaaaa    7980
ggaggccctg gtcatgaaga acccgtgttg gtgcaaagct atgggtggaa catagtccgt    8040
cttaagagtg gggtggacgt cttttcatatg gcggctgagc cgtgtgacac gttgctgtgt    8100
gacataggtg agtcatcatc tagtcctgaa gtggaagaag cacggacgct cagagtcctc    8160
tccatggtgg gggattggct tgaaaaaaga ccaggagcct tttgtataaa agtgttgtgc    8220
ccatacacca gcactatgat ggaaaccctg agcgactgc agcgtaggta tggggagga    8280 ctggtcagag tgccactctc ccgcaactct acacatgaga tgtactgggt ctctggagcg    8340
aaaagcaaca ccataaaaag tgtgtccacc acgagccagc tcctcttggg gcgcatggac    8400
```

```
gggcctagga ggccagtgaa atatgaggag gatgtgaatc tcggctctgg cacgcgggct   8460
gtggtaagct gcgctgaagc tcccaacatg aagatcattg gtaaccgcat tgaaaggatc   8520
cgcgctgaga aagcggaaac gtggttcttt gacgagaacc acccatatag gacatgggct   8580
taccatggaa gctatgatgc cgccacacaa gggtcagcgt cctctctaat aaacggggtt   8640
gtcaggctcc tgtcaaaacc ctgggatgtg gtgactggag tcacaggaat agccatgacc   8700
gacaccacac cgtatggtca gcaaagagtt ttcaaggaaa aagtggacac tagggtgcca   8760
gacccccaag aaggcactcg tcaggttatg agcatggtct cttcctggtt gtggaaagag   8820
ctaggcaaac acaaacggcc acgagtctgt accaaagaag agttcatcaa caaggttcgt   8880
agcaatgcag cattaggggc aatatttgaa gaggaaaaag agtggaagac tgcagtggaa   8940
gctgtgaacg atccaaggtt ctgggctcta gtggacaagg aaagagagca ccacctgaga   9000
ggagagtgcc agagttgtgt gtacatcaca atgggaaaaa gagaaaagaa caaggggaa    9060
tttggaaagg ccaagggcag ccgcgccatc tggtatatgt ggctagggc tagatttcta    9120
gagttcgaag cccttggatt cttgaacgag gatcactgga tggggagaga gaactcagga   9180
ggtggtgttg aagggctggg attacaaaga ctcggatatg tcctagaaga gatgagtcgc   9240
ataccaggag gaaggatgta tgcagatgac actgctggct gggacacccg catcagcagg   9300
tttgatctgg agaatgaagc tctaatcacc aaccaaatgg agaaagggca cagggccttg   9360
gcattggcca taatcaagta cacataccaa aacaaagtgg taaaggtcct tagaccagct   9420
gaaaaaggga gacagttat ggacattatt tcgagacaag accaaggggg agcggacaa     9480
gttgtcactt acgctctcaa cacatttacc aacctagtgg tgcaactcat tcggaatatg   9540
gaggctgagg aagttctaga gatgcaagac ttgtggctgc tgcggaggtc agagaaagtg   9600
accaactggt tgcagagcaa cggatgggat aggctcaaac gaatggcggt cagtggagat   9660
gattgcgttg tgaaaccaat tgatgatagg tttgcacatg ccctcaggtt cttgaatgat   9720
atgggaaaag ttaggaagga cacacaagag tggaaaccct caactggatg ggacaactgg   9780
gaagaagttc ccttctgctc ccaccacttc aacaagctcc atctcaagga cgggaggtcc   9840
attgtggttc cctgccgcca ccaagatgaa ctgattggcc gggcccgcgt ctctccaggg   9900
gcgggatgga gcatccggga gactgcttgc ctagcaaaat catatgcgca aatgtggcag   9960
ctcctttatt tccacagaag ggacctccga ctgatggcca atgccatttg ttcatctgtg   10020
ccagttgact gggttccaac tgggagaact acctggtcaa tccatggaaa gggagaatgg   10080
atgaccactg aagacatgct tgtggcgtgg aacagagtgt ggattgagga gaacgaccac   10140
atggaagaca gacccccagt cacgaaatgg acagacattc cctatttggg aaaagggaa    10200
gacttgtggt gtgatctct cataggggcac agaccgcgca ccacctgggc tgagaacatt   10260
aaaaacacag tcaacatggt gcgcaggatc ataggtgatg aagaaaagta catggactac   10320
ctatccaccc aagttcgcta cttgggtgaa gaagggtcta cacctggagt gctgtaagca   10380
ccaatcttaa tgttgtcagg cctgctagtc agccacagct tggggaaagc tgtgcagcct   10440
gtgacccccc caggagaagc tgggaaacca agcctatagt caggccgaga acgccatggc   10500
acggaagaag ccatgctgcc tgtgagcccc tcagaggaca ctgagtcaaa aaccccacg    10560
cgcttggagg cgcaggatgg gaaaagaagg tggcgacctt ccccacccTT caatctgggg   10620
cctgaactgg agatcagctg tggatctcca gaagagggac tagtggttag aggaga       10676
```

<210> SEQ ID NO 11

<211> LENGTH: 10807
<212> TYPE: DNA
<213> ORGANISM: Zika virus

<400> SEQUENCE: 11

```
agttgttgat ctgtgtgagt cagactgcga cagttcgagt ctgaagcgag agctaacaac      60
agtatcaaca ggtttaattt ggatttggaa acgagagttt ctggtcatga aaacccaaa     120
gaagaaatcc ggaggattcc ggattgtcaa tatgctaaaa cgcggagtag cccgtgtaaa    180
ccccttggga ggtttgaaga ggttgccagc cggacttctg ctgggtcatg gacccatcag    240
aatggttttg gcgatactag cctttttgag atttacagca atcaagccat cactgggcct    300
tatcaacaga tggggttccg tggggaaaaa agaggctatg gaaataataa gaagttcaa    360
gaaagatctt gctgccatgt tgagaataat caatgctagg aaagagagga gagacgtgg    420
cgcagacacc agcatcggaa tcattggcct cctgctgact acagccatgg cagcagagat    480
cactagacgc gggagtgcat actacatgta cttggatagg agcgatgccg gaaggccat    540
ttcgtttgct accacattgg gagtgaacaa gtgccacgta cagatcatgg acctcgggca    600
catgtgtgac gccaccatga gttatgagtg ccctatgctg gatgagggag tggaaccaga    660
tgatgtcgat tgctggtgca acacgacatc aacttgggtt gtgtacggaa cctgtcatca    720
caaaaaggt gaggcacggc gatctagaag agccgtgacg ctcccttctc actctacaag    780
gaagttgcaa acgcggtcgc agacctggtt agaatcaaga gaatacacga agcacttgat    840
caaggttgaa actggatat tcaggaaccc cgggtttgcg ctagtggccg ttgccattgc    900
ctggcttttg ggaagctcga cgagccaaaa agtcatatac ttggtcatga tactgctgat    960
tgccccggca tacagtatca ggtgcattgg agtcagcaat agagacttcg tggagggcat   1020
gtcaggtggg acctgggttg atgttgtctt ggaacatgga ggctgcgtta ccgtgatggc   1080
acaggacaag ccaacagttg acatagagtt ggtcacgacg acggttagta acatggccga   1140
ggtaagatcc tattgctacg aggcatcgat atcggacatg gcttcggaca gtcgttgccc   1200
aacacaaggt gaagcctacc ttgacaagca atcagacact caatatgtct gcaaaagaac   1260
attagtggac agaggttggg gaacggttg tggacttttt ggcaaaggga gcttggtgac   1320
atgtgccaag tttacgtgtt ctaagaagat gaccgggaag agcattcaac cggaaaatct   1380
ggagtatcgg ataatgctat cagtgcatgg ctcccagcat agcgggatga ctgtcaatga   1440
tataggatat gaaactgacg aaaatagagc gaaagtcgag gttacgccta attccaag    1500
agcggaagca accttgggag ctttggaag cttaggactt gactgtgaac caaggacagg   1560
ccttgacttt tcagatctgt attcctgac catgaacaat aagcattggt tggtgcacaa   1620
agagtggttt catgacatcc cattgccttg gcatgctggg gcagacactg aactccaca   1680
ctggaacaac aaagaggcat tggtagaatt caaggatgcc cacgccaaga ggcaaaccgt   1740
cgtcgttctg gggagccagg aaggagccgt tcacacggct ctcgctggag ctctagaggc   1800
tgagatggat ggtgcaaagg gaagctgtt ctctggccat ttgaaatgcc gcctaaaaat   1860
ggacaagctt agattgaagg gcgtgtcata ttccttgtgc actgcggcat tcacattcac   1920
caaggtccca gctgaaacac tgcatggaac agtcacagtg gaggtgcagt atgcagggac   1980
agatggaccc tgcaagatcc cagtccagat ggcggtggac atgcagaccc tgaccccagt   2040
tggaaggctg ataaccgcca accccgtgat tactgaaagc actgagaact caaagatgat   2100
gttggagctt gacccaccat ttggggattc ttacattgtc ataggagttg gggacaagaa   2160
aatcacccac cactggcata ggagtggtag caccatcgga aaggcatttg aggccactgt   2220
```

```
gagaggcgcc aagagaatgg cagtcctggg ggatacagcc tgggacttcg gatcagtcgg    2280
gggtgtgttc aactcactgg gtaagggcat tcaccagatt tttggagcag ccttcaaatc    2340
actgtttgga ggaatgtcct ggttctcaca gatcctcata ggcacgctgc tagtgtggtt    2400
aggtttgaac acaaagaatg gatctatctc cctcacatgc ttggccctgg ggggagtgat    2460
gatcttcctc tccacggctg tttctgctga cgtggggtgc tcagtggact tctcaaaaaa    2520
ggaaacgaga tgtggcacgg gggtattcat ctataatgat gttgaagcct ggagggaccg    2580
gtacaagtac catcctgact ccccccgcag attggcagca gcagtcaagc aggcctggga    2640
agaggggatc tgtgggatct catccgtttc aagaatggaa acatcatgt ggaaatcagt     2700 agaaggggag ctcaatgcta tcctagagga gaatggagtt caactgacag ttgttgtggg    2760
atctgtaaaa aacccatgt ggagaggtcc acaaagattg ccagtgcctg tgaatgagct     2820
gccccatggc tggaaagcct gggggaaatc gtattttgtt agggcggcaa agaccaacaa    2880
cagttttgtt gtcgacggtg acacactgaa ggaatgtccg cttgagcaca gagcatggaa    2940 tagtttttctt gtggaggatc acgggtttgg agtcttccac accagtgtct ggcttaaggt    3000
cagagaagat tactcattag aatgtgaccc agccgtcata ggaacagctg ttaagggaag    3060
ggaggccgcg cacagtgatc tgggctattg gattgaaagt gaaaagaatg acacatggag    3120
gctgaagagg gcccacctga ttgagatgaa aacatgtgaa tggccaaagt ctcacacatt    3180
gtggacagat ggagtagaag aaagtgatct tatcataccc aagtctttag ctggtccact    3240
cagccaccac aacaccagag agggttacag aacccaagtg aaagggccat ggcacagtga    3300
agagcttgaa atccggtttg aggaatgtcc aggcaccaag gtttacgtgg aggagacatg    3360
cggaactaga ggaccatctc tgagatcaac tactgcaagt ggaagggtca ttgaggaatg    3420
gtgctgtagg gaatgcacaa tgcccccact atcgtttcga gcaaaagacg gctgctggta    3480
tggaatggag ataaggccca ggaaagaacc agagagcaac ttagtgaggt caatggtgac    3540 agcgggtca accgatcata tggaccactt ctctcttgga gtgcttgtga ttctactcat     3600
ggtgcaggag gggttgaaga agagaatgac cacaaagatc atcatgagca catcaatggc    3660
agtgctggta gtcatgatct tgggaggatt ttcaatgagt gacctggcca agcttgtgat    3720
cctgatgggt gctactttcg cagaaatgaa cactggagga gatgtagctc acttggcatt    3780
ggtagcggca tttaaagtca gaccagcctt gctggtctcc ttcattttca gagccaattg    3840
gacaccccgt gagagcatgc tgctagccct ggcttcgtgt cttctgcaaa ctgcgatctc    3900
tgctcttgaa ggtgacttga tggtcctcat taatggattt gctttggcct ggttggcaat    3960
tcgagcaatg gccgtgccac gcactgacaa catcgctcta ccaatcttgg ctgctctaac    4020
accactagct cgaggcacac tgctcgtggc atggagagcg ggcctggcta cttgtgggag    4080
gatcatgctc ctctccctga aagggaaagg tagtgtgaag aagaacctgc catttgtcat    4140 ggcccttggga ttgacagctg tgagggtagt agaccctatt aatgtggtag actactgtt   4200 actcacaagg agtgggaagc ggagctggcc ccctagtgaa gttctcacag ccgttggcct    4260
gatatgtgca ctggcggag gtttgccaa ggcagacatt gagatggctg gacccatggc     4320
tgcagtaggc ttgctaattg tcagctatgt ggtctcggga aagagtgtgg acatgtacat    4380
tgaaagagca ggtgacatca catgggaaaa ggacgcggaa gtcactggaa acagtcctcg    4440
gcttgacgtg gcactggatg agagtggtga tttctcctgt gtagaggaag atggtccacc    4500
catgagagag atcatactta aggtggtcct gatggccatc tgtggcatga acccaatagc    4560
```

```
tataccttttt gctgcaggag cgtggtatgt gtatgtgaag actgggaaaa ggagtggcgc    4620
cctctgggac gtgcctgctc ccaaagaagt gaagaaagga gagaccacag atggagtgta    4680
cagagtgatg actcgcagac tgctaggttc aacacaggtt ggagtgggag tcatgcaaga    4740
gggagtcttc cacaccatgt ggcacgttac aaaaggagcc gcactgagga gcggtgaggg    4800
aagacttgat ccatactggg gggatgtcaa gcaggacttg gtgtcatact gtgggccttg    4860
gaagttggat gcagcttggg atggactcag cgaggtacag cttttggccg tacctcccgg    4920
agagagggcc agaaacattc agaccctgcc tggaatattc aagacaaagg acggggacat    4980
cggagcagtt gctctggact accctgcagg gacctcagga tctccgatcc tagacaaatg    5040
tggaagagtg ataggactct atggcaatgg ggttgtgatc aagaatggaa gctatgttag    5100
tgctataacc cagggaaaga gggaggagga gactccggtt gaatgtttcg aaccctcgat    5160
gctgaagaag aagcagctaa ctgtcttgga tctgcatcca ggagccggaa aaaccaggag    5220
agttcttcct gaaatagtcc gtgaagccat aaaaaagaga ctccggacag tgatcttggc    5280
accaactagg gttgtcgctg ctgagatgga ggaggccttg agaggacttc cggtgcgtta    5340
catgacaaca gcagtcaacg tcacccattc tgggacagaa atcgttgatt tgatgtgcca    5400
tgccactttc acttcacgct tactacaacc catcagagtc cctaattaca atctctacat    5460
catggatgaa gcccacttca cagacccctc aagtatagct gcaagaggat atatatcaac    5520
aagggttgaa atgggcgagg cggctgccat ttttatgact gccacaccac caggaacccg    5580
tgatgcgttt cctgactcta actcaccaat catggacaca gaagtggaag tcccagagag    5640
agcctggagc tcaggctttg attgggtgac agaccattct gggaaaacag tttggttcgt    5700
tccaagcgtg agaaacggaa atgaaatcgc agcctgtctg acaaaggctg gaaagcgggt    5760
catacagctc agcaggaaga cttttgagac agaatttcag aaaacaaaaa atcaagagtg    5820
ggactttgtc ataacaactg acatctcaga gatgggcgcc aacttcaagg ctgaccgggt    5880
catagactct aggagatgcc taaaaccagt catacttgat ggtgagagag tcatcttggc    5940
tgggcccatg cctgtcacgc atgctagtgc tgctcagagg agaggacgta taggcaggaa    6000
ccctaacaaa cctggagatg agtacatgta tggaggtggg tgtgcagaga ctgatgaagg    6060
ccatgcacac tggcttgaag caagaatgct tcttgacaac atctacctcc aggatggcct    6120
catagcctcg ctctatcggc ctgaggccga taaggtagcc gccattgagg gagagtttaa    6180
gctgaggaca gagcaaagga gaccttcgt ggaactcatg aagagaggag accttcccgt    6240
ctggctagcc tatcaggttg catctgccgg aataacttac acagacagaa gatggtgctt    6300
tgatggcaca accaacaaca ccataatgga agacagcgta ccagcagagg tgtggacaaa    6360
gtatggagag aagagagtgc tcaaaccgag atggatggat gctagggtct gttcagacca    6420
tgcggccctg aagtcgttca aagaattcgc cgctggaaaa agaggagcgg ctttgggagt    6480
aatggaggcc ctgggaacac tgccaggaca catgacagag aggtttcagg aagccattga    6540
caacctcgcc gtgctcatgc gagcagagac tggaagcagg ccttataagg cagcggcagc    6600
ccaactgccg gagaccctag agaccattat gctcttaggt ttgctgggaa cagtttcact    6660
ggggatcttc ttcgtcttga tgcggaataa gggcatcggg aagatgggct ttggaatggt    6720
aacccttggg gccagtgcat ggctcatgtg gctttcggaa attgaaccag ccagaattgc    6780
atgtgtcctc attgttgtgt ttttattact ggtggtgctc ataccgagc cagagaagca    6840 aagatctccc caagataacc agatggcaat tatcatcatg gtggcagtgg gccttctagg    6900
tttgataact gcaaacgaac ttggatggct ggaaagaaca aaaaatgaca tagctcatct    6960
```

```
aatgggaagg agagaagaag gagcaaccat gggattctca atggacattg atctgcggcc    7020
agcctccgcc tgggctatct atgccgcatt gacaactctc atcacccccag ctgtccaaca   7080 tgcggtaacc acttcataca acaactactc cttaatggcg atggccacac aagctggagt   7140
gctgtttggc atgggcaaag ggatgccatt ttatgcatgg gaccttggag tcccgctgct   7200
aatgatgggt tgctattcac aattaacacc cctgactctg atagtagcta tcattctgct   7260
tgtggcgcac tacatgtact tgatcccagg cctacaagcg gcagcagcgc gtgctgccca   7320
gaaaaggaca gcagctggca tcatgaagaa tcccgttgtg gatggaatag tggtaactga   7380
cattgacaca atgacaatag accccccaggt ggagaagaag atgggacaag tgttactcat   7440
agcagtagcc atctccagtg ctgtgctgct gcggaccgcc tggggatggg gggaggctgg   7500
agctctgatc acagcagcga cctccacctt gtgggaaggc tctccaaaca aatactggaa   7560
ctcctctaca gccacctcac tgtgcaacat cttcagagga agctatctgg caggagcttc   7620
ccttatctat acagtgacga gaaacgctgg cctggttaag agacgtggag gtgggacggg   7680
agagactctg ggagagaagt ggaaagctcg tctgaatcag atgtcggccc tggagttcta   7740
ctcttataaa aagtcaggta tcactgaagt gtgtagagag gaggctcgcc gtgccctcaa   7800
ggatggagtg gccacaggag gacatgccgt atcccgggga agtgcaaagc tcagatggtt   7860
ggtggagaga ggatatctgc agccctatgg gaaggttgtt gacctcggat gtggcagagg   7920
gggctggagc tattatgccg ccaccatccg caaagtgcag gaggtgagag gatacacaaa   7980
gggaggtccc ggtcatgaag aacccatgct ggtgcaaagc tatgggtgga acatagttcg   8040
tctcaagagt ggagtggacg tcttccacat ggcggctgag ccgtgtgaca ctctgctgtg   8100
tgacataggt gagtcatcat ctagtcctga agtggaagag acacgaacac tcagagtgct   8160
ctctatggtg ggggactggc ttgaaaaaag accagggggcc ttctgtataa aggtgctgtg   8220
cccatacacc agcactatga tggaaaccat ggagcgactg caactaggc atggggagg    8280 attagtcaga gtgccattgt ctcgcaactc cacacatgag atgtactggg tctctggggc   8340
aaagagcaac atcataaaaa gtgtgtccac cacaagtcag ctcctcctgg gacgcatgga   8400
tggccccagg aggccagtga aatatgagga ggatgtgaac ctcggctcgg gtacacgagc   8460
tgtggcaagc tgtgctgagg ctcctaacat gaaaatcatc ggcaggcgca ttgagagaat   8520
ccgcaatgaa catgcagaaa catggtttct tgatgaaaac cacccataca ggacatgggc   8580
ctaccatggg agctacgaag ccccccacgca aggatcagcg tcttccctcg tgaacggggt   8640
tgttagactc ctgtcaaagc cttggacgt ggtgactgga gttacaggaa tagccatgac    8700
tgacaccaca ccatacggcc aacaaagagt cttcaaagaa aaagtggaca ccagggtgcc   8760
agatccccaa gaaggcactc gccaggtaat gaacatagtc tcttcctggc tgtggaagga   8820
gctggggaaa cgcaagcggc cacgcgtctg caccaaagaa gagtttatca caaggtgcg   8880 cagcaatgca gcactgggag caatattga agaggaaaaa gaatgaaga cggctgtgga    8940 agctgtgaat gatccaaggt tttgggccct agtggatagg gagagagaac accacctgag   9000
aggagagtgt cacagctgtg tgtacaacat gatgggaaaa agagaaaaga agcaaggaga   9060
gttcgggaaa gcaaaaggta gccgcgccat ctggtacatg tggttgggag ccagattctt   9120
ggagtttgaa gcccttggat tcttgaacga ggaccattgg atgggaagag aaaactcagg   9180
aggtggagtc gaagggttag gattgcaaag acttggatac attctagaag aaatgaatcg   9240
ggcaccagga ggaaagatgt acgcagatga cactgctggc tgggacaccc gcattagtaa   9300
```

```
gtttgatctg gagaatgaag ctctgattac caaccaaatg gaggaagggc acagaactct      9360
ggcgttggcc gtgattaaat acacatacca aaacaaagtg gtgaaggttc tcagaccagc      9420
tgaaggagga aaaacagtta tggacatcat ttcaagacaa gaccagagag ggagtggaca      9480
agttgtcact tatgctctca acacattcac caacttggtg gtgcagctta tccggaacat      9540
ggaagctgag gaagtgttag agatgcaaga cttatggttg ttgaggaagc cagagaaagt      9600
gaccagatgg ttgcagagca atggatggga tagactcaaa cgaatggcgg tcagtggaga      9660
tgactgcgtt gtgaagccaa tcgatgatag gtttgcacat gccctcaggt tcttgaatga      9720
catgggaaaa gttaggaaag acacacagga gtggaaaccc tcgactggat ggagcaattg      9780
ggaagaagtc ccgttctgct cccaccactt caacaagctg tacctcaagg atgggagatc      9840
cattgtggtc ccttgccgcc accaagatga actgattggc cgagctcgcg tctcaccagg      9900
ggcaggatgg agcatccggg agactgcctg tcttgcaaaa tcatatgcgc agatgtggca      9960
gctcctttat ttccacagaa gagaccttcg actgatggct aatgccattt gctcggctgt     10020
gccagttgac tgggtaccaa ctgggagaac cacctggtca atccatggaa agggagaatg     10080
gatgaccact gaggacatgc tcatggtgtg gaatagagtg tggattgagg agaacgacca     10140
tatggaggac aagactcctg taacaaaatg gacagacatt ccctatctag gaaaaaggga     10200
ggacttatgg tgtggatccc ttataggggca cagaccccgc accacttggg ctgaaaacat     10260
caaagacaca gtcaacatgg tgcgcaggat cataggtgat gaagaaaagt acatggacta     10320
tctatccacc caagtccgct acttgggtga ggaagggtcc acacccggag tgttgtaagc     10380
accaatttta gtgttgtcag gcctgctagt cagccacagt ttggggaaag ctgtgcagcc     10440
tgtaaccccc ccaggagaag ctgggaaacc aagctcatag tcaggccgag aacgccatgg     10500 cacgaagaa gccatgctgc ctgtgagccc ctcagaggac actgagtcaa aaaccccac     10560 gcgcttggaa gcgcaggatg ggaaaagaag gtggcgacct tccccaccct tcaatctggg     10620
gcctgaactg gagactagct gtgaatctcc agcagaggga ctagtggtta gaggagaccc     10680
cccggaaaac gcaaaacagc atattgacgc tgggaaagac cagagactcc atgagtttcc     10740
accacgctgg ccgccaggca cagatcgccg aacagcggcg ccggtgtgg ggaaatccat     10800 ggtttct                                                              10807
```

<210> SEQ ID NO 12
<211> LENGTH: 10794
<212> TYPE: DNA
<213> ORGANISM: Zika virus

<400> SEQUENCE: 12

```
agttgttgat ctgtgtgagt cagactgcga cagttcgagt ctgaagcgag agctaacaac       60
agtatcaaca ggtttaattt ggatttggaa acgagagttt ctggtcatga aaaaccccaa      120
agaagaaatc cggaggatcc ggattgtcaa tatgctaaaa cgcggagtag cccgtgtaaa      180
ccccttggga ggtttgaaga ggttgccagc cggacttctg ctgggtcatg gacccatcag      240
aatggttttg gcgatactag ccttttttgag atttacagca atcaagccat cactgggcct      300
tatcaacaga tggggttccg tggggaaaaa agaggctatg gaaataataa agaagttcaa      360
gaaagatctt gctgccatgt tgagaataat caatgctagg aaagagagga agagacgtgg      420
cgcagacacc agcatcggaa tcattggcct cctgctgact acagccatgg cagcagagat      480
cactagacgc gggagtgcat actacatgta cttggatagg agcgatgccg ggaaggccat      540
ttcgtttgct accacattgg gagtgaacaa gtgccacgta cagatcatgg acctcgggca      600
```

```
catgtgtgac gccaccatga gttatgagtg ccctatgctg gatgagggag tggaaccaga      660
tgatgtcgat tgctggtgca acacgacatc aacttgggtt gtgtacggaa cctgtcatca      720
caaaaaaggt gaggcacggc gatctagaag agccgtgacg ctcccttctc actctacaag      780
gaagttgcaa acgcggtcgc agacctggtt agaatcaaga gaatacacga agcacttgat      840
caaggttgaa aactggatat tcaggaaccc cgggtttgcg ctagtggccg ttgccattgc      900
ctggcttttg ggaagctcga cgagccaaaa agtcatatac ttggtcatga tactgctgat      960
tgccccggca tacagtatca ggtgcattgg agtcagcaat agagacttcg tggagggcat     1020
gtcaggtggg acctggggttg atgttgtctt ggaacatgga ggctgcgtta ccgtgatggc     1080
acaggacaag ccaacagtcg acatagagtt ggtcacgacg acggttagta acatggccga     1140
ggtaagatcc tattgctacg aggcatcgat atcggacatg gcttcggaca gtcgttgccc     1200
aacacaaggt gaagcctacc ttgacaagca atcagacact caatatgtct gcaaaagaac     1260
attagtggac agaggttggg gaaacggttg tggacttttt ggcaaaggga gcttggtgac     1320
atgtgccaag tttacgtgtt ctaagaagat gaccgggaag agcattcaac cggaaaatct     1380
ggagtatcgg ataatgctat cagtgcatgg ctcccagcat agcgggatga ttggatatga     1440
aactgacgaa gatagagcga aagtcgaggt tacgcctaat tcaccaagag cggaagcaac     1500
cttgggaggc tttggaagct taggacttga ctgtgaacca aggacaggcc ttgactttttc     1560
agatctgtat tacctgacca tgaacaataa gcattggttg gtgcacaaag agtggtttca     1620
tgacatccca ttgccttggc atgctggggc agacaccgga actccacact ggaacaacaa     1680
agaggcattg gtagaattca aggatgccca cgccaagagg caaaccgtcg tcgttctggg     1740
gagccaggaa ggagccgttc acggctctct cgctggagct ctagaggctg agatggatgg     1800
tgcaaaggga aggctgttct ctggccatttt gaaatgccgc ctaaaaatgg acaagcttag     1860
attgaagggc gtgtcatatt ccttgtgcac tgcggcattc acattcacca aggtcccagc     1920
tgaaacactg catggaacag tcacagtgga ggtgcagtat gcaggacag atggaccctg     1980
caagatccca gtccagatgg cggtggacat gcagaccctg acccccagttg gaaggctgat     2040
aaccgccaac cccgtgatta ctgaaagcac tgagaactca aagatgatgt ggagcttga     2100
cccaccattt ggggattctt acattgtcat aggagttggg gacaagaaaa tcacccacca     2160
ctggcatagg agtggtagca ccatcggaaa ggcatttgag gccactgtga gaggcgccaa     2220
gagaatggca gtcctggggg atacagcctg ggacttcgga tcagtcgggg gtgtgttcaa     2280
ctcactgggt aagggcattc accagatttt tggagcagcc ttcaaatcac tgtttggagg     2340
aatgtcctgg ttctcacaga tcctcatagg cacgctgcta gtgtggttag gtttgaacac     2400
aaagaatgga tctatctccc tcacatgctt ggccctgggg ggagtgatga tcttcctctc     2460
cacggctgtt tctgctgacg tggggtgctc agtggacttc tcaaaaaagg aaacgagatg     2520
tggcacgggg gtattcatct ataatgatgt tgaagcctgg agggaccggt acaagtacca     2580
tcctgactcc ccccgcagat tggcagcagc agtcaagcag gcctgggaag aggggatctg     2640
tgggatctca tccgtttcaa gaatggaaaa catcatgtgg aaatcagtag aaggggagct     2700
caatgctatc ctagaggaga atggagttca actgacagtt gttgtggat ctgtaaaaaa     2760
ccccatgtgg agaggtccac aaagattgcc agtgcctgtg aatgagctgc ccatggctg     2820
gaaagcctgg gggaaatcgt attttgttag ggcggcaaag accaacaaca gttttgttgt     2880
cgacggtgac acactgaagg aatgtccgct tgagcacaga gcatggaata gttttcttgt     2940
```

```
ggaggatcac gggtttggag tcttccacac cagtgtctgg cttaaggtca gagaagatta      3000
ctcattagaa tgtgacccag ccgtcatagg aacagctgtt aagggaaggg aggccgcgca      3060
cagtgatctg ggctattgga ttgaaagtga aaagaatgac acatggaggc tgaagagggc      3120
ccacctgatt gagatgaaaa catgtgaatg gccaaagtct cacacattgt ggacagatgg      3180
agtagaagaa agtgatctta tcatacccaa gtctttagct ggtccactca gccaccacaa      3240
caccagagag ggttacagaa cccaagtgaa agggccatgg cacagtgaag agcttgaaat      3300
ccggtttgag gaatgtccag gcaccaaggt ttacgtggag gagacatgcg gaactagagg      3360
accatctctg agatcaacta ctgcaagtgg aagggtcatt gaggaatggt gctgtaggga      3420
atgcacaatg ccccccactat cgtttcgagc aaaagacggc tgctggtatg gaatggagat      3480
aaggcccagg aaagaaccag agagcaactt agtgaggtca atggtgacag cggggtcaac      3540
cgatcatatg gaccacttct ctcttggagt gcttgtgatt ctactcatgg tgcaggaggg      3600
gttgaagaag agaatgacca caaagatcat catgagcaca tcaatggcag tgctggtagt      3660
catgatcttg ggaggatttt caatgagtga cctggccaag cttgtgatcc tgatgggtgc      3720
tactttcgca gaaatgaaca ctggaggaga tgtagctcac ttggcattgg tagcggcatt      3780
taaagtcaga ccagccttgc tggtctcctt cattttcaga gccaattgga cccccgtga      3840
gagcatgctg ctagccctgg cttcgtgtct tctgcaaact gcgatctctg ctcttgaagg      3900
tgacttgatg gtcctcatta atggatttgc tttggcctgg ttggcaattc gagcaatggc      3960
cgtgccacgc actgacaaca tcgctctacc aatcttggct gctctaacac cactagctcg      4020
aggcacactc tcgtggcat ggagagcggg cctggctact tgtggaggga tcatgctcct      4080
ctccctgaaa gggaaaggta gtgtgaagaa gaacctgcca tttgtcatgg ccctgggatt      4140
gacagctgtg agggtagtag accctattaa tgtggtagga ctactgttac tcacaaggag      4200
tgggaagcgg agctggcccc ctagtgaagt tctcacagcc gttggcctga tatgtgcact      4260
ggccggaggg tttgccaagg cagacattga tgggctgga cccatggctg cagtaggctt      4320
gctaattgtc agctatgtgg tctcgggaaa gagtgtggac atgtacattg aaagagcagg      4380
tgacatcaca tgggaaaagg acgcggaagt cactggaaac agtcctcggc ttgacgtggc      4440
actggatgag agtggtgact tctccttggt agaggaagat ggtccaccca tgagagagat      4500
catactcaag gtggtcctga tggccatctg tggcatgaac ccaatagcta accttttgc      4560
tgcaggagcg tggtatgtgt atgtgaagac tgggaaaagg agtggcgccc tctgggacgt      4620
gcctgctccc aaagaagtga agaaaggaga gaccacagat ggagtgtaca gagtgatgac      4680
tcgcagactg ctaggttcaa cacaggttgg agtgggagtc atgcaagagg gagtcttcca      4740
caccatgtgg cacgttacaa aaggagccgc actgaggagc ggtgagggaa gacttgatcc      4800
atactggggg gatgtcaagc aggacttggt gtcatactgt gggccttgga gttggatgc      4860
agcttgggat ggactcagcg aggtacagct tttggccgta cctccggag agagggccag      4920
aaacattcag accctgcctg gaatattcaa gacaaaggac gggacatcg gagcagttgc      4980
tctggactac cctgcaggga cctcaggatc tccgatccta gacaaatgtg aagagtgat      5040
aggactctat ggcaatgggg ttgtgatcaa gaatggaagc tatgttagtg ctataaccca      5100
gggaaagagg gaggaggaga ctccggttga atgtttcgaa ccctcgatgc tgaagaagaa      5160
gcagctaact gtcttggatc tgcatccagg agccggaaaa accaggagag ttcttcctga      5220
aatagtccgt gaagccataa aaagagagact ccggacagtg atcttggcac caactagggt      5280
tgtcgctgct gagatggagg aggccttgag aggacttccg gtgcgttaca tgacaacagc      5340
```

```
agtcaacgtc acccattctg ggacagaaat cgttgatttg atgtgccatg ccactttcac    5400
ttcacgctta ctacaaccca tcagagtccc taattacaat ctcaacatca tggatgaagc    5460
ccacttcaca gacccctcaa gtatagctgc aagaggatac atatcaacaa gggttgaaat    5520
gggcgaggcg gctgccattt ttatgactgc cacaccacca ggaacccgtg atgcgtttcc    5580
tgactctaac tcaccaatca tggacacaga agtggaagtc ccagagagag cctggagctc    5640
aggctttgat tgggtgacag accattctgg gaaaacagtt tggttcgttc caagcgtgag    5700
aaacggaaat gaaatcgcag cctgtctgac aaaggctgga aagcgggtca tacagctcag    5760
caggaagact tttgagacag aatttcagaa aacaaaaaat caagagtggg actttgtcat    5820
aacaactgac atctcagaga tgggcgccaa cttcaaggct gaccgggtca tagactctag    5880
gagatgccta aaaccagtca tacttgatgg tgagagagtc atcttggctg ggcccatgcc    5940
tgtcacgcat gctagtgctg ctcagaggag aggacgtata ggcaggaacc ctaacaaacc    6000
tggagatgag tacatgtatg gaggtgggtg tgcagagact gatgaaggcc atgcacactg    6060
gcttgaagca agaatgcttc ttgacaacat ctacctccag gatggcctca tagcctcgct    6120
ctatcggcct gaggccgata aggtagccgc cattgaggga gagtttaagc tgaggacaga    6180
gcaaaggaag accttcgtgg aactcatgaa gagaggagac cttcccgtct ggctagccta    6240
tcaggttgca tctgccggaa taacttacac agacagaaga tggtgctttg atggcacaac    6300
caacaacacc ataatggaag acagtgtacc agcagaggtt tggacaaagt atggagagaa    6360
gagagtgctc aaaccgagat ggatggatgc tagggtctgt tcagaccatg cggccctgaa    6420
gtcgttcaaa gaattcgccg ctggaaaaag aggagcggct ttgggagtaa tggaggccct    6480
gggaacactg ccaggacaca tgacagagag gtttcaggaa gccattgaca acctcgccgt    6540
gctcatgcga gcagagactg gaagcaggcc ttataaggca cggcagccc aactgccgga    6600 gacccctagag accattatgc tcttaggttt gctgggaaca gtttcactgg ggatcttctt    6660
cgtcttgatg cggaataagg gcatcgggaa gatgggcttt ggaatggtaa cccttgggc    6720 cagtgcatgg ctcatgtggc tttcggaaat tgaaccagcc agaattgcat gtgtcctcat    6780
tgttgtgttt ttattactgg tggtgctcat acccgagcca gagaagcaaa gatctccca    6840 agataaccag atggcaatta tcatcatggt ggcagtgggc cttctaggtt tgataactgc    6900
aaacgaactt ggatggctgg aaagaacaaa aaatgacata gctcatcaa tgggaaggag    6960 agaagaagga gcaaccatgg gattctcaat ggacattgat ctgcggccag cctccgcctg    7020
ggctatctat gccgcattga caactctcat cacccccagct gtccaacatg cggtaaccac    7080
ttcatacaac aactactcct taatggcgat ggccacacaa gctggagtgc tgtttggcat    7140
gggcaaaggg atgccattta tgcatggga ccttggagtc ccgctgctaa tgatgggttg    7200
ctattcacaa ttaacaccc tgactctgat agtagctatc attctgcttg tggcgcacta    7260
catgtacttg atcccaggcc tacaagcggc agcagcgcgt gctgcccaga aaggacagc    7320 agctggcatc atgaagaatc cgttgtgga tggaatagtg gtaactgaca ttgacacaat    7380
gacaatagac ccccaggtgg agaagaagat gggacaagtg ttactcatag cagtagccat    7440
ctccagtgct gtgctgctgc ggaccgcctg ggatggggg gaggctggag ctctgatcac    7500
agcagcgacc tccaccttgt gggaaggctc tccaaacaaa tactggaact cctctacagc    7560
cacctcactg tgcaacatct tcagaggaag ctatctggca ggagcttccc ttatctatac    7620
agtgacgaga aacgctggcc tggttaagag acgtggaggt gggacgggag agactctggg    7680
```

```
agagaagtgg aaagctcgtc tgaatcagat gtcggccctg gagttctact cttataaaaa   7740
gtcaggtatc actgaagtgt gtagagagga ggctcgccgt gccctcaagg atggagtggc   7800
cacaggagga catgccgtat cccgggaag tgcaaagatc agatggttgg aggagagagg   7860
atatctgcag ccctatggga aggttgttga cctcggatgt ggcagagggg gctggagcta   7920
ttatgccgcc accatccgca aagtgcagga ggtgagagga tacacaaagg aggtcccgg    7980
tcatgaagaa cccatgctgg tgcaaagcta tgggtggaac atagttcgtc tcaagagtgg   8040
agtggacgtc ttccacatgg cggctgagcc gtgtgacact ctgctgtgtg acataggtga   8100
gtcatcatct agtcctgaag tggaagagac acgaacactc agagtgctct ctatggtggg   8160
ggactggctt gaaaaaagac caggggcctt ctgtataaag gtgctgtgcc catacaccag   8220
cactatgatg gaaccatgg agcgactgca acgtaggcat gggggaggat tagtcagagt    8280
gccattgtgt cgcaactcca cacatgagat gtactgggtc tctggggcaa agagcaacat   8340
cataaaaagt gtgtccacca caagtcagct cctcctggga cgcatggatg cccccaggag   8400
gccagtgaaa tatgaggagg atgtgaacct cggctcgggt acacgagctg tggcaagctg   8460
tgctgaggct cctaacatga aaatcatcgg caggcgcatt gagagaatcc gcaatgaaca   8520
tgcagaaaca tggtttcttg atgaaaacca cccatacagg acatgggcct accatgggag   8580
ctacgaagcc cccacgcaag atcagcgtc ttccctcgtg aacggggttg ttagactcct    8640
gtcaaagcct tgggacgtgg tgactggagt tacaggaata gccatgactg acaccacacc   8700
atacggccaa caaagagtct tcaaagaaaa agtggacacc agggtgccag atccccaaga   8760
aggcactcgc caggtaatga acatagtctc ttcctggctg tggaaggagc tggggaaacg   8820
caagcggcca cgcgtctgca ccaaagaaga gtttatcaac aaggtgcgca gcaatgcagc   8880
actgggagca atatttgaag aggaaaaaga atggaagacg gctgtggaag ctgtgaatga   8940
tccaaggttt tgggcctag tggatggga gagagaacac cacctgagag gagagtgtca    9000
cagctgtgtg tacaacatga tgggaaaaag agaaaagaag caaggagagt tcgggaaagc   9060
aaaaggtagc cgcgccatct ggtacatgtg gttgggagcc agattcttgg agtttgaagc   9120
ccttggattc ttgaacgagg accattggat gggaagagaa aactcaggag gtggagtcga   9180
agggttagga ttgcaaagac ttggatacat tctagaagaa atgaatcggg caccaggagg   9240
aaagatgtac gcagatgaca ctgctggctg ggacacccgc attagtaagt ttgatctgga   9300
gaatgaagct ctgattacca ccaaatgga ggaagggcac agaactctgg cgttggccgt    9360
gattaaatac acataccaaa acaaagtggt gaaggttctc agaccagctg aaggaggaaa   9420
aacagttatg gacatcattt caagacaaga ccagagaggg agtggacaag ttgtcactta   9480
tgctctcaac acattcacca acttggtggt gcagcttatc cggaacatgg aagctgagga   9540
agtgttagag atgcaagact tatggttgtt gaggaagcca gagaaagtga ccagatggtt   9600
gcagagcaat ggatgggata gactcaaacg aatggcggtc agtggagatg actgcgttgt   9660
gaagccaatc gatgataggt ttgcacatgc cctcaggttc ttgaatgaca tgggaaaagt   9720
taggaaagac acacaggagt ggaaaccctc gactggatgg agcaattggg aagaagtccc   9780
gttctgctcc caccacttca acaagctgta cctcaaggat gggagatcca ttgtggtccc   9840
ttgccgccac caagatgaac tgattggccg agctcgcgtc tcaccagggg caggatggag   9900
catccgggag actgcctgtc ttgcaaaatc atatgcgcag atgtggcagc tcctttattt   9960
ccacagaaga gaccttcgac tgatggctaa tgccatttgc tcggctgtgc cagttgactg  10020
ggtaccaact gggagaacca cctggtcaat ccatggaaag ggagaatgga tgaccactga  10080
```

```
ggacatgctc atggtgtgga atagagtgtg gattgaggag aacgaccata tggaggacaa    10140
gactcctgta acaaaatgga cagacattcc ctatctagga aaaagggagg acttatggtg    10200
tggatccctt atagggcaca gaccccgcac cacttgggct gaaaacatca agacacagt    10260 caacatggtg cgcaggatca taggtgatga agaaaagtac atggactatc tatccaccca    10320
agtccgctac ttgggtgagg aagggtccac acccggagtg ttgtaagcac caattttagt    10380
gttgtcaggc ctgctagtca gccacagttt ggggaaagct gtgcagcctg taaccccccc    10440
aggagaagct gggaaaccaa gctcatagtc aggccgagaa cgccatggca cggaagaagc    10500
catgctgcct gtgagcccct cagagacac tgagtcaaaa acccacgc gcttggaagc    10560 gcaggatggg aaaagaaggt ggcgaccttc cccacccttc aatctggggc ctgaactgga    10620
gactagctgt gaatctccag cagagggact agtggttaga ggagaccccc cggaaaacgc    10680
aaaacagcat attgacgtgg gaaagaccag agactccatg agtttccacc acgctggccg    10740
ccaggcacag atcgccgaac ttcggcggcc ggtgtgggga aatccatggt ttct    10794

<210> SEQ ID NO 13
<211> LENGTH: 10617
<212> TYPE: DNA
<213> ORGANISM: Zika virus

<400> SEQUENCE: 13
agtatcaaca ggttttatttt tggatttgga aacgagagtt tctggtcatg aaaaacccaa      60
aaaagaaatc cggaggattc cggattgtca atatgctaaa acgcggagta gcccgtgtga     120 gccccttttgg gggcttgaag aggctgccag ccggacttct gctgggtcat gggcccatca     180
ggatggtctt ggcgattcta gccttttttga gattcacggc aatcaagcca tcactgggtc     240
tcatcaatag atggggttca gtggggaaaa aagaggctat ggaaataata aagaagttca     300
agaaagatct ggctgccatg ctgagaataa tcaatgctag gaaggagaag aagagacgag     360
gcgcagatac tagtgtcgga attgttggcc tcctgctgac cacagctatg gcagcggagg     420
tcactagacg tgggagtgca tactatatgt acttggacag aaacgacgct ggggaggcca     480
tatcttttcc aaccacattg gggatgaata agtgttatat acagatcatg gatcttggac     540
acatgtgtga tgccaccatg agctatgaat gccctatgct ggatgagggg gtggaaccag     600
atgacgtcga ttgttggtgc aacacgacgt caacttgggt tgtgtacgga acctgccatc     660
acaaaaaagg tgaagcacgg agatctagaa gagctgtgac gctcccctcc cattccacta     720
ggaagctgca aacgcggtcg caaacctggt tggaatcaag agaatacaca aagcacttga     780
ttagagtcga aaattggata ttcaggaacc ctggcttcgc gttagcagca gctgccatcg     840
cttggctttt gggaagctca acgagccaaa aagtcatata cttggtcatg atactgctga     900
ttgccccggc atacagcatc aggtgcatag gagtcagcaa tagggacttt gtggaaggta     960
tgtcaggtgg gacttgggtt gatgttgtct tggaacatgg aggttgtgtc accgtaatgg    1020
cacaggacaa accgactgtc gacatagagc tggttacaac aacagtcagc aacatggcgg    1080
aggtaagatc ctactgctat gaggcatcaa tatcggacat ggcttcggac agccgctgcc    1140
caacacaagg tgaagcctac cttgacaagc aatcagacac tcaatatgtc tgcaaaagaa    1200
cgttagtgga cagaggctgg ggaaatggat gtggactttt tggcaaaggg agcctggtga    1260
catgcgctaa gtttgcatgc tccaagaaaa tgaccgggaa gagcatccag ccagagaatc    1320
tggagtaccg gataatgctg tcagttcatg gctcccagca cagtgggatg atcgttaatg    1380
```

```
acacaggaca tgaaactgat gagaatagag cgaaggttga gataacgccc aattcaccaa    1440
gagccgaagc caccctgggg ggttttggaa gcctaggact tgattgtgaa ccgaggacag    1500
gccttgactt ttcagatttg tattacttga ctatgaataa caagcactgg ttggttcaca    1560
aggagtggtt ccacgacatt ccattacctt ggcacgctgg ggcagacacc ggaactccac    1620
actggaacaa caaagaagca ctggtagagt tcaaggacgc acatgccaaa aggcaaactg    1680
tcgtggttct agggagtcaa gaaggagcag ttcacacggc ccttgctgga gctctggagg    1740
ctgagatgga tggtgcaaag ggaaggctgt cctctggcca cttgaaatgt cgcctgaaaa    1800
tggataaact tagattgaag ggcgtgtcat actccttgtg taccgcagcg ttcacattca    1860
ccaagatccc ggctgaaaca ctgcacggga cagtcacagt ggaggtacag tacgcaggga    1920
cagatggacc ttgcaaggtt ccagctcaga tggcggtgga catgcaaact ctgaccccag    1980
ttgggaggtt gataaccgct aaccccgtaa tcactgaaag cactgagaac tctaagatga    2040
tgctggaact tgatccacca tttggggact cttacattgt cataggagtc ggggagaaga    2100
agatcaccca ccactggcac aggagtggca gcaccattgg aaaagcattt gaagccactg    2160
tgagaggtgc caagagaatg gcagtcttgg gagacacagc ctgggacttt ggatcagttg    2220
gaggcgctct caactcattg ggcaagggca tccatcaaat ttttggagca gctttcaaat    2280
cattgtttgg aggaatgtcc tggttctcac aaattctcat tggaacgttg ctgatgtggt    2340
tgggtctgaa cacaaagaat ggatctattt cccttatgtg cttggcctta ggggagtgt    2400 tgatcttctt atccacagct gtctctgctg atgtggggtg ctcggtggac ttctcaaaga    2460
aggagacgag atgcggtaca ggggtgttcg tctataacga cgttgaagcc tggagggaca    2520
ggtacaagta ccatcctgac tcccccgta gattggcagc agcagtcaag caagcctggg    2580
aagatggtat ctgtgggatc tcctctgttt caagaatgga aaacatcatg tggagatcag    2640
tagaagggga gctcaacgca atcctggaag agaatggagt tcaactgacg gtcgttgtgg    2700
gatctgtaaa aaaccccatg tggagaggtc cacagagatt gcccgtgcct gtgaacgagc    2760
tgccccacgg ctggaaggct tgggggaaat cgtacttcgt cagagcagca aagacaaata    2820
acagctttgt cgtggatggt gacacactga aggaatgccc actcaaacat agagcatgga    2880
acagctttct tgtggaggat catgggttcg gggtatttca cactagtgtc tggctcaagg    2940
ttagagaaga ttattcatta gagtgtgatc cagccgttat tggaacagct gttaagggaa    3000
aggaggctgt acacagtgat ctaggctact ggattgagag tgagaagaat gacacatgga    3060
ggctgaagag ggcccatctg atcgagatga aaacatgtga atggccaaag tcccacacat    3120
tgtggacaga tggaatagaa gagagtgatc tgatcatacc caagtctta gctgggccac    3180 tcagccatca caataccaga gagggctaca ggacccaaat gaaagggcca tggcacagtg    3240
aagagcttga aattcggttt gaggaatgcc caggcactaa ggtccacgtg gaggaaacat    3300
gtggaacaag aggaccatct ctgagatcaa ccactgcaag cggaagggtg atcgaggaat    3360
ggtgctgcag ggagtgcaca atgccccac tgtcgttccg ggctaaagat ggctgttggt    3420
atggaatgga gataaggccc aggaaagaac cagaaagtaa cttagtaagg tcaatggtga    3480
ctgcaggatc aactgatcac atggatcact ctcccttgg agtgcttgtg attctgctca    3540
tggtgcagga agggctgaag aagagaatga ccacaaagat catcataagc catcgatgg    3600 cagtgctggt agctatgatc ctgggaggat tttcaatgag tgacctggct aagcttgcaa    3660
ttttgatggg tgccaccttc gcggaaatga acactggagg agatgtagct catctggcgc    3720
tgatagcggc attcaaagtc agaccagcgt tgctggtatc tttcatcttc agagctaatt    3780
```

```
ggacacccg tgaaagcatg ctgctggcct tggcctcgtg tcttttgcaa actgcgatct    3840
ccgccttgga aggcgacctg atggttctca tcaatggttt tgctttggcc tggttggcaa    3900
tacgagcgat ggttgttcca cgcactgata acatcacctt ggcaatcctg gctgctctga    3960
caccactggc ccgggcaca ctgcttgtgg cgtggagagc aggccttgct acttgcgggg    4020
ggtttatgct cctctctctg aagggaaaag gcagtgtgaa gaagaactta ccatttgtca    4080
tggccctggg actaaccgct gtgaggctgg tcgaccccat caacgtggtg ggactgctgt    4140
tgctcacaag gagtgggaag cggagctggc cccctagcga agtactcaca gctgttggcc    4200
tgatatgcgc attggctgga gggttcgcca aggcagatat agagatggct gggcccatgg    4260
ccgcggtcgg tctgctaatt gtcagttacg tggtctcagg aaagagtgtg acatgtaca    4320 ttgaaagagc aggtgacatc acatgggaaa aagatgcgga agtcactgga aacagtcccc    4380
ggctcgatgt ggcgctagat gagagtggtg atttctccct ggtggaggat gacggtcccc    4440
ccatgagaga gatcatactc aaggtggtcc tgatgaccat ctgtggcatg aacccaatag    4500 ccatacccctt tgcagctgga gcgtggtacg tatacgtgaa gactggaaaa aggagtggtg    4560
ctctatggga tgtgcctgct cccaaggaag taaaaaggg ggagaccaca gatggagtgt    4620
acagagtaat gactcgtaga ctgctaggtt caacacaagt tggagtggga gttatgcaag    4680 aggggtctt tcacactatg tggcacgtca caaaaggatc cgcgctgaga agcggtgaag    4740
ggagacttga tccatactgg ggagatgtca agcaggatct ggtgtcatac tgtggtccat    4800
ggaagctaga tgccgcctgg gacgggcaca gcgaggtgca gctcttggcc gtgccccccg    4860
gagagagagc gaggaacatc cagactctgc ccggaatatt taagacaaag gatggggaca    4920
ttggagcggt tgcgctggat tacccagcag gaacttcagg atctccaatc ctagacaagt    4980
gtgggagagt gataggactt tatggcaatg gggtcgtgat caaaaatggg agttatgtta    5040
gtgccatcac ccaagggagg agggaggaag agactcctgt tgagtgcttc gagccttcga    5100
tgctgaagaa gaagcagcta actgtcttag acttgcatcc tggagctggg aaaaccagga    5160
gagttcttcc tgaaatagtc cgtgaagcca taaaaacaag actccgtact gtgatcttag    5220
ctccaaccag ggttgtcgct gctgaaatgg aggaagcccct tagagggctt ccagtgcgtt    5280
atatgacaac agcagtcaat gtcacccact ctggaacaga aatcgtcgac ttaatgtgcc    5340
atgccaccct cacttcacgt ctactacagc caatcagagt ccccaactat aatctgtata    5400
ttatggatga ggcccacttc acagatccct caagtatagc agcaagagga tacatttcaa    5460
caagggttga gatgggcgag gcggctgcca tcttcatgac cgccacgcca ccaggaaccc    5520
gtgacgcatt tccggactcc aactcaccaa ttatggacac cgaagtggaa gtcccagaga    5580
gagcctggag ctcaggcttt gattgggtga cggatcattc tggaaaaaca gtttggttttg    5640 ttccaagcgt gaggaacggc aatgagatcg cagcttgtct gacaaaggct ggaaaacggg    5700
tcatacagct cagcagaaag acttttgaga cagagttcca gaaaacaaaa catcaagagt    5760
gggactttgt cgtgacaact gacatttcag agatgggcgc caactttaaa gctgaccgtg    5820
tcatagattc caggagatgc ctaaagccgg tcatacttga tggcgagaga gtcattctgg    5880
ctggacccat gcctgtcaca catgccgcg ctgcccagag gaggggcgc ataggcagga    5940 atcccaacaa acctggagat gagtatctgt atggaggtgg gtgcgcagag actgacgaag    6000
accatgcaca ctggcttgaa gcaagaatgc tccttgacaa tatttacctc caagatggcc    6060
tcatagcctc gctctatcga cctgaggccg acaaagtagc agccattgag ggagagttca    6120
```

```
agcttaggac ggagcaaagg aagacctttg tggaactcat gaaaagagga gatcttcctg      6180
tttggctggc ctatcaggtt gcatctgccg gaataaccta cacagataga agatggtgct      6240
ttgatggcac gaccaacaac accataatgg aagacagtgt gccggcagag gtgtggacca      6300
gacacggaga gaaaagagtg ctcaaaccga ggtggatgga cgccagagtt tgttcagatc      6360
atgcggccct gaagtcattc aaggagtttg ccgctgggaa aagaggagcg gcttttggag      6420
tgatggaagc cctgggaaca ctgccaggac acatgacaga gagattccag gaagccattg      6480
acaacctcgc tgtgctcatg cgggcagaga ctggaagcag gccttacaaa gccgcggcgg      6540
cccaattgcc ggagacccta gagaccatta tgcttttggg gttgctggga acagtctcgc      6600
tgggaatctt tttcgtcttg atgaggaaca agggcatagg gaagatgggc tttggaatgg      6660
tgactcttgg ggccagcgca tggctcatgt ggctctcgga aattgagcca gccagaattg      6720
catgtgtcct cattgttgtg ttcctattgc tggtggtgct catacctgag ccagaaaagc      6780
aaagatctcc ccaggacaac caaatggcaa tcatcatcat ggtagcagta ggtcttctgg      6840
gcttgattac cgccaatgaa ctcggatggt tggagagaac aaaagagtgac ctaagccatc      6900 taatgggaag gagagaggag ggggcaacca taggattctc aatggacatt gacctgcggc      6960
cagcctcagc ttgggccatc tatgctgcct tgacaacttt cattacccca gccgtccaac      7020
atgcagtgac cacttcatac aacaactact ccttaatggc gatggccacg caagctggag      7080
tgttgtttgg tatgggcaaa gggatgccat tctacgcatg ggactttgga gtcccgctgc      7140
taatgatagg ttgctactca caattaacac ccctgaccct aatagtggcc atcattttgc      7200
tcgtggcgca ctacatgtac ttgatcccag ggctgcaggc agcagctgcg cgtgctgccc      7260
agaagagaac ggcagctggc atcatgaaga accctgttgt ggatggaata gtggtgactg      7320
acattgacac aatgacaatt gaccccaag tggagaaaaa gatgggacag gtgctactca      7380
tagcagtagc cgtctccagc gccatactgt cgcggaccgc ctgggggtgg ggggaggctg      7440
gggccctgat cacagcggca acttccactt tgtgggaagg ctctccgaac aagtactgga      7500
actcctctac agccacttca ctgtgtaaca tttttagggg aagttacttg gctggagctt      7560
ctctaatcta cacagtaaca agaaacgctg gcttggtcaa gagacgtggg ggtggaacag      7620
gagagaccct gggagagaaa tggaaggccc gcttgaacca gatgtcggcc ctggagttct      7680
actcctacaa aaagtcaggc atcaccgagg tgtgcagaga agaggcccgc cgcgccctca      7740
aggacggtgt ggcaacggga ggccatgctg tgtcccgagg aagtgcaaag ctgagatggt      7800
tggtggagcg gggatacctg cagccctatg gaaaggtcat tgatcttgga tgtggcagag      7860 gggctggag ttactacgcc gccaccatcc gcaaagttca agaagtgaaa ggatacacaa      7920
aaggaggccc tggtcatgaa gaacccatgt tggtgcaaag ctatgggtgg aacatagtcc      7980
gtcttaagag tggggtggac gtcttcata tggcggctga gccgtgtgac acgttgctgt      8040
gtgacatagg tgagtcatca tctagtcctg aagtggaaga agcacggacg ctcagagtcc      8100
tctccatggt ggggattgg cttgaaaaaa gaccaggagc cttttgtata aaagtgttgt      8160
gcccatacac cagcactatg atggaaaccc tggagcgact gcagcgtagg tatggggag      8220 gactggtcag agtgccactc tcccgcaact ctacacatga gatgtactgg gtctctggag      8280
cgaaaagcaa caccataaaa agtgtgtcca ccacgagcca gctcctcttg gggcgcatgg      8340
acgggcccag gaggccagtg aaatatgagg aggatgtgaa tctcggctct ggcacgcggg      8400
ctgtggtaag ctgcgctgaa gctccccaaca tgaagatcat tggtaaccgc attgaaagga      8460
tccgcagtga gcacgcggaa acgtggttct ttgacgagaa ccacccatat aggacatggg      8520
```

-continued

```
cttaccatgg aagctatgag gcccccacac aagggtcagc gtcctctcta ataaacgggg   8580
ttgtcaggct cctgtcaaaa ccctgggatg tggtgactgg agtcacagga atagccatga   8640
ccgacaccac accgtatggt cagcaaagag ttttcaagga aaaagtggac actagggtgc   8700
cagaccccca agaaggcact cgtcaggtta tgagcatggt ctcttcctgg ttgtggaaag   8760
agctaggcaa acacaaacgg ccacgagtct gtaccaaaga agagttcatc aacaaggttc   8820
gtagcaatgc agcattaggg gcaatatttg aagaggaaaa agagtggaag actgcagtgg   8880
aagctgtgaa cgatccaagg ttctgggctc tagtggacaa ggaaagagag caccacctga   8940
gaggagagtg ccagagttgt gtgtacaaca tgatgggaaa aagagaaaag aaacaagggg   9000
aatttggaaa ggccaagggc agccgcgcca tctggtatat gtggctaggg gctagatttc   9060
tagagttcga agcccttgga ttcttgaacg aggatcactg gatggggaga gagaactcag   9120
gaggtggtgt tgaagggctg ggattacaaa gactcggata tgtcctagaa gagatgagtc   9180
gcataccagg aggaaggatg tatgcagatg acactgctgg ctgggacacc cgcatcagca   9240
ggtttgatct ggagaatgaa gctctaatca ccaaccaaat ggagaaaggg cacagggcct   9300
tggcattggc cataatcaag tacacatacc aaaacaaagt ggtaaaggtc cttagaccag   9360
ctgaaaaagg gaagacagtt atggacatta tttcgagaca agaccaaagg gggagcggac   9420
aagttgtcac ttacgctctt aacacattta ccaacctagt ggtgcaactc attcggaata   9480
tggaggctga ggaagttcta gagatgcaag acttgtggct gctgcggagg tcagagaaag   9540
tgaccaactg gttgcagagc aacggatggg ataggctcaa acgaatggca gtcagtggag   9600
atgattgcgt tgtgaagcca attgatgata ggtttgcaca tgccctcagg ttcttgaatg   9660
atatgggaaa agttaggaag gacacacaag agtggaaacc ctcaactgga tgggacaact   9720
gggaagaagt tccgttttgc tcccaccact tcaacaagct ccatctcaag gacgggaggt   9780
ccattgtggt tccctgccgc caccaagatg aactgattgg ccgggcccgc gtctctccag   9840
ggcgggatg gagcatccgg gagactgctt gcctagcaaa atcatatgcg caaatgtggc   9900
agctccttta tttccacaga agggacctcc gactgatggc caatgccatt tgttcatctg   9960
tgccagttga ctgggttcca actgggagaa ctacctggtc aatccatgga aagggagaat  10020
ggatgaccac tgaagacatg cttgtggtgt ggaacagagt gtggattgag gagaacgacc  10080
acatggaaga caagacccca gttacgaaat ggacagacat tccctatttg ggaaaaaggg  10140
aagacttgtg gtgtggatct ctcatagggc acagaccgcg caccacctgg gctgagaaca  10200
ttaaaaacac agtcaacatg gtgcgcagga tcataggtga tgaagaaaag tacatggact  10260
acctatccac ccaagttcgc tacttgggtg aagaagggtc tacacctgga gtgctgtaag  10320
caccaatctt agtgttgtca ggcctgctag tcagccacag cttggggaaa gctgtgcagc  10380
ctgtgacccc cccaggagaa gctgggaaac caagcctata gtcaggccga gaacgccatg  10440
gcacggaaga agccatgctg cctgtgagcc cctcagagga cactgagtca aaaaacccca  10500
cgcgcttgga ggcgcaggat gggaaaagaa ggtggcgacc ttccccaccc ttcaatctgg  10560
ggcctgaact ggagatcagc tgtggatctc cagaagaggg actagtggtt agaggag     10617
```

<210> SEQ ID NO 14
<211> LENGTH: 498
<212> TYPE: PRT
<213> ORGANISM: Zika virus

<400> SEQUENCE: 14

```
Ile Arg Cys Ile Gly Val Ser Asn Arg Asp Phe Val Glu Gly Met Ser
 1               5                  10                  15

Gly Gly Thr Trp Val Asp Val Val Leu Glu His Gly Gly Cys Val Thr
             20                  25                  30

Val Met Ala Gln Asp Lys Pro Thr Val Asp Ile Glu Leu Val Thr Thr
             35                  40                  45

Thr Val Ser Asn Met Ala Glu Val Arg Ser Tyr Cys Tyr Glu Ala Ser
 50                  55                  60

Ile Ser Asp Met Ala Ser Asp Ser Arg Cys Pro Thr Gln Gly Glu Ala
 65                  70                  75                  80

Tyr Leu Asp Lys Gln Ser Asp Thr Gln Tyr Val Cys Lys Arg Thr Leu
                 85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
            115                 120                 125

Ser Ile Gln Pro Glu Asn Leu Glu Tyr Arg Ile Met Leu Ser Val His
            130                 135                 140

Gly Ser Gln His Ser Gly Met Ile Val Asn Asp Glu Asn Arg Ala Lys
145                 150                 155                 160

Val Glu Val Thr Pro Asn Ser Pro Arg Ala Glu Ala Thr Leu Gly Gly
                165                 170                 175

Phe Gly Ser Leu Gly Leu Asp Cys Glu Pro Arg Thr Gly Leu Asp Phe
            180                 185                 190

Ser Asp Leu Tyr Tyr Leu Thr Met Asn Asn Lys His Trp Leu Val His
            195                 200                 205

Lys Glu Trp Phe His Asp Ile Pro Leu Pro Trp His Ala Gly Ala Asp
210                 215                 220

Thr Gly Thr Pro His Trp Asn Asn Lys Glu Ala Leu Val Glu Phe Lys
225                 230                 235                 240

Asp Ala His Ala Lys Arg Gln Thr Val Val Leu Gly Ser Gln Glu
                245                 250                 255

Gly Ala Val His Thr Ala Leu Ala Gly Ala Leu Glu Ala Glu Met Asp
            260                 265                 270

Gly Ala Lys Gly Arg Leu Phe Ser Gly His Leu Lys Cys Arg Leu Lys
            275                 280                 285

Met Asp Lys Leu Arg Leu Lys Gly Val Ser Tyr Ser Leu Cys Thr Ala
            290                 295                 300

Ala Phe Thr Phe Thr Lys Val Pro Ala Glu Thr Leu His Gly Thr Val
305                 310                 315                 320

Thr Val Glu Val Gln Tyr Ala Gly Thr Asp Gly Pro Cys Lys Val Pro
                325                 330                 335

Ala Gln Met Ala Val Asp Met Gln Thr Leu Thr Pro Val Gly Arg Leu
            340                 345                 350

Ile Thr Ala Asn Pro Val Ile Thr Glu Ser Thr Glu Asn Ser Lys Met
            355                 360                 365

Met Leu Glu Leu Asp Pro Pro Phe Gly Asp Ser Tyr Ile Val Ile Gly
            370                 375                 380

Val Gly Asp Lys Lys Ile Thr His His Trp His Arg Ser Gly Ser Thr
385                 390                 395                 400

Ile Gly Lys Ala Phe Glu Ala Thr Val Arg Gly Ala Lys Arg Met Ala
                405                 410                 415

Val Leu Gly Asp Thr Ala Trp Asp Phe Gly Ser Val Gly Gly Val Phe
```

```
                    420                 425                 430
Asn Ser Leu Gly Lys Gly Ile His Gln Ile Phe Gly Ala Ala Phe Lys
            435                 440                 445

Ser Leu Phe Gly Gly Met Ser Trp Phe Ser Gln Ile Leu Ile Gly Thr
        450                 455                 460

Leu Leu Val Trp Leu Gly Leu Asn Thr Lys Asn Gly Ser Ile Ser Leu
465                 470                 475                 480

Thr Cys Leu Ala Leu Gly Gly Val Met Ile Phe Leu Ser Thr Ala Val
                485                 490                 495

Ser Ala

<210> SEQ ID NO 15
<211> LENGTH: 498
<212> TYPE: PRT
<213> ORGANISM: Zika virus

<400> SEQUENCE: 15

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Glu Asn Arg Ala Lys
145                 150                 155                 160

Val Glu Val Thr Pro Asn Ser Pro Arg Ala Glu Ala Thr Leu Gly Gly
                165                 170                 175

Phe Gly Ser Leu Gly Leu Asp Cys Glu Pro Arg Thr Gly Leu Asp Phe
            180                 185                 190

Ser Asp Leu Tyr Tyr Leu Thr Met Asn Asn Lys His Trp Leu Val His
        195                 200                 205

Lys Glu Trp Phe His Asp Ile Pro Leu Pro Trp His Ser Gly Ala Asp
    210                 215                 220

Thr Glu Thr Pro His Trp Asn Asn Lys Glu Ala Leu Val Glu Phe Lys
225                 230                 235                 240

Asp Ala His Ala Lys Arg Gln Thr Val Val Leu Gly Ser Gln Glu
                245                 250                 255

Gly Ala Val His Thr Ala Leu Ala Gly Ala Leu Glu Ala Glu Met Asp
            260                 265                 270

Gly Ala Lys Gly Arg Leu Ser Ser Gly His Leu Lys Cys Arg Leu Lys
        275                 280                 285

Met Asp Lys Leu Arg Leu Lys Gly Val Ser Tyr Ser Leu Cys Thr Ala
```

```
                290                 295                 300
Ala Phe Thr Phe Thr Lys Val Pro Ala Glu Thr Leu His Gly Thr Val
305                 310                 315                 320

Thr Val Glu Val Gln Tyr Ala Gly Arg Asp Gly Pro Cys Lys Val Pro
                325                 330                 335

Ala Gln Met Ala Val Asp Met Gln Thr Leu Thr Pro Val Gly Arg Leu
                340                 345                 350

Ile Thr Ala Asn Pro Val Ile Thr Glu Ser Thr Glu Asn Ser Lys Met
                355                 360                 365

Met Leu Glu Leu Asp Pro Pro Phe Gly Asp Ser Tyr Ile Val Ile Gly
            370                 375                 380

Val Gly Asp Lys Lys Ile Thr His His Trp His Arg Ser Gly Ser Ile
385                 390                 395                 400

Ile Gly Lys Ala Phe Glu Ala Thr Val Arg Gly Ala Lys Arg Met Ala
                405                 410                 415

Val Leu Gly Asp Thr Ala Trp Asp Phe Gly Ser Val Gly Gly Val Phe
                420                 425                 430

Asn Ser Leu Gly Lys Gly Ile His Gln Ile Phe Gly Ala Ala Phe Lys
                435                 440                 445

Ser Leu Phe Gly Gly Met Ser Trp Phe Ser Gln Ile Leu Ile Gly Thr
            450                 455                 460

Leu Leu Val Trp Leu Gly Leu Asn Thr Lys Asn Gly Ser Ile Ser Leu
465                 470                 475                 480

Thr Cys Leu Ala Leu Gly Gly Val Met Ile Phe Leu Ser Thr Ala Val
                485                 490                 495

Ser Ala

<210> SEQ ID NO 16
<211> LENGTH: 504
<212> TYPE: PRT
<213> ORGANISM: Zika virus
<220> FEATURE:
<221> NAME/KEY: misc_feature
<222> LOCATION: (156)..(162)
<223> OTHER INFORMATION: X=any amino acid

<400> SEQUENCE: 16

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
        50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
                100                 105                 110

Leu Val Thr Cys Ala Lys Phe Thr Cys Ser Lys Lys Met Thr Gly Lys
            115                 120                 125

Ser Ile Gln Pro Glu Asn Leu Glu Tyr Arg Ile Met Leu Ser Val His
        130                 135                 140
```

```
Gly Ser Gln His Ser Gly Met Ile Val Asn Asp Xaa Xaa Xaa Xaa
145                 150                 155                 160

Xaa Xaa Asn Arg Ala Glu Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500
```

<210> SEQ ID NO 17
<211> LENGTH: 504
<212> TYPE: PRT
<213> ORGANISM: Zika virus
<220> FEATURE:
<221> NAME/KEY: misc_feature
<222> LOCATION: (152)..(156)
<223> OTHER INFORMATION: X=any amino acid

```
<400> SEQUENCE: 17

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Xaa Xaa Xaa Xaa Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Arg Leu Val Arg Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

Leu Lys Lys Gly Ser Ser Ile Gly Lys Ala Phe Glu Ala Thr Val Arg
                405                 410                 415
```

-continued

Gly Ala Lys Arg Met Ala Val Leu Gly Asp Thr Ala Trp Asp Phe Gly
            420                 425                 430

Ser Val Gly Val Phe Asn Ser Leu Gly Lys Gly Val His Gln Ile
    435                 440                 445

Phe Gly Ala Ala Phe Lys Ser Leu Phe Gly Gly Met Ser Trp Phe Ser
450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500

<210> SEQ ID NO 18
<211> LENGTH: 504
<212> TYPE: PRT
<213> ORGANISM: Zika virus

<400> SEQUENCE: 18

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His

```
                   275                 280                 285
Leu Lys Cys Arg Leu Lys Met Asp Lys Leu Arg Leu Lys Gly Val Ser
290                 295                 300
Tyr Ser Leu Cys Thr Ala Ala Phe Thr Phe Thr Lys Val Pro Ala Glu
305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
            340                 345                 350
Thr Pro Val Gly Arg Leu Ile Thr Ala Asn Pro Val Ile Thr Glu Ser
        355                 360                 365
Thr Glu Asn Ser Lys Met Met Leu Glu Leu Asp Pro Pro Phe Gly Asp
370                 375                 380
Ser Tyr Ile Val Ile Gly Val Gly Asp Lys Lys Ile Thr His His Trp
385                 390                 395                 400
His Arg Ser Gly Ser Thr Ile Gly Lys Ala Phe Glu Ala Thr Val Arg
                405                 410                 415
Gly Ala Lys Arg Met Ala Val Leu Gly Asp Thr Ala Trp Asp Phe Gly
            420                 425                 430
Ser Val Gly Gly Val Phe Asn Ser Leu Gly Lys Gly Ile His Gln Ile
        435                 440                 445
Phe Gly Ala Ala Phe Lys Ser Leu Phe Gly Gly Met Ser Trp Phe Ser
    450                 455                 460
Gln Ile Leu Ile Gly Thr Leu Leu Val Trp Leu Gly Leu Asn Thr Lys
465                 470                 475                 480
Asn Gly Ser Ile Ser Leu Thr Cys Leu Ala Leu Gly Gly Val Met Ile
                485                 490                 495
Phe Leu Ser Thr Ala Val Ser Ala
            500

<210> SEQ ID NO 19
<211> LENGTH: 504
<212> TYPE: PRT
<213> ORGANISM: Zika virus

<400> SEQUENCE: 19

Ile Arg Cys Ile Gly Val Ser Asn Arg Asp Phe Val Glu Gly Met Ser
1               5                   10                  15
Gly Gly Thr Trp Val Asp Val Val Leu Glu His Gly Gly Cys Val Thr
            20                  25                  30
Val Met Ala Gln Asp Lys Pro Thr Val Asp Ile Glu Leu Val Thr Thr
        35                  40                  45
Thr Val Ser Asn Met Ala Glu Val Arg Ser Tyr Cys Tyr Glu Ala Ser
    50                  55                  60
Ile Ser Asp Met Ala Ser Asp Ser Arg Cys Pro Thr Gln Gly Glu Ala
65                  70                  75                  80
Tyr Leu Asp Lys Gln Ser Asp Thr Gln Tyr Val Cys Lys Arg Thr Leu
                85                  90                  95
Val Asp Arg Gly Trp Gly Asn Gly Cys Gly Leu Phe Gly Lys Gly Ser
            100                 105                 110
Leu Val Thr Cys Ala Lys Phe Thr Cys Ser Lys Lys Met Thr Gly Lys
        115                 120                 125
Ser Ile Gln Pro Glu Asn Leu Glu Tyr Arg Ile Met Leu Ser Val His
    130                 135                 140
```

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
165 170 175

Glu Ala Thr Leu Gly Gly Phe Gly Ser Leu Gly Leu Asp Cys Glu Pro
180 185 190

Arg Thr Gly Leu Asp Phe Ser Asp Leu Tyr Tyr Leu Thr Met Asn Asn
195 200 205

Lys His Trp Leu Val His Lys Glu Trp Phe His Asp Ile Pro Leu Pro
210 215 220

Trp His Ala Gly Ala Asp Thr Gly Thr Pro His Trp Asn Asn Lys Glu
225 230 235 240

Ala Leu Val Glu Phe Lys Asp Ala His Ala Lys Arg Gln Thr Val Val
245 250 255

Val Leu Gly Ser Gln Glu Gly Ala Val His Thr Ala Leu Ala Gly Ala
260 265 270

Leu Glu Ala Glu Met Asp Gly Ala Lys Gly Arg Leu Phe Ser Gly His
275 280 285

Leu Lys Cys Arg Leu Lys Met Asp Lys Leu Arg Leu Lys Gly Val Ser
290 295 300

Tyr Ser Leu Cys Thr Ala Ala Phe Thr Phe Thr Lys Val Pro Ala Glu
305 310 315 320

Thr Leu His Gly Thr Val Thr Val Glu Val Gln Tyr Ala Gly Thr Asp
325 330 335

Gly Pro Cys Lys Val Pro Ala Gln Met Ala Val Asp Met Gln Thr Leu
340 345 350

Thr Pro Val Gly Arg Leu Ile Thr Ala Asn Pro Val Ile Thr Glu Ser
355 360 365

Thr Glu Asn Ser Lys Met Met Leu Glu Leu Asp Pro Pro Phe Gly Asp
370 375 380

Ser Tyr Ile Val Ile Gly Val Gly Asp Lys Lys Ile Thr His His Trp
385 390 395 400

His Arg Ser Gly Ser Thr Ile Gly Lys Ala Phe Glu Ala Thr Val Arg
405 410 415

Gly Ala Lys Arg Met Ala Val Leu Gly Asp Thr Ala Trp Asp Phe Gly
420 425 430

Ser Val Gly Gly Val Phe Asn Ser Leu Gly Lys Gly Ile His Gln Ile
435 440 445

Phe Gly Ala Ala Phe Lys Ser Leu Phe Gly Gly Met Ser Trp Phe Ser
450 455 460

Gln Ile Leu Ile Gly Thr Leu Leu Val Trp Leu Gly Leu Asn Thr Lys
465 470 475 480

Asn Gly Ser Ile Ser Leu Thr Cys Leu Ala Leu Gly Gly Val Met Ile
485 490 495

Phe Leu Ser Thr Ala Val Ser Ala
500

<210> SEQ ID NO 20
<211> LENGTH: 504
<212> TYPE: PRT
<213> ORGANISM: Zika virus

<400> SEQUENCE: 20

Ile Arg Cys Ile Gly Val Ser Asn Arg Asp Phe Val Glu Gly Met Ser
1 5 10 15

-continued

Gly Gly Thr Trp Val Asp Val Leu Glu His Gly Gly Cys Val Thr
         20              25              30

Val Met Ala Gln Asp Lys Pro Thr Val Asp Ile Glu Leu Val Thr Thr
         35              40              45

Thr Val Ser Asn Met Ala Glu Val Arg Ser Tyr Cys Tyr Glu Ala Ser
50              55              60

Ile Ser Asp Met Ala Ser Asp Ser Arg Cys Pro Thr Gln Gly Glu Ala
65              70              75              80

Tyr Leu Asp Lys Gln Ser Asp Thr Gln Tyr Val Cys Lys Arg Thr Leu
             85              90              95

Val Asp Arg Gly Trp Gly Asn Gly Cys Gly Leu Phe Gly Lys Gly Ser
            100             105             110

Leu Val Thr Cys Ala Lys Phe Thr Cys Ser Lys Lys Met Thr Gly Lys
            115             120             125

Ser Ile Gln Pro Glu Asn Leu Glu Tyr Arg Ile Met Leu Ser Val His
        130             135             140

Gly Ser Gln His Ser Gly Met Ile Val Asn Asp Ile Gly His Glu Thr
145             150             155             160

Asp Glu Asn Arg Ala Lys Val Glu Val Thr Pro Asn Ser Pro Arg Ala
                165             170             175

Glu Ala Thr Leu Gly Gly Phe Gly Ser Leu Gly Leu Asp Cys Glu Pro
            180             185             190

Arg Thr Gly Leu Asp Phe Ser Asp Leu Tyr Tyr Leu Thr Met Asn Asn
        195             200             205

Lys His Trp Leu Val His Lys Glu Trp Phe His Asp Ile Pro Leu Pro
        210             215             220

Trp His Ala Gly Ala Asp Thr Gly Thr Pro His Trp Asn Asn Lys Glu
225             230             235             240

Ala Leu Val Glu Phe Lys Asp Ala His Ala Lys Arg Gln Thr Val Val
            245             250             255

Val Leu Gly Ser Gln Glu Gly Ala Val His Thr Ala Leu Ala Gly Ala
            260             265             270

Leu Glu Ala Glu Met Asp Gly Ala Lys Gly Arg Leu Phe Ser Gly His
            275             280             285

Leu Lys Cys Arg Leu Lys Met Asp Lys Leu Arg Leu Lys Gly Val Ser
        290             295             300

Tyr Ser Leu Cys Thr Ala Ala Phe Thr Phe Thr Lys Val Pro Ala Glu
305             310             315             320

Thr Leu His Gly Thr Val Thr Val Glu Val Gln Tyr Ala Gly Thr Asp
            325             330             335

Gly Pro Cys Lys Val Pro Ala Gln Met Ala Val Asp Met Gln Thr Leu
            340             345             350

Thr Pro Val Gly Arg Leu Ile Thr Ala Asn Pro Val Ile Thr Glu Ser
        355             360             365

Thr Glu Asn Ser Lys Met Met Leu Glu Leu Asp Pro Pro Phe Gly Asp
        370             375             380

Ser Tyr Ile Val Ile Gly Val Gly Asp Lys Lys Ile Thr His His Trp
385             390             395             400

His Arg Ser Gly Ser Thr Ile Gly Lys Ala Phe Glu Ala Thr Val Arg
            405             410             415

Gly Ala Lys Arg Met Ala Val Leu Gly Asp Thr Ala Trp Asp Phe Gly
            420             425             430

Ser Val Gly Val Phe Asn Ser Leu Gly Lys Gly Val His Gln Ile
          435                 440                 445

Phe Gly Ala Ala Phe Lys Ser Leu Phe Gly Gly Met Ser Trp Phe Ser
450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
              485                 490                 495

Phe Leu Ser Thr Ala Val Ser Ala
          500

<210> SEQ ID NO 21
<211> LENGTH: 504
<212> TYPE: PRT
<213> ORGANISM: Zika virus

<400> SEQUENCE: 21

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

-continued

```
Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Val His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
                500

<210> SEQ ID NO 22
<211> LENGTH: 504
<212> TYPE: PRT
<213> ORGANISM: Zika virus

<400> SEQUENCE: 22

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
        50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Val Thr Pro Asn Ser Pro Arg Ala
```

| | | | | | 165 | | | | 170 | | | | 175 | | |
|---|---|---|---|---|---|---|---|---|---|---|---|---|---|---|---|

Glu Ala Thr Leu Gly Gly Phe Gly Ser Leu Gly Leu Asp Cys Glu Pro
               180                   185               190

Arg Thr Gly Leu Asp Phe Ser Asp Leu Tyr Tyr Leu Thr Met Asn Asn
            195                  200                 205

Lys His Trp Leu Val His Lys Glu Trp Phe His Asp Ile Pro Leu Pro
210                  215                 220

Trp His Ala Gly Ala Asp Thr Gly Thr Pro His Trp Asn Asn Lys Glu
225                  230                 235               240

Ala Leu Val Glu Phe Lys Asp Ala His Ala Lys Arg Gln Thr Val Val
            245                  250                 255

Val Leu Gly Ser Gln Glu Gly Ala Val His Thr Ala Leu Ala Gly Ala
            260                  265                 270

Leu Glu Ala Glu Met Asp Gly Ala Lys Gly Arg Leu Phe Ser Gly His
            275                  280                 285

Leu Lys Cys Arg Leu Lys Met Asp Lys Leu Arg Leu Lys Gly Val Ser
            290                  295                 300

Tyr Ser Leu Cys Thr Ala Ala Phe Thr Phe Thr Lys Val Pro Ala Glu
305                  310                 315               320

Thr Leu His Gly Thr Val Thr Val Glu Val Gln Tyr Ala Gly Thr Asp
            325                  330                 335

Gly Pro Cys Lys Val Pro Ala Gln Met Ala Val Asp Met Gln Thr Leu
            340                  345                 350

Thr Pro Val Gly Arg Leu Ile Thr Ala Asn Pro Val Ile Thr Glu Ser
            355                  360                 365

Thr Glu Asn Ser Lys Met Met Leu Glu Leu Asp Pro Pro Phe Gly Asp
            370                  375                 380

Ser Tyr Ile Val Ile Gly Val Gly Asp Lys Lys Ile Thr His His Trp
385                  390                 395               400

His Arg Ser Gly Ser Thr Ile Gly Lys Ala Phe Glu Ala Thr Val Arg
            405                  410                 415

Gly Ala Lys Arg Met Ala Val Leu Gly Asp Thr Ala Trp Asp Phe Gly
            420                  425                 430

Ser Val Gly Gly Val Phe Asn Ser Leu Gly Lys Gly Ile His Gln Ile
            435                  440                 445

Phe Gly Ala Ala Phe Lys Ser Leu Phe Gly Gly Met Ser Trp Phe Ser
            450                  455                 460

Gln Ile Leu Ile Gly Thr Leu Leu Val Trp Leu Gly Leu Asn Thr Lys
465                  470                 475               480

Asn Gly Ser Ile Ser Leu Thr Cys Leu Ala Leu Gly Gly Val Met Ile
            485                  490                 495

Phe Leu Ser Thr Ala Val Ser Ala
            500

```
<210> SEQ ID NO 23
<211> LENGTH: 504
<212> TYPE: PRT
<213> ORGANISM: Zika virus

<400> SEQUENCE: 23

```
Val Met Ala Gln Asp Lys Pro Thr Val Asp Ile Glu Leu Val Thr Thr
             35                  40                  45

Thr Val Ser Asn Met Ala Glu Val Arg Ser Tyr Cys Tyr Glu Ala Ser
 50                  55                  60

Ile Ser Asp Met Ala Ser Asp Ser Arg Cys Pro Thr Gln Gly Glu Ala
 65                  70                  75                  80

Tyr Leu Asp Lys Gln Ser Asp Thr Gln Tyr Val Cys Lys Arg Thr Leu
                 85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
            115                 120                 125

Ser Ile Gln Pro Glu Asn Leu Glu Tyr Arg Ile Met Leu Ser Val His
130                 135                 140

Gly Ser Gln His Ser Gly Met Thr Val Asn Asp Ile Gly Tyr Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
            195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Lys Leu Phe Ser Gly His
            275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Ile Pro Val Gln Met Ala Val Asp Met Gln Thr Leu
            340                 345                 350

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
            435                 440                 445

Phe Gly Ala Ala Phe Lys Ser Leu Phe Gly Gly Met Ser Trp Phe Ser
```

```
              450                 455                 460
Gln Ile Leu Ile Gly Thr Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500

<210> SEQ ID NO 24
<211> LENGTH: 504
<212> TYPE: PRT
<213> ORGANISM: Zika virus

<400> SEQUENCE: 24

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
130                 135                 140

Gly Ser Gln His Ser Gly Met Thr Val Asn Asp Ile Gly Tyr Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Lys Leu Phe Ser Gly His
        275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Val Pro Ala Glu
305                 310                 315                 320
```

Thr Leu His Gly Thr Val Thr Val Glu Val Gln Tyr Ala Gly Thr Asp
            325                 330                 335

Gly Pro Cys Lys Ile Pro Val Gln Met Ala Val Asp Met Gln Thr Leu
        340                 345                 350

Thr Pro Val Gly Arg Leu Ile Thr Ala Asn Pro Val Ile Thr Glu Ser
    355                 360                 365

Thr Glu Asn Ser Lys Met Met Leu Glu Leu Asp Pro Pro Phe Gly Asp
370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500

<210> SEQ ID NO 25
<211> LENGTH: 504
<212> TYPE: PRT
<213> ORGANISM: Zika virus

<400> SEQUENCE: 25

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly Tyr Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

```
Arg Thr Gly Leu Asp Phe Ser Asp Leu Tyr Tyr Leu Thr Met Asn Asn
            195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
            245                 250                 255

Val Leu Gly Ser Gln Glu Gly Ala Val His Thr Ala Leu Ala Gly Ala
        260                 265                 270

Leu Glu Ala Glu Met Asp Gly Ala Lys Gly Lys Leu Phe Ser Gly His
            275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
            325                 330                 335

Gly Pro Cys Lys Ile Pro Val Gln Met Ala Val Asp Met Gln Thr Leu
        340                 345                 350

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
            405                 410                 415

Gly Ala Lys Arg Met Ala Val Leu Gly Asp Thr Ala Trp Asp Phe Gly
        420                 425                 430

Ser Val Gly Gly Val Phe Asn Ser Leu Gly Lys Gly Ile His Gln Ile
            435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
            485                 490                 495

Phe Leu Ser Thr Ala Val Ser Ala
            500

<210> SEQ ID NO 26
<211> LENGTH: 504
<212> TYPE: PRT
<213> ORGANISM: Zika virus

<400> SEQUENCE: 26

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
```

```
              50                  55                  60
Ile Ser Asp Met Ala Ser Asp Ser Arg Cys Pro Thr Gln Gly Glu Ala
 65                  70                  75                  80

Tyr Leu Asp Lys Gln Ser Asp Thr Gln Tyr Val Cys Lys Arg Thr Leu
                 85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Met Thr Gly Lys
            115                 120                 125

Ser Ile Gln Pro Glu Asn Leu Glu Tyr Arg Ile Met Leu Ser Val His
            130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
            195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
            275                 280                 285

Leu Lys Cys Arg Leu Lys Met Asp Lys Leu Arg Leu Lys Gly Val Ser
            290                 295                 300

Tyr Ser Leu Cys Thr Ala Val Cys Thr Ala Ala Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
            370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
            435                 440                 445

Phe Gly Ala Ala Phe Lys Ser Leu Phe Gly Gly Met Ser Trp Phe Ser
            450                 455                 460

Gln Ile Leu Ile Gly Thr Leu Leu Val Trp Leu Gly Leu Asn Thr Lys
465                 470                 475                 480
```

```
Asn Gly Ser Ile Ser Leu Thr Cys Leu Ala Leu Gly Gly Val Met Ile
                485                 490                 495
Phe Leu Ser Thr Ala Val Ser Ala
            500

<210> SEQ ID NO 27
<211> LENGTH: 500
<212> TYPE: PRT
<213> ORGANISM: Zika virus

<400> SEQUENCE: 27

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
        50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
130                 135                 140

Gly Ser Gln His Ser Gly Met Ile Gly Tyr Glu Thr Asp Glu Asp Arg
145                 150                 155                 160

Ala Lys Val Glu Val Thr Pro Asn Ser Pro Arg Ala Glu Ala Thr Leu
                165                 170                 175

Gly Gly Phe Gly Ser Leu Gly Leu Asp Cys Glu Pro Arg Thr Gly Leu
            180                 185                 190

Asp Phe Ser Asp Leu Tyr Tyr Leu Thr Met Asn Asn Lys His Trp Leu
        195                 200                 205

Val His Lys Glu Trp Phe His Asp Ile Pro Leu Pro Trp His Ala Gly
210                 215                 220

Ala Asp Thr Gly Thr Pro His Trp Asn Asn Lys Glu Ala Leu Val Glu
225                 230                 235                 240

Phe Lys Asp Ala His Ala Lys Arg Gln Thr Val Val Val Leu Gly Ser
                245                 250                 255

Gln Glu Gly Ala Val His Thr Ala Leu Ala Gly Ala Leu Glu Ala Glu
            260                 265                 270

Met Asp Gly Ala Lys Gly Arg Leu Phe Ser Gly His Leu Lys Cys Arg
        275                 280                 285

Leu Lys Met Asp Lys Leu Arg Leu Lys Gly Val Ser Tyr Ser Leu Cys
290                 295                 300

Thr Ala Ala Phe Thr Phe Thr Lys Val Pro Ala Glu Thr Leu His Gly
305                 310                 315                 320

Thr Val Thr Val Glu Val Gln Tyr Ala Gly Thr Asp Gly Pro Cys Lys
                325                 330                 335

Ile Pro Val Gln Met Ala Val Asp Met Gln Thr Leu Thr Pro Val Gly
```

```
                    340                 345                 350
Arg Leu Ile Thr Ala Asn Pro Val Ile Thr Glu Ser Thr Glu Asn Ser
            355                 360                 365

Lys Met Met Leu Glu Leu Asp Pro Pro Phe Gly Asp Ser Tyr Ile Val
        370                 375                 380

Ile Gly Val Gly Asp Lys Lys Ile Thr His His Trp His Arg Ser Gly
385                 390                 395                 400

Ser Thr Ile Gly Lys Ala Phe Glu Ala Thr Val Arg Gly Ala Lys Arg
            405                 410                 415

Met Ala Val Leu Gly Asp Thr Ala Trp Asp Phe Gly Ser Val Gly Gly
        420                 425                 430

Val Phe Asn Ser Leu Gly Lys Gly Ile His Gln Ile Phe Gly Ala Ala
            435                 440                 445

Phe Lys Ser Leu Phe Gly Gly Met Ser Trp Phe Ser Gln Ile Leu Ile
        450                 455                 460

Gly Thr Leu Leu Val Trp Leu Gly Leu Asn Thr Lys Asn Gly Ser Ile
465                 470                 475                 480

Ser Leu Thr Cys Leu Ala Leu Gly Gly Val Met Ile Phe Leu Ser Thr
            485                 490                 495

Ala Val Ser Ala
        500

<210> SEQ ID NO 28
<211> LENGTH: 500
<212> TYPE: PRT
<213> ORGANISM: Zika virus

<400> SEQUENCE: 28

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Gly Tyr Glu Thr Asp Glu Asp Arg
145                 150                 155                 160

Ala Lys Val Glu Val Thr Pro Asn Ser Pro Arg Ala Glu Ala Thr Leu
                165                 170                 175

Gly Gly Phe Gly Ser Leu Gly Leu Asp Cys Glu Pro Arg Thr Gly Leu
            180                 185                 190

Asp Phe Ser Asp Leu Tyr Tyr Leu Thr Met Asn Asn Lys His Trp Leu
        195                 200                 205
```

Val His Lys Glu Trp Phe His Asp Ile Pro Leu Pro Trp His Ala Gly
210                 215                 220

Ala Asp Thr Gly Thr Pro His Trp Asn Asn Lys Glu Ala Leu Val Glu
225                 230                 235                 240

Phe Lys Asp Ala His Ala Lys Arg Gln Thr Val Val Leu Gly Ser
                245                 250                 255

Gln Glu Gly Ala Val His Thr Ala Leu Ala Gly Ala Leu Glu Ala Glu
                260                 265                 270

Met Asp Gly Ala Lys Gly Arg Leu Phe Ser Gly His Leu Lys Cys Arg
                275                 280                 285

Leu Lys Met Asp Lys Leu Arg Leu Lys Gly Val Ser Tyr Ser Leu Cys
290                 295                 300

Thr Ala Ala Phe Thr Phe Thr Lys Val Pro Ala Glu Thr Leu His Gly
305                 310                 315                 320

Thr Val Thr Val Glu Val Gln Tyr Ala Gly Thr Asp Gly Pro Cys Lys
                325                 330                 335

Ile Pro Val Gln Met Ala Val Asp Met Gln Thr Leu Thr Pro Val Gly
                340                 345                 350

Arg Leu Ile Thr Ala Asn Pro Val Ile Thr Glu Ser Thr Glu Asn Ser
                355                 360                 365

Lys Met Met Leu Glu Leu Asp Pro Pro Phe Gly Asp Ser Tyr Ile Val
370                 375                 380

Ile Gly Val Gly Asp Lys Lys Ile Thr His His Trp His Arg Ser Gly
385                 390                 395                 400

Ser Thr Ile Gly Lys Ala Phe Glu Ala Thr Val Arg Gly Ala Lys Arg
                405                 410                 415

Met Ala Val Leu Gly Asp Thr Ala Trp Asp Phe Gly Ser Val Gly Gly
                420                 425                 430

Val Phe Asn Ser Leu Gly Lys Gly Ile His Gln Ile Phe Gly Ala Ala
                435                 440                 445

Phe Lys Ser Leu Phe Gly Gly Met Ser Trp Phe Ser Gln Ile Leu Ile
                450                 455                 460

Gly Thr Leu Leu Val Trp Leu Gly Leu Asn Thr Lys Asn Gly Ser Ile
465                 470                 475                 480

Ser Leu Thr Cys Leu Ala Leu Gly Gly Val Met Ile Phe Leu Ser Thr
                485                 490                 495

Ala Val Ser Ala
                500

<210> SEQ ID NO 29
<211> LENGTH: 500
<212> TYPE: PRT
<213> ORGANISM: Zika virus

<400> SEQUENCE: 29

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
                35                  40                  45

Thr Val Ser Asn Met Ala Glu Val Arg Ser Tyr Cys Tyr Glu Ala Ser
50                  55                  60

Ile Ser Asp Met Ala Ser Asp Ser Arg Cys Pro Thr Gln Gly Glu Ala
65                  70                  75                  80

-continued

```
Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
130                 135                 140

Gly Ser Gln His Ser Gly Met Ile Gly Tyr Glu Thr Asp Glu Asp Arg
145                 150                 155                 160

Ala Lys Val Glu Val Thr Pro Asn Ser Pro Arg Ala Glu Ala Thr Leu
                165                 170                 175

Gly Gly Phe Gly Ser Leu Gly Leu Asp Cys Glu Pro Arg Thr Gly Leu
            180                 185                 190

Asp Phe Ser Asp Leu Tyr Tyr Leu Thr Met Asn Asn Lys His Trp Leu
        195                 200                 205

Val His Lys Glu Trp Phe His Asp Ile Pro Leu Pro Trp His Ala Gly
    210                 215                 220

Ala Asp Thr Gly Thr Pro His Trp Asn Asn Lys Glu Ala Leu Val Glu
225                 230                 235                 240

Phe Lys Asp Ala His Ala Lys Arg Gln Thr Val Val Val Leu Gly Ser
                245                 250                 255

Gln Glu Gly Ala Val His Thr Ala Leu Ala Gly Ala Leu Glu Ala Glu
            260                 265                 270

Met Asp Gly Ala Lys Gly Arg Leu Phe Ser Gly His Leu Lys Cys Arg
        275                 280                 285

Leu Lys Met Asp Lys Leu Arg Leu Lys Gly Val Ser Tyr Ser Leu Cys
    290                 295                 300

Thr Ala Ala Phe Thr Phe Thr Lys Val Pro Ala Glu Thr Leu His Gly
305                 310                 315                 320

Thr Val Thr Val Glu Val Gln Tyr Ala Gly Thr Asp Gly Pro Cys Lys
                325                 330                 335

Ile Pro Val Gln Met Ala Val Asp Met Gln Thr Leu Thr Pro Val Gly
            340                 345                 350

Arg Leu Ile Thr Ala Asn Pro Val Ile Thr Glu Ser Thr Glu Asn Ser
        355                 360                 365

Lys Met Met Leu Glu Leu Asp Pro Pro Phe Gly Asp Ser Tyr Ile Val
    370                 375                 380

Ile Gly Val Gly Asp Lys Lys Ile Thr His His Trp His Arg Ser Gly
385                 390                 395                 400

Ser Thr Ile Gly Lys Ala Phe Glu Ala Thr Val Arg Gly Ala Lys Arg
                405                 410                 415

Met Ala Val Leu Gly Asp Thr Ala Trp Asp Phe Gly Ser Val Gly Gly
            420                 425                 430

Val Phe Asn Ser Leu Gly Lys Gly Ile His Gln Ile Phe Gly Ala Ala
        435                 440                 445

Phe Lys Ser Leu Phe Gly Gly Met Ser Trp Phe Ser Gln Ile Leu Ile
    450                 455                 460

Gly Thr Leu Leu Val Trp Leu Gly Leu Asn Thr Lys Asn Gly Ser Ile
465                 470                 475                 480

Ser Leu Thr Cys Leu Ala Leu Gly Gly Val Met Ile Phe Leu Ser Thr
                485                 490                 495
```

Ala Val Ser Ala
        500

<210> SEQ ID NO 30
<211> LENGTH: 504
<212> TYPE: PRT
<213> ORGANISM: Zika virus

<400> SEQUENCE: 30

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Thr Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Gly
        355                 360                 365

```
Thr Glu Asn Ser Lys Met Met Leu Glu Leu Asp Pro Pro Phe Gly Asp
            370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Leu Asn Ser Leu Gly Lys Gly Ile His Gln Ile
            435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 31
<211> LENGTH: 504
<212> TYPE: PRT
<213> ORGANISM: Zika virus

<400> SEQUENCE: 31

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
            115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
            195                 200                 205

Lys His Trp Leu Val His Lys Glu Trp Phe His Asp Ile Pro Leu Pro
    210                 215                 220

Trp His Thr Gly Ala Asp Thr Gly Thr Pro His Trp Asn Asn Lys Glu
```

```
                225                 230                 235                 240
Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
                260                 265                 270

Leu Glu Ala Glu Met Asp Gly Ala Lys Gly Arg Leu Ser Ser Gly His
                275                 280                 285

Leu Lys Cys Arg Leu Lys Met Asp Lys Leu Arg Leu Lys Gly Val Ser
                290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
                340                 345                 350

Thr Pro Val Gly Arg Leu Ile Thr Ala Asn Pro Val Ile Thr Glu Gly
                355                 360                 365

Thr Glu Asn Ser Lys Met Met Leu Glu Leu Asp Pro Pro Phe Gly Asp
                370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
                420                 425                 430

Ser Val Gly Gly Val Leu Asn Ser Leu Gly Lys Gly Ile His Gln Ile
                435                 440                 445

Phe Gly Ala Ala Phe Lys Ser Leu Phe Gly Gly Met Ser Trp Phe Ser
                450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
                500

<210> SEQ ID NO 32
<211> LENGTH: 504
<212> TYPE: PRT
<213> ORGANISM: Zika virus

<400> SEQUENCE: 32

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
        50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95
```

```
Val Asp Arg Gly Trp Gly Asn Gly Cys Gly Leu Phe Gly Lys Gly Ser
            100                 105                 110
Leu Val Thr Cys Ala Lys Phe Ala Cys Ser Lys Lys Met Thr Gly Lys
        115                 120                 125
Ser Ile Gln Pro Glu Asn Leu Glu Tyr Arg Ile Met Leu Ser Val His
    130                 135                 140
Gly Ser Gln His Ser Gly Met Ile Val Asn Asp Thr Gly His Glu Thr
145                 150                 155                 160
Asp Glu Asn Arg Ala Lys Val Glu Ile Thr Pro Asn Ser Pro Arg Ala
                165                 170                 175
Glu Ala Thr Leu Gly Gly Phe Gly Ser Leu Gly Leu Asp Cys Glu Pro
            180                 185                 190
Arg Thr Gly Leu Asp Phe Ser Asp Leu Tyr Tyr Leu Thr Met Asn Asn
        195                 200                 205
Lys His Trp Leu Val His Lys Glu Trp Phe His Asp Ile Pro Leu Pro
    210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Val Val
                245                 250                 255
Val Leu Gly Ser Gln Glu Gly Ala Val His Thr Ala Leu Ala Gly Ala
            260                 265                 270
Leu Glu Ala Glu Met Asp Gly Ala Lys Gly Arg Leu Ser Ser Gly His
        275                 280                 285
Leu Lys Cys Arg Leu Lys Met Asp Lys Leu Arg Leu Lys Gly Val Ser
    290                 295                 300
Tyr Ser Leu Cys Thr Ala Ala Phe Thr Phe Thr Lys Ile Pro Ala Glu
305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
            340                 345                 350
Thr Pro Val Gly Arg Leu Ile Thr Ala Asn Pro Val Ile Thr Glu Ser
        355                 360                 365
Thr Glu Asn Ser Lys Met Met Leu Glu Leu Asp Pro Pro Phe Gly Asp
    370                 375                 380
Ser Tyr Ile Val Ile Gly Val Gly Glu Lys Lys Ile Thr His His Trp
385                 390                 395                 400
His Arg Ser Gly Ser Thr Ile Gly Lys Ala Phe Glu Ala Thr Val Arg
                405                 410                 415
Gly Ala Lys Arg Met Ala Val Leu Gly Asp Thr Ala Trp Asp Phe Gly
            420                 425                 430
Ser Val Gly Gly Ala Leu Asn Ser Leu Gly Lys Gly Ile His Gln Ile
        435                 440                 445
Phe Gly Ala Ala Phe Lys Ser Leu Phe Gly Gly Met Ser Trp Phe Ser
    450                 455                 460
Gln Ile Leu Ile Gly Thr Leu Leu Met Trp Leu Gly Leu Asn Thr Lys
465                 470                 475                 480
Asn Gly Ser Ile Ser Leu Met Cys Leu Ala Leu Gly Gly Val Leu Ile
                485                 490                 495
Phe Leu Ser Thr Ala Val Ser Ala
            500
```

```
<210> SEQ ID NO 33
<211> LENGTH: 504
<212> TYPE: PRT
<213> ORGANISM: Zika virus

<400> SEQUENCE: 33

```
Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
            405                 410                 415

Gly Ala Lys Arg Met Ala Val Leu Gly Asp Thr Ala Trp Asp Phe Gly
        420                 425                 430

Ser Val Gly Gly Ala Leu Asn Ser Leu Gly Lys Gly Ile His Gln Ile
    435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
                500

<210> SEQ ID NO 34
<211> LENGTH: 504
<212> TYPE: PRT
<213> ORGANISM: Zika virus

<400> SEQUENCE: 34

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255
```

```
Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 35
<211> LENGTH: 504
<212> TYPE: PRT
<213> ORGANISM: Zika virus

<400> SEQUENCE: 35

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
```

```
            115                 120                 125
Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 36
<211> LENGTH: 504
<212> TYPE: PRT
<213> ORGANISM: Zika virus
```

<400> SEQUENCE: 36

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
```

-continued

```
                    405                 410                 415
Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 37
<211> LENGTH: 504
<212> TYPE: PRT
<213> ORGANISM: Zika virus

<400> SEQUENCE: 37

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270
```

-continued

```
Leu Glu Ala Glu Met Asp Gly Ala Lys Gly Arg Leu Ser Gly His
            275                 280                 285

Leu Lys Cys Arg Leu Lys Met Asp Lys Leu Arg Leu Lys Gly Val Ser
            290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
                340                 345                 350

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
                420                 425                 430

Ser Val Gly Gly Ala Leu Asn Ser Leu Gly Lys Gly Ile His Gln Ile
            435                 440                 445

Phe Gly Ala Ala Phe Lys Ser Leu Phe Gly Gly Met Ser Trp Phe Ser
            450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 38
<211> LENGTH: 504
<212> TYPE: PRT
<213> ORGANISM: Zika virus

<400> SEQUENCE: 38

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140
```

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
            165                 170                 175

Glu Ala Thr Leu Gly Gly Phe Gly Ser Leu Gly Leu Asp Cys Glu Pro
        180                 185                 190

Arg Thr Gly Leu Asp Phe Ser Asp Leu Tyr Tyr Leu Thr Met Asn Asn
    195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 39
<211> LENGTH: 504
<212> TYPE: PRT
<213> ORGANISM: Zika virus

<400> SEQUENCE: 39

Ile Arg Cys Ile Gly Val Ser Asn Arg Asp Phe Val Glu Gly Met Ser

-continued

```
1               5                   10                  15
Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
            115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
            195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
            275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430
```

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 40
<211> LENGTH: 504
<212> TYPE: PRT
<213> ORGANISM: Zika virus

<400> SEQUENCE: 40

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser

```
                290                 295                 300
Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
                340                 345                 350

Thr Pro Val Gly Arg Leu Ile Thr Ala Asn Pro Val Ile Thr Glu Ser
                355                 360                 365

Thr Glu Asn Ser Lys Met Met Leu Glu Leu Asp Pro Pro Phe Gly Asp
                370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
                420                 425                 430

Ser Val Gly Gly Ala Leu Asn Ser Leu Gly Lys Gly Ile His Gln Ile
                435                 440                 445

Phe Gly Ala Ala Phe Lys Ser Leu Phe Gly Gly Met Ser Trp Phe Ser
                450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
                500

<210> SEQ ID NO 41
<211> LENGTH: 504
<212> TYPE: PRT
<213> ORGANISM: Zika virus

<400> SEQUENCE: 41

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
                35                  40                  45

Thr Val Ser Asn Met Ala Glu Val Arg Ser Tyr Cys Tyr Glu Ala Ser
                50                  55                  60

Ile Ser Asp Met Ala Ser Asp Ser Arg Cys Pro Thr Gln Gly Glu Ala
65              70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
                100                 105                 110

Leu Val Thr Cys Ala Lys Phe Ala Cys Ser Lys Lys Met Thr Gly Lys
                115                 120                 125

Ser Ile Gln Pro Glu Asn Leu Glu Tyr Arg Ile Met Leu Ser Val His
                130                 135                 140

Gly Ser Gln His Ser Gly Met Ile Val Asn Asp Thr Gly His Glu Thr
145                 150                 155                 160
```

```
Asp Glu Asn Arg Ala Lys Val Glu Ile Thr Pro Asn Ser Pro Arg Ala
            165                 170                 175

Glu Ala Thr Leu Gly Gly Phe Gly Ser Leu Gly Leu Asp Cys Glu Pro
        180                 185                 190

Arg Thr Gly Leu Asp Phe Ser Asp Leu Tyr Tyr Leu Thr Met Asn Asn
    195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 42
<211> LENGTH: 504
<212> TYPE: PRT
<213> ORGANISM: Zika virus

<400> SEQUENCE: 42

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30
```

```
Val Met Ala Gln Asp Lys Pro Thr Val Asp Ile Glu Leu Val Thr Thr
        35                  40                  45
Thr Val Ser Asn Met Ala Glu Val Arg Ser Tyr Cys Tyr Glu Ala Ser
 50                  55                  60
Ile Ser Asp Met Ala Ser Asp Ser Arg Cys Pro Thr Gln Gly Glu Ala
 65                  70                  75                  80
Tyr Leu Asp Lys Gln Ser Asp Thr Gln Tyr Val Cys Lys Arg Thr Leu
                 85                  90                  95
Val Asp Arg Gly Trp Gly Asn Gly Cys Gly Leu Phe Gly Lys Gly Ser
            100                 105                 110
Leu Val Thr Cys Ala Lys Phe Ala Cys Ser Lys Lys Met Thr Gly Lys
            115                 120                 125
Ser Ile Gln Pro Glu Asn Leu Glu Tyr Arg Ile Met Leu Ser Val His
130                 135                 140
Gly Ser Gln His Ser Gly Met Ile Val Asn Asp Thr Gly His Glu Thr
145                 150                 155                 160
Asp Glu Asn Arg Ala Lys Val Glu Ile Thr Pro Asn Ser Pro Arg Ala
                165                 170                 175
Glu Ala Thr Leu Gly Gly Phe Gly Ser Leu Gly Leu Asp Cys Glu Pro
            180                 185                 190
Arg Thr Gly Leu Asp Phe Ser Asp Leu Tyr Tyr Leu Thr Met Asn Asn
            195                 200                 205
Lys His Trp Leu Val His Lys Glu Trp Phe His Asp Ile Pro Leu Pro
            210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Val Val
                245                 250                 255
Val Leu Gly Ser Gln Glu Gly Ala Val His Thr Ala Leu Ala Gly Ala
            260                 265                 270
Leu Glu Ala Glu Met Asp Gly Ala Lys Gly Arg Leu Ser Ser Gly His
            275                 280                 285
Leu Lys Cys Arg Leu Lys Met Asp Lys Leu Arg Leu Lys Gly Val Ser
            290                 295                 300
Tyr Ser Leu Cys Thr Ala Ala Phe Thr Phe Thr Lys Ile Pro Ala Glu
305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
            340                 345                 350
Thr Pro Val Gly Arg Leu Ile Thr Ala Asn Pro Val Ile Thr Glu Ser
            355                 360                 365
Thr Glu Asn Ser Lys Met Met Leu Glu Leu Asp Pro Pro Phe Gly Asp
            370                 375                 380
Ser Tyr Ile Val Ile Gly Val Gly Glu Lys Lys Ile Thr His His Trp
385                 390                 395                 400
His Arg Ser Gly Ser Thr Ile Gly Lys Ala Phe Glu Ala Thr Val Arg
                405                 410                 415
Gly Ala Lys Arg Met Ala Val Leu Gly Asp Thr Ala Trp Asp Phe Gly
            420                 425                 430
Ser Val Gly Gly Ala Leu Asn Ser Leu Gly Lys Gly Ile His Gln Ile
            435                 440                 445
```

```
Phe Gly Ala Ala Phe Lys Ser Leu Phe Gly Gly Met Ser Trp Phe Ser
        450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 43
<211> LENGTH: 504
<212> TYPE: PRT
<213> ORGANISM: Zika virus

<400> SEQUENCE: 43

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320
```

```
Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 44
<211> LENGTH: 504
<212> TYPE: PRT
<213> ORGANISM: Zika virus

<400> SEQUENCE: 44

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
```

```
                 180                 185                 190
Arg Thr Gly Leu Asp Phe Ser Asp Leu Tyr Tyr Leu Thr Met Asn Asn
             195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
             245                 250                 255

Val Leu Gly Ser Gln Glu Gly Ala Val His Thr Ala Leu Ala Gly Ala
         260                 265                 270

Leu Glu Ala Glu Met Asp Gly Ala Lys Gly Arg Leu Ser Ser Gly His
     275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
             325                 330                 335

Gly Pro Cys Lys Val Pro Ala Gln Met Ala Val Asp Met Gln Thr Leu
         340                 345                 350

Thr Pro Val Gly Arg Leu Ile Thr Ala Asn Pro Val Ile Thr Glu Ser
     355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
             405                 410                 415

Gly Ala Lys Arg Met Ala Val Leu Gly Asp Thr Ala Trp Asp Phe Gly
         420                 425                 430

Ser Val Gly Gly Ala Leu Asn Ser Leu Gly Lys Gly Ile His Gln Ile
     435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
             485                 490                 495

Phe Leu Ser Thr Ala Val Ser Ala
         500

<210> SEQ ID NO 45
<211> LENGTH: 504
<212> TYPE: PRT
<213> ORGANISM: Zika virus

<400> SEQUENCE: 45

Ile Arg Cys Ile Gly Val Ser Asn Arg Asp Phe Val Glu Gly Met Ser
1               5                  10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45
```

```
Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
```

465                 470                 475                 480
Asn Gly Ser Ile Ser Leu Met Cys Leu Ala Leu Gly Gly Val Leu Ile
                    485                 490                 495
Phe Leu Ser Thr Ala Val Ser Ala
                    500

<210> SEQ ID NO 46
<211> LENGTH: 504
<212> TYPE: PRT
<213> ORGANISM: Zika virus

<400> SEQUENCE: 46

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
        50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

```
Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
        370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Met Ser Trp Phe Ser
        450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 47
<211> LENGTH: 504
<212> TYPE: PRT
<213> ORGANISM: Zika virus

<400> SEQUENCE: 47

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205
```

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
            245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 48
<211> LENGTH: 504
<212> TYPE: PRT
<213> ORGANISM: Zika virus

<400> SEQUENCE: 48

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
50                  55                  60

Ile Ser Asp Met Ala Ser Asp Ser Arg Cys Pro Thr Gln Gly Glu Ala

```
            65                  70                  75                  80
Tyr Leu Asp Lys Gln Ser Asp Thr Gln Tyr Val Cys Lys Arg Thr Leu
                    85                  90                  95
Val Asp Arg Gly Trp Gly Asn Gly Cys Gly Leu Phe Gly Lys Gly Ser
                100                 105                 110
Leu Val Thr Cys Ala Lys Phe Ala Cys Ser Lys Lys Met Thr Gly Lys
                115                 120                 125
Ser Ile Gln Pro Glu Asn Leu Glu Tyr Arg Ile Met Leu Ser Val His
            130                 135                 140
Gly Ser Gln His Ser Gly Met Ile Val Asn Asp Thr Gly His Glu Thr
145                 150                 155                 160
Asp Glu Asn Arg Ala Lys Val Glu Ile Thr Pro Asn Ser Pro Arg Ala
                165                 170                 175
Glu Ala Thr Leu Gly Gly Phe Gly Ser Leu Gly Leu Asp Cys Glu Pro
                180                 185                 190
Arg Thr Gly Leu Asp Phe Ser Asp Leu Tyr Tyr Leu Thr Met Asn Asn
                195                 200                 205
Lys His Trp Leu Val His Lys Glu Trp Phe His Asp Ile Pro Leu Pro
            210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Val Val
                245                 250                 255
Val Leu Gly Ser Gln Glu Gly Ala Val His Thr Ala Leu Ala Gly Ala
                260                 265                 270
Leu Glu Ala Glu Met Asp Gly Ala Lys Gly Arg Leu Ser Ser Gly His
                275                 280                 285
Leu Lys Cys Arg Leu Lys Met Asp Lys Leu Arg Leu Lys Gly Val Ser
            290                 295                 300
Tyr Ser Leu Cys Thr Ala Ala Phe Thr Phe Thr Lys Ile Pro Ala Glu
305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
                340                 345                 350
Thr Pro Val Gly Arg Leu Ile Thr Ala Asn Pro Val Ile Thr Glu Ser
                355                 360                 365
Thr Glu Asn Ser Lys Met Met Leu Glu Leu Asp Pro Pro Phe Gly Asp
            370                 375                 380
Ser Tyr Ile Val Ile Gly Val Gly Glu Lys Lys Ile Thr His His Trp
385                 390                 395                 400
His Arg Ser Gly Ser Thr Ile Gly Lys Ala Phe Glu Ala Thr Val Arg
                405                 410                 415
Gly Ala Lys Arg Met Ala Val Leu Gly Asp Thr Ala Trp Asp Phe Gly
                420                 425                 430
Ser Val Gly Gly Ala Leu Asn Ser Leu Gly Lys Gly Ile His Gln Ile
                435                 440                 445
Phe Gly Ala Ala Phe Lys Ser Leu Phe Gly Gly Met Ser Trp Phe Ser
            450                 455                 460
Gln Ile Leu Ile Gly Thr Leu Leu Met Trp Leu Gly Leu Asn Thr Lys
465                 470                 475                 480
Asn Gly Ser Ile Ser Leu Met Cys Leu Ala Leu Gly Gly Val Leu Ile
                485                 490                 495
```

Phe Leu Ser Thr Ala Val Ser Ala
            500

<210> SEQ ID NO 49
<211> LENGTH: 504
<212> TYPE: PRT
<213> ORGANISM: Zika virus

<400> SEQUENCE: 49

Ile Arg Cys Ile Gly Val Ser Asn Arg Asp Phe Val Glu Gly Met Ser
1               5                   10                  15

Gly Gly Thr Trp Val Asp Ile Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser

```
                355                 360                 365
Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
                500

<210> SEQ ID NO 50
<211> LENGTH: 504
<212> TYPE: PRT
<213> ORGANISM: Zika virus

<400> SEQUENCE: 50

Ile Arg Cys Ile Gly Val Ser Asn Arg Asp Phe Val Glu Gly Met Ser
1               5                   10                  15

Gly Gly Thr Trp Val Asp Ile Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220
```

```
Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
            245                 250                 255

Val Leu Gly Ser Gln Glu Gly Ala Val His Thr Ala Leu Ala Gly Ala
        260                 265                 270

Leu Glu Ala Glu Met Asp Gly Ala Lys Gly Arg Leu Ser Ser Gly His
    275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
            325                 330                 335

Gly Pro Cys Lys Val Pro Ala Gln Met Ala Val Asp Met Gln Thr Leu
        340                 345                 350

Thr Pro Val Gly Arg Leu Ile Thr Ala Asn Pro Val Ile Thr Glu Ser
    355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
            405                 410                 415

Gly Ala Lys Arg Met Ala Val Leu Gly Asp Thr Ala Trp Asp Phe Gly
        420                 425                 430

Ser Val Gly Gly Ala Leu Asn Ser Leu Gly Lys Gly Ile His Gln Ile
    435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
            485                 490                 495

Phe Leu Ser Thr Ala Val Ser Ala
            500

<210> SEQ ID NO 51
<211> LENGTH: 504
<212> TYPE: PRT
<213> ORGANISM: Zika virus

<400> SEQUENCE: 51

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Th

```
Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 52
<211> LENGTH: 504
<212> TYPE: PRT
<213> ORGANISM: Zika virus

<400> SEQUENCE: 52

```

```
Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
            405                 410                 415

Gly Ala Lys Arg Met Ala Val Leu Gly Asp Thr Ala Trp Asp Phe Gly
        420                 425                 430

Ser Val Gly Gly Ala Leu Asn Ser Leu Gly Lys Gly Ile His Gln Ile
    435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 53
<211> LENGTH: 504
<212> TYPE: PRT
<213> ORGANISM: Zika virus

<400> SEQUENCE: 53

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
```

245                 250                 255
Val Leu Gly Thr Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 54
<211> LENGTH: 504
<212> TYPE: PRT
<213> ORGANISM: Zika virus

<400> SEQUENCE: 54

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
            115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Arg Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 55
<211> LENGTH: 504
<212> TYPE: PRT

<213> ORGANISM: Zika virus

<400> SEQUENCE: 55

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

```
His Arg Ser Gly Ser Thr Ile Gly Lys Ala Phe Glu Ala Thr Val Arg
                405                 410                 415
Gly Ala Lys Arg Met Ala Val Leu Gly Asp Thr Ala Trp Asp Phe Gly
            420                 425                 430
Ser Val Gly Gly Ala Leu Asn Ser Leu Gly Lys Gly Ile His Gln Ile
        435                 440                 445
Phe Gly Ala Ala Phe Lys Ser Leu Phe Gly Gly Met Ser Trp Phe Ser
    450                 455                 460
Gln Ile Leu Ile Gly Thr Leu Leu Val Trp Leu Gly Leu Asn Thr Lys
465                 470                 475                 480
Asn Gly Ser Ile Ser Leu Met Cys Leu Ala Leu Gly Gly Val Leu Ile
                485                 490                 495
Phe Leu Ser Thr Ala Val Ser Ala
                500

<210> SEQ ID NO 56
<211> LENGTH: 504
<212> TYPE: PRT
<213> ORGANISM: Zika virus

<400> SEQUENCE: 56

Ile Arg Cys Ile Gly Val Ser Asn Arg Asp Phe Val Glu Gly Met Ser
1               5                   10                  15
Gly Gly Thr Trp Val Asp Val Val Leu Glu His Gly Gly Cys Val Thr
            20                  25                  30
Val Met Ala Gln Asp Lys Pro Thr Val Asp Ile Glu Leu Val Thr Thr
        35                  40                  45
Thr Val Ser Asn Met Ala Glu Val Arg Ser Tyr Cys Tyr Glu Ala Ser
    50                  55                  60
Ile Ser Asp Met Ala Ser Asp Ser Arg Cys Pro Thr Gln Gly Glu Ala
65                  70                  75                  80
Tyr Leu Asp Lys Gln Ser Asp Thr Gln Tyr Val Cys Lys Arg Thr Leu
                85                  90                  95
Val Asp Arg Gly Trp Gly Asn Gly Cys Gly Leu Phe Gly Lys Gly Ser
            100                 105                 110
Leu Val Thr Cys Ala Lys Phe Ala Cys Ser Lys Lys Met Thr Gly Lys
        115                 120                 125
Ser Ile Gln Pro Glu Asn Leu Glu Tyr Arg Ile Met Leu Ser Val His
    130                 135                 140
Gly Ser Gln His Ser Gly Met Ile Val Asn Asp Thr Gly His Glu Thr
145                 150                 155                 160
Asp Glu Asn Arg Ala Lys Val Glu Ile Thr Pro Asn Ser Pro Arg Ala
                165                 170                 175
Glu Ala Thr Leu Gly Gly Phe Gly Ser Leu Gly Leu Asp Cys Glu Pro
            180                 185                 190
Arg Thr Gly Leu Asp Phe Ser Asp Leu Tyr Tyr Leu Thr Met Asn Asn
        195                 200                 205
Lys His Trp Leu Val His Lys Glu Trp Phe His Asp Ile Pro Leu Pro
    210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Val Val
                245                 250                 255
Val Leu Gly Ser Gln Glu Gly Ala Val His Thr Ala Leu Ala Gly Ala
            260                 265                 270
```

-continued

Leu Glu Ala Glu Met Asp Gly Ala Lys Gly Arg Leu Ser Ser Gly His
            275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
            435                 440                 445

Phe Gly Ala Ala Phe Lys Ser Leu Phe Gly Gly Met Ser Trp Phe Ser
            450                 455                 460

Gln Ile Leu Ile Gly Thr Leu Leu Met Trp Leu Gly Leu Asn Ala Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
                500

<210> SEQ ID NO 57
<211> LENGTH: 504
<212> TYPE: PRT
<213> ORGANISM: Zika virus

<400> SEQUENCE: 57

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
            115                 120                 125

Ser Ile Gln Pro Glu Asn Leu Glu Tyr Arg Ile Met Leu Ser Val His

```
                130                 135                 140
Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
                180                 185                 190

Arg Thr Gly Leu Asp Phe Ser Asp Leu Tyr Tyr Leu Thr Met Asn Asn
                195                 200                 205

Lys His Trp Leu Val His Lys Glu Trp Phe His Asp Ile Pro Leu Pro
            210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
                260                 265                 270

Leu Glu Ala Glu Met Asp Gly Ala Lys Gly Arg Leu Ser Ser Gly His
                275                 280                 285

Leu Lys Cys Arg Leu Lys Met Asp Lys Leu Arg Leu Lys Gly Val Ser
            290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
                340                 345                 350

Thr Pro Val Gly Arg Leu Ile Thr Ala Asn Pro Val Ile Thr Glu Ser
                355                 360                 365

Thr Glu Asn Ser Lys Met Met Leu Glu Leu Asp Pro Pro Phe Gly Asp
            370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
                420                 425                 430

Ser Val Gly Gly Ala Leu Asn Ser Leu Gly Lys Gly Ile His Gln Ile
                435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Ala Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
                500

<210> SEQ ID NO 58
<211> LENGTH: 504
<212> TYPE: PRT
<213> ORGANISM: Zika virus

<400> SEQUENCE: 58
```

```
Ile Arg Cys Ile Gly Val Ser Asn Arg Asp Phe Val Glu Gly Met Ser
1               5                   10                  15

Gly Gly Thr Trp Val Asp Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Thr Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
```

```
                420                 425                 430
Ser Val Gly Gly Ala Leu Asn Ser Leu Gly Lys Gly Ile His Gln Ile
            435                 440                 445

Phe Gly Ala Ala Phe Lys Ser Leu Phe Gly Gly Met Ser Trp Phe Ser
        450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
                500

<210> SEQ ID NO 59
<211> LENGTH: 504
<212> TYPE: PRT
<213> ORGANISM: Zika virus

<400> SEQUENCE: 59

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Gly Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285
```

```
Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
                355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Le

```
Asp Glu Asn Arg Ala Lys Val Glu Ile Thr Pro Asn Ser Pro Arg Ala
            165                 170                 175

Glu Ala Thr Leu Gly Gly Phe Gly Ser Leu Gly Leu Asp Cys Glu Pro
        180                 185                 190

Arg Thr Gly Leu Asp Phe Ser Asp Leu Tyr Tyr Leu Thr Met Asn Asn
    195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Leu Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 61
<211> LENGTH: 504
<212> TYPE: PRT
<213> ORGANISM: Zika virus

<400> SEQUENCE: 61

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
```

```
                20                  25                  30
Val Met Ala Gln Asp Lys Pro Ala Val Asp Ile Glu Leu Val Thr Thr
            35                  40                  45
Thr Val Ser Asn Met Ala Glu Val Arg Ser Tyr Cys Tyr Glu Ala Ser
        50                  55                  60
Ile Ser Asp Met Ala Ser Asp Ser Arg Cys Pro Thr Gln Gly Glu Ala
65                  70                  75                  80
Tyr Leu Asp Lys Gln Ser Asp Thr Gln Tyr Val Cys Lys Arg Thr Leu
                85                  90                  95
Val Asp Arg Gly Trp Gly Asn Gly Cys Gly Leu Phe Gly Lys Gly Ser
            100                 105                 110
Leu Val Thr Cys Ala Lys Phe Ala Cys Ser Lys Lys Met Thr Gly Lys
        115                 120                 125
Ser Ile Gln Pro Glu Asn Leu Glu Tyr Arg Ile Met Leu Ser Val His
    130                 135                 140
Gly Ser Gln His Ser Gly Met Ile Val Asn Asp Thr Gly His Glu Thr
145                 150                 155                 160
Asp Glu Asn Arg Ala Lys Val Glu Ile Thr Pro Asn Ser Pro Arg Ala
                165                 170                 175
Glu Ala Thr Leu Gly Gly Phe Gly Ser Leu Gly Leu Asp Cys Glu Pro
            180                 185                 190
Arg Thr Gly Leu Asp Phe Ser Asp Leu Tyr Tyr Leu Thr Met Asn Asn
        195                 200                 205
Lys His Trp Leu Val His Lys Glu Trp Phe His Asp Ile Pro Leu Pro
    210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Val Val
                245                 250                 255
Val Leu Gly Ser Gln Glu Gly Ala Val His Thr Ala Leu Ala Gly Ala
            260                 265                 270
Leu Glu Ala Glu Met Asp Gly Ala Lys Gly Arg Leu Ser Ser Gly His
        275                 280                 285
Leu Lys Cys Arg Leu Lys Met Asp Lys Leu Arg Leu Lys Gly Val Ser
    290                 295                 300
Tyr Ser Leu Cys Thr Ala Ala Phe Thr Phe Thr Lys Ile Pro Ala Glu
305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
            340                 345                 350
Thr Pro Val Gly Arg Leu Ile Thr Ala Asn Pro Val Ile Thr Glu Ser
        355                 360                 365
Thr Glu Asn Ser Lys Met Met Leu Glu Leu Asp Pro Pro Phe Gly Asp
    370                 375                 380
Ser Tyr Ile Val Ile Gly Val Gly Glu Lys Lys Ile Thr His His Trp
385                 390                 395                 400
His Arg Ser Gly Ser Thr Ile Gly Lys Ala Phe Glu Ala Thr Val Arg
                405                 410                 415
Gly Ala Lys Arg Met Ala Val Leu Gly Asp Thr Ala Trp Asp Phe Gly
            420                 425                 430
Ser Val Gly Gly Ala Leu Asn Ser Leu Gly Lys Gly Ile His Gln Ile
        435                 440                 445
```

```
Phe Gly Ala Ala Phe Lys Ser Leu Phe Gly Gly Met Ser Trp Phe Ser
        450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Leu Ile
                485                 490                 495

Phe Leu Ser Thr Ala Val Ser Ala
            500

<210> SEQ ID NO 62
<211> LENGTH: 504
<212> TYPE: PRT
<213> ORGANISM: Zika virus

<400> SEQUENCE: 62

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
```

-continued

```
                305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
                340                 345                 350
Thr Pro Val Gly Arg Leu Ile Thr Ala Asn Pro Val Ile Thr Glu Ser
                355                 360                 365
Thr Glu Asn Ser Lys Met Met Leu Glu Leu Asp Pro Pro Phe Gly Asp
                370                 375                 380
Ser Tyr Ile Val Ile Gly Val Gly Glu Lys Lys Ile Thr His His Trp
385                 390                 395                 400
His Arg Ser Gly Ser Thr Ile Gly Lys Ala Phe Glu Ala Thr Val Arg
                405                 410                 415
Gly Ala Lys Arg Met Ala Val Leu Gly Asp Thr Ala Trp Asp Phe Gly
                420                 425                 430
Ser Val Gly Gly Ala Leu Asn Ser Leu Gly Lys Gly Ile His Gln Ile
                435                 440                 445
Phe Gly Ala Ala Phe Lys Ser Leu Phe Gly Gly Met Ser Trp Phe Ser
                450                 455                 460
Gln Ile Leu Ile Gly Thr Leu Leu Val Trp Leu Gly Leu Asn Thr Lys
465                 470                 475                 480
Asn Gly Ser Ile Ser Leu Thr Cys Leu Ala Leu Gly Gly Val Leu Ile
                485                 490                 495
Phe Leu Ser Thr Ala Val Ser Ala
                500

<210> SEQ ID NO 63
<211> LENGTH: 504
<212> TYPE: PRT
<213> ORGANISM: Zika virus

<400> SEQUENCE: 63

Ile Arg Cys Ile Gly Val Ser Asn Arg Asp Phe Val Glu Gly Met Ser
1               5                   10                  15
Gly Gly Thr Trp Val Asp Val Val Leu Glu His Gly Gly Cys Val Thr
                20                  25                  30
Val Met Ala Gln Asp Lys Pro Thr Val Asp Ile Glu Leu Val Thr Thr
                35                  40                  45
Thr Val Ser Asn Met Ala Glu Val Arg Ser Tyr Cys Tyr Glu Ala Ser
                50                  55                  60
Ile Ser Asp Met Ala Ser Asp Ser Arg Cys Pro Thr Gln Gly Glu Ala
65                  70                  75                  80
Tyr Leu Asp Lys Gln Ser Asp Thr Gln Tyr Val Cys Lys Arg Thr Leu
                85                  90                  95
Val Asp Arg Gly Trp Gly Asn Gly Cys Gly Leu Phe Gly Lys Gly Ser
                100                 105                 110
Leu Val Thr Cys Ala Lys Phe Ala Cys Ser Lys Lys Met Thr Gly Lys
                115                 120                 125
Ser Ile Gln Pro Glu Asn Leu Glu Tyr Arg Ile Met Leu Ser Val His
                130                 135                 140
Gly Ser Gln His Ser Gly Met Ile Val Asn Asp Thr Gly His Glu Thr
145                 150                 155                 160
Asp Glu Asn Arg Ala Lys Val Glu Ile Thr Pro Asn Ser Pro Arg Ala
                165                 170                 175
```

```
Glu Ala Thr Leu Gly Gly Phe Gly Ser Leu Gly Leu Asp Cys Glu Pro
                180                 185                 190

Arg Thr Gly Leu Asp Phe Ser Asp Leu Tyr Tyr Leu Thr Met Asn Asn
            195                 200                 205

Lys His Trp Leu Val His Lys Glu Trp Phe His Asp Ile Pro Leu Pro
        210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Leu Ile
                485                 490                 495

Phe Leu Ser Thr Ala Val Ser Ala
            500

<210> SEQ ID NO 64
<211> LENGTH: 504
<212> TYPE: PRT
<213> ORGANISM: Zika virus

<400> SEQUENCE: 64

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Ser Thr
        35                  40                  45
```

```
Thr Val Ser Asn Met Ala Glu Val Arg Ser Tyr Cys Tyr Glu Ala Thr
     50              55                  60
Ile Ser Asp Ile Ala Ser Asp Ser Arg Cys Pro Thr Gln Gly Glu Ala
65              70                  75                  80
Tyr Leu Asp Lys Gln Ser Asp Thr Gln Tyr Val Cys Lys Arg Thr Leu
             85                  90                  95
Val Asp Arg Gly Trp Gly Asn Gly Cys Gly Leu Phe Gly Lys Gly Ser
         100                 105                 110
Leu Val Thr Cys Ala Lys Phe Ala Cys Ser Lys Lys Met Thr Gly Lys
     115                 120                 125
Ser Ile Gln Pro Glu Asn Leu Glu Tyr Arg Ile Met Leu Ser Val His
130                 135                 140
Gly Ser Gln His Ser Gly Met Ile Val Asn Asp Thr Gly His Glu Thr
145                 150                 155                 160
Asp Glu Asn Arg Ala Lys Val Glu Ile Thr Pro Asn Ser Pro Arg Ala
             165                 170                 175
Glu Ala Thr Leu Gly Gly Phe Gly Ser Leu Gly Leu Asp Cys Glu Pro
         180                 185                 190
Arg Thr Gly Leu Asp Phe Ser Asp Leu Tyr Tyr Leu Thr Met Asn Asn
     195                 200                 205
Lys His Trp Leu Val His Lys Glu Trp Phe His Asp Ile Pro Leu Pro
     210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Ala Val
             245                 250                 255
Val Leu Gly Ser Gln Glu Gly Ala Val His Thr Ala Leu Ala Gly Ala
         260                 265                 270
Leu Glu Ala Glu Met Asp Gly Ala Lys Gly Arg Leu Ser Ser Gly His
     275                 280                 285
Leu Lys Cys Arg Leu Lys Met Asp Lys Leu Arg Leu Lys Gly Val Ser
     290                 295                 300
Tyr Ser Leu Cys Thr Ala Ala Phe Thr Phe Thr Lys Ile Pro Ala Glu
305                 310                 315                 320
Thr Leu His Gly Thr Val Thr Val Glu Val Gln Tyr Ala Gly Thr Asp
             325                 330                 335
Gly Pro Cys Lys Val Pro Ala Gln Met Ala Val Asp Met Gln Thr Leu
         340                 345                 350
Thr Pro Val Gly Arg Leu Ile Thr Ala Asn Pro Val Ile Thr Glu Ser
     355                 360                 365
Thr Glu Asn Ser Lys Met Met Leu Glu Leu Asp Pro Pro Phe Gly Asp
     370                 375                 380
Ser Tyr Ile Val Ile Gly Val Gly Glu Lys Lys Ile Thr His His Trp
385                 390                 395                 400
His Arg Ser Gly Ser Thr Ile Gly Lys Ala Phe Glu Ala Thr Val Arg
             405                 410                 415
Gly Ala Lys Arg Met Ala Val Leu Gly Asp Thr Ala Trp Asp Phe Gly
         420                 425                 430
Ser Val Gly Gly Ala Leu Asn Ser Leu Gly Lys Gly Ile His Gln Ile
     435                 440                 445
Phe Gly Ala Ala Phe Lys Ser Leu Phe Gly Gly Met Ser Trp Phe Ser
450                 455                 460
```

```
Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
            485                 490                 495

Phe Leu Ser Thr Ala Val Ser Ala
            500

<210> SEQ ID NO 65
<211> LENGTH: 504
<212> TYPE: PRT
<213> ORGANISM: Zika virus
<220> FEATURE:
<221> NAME/KEY: misc_feature
<222> LOCATION: (1)..(504)
<223> OTHER INFORMATION: X=any amino acid

<400> SEQUENCE: 65

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Xaa Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
```

```
            305                 310                 315                 320
        Thr Leu His Gly Thr Val Thr Val Glu Val Gln Tyr Ala Gly Thr Asp
                        325                 330                 335

Gly Pro Cys Lys Val Pro Ala Gln Met Ala Val Asp Met Gln Thr Leu
                    340                 345                 350

Thr Pro Val Gly Arg Leu Ile Thr Ala Asn Pro Val Ile Thr Glu Ser
                        355                 360                 365

Thr Glu Asn Ser Lys Met Met Leu Glu Leu Asp Pro Pro Phe Gly Asp
                    370                 375                 380

Ser Tyr Ile Val Ile Gly Val Gly Asp Lys Lys Ile Thr His His Trp
        385                 390                 395                 400

Xaa Arg Ser Gly Ser Thr Ile Gly Lys Ala Phe Glu Ala Thr Val Arg
                        405                 410                 415

Gly Ala Lys Arg Met Ala Val Leu Gly Asp Thr Ala Trp Asp Phe Gly
                    420                 425                 430

Ser Val Gly Gly Ala Leu Asn Ser Leu Gly Lys Gly Ile His Gln Ile
                    435                 440                 445

Phe Gly Ala Ala Phe Lys Ser Leu Phe Gly Gly Met Ser Trp Phe Ser
                    450                 455                 460

Gln Ile Leu Ile Gly Thr Leu Leu Val Trp Leu Gly Leu Asn Thr Lys
        465                 470                 475                 480

Asn Gly Ser Ile Ser Leu Thr Cys Leu Ala Leu Gly Gly Val Leu Ile
                        485                 490                 495

Phe Leu Ser Thr Ala Val Ser Ala
                    500

<210> SEQ ID NO 66
<211> LENGTH: 504
<212> TYPE: PRT
<213> ORGANISM: Zika virus

<400> SEQUENCE: 66

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Ala Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
        50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Leu Val Asn Asp Thr Gly His Glu Thr
145                 150                 155                 160

Asp Glu Asn Arg Ala Lys Val Glu Ile Thr Pro Asn Ser Pro Arg Ala
                165                 170                 175
```

```
Glu Ala Thr Leu Gly Gly Phe Gly Ser Leu Gly Leu Asp Cys Glu Pro
                180                 185                 190

Arg Thr Gly Leu Asp Phe Ser Asp Leu Tyr Tyr Leu Thr Met Asn Asn
            195                 200                 205

Lys His Trp Leu Ala His Lys Glu Trp Phe His Asp Ile Pro Leu Pro
        210                 215                 220

Trp His Ala Gly Ala Ala Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Val Asp Gly Thr Val Thr Val Glu Gly Gln Tyr Gly Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Ile Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Gly
            500

<210> SEQ ID NO 67
<211> LENGTH: 504
<212> TYPE: PRT
<213> ORGANISM: Zika virus

<400> SEQUENCE: 67

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Ala Met Ala Gln Asp Lys Pro Thr Val Asp Ile Glu Leu Val Thr Thr
            35                  40                  45
```

```
Thr Val Ser Asn Met Ala Glu Val Arg Ser Tyr Cys Tyr Glu Ala Ser
         50                  55                  60

Ile Ser Asp Met Ala Ser Asp Ser Arg Cys Pro Thr Gln Gly Glu Ala
 65                  70                  75                  80

Tyr Leu Asp Lys Gln Ser Asp Thr Gln Tyr Val Cys Lys Arg Thr Leu
                 85                  90                  95

Val Asp Arg Gly Trp Gly Asn Gly Cys Gly Leu Phe Gly Lys Gly Ser
             100                 105                 110

Leu Val Thr Cys Ala Lys Phe Ala Cys Ser Lys Lys Met Thr Gly Lys
         115                 120                 125

Ser Ile Gln Pro Glu Asn Leu Glu Tyr Arg Ile Met Leu Ser Val His
     130                 135                 140

Gly Ser Gln His Ser Gly Met Leu Val Asn Asp Thr Gly His Glu Thr
145                 150                 155                 160

Asp Glu Asn Arg Ala Lys Val Glu Ile Thr Pro Asn Ser Pro Arg Ala
                 165                 170                 175

Glu Ala Thr Leu Gly Gly Phe Gly Ser Leu Gly Leu Asp Cys Glu Pro
             180                 185                 190

Arg Thr Gly Leu Asp Phe Ser Asp Leu Tyr Tyr Leu Thr Met Asn Asn
         195                 200                 205

Lys His Trp Leu Ala His Lys Glu Trp Phe His Asp Ile Pro Leu Pro
     210                 215                 220

Trp His Ala Gly Ala Ala Thr Gly Thr Pro His Trp Asn Asn Lys Glu
225                 230                 235                 240

Ala Leu Val Glu Phe Lys Asp Ala His Ala Lys Arg Gln Thr Val Val
                 245                 250                 255

Val Leu Gly Ser Gln Glu Gly Ala Val His Thr Ala Leu Ala Gly Ala
             260                 265                 270

Leu Glu Ala Glu Met Asp Gly Ala Lys Gly Arg Leu Ser Ser Gly His
         275                 280                 285

Leu Lys Cys Arg Leu Lys Met Asp Lys Leu Arg Leu Lys Gly Val Ser
     290                 295                 300

Tyr Ser Leu Cys Thr Ala Ala Phe Thr Phe Thr Lys Ile Pro Ala Glu
305                 310                 315                 320

Thr Val Asp Gly Thr Val Thr Val Glu Gly Gln Tyr Gly Gly Thr Asp
                 325                 330                 335

Gly Pro Cys Lys Val Pro Ala Gln Met Ala Val Asp Met Gln Thr Leu
             340                 345                 350

Thr Pro Val Gly Arg Leu Ile Thr Ala Asn Pro Val Ile Thr Glu Ser
         355                 360                 365

Thr Glu Asn Ser Lys Met Met Leu Glu Leu Asp Pro Pro Phe Gly Asp
     370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                 405                 410                 415

Gly Ala Lys Arg Met Ala Val Leu Gly Asp Thr Ala Trp Asp Phe Gly
             420                 425                 430

Ser Val Gly Gly Ala Leu Asn Ser Leu Gly Lys Gly Ile His Gln Ile
         435                 440                 445

Ile Gly Ala Ala Phe Lys Ser Leu Phe Gly Gly Met Ser Trp Phe Ser
     450                 455                 460
```

```
Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
            485                 490                 495

Phe Leu Ser Thr Ala Val Ser Gly
            500

<210> SEQ ID NO 68
<211> LENGTH: 504
<212> TYPE: PRT
<213> ORGANISM: Zika virus

<400> SEQUENCE: 68

Ile Ser Cys Ile Gly Val Ser Asn Arg Asp Leu Val Glu Gly Met Ser
1               5                   10                  15

Gly Gly Thr Trp Val Asp Val Val Leu Glu His Gly Gly Cys Val Thr
            20                  25                  30

Glu Met Ala Gln Asp Lys Pro Thr Val Asp Ile Glu Leu Val Thr Met
        35                  40                  45

Thr Val Ser Asn Met Ala Glu Val Arg Ser Tyr Cys Tyr Glu Ala Ser
50                  55                  60

Leu Ser Asp Met Ala Ser Asp Ser Arg Cys Pro Thr Gln Gly Glu Pro
65                  70                  75                  80

Ser Leu Asp Lys Gln Ser Asp Thr Gln Ser Val Cys Lys Arg Thr Leu
                85                  90                  95

Gly Asp Arg Gly Trp Gly Asn Gly Cys Gly Ile Phe Gly Lys Gly Ser
            100                 105                 110

Leu Val Thr Cys Ser Lys Phe Thr Cys Cys Lys Lys Met Pro Gly Lys
        115                 120                 125

Ser Ile Gln Pro Glu Asn Leu Glu Tyr Arg Ile Met Leu Pro Val His
130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Ser Ala Gly Thr Asp
                325                 330                 335
```

```
Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
        370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
            435                 440                 445

Phe Gly Ala Ala Phe Lys Ser Leu Phe Gly Gly Met Ser Trp Phe Ser
        450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500

<210> SEQ ID NO 69
<211> LENGTH: 498
<212> TYPE: PRT
<213> ORGANISM: Zika virus

<400> SEQUENCE: 69

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Glu Asn Arg Ala Lys
145                 150                 155                 160

Val Glu Val Thr Pro Asn Ser Pro Arg Ala Glu Ala Thr Leu Gly Gly
                165                 170                 175

Phe Gly Ser Leu Gly Leu Asp Cys Glu Pro Arg Thr Gly Leu Asp Phe
            180                 185                 190

Ser Asp Leu Tyr Tyr Leu Thr Met Asn Asn Lys His Trp Leu Val His
```

-continued

```
                195                 200                 205
Lys Glu Trp Phe His Asp Ile Pro Leu Pro Trp His Ala Gly Ala Asp
210                 215                 220

Thr Gly Thr Pro His Trp Asn Asn Lys Glu Ala Leu Val Glu Phe Lys
225                 230                 235                 240

Asp Ala His Ala Lys Arg Gln Thr Val Val Leu Gly Ser Gln Glu
                245                 250                 255

Gly Ala Val His Thr Ala Leu Ala Gly Ala Leu Glu Ala Glu Met Asp
                260                 265                 270

Gly Ala Lys Gly Arg Leu Phe Ser Gly His Leu Lys Cys Arg Leu Lys
            275                 280                 285

Met Asp Lys Leu Arg Leu Lys Gly Val Ser Tyr Ser Leu Cys Thr Ala
290                 295                 300

Ala Phe Thr Phe Thr Lys Val Pro Ala Glu Thr Leu His Gly Thr Val
305                 310                 315                 320

Thr Val Glu Val Gln Tyr Ala Gly Thr Asp Gly Pro Cys Lys Val Pro
                325                 330                 335

Ala Gln Met Ala Val Asp Met Gln Thr Leu Thr Pro Val Gly Arg Leu
                340                 345                 350

Ile Thr Ala Asn Pro Val Ile Thr Glu Ser Thr Glu Asn Ser Lys Met
            355                 360                 365

Met Leu Glu Leu Asp Pro Pro Phe Gly Asp Ser Tyr Ile Val Ile Gly
370                 375                 380

Val Gly Asp Lys Lys Ile Thr His His Trp His Arg Ser Gly Ser Thr
385                 390                 395                 400

Ile Gly Lys Ala Phe Glu Ala Thr Val Arg Gly Ala Lys Arg Met Ala
                405                 410                 415

Val Leu Gly Asp Thr Ala Trp Asp Phe Gly Ser Val Gly Gly Val Phe
                420                 425                 430

Asn Ser Leu Gly Lys Gly Ile His Gln Ile Phe Gly Ala Ala Phe Lys
            435                 440                 445

Ser Leu Phe Gly Gly Met Ser Trp Phe Ser Gln Ile Leu Ile Gly Thr
450                 455                 460

Leu Leu Val Trp Leu Gly Leu Asn Thr Lys Asn Gly Ser Ile Ser Leu
465                 470                 475                 480

Thr Cys Leu Ala Leu Gly Gly Val Met Ile Phe Leu Ser Thr Ala Val
                485                 490                 495

Ser Ala
```

<210> SEQ ID NO 70
<211> LENGTH: 26
<212> TYPE: DNA
<213> ORGANISM: Artificial Sequence
<220> FEATURE:
<223> OTHER INFORMATION: 1-26 n=inosine
<220> FEATURE:
<221> NAME/KEY: misc_feature
<222> LOCATION: (1)..(26)
<223> OTHER INFORMATION: n=inosine

<400> SEQUENCE: 70
ncncncncnc ncncncncnc ncncnc                                     26

<210> SEQ ID NO 71
<211> LENGTH: 11
<212> TYPE: PRT
<213> ORGANISM: Artificial Sequence
<220> FEATURE:
<223> OTHER INFORMATION: synthetic peptide

<400> SEQUENCE: 71

Lys Leu Lys Leu Leu Leu Leu Leu Lys Leu Lys
1               5                   10

<210> SEQ ID NO 72
<211> LENGTH: 11840
<212> TYPE: DNA
<213> ORGANISM: Chikungunya virus

<400> SEQUENCE: 72

| | | | | | |
|---|---|---|---|---|---|
| atggctgcgt | gagacacacg | tagcctacca | gtttcttact | gctctactct | gcaaagcaag | 60 |
| agattaataa | cccatcatgg | atcctgtgta | cgtggacata | gacgctgaca | gcgcctttt | 120 |
| gaaggccctg | caacgtgcgt | accccatgtt | tgaggtggaa | ccaaggcagg | tcacaccgaa | 180 |
| tgaccatgct | aatgctagag | cgttctcgca | tctagctata | aaactaatag | agcaggaaat | 240 |
| tgaccccgac | tcaaccatcc | tggatatcgg | cagtgcgcca | gcaaggagga | tgatgtcgga | 300 |
| caggaagtac | cactgcgtct | gcccgatgcg | cagtgcggaa | gatcccgaga | gactcgccaa | 360 |
| ttatgcgaga | aagctagcat | ctgccgcagg | aaaagtcctg | gacagaaaca | tctctggaaa | 420 |
| gatcggggac | ttacaagcag | taatggccgt | gccagacacg | gagacgccaa | cattctgctt | 480 |
| acacacagac | gtctcatgta | gacagagagc | agacgtcgct | ataccaagac | gtctatgc | 540 |
| tgtacacgca | cccacgtcgc | tataccacca | ggcgattaaa | ggggtccgag | tggcgtactg | 600 |
| ggttgggttc | gacacaaccc | cgttcatgta | caatgccatg | cgggtgcct | accctcata | 660 |
| ctcgacaaac | tgggcagatg | agcaggtact | gaaggctaag | aacataggat | tatgttcaac | 720 |
| agacctgacg | gaaggtagac | gaggcaagtt | gtctattatg | agagggaaaa | agctaaaacc | 780 |
| gtgcgaccgt | gtgctgttct | cagtagggtc | aacgctctac | ccggaaagcc | gcaagctact | 840 |
| taagagctgg | cacctgccat | cggtgttcca | tttaaagggc | aaactcagct | tcacatgccg | 900 |
| ctgtgataca | gtggtttcgt | gtgagggcta | cgtcgttaag | agaataacga | tgagcccagg | 960 |
| cctttatgga | aaaaccacag | gtatgcggt | aacccaccac | gcagacgat | tcctgatgtg | 1020 |
| caagactacc | gacacggttg | acggcgaaag | artgtcattc | tcggtgtgca | catacgtgcc | 1080 |
| ggcgaccatt | tgtgatcaaa | tgaccggcat | ccttgctaca | gaagtcacgc | cggaggatgc | 1140 |
| acagaagctg | ttggtggggc | tgaaccagag | aatagtggtt | aacggcagaa | cgcaacggaa | 1200 |
| tacgaacacc | atgaaaaatt | atctgcttcc | cgtggtcgcc | caagccttca | gtaagtgggc | 1260 |
| aaaggagtgc | cggaaagaca | tggaagatga | aaaactcctg | ggggtcagag | aagaacact | 1320 |
| gacctgctgc | tgtctctatg | gcattcaagaa | gcagaaaaca | cacacggtct | acaagaggcc | 1380 |
| tgatacccag | tcaattcaga | aggttcaggc | cgagtttgac | agctttgtgg | taccgagtct | 1440 |
| gtggtcgtcc | gggttgtcaa | tccctttgag | gactagaatc | aaatggttgt | taagcaaggt | 1500 |
| gccaaaaacc | gacctgatcc | catacagcgg | agacgcccga | gaagcccggg | acgcagaaaa | 1560 |
| agaagcagag | gaagaacgag | aagcagaact | gactcgcgaa | gccctaccac | ctctacaggc | 1620 |
| agcacaggaa | gatgttcagg | tcgaaatcga | cgtggaacag | cttgaggaca | gagcgggcgc | 1680 |
| aggaataata | gagactccga | gaggagctat | caaagttact | gcccaaccaa | cagaccacgt | 1740 |
| cgtgggagag | tacctggtac | tctcccgca | gaccgtacta | cgtagccaga | agctcagtct | 1800 |
| gattcacgct | ttggcggagc | aagtgaagac | gtgcacgcac | aacggacgag | cagggaggta | 1860 |
| tgcggtcgaa | gcgtacgacg | gccgagtcct | agtgccctca | ggctatgcaa | tctcgcctga | 1920 |

```
agacttccag agtctaagcg aaagcgcaac gatggtgtat aacgaaagag agttcgtaaa    1980
cagaaagcta caccatattg cgatgcacgg accagccctg aacaccgacg aagagtcgta    2040
tgagctggtg agggcagaga ggacagaaca cgagtacgtc tacgacgtgg atcagagaag    2100
atgctgtaag aaggaagaag ccgcaggact ggtactggtg ggcgacttga ctaatccgcc    2160
ctaccacgaa ttcgcatatg aagggctaaa atccgccct gcctgccat acaaaattgc      2220 agtcatagga gtcttcggag taccgggatc tggcaagtca gctattatca agaacctagt    2280
taccaggcag gacctggtga ctagcggaaa gaaagaaaac tgccaagaaa tcaccaccga    2340
cgtgatgaga cagagaggtc tagagatatc tgcacgtacg gttgactcgc tgctcttgaa    2400
tggatgcaac agaccagtcg acgtgttgta cgtagacgag gcgtttgcgt gccactctgg    2460
aacgctactt gctttgatcg ccttggtgag accaaggcag aaagttgtac tttgtggtga    2520
cccgaagcag tgcggcttct tcaatatgat gcagatgaaa gtcaactata atcacaacat    2580
ctgcacccaa gtgtaccaca aaagtatctc caggcggtgt acactgcctg tgaccgccat    2640
tgtgtcatcg ttgcattacg aaggcaaaat gcgcactacg aatgagtaca acaagccgat    2700
tgtagtggac actacaggct caacaaaacc tgaccctgga gacctcgtgt taacgtgctt    2760
cagagggtgg gttaaacaac tgcaaattga ctatcgtgga tacgaggtca tgacagcagc    2820
cgcatcccaa gggttaacca gaaaggagt ttacgcagtt agacaaaaag ttaatgaaaa      2880
cccgctctat gcatcaacgt cagagcacgt caacgtactc ctaacgcgta cggaaggtaa    2940
actggtatgg aagacacttt ccggcgaccc gtggataaag acgctgcaga acccaccgaa    3000
aggaaacttc aaagcaacta ttaaggagtg ggaggtggag catgcatcaa taatggcggg    3060
catctgcagt caccaaatga ccttcgatac attccaaaat aaagccaacg tttgttgggc    3120
taagagcttg gtccctatcc tcgaaacagc ggggataaaa ctaaatgata ggcagtggtc    3180
tcagataatt caagccttca agaagacaa agcatactca cctgaagtag ccctgaatga     3240
aatatgtacg cgcatgtatg gggtggatct agacagcggg ctattttcta aaccgttggt    3300
gtctgtgtat tacgcggata accactggga taataggcct ggagggaaaa tgttcgatt     3360 taaccccgag gcagcatcca ttctagaaag aaagtatcca ttcacaaaag ggaagtggaa    3420
catcaacaag cagatctgcg tgactaccag gaggatagaa gactttaacc ctaccaccaa    3480
catcataccg gccaacagga gactaccaca ctcattagtg gccgaacacc gcccagtaaa    3540
aggggaaaga atggaatggc tggttaacaa gataaacggc caccacgtgc tcctggtcag    3600
tggctataac cttgcactgc ctactaagag agtcacttgg gtagcgccgt taggtgtccg    3660
cggagcggac tacacataca acctagagtt gggtctgcca gcaacgcttg gtaggtatga    3720
cctagtggtc ataaacatcc acaccctttt tcgcatacac cattccaac agtgcgtcga     3780 ccacgcaatg aaactgcaaa tgctcggggg tgactcattg agactgctca accgggcgg     3840 ctctctattg atcagagcat atggttacgc agatagaacc agtgaacgag tcatctgcgt    3900
attgggacgc aagtttagat cgtctagagc gttgaaacca ccatgtgtca ccagcaacac    3960
tgagatgttt ttcctattca gcaactttga caatggcaga aggaatttca caactcatgt    4020
catgaacaat caactgaatg cagccttcgt aggacaggtc acccgagcag gatgtgcacc    4080
gtcgtaccgg gtaaaacgca tggacatcgc gaagaacgat gaagagtgcg tagtcaacgc    4140
cgctaaccct cgcgggttac cgggtgrcgg tgtttgcaag gcagtataca aaaatggcc     4200 ggagtccttt aagaacagtg caacaccagt gggaaccgca aaaacagtta tgtgcggtac    4260
```

```
gtatccagta atccacgctg ttggaccaaa cttctctaat tattcggagt ctgaagggga    4320
ccgggaattg gcagctgcct atcgagaagt cgcaaaggaa gtaactaggc tgggagtaaa    4380
tagtgtagct atacctctcc tctccacagg tgtatactca ggagggaaag acaggctgac    4440
ccagtcactg aaccacctct ttacagccat ggactcgacg gatgcagacg tggtcatcta    4500
ctgccgcgac aaagaatggg agaagaaaat atctgaggcc atacagatgc ggacccaagt    4560
agagctgctg gatgagcaca tctccataga ctgcgatatt gttcgcgtgc accctgacag    4620
cagcttggca ggcagaaaag gatacagcac cacggaaggc gcactgtact catatctaga    4680
agggacccgt tttcatcaga cggctgtgga tatggcggag atacatacta tgtggccaaa    4740
gcaaacagag gccaatgagc aagtctgcct atatgccctg ggggaaagta ttgaatcgat    4800
caggcagaaa tgcccggtgg atgatgcaga cgcatcatct ccccccaaaa ctgtcccgtg    4860
cctttgccgt tacgctatga ctccagaacg cgtcacccgg cttcgcatga accacgtcac    4920
aagcataatt gtgtgttctt cgtttcccct cccaaagtac aaaatagaag gagtgcaaaa    4980
agtcaaatgc tctaaggtaa tgctatttga ccacaacgtg ccatcgcgcg taagtccaag    5040
ggaatataka tcttcccagg agtctgcaca ggaggcgagt acaatcacgt cactgacgca    5100
tagtcaattc gacctaagcg ttgatggcga gatactgccc gtcccgtcag acctggatgc    5160
tgacgcccca gccctagaac cagcactaga cgacggggcg acacacacgc tgccatccac    5220
aaccggaaac cttgcggccg tgtctgattg ggtaatgagc accgtacctg tcgcgccgcc    5280
cagaagaagg cgagggagaa acctgactgt gacatgtgac gagagagaag ggaatataac    5340
acccatggct agcgtccgat tctttagggc agagctgtgt ccggtcgtac aagaaacagc    5400
ggagacgcgt gacacagcaa tgtctcttca ggcaccaccg agtaccgcca cggaaccgaa    5460
tcatccgccg atctccttcg gagcatcaag cgagacgttc cccattacat ttggggactt    5520
caacgaagga gaaatcgaaa gcttgtcttc tgagctacta actttcggag acttcttacc    5580
aggagaagtg gatgacttga cagacagcga ctggtccacg tgctcagaca cggacgacga    5640
gttatgacta gacagggcag gtgggtatat attctcgtcg gacaccggtc caggtcattt    5700
acaacagaag tcagtacgcc agtcagtgct gccggtgaac accctggagg aagtccacga    5760
ggagaagtgt tacccaccta agctggatga agcaaaggag caactattac ttaagaaact    5820
ccaggagagt gcatccatgg ccaacagaag caggtatcag tcgcgcaaag tagaaaacat    5880
gaaagcagca atcatccaga gactaaagag aggctgtaga ctatacttaa tgtcagagac    5940
cccaaaagtc cctacttacc ggactacata tccggcgcct gtgtactcgc ctccgatcaa    6000
cgtccgattg tccaatcccg agtccgcagt ggcagcatgc aatgagttct agctagaaa     6060 ctatccaact gtctcatcat accaaattac cgacgagtat gatgcatatc tagacatggt    6120
ggacgggtcg gagagttgcc tggaccgagc gacattcaat ccgtcaaaac tcaggagcta    6180
cccgaaacag cacgcttacc acgcgccctc catcagaagc gctgtaccgt ccccattcca    6240
gaacacacta cagaatgtac tggcagcagc cacgaaaaga aactgcaacg tcacacagat    6300
gagggaatta cccactttgg actcagcagt attcaacgtg gagtgtttca aaaattcgc     6360 atgcaaccaa gaatactggg aagaatttgc tgccagccct attaggataa caactgagaa    6420
tttagcaacc tatgttacta aactaaaagg gccaaaagca gcagcgctat tcgcaaaaac    6480
ccataatcta ctgccactac aggaagtacc aatggatagg ttcacagtag atatgaaaag    6540
ggacgtaaag gtgactcctg gtacaaagca tacagaggaa agacctaagg tgcaggttat    6600
acaggcggct gaacccttgg cgacagcata cctatgtggg attcacagag agctggttag    6660
```

```
gaggctgaac gccgtcctcc tacccaatgt acatacacta tttgacatgt ctgccgagga    6720
tttcgatgcc atcatagccg cacactttaa gccaggagac actgttttgg aaacggacat    6780
agcctccttt gataagagcc aagatgattc acttgcgctt actgctttga tgctgttaga    6840
ggatttaggg gtggatcact ccctgctgga cttgatagag gctgctttcg gagagatttc    6900
cagctgtcac ctaccgacag gtacgcgctt caagttcggc gccatgatga atcaggtat    6960 gttcctaact ctgttcgtca acacattgtt aaacatcacc atcgccagcc gagtgctgga    7020
agatcgtctg acaaaatccg cgtgcgcggc cttcatcggc gacgacaaca taatacatgg    7080
agtcgtctcc gatgaattga tggcagccag atgtgccact tggatgaaca tggaagtgaa    7140
gatcatagat gcagttgtat ccttgaaagc cccttacttt tgtggagggt ttatactgca    7200
cgatactgtg acaggaacag cttgcagagt ggcagacccg ctaaaaaggc ttttaaact    7260 gggcaaaccg ctagcggcag gtgacgaaca agatgaagat agaagacgag cgctggctga    7320
cgaagtgatc agatggcaac gaacagggct aattgatgag ctggagaaag cggtatactc    7380
taggtacgaa gtgcagggta tatcagttgt ggtaatgtcc atggccacct ttgcaagctc    7440
cagatccaac ttcgagaagc tcagaggacc cgtcataact ttgtacgcg gtcctaaata    7500 ggtacgcact acagctacct attttgcaga agccgacagc aagtatctaa acactaatca    7560
gctacaatgg agttcatccc aacccaaact ttttacaata ggaggtacca gcctcgaccc    7620
tggactccgc gccctactat ccaagtcatc aggcccagac cgcgccctca gaggcaagct    7680
gggcaacttg cccagctgat ctcagcagtt aataaactga caatgcgcgc ggtaccccaa    7740
cagaagccac gcaggaatcg gaagaataag aagcaaaagc aaaacaaca ggcgccacaa    7800 aacaacacaa atcaaaagaa gcagccacct aaaaagaaac cggctcaaaa gaaaagaag    7860 ccgggccgca gagagaggat gtgcatgaaa atcgaaaatg attgtatttt cgaagtcaag    7920
cacgaaggta aggtaacagg ttacgcgtgc ctggtggggg acaaagtaat gaaaccagca    7980
cacgtaaagg ggaccatcga taacgcggac ctggccaaac tggcctttaa gcggtcatct    8040
aagtatgacc ttgaatgcgc gcagataccc gtgcacatga agtccgacgc ttcgaagttc    8100
acccatgaga aaccggaggg gtactacaac tggcaccacg gagcagtaca gtactcagga    8160
ggccggttca ccatccctac aggtgctggc aaaccagggg acagcggcag accgatcttc    8220
gacaacaagg gacgcgtggt ggccatagtc ttaggaggag ctaatgaagg agcccgtaca    8280
gccctctcgg tggtgacctg gaataaagac attgtcacta aaatcacccc cgaggggggcc    8340 gaagagtgga gtcttgccat cccagttatg tgcctgttgg caaacaccac gttccctgc    8400 tcccagcccc cttgcacgcc ctgctgctac gaaaaggaac cggaggaaac cctacgcatg    8460
cttgaggaca acgtcatgag acctgggtac tatcagctgc tacaagcatc cttaacatgt    8520
tctccccacc gccagcgacg cagcaccaag gacaacttca atgtctataa agccacaaga    8580
ccatacttag ctcactgtcc cgactgtgga gaagggcact cgtgccatag tcccgtagca    8640
ctagaacgca tcagaaatga agcgacagac gggacgctga aaatccaggt ctccttgcaa    8700
atcggaataa agacggatga cagccacgat tggaccaagc tgcgttatat ggacaaccac    8760
atgccagcag acgcagagag ggcggggcta tttgtaagaa catcagcacc gtgtacgatt    8820
actggaacaa tgggacactt catcctggcc cgatgtccaa aggggaaac tctgacggtg    8880 ggattcactg acagtaggaa gattagtcac tcatgtacgc acccatttca ccacgaccct    8940
cctgtgatag gtcgggaaaa attccattcc cgaccgcagc acggtaaaga gctaccttgc    9000
```

```
agcacgtacg tgcagagcac cgccgcaact accgaggaga tagaggtaca catgccccca    9060
gacacccctg atcgcacatt aatgtcacaa cagtccggca acgtaaagat cacagtcaat    9120
ggccagacgg tgcggtacaa gtgtaattgc ggtggctcaa atgaaggact aacaactaca    9180
gacaaagtga ttaataactg caaggttgat caatgtcatg ccgcggtcac caatcacaaa    9240
aagtggcagt ataactcccc tctggtcccg cgtaatgctg aacttgggga ccgaaaagga    9300
aaaattcaca tcccgtttcc gctggcaaat gtaacatgca gggtgcctaa agcaaggaac    9360
cccaccgtga cgtacgggaa aaaccaagtc atcatgctac tgtatcctga ccacccaaca    9420
ctcctgtcct accggaatat gggagaagaa ccaaactatc aagaagagtg ggtgatgcat    9480
aagaaggaag tcgtgctaac cgtgccgact gaagggctcg aggtcacgtg gggcaacaac    9540
gagccgtata agtattggcc gcagttatct acaaacggta cagcccatgg ccacccgcat    9600
gagataattc tgtattatta tgagctgtac cccactatga ctgtagtagt tgtgtcagtg    9660
gccacgttca tactcctgtc gatggtgggt atggcagcgg ggatgtgcat gtgtgcacga    9720
cgcagatgca tcacaccgta tgaactgaca ccaggagcta ccgtcccttt cctgcttagc    9780
ctaatatgct gcatcagaac agctaaagcg ccacatacc aagaggctgc gatatacctg    9840
tggaacgagc agcaaccttt gttttggcta caagcccttaa ttccgctggc agccctgatt    9900
gttctatgca actgtctgag actcttacca tgctgctgta aaacgttggc ttttttagcc    9960
gtaatgagcg tcggtgccca cactgtgagc gcgtacgaac acgtaacagt gatcccgaac   10020
acggtgggag taccgtataa gactctagtc aatagacctg gctacagccc catggtattg   10080 gagatgaac tactgtcagt cactttggag ccaacactat cgcttgatta catcacgtgc   10140
gagtacaaaa ccgtcatccc gtctccgtac gtgaagtgct gcggtacagc agagtgcaag   10200
gacaaaaacc tacctgacta cagctgtaag gtcttcaccg cgtctaccc atttatgtgg   10260 ggcggcgcct actgcttctg cgacgctgaa acacgcagt tgagcgaagc acacgtggag   10320
aagtccgaat catgcaaaac agaatttgca tcagcataca gggctcatac cgcatctgca   10380
tcagctaagc tccgcgtcct ttaccaagga aataacatca ctgtaactgc ctatgcaaac   10440
ggcgaccatg ccgtcacagt taaggacgcc aaattcattg tggggccaat gtcttcagcc   10500
tggacacctt tcgacaacaa aattgtggtg tacaaaggtg acgtctataa catggactac   10560 ccgcccttttg cgcaggaag accaggacaa tttggcgata tccaaagtcg cacacctgag   10620
agtaaagacg tctatgctaa tacacaactg gtactgcaga gaccggctgt gggtacggta   10680
cacgtgccat actctcaggc accatctggc tttaagtatt ggctaaaaga acgcggggcg   10740
tcgctgcagc acacagcacc atttggctgc caaatagcaa caaacccggt aagagcggtg   10800
aactgcgccg tagggaacat gcccatctcc atcgacatac cggaagcggc cttcactagg   10860
gtcgtcgacg cgccctcttt aacggacatg tcgtgcgagg taccagcctg cacccattcc   10920
tcagactttg ggggcgtcgc cattattaaa tatgcagcca gcaagaaagg caagtgtgcg   10980
gtgcattcga tgactaacgc cgtcactatt cgggaagctg agatagaagt tgaagggaat   11040
tctcagctgc aaatctcttt ctcgacggcc ttagccagcg ccgaattccg cgtacaagtc   11100
tgttctacac aagtacactg tgcagccgag tgccacccc cgaaggacca catagtcaac   11160
tacccggcgt cacataccac cctcgggggtc caggacatct ccgctacggc gatgtcatgg   11220
gtgcagaaga tcacgggagg tgtgggactg gttgttgctg ttgccgcact gattctaatc   11280
gtggtgctat gcgtgtcgtt cagcaggcac taacttgaca attaagtatg aaggtatatg   11340
tgtcccctaa gagacacact gtacatagca aataatctat agatcaaagg gctacgcaac   11400
```

-continued

| | |
|---|---|
| ccctgaatag taacaaaata caaaatcact aaaaattata aaaacagaaa aatacataaa | 11460 |
| taggtatacg tgtcccctaa gagacacatt gtatgtaggt gataagtata gatcaaaggg | 11520 |
| ccgaataacc cctgaatagt aacaaaatat gaaaatcaat aaaaatcata aaatagaaaa | 11580 |
| accataaaca gaagtagttc aaagggctat aaaacccctg aatagtaaca aaacataaaa | 11640 |
| ttaataaaaa tcaaatgaat accataattg gcaaacggaa gagatgtagg tacttaagct | 11700 |
| tcctaaaagc agccgaactc actttgagaa gtaggcatag cataccgaac tcttccacga | 11760 |
| ttctccgaac ccacagggac gtaggagatg ttattttgtt tttaatattt caaaaaaaaa | 11820 |
| aaaaaaaaaa aaaaaaaaaa | 11840 |

<210> SEQ ID NO 73
<211> LENGTH: 10863
<212> TYPE: DNA
<213> ORGANISM: Japanese encephalitis virus

<400> SEQUENCE: 73

| | |
|---|---|
| tttaaacagt tttttagaac ggaagataac catgactaaa aaaccaggag ggcccggtaa | 60 |
| aaaccgggct atcaatatgc tgaaacgcgg cctaccccgc gtattcccac tagtgggagt | 120 |
| gaagagggta gtaatgagct tgttggacgg cagagggcca gtacgtttcg tgctggctct | 180 |
| tatcacgttc ttcaagttta cagcattagc cccgaccaag gcgcttttag ccgatggaa | 240 |
| agcagtggaa aagagtgtgg caatgaaaca tcttactagt ttcaaacgag aacttggaac | 300 |
| actcattgac gccgtgaaca gcgggggcag aaagcaaaac aaaagaggag gaaatgaagg | 360 |
| ctcaatcatg tggctcgcga gcttggcagt tgtcatagct tgtgcaggag ccatgaagtt | 420 |
| gtcgaatttc caggggaagc ttttgatgac catcaacaac acggacattg cagacgttat | 480 |
| cgtgattccc acctcaaaag gagagaacag atgctgggtc cgggcaatcg acgtcggcta | 540 |
| catgtgtgag gacactatca cgtacgaatg tcctaagctt accatgggca atgatccaga | 600 |
| ggatgtggat tgctggtgtg acaaccaaga agtctacgtc caatatggac ggtgcacgcg | 660 |
| gaccaggcat tccaagcgaa gcaggagatc cgtgtcggtc caaacacatg gggagagttc | 720 |
| actagtgaat aaaaaagagg cttggctgga ttcaacgaaa gccacacgat atctcatgaa | 780 |
| aactgagaac tggatcataa ggaatcctgg ctatgctttc ctggcggcgg tacttggctg | 840 |
| gatgcttggc agtaacaacg gtcaacgcgt ggtatttacc atcctcctgc tgttggtcgc | 900 |
| tccggcttac agttttaatt gtctgggaat gggcaatcgt gacttcatag aaggagccag | 960 |
| tggagccact tgggtggact tggtgctaga aggagatagc tgcttgacaa tcatggcaaa | 1020 |
| cgacaaacca acattggacg tccgcatgat taacatcgaa gctagccaac ttgctgaggt | 1080 |
| cagaagttac tgctatcatg cttcagtcac tgacatctcg acggtggctc ggtgccccac | 1140 |
| gactggagaa gcccacaacg agaagcgagc tgatagtagc tatgtgtgca aacaaggctt | 1200 |
| cactgaccgt gggtgggca acggatgtgg acttttcggg aagggaagca ttgacacatg | 1260 |
| tgcaaaattc tcctgcacca gtaaagcgat tgggagaaca atccagccag aaaacatcaa | 1320 |
| atacgaagtt ggcattttg tgcatggaac caccacttcg gaaaaccatg gaaattattc | 1380 |
| agcgcaagtt ggggcgtccc aggcggcaaa gtttacagta acacccaatg ctccttcgat | 1440 |
| aaccctcaaa cttggtgact acggagaagt cacactggac tgtgagccaa ggagtggact | 1500 |
| gaacactgaa gcgttttacg tcatgaccgt ggggtcaaag tcatttctgg tccataggga | 1560 |
| gtggtttcat gacctcgctc tcccctggac gtccccttcg agcacagcgt ggagaaacag | 1620 |

| | | | | | |
|---|---|---|---|---|---|
| agaactcctc | atggaatttg | aaggggcgca | cgccacaaaa | cagtccgttg | ttgctcttgg | 1680 |
| gtcacaggaa | ggaggcctcc | atcaggcgtt | ggcaggagcc | atcgtggtgg | agtactcaag | 1740 |
| ctcagtgaag | ttaacatcag | gccacctgaa | atgtaggctg | aaaatggaca | aactggctct | 1800 |
| gaaaggcaca | acctatggca | tgtgtacaga | aaaattctcg | ttcgcgaaaa | atccggcgga | 1860 |
| cactggtcac | ggaacagttg | tcattgaact | ctcctactct | gggagtgatg | gcccctgcaa | 1920 |
| aattccgatt | gtttccgttg | cgagcctcaa | tgacatgacc | cccgttgggc | ggctggtgac | 1980 |
| agtgaacccc | ttcgtcgcga | cttccagtgc | caactcaaag | gtgctggtcg | agatggaacc | 2040 |
| ccccttcgga | gactcctaca | tcgtagttgg | aaggggagac | aagcagatca | accaccattg | 2100 |
| gcacaaagct | ggaagcacgc | tgggcaaggc | cttttcaaca | actttgaagg | gagctcaaag | 2160 |
| actggcagcg | ttgggcgaca | cagcctggga | cttggctct | attggagggg | tcttcaactc | 2220 |
| cataggaaaa | gccgttcacc | aagtgtttgg | tggtgccttc | agaacactct | ttgggggaat | 2280 |
| gtcttggatc | acacaagggc | taatgggtgc | cctactgctc | tggatgggcg | tcaacgcacg | 2340 |
| agaccgatca | attgctttgg | ccttcttagc | cacaggggt | gtgctcgtgt | tcttagcgac | 2400 |
| caatgtgcat | gctgacactg | gatgtgccat | tgacatcaca | agaaaagaga | tgagatgtgg | 2460 |
| aagtggcatc | ttcgtgcaca | acgacgtgga | agcctgggtg | gataggtata | aatatttgcc | 2520 |
| agaaacgccc | agatccctag | cgaagatcgt | ccacaaagcg | cacaaggaag | gcgtgtgcgg | 2580 |
| agtcagatct | gtcactagac | tggagcacca | aatgtgggaa | gccgtacggg | acgaattgaa | 2640 |
| cgtcctgctc | aaagagaatg | cagtggacct | cagtgtggtt | gtgaacaagc | ccgtgggaag | 2700 |
| atatcgctca | gccctaaac | gcctatccat | gacgcaagag | aagtttgaaa | tgggctggaa | 2760 |
| agcatgggga | aaaagcattc | tctttgcccc | ggaattggct | aactccacat | ttgtcgtaga | 2820 |
| tggacctgag | acaaaggaat | gccctgatga | gcacagagct | tggaacagca | tgcaaatcga | 2880 |
| agacttcggc | tttggcatca | catcaaccgg | tgtgtggctg | aaaattagag | aggagagcac | 2940 |
| tgacgagtgt | gatggagcga | tcataggcac | ggctgtcaaa | ggacatgtgg | cagtccatag | 3000 |
| tgacttgtcg | tactggattg | agagtcgcta | caacgacaca | tggaaacttg | agagggcagt | 3060 |
| ctttggagag | gtcaaatctt | gcacttggcc | agagacacac | acccttggg | gagatgatgt | 3120 |
| tgaggaaagt | gaactcatca | ttccgcacac | catagccgga | ccaaaaagca | agcacaatcg | 3180 |
| gagggaaggg | tataagacac | aaaaccaggg | accttgggat | gagaatggca | tagtcttgga | 3240 |
| ctttgattat | tgcccaggga | caaaagtcac | cattacagag | gattgtggca | agagaggccc | 3300 |
| ttcggtcaga | accactactg | acagtggaaa | gttgatcact | gactggtgct | gtcgcagttg | 3360 |
| ctcccttccg | cccctacgat | tccggacaga | aaatggctgc | tggtacggaa | tggaaatcag | 3420 |
| acctgttagg | catgatgaaa | caacactcgt | cagatcacag | gttgatgctt | tcaatggtga | 3480 |
| aatggttgac | ccttttcagc | tgggccttct | ggtgatgttt | ctggccaccc | aggaggtcct | 3540 |
| tcgcaagagg | tggacggcca | gattgaccat | tcctgcggtt | ttgggggccc | tacttgtgct | 3600 |
| gatgcttggg | ggcatcactt | acactgattt | ggcgaggtat | gtggtgctag | tcgctgctgc | 3660 |
| tttcgcagag | gccaacagtg | gaggagacgt | cctgcacctt | gctttgattg | ccgttttaa | 3720 |
| gatccaacca | gcatttctag | tgatgaacat | gcttagcacg | agatggacga | accaagaaaa | 3780 |
| cgtggttctg | gtcctagggg | ctgccttttt | ccaattggcc | tcagtagatc | tgcaaatagg | 3840 |
| agtccacgga | atcctgaatg | ccgccgctat | agcatggatg | attgtccgag | cgatcacctt | 3900 |
| ccccacaacc | tcctccgtca | ccatgccagt | cttagcgctt | ctaactccgg | ggatgagggc | 3960 |
| tctataccta | gacacttaca | gaatcatcct | cctcgtcata | gggatttgct | ccctgctgca | 4020 |

```
cgagaggaaa aagaccatgg caaaaaagaa aggagctgta ctcttgggct tagcgctcac   4080
atccactgga tggttctcgc ccaccactat agctgccgga ctaatggtct gcaacccaaa   4140
caagaagaga gggtggccag ctactgagtt tttgtcggca gttggattga tgtttgccat   4200
cgtaggtggt ttggccgagt tggatattga atccatgtca ataccttca tgctggcagg    4260 tctcatggca gtgtcctacg tggtgtcagg aaaagcaaca gatatgtggc ttgaacgggc   4320
cgccgacatc agctgggaga tggatgctgc aatcacagga agcagtcgga ggctggatgt   4380
gaaactggat gatgacggag attttcactt gattgatgat cccggtgttc catggaaggt   4440
ctgggtcctg cgcatgtctt gcattggctt agccgccctc acgccttggg ccatcgttcc   4500
cgccgctttc ggttattggc tcactttaaa aacaacaaaa agagggggcg tgttttggga   4560
cacgccatcc ccaaaacctt gctcaaaagg agacaccact acaggagtct accgaattat   4620
ggctagaggg attcttggca cttaccaggc cggcgtcgga gtcatgtacg agaatgtttt   4680
ccacacacta tggcacacaa ctagaggagc agccattatg agtggagaag gaaaattgac   4740
gccatactgg ggtagtgtga gagaagaccg catagcttac ggaggcccat ggaggtttga   4800
ccgaaaatgg aatggaacag atgacgtgca agtgatcgtg gtagaaccgg ggaaggctgc   4860
agtaaacatc cagacaaaac caggagtgtt tcggactccc ttcggggagg ttggggctgt   4920
tagtctggat tacccgcgag gaacatccgg ctcacccatt ctggattcca atggagacat   4980
tataggccta tacggcaatg gagttgagct tggcgatggc tcatacgtca gcgccatcgt   5040
gcagggtgac cgtcaggagg aaccagtccc agaagcttac accccaaaca tgttgagaaa   5100
gagacagatg actgtgctag atttgcaccc tggttcaggg aaaaccagga aaattctgcc   5160
acaaataatt aaggacgcta tccagcagcg cctaagaaca gctgtgttgg caccgacgcg   5220
ggtggtagca gcagaaatgg cagaagcttt gagagggctc ccagtacgat atcaaacttc   5280
agcagtgcag agagagcacc aagggaatga aatagtggat gtgatgtgcc acgccactct   5340
gacccataga ctgatgtcac cgaacagagt gcccaactac aacctatttg tcatggatga   5400
agctcatttc accgacccag ccagtatagc cgcacgagga tacattgcta ccaaggtgga   5460 attagggag gcagcagcca tctttatgac agcgaccccg cctggaacca cggatccttt   5520
tcctgactca aatgccccaa tccatgattt gcaagatgag ataccagaca gggcatggag   5580
cagtggatac gaatggatca cagaatatgc gggtaaaacc gtgtggtttg tggcgagcgt   5640
aaaaatgggg aatgagattg caatgtgcct ccaaagagcg gggaaaaagg tcatccaact   5700
caaccgcaag tcctatgaca cagaataccc aaaatgtaag aatggagact gggatttgt    5760 cattaccacc gacatctctg aaatgggggc caacttcggt gcgagcaggg tcatcgactg   5820
tagaaagagc gtgaaaccca ccatcttaga agagggagaa ggcagagtca tcctcggaaa   5880
cccatctccc ataaccagtg caagcgcagc tcaacggagg ggcagagtag cagaaacccc   5940
caaccaagtt ggagatgaat accactatgg ggggctacc agtgaagatg acagtaacct   6000
agcccattgg acagaggcaa agatcatgtt agacaacata cacatgccca atggactggt   6060
ggcccagctc tatggaccag agagggaaaa ggctttcaca atggatggcg aataccgtct   6120
cagaggtgaa gaaagaaaa acttcttaga gctgcttagg acggctgacc tcccggtgtg   6180
gctggcctac aagtggcgt ccaatggcat tcagtacacc gacagaaagt ggtgttttga   6240
tgggccgcgt acgaatgcca tactggagga caacaccgag gtagagatag tcaccgggat   6300
gggtgagagg aaaatcctca agccgagatg gcttgatgca agagtttatg cagatcacca   6360
```

```
agccctcaag tggttcaaag actttgcagc agggaagaga tcagccgtta gcttcataga   6420
ggtgctcggt cgcatgcctg agcatttcat gggaaagacg cgggaagctt tagacaccat   6480
gtacttggtt gcaacggctg agaaaggtgg gaaagcacac cgaatggctc tcgaagagct   6540
gccagatgca ctggaaacca tcacacttat tgtcgccatt actgtgatga caggaggatt   6600
cttcctacta atgatgcagc gaaagggtat agggaagatg ggtcttggag ctctagtgct   6660
cacgctagct accttcttcc tgtgggcggc agaggttcct ggaaccaaaa tagcagggac   6720
cctgctgatc gccctgctgc tgatggtggt tctcatccca gaaccggaaa aacagaggtc   6780
acagacagat aaccaactgg cggtgtttct catctgtgtc ttgaccgtgg ttggagtggt   6840
ggcagcaaac gagtacggga tgctagaaaa aaccaaagca gatctcaaga gcatgtttgg   6900
cggaaagacg caggcatcag gactgactgg attgccaagc atggcactgg acctgcgtcc   6960
agccacagcc tgggcactgt atgggggag cacagtcgtg ctaaccctc ttctgaagca   7020
cctgatcacg tcggaatacg tcaccacatc gctagcctca attaactcac aagctggctc   7080
attattcgtc ttgccacgag gcgtgccttt taccgaccta gacttgaccg ttggcctcgt   7140
cttccttggc tgttggggtc aaatcaccct cacaacgttt ctgacagcca tggttctggc   7200
gacacttcac tatgggtaca tgctccctgg atggcaagca aagcactca gggctgccca   7260
gagaaggaca gcggctggaa taatgaagaa tgccgttgtt gacggaatgg tcgccactga   7320
tgtgcctgaa ctgaaagga ctactcctct gatgcaaaag aaagtcggac aggtgctcct   7380
catagggta agcgtggcag cgttcctcgt caaccctaat gtcaccactg tgagagaagc   7440
aggggtgttg gtgacggcgg ctacgcttac tttgtgggac aatggagcca gtgccgtttg   7500
gaattccacc acagccacgg gactctgcca tgtcatgcga ggtagctacc tggctggagg   7560
ctccattgct tggactctca tcaagaacgc tgataagccc tccttgaaaa ggggaaggcc   7620
tgggggcagg acgctagggg agcagtggaa ggaaaaacta atgccatga gcagagaaga   7680
gtttttttaaa taccggagag aggccataat cgaggtggac cgcactgaag cacgcagggc   7740
cagacgtgaa ataacatag tgggaggaca tccggtttcg cgaggctcag caaaactccg   7800
ttggctcgtg gagaaaggat ttgtctcgcc aataggaaaa gtcattgatc tagggtgtgg   7860
gcgtggagga tggagctact acgcagcaac cctgaagaag gtccaggaag tcagaggata   7920
cacgaaaggt gggcgggac atgaagaacc gatgctcatg cagagctacg gctggaacct   7980
ggtctccctg aagagtggag tggacgtgtt ttacaaacct tcagagccca gtgacaccct   8040
gttctgtgac ataggggaat cctccccaag tccagaagta gaagaacaac gcacactacg   8100
cgtcctagag atgacatctg actggttgca ccgaggacct agagagttct gcattaaagt   8160
tctctgccct tacatgccca aggttataga aaaaatggaa gttctgcagc gccgcttcgg   8220
aggtgggcta gtgcgtctcc ccctgtcccg aaactccaat cacgagatgt attgggttag   8280
tggagccgct ggcaatgtgg tgcacgctgt gaacatgacc agccaggtac tactggggcg   8340
aatggatcgc acagtgtgga gggccaaa gtatgaggaa gatgtcaacc tagggagcgg   8400
aacaagagcc gtgggaaagg gagaagtcca tagcaatcag gagaaaatca agaagagaat   8460
ccagaagctt aaagaagaat cgccacaac gtggcacaaa gaccctgagc atccataccg   8520
cacttggaca taccacggaa gctatgaagt gaaggctact ggctcagcca gctctctcgt   8580
caacggagtg gtgaagctca tgagcaaacc ttgggacgcc attgccaacg tcaccaccat   8640
ggccatgact gacaccaccc cttttggaca gcaaagagtt ttcaaggaga agttgacac    8700
gaaggctcct gagccaccag ctggagccaa ggaagtgctc aacgagacca ccaactggct   8760
```

-continued

```
gtgggcccac ttgtcacggg aaaaaagacc ccgcttgtgc accaaggaag aattcataaa    8820
gaaagtcaac agcaacgcgg ctcttggagc agtgttcgct gaacagaatc aatggagcac    8880
ggcgcgtgag gctgtggatg acccgcggtt tgggagatg gttgatgaag agagggaaaa    8940
ccatctgcga ggagagtgtc acacatgtat ctacaacatg atgggaaaaa gagagaagaa    9000
gcctggagag tttggaaaag ctaaaggaag cagggccatt tggttcatgt ggcttggagc    9060
acggtatcta gagtttgaag cttttgggtt cctgaatgaa gaccattggc tgagccgaga    9120
gaattcagga ggtggagtgg aaggctcagg cgtccaaaag ctgggataca tcctccgtga    9180
catagcagga aagcaaggag ggaaaatgta cgctgatgat accgccgggt gggacactag    9240
aattaccaga actgatttag aaaatgaagc taaggtactg gagctcctag acggtgaaca    9300
ccgcatgctc gcccgagcca taattgaact gacttacagg cacaaagtgg tcaaggtcat    9360
gagacctgca gcagaaggaa agaccgtgat ggacgtgata tcaagagaag atcaaagggg    9420
gagtggacag gtggtcactt atgctcttaa cactttcacg aacatcgctg tccagctcgt    9480
caggctgatg gaggctgagg gggtcattgg accacaacac ttggaacagc tacctaggaa    9540
aaacaagata gctgtcagga cctggctctt tgagaatgga gaggagagag tgaccaggat    9600
ggcgatcagc ggagacgact gtgtcgtcaa gccgctggac gacagattcg ccacagccct    9660
ccacttcctc aacgcaatgt caaaggtcag aaaagacatc caggaatgga gccttcgca    9720
tggctggcac gattggcagc aagttcccctt ctgctctaac cattttcagg agattgtgat    9780
gaaagatgga aggagtatag ttgtcccgtg cagaggacag gatgagctga taggcagggc    9840
tcgcatctct ccaggagctg gatggaatgt gaaggacaca gcttgcctgg ccaaagcata    9900
tgcacagatg tggctactcc tatacttcca tcgcagggac ttgcgtctca tggcaaatgc    9960
gatttgctca gcagtgccag tggattgggt gcccacaggc aggacatcct ggtcaataca   10020
ctcgaaagga gagtggatga ccacggaaga catgctgcag gtctggaaca gagtctggat   10080
tgaagaaaat gaatggatga tggacaagac tccaatcaca agctggacag acgttccgta   10140
tgtgggaaag cgtgaggaca tctggtgtgg cagcctcatc ggaacgcgat ccagagcaac   10200
ctgggctgag aacatctatg cggcgataaa ccaggttaga gctgtcattg ggaaagaaaa   10260
ttatgttgac tacatgacct cactcaggag atacgaagac gtcttgatcc aggaagacag   10320
ggtcatctag tgtgatttaa ggtagaaaag tagactatgt aaataatgta atgagaaaa   10380
tgcatgcata tggagtcagg ccagcaaaag ctgccaccgg atactgggta gacggtgctg   10440
cctgcgtctc agtcccagga ggactgggtt aacaaatctg acaacagaaa gtgagaaagc   10500
cctcagaacc gtctcggaag taggtccctg ctcactggaa gttgaaagac caacgtcagg   10560
ccacaaattt gtgccactcc gctagggagt gcggcctgcg cagccccagg aggactgggt   10620
taccaaagcc gttgaggccc ccacggccca agcctcgtct aggatgcaat agacgaggtg   10680
taaggactag aggttagagg agaccccgtg gaaacaacaa catgcggccc aagcccccctc   10740
gaagctgtag aggaggtgga aggactagag gttagaggag accccgcatt tgcatcaaac   10800
agcatattga cacctgggaa tagactggga gatcttctgc tctatctcaa catcagctac   10860
tag                                                                 10863
```

<210> SEQ ID NO 74
<211> LENGTH: 10977
<212> TYPE: DNA
<213> ORGANISM: Japanese encephalitis virus

<400> SEQUENCE: 74

```
agaagtttat ctgtgtgaac ttcttggctt agtatcgtag agaagaatcg agagattagt      60
gcagtttaaa cagttttta gaacggaaga taaccatgac taaaaaacca ggagggcccg      120
gtaaaaaccg ggctatcaat atgctgaaac gcggcctacc ccgcgtattc ccactagtgg     180
gagtgaagag ggtagtaatg agcttgttgg acggcagagg gccagtacgt ttcgtgctgg     240
ctcttatcac gttcttcaag tttacagcat tagccccgac caaggcgctt tcaggccgat     300
ggaaagcagt ggaaagagt gtggcaatga acatcttac tagtttcaaa cgagaacttg       360
gaacactcat tgacgccgtg aacaagcggg gcagaaagca aaacaaaaga ggaggaaatg     420
aaggctcaat catgtggctc gcgagcttgg cagttgtcat agcttgtgca ggagccatga     480
agttgtcgaa tttccagggg aagcttttga tgaccatcaa caacacggac attgcagacg     540
ttatcgtgat tcccacctca aaaggagaga acagatgctg ggtccgggca atcgacgtcg     600
gctacatgtg tgaggacact atcacgtacg aatgtcctaa gcttaccatg ggcaatgatc     660
cagaggatgt ggattgctgg tgtgacaacc aagaagtcta cgtccaatat ggacggtgca     720
cgcggaccag gcattccaag cgaagcagga gatccgtgtc ggtccaaaca catggggaga     780
gttcactagt gaataaaaaa gaggcttggc tggattcaac gaaagccaca cgatatctca     840
tgaaaactga gaactggatc ataaggaatc ctggctatgc tttcctggcg gcggtacttg     900
gctggatgct tggcagtaac aacggtcaac gcgtggtatt taccatcctc ctgctgttgg     960
tcgctccggc ttacagtttt aattgtctgg gaatgggcaa tcgtgacttc atagaaggag    1020
ccagtgggag cacttgggtg gacttggtgc tagaaggaga cagctgcttg acaatcatgg    1080
caaacgacaa accaacattg gacgtccgca tgattaacat cgaagctagc caacttgctg    1140
aggtcagaag ttactgctat catgcttcag tcactgacat ctcgacggtg gctcggtgcc    1200
ccacgactgg agaagcccac aacgagaagc gagctgatag tagctatgtg tgcaaacaag    1260
gcttcactga ccgtgggtgg ggcaacggat gtggattttt cgggaaggga agcattgaca    1320
catgtgcaaa attctcctgc accagtaaag cgattgggag aacaatccag ccagaaaaca    1380
tcaaatacaa agttggcatt tttgtgcatg gaaccaccac ttcggaaaac catgggaatt    1440
attcagcgca agttggggcg tcccaggcgg caaagtttac agtaacaccc aatgctcctt    1500
cggtagccct caaacttggt gactacgag aagtcacact ggactgtgag ccaaggagtg     1560
gactgaacac tgaagcgttt tacgtcatga ccgtgggtc aaagtcattt ctggtccata     1620
gggagtggtt tcatgacctc gctctcccct ggacgtcccc ttcgagcaca gcgtggagaa    1680
acagagaact cctcatggaa tttgaagggg cgcacgccac aaaacagtcc gttgttgctc    1740
ttgggtcaca ggaaggaggc ctccatcatg cgttggcagg agccatcgtg gtggagtact    1800
caagctcagt gatgttaaca tcaggccacc tgaaatgtag gctgaaaatg gacaaactgg    1860
ctctgaaagg cacaacctat ggcatgtgta cagaaaaatt ctcgttcgcg aaaaatccgg    1920
tggacactgg tcacggaaca gttgtcattg aactctccta ctctgggagt gatggcccct    1980
gcaaaattcc gattgtttcc gttgcgagcc tcaatgacat gaccccgtt gggcggctgg     2040
tgacagtgaa cccccttcgtc gcgacttcca gtgccaactc aaaggtgctg gtcgagatgg    2100
aaccccccctt cggagactcc tacatcgtag ttggaagggg agacaagcag atcaaccacc    2160
attggcacaa agctggaagc acgctgggca aggccttttc aacaactttg aagggagctc    2220
aaagactggc agcgttgggc gacacagcct gggactttgg ctctattgga ggggtcttca    2280
actccatagg aagagccgtt caccaagtgt ttggtggtgc cttcagaaca ctctttgggg    2340
```

```
gaatgtcttg gatcacacaa gggctaatgg gtgccctact gctctggatg ggcgtcaacg   2400
cacgagaccg atcaattgct ttggccttct tagccacagg aggtgtgctc gtgttcttag   2460
cgaccaatgt gcatgctgac actggatgtg ccattgacat cacaagaaaa gagatgagat   2520
gtggaagtgg catcttcgtg cacaacgacg tggaagcctg ggtggatagg tataaatatt   2580
tgccagaaac gcccagatcc ctagcgaaga tcgtccacaa agcgcacaag gaaggcgtgt   2640
gcggagtcag atctgtcact agactggagc accaaatgtg ggaagccgta agggacgaat   2700
tgaacgtcct gctcaaagag aatgcagtgg acctcagtgt ggttgtgaac aagcccgtgg   2760
gaagatatcg ctcagcccct aaacgcctat ccatgacgca agagaagttt gaaatgggct   2820
ggaaagcatg gggaaaaagc atcctctttg ccccggaatt ggctaactcc acatttgtcg   2880
tagatggacc tgagacaaag gaatgccctg atgagcacag agcttggaac agcatgcaaa   2940
tcgaagactt cggctttggc atcacatcaa cccgtgtgtg gctgaaaatt agagaggaga   3000
gcactgacga gtgtgatgga gcgatcatag gcacggctgt caaggacat gtggcagtcc   3060 atagtgactt gtcgtactgg attgagagtc gctacaacga cacatggaaa cttgagaggg   3120
cagtctttgg agaggtcaaa tcttgcactt ggccagagac acacacccctt tggggagatg   3180 atgttgagga aagtgaactc atcattccgc acaccatagc cggaccaaaa agcaagcaca   3240
atcggaggga agggtataag acacaaaacc agggaccttg ggatgagaat ggcatagtct   3300
tggactttga ttattgccca gggacaaaag tcaccattac agaggattgt agcaagagag   3360
gcccttcggt cagaaccact actgacagtg gaaagttgat cactgactgg tgctgtcgca   3420
gttgctccct tccgcccta cgattccgga cagaaaatgg ctgctggtac ggaatggaaa   3480
tcagacctgt tatgcatgat gaaacaacac tcgtcagatc acaggttcat gctttcaaag   3540
gtgaaatggt tgacccttt cagctgggcc ttctggtgat gtttctggcc acccaggaag   3600
tccttcgcaa gaggtggacg gccagattga ccattcctgc ggttttgggg gtcctacttg   3660
tgctgatgct tgggggtatc acttacactg atttggcgag gtatgtggtg ctagtcgctg   3720
ctgctttcgc agaggccaac agtggaggag acgtcctgca ccttgctttg attgctgttt   3780
ttaagatcca accagcattt ttagtgatga acatgcttag cacgagatgg acgaaccaag   3840
aaaacgtggt tctggtccta ggggctgcct ttttccaatt ggcctcagta gatctgcaaa   3900
taggagtcca cggaatcctg aatgccgccg ctatagcatg gatgattgtc gagcgatca   3960 ccttccccac aacctcctcc gtcaccatgc cagtcttagc gcttctaact ccggggatga   4020
gggctctata cctagacact tacagaatca tcctcctcgt catagggatt tgctccctgc   4080
tgcacgagag gaaaaagacc atggcgaaaa agaaggagc tgtactcttg ggcttagcgc   4140
tcacatccac tggatggttc tcgcccacca ctatagctgc cggactaatg gtctgcaacc   4200
caaacaagaa gagagggtgg ccagctactg agttttttgtc ggcagttgga ttgatgtttg   4260
ccatcgtagg tggtttggcc gagttggata ttgaatccat gtcaataccc ttcatgctgg   4320
caggtctcat ggcagtgtcc tacgtggtgt caggaaaagc aacagatatg tggcttgaac   4380
gggccgccga catcagctgg gatatgggtg ctgcaatcac aggaagcagt cggaggctgg   4440
atgtgaaact ggatgatgac ggagatttc acttgattga tgatcccggt gttccatgga   4500
aggtctgggt cctgcgcatg tcttgcattg gcttagccgc cctcacgcct tgggccatcg   4560
ttcccgccgc tttcggttat tggctcactt taaaaacaac aaaaagaggg ggcgtgtttt   4620
gggacacgcc atccccaaaa ccttgctcaa aaggagacac cactacagga gtctaccgaa   4680
```

-continued

```
ttatggctag agggattctt ggcacttacc aggccggcgt cggagtcatg tacgagaatg    4740
ttttccacac actatggcac acaactagag gagcagccat tgtgagtgga gaaggaaaat    4800
tgacgccata ctggggtagt gtgaaagaag accgcatagc ttacggaggc ccatggaggt    4860
ttgaccgaaa atggaatgga acagatgacg tgcaagtgat cgtggtagaa ccggggaagg    4920
gcgcagtaaa catccagaca aaaccaggag tgtttcggac tcccttcggg gaggttgggg    4980
ctgttagtct ggattacccg cgaggaacat ccggctcacc cattctggat tccaatggag    5040
acattatagg cctatacggc aatggagttg agcttggcga tggctcatac gtcagcgcca    5100
tcgtgcaggt tgaccgtcag gaggaaccag tcccagaagc ttacccccca acatgttga    5160 gaaagagaca gatgactgtg ctagatttgc accctggttc agggaaaacc aggaaaattc    5220
tgccacaaat aattaaggac gctatccagc agcgcctaag aacagctgtg ttggcaccga    5280
cgcgggtggt agcagcagaa atggcagaag ctttgagagg gctcccagta cgatatcaaa    5340
cttcagcagt gcagagagag caccaaggga tgaaatagt ggatgtgatg tgccacgcca    5400
ctctgaccca tagactgatg tcaccgaaca gagtgcccaa ctacaaccta tttgtcatgg    5460
atgaagctca tttcaccgac ccagccagta tagccgcacg aggatacatt gctaccaagg    5520
tggaattagg ggaggcagca gccatctttta tgacagcgac cccgcctgga accacggatc    5580
cttttcctga ctcaaatgcc ccaatccatg atttgcaaga tgagatacca gacagggcat    5640
ggagcagtgg atacgaatgg atcacagaat atgcgggtaa aaccgtgtgg tttgtggcga    5700
gcgtaaaaat ggggaatgag attgcaatgt gcctccaaag agcggggaaa aaggtcatcc    5760
aactcaaccg caagtcctat gacacagaat acccaaaatg taagaatgga gactgggatt    5820 tgtcattac caccgacatc tctgaaatgg gggccaactt cggtgcgagc agggtcatcg    5880
actgtagaaa gagcgtgaaa cccaccatct tagaagaggg agaaggcaga gtcatcctcg    5940
gaaacccatc tcccataacc agtgcaagcg cagctcaacg gagggggaga gtaggcagaa    6000
accccaatca agttggagat gaataccact atggggggc taccagtgaa gatgacagta    6060
acctagccca ttggacagag gcaaagatca tgttagacaa catacacatg cccaatggac    6120
tggtggccca gctctatgga ccagagaggg aaaaggcttt cacaatggat ggcgaatacc    6180
gtctcagagg tgaagaaaag aaaaacttct tagagctgct taggacggct gacctcccgg    6240
tgtggctggc ctacaaggtg gcgtccaatg gcattcagta caccgacaga aagtggtgtt    6300
ttgatgggcc gcgtacgaat gccatactgg aggacaacac cgaggtagag atagtcaccc    6360
ggatgggtga gaggaaaatc ctcaagccga gatggcttga tgcaagagtt tatgcagatc    6420
accaggccct caagtggttc aaagactttg cagcgggaa gagatcagcc gttagcttca    6480
tagaggtgct cggtcgcatg cctgagcatt tcatgggaaa gacgcgggaa gctttagaca    6540
ccatgtactt ggttgcaacg gctgagaaag gtgggaaagc acaccgaatg ctctcgaag    6600 agctgccaga tgcactggaa accatcacac ttattgtcgc cattactgtg atgacaggag    6660
gattcttcct actaatgatg cagcgaaagg gtataggaa gatgggtctt ggagctctag    6720
tgctcacact agctaccttc ttcctgtggg cggcagaggt tcctggaacc aaaatagcag    6780 ggacctgct gatcgccctg ctgctgatgg tggttctcat cccagaaccg gaaaaacaga    6840
ggtcacagac agataaccaa ctggcggtgt ttctcatctg tgtcttgacc gtggttggag    6900
tggtggcagc aaacgagtac gggatgctag aaaaaaccaa agcggatctc aagagcatgt    6960
ttggcggaaa gacgcaggca tcaggactga ctggattgcc aagcatggca ctggacctgc    7020
gtccagccac agcctgggca ctgtatgggg ggagcacagt cgtgctaacc cctcttctga    7080
```

```
agcacctgat cacgtcggaa tacgtcacca catcgctagc ttcaattaac tcacaagctg   7140
gctcattatt cgtcttgcca cgaggcgtgc cttttaccga cctagacttg actgttggcc   7200
tcgtcttcct tggctgttgg ggtcaagtca ccctcacaac gtttctgaca gccatggttc   7260
tggcgacact tcactatggg tacatgctcc ctggatggca agcagaagca ctcaggctg    7320 cccagagaag gacagcggct ggaataatga agaatgccgt tgttgacgga atggtcgcca   7380
ctgatgtgcc tgaactggaa aggactactc tctgatgca aaagaaagtc ggacaggtgc    7440
tcctcatagg ggtaagcgtg gcagcgttcc tcgtcaaccc taatgtcacc actgtgagag   7500 aagcagcgggt gttggtgacg gcggctacgc ttactttgtg ggacaatgga gccagtgccg  7560
tttggaattc caccacagcc acgggactct gccatgtcat gcgaggtagc tacctggctg   7620
gaggctccat tgcttggact ctcatcaaga acgctgataa gccctccttg aaaaggggaa   7680
ggcctggggg caggacgcta ggggagcagt ggaaggaaaa actaaatgcc atgagtagag   7740
aagagttttt taaataccgg agagaggcca aatcgaggt ggaccgcact gaagcacgca    7800
gggccagacg tgaaaataac atagtgggag acatccggt ttcgcgaggc tcagcaaaac    7860
tccgttggct cgtggagaaa ggatttgtct cgccaatagg aaaagtcatt gatctagggt   7920
gtgggcgtgg aggatggagc tactacgcag caaccctgaa gaaggtccag gaagtcagag   7980
gatacacgaa aggtggggcg ggacatgaag aaccgatgct catgcagagc tacggctgga   8040
acctggtctc cctgaagagt ggagtggacg tgttttacaa accttcagag cccagtgata   8100
ccctgttctg tgacataggg gaatcctccc caagtccaga agtagaagaa caacgcacac   8160
tacgcgtcct agagatgaca tctgactggt tgcaccgagg acctagagag ttctgcatta   8220
aagttctctg cccttacatg cccaaggtta tagaaaaaat ggaagttctg cagcgtcgct   8280
tcggaggtgg gctagtgcgt ctcccctgt cccgaaactc caatcacgag atgtattggg    8340
ttagtggagc cgctggcaat gtggtgcacg ctgtgaacat gaccagccag gtattactgg   8400
ggcgaatgga tcgcacagtg tggagagggc caaagtatga ggaagatgtc aacctaggga   8460
gcggaacaag agccgtggga aagggagaag tccatagcaa tcaggagaaa atcaagaaga   8520
gaatccagaa gcttaaagaa gaattcgcca caacgtggca caaagaccct gagcatccat   8580
accgcacttg gacataccac ggaagctatg aagtgaaggc tactggctca gccagctctc   8640
tcgtcaacgg agtggtgaag ctcatgagca accttgggac cgccattgcc aacgtcacca   8700
ccatggccat gactgacacc ccccttttg gacagcaaag agtttttcaag gagaaagttg   8760 acacgaaggc tcctgagcca ccagctggag ccaaggaagt gctcaacgag accaccaact   8820
ggctgtgggc ctacttgtca cgggaaaaaa gaccccgctt gtgcaccaag gaagaattca   8880
ttaagaaagt taacagcaac gcggctcttg gagcagtgtt cgctgaacag aatcaatgga   8940
gcacggcgcg tgaggctgtg gatgacccgc ggttttggga gatggttgat gaagagaggg   9000
aaaaccatct gcgaggagag tgtcacacat gtatctacaa catgatggga aaaagagaga   9060
agaagcctgg agagtttgga aaagctaaag gaagcagggc catttggttc atgtggcttg   9120
gagcacggta tctagagttt gaagctttgg ggttcctgaa tgaagaccat tggctgagcc   9180
gagagaattc aggaggtgga gtggaaggct caggcgtcca aaagctggga tacatcctcc   9240
gtgacatagc aggaaagcaa ggagggaaaa tgtacgctga tgataccgcc gggtgggaca   9300
ctagaattac cagaactgat ttagaaaatg aagctaaggt actggagctc ctagacggtg   9360
aacaccgcat gctcgcccga gccataattg aactgactta caggcacaaa gtggtcaagg   9420
```

```
tcatgagacc tgcagcagaa ggaaagaccg tgatggacgt gatatcaaga gaagatcaaa    9480
gggggagtgg acaggtggtc acttatgctc ttaacacttt cacgaacatc gctgtccagc    9540
tcgtcaggct gatggaggct gaggggggtca ttggaccaca acacttggaa catctaccta   9600
```
*(line 9600 shown as written)*

```
ggaaaaacaa gatagctgtc aggacctggc tctttgagaa tggagaggag agagtgacca    9660
ggatggcgat cagcggagac gactgtgccg tcaaaccgct ggacgacaga ttcgccacag    9720
ccctccactt cctcaacgca atgtcaaagg tcagaaaaga catccaggaa tggaagcctt    9780
cgcatggctg gcacgattgg cagcaagttc ccttctgttc taaccatttt caggagattg    9840
tgatgaaaga tggaaggagt atagttgtcc cgtgcagagg acaggatgag ctgataggca    9900
gggctcgcat ctctcctgga gctggatgga atgtgaagga cacagcttgc ctggccaaag    9960
catatgcaca gatgtggcta ctcctatact tccatcgcag ggacttgcgt ctcatggcaa   10020
atgcgatttg ctcagcagtg ccagtagatt gggtgcccac aggcaggaca tcctggtcaa   10080
tacactcgaa aggagagtgg atgaccacgg aagacatgct gcaggtctgg aacagagttt   10140
ggattgaaga aaatgaatgg atgatggaca agactccaat cacaagctgg acagacgttc   10200
cgtatgtggg aaagcgcgag gacatctggt gtggcagcct catcggaacg cgatccagag   10260
caacctgggc tgagaacatc tatgcggcga taaaccaggt tagagctgtc attgggaaag   10320
aaaattatgt tgactacatg acctcactca ggagatacga agacgtcttg atccaggaag   10380
acagggtcat ctagtgtgat ttaaggtaga aaagtagact atgtaaacaa tgtaaatgag   10440
aaaatgcatg catatggagt caggccagca aaagctgcca ccggatactg ggtagacggt   10500
gctgcctgcg tctcagtccc aggaggactg ggttaacaaa tctgacaaca gaaagtgaga   10560
aagccctcag aaccgtctcg gaagtaggtc cctgctcact ggaagttgaa agaccaacgt   10620
caggccacaa atttgtgcca ctccgctagg gagtgcggcc tgcgcagccc caggaggact   10680
gggttaccaa agccgttgag gcccccacgg cccaagcctc gtctaggatg caatagacga   10740
ggtgtaagga ctagaggtta gaggagaccc cgtggaaaca caacatgcg gcccaagccc   10800
```
*(last group shown as written on the page)*

```
cctcgaagct gtagaggagg tggaaggact agaggttaga ggagaccccg catttgcatc   10860
aaacagcata ttgacacctg gaatagact gggagatctt ctgctctatc tcaacatcag   10920
ctactaggca cagagcgccg aagtatgtag ctggtggtga ggaagaacac aggatct      10977
```

<210> SEQ ID NO 75
<211> LENGTH: 10976
<212> TYPE: DNA
<213> ORGANISM: Japanese encephalitis virus

<400> SEQUENCE: 75

```
agaagtttat ctgtgtgaac ttcttggctt agtatcgtag agaagaatcg agagattagt      60
gcagtttaaa cagttttta gaacggaaga taaccatgac taaaaaacca ggagggcccg      120
gtaaaaaccg ggctatcaat atgctgaaac gcggcctacc ccgcgtattc ccactagtgg     180
gagtgaagag ggtagtaatg agcttgttgg acggcagagg gccagtacgt tcgtgctgg      240 ctcttatcac gttcttcaag tttacagcat tagccccgac caaggcgctt tcaggccgat     300
ggaaagcagt ggaaaagagt gtggcaatga acatcttac tagtttcaaa cgagaacttg     360
gaacactcat tgacgccgtg aacaagcggg gcagaaagca aaacaaaga ggaggaaatg     420 aaggctcaat catgtggctc gcgagcttgg cagttgtcat agcttgtgca ggagccatga     480
agttgtcgaa tttccagggg aagcttttga tgaccatcaa caacacggac attgcagacg     540
ttatcgtgat tcccacctca aaaggagaga acagatgctg ggtccgggca atcgacgtcg     600
```

-continued

```
gctacatgtg tgaggacact atcacgtacg aatgtcctaa gcttaccatg ggcaatgatc    660
cagaggatgt ggattgctgg tgtgacaacc aagaagtcta cgtccaatat ggacggtgca    720
cgcggaccag gcattccaag cgaagcagga gatccgtgtc ggtccaaaca catggggaga    780
gttcactagt gaataaaaaa gaggcttggc tggattcaac gaaagccaca cgatatctca    840
tgaaaactga gaactggatc ataaggaatc ctggctatgc tttcctggcg gcggtacttg    900
gctggatgct tggcagtaac aacggtcaac gcgtggtatt taccatcctc ctgctgttgg    960
tcgctccggc ttacagtttt aattgtctgg gaatgggcaa tcgtgacttc atagaaggag   1020 ccagtgggagc cacttgggtg gacttggtgc tagaaggaga cagctgcttg acaatcatgg   1080
caaacgacaa accaacattg gacgtccgca tgattaacat cgaagctagc caacttgctg   1140
aggtcagaag ttactgctat catgcttcag tcactgacat ctcgacggtg gctcggtgcc   1200
ccacgactgg agaagcccac aacgagaagc gagctgatag tagctatgtg tgcaaacaag   1260
gcttcactga ccgtgggtgg ggcaacggat gtggattttt cgggaaggga agcattgaca   1320
catgtgcaaa attctcctgc accagtaaag cgattgggag aacaatccag ccagaaaaca   1380
tcaaatacaa agttggcatt tttgtgcatg gaaccaccac ttcggaaaac catgggaatt   1440
attcagcgca agttggggcg tcccaggcgg caaagtttac agtaacaccc aatgctcctt   1500
cggtagccct caaacttggt gactacggag aagtcacact ggactgtgag ccaaggagtg   1560
gactgaacac tgaagcgttt tacgtcatga ccgtggggtc aaagtcattt ctggtccata   1620
gggagtggtt tcatgacctc gctctcccct ggacgtcccc ttcgagcaca gcgtggagaa   1680
acagagaact cctcatggaa tttgaagggg cgcacgccac aaaacagtcc gttgttgctc   1740
ttgggtcaca ggaaggaggc ctccatcatg cgttggcagg agccatcgtg gtggagtact   1800
caagctcagt gatgttaaca tcaggccacc tgaaatgtag gctgaaaatg acaaactgg   1860 ctctgaaagg cacaacctat ggcatgtgta cagaaaaatt ctcgttcgcg aaaaatccgg   1920
tggacactgg tcacggaaca gttgtcattg aactctccta ctctgggagt gatggcccct   1980
gcaaaattcc gattgtttcc gttgcgagcc tcaatgacat gaccccgttt gggcggctgg   2040
tgacagtgaa ccccttcgtc gcgacttcca gtgccaactc aaaggtgctg gtcgagatgg   2100 aaccccccctt cggagactcc tacatcgtag ttggaagggg agacaagcag atcaaccacc   2160
attggcacaa agctggaagc acgctgggca aggccttttc aacaactttg aagggagctc   2220
aaagactggc agcgttgggc gacacagcct gggactttgg ctctattgga ggggtcttca   2280
actccatagg aagagccgtt caccaagtgt tggtgatgc cttcagaaca ctctttgggg   2340
gaatgtcttg gatcacacaa gggctaatgg gtgccctact gctctggatg ggcgtcaacg   2400
cacgagaccg atcaattgct ttggccttct tagccacagg aggtgtgctc gtgttcttag   2460
cgaccaatgt gcatgctgac actggatgtg ccattgacat cacaagaaaa gagatgagat   2520
gtggaagtgg catcttcgtg cacaacgacg tggaagcctg ggtggatagg tataaatatt   2580
tgccagaaac gcccagatcc ctagcgaaga tcgtccacaa agcgcacaag gaaggcgtgt   2640
gcggagtcag atctgtcact agactggagc accaaatgtg ggaagccgta agggacgaat   2700
tgaacgtcct gctcaaagag aatgcagtgg acctcagtgt ggttgtgaac aagcccgtgg   2760
gaagatatcg ctcagcccct aaacgcctat ccatgacgca agagaagttt gaaatgggct   2820
ggaaagcatg gggaaaaagc atcctctttg ccccggaatt ggctaactcc acatttgtcg   2880
tagatggacc tgagacaaag gaatgccctg atgagcacag agcttggaac agcatgcaaa   2940
```

```
tcgaagactt cggctttggc atcacatcaa cccgtgtgtg gctgaaaatt agagaggaga    3000
gcactgacga gtgtgatgga gcgatcatag gcacggctgt caaaggacat gtggcagtcc    3060
atagtgactt gtcgtactgg attgagagtc gctacaacga cacatggaaa cttgagaggg    3120
cagtctttgg agaggtcaaa tcttgcactt ggccagagac acacacccctt tggggagatg   3180 atgttgagga aagtgaactc atcattccgc acaccatagc cggaccaaaa agcaagcaca    3240
atcggaggga agggtataag acacaaaacc agggaccttg ggatgagaat ggcatagtct    3300
tggactttga ttattgccca gggacaaaag tcaccattac agaggattgt agcaagagag    3360
gcccttcggt cagaaccact actgacagtg gaaagttgat cactgactgg tgctgtcgca    3420
gttgctccct tccgccccta cgattccgga cagaaaatgg ctgctggtac ggaatggaaa    3480
tcagacctgt tatgcatgat gaaacaacac tcgtcagatc acaggttcat gctttcaaag    3540
gtgaaatggt tgacccttttt cagctgggcc ttctggtgat gtttctggcc acccaggaag   3600
tccttcgcaa gaggtggacg ccagattga ccattcctgc ggttttgggg gtcctacttg    3660
tgctgatgct tgggggtatc acttacactg atttggcgag gtatgtggtg ctagtcgctg    3720
ctgctttcgc agaggccaac agtggaggag acgtcctgca ccttgctttg attgctgttt    3780
ttaagatcca accagcattt ttagtgatga acatgcttag cacgagatgg acgaaccaag    3840
aaaacgtggt tctggtccta ggggctgcct ttttccaatt ggcctcagta gatctgcaaa    3900
taggagtcca cggaatcctg aatgccgccg ctatagcatg gatgattgtc cgagcgatca    3960 ccttcccccac aacctcctcc gtcaccatgc cagtcttagc gcttctaact ccggggatga    4020
gggctctata cctagacact tacagaatca tcctcctcgt catagggatt tgctccctgc    4080
tgcacgagag gaaaaagacc atggcgaaaa agaaggagc tgtactcttg ggcttagcgc     4140
tcacatccac tggatggttc tcgcccacca ctatagctgc cggactaatg gtctgcaacc    4200
caaacaagaa gagagggtgg ccagctactg agttttttgtc ggcagttgga ttgatgtttg   4260
ccatcgtagg tggtttggcc gagttggata ttgaatccat gtcaataccc ttcatgctgg    4320
caggtctcat ggcagtgtcc tacgtggtgt caggaaaagc aacagatatg tggcttgaac    4380
gggccgccga catcagctgg gatatgggtg ctgcaatcac aggaagcagt cggaggctgg    4440
atgtgaaact ggatgatgac ggagattttc acttcattga tgatcccggt gttccatgga    4500
aggtctgggg cctgcgcatg tcttgcattg gcttagccgc cctcacgcct tgggccatcg    4560
ttcccgccgc tttcggttat tggctcactt taaaaacaac aaaaagaggg ggcgtgtttt    4620
gggacacgcc atccccaaaa ccttgctcaa aaggagacac cactacagga gtctaccgaa    4680
ttatggctag agggattctt ggcacttacc aggccggcgt cggagtcatg tacgagaatg    4740 tttttccacac actatggcac acaactagag gagcagccat tgtgagtgga gaaggaaaat    4800
tgacgccata ctggggtagt gtgaaagaag accgcatagc ttacggaggc ccatggaggt    4860
ttgaccgaaa atgaatggga acagatgacg tgcaagtgat cgtggtagaa ccggggaagg    4920
gcgcagtaaa catccagaca aaaccaggag tgtttcggac tcccttcggg gaggttgggg    4980
ctgttagtct ggattacccg cgaggaacat ccggctcacc cattctggat tccaatggag    5040
acattatagg cctatacggc aatggagttg agcttggcga tggctcatac gtcagcgcca    5100
tcgtgcaggg tgaccgtcag gaggaaccag tcccagaagc ttacacccca aacatgttga    5160
gaaagagaca gatgactgtg ctagatttgc accctggttc agggaaaacc aggaaaattc    5220
tgccacaaat aattaaggac gctatccagc agcgcctaag aacagctgtg ttggcaccga    5280
cgcgggtggt agcagcagaa atggcagaag ttttgagagg gctcccagta cgatatcaaa    5340
```

```
cttcagcagt gcagagagag caccaaggga atgaaatagt ggatgtgatg tgccacgcca   5400
ctctgaccca tagactgatg tcaccgaaca gagtgcccaa ctacaaccta tttgtcatgg   5460
atgaagctca tttcaccgac ccagccagta tagccgcacg aggatacatt gctaccaagg   5520
tggaattagg ggaggcagca gccatcttta tgacagcgac cccgcctgga accacggatc   5580
cttttcctga ctcaaatgcc ccaatccatg atttgcaaga tgagatacca gacagggcat   5640
ggagcagtgg atacgaatgg atcacagaat atgcgggtaa aaccgtgtgg tttgtggcga   5700
gcgtaaaaat ggggaatgag attgcaatgt gcctccaaag agcggggaaa aaggtcatcc   5760
aactcaaccg caagtcctat gacacagaat acccaaaatg taagaatgga gactgggatt   5820
ttgtcattac caccgacatc tctgaaatgg gggccaactt cggtgcgagc agggtcatcg   5880
actgtagaaa gagcgtgaaa cccaccatct tagaagaggg agaaggcaga gtcatcctcg   5940
gaaacccatc tcccataacc agtgcaagcg cagctcaacg gaggggcaga gtaggcagaa   6000
accccaatca agttggagat gaataccact atgggggggc taccagtgaa gatgacagta   6060
acctagccca ttggacagag gcaaagatca tgttagacaa catacacatg cccaatggac   6120
tggtggccca gctctatgga ccagagaggg aaaaggcttt cacaatggat ggcgaatacc   6180
gtctcagagg tgaagaaaag aaaaacttct agagctgct taggacggct gacctcccgg   6240
tgtggctggc ctacaaggtg gcgtccaatg gcattcagta caccgacaga agtggtgtt   6300
ttgatgggcc gcgtacgaat gccatactgg aggacaacac cgaggtagag atagtcaccc   6360
ggatgggtga gaggaaaatc ctcaagccga gatggcttga tgcaagagtt tatgcagatc   6420
accaggccct caagtggttc aaagactttg cagcagggaa gagatcagcc gttagcttca   6480
tagaggtgct cggtcgcatg cctgagcatt tcatgggaaa gacgcgggaa gctttagaca   6540
ccatgtactt ggttgcaacg gctgagaaag gtgggaaagc acaccgaatg gctctcgaag   6600
agctgccaga tgcactggaa accatcacac ttattgtcgc cattactgtg atgacaggag   6660
gattcttcct actaatgatg cagcgaaagg gtataggaaa gatgggtctt ggagctctag   6720
tgctcacact agctaccttc ttcctgtggg cggcagaggt tcctggaacc aaaatagcag   6780
ggaccctgct gatcgccctg ctgctgatgg tggttctcat cccagaaccg gaaaaacaga   6840
ggtcacagac agataaccaa ctggcggtgt ttctcatctg tgtcttgacc gtggttggag   6900
tggtggcagc aaacgagtac gggatgctag aaaaaaccaa agcggatctc aagagcatgt   6960
ttggcggaaa gacgcaggca tcaggactga ctggattgcc aagcatggca ctggacctgc   7020
gtccagccac agcctgggca ctgtatgggg ggagcacagt cgtgctaacc cctcttctga   7080
agcacctgat cacgtcggaa tacgtcacca catcgctagc ttcaattaac tcacaagctg   7140
gctcattatt cgtcttgcca cgaggcgtgc ctttttaccga cctagacttg actgttggcc   7200
tcgtcttcct tggctgttgg ggtcaagtca ccctcacaac gtttctgaca gccatggttc   7260
tggcgacact tcactatggg tacatgctcc tggatggca agcagaagca ctcagggctg   7320
cccagagaag gacagcggct ggaataatga agaatgccgt tgttgacgga atggtcgcca   7380
ctgatgtgcc tgaactggaa aggactactc ctctgatgca aagaaagtc ggacaggtgc   7440
tcctcatagg ggtaagcgtg gcagcgttcc tcgtcaaccc taatgtcacc actgtgagag   7500
aagcaggggt gttggtgacg gcggctacgc ttacttgtg ggacaatgga gccagtgccg   7560
tttggaattc caccacagcc acgggactct gccatgtcat gcgaggtagc tacctggctg   7620
gaggctccat tgcttggact ctcatcaaga acgctgataa gccctccttg aaaaggggaa   7680
```

```
ggcctggggg caggacgcta ggggagcagt ggaaggaaaa actaaatgcc atgagtagag    7740
aagagttttt taaataccgg agagagggca taatcgaggt ggaccgcact gaagcacgca    7800
gggccagaag tgaaaataac atagtgggag gacatccggt ttcgcgaggc tcagcaaaac    7860
tccgttggct tgtggagaaa ggatttgtct cgccaatagg aaaagtcatt gatctagggt    7920
gtgggcgtgg aggatggagc tactacgcag caaccctgaa gaaggtccag gaagtcagag    7980
gatacacgaa aggtggggcg ggacatgaag aaccgatgct catgcagagc tacggctgga    8040
acctggtctc cctgaagagt ggagtggacg tgttttacaa accttcagag cccagtgata    8100
ccctgttctg tgacataggg gaatcctccc caagtccaga agtagaagaa caacgcacac    8160
tacgcgtcct agagatgaca tctgactggt tgcaccgagg acctagagag ttctgcatta    8220
aagttctctg cccttacatg cccaaggtta tagaaaaaat tgaagttctg cagcgccgct    8280
tcggaggtgg gctagtgcgt ctcccccctgt cccgaaactc caatcacgag atgtattggg    8340
ttagtggagc cgctggcaat gtggtgcacg ctgtgaacat gaccagccag gtattactgg    8400
ggcgaatgga tcgcacagtg tggagagggc caaagtatga ggaagatgtc aacctaggga    8460
gcggaacaag agccgtggga agggagaag tccatagcaa tcaggagaaa atcaagaaga    8520
gaatccagaa gcttaaagaa gaattcgcca caacgtggca caaagaccct gagcatccat    8580
accgcacttg gacataccac ggaagctatg aagtgaaggc tactggctca gccagctctc    8640
tcgtcaacgg agtggtgaag ctcatgagca aaccttggga cgccattgcc aacgtcacca    8700
ccatggccat gactgacacc accccttttg gacagcaaag agttttcaag gagaaagttg    8760
acacgaaggc tcctgagcca ccagctggag ccaaggaagt gctcaacgag accaccaact    8820
ggctgtgggc ctacttgtca cgggaaaaaa gaccccgctt gtgcaccaag gaagaattca    8880
ttaagaaagt taacagcaac gcggctcttg gagcagtgtt cgctgaacag aatcaatgga    8940
gcacggcgcg tgaggctgtg gatgacccgc ggttttggga gatggttgat gaagagaggg    9000
aaaaccatct gcgaggagag tgtcacacat gtatctacaa catgatggga aaaagagaga    9060
agaagcctgg agagtttgga aaagctaaag gaagcagggc catttggttc atgtggcttg    9120
gagcacggta tctagagttt gaagctttgg ggttcctgaa tgaagaccat tggctgagcc    9180
gagagaattc aggaggtgga gtggaaggct caggcgtcca aaagctggga tacatcctcc    9240
gtgacatagc aggaaagcaa ggagggaaaa tgtacgctga tgataccgcc gggtgggaca    9300
ctagaattac cagaactgat ttagaaaatg aagctaaggt actggagctc ctagacggtg    9360
aacaccgcat gctcgcccga gccataattg aactgactta caggcacaaa gtggtcaagg    9420
tcatgagacc tgcagcagaa ggaaagaccg tgatggacgt gatatcaaga gaagatcaaa    9480
gggggagtgg acaggtggtc acttatgctc ttaacacttt cacgaacatc gctgtccagc    9540
tcgtcaggct gatggaggct gagggggtca ttggaccaca acacttggaa catctaccta    9600
ggaaaaacaa gatagctgtc aggacctggc tctttgagaa tggagaggag agagtgacca    9660
ggatggcgat cagcggagac gactgtgccg tcaaaccgct ggacgacaga ttcgccacag    9720
ccctccactt cctcaacgca atgtcaaagg tcagaaaaga catccaggaa tggaagcctt    9780 cgcatgctg gcacgattgg cagcaagttc ccttctgttc taaccatttt caggagattg    9840
tgatgaaaga tggaaggagt atagttgtcc cgtgcagagg acaggatgag ctgataggca    9900
gggctcgcat ctctccagga gctggatgga atgtgaagga cacagcttgc ctgcccaaag    9960
catatgcaca aatgtgggta ctcctatact tccaccgcag ggacttgcgt ctcatggcaa   10020
atgcgatttg ctcagcagtg ccagtagatt gggtgccacc aggcaggaca tcctggtcaa   10080
```

```
tacactcgaa aggagagtgg atgaccacgg aagacatgct gcaggtctgg aacagagttt    10140
ggattgaaga aaatgaatgg atgatggaca agactccaat cacaagctgg acagacgttc    10200
cgtatgtggg aaagcgcgag gacatctggt gtggcagcct catcggaacg cgatccagag    10260
caacctgggc tgagaacatc tatgcggcga taaaccaggt tagagctgtc attgggaaag    10320
aaaattatgt tgactacatg acctcactca ggagatacga agacgtcttg atccaggaag    10380
acagggtcat ctagtgtgat ttaaggtaga aaagtagact atgtaaacaa tgtaaatgag    10440
aaaatgcatg catatggagt caggccagca aaagctgcca ccggatactg gtagacggt     10500 gctgcctgcg tctcagtccc aggaggactg ggttaacaaa tctgacaaca gaaagtgaga    10560
aagccctcag aactgtctcg gaagtaggtc cctgctcact ggaagttgaa agaccaacgt    10620
caggccacaa atttgtgcca ctccgctagg gagtgcggcc tgcgcagccc caggaggact    10680
gggttaccaa agccgttgag cccccacggc ccaagcctcg tctaggatgc aatagacgag    10740
gtgtaaggac tagaggttag aggagacccc gtggaaacaa caacatgcgg cccaagcccc    10800
ctcgaagctg tagaggaggt ggaaggacta gaggttagag gagacccgc atttgcatca     10860 aacagcatat tgacacctgg gaatagactg ggagatcttc tgctctatct caacatcagc    10920
tactaggcac agagcgccga agtatgtacg tggtggtgag gaagaacaca ggatct        10976
```

<210> SEQ ID NO 76
<211> LENGTH: 10838
<212> TYPE: DNA
<213> ORGANISM: Yellow fever virus

<400> SEQUENCE: 76

```
gtgctaattg aggtgcattg gtctgcaaat cgagttgcta ggcaataaac acatttggat      60
taattttaat cgttcgttga gcgattagca gagaactgac cagaacatgt ctggtcgtaa     120
agctcaggga aaaccctggg gcgtcaatat ggtacgacga ggagttcgct ccttgtcaaa     180
caaaataaaa caaaaaacaa aacaaattgg aaacagacct ggaccttcaa gaggtgttca     240
aggatttatc ttttcttttt tgttcaacat tttgactgga aaaagatca cagcccacct      300 aaagaggttg tggaaaatgc tggacccaag acaaggcttg gctgttctaa ggaaagtcaa     360
gagagtggtg ccagtttga tgagaggatt gtcctcaagg aaacgccgtt cccatgatgt      420
tctgactgtg caattcctaa ttttgggaat gctgttgatg acgggtggag tgaccttggt     480
gcggaaaaac agatggttgc tcctaaatgt gacatctgag gacctcggga aaacattctc     540
tgtgggcaca ggcaactgca caacaaacat tttggaagcc aagtactggt gcccagactc     600
aatggaatac aactgtccca atctcagtcc aagagaggag ccagatgaca ttgattgctg     660
gtgctatggg gtggaaaacg ttagagtcgc atatggtaag tgtgactcag caggcaggtc     720
taggaggtca agaagggcca ttgacttgcc tacgcatgaa accatggtt tgaagacccg      780 gcaagaaaaa tggatgactg gaagaatggg tgaaaggcaa ctccaaaaga ttgagagatg     840
gttcgtgagg aaccccttt tgcagtgac ggctctgacc attgcctacc ttgtgggaag       900
caacatgacg caacgagtcg tgattgccct actggtcttg gctgttggtc cggcctactc     960
agctcactgc attggaatta ctgacaggga tttcattgag ggggtgcatg gaggaacttg    1020
ggtttcagct accctggagc aagacaagtg tgtcactgtt atggccctg acaagccttc     1080 attggacatc tcactagaga cagtagccat tgatagacct gctgaggtga ggaaagtgtg    1140
ttacaatgca gttctcactc atgtgaagat taatgacaag tgccccagca ctggagaggc    1200
```

-continued

```
ccacctagct gaagagaacg aaggggacaa tgcgtgcaag cgcacttatt ctgatagagg      1260
ctggggcaat ggctgtggcc tatttgggaa agggagcatt gtggcatgcg ccaaattcac      1320
ttgtgccaaa tccatgagtt tgtttgaggt tgatcagacc aaaattcagt atgtcatcag      1380
agcacaattg catgtagggg ccaagcagga aaattggact accgacatta agactctcaa      1440
gtttgatgcc ctgtcaggct cccaggaagt cgagttcatt gggtatggaa aagctacact      1500
ggaatgccag gtgcaaactg cggtggactt tggtaacagt tacatcgctg agatggaaac      1560
agagagctgg atagtggaca gacagtgggc ccaggacttg accctgccat ggcagagtgg      1620
aagtggcggg gtgtggagag agatgcatca tcttgtcgaa tttgaacctc gcatgccgc      1680
cactatcaga gtactggccc tgggaaacca ggaaggctcc ttgaaaacag ctcttactgg      1740
cgcaatgagg gttacaaagg acacaaatga caacaacctt tacaaactac atggtggaca      1800
tgtttcttgc agagtgaaat tgtcagcttt gacactcaag gggacatcct acaaaatatg      1860
cactgacaaa atgttttttg tcaagaaccc aactgacact ggccatggca tgttgtgat       1920
gcaggtgaaa gtgtcaaaag gagcccctg caggattcca gtgatagtag ctgatgatct       1980
tacagcggca atcaataaag gcattttggt tacagttaac cccatcgcct caaccaatga      2040
tgatgaagtg ctgattgagg tgaacccacc ttttggagac agctacatta tcgttgggag      2100
aggagattca cgtctcactt accagtggca caagaggga agctcaatag gaaagttgtt       2160
cactcagacc atgaaaggcg tggaacgcct ggccgtcatg ggagacaccg cctgggattt      2220
cagctccgct ggagggttct tcacttcggt tgggaaagga attcatacgg tgtttggctc      2280
tgcctttcag gggctatttg gcggcttgaa ctggataaca aaggtcatca tggggcggt       2340
acttatatgg gttggcatca acacaagaaa catgacaatg tccatgagca tgatcttggt      2400
aggagtgatc atgatgtttt tgtctctagg agttggggcg gatcaaggat gcgccatcaa      2460
ctttggcaag agagagctca gtgcggaga tggtatcttc atatttagag actctgatga      2520
ctggctgaac aagtactcat actatccaga agatcctgtg aagcttgcat caatagtgaa      2580
agcctctttt gaagaaggga gtgtggcct aaattcagtt gactcccttg agcatgagat      2640
gtggagaagc agggcagatg agatcaatgc catttttgag gaaaacgagg tggacatttc      2700
tgttgtcgtg caggatccaa agaatgttta ccagagagga actcatccat tttccagaat      2760
tcggatggt ctgcagtatg gttggaagac ttggggtaag aaccttgtgt ctctccccagg      2820
gaggaagaat ggaagcttca tcatagatgg aaagtccagg aaagaatgcc cgttttcaaa      2880
ccgggtctgg aattctttcc agatagagga gtttgggacg ggagtgttca ccacacgcgt      2940
gtacatggac gcagtctttg aatacaccat agactgcgat ggatctatct ggggtgcagc      3000
ggtgaacgga aaaagagtg cccatggctc tccaacattt tggatgggaa gtcatgaagt      3060
aaatgggaca tggatgatcc acaccttgga ggcattagat tacaaggagt gtgagtggcc      3120
actgacacat acgattggaa catcagttga agagagtgaa atgttcatgc cgagatcaat      3180
cggaggccca gttagctctc acaatcatat ccctggatac aaggttcaga cgaacggacc      3240
ttggatgcag gtaccactag aagtgaagag agaagcttgc ccagggacta gcgtgatcat      3300
tgatggcaac tgtgatggac ggggaaaatc aaccagatcc accacggata gcgggaaagt      3360
tattcctgaa tggtgttgcc gctcctgcac aatgccgcct gtgagcttcc atggtagtga      3420
tgggtgttgg tatcccatgg aaattaggcc aaggaaaacg catgaaagcc atctggtgcg      3480
ctcctggggtt acagctggag aaatacatgc tgtccctttt ggtttggtga gcatgatgat      3540
agcaatggaa gtggtcctaa ggaaaagaca gggaccaaag caaatgttgg ttggaggagt      3600
```

```
agtgctcttg ggagcaatgc tggtcgggca agtaactctc cttgatttgc tgaaactcac   3660
agtggctgtg ggattgcatt tccatgagat gaacaatgga ggagacgcca tgtatatggc   3720
gttgattgct gccttttcaa tcagaccagg gctgctcatc ggctttgggc tcaggaccct   3780
atggagccct cgggaacgcc ttgtgctgac cctaggagca gccatggtgg agattgcctt   3840
gggtggcgtg atgggcggcc tgtggaagta tctaaatgca gtttctctct gcatcctgac   3900
aataaatgct gttgcttcta ggaaagcatc aaataccatc ttgcccctca tggctctgtt   3960
gacacctgtc actatggctg aggtgagact tgccgcaatg ttcttttgtg ccgtggttat   4020 catagggtc cttcaccaga atttcaagga cacctccatg cagaagacta tacctctggt   4080
ggccctcaca ctcacatctt acctgggctt gacacaacct tttttgggcc tgtgtgcatt   4140
tctggcaacc cgcatatttg ggcgaaggag tatcccagtg aatgaggcac tcgcagcagc   4200
tggtctagtg ggagtgctgg caggactggc ttttcaggag atggagaact tccttggtcc   4260
gattgcagtt ggaggactcc tgatgatgct ggttagcgtg gctgggaggg tggatgggct   4320
agagctcaag aagcttggtg aagtttcatg ggaagaggag gcggagatca gcgggagttc   4380
cgcccgctat gatgtggcac tcagtgaaca aggggagttc aagctgcttt ctgaagagaa   4440
agtgccatgg gaccaggttg tgatgacctc gctggccttg gttggggctg ccctccatcc   4500
atttgctctt ctgctggtcc ttgctgggtg gctgtttcat gtcaggggag ctaggagaag   4560 tgggatgtc ttgtgggata ttcccactcc taagatcatc gaggaatgtg aacatctgga   4620
ggatgggatt tatggcatat tccagtcaac cttcttgggg gcctcccagc gaggagtggg   4680
agtggcacag ggaggggtgt tccacacaat gtggcatgtc acaagaggag ctttccttgt   4740
caggaatggc aagaagttga ttccatcttg ggcttcagta aaggaagacc ttgtcgccta   4800
tggtggctca tggaagttgg aaggcagatg ggatggagag gaagaggtcc agttgatcgc   4860
ggctgttcca ggaaagaacg tggtcaacgt ccagacaaaa ccgagcttgt tcaaagtgag   4920
gaatggggga gaaatcgggg ctgtcgctct tgactatccg agtggcactt caggatctcc   4980
tattgttaac aggaacggag aggtgattgg gctgtacggc aatggcatcc ttgtcggtga   5040
caactccttc gtgtccgcca tatcccagac tgaggtgaag gaagaaggaa aggaggagct   5100
ccaagagatc ccgacaatgc taaagaaagg aatgacaact gtccttgatt ttcatcctgg   5160
agctgggaag acaagacgtt tcctcccaca gatcttggcc gagtgcgcac ggagacgctt   5220
gcgcactctt gtgttggccc ccaccagggt tgttctttct gaaatgaagg aggcttttca   5280
cggcctggac gtgaaattcc acacacaggc ttttttccgct cacggcagcg ggagagaagt   5340
cattgatgct atgtgccatg ccaccctaac ttacaggatg ttggaaccaa ctagggttgt   5400
taactgggaa gtgatcatta tggatgaagc ccatttttg gatccagcta gcatagccgc   5460
tagaggttgg gcagcgcaca gagctagggc aaatgaaagt gcaacaatct tgatgacagc   5520
cacaccgcct gggactagtg atgaatttcc acattcaaat ggtgaaatag aagatgttca   5580
aacggacata cccagtgagc cctggaacac agggcatgac tggatcctgg ctgacaaaag   5640
gcccacggca tggttccttc catccatcag agctgcaaat gtcatggctg cctctttgcg   5700
taaggctgga aagagtgtgg tggtcctgaa caggaaaacc tttgagagag aatacccac   5760 gataaagcag aagaaacctg actttatatt ggccactgac atagctgaaa tgggagccaa   5820
cctttgcgtg gagcgagtgc tggattgcag gacggctttt aagcctgtgc ttgtggatga   5880
agggaggaag gtggcaataa aagggccact tcgtatctcc gcatcctctg ctgctcaaag   5940
```

-continued

```
gaggggggcgc attgggagaa atcccaacag agatggagac tcatactact attctgagcc    6000
tacaagtgaa aataatgccc accacgtctg ctggttggag gcctcaatgc tcttggacaa    6060
catggaggtg aggggtggaa tggtcgcccc actctatggc gttgaaggaa ctaaaacacc    6120
agtttcccct ggtgaaatga gactgaggga tgaccagagg aaagtcttca gagaactagt    6180
gaggaattgt gacctgcccg tttggctttc gtggcaagtg gccaaggctg gtttgaagac    6240
gaatgatcgt aagtggtgtt ttgaaggccc tgaggaacat gagatcttga atgacagcgg    6300
tgaaacagtg aagtgcaggg ctcctggagg agcaaagaag cctctgcgcc caaggtggtg    6360
tgatgaaagg gtgtcatctg accagagtgc gctgtctgaa tttattaagt ttgctgaagg    6420
taggagggga gctgctgaag tgctagttgt gctgagtgaa ctccctgatt tcctggctaa    6480
aaaaggtgga gaggcaatgg ataccatcag tgtgtttctc cactctgagg aaggctctag    6540
ggcttaccgc aatgcactat caatgatgcc tgaggcaatg acaatagtca tgctgtttat    6600
actggctgga ctactgacat cgggaatggt catcttttc atgtctccca aaggcatcag    6660
tagaatgtct atggcgatgg gcacaatggc cggctgtgga tatctcatgt tccttggagg    6720
cgtcaaaccc actcacatct cctatatcat gctcatattc tttgtcctga tggtggttgt    6780
gatccccgag ccagggcaac aaaggtccat ccaagacaac caagtggcat acctcattat    6840
tggcatcctg acgctggttt cagcggtggc agccaacgag ctaggcatgc tggagaaaac    6900
caaagaggac ctctttggga agaagaactt aattccatct agtgcttcac cctggagttg    6960
gccggatctt gacctgaagc caggagctgc ctggacagtg tacgttggca ttgttacaat    7020
gctctctcca atgttgcacc actggatcaa agtcgaatat ggcaacctgt ctctgtctgg    7080
aatagcccag tcagcctcag tcctttcttt catggacaag gggataccat tcatgaagat    7140
gaatatctcg gtcataatgc tgctggtcag tggctggaat tcaataacag tgatgcctct    7200
gctctgtggc ataggtgcg ccatgctcca ctggtctctc attttacctg gaatcaaagc    7260
gcagcagtca aagcttgcac agagaagggt gttccatggc gttgccaaga accctgtggt    7320
tgatgggaat ccaacagttg acattgagga agctcctgaa atgcctgccc tttatgagaa    7380
gaaactggct ctatatctcc ttcttgctct cagcctagct tctgttgcca tgtgcagaac    7440
gccccttttca ttggctgaag gcattgtcct agcatcagct gccctagggc cgctcataga    7500
gggaaacacc agccttcttt ggaatggacc catggctgtc tccatgacag gagtcatgag    7560
ggggaatcac tatgcttttg tgggagtcat gtacaatcta tggaagatga aaactggacg    7620
ccggggagc gcgaatggaa aaactttggg tgaagtctgg aagagggaac tgaatctgtt    7680
ggacaagcga cagtttgagt tgtataaaag gaccgacatt gtggaggtgg atcgtgatac    7740
ggcacgcagg catttggccg aagggaaggt ggacaccggg gtggcggtct ccaggggggac    7800
cgcaaagtta aggtggttcc atgagcgtgg ctatgtcaag ctggaaggta gggtgattga    7860
cctggggtgt ggccgcggag ctggtgttta ctacgctgct gcgcaaaagg aagtgagtgg    7920
ggtcaaagga tttactcttg aagagacgg ccatgagaaa cccatgaatg tgcaaagtct    7980
gggatggaac atcatcacct tcaaggacaa aactgatatc caccgcctag aaccagtgaa    8040
atgtgacacc cttttgtgtg acattggaga gtcatcatcg tcatcggtca cagagggga    8100
aaggaccgtg agagttcttg atactgtaga aaatggctg gcttgtgggg ttgacaactt    8160
ctgtgtgaag gtgttagctc catacatgcc agatgttctc gagaaactgg aattgctcca    8220
aaggaggttt ggcggaacag tgatcaggaa ccctctctcc aggaattcca ctcatgaaat    8280
gtactacgtg tctggagccc gcagcaatgt cacatttact gtgaaccaaa catcccgcct    8340
```

```
cctgatgagg agaatgaggc gtccaactgg aaaagtgacc ctggaggctg acgtcatcct    8400
cccaattggg acacgcagtg ttgagacaga caagggaccc ctggacaaag aggccataga    8460
agaaagggtt gagaggataa aatctgagta catgacctct tggttttatg acaatgacaa    8520
cccctacagg acctggcact actgtggctc ctatgtcaca aaaacctcag gaagtgcggc    8580
gagcatggta aatggtgtta ttaaaattct gacatatcca tgggacagga tagaggaggt    8640
cacaagaatg gcaatgactg acacaacccc ttttggacag caaagagtgt ttaaagaaaa    8700
agttgacacc agagcaaagg atccaccagc gggaactagg aagatcatga aagttgtcaa    8760
caggtggctg ttccgccacc tggccagaga aagaaccccc agactgtgca caaggaaga     8820
atttattgca aaagtccgaa gtcatgcagc cattggagct tacctggaag aacaagaaca    8880
gtggaagact gccaatgagg ctgtccaaga cccaaagttc tgggaactgg tggatgaaga    8940
aaggaagctg caccaacaag gcaggtgtcg gacttgtgtg tacaacatga tggggaaaag    9000
agagaagaag ctgtcagagt ttgggaaagc aaagggaagc cgtgccatat ggtatatgtg    9060
gctgggagcg cggtatcttg agtttgaggc cctgggattc ctgaatgagg accattgggc    9120
ttccagggaa aactcaggag gaggagtgga aggcattggc ttacaatacc taggatatgt    9180
gatcagagac ctggctgcaa tggatggtgg tggattctac gcggatgaca ccgctggatg    9240
ggacacgcgc atcacagagg cagaccttga tgatgaacag gagatcttga actacatgag    9300
cccacatcac aaaaaactgg cacaagcagt gatggaaatg acatacaaga caaagtggt    9360
gaaagtgttg agaccagccc caggagggaa agcctacatg gatgtcataa gtcgacgaga    9420
ccagagagga tccgggcagg tagtgactta tgctctgaac accatcacca acttgaaagt    9480
ccaattgatc agaatggcag aagcagagat ggtgatacat caccaacatg ttcaagattg    9540
tgatgaatca gttctgacca ggctggaggc atggctcact gagcacggat gtaacagact    9600
gaagaggatg gcggtgagtg gagacgactg tgtggtccgg cccatcgatg acaggttcgg    9660
cctggccctg tcccatctca cgccatgtc caaggttaga aaggacatat ctgaatggca     9720
gccatcaaaa gggtggaatg attgggaaa tgtgcccttc tgttcccacc acttccatga     9780
actacagctg aaggatggca ggaggattgt ggtgccttgc cgagaacagg acgagctcat    9840
tgggagagga agggtgtctc caggaaacgg ctggatgatc aaggaaacag cttgcctcag    9900
caaagcctat gccaacatgt ggtcactgat gtattttcac aaaagggaca tgaggctact    9960
gtcattggct gtttcctcag ctgttcccac ctcatggggtt ccacaaggac gcacaacatg   10020
gtcgattcat gggaaagggg agtggatgac cacggaagac atgcttgagg tgtggaacag   10080
agtatggata accaacaacc cacacatgca ggacaagaca atggtgaaaa aatggagaga   10140
tgtcccttat ctaaccaaga acaagacaa gctgtgcgga tcactgattg gaatgaccaa    10200
tagggccacc tgggcctccc acatccattt ggtcatccat cgtatccgaa cgctgattgg   10260
acaggagaaa tacactgact acctaacagt catggacagg tattctgtgg atgctgacct   10320
gcaactgggt gagcttatct gaaacaccat ctaacaggaa taaccgggat acaaaccacg   10380
ggtggagaac cggactcccc acaacctgaa accgggatat aaaccacggc tggagaaccg   10440
gactccgcac ttaaaatgaa acagaaaccg ggataaaaac tacggatgga gaaccggact   10500
ccacacattg agacagaaga agttgtcagc ccagaaccc acacgagttt tgccactgct    10560
aagctgtgag gcagtgcagg ctgggacagc cgacctccag gttgcgaaaa acctggtttc   10620
tgggacctcc caccccagag taaaagaac ggagcctccg ctaccaccct cccacgtggt    10680
```

```
ggtagaaaga cggggtctag aggttagagg agaccctcca gggaacaaat agtgggacca   10740
tattgacgcc agggaaagac cggagtggtt ctctgctttt cctccagagg tctgtgagca   10800
cagtttgctc aagaataagc agacctttgg atgacaaa                           10838

<210> SEQ ID NO 77
<211> LENGTH: 11674
<212> TYPE: DNA
<213> ORGANISM: Chikungunya virus

<400> SEQUENCE: 77
gatggctgcg tgagacacac gtagcctacc agtttcttac tgctctactc tgcaaagcaa     60
gagattaata acccatcatg gatcctgtgt acgtggacat agacgctgac agcgcctttt    120
tgaaggccct gcaacgtgcg tacccccatg ttgaggtgga accaaggcag gtcacaccga    180
atgaccatgc taatgctaga gcgttctcgc atctagctat aaaactaata gagcaggaaa    240
ttgaccccga ctcaaccatc ctggatatcg cagtgcgcc agcaaggagg atgatgtcgg    300
acaggaagta ccactgcgtc tgcccgatgc gcagtgcgga agatcccgag agactcgcca    360
attatgcgag aaagctagca tctgccgcag gaaaagtcct ggacagaaac atctctggaa    420
agatcgggga cttacaagca gtaatggccg tgccagacac ggagacgcca acattctgct    480
tacacacaga cgtctcatgt agacagagag cagacgtcgc tataccaa gacgtctatg    540 ctgtacacgc acccacgtcg ctataccacc aggcgattaa aggggtccga gtggcgtact    600
gggttgggtt cgacacaacc ccgttcatgt acaatgccat ggcgggtgcc taccctcat    660 actcgacaaa ctgggcagat gagcaggtac tgaaggctaa aacatagga ttatgttcaa    720 cagacctgac ggaaggtaga cgaggcaagt tgtctattat gagagggaaa aagctaaaac    780
cgtgcgaccg tgtgctgttc tcagtagggt caacgctcta cccggaaagc cgcaagctac    840
ttaagagctg gcacctgcca tcggtgttcc atttaaaggg caaactcagc ttcacatgcc    900
gctgtgatac agtggtttcg tgtgagggct acgtcgttaa gagaataacg atgagcccag    960 gccctttatgg aaaaaccaca gggtatgcgg taacccacca cgcagacgga ttcctgatgt   1020
gcaagactac cgacacggtt gacggcgaaa gaatgtcatt ctcggtgtgc acatacgtgc   1080
cggcgaccat ttgtgatcaa atgaccggca tccttgctac agaagtcacg ccggaggatg   1140
cacagaagct gttggtgggg ctgaaccaga gaatagtggt taacggcaga acgcaacgga   1200
atacgaacac catgaaaaat tatctgcttc ccgtggtcgc ccaagccttc agtaagtggg   1260
caaaggagtg ccgaaagac atggaagatg aaaaactcct ggggtcaga gaaagaacac   1320 tgaccctgctg ctgtctatgg gcattcaaga agcagaaaac acacacggtc tacaagaggc   1380 ctgatacccca gtcaattcag aaggttcagg ccgagtttga cagctttgtg gtaccgagtc   1440
tgtggtcgtc cgggttgtca atcccctttga ggactagaat caaatggttg ttaagcaagg   1500
tgccaaaaac cgacctgatc ccatacagcg gagacgcccg agaagcccgg gacgcagaaa   1560
aagaagcaga ggaagaacga gaagcagaac tgactcgcga agccctacca cctctacagg   1620
cagcacagga agatgttcag gtcgaaatcg acgtggaaca gcttgaggac agagcgggcg   1680
caggaataat agagactccg agaggagcta tcaaagttac tgcccaacca acagaccacg   1740
tcgtgggaga gtacctggta ctctccccgc agaccgtact acgtagccag aagctcagtc   1800
tgattcacgc tttggcggag caagtgaaga cgtgcacgca caacggacga gcagggaggt   1860
atgcggtcga agcgtacgac ggccgagtcc tagtgccctc aggctatgca atctcgcctg   1920
aagacttcca gagtctaagc gaaagcgcaa cgatggtgta taacgaaaga gagttcgtaa   1980
```

```
acagaaagct acaccatatt gcgatgcacg gaccagccct gaacaccgac gaagagtcgt    2040
atgagctggt gagggcagag aggacagaac acgagtacgt ctacgacgtg gatcagagaa    2100
gatgctgtaa gaaggaagaa gccgcaggac tggtactggt gggcgacttg actaatccgc    2160
cctaccacga attcgcatat gaagggctaa aaatccgccc tgcctgccca tacaaaattg    2220
cagtcatagg agtcttcgga gtaccgggat ctggcaagtc agctattatc aagaacctag    2280
ttaccaggca ggacctggtg actagcggaa agaaagaaaa ctgccaagaa atcaccaccg    2340
acgtgatgag acagagaggt ctagagatat ctgcacgtac ggttgactcg ctgctcttga    2400
atggatgcaa cagaccagtc gacgtgttgt acgtagacga ggcgtttgcg tgccactctg    2460
gaacgctact tgctttgatc gccttggtga gaccaaggca gaaagttgta ctttgtggtg    2520
acccgaagca gtgcggcttc ttcaatatga tgcagatgaa agtcaactat aatcacaaca    2580
tctgcaccca agtgtaccac aaaagtatct ccaggcggtg tacactgcct gtgaccgcca    2640
ttgtgtcatc gttgcattac gaaggcaaaa tgcgcactac gaatgagtac aacaagccga    2700
ttgtagtgga cactacaggc tcaacaaaac ctgaccctgg agacctcgtg ttaacgtgct    2760
tcagagggtg ggttaaacaa ctgcaaattg actatcgtgg atacgaggtc atgacagcag    2820
ccgcatccca agggttaacc agaaaaggag tttacgcagt tagacaaaaa gttaatgaaa    2880
acccgctcta tgcatcaacg tcagagcacg tcaacgtact cctaacgcgt acggaaggta    2940
aactggtatg gaagacactt tccggcgacc cgtggataaa gacgctgcag aacccaccga    3000
aaggaaactt caaagcaact attaaggagt gggaggtgga gcatgcatca ataatggcgg    3060
gcatctgcag tcaccaaatg accttcgata cattccaaaa taaagccaac gtttgttggg    3120
ctaagagctt ggtccctatc ctcgaaacag cggggataaa actaaatgat aggcagtggt    3180
ctcagataat tcaagccttc aaagaagaca aagcatactc acctgaagta gccctgaatg    3240
aaatatgtac gcgcatgtat ggggtggatc tagacagcgg gctattttct aaaccgttgg    3300
tgtctgtgta ttacgcggat aaccactggg ataataggcc tggagggaaa atgttcggat    3360 ttaacccga ggcagcatcc attctagaaa gaaagtatcc attcacaaaa gggaagtgga    3420
acatcaacaa gcagatctgc gtgactacca ggaggataga agactttaac cctaccacca    3480
acatcatacc ggccaacagg agactaccac actcattagt ggccgaacac cgcccagtaa    3540
aaggggaaag aatggaatgg ctggttaaca agataaacgg ccaccacgtg ctcctggtca    3600
gtggctataa ccttgcactg cctactaaga gagtcacttg ggtagcgccg ttaggtgtcc    3660
gcggagcgga ctacacatac aacctagagt tgggtctgcc agcaacgctt ggtaggtatg    3720
acctagtggt cataaacatc cacacacctt ttcgcataca ccattaccaa cagtgcgtcg    3780
accacgcaat gaaactgcaa atgctcgggg gtgactcatt gagactgctc aaaccgggcg    3840
gctctctatt gatcagagca tatggttacg cagatagaac cagtgaacga gtcatctgcg    3900
tattgggacg caagtttaga tcgtctagag cgttgaaacc accatgtgtc accagcaaca    3960
ctgagatgtt tttcctattc agcaactttg acaatggcag aaggaatttc acaactcatg    4020
tcatgaacaa tcaactgaat gcagccttcg taggacaggt cacccgagca ggatgtgcac    4080
cgtcgtaccg ggtaaaacgc atggacatcg cgaagaacga tgaagagtgc gtagtcaacg    4140
ccgctaaccc tcgcgggtta ccgggtggcg gtgtttgcaa ggcagtatac aaaaaatggc    4200
cggagtcctt taagaacagt gcaacaccag tgggaaccgc aaaaacagtt atgtgcggta    4260
cgtatccagt aatccacgct gttggaccaa acttctctaa ttattcggag tctgaagggg    4320
```

```
accgggaatt ggcagctgcc tatcgagaag tcgcaaagga agtaactagg ctgggagtaa    4380
atagtgtagc tataccctctc ctctccacag gtgtatactc aggagggaaa gacaggctga    4440
cccagtcact gaaccacctc tttacagcca tggactcgac ggatgcagac gtggtcatct    4500
actgccgcga caaagaatgg gagaagaaaa tatctgaggc catacagatg cggacccaag    4560
tagagctgct ggatgagcac atctccatag actgcgatat tgttcgcgtg caccctgaca    4620
gcagcttggc aggcagaaaa ggatacagca ccacggaagg cgcactgtac tcatatctag    4680
aagggacccg ttttcatcag acggctgtgg atatggcgga gatacatact atgtggccaa    4740
agcaaacaga ggccaatgag caagtctgcc tatatgccct gggggaaagt attgaatcga    4800
tcaggcagaa atgcccggtg gatgatgcag acgcatcatc tcccccccaaa actgtcccgt    4860 gcctttgccg ttacgctatg actccagaac gcgtcacccg gcttcgcatg aaccacgtca    4920
caagcataat tgtgtgttct tcgtttcccc tcccaaagta caaaatagaa ggagtgcaaa    4980
aagtcaaatg ctctaaggta atgctatttg accacaacgt gccatcgcgc gtaagtccaa    5040
gggcttatag aggtgccgct gccggtaacc ttgcggccgt gtctgattgg gtaatgagca    5100
ccgtacctgt cgcgccgccc agaagaaggc gagggagaaa cctgactgtg acatgtgacg    5160
agagagaagg gaatataaca cccatggcta gcgtccgatt cttaggca gagctgtgtc    5220 cggtcgtaca agaaacagcg gagacgcgtg acacagcaat gtctcttcag gcaccaccga    5280
gtaccgccac ggaaccgaat catccgccga tctccttcgg agcatcaagc gagacgttcc    5340
ccattacatt tggggacttc aacgaaggag aaatcgaaag cttgtcttct gagctactaa    5400
ctttcggaga cttcttacca ggagaagtgg atgacttgac agacagcgac tggtccacgt    5460
gctcagacac ggacgacgag ttaagactag acagggcagg tgggtatata ttctcgtcgg    5520
acaccggtcc aggtcattta caacagaagt cagtacgcca gtcagtgctg ccggtgaaca    5580
ccctggagga agtccacgag gagaagtgtt acccaccta gctggatgaa gcaaaggagc    5640
aactattact taagaaactc caggagagtg catccatggc caacagaagc aggtatcagt    5700
cgcgcaaagt agaaaacatg aaagcagcaa tcatccagag actaaagaga ggctgtagac    5760
tatacttaat gtcagagacc ccaaaagtcc ctacttaccg gactacatat ccggcgcctg    5820
tgtactcgcc tccgatcaac gtccgattgt ccaatcccga gtccgcagtg gcagcatgca    5880
atgagttctt agctagaaac tatccaactg tctcatcata ccaaattacc gacgagtatg    5940
atgcatatct agacatggtg gacgggtcgg agagttgcct ggaccgagcg acattcaatc    6000
cgtcaaaact caggagctac ccgaaacagc acgcttacca cgcgccctcc atcagaagcg    6060
ctgtaccgtc cccattccag aacacactac agaatgtact ggcagcagcc acgaaaagaa    6120
actgcaacgt cacacagatg agggaattac ccactttgga ctcagcagta ttcaacgtgg    6180
agtgtttcaa aaaattcgca tgcaaccaag aatactggga agaatttgct gccagcccta    6240
ttaggataac aactgagaat ttagcaacct atgttactaa actaaaaggg ccaaaagcag    6300
cagcgctatt cgcaaaaacc cataatctac tgccactaca ggaagtacca atggataggt    6360
tcacagtaga tatgaaaagg gacgtaaagg tgactcctgg tacaaagcat acagaggaaa    6420
gacctaaggt gcaggttata caggcggctg aaccccttgg cacagcatac ctatgtggga    6480
ttcacagaga gctggttagg aggctgaacg ccgtcctcct acccaatgta catacactat    6540
ttgacatgtc tgccgaggat ttcgatgcca tcatagccgc cactttaagc caggagaca    6600 ctgttttgga aacggacata gcctcctttg ataagagcca agatgattca cttgcgctta    6660
ctgctttgat gctgttagag gatttagggg tggatcactc cctgctggac ttgatagagg    6720
```

```
ctgctttcgg agagatttcc agctgtcacc taccgacagg tacgcgcttc aagttcggcg    6780
ccatgatgaa atcaggtatg ttcctaactc tgttcgtcaa cacattgtta aacatcacca    6840
tcgccagccg agtgctggaa gatcgtctga caaaatccgc gtgcgcggcc ttcatcggcg    6900
acgacaacat aatacatgga gtcgtctccg atgaattgat ggcagccaga tgtgccactt    6960
ggatgaacat ggaagtgaag atcatagatg cagttgtatc cttgaaagcc ccttactttt    7020
gtggagggtt tatactgcac gatactgtga caggaacagc ttgcagagtg cagacccgc     7080
taaaaaggct ttttaaactg ggcaaaccgc tagcggcagg tgacgaacaa gatgaagata    7140
gaagacgagc gctggctgac gaagtgatca gatggcaacg aacagggcta attgatgagc    7200
tggagaaagc ggtatactct aggtacgaag tgcagggtat atcagttgtg gtaatgtcca    7260
tggccacctt tgcaagctcc agatccaact tcgagaagct cagaggaccc gtcataactt    7320
tgtacggcgg tcctaaatag gtacgcacta cagctaccta ttttgcagaa gccgacagca    7380
agtatctaaa cactaatcag ctacaatgga gttcatccca acccaaactt tttacaatag    7440
gaggtaccag cctcgaccct ggactccgcg ccctactatc caagtcatca ggcccagacc    7500
gcgccctcag aggcaagctg gcaacttgcc cagctgatc tcagcagtta ataaactgac     7560
aatgcgcgcg gtaccacaac agaagccacg caggaatcgg aagaataaga agcaaaagca    7620
aaacaacag gcgccacaaa acaacacaaa tcaaaagaag cagccaccta aaaagaaacc     7680
ggctcaaaag aaaagaagc cgggccgcag agagaggatg tgcatgaaaa tcgaaaatga    7740
ttgtattttc gaagtcaagc acgaaggtaa ggtaacaggt tacgcgtgcc tggtgggga    7800
caaagtaatg aaaccagcac acgtaaaggg gaccatcgat aacgcggacc tggccaaact    7860
ggcctttaag cggtcatcta agtatgacct tgaatgcgcg cagataccg tgcacatgaa     7920
gtccgacgct tcgaagttca cccatgagaa accggagggg tactacaact ggcaccacgg    7980
agcagtacag tactcaggag gccggttcac catccctaca ggtgctggca accagggga    8040
cagcggcaga ccgatcttcg acaacaaggg acgcgtggtg gccatagtct taggaggagc    8100
taatgaagga gcccgtacag ccctctcggt ggtgacctgg aataaagaca ttgtcactaa    8160
aatcaccccc gagggggccg aagagtggag tcttgccatc ccagttatgt gcctgttggc    8220
aaacaccacg ttccccctgct cccagccccc ttgcacgccc tgctgctacg aaaaggaacc    8280
ggaggaaacc ctacgcatgc ttgaggacaa cgtcatgaga cctgggtact atcagctgct    8340
acaagcatcc ttaacatgtt ctccccaccg ccagcgacgc agcaccaagg acaacttcaa    8400
tgtctataaa gccacaagac catacttagc tcactgtccc gactgtggag aagggcactc    8460
gtgccatagt cccgtagcac tagaacgcat cagaaatgaa gcgacagacg ggacgctgaa    8520
aatccaggtc tccttgcaaa tcggaataaa gacggatgac agccacgatt ggaccaagct    8580
gcgttatatg gacaaccaca tgccagcaga cgcagagagg gcggggctat ttgtaagaac    8640
atcagcaccg tgtacgatta ctggaacaat gggacactttc atcctggccc gatgtccaaa    8700
aggggaaact ctgacggtgg gattcactga cagtaggaag attagtcact catgtacgca    8760
cccatttcac cacgaccctc ctgtgatagg tcgggaaaaa ttccattccc gaccgcagca    8820
cggtaaagag ctaccttgca gcacgtacgt gcagagcacc gccgcaacta ccgaggagat    8880
agaggtacac atgcccccag acacccctga tcgcacatta atgtcacaac agtccggcaa    8940
cgtaaagatc acagtcaatg gccagacggt gcggtacaag tgtaattgcg gtggctcaaa    9000
tgaaggacta acaactacag acaaagtgat taataactgc aaggttgatc aatgtcatgc    9060
```

```
cgcggtcacc aatcacaaaa agtggcagta taactcccct ctggtcccgc gtaatgctga   9120
acttggggac cgaaaaggaa aaattcacat cccgtttccg ctggcaaatg taacatgcag   9180
ggtgcctaaa gcaaggaacc ccaccgtgac gtacgggaaa aaccaagtca tcatgctact   9240
gtatcctgac cacccaacac tcctgtccta ccggaatatg ggagaagaac caaactatca   9300
agaagagtgg gtgatgcata agaaggaagt cgtgctaacc gtgccgactg aagggctcga   9360
ggtcacgtgg ggcaacaacg agccgtataa gtattggccg cagttatcta caaacggtac   9420
agcccatggc cacccgcatg agataattct gtattattat gagctgtacc ccactatgac   9480
tgtagtagtt gtgtcagtgg ccacgttcat actcctgtcg atggtgggta tggcagcggg   9540
gatgtgcatg tgtgcacgac gcagatgcat cacaccgtat gaactgacac caggagctac   9600
cgtccctttc ctgcttagcc taatatgctg catcagaaca gctaaagcgg ccacatacca   9660
agaggctgcg atatacctgt ggaacgagca gcaacctttg ttttggctac aagcccttat   9720
tccgctggca gccctgattg ttctatgcaa ctgtctgaga ctcttaccat gctgctgtaa   9780
aacgttggct tttttagccg taatgagcgt cggtgcccac actgtgagcg cgtacgaaca   9840
cgtaacagtg atcccgaaca cggtgggagt accgtataag actctagtca atagacctgg   9900
ctacagcccc atggtattgg agatggaact actgtcagtc actttggagc caacactatc   9960
gcttgattac atcacgtgcg agtacaaaac cgtcatcccg tctccgtacg tgaagtgctg  10020
cggtacagca gagtgcaagg acaaaaacct acctgactac agctgtaagg tcttcaccgg  10080
cgtctaccca tttatgtggg gcggcgccta ctgcttctgc gacgctgaaa acacgcagtt  10140
gagcgaagca cacgtggaga agtccgaatc atgcaaaaca gaatttgcat cagcatacag  10200
ggctcatacc gcatctgcat cagctaagct ccgcgtcctt taccaaggaa ataacatcac  10260
tgtaactgcc tatgcaaacg gcgaccatgc cgtcacagtt aaggacgcca aattcattgt  10320
ggggccaatg tcttcagcct ggacaccttt cgacaacaaa attgtggtgt acaaaggtga  10380
cgtctataac atggactacc cgccctttgg cgcaggaaga ccaggacaat ttggcgatat  10440
ccaaagtcgc acacctgaga gtaaagacgt ctatgctaat acacaactgg tactgcagag  10500
accggctgtg ggtacggtac acgtgccata ctctcaggca ccatctggct ttaagtattg  10560
gctaaaagaa cgcggggcgt cgctgcagca cacagcacca tttggctgcc aaatagcaac  10620
aaacccggta agagcggtga actgcgccgt agggaacatg cccatctcca tcgacatacc  10680
ggaagcggcc ttcactaggg tcgtcgacgc gccctcttta acggacatgt cgtgcgaggt  10740
accagcctgc acccattcct cagactttgg gggcgtcgcc attattaaat atgcagccag  10800
caagaaaggc aagtgtgcgg tgcattcgat gactaacgcc gtcactattc gggaagctga  10860
gatagaagtt gaagggaatt ctcagctgca aatctctttc tcgacggcct tagccagcgc  10920
cgaattccgc gtacaagtct gttctacaca agtacactgt gcagccgagt gccaccccc   10980 gaaggaccac atagtcaact acccggcgtc acataccacc ctcggggtcc aggacatctc  11040
cgctacggcg atgtcatggg tgcagaagat cacgggaggt gtgggactgg ttgttgctgt  11100
tgccgcactg attctaatcg tggtgctatg cgtgtcgttc agcaggcact aacttgacaa  11160
ttaagtatga aggtatatgt gtcccctaag agacacactg tacatagcaa ataatctata  11220
gatcaaaggg ctacgcaacc cctgaatagt aacaaaatac aaaatcacta aaaattataa  11280
aaacagaaaa atacataaat aggtatacgt gtcccctaag agacacattg tatgtaggtg  11340
ataagtatag atcaaagggc cgaataaccc ctgaatagta acaaaatatg aaaatcaata  11400
aaaatcataa aatagaaaaa ccataaacag aagtagttca aagggctata aaaccccctga 11460
```

-continued

| | |
|---|---|
| atagtaacaa aacataaaat taataaaaat caaatgaata ccataattgg caaacggaag | 11520 |
| agatgtaggt acttaagctt cctaaaagca gccgaactca ctttgagaag taggcatagc | 11580 |
| ataccgaact cttccacgat tctccgaacc cacagggacg taggagatgt tattttgttt | 11640 |
| ttaatatttc aaaaaaaaaa aaaaaaaaaa aaaa | 11674 |

<210> SEQ ID NO 78
<211> LENGTH: 10773
<212> TYPE: DNA
<213> ORGANISM: Zika virus

<400> SEQUENCE: 78

| | |
|---|---|
| cagactgcga cagttcgagt ttgaagcgaa agctagcaac agtatcaaca ggttttattt | 60 |
| tggatttgga aacgagagtt tctggtcatg aaaaacccaa aaaagaaatc cggaggattc | 120 |
| cggattgtca atatgctaaa acgcggagta gcccgtgtga gcccctttgg gggcttgaag | 180 |
| aggctgccag ccggacttct gctgggtcat gggcccatca ggatggtctt ggcgattcta | 240 |
| gccttttga gattcacggc aatcaagcca tcactgggtc tcatcaatag atggggttca | 300 |
| gtggggaaaa aagaggctat ggaaataata aagaagttca gaaagatct ggctgccatg | 360 |
| ctgagaataa tcaatgctag gaaggagaag aagagacgag gcgcagatac tagtgtcgga | 420 |
| attgttggcc tcctgctgac cacagctatg gcagcgagg tcactagacg tgggagtgca | 480 |
| tactatatgt acttggacag aaacgacgct ggggaggcca tatcttttcc aaccacattg | 540 |
| gggatgaata gtgttatat acagatcatg gatcttggac acatgtgtga tgccaccatg | 600 |
| agctatgaat gccctatgct ggatgagggg gtggaaccag atgacgtcga ttgttggtgc | 660 |
| aacacgacgt caacttgggt tgtgtacgga acctgccatc acaaaaaagg tgaagcacgg | 720 |
| agatctagaa gagctgtgac gctcccctcc cattccacta ggaagctgca aacgcggtcg | 780 |
| caaacctggt tggaatcaag agaatacaca aagcacttga ttagagtcga aaattggata | 840 |
| ttcaggaacc ctggcttcgc gttagcagca gctgccatcg cttggcttt gggaagctca | 900 |
| acgagccaaa aagtcatata cttggtcatg atactgctga ttgccccggc atacagcatc | 960 |
| aggtgcatag gagtcagcaa tagggacttt gtggaaggta tgtcaggtgg gacttgggtt | 1020 |
| gatgttgtct tggaacatgg aggttgtgtc accgtaatgg cacaggacaa accgactgtc | 1080 |
| gacatagagc tggttacaac aacagtcagc aacatggcgg aggtaagatc ctactgctat | 1140 |
| gaggcatcaa tatcggacat ggcttcggac agccgctgcc caacacaagg tgaagcctac | 1200 |
| cttgacaagc aatcagacac tcaatatgtc tgcaaaagaa cgttagtgga cagaggctgg | 1260 |
| ggaaatggat gtggactttt tggcaaaggg agcctggtga catgcgctaa gtttgcatgc | 1320 |
| tccaagaaaa tgaccgggaa gagcatccag ccagagaatc tggagtaccg gataatgctg | 1380 |
| tcagttcatg gctcccagca cagtgggatg atcgttaatg acacaggaca tgaaactgat | 1440 |
| gagaatagag cgaaggttga gataacgccc aattccacaa gagccgaagc caccctgggg | 1500 |
| ggttttggaa gcctaggact tgattgtgaa ccgaggacag gccttgactt ttcagatttg | 1560 |
| tattacttga ctatgaataa caagcactgg ttggttcaca aggagtggtt ccacgacatt | 1620 |
| ccattacctt ggcacgctgg ggcagacacc ggaactccac actggaacaa caaagaagca | 1680 |
| ctggtagagt tcaaggacgc acatgccaaa aggcaaactg tcgtggttct agggagtcaa | 1740 |
| gaaggagcag ttcacacggc ccttgctgga gctctgaggg ctgagatgga tggtgcaaag | 1800 |
| ggaaggctgt cctctggcca cttgaaatgt cgcctgaaaa tggataaact tagattgaag | 1860 |

```
ggcgtgtcat actccttgtg taccgcagcg ttcacattca ccaagatccc ggctgaaaca    1920
ctgcacggga cagtcacagt ggaggtacag tacgcaggga cagatggacc ttgcaaggtt    1980
ccagctcaga tggcggtgga catgcaaact ctgacccag ttgggaggtt gataaccgct     2040
aaccccgtaa tcactgaaag cactgagaac tctaagatga tgctggaact tgatccacca    2100
tttggggact cttacattgt cataggagtc ggggagaaga agatcaccca ccactggcac    2160
aggagtggca gcaccattgg aaaagcattt gaagccactg tgagaggtgc caagagaatg    2220
gcagtcttgg gagacacagc ctgggacttt ggatcagttg gaggcgctct caactcattg    2280
ggcaagggca tccatcaaat ttttggagca gctttcaaat cattgtttgg aggaatgtcc    2340
tggttctcac aaattctcat tggaacgttg ctgatgtggt tgggtctgaa cacaaagaat    2400
ggatctattt cccttatgtg cttggcctta ggggagtgt tgatcttctt atccacagct    2460
gtctctgctg atgtggggtg ctcggtggac ttctcaaaga aggagacgag atgcggtaca    2520
ggggtgttcg tctataacga cgttgaagcc tggagggaca ggtacaagta ccatcctgac    2580 tcccccgta gattggcagc agcagtcaag caagcctggg aagatggtat ctgtgggatc    2640
tcctctgttt caagaatgga aaacatcatg tggagatcag tagaagggga gctcaacgca    2700
atcctggaag agaatggagt tcaactgacg gtcgttgtgg gatctgtaaa aaccccatg     2760 tggagaggtc cacagagatt gcccgtgcct gtgaacgagc tgccccacgg ctggaaggct    2820
tgggggaaat cgtacttcgt cagagcagca agacaaata acagctttgt cgtggatggt     2880
gacacactga aggaatgccc actcaaacat agagcatgga acagctttct tgtggaggat    2940
catgggttcg gggtatttca cactagtgtc tggctcaagg ttagagaaga ttattcatta    3000
gagtgtgatc cagccgttat tggaacagct gttaagggaa aggaggctgt acacagtgat    3060
ctaggctact ggattgagag tgagaagaat gacacatgga ggctgaagag ggcccatctg    3120
atcgagatga aaacatgtga atggccaaag tcccacacat tgtggacaga tggaatagaa    3180
gagagtgatc tgatcatacc caagtcttta gctgggccac tcagccatca aataccaga    3240 gagggctaca ggacccaaat gaaagggcca tggcacagtg aagagcttga aattcggttt    3300
gaggaatgcc caggcactaa ggtccacgtg gaggaaacat gtggaacaag aggaccatct    3360
ctgagatcaa ccactgcaag cggaagggtg atcgaggaat ggtgctgcag ggagtgcaca    3420 atgccccac tgtcgttccg ggctaaagat ggctgttggt atggaatgga gataaggccc     3480
aggaaagaac cagaaagtaa cttagtaagg tcaatggtga ctgcaggatc aactgatcac    3540
atggatcact tctcccttgg agtgcttgtg attctgctca tggtgcagga agggctgaag    3600
aagagaatga ccacaaagat catcataagc acatcgatgg cagtgctggt agctatgatc    3660
ctgggaggat tttcaatgag tgacctggct aagcttgcaa ttttgatggg tgccaccttc    3720
gcggaaatga acactggagg agatgtagct catctggcgc tgatagcggc attcaaagtc    3780
agaccagcgt tgctggtatc tttcatcttc agagctaatt ggacacccg tgaaagcatg    3840 ctgctggcct tggcctcgtg tcttttgcaa actgcgatct ccgccttgga aggcgacctg    3900
atggttctca tcaatggttt tgctttggcc tggttggcaa tacgagcgat ggttgttcca    3960
cgcactgata acatcacctt ggcaatcctg gctgctctga caccactggc ccggggcaca    4020
ctgcttgtgg cgtggagagc aggccttgct acttgcgggg ggtttatgct cctctctctg    4080
aagggaaaag gcagtgtgaa gaagaactta ccatttgtca tggcccctgg gactaaccgct  4140 gtgaggctgt cgaccccat caacgtgtg ggactgctgt tgctcacaag gagtgggaag      4200
cggagctggc ccctagcga agtactcaca gctgttggcc tgatatgcgc attggctgga    4260
```

```
gggttcgcca aggcagatat agagatggct gggcccatgg ccgcggtcgg tctgctaatt    4320
gtcagttacg tggtctcagg aaagagtgtg gacatgtaca ttgaaagagc aggtgacatc    4380
acatgggaaa aagatgcgga agtcactgga acagtcccc ggctcgatgt ggcgctagat    4440
gagagtggtg atttctccct ggtggaggat acggtcccc ccatgagaga gatcatactc    4500
aaggtggtcc tgatgaccat ctgtggcatg aacccaatag ccatacccct tgcagctgga    4560
gcgtggtacg tatacgtgaa gactggaaaa aggagtggtg ctctatggga tgtgcctgct    4620
cccaaggaag taaaaaggg ggagaccaca gatggagtgt acagagtaat gactcgtaga    4680
ctgctaggtt caacacaagt tggagtggga gttatgcaag agggggtctt tcacactatg    4740
tggcacgtca caaaggatc cgcgctgaga agcggtgaag ggagacttga tccatactgg    4800
ggagatgtca agcaggatct ggtgtcatac tgtggtccat ggaagctaga tgccgcctgg    4860
gacgggcaca gcgaggtgca gctcttggcc gtgccccccg agagagagc gaggaacatc    4920
cagactctgc ccggaatatt taagacaaag gatgggggaca ttggagcggt tgcgctggat    4980
tacccagcag gaacttcagg atctccaatc ctagacaagt gtgggagagt gataggactt    5040
tatggcaatg gggtcgtgat caaaaatggg agttatgtta gtgccatcac ccaagggagg    5100
agggaggaag agactcctgt tgagtgcttc gagccttcga tgctgaagaa gaagcagcta    5160
actgtcttag acttgcatcc tggagctggg aaaaccagga gagttcttcc tgaaatagtc    5220
cgtgaagcca taaaaacaag actccgtact gtgatcttag ctccaaccag ggttgtcgct    5280
gctgaaatgg aggaagccct tagagggctt ccagtgcgtt atatgacaac agcagtcaat    5340
gtcacccact ctggaacaga aatcgtcgac ttaatgtgcc atgccacctt cacttcacgt    5400
ctactacagc caatcagagt ccccaactat aatctgtata ttatggatga ggcccacttc    5460
acagatcct caagtatagc agcaagagga tacatttcaa caagggttga gatgggcgag    5520
gcggctgcca tcttcatgac cgccacgcca ccaggaaccc gtgacgcatt tccggactcc    5580
aactcaccaa ttatggacac cgaagtggaa gtcccagaga gagcctggag ctcaggcttt    5640
gattgggtga cggatcattc tggaaaaaca gtttggtttg ttccaagcgt gaggaacggc    5700
aatgagatcg cagcttgtct gacaaaggct ggaaaacggg tcatacagct cagcagaaag    5760
acttttgaga cagagttcca gaaaacaaaa catcaagagt gggactttgt cgtgacaact    5820
gacatttcag agatgggcgc caactttaaa gctgaccgtg tcatagattc caggagatgc    5880
ctaaagccgg tcatacttga tggcgagaga gtcattctgg ctggacccat gcctgtcaca    5940
catgccagcg ctgcccagag agggggggcgc ataggcagga tcccaacaa acctggagat    6000
gagtatctgt atggaggtgg gtgcgcagag actgacgaag accatgcaca ctggcttgaa    6060
gcaagaatgc tccttgacaa tatttacctc caagatggcc tcatagcctc gctctatcga    6120
cctgaggccg acaaagtagc agccattgag ggagagttca gcttaggac ggagcaaagg    6180
aagacctttg tggaactcat gaaaagagga gatcttcctg tttggctggc ctatcaggtt    6240
gcatctgccg aataaccta cacagataga agatggctgc ttgatggcac gaccaacaac    6300
accataatgg aagacagtgt gccggcagag gtgtggacca gacacggaga gaaaagagtg    6360
ctcaaaccga ggtggatgga cgccagagtt tgttcagatc atgcggccct gaagtcattc    6420
aaggagtttg ccgctgggaa aagaggagcg gcttttggag tgatggaagc cctgggaaca    6480
ctgccaggac acatgacaga gagattccag gaagccattg acaacctcgc tgtgctcatg    6540
cgggcagaga ctggaagcag gccttacaaa gccgcggcgg cccaattgcc ggagacccta    6600
```

```
gagaccatta tgcttttggg gttgctggga acagtctcgc tgggaatctt tttcgtcttg    6660
atgaggaaca agggcatagg gaagatgggc tttggaatgg tgactcttgg ggccagcgca    6720
tggctcatgt ggctctcgga aattgagcca gccagaattg catgtgtcct cattgttgtg    6780
ttcctattgc tggtggtgct catacctgag ccagaaaagc aaagatctcc ccaggacaac    6840
caaatggcaa tcatcatcat ggtagcagta ggtcttctgg gcttgattac cgccaatgaa    6900
ctcggatggt tggagagaac aaagagtgac ctaagccatc taatgggaag agagaggag    6960 ggggcaacca taggattctc aatggacatt gacctgcggc cagcctcagc ttgggccatc    7020
tatgctgcct tgacaacttt cattacccca gccgtccaac atgcagtgac cacttcatac    7080
aacaactact ccttaatggc gatggccacg caagctggag tgttgtttgg tatgggcaaa    7140
gggatgccat tctacgcatg ggactttgga gtcccgctgc taatgatagg ttgctactca    7200
caattaacac ccctgaccct aatagtggcc atcatttttgc tcgtggcgca ctacatgtac    7260
ttgatcccag gctgcaggc agcagctgcg cgtgctgccc agaagagaac ggcagctggc    7320
atcatgaaga accctgttgt ggatggaata gtggtgactg acattgacac aatgacaatt    7380
gacccccaag tggagaaaaa gatgggacag gtgctactca tagcagtagc cgtctccagc    7440
gccatactgt cgcggaccgc ctgggggtgg ggggaggctg gggccctgat cacagcggca    7500
acttccactt tgtgggaagg ctctccgaac aagtactgga actcctctac agccacttca    7560
ctgtgtaaca ttttaggg aagttacttg gctggagctt ctctaatcta cacagtaaca    7620
agaaacgctg gcttggtcaa gagacgtggg ggtggaacag agagaccct gggagagaaa    7680 tggaaggccc gcttgaacca gatgtcggcc ctggagttct actcctacaa aaagtcaggc    7740
atcaccgagg tgtgcagaga agaggcccgc cgcgccctca aggacggtgt ggcaacggga    7800
ggccatgctg tgtcccgagg aagtgcaaag ctgagatggt tggtggagcg gggatacctg    7860
cagccctatg gaaaggtcat tgatcttgga tgtggcagag ggggctggag ttactacgcc    7920
gccaccatcc gcaaagttca agaagtgaaa ggatacacaa aaggaggccc tggtcatgaa    7980
gaacccatgt tggtgcaaag ctatgggtgg aacatagtcc gtcttaagag tggggtggac    8040
gtctttcata tggcggctga gccgtgtgac acgttgctgt gtgacatagg tgagtcatca    8100
tctagtcctg aagtggaaga agcacggacg ctcagagtcc tctccatggt gggggattgg    8160
cttgaaaaaa gaccaggagc cttttgtata aaagtgttgt gcccatacac cagcactatg    8220
atggaaaccc tggagcgact gcagcgtagg tatgggggag gactggtcag agtgccactc    8280
tcccgcaact ctacacatga gatgtactgg gtctctggag cgaaaagcaa caccataaaa    8340
agtgtgtcca ccacgagcca gctcctcttg gggcgcatgg acgggcccag gaggccagtg    8400
aaatatgagg aggatgtgaa tctcggctct ggcacgcggg ctgtggtaag ctgcgctgaa    8460
gctcccaaca tgaagatcat tggtaaccgc attgaaagga tccgcagtga gcacgcggaa    8520
acgtggttct ttgacgagaa ccacccatat aggacatggg cttaccatgg aagctatgag    8580
gcccccacac aagggtcagc gtcctctcta ataaacgggg ttgtcaggct cctgtcaaaa    8640
ccctgggatg tggtgactgg agtcacagga atagccatga ccgacaccac accgtatggt    8700
cagcaaagag ttttcaagga aaagtggac actagggtgc agaccccca agaaggcact    8760 cgtcaggtta tgagcatggt ctcttcctgg ttgtggaaag agctaggcaa acacaaacgg    8820
ccacgagtct gtaccaaaga agagttcatc aacaaggttc gtagcaatgc agcattaggg    8880
gcaatatttg aagaggaaaa agagtggaag actgcagtgg aagctgtgaa cgatccaagg    8940 ttctggggctc tagtggacaa ggaaagagag caccacctga gggagagtg ccagagttgt    9000
```

-continued

```
gtgtacaaca tgatgggaaa aagagaaaag aaacaagggg aatttggaaa ggccaagggc   9060
agccgcgcca tctggtatat gtggctaggg gctagatttc tagagttcga agcccttgga   9120
ttcttgaacg aggatcactg gatggggaga gagaactcag gaggtggtgt tgaagggctg   9180
ggattacaaa gactcggata tgtcctagaa gagatgagtc gcataccagg aggaaggatg   9240
tatgcagatg acactgctgg ctgggacacc cgcatcagca ggtttgatct ggagaatgaa   9300
gctctaatca ccaaccaaat ggagaaaggg cacagggcct tggcattggc cataatcaag   9360
tacacatacc aaaacaaagt ggtaaaggtc cttagaccag ctgaaaaagg gaagacagtt   9420
atggacatta tttcgagaca agaccaaagg gggagcggac aagttgtcac ttacgctctt   9480
aacacattta ccaacctagt ggtgcaactc attcggaata tggaggctga ggaagttcta   9540
gagatgcaag acttgtggct gctgcggagg tcagagaaaa tgaccaactg gttgcagagc   9600
aacggatggg ataggctcaa acgaatggca gtcagtggag atgattgcgt tgtgaagcca   9660
attgatgata ggtttgcaca tgccctcagg ttcttgaatg atatgggaaa agttaggaag   9720
gacacacaag agtggaaacc ctcaactgga tgggacaact gggaagaagt tccgttttgc   9780
tcccaccact tcaacaagct ccatctcaag gacgggaggt ccattgtggt tcccctgccgc   9840 caccaagatg aactgattgg ccgggcccgc gtctctccag gggcgggatg gagcatccgg   9900
gagactgctt gcctagcaaa atcatatgcg caaatgtggc agctccttta tttccacaga   9960
agggacctcc gactgatggc caatgccatt tgttcatctg tgccagttga ctgggttcca  10020
actgggagaa ctacctggtc aatccatgga aaggagaat ggatgaccac tgaagacatg  10080
cttgtggtgt ggaacagagt gtggattgag agaacgacc acatggaaga caagaccccca  10140 gttacgaaat ggacagacat tccctatttg ggaaaaaggg aagacttgtg gtgtggatct  10200 ctcataggg acagaccgcg caccacctgg gctgagaaca ttaaaaacac agtcaacatg  10260
gtgcgcagga tcataggtga tgaagaaaag tacatggact acctatccac ccaagttcgc  10320
tacttgggtg aagaagggtc tacacctgga gtgctgtaag caccaatctt agtgttgtca  10380
ggcctgctag tcagccacag cttggggaaa gctgtgcagc ctgtgacccc cccaggagaa  10440
gctgggaaac caagcctata gtcaggccga gaacgccatg gcacggaaga agccatgctg  10500
cctgtgagcc cctcagagga cactgagtca aaaaaccccca cgcgcttgga ggcgcaggat  10560
gggaaaagaa ggtggcgacc ttcccccaccc ttcaatctgg ggcctgaact ggagatcagc  10620
tgtggatctc cagaagaggg actagtggtt agaggagacc ccccggaaaa cgcaaaacag  10680
catattgacg ctgggaaaga ccagagactc catgagtttc caccacgctg ccgccaggc  10740 acagatcgcc gaatagcggc ggccggtgtg ggg                               10773
```

<210> SEQ ID NO 79
<211> LENGTH: 3423
<212> TYPE: PRT
<213> ORGANISM: Zika virus

<400> SEQUENCE: 79

```
Met Lys Asn Pro Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
```

```
                50                  55                  60
Leu Ile Asn Arg Trp Gly Ser Val Gly Lys Lys Glu Ala Met Glu Ile
 65                  70                  75                  80

Ile Lys Lys Phe Lys Lys Asp Leu Ala Ala Met Leu Arg Ile Ile Asn
                 85                  90                  95

Ala Arg Lys Glu Lys Lys Arg Arg Gly Ala Asp Thr Ser Val Gly Ile
                100                 105                 110

Val Gly Leu Leu Leu Thr Thr Ala Met Ala Ala Glu Val Thr Arg Arg
                115                 120                 125

Gly Ser Ala Tyr Tyr Met Tyr Leu Asp Arg Asn Asp Ala Gly Glu Ala
                130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
                180                 185                 190

Thr Thr Ser Thr Trp Val Val Tyr Gly Thr Cys His His Lys Lys Gly
                195                 200                 205

Glu Ala Arg Arg Ser Arg Arg Ala Val Thr Leu Pro Ser His Ser Thr
210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
                260                 265                 270

Ser Gln Lys Val Ile Tyr Leu Val Met Ile Leu Leu Ile Ala Pro Ala
                275                 280                 285

Tyr Ser Ile Arg Cys Ile Gly Val Ser Asn Arg Asp Phe Val Glu Gly
                290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
                340                 345                 350

Ala Ser Ile Ser Asp Met Ala Ser Asp Ser Arg Cys Pro Thr Gln Gly
                355                 360                 365

Glu Ala Tyr Leu Asp Lys Gln Ser Asp Thr Gln Tyr Val Cys Lys Arg
                370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
                420                 425                 430

Val His Gly Ser Gln His Ser Gly Met Ile Val Asn Asp Thr Gly His
                435                 440                 445

Glu Thr Asp Glu Asn Arg Ala Lys Val Glu Ile Thr Pro Asn Ser Pro
450                 455                 460

Arg Ala Glu Ala Thr Leu Gly Gly Phe Gly Ser Leu Gly Leu Asp Cys
465                 470                 475                 480
```

-continued

Glu Pro Arg Thr Gly Leu Asp Phe Ser Asp Leu Tyr Tyr Leu Thr Met
            485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
            515                 520                 525

Lys Glu Ala Leu Val Glu Phe Lys Asp Ala His Ala Lys Arg Gln Thr
            530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
            595                 600                 605

Ala Glu Thr Leu His Gly Thr Val Thr Val Glu Val Gln Tyr Ala Gly
            610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
            675                 680                 685

His Trp His Arg Ser Gly Ser Thr Ile Gly Lys Ala Phe Glu Ala Thr
            690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
            755                 760                 765

Thr Lys Asn Gly Ser Ile Ser Leu Met Cys Leu Ala Leu Gly Gly Val
            770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
            820                 825                 830

Pro Arg Arg Leu Ala Ala Ala Val Lys Gln Ala Trp Glu Asp Gly Ile
            835                 840                 845

Cys Gly Ile Ser Ser Val Ser Arg Met Glu Asn Ile Met Trp Arg Ser
            850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895

-continued

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
            915                 920                 925

Val Asp Gly Asp Thr Leu Lys Glu Cys Pro Leu Lys His Arg Ala Trp
        930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Lys Glu Ala Val His Ser Asp Leu
            980                 985                 990

Gly Tyr Trp Ile Glu Ser Glu Lys Asn Asp Thr Trp Arg Leu Lys Arg
            995                 1000                1005

Ala His Leu Ile Glu Met Lys Thr Cys Glu Trp Pro Lys Ser His
        1010                1015                1020

Thr Leu Trp Thr Asp Gly Ile Glu Glu Ser Asp Leu Ile Ile Pro
        1025                1030                1035

Lys Ser Leu Ala Gly Pro Leu Ser His His Asn Thr Arg Glu Gly
        1040                1045                1050

Tyr Arg Thr Gln Met Lys Gly Pro Trp His Ser Glu Glu Leu Glu
        1055                1060                1065

Ile Arg Phe Glu Glu Cys Pro Gly Thr Lys Val His Val Glu Glu
        1070                1075                1080

Thr Cys Gly Thr Arg Gly Pro Ser Leu Arg Ser Thr Thr Ala Ser
        1085                1090                1095

Gly Arg Val Ile Glu Glu Trp Cys Cys Arg Glu Cys Thr Met Pro
        1100                1105                1110

Pro Leu Ser Phe Arg Ala Lys Asp Gly Cys Trp Tyr Gly Met Glu
        1115                1120                1125

Ile Arg Pro Arg Lys Glu Pro Glu Ser Asn Leu Val Arg Ser Met
        1130                1135                1140

Val Thr Ala Gly Ser Thr Asp His Met Asp His Phe Ser Leu Gly
        1145                1150                1155

Val Leu Val Ile Leu Leu Met Val Gln Glu Gly Leu Lys Lys Arg
        1160                1165                1170

Met Thr Thr Lys Ile Ile Ile Ser Thr Ser Met Ala Val Leu Val
        1175                1180                1185

Ala Met Ile Leu Gly Gly Phe Ser Met Ser Asp Leu Ala Lys Leu
        1190                1195                1200

Ala Ile Leu Met Gly Ala Thr Phe Ala Glu Met Asn Thr Gly Gly
        1205                1210                1215

Asp Val Ala His Leu Ala Leu Ile Ala Ala Phe Lys Val Arg Pro
        1220                1225                1230

Ala Leu Leu Val Ser Phe Ile Phe Arg Ala Asn Trp Thr Pro Arg
        1235                1240                1245

Glu Ser Met Leu Leu Ala Leu Ala Ser Cys Leu Leu Gln Thr Ala
        1250                1255                1260

Ile Ser Ala Leu Glu Gly Asp Leu Met Val Leu Ile Asn Gly Phe
        1265                1270                1275

Ala Leu Ala Trp Leu Ala Ile Arg Ala Met Val Val Pro Arg Thr
        1280                1285                1290

Asp Asn Ile Thr Leu Ala Ile Leu Ala Ala Leu Thr Pro Leu Ala

```
              1295                1300                1305
Arg Gly  Thr Leu Leu Val Ala  Trp Arg Ala Gly Leu  Ala Thr Cys
    1310                1315                1320

Gly Gly  Phe Met Leu Leu Ser  Leu Lys Gly Lys Gly  Ser Val Lys
    1325                1330                1335

Lys Asn  Leu Pro Phe Val Met  Ala Leu Gly Leu Thr  Ala Val Arg
    1340                1345                1350

Leu Val  Asp Pro Ile Asn Val  Val Gly Leu Leu Leu  Leu Thr Arg
    1355                1360                1365

Ser Gly  Lys Arg Ser Trp Pro  Pro Ser Glu Val Leu  Thr Ala Val
    1370                1375                1380

Gly Leu  Ile Cys Ala Leu Ala  Gly Gly Phe Ala Lys  Ala Asp Ile
    1385                1390                1395

Glu Met  Ala Gly Pro Met Ala  Ala Val Gly Leu Leu  Ile Val Ser
    1400                1405                1410

Tyr Val  Val Ser Gly Lys Ser  Val Asp Met Tyr Ile  Glu Arg Ala
    1415                1420                1425

Gly Asp  Ile Thr Trp Glu Lys  Asp Ala Glu Val Thr  Gly Asn Ser
    1430                1435                1440

Pro Arg  Leu Asp Val Ala Leu  Asp Glu Ser Gly Asp  Phe Ser Leu
    1445                1450                1455

Val Glu  Asp Asp Gly Pro Pro  Met Arg Glu Ile Ile  Leu Lys Val
    1460                1465                1470

Val Leu  Met Thr Ile Cys Gly  Met Asn Pro Ile Ala  Ile Pro Phe
    1475                1480                1485

Ala Ala  Gly Ala Trp Tyr Val  Tyr Val Lys Thr Gly  Lys Arg Ser
    1490                1495                1500

Gly Ala  Leu Trp Asp Val Pro  Ala Pro Lys Glu Val  Lys Lys Gly
    1505                1510                1515

Glu Thr  Thr Asp Gly Val Tyr  Arg Val Met Thr Arg  Arg Leu Leu
    1520                1525                1530

Gly Ser  Thr Gln Val Gly Val  Gly Val Met Gln Glu  Gly Val Phe
    1535                1540                1545

His Thr  Met Trp His Val Thr  Lys Gly Ser Ala Leu  Arg Ser Gly
    1550                1555                1560

Glu Gly  Arg Leu Asp Pro Tyr  Trp Gly Asp Val Lys  Gln Asp Leu
    1565                1570                1575

Val Ser  Tyr Cys Gly Pro Trp  Lys Leu Asp Ala Ala  Trp Asp Gly
    1580                1585                1590

His Ser  Glu Val Gln Leu Leu  Ala Val Pro Pro Gly  Glu Arg Ala
    1595                1600                1605

Arg Asn  Ile Gln Thr Leu Pro  Gly Ile Phe Lys Thr  Lys Asp Gly
    1610                1615                1620

Asp Ile  Gly Ala Val Ala Leu  Asp Tyr Pro Ala Gly  Thr Ser Gly
    1625                1630                1635

Ser Pro  Ile Leu Asp Lys Cys  Gly Arg Val Ile Gly  Leu Tyr Gly
    1640                1645                1650

Asn Gly  Val Val Ile Lys Asn  Gly Ser Tyr Val Ser  Ala Ile Thr
    1655                1660                1665

Gln Gly  Arg Arg Glu Glu Glu  Thr Pro Val Glu Cys  Phe Glu Pro
    1670                1675                1680

Ser Met  Leu Lys Lys Lys Gln  Leu Thr Val Leu Asp  Leu His Pro
    1685                1690                1695
```

-continued

```
Gly Ala Gly Lys Thr Arg Arg Val Leu Pro Glu Ile Val Arg Glu
    1700              1705                1710

Ala Ile Lys Thr Arg Leu Arg Thr Val Ile Leu Ala Pro Thr Arg
    1715              1720                1725

Val Val Ala Ala Glu Met Glu Glu Ala Leu Arg Gly Leu Pro Val
    1730              1735                1740

Arg Tyr Met Thr Thr Ala Val Asn Val Thr His Ser Gly Thr Glu
    1745              1750                1755

Ile Val Asp Leu Met Cys His Ala Thr Phe Thr Ser Arg Leu Leu
    1760              1765                1770

Gln Pro Ile Arg Val Pro Asn Tyr Asn Leu Tyr Ile Met Asp Glu
    1775              1780                1785

Ala His Phe Thr Asp Pro Ser Ser Ile Ala Ala Arg Gly Tyr Ile
    1790              1795                1800

Ser Thr Arg Val Glu Met Gly Glu Ala Ala Ile Phe Met Thr
    1805              1810                1815

Ala Thr Pro Pro Gly Thr Arg Asp Ala Phe Pro Asp Ser Asn Ser
    1820              1825                1830

Pro Ile Met Asp Thr Glu Val Glu Val Pro Glu Arg Ala Trp Ser
    1835              1840                1845

Ser Gly Phe Asp Trp Val Thr Asp His Ser Gly Lys Thr Val Trp
    1850              1855                1860

Phe Val Pro Ser Val Arg Asn Gly Asn Glu Ile Ala Ala Cys Leu
    1865              1870                1875

Thr Lys Ala Gly Lys Arg Val Ile Gln Leu Ser Arg Lys Thr Phe
    1880              1885                1890

Glu Thr Glu Phe Gln Lys Thr Lys His Gln Glu Trp Asp Phe Val
    1895              1900                1905

Val Thr Thr Asp Ile Ser Glu Met Gly Ala Asn Phe Lys Ala Asp
    1910              1915                1920

Arg Val Ile Asp Ser Arg Arg Cys Leu Lys Pro Val Ile Leu Asp
    1925              1930                1935

Gly Glu Arg Val Ile Leu Ala Gly Pro Met Pro Val Thr His Ala
    1940              1945                1950

Ser Ala Ala Gln Arg Arg Gly Arg Ile Gly Arg Asn Pro Asn Lys
    1955              1960                1965

Pro Gly Asp Glu Tyr Leu Tyr Gly Gly Gly Cys Ala Glu Thr Asp
    1970              1975                1980

Glu Asp His Ala His Trp Leu Glu Ala Arg Met Leu Leu Asp Asn
    1985              1990                1995

Ile Tyr Leu Gln Asp Gly Leu Ile Ala Ser Leu Tyr Arg Pro Glu
    2000              2005                2010

Ala Asp Lys Val Ala Ala Ile Glu Gly Glu Phe Lys Leu Arg Thr
    2015              2020                2025

Glu Gln Arg Lys Thr Phe Val Glu Leu Met Lys Arg Gly Asp Leu
    2030              2035                2040

Pro Val Trp Leu Ala Tyr Gln Val Ala Ser Ala Gly Ile Thr Tyr
    2045              2050                2055

Thr Asp Arg Arg Trp Cys Phe Asp Gly Thr Thr Asn Asn Thr Ile
    2060              2065                2070

Met Glu Asp Ser Val Pro Ala Glu Val Trp Thr Arg His Gly Glu
    2075              2080                2085
```

```
Lys Arg Val Leu Lys Pro Arg Trp Met Asp Ala Arg Val Cys Ser
2090                2095                2100

Asp His Ala Ala Leu Lys Ser Phe Lys Glu Phe Ala Ala Gly Lys
2105                2110                2115

Arg Gly Ala Ala Phe Gly Val Met Glu Ala Leu Gly Thr Leu Pro
2120                2125                2130

Gly His Met Thr Glu Arg Phe Gln Glu Ala Ile Asp Asn Leu Ala
2135                2140                2145

Val Leu Met Arg Ala Glu Thr Gly Ser Arg Pro Tyr Lys Ala Ala
2150                2155                2160

Ala Ala Gln Leu Pro Glu Thr Leu Glu Thr Ile Met Leu Leu Gly
2165                2170                2175

Leu Leu Gly Thr Val Ser Leu Gly Ile Phe Phe Val Leu Met Arg
2180                2185                2190

Asn Lys Gly Ile Gly Lys Met Gly Phe Gly Met Val Thr Leu Gly
2195                2200                2205

Ala Ser Ala Trp Leu Met Trp Leu Ser Glu Ile Glu Pro Ala Arg
2210                2215                2220

Ile Ala Cys Val Leu Ile Val Val Phe Leu Leu Leu Val Val Leu
2225                2230                2235

Ile Pro Glu Pro Glu Lys Gln Arg Ser Pro Gln Asp Asn Gln Met
2240                2245                2250

Ala Ile Ile Ile Met Val Ala Val Gly Leu Leu Gly Leu Ile Thr
2255                2260                2265

Ala Asn Glu Leu Gly Trp Leu Glu Arg Thr Lys Ser Asp Leu Ser
2270                2275                2280

His Leu Met Gly Arg Arg Glu Glu Gly Ala Thr Ile Gly Phe Ser
2285                2290                2295

Met Asp Ile Asp Leu Arg Pro Ala Ser Ala Trp Ala Ile Tyr Ala
2300                2305                2310

Ala Leu Thr Thr Phe Ile Thr Pro Ala Val Gln His Ala Val Thr
2315                2320                2325

Thr Ser Tyr Asn Asn Tyr Ser Leu Met Ala Met Ala Thr Gln Ala
2330                2335                2340

Gly Val Leu Phe Gly Met Gly Lys Gly Met Pro Phe Tyr Ala Trp
2345                2350                2355

Asp Phe Gly Val Pro Leu Leu Met Ile Gly Cys Tyr Ser Gln Leu
2360                2365                2370

Thr Pro Leu Thr Leu Ile Val Ala Ile Ile Leu Leu Val Ala His
2375                2380                2385

Tyr Met Tyr Leu Ile Pro Gly Leu Gln Ala Ala Ala Arg Ala
2390                2395                2400

Ala Gln Lys Arg Thr Ala Ala Gly Ile Met Lys Asn Pro Val Val
2405                2410                2415

Asp Gly Ile Val Val Thr Asp Ile Asp Thr Met Thr Ile Asp Pro
2420                2425                2430

Gln Val Glu Lys Lys Met Gly Gln Val Leu Leu Ile Ala Val Ala
2435                2440                2445

Val Ser Ser Ala Ile Leu Ser Arg Thr Ala Trp Gly Trp Gly Glu
2450                2455                2460

Ala Gly Ala Leu Ile Thr Ala Ala Thr Ser Thr Leu Trp Glu Gly
2465                2470                2475

Ser Pro Asn Lys Tyr Trp Asn Ser Ser Thr Ala Thr Ser Leu Cys
```

-continued

```
                2480                2485                2490
Asn Ile Phe Arg Gly Ser Tyr Leu Ala Gly Ala Ser Leu Ile Tyr
        2495                2500                2505
Thr Val Thr Arg Asn Ala Gly Leu Val Lys Arg Arg Gly Gly Gly
    2510                2515                2520
Thr Gly Glu Thr Leu Gly Glu Lys Trp Lys Ala Arg Leu Asn Gln
    2525                2530                2535
Met Ser Ala Leu Glu Phe Tyr Ser Tyr Lys Lys Ser Gly Ile Thr
    2540                2545                2550
Glu Val Cys Arg Glu Glu Ala Arg Arg Ala Leu Lys Asp Gly Val
    2555                2560                2565
Ala Thr Gly Gly His Ala Val Ser Arg Gly Ser Ala Lys Leu Arg
    2570                2575                2580
Trp Leu Val Glu Arg Gly Tyr Leu Gln Pro Tyr Gly Lys Val Ile
    2585                2590                2595
Asp Leu Gly Cys Gly Arg Gly Gly Trp Ser Tyr Tyr Ala Ala Thr
    2600                2605                2610
Ile Arg Lys Val Gln Glu Val Lys Gly Tyr Thr Lys Gly Gly Pro
    2615                2620                2625
Gly His Glu Glu Pro Met Leu Val Gln Ser Tyr Gly Trp Asn Ile
    2630                2635                2640
Val Arg Leu Lys Ser Gly Val Asp Val Phe His Met Ala Ala Glu
    2645                2650                2655
Pro Cys Asp Thr Leu Leu Cys Asp Ile Gly Glu Ser Ser Ser Ser
    2660                2665                2670
Pro Glu Val Glu Glu Ala Arg Thr Leu Arg Val Leu Ser Met Val
    2675                2680                2685
Gly Asp Trp Leu Glu Lys Arg Pro Gly Ala Phe Cys Ile Lys Val
    2690                2695                2700
Leu Cys Pro Tyr Thr Ser Thr Met Met Glu Thr Leu Glu Arg Leu
    2705                2710                2715
Gln Arg Arg Tyr Gly Gly Gly Leu Val Arg Val Pro Leu Ser Arg
    2720                2725                2730
Asn Ser Thr His Glu Met Tyr Trp Val Ser Gly Ala Lys Ser Asn
    2735                2740                2745
Thr Ile Lys Ser Val Ser Thr Thr Ser Gln Leu Leu Leu Gly Arg
    2750                2755                2760
Met Asp Gly Pro Arg Arg Pro Val Lys Tyr Glu Glu Asp Val Asn
    2765                2770                2775
Leu Gly Ser Gly Thr Arg Ala Val Val Ser Cys Ala Glu Ala Pro
    2780                2785                2790
Asn Met Lys Ile Ile Gly Asn Arg Ile Glu Arg Ile Arg Ser Glu
    2795                2800                2805
His Ala Glu Thr Trp Phe Phe Asp Glu Asn His Pro Tyr Arg Thr
    2810                2815                2820
Trp Ala Tyr His Gly Ser Tyr Glu Ala Pro Thr Gln Gly Ser Ala
    2825                2830                2835
Ser Ser Leu Ile Asn Gly Val Val Arg Leu Leu Ser Lys Pro Trp
    2840                2845                2850
Asp Val Val Thr Gly Val Thr Gly Ile Ala Met Thr Asp Thr Thr
    2855                2860                2865
Pro Tyr Gly Gln Gln Arg Val Phe Lys Glu Lys Val Asp Thr Arg
    2870                2875                2880
```

-continued

Val Pro Asp Pro Gln Glu Gly Thr Arg Gln Val Met Ser Met Val
2885              2890              2895

Ser Ser Trp Leu Trp Lys Glu Leu Gly Lys His Lys Arg Pro Arg
2900              2905              2910

Val Cys Thr Lys Glu Glu Phe Ile Asn Lys Val Arg Ser Asn Ala
2915              2920              2925

Ala Leu Gly Ala Ile Phe Glu Glu Lys Glu Trp Lys Thr Ala
2930              2935              2940

Val Glu Ala Val Asn Asp Pro Arg Phe Trp Ala Leu Val Asp Lys
2945              2950              2955

Glu Arg Glu His His Leu Arg Gly Glu Cys Gln Ser Cys Val Tyr
2960              2965              2970

Asn Met Met Gly Lys Arg Glu Lys Lys Gln Gly Glu Phe Gly Lys
2975              2980              2985

Ala Lys Gly Ser Arg Ala Ile Trp Tyr Met Trp Leu Gly Ala Arg
2990              2995              3000

Phe Leu Glu Phe Glu Ala Leu Gly Phe Leu Asn Glu Asp His Trp
3005              3010              3015

Met Gly Arg Glu Asn Ser Gly Gly Gly Val Glu Gly Leu Gly Leu
3020              3025              3030

Gln Arg Leu Gly Tyr Val Leu Glu Glu Met Ser Arg Ile Pro Gly
3035              3040              3045

Gly Arg Met Tyr Ala Asp Asp Thr Ala Gly Trp Asp Thr Arg Ile
3050              3055              3060

Ser Arg Phe Asp Leu Glu Asn Glu Ala Leu Ile Thr Asn Gln Met
3065              3070              3075

Glu Lys Gly His Arg Ala Leu Ala Leu Ala Ile Ile Lys Tyr Thr
3080              3085              3090

Tyr Gln Asn Lys Val Val Lys Val Leu Arg Pro Ala Glu Lys Gly
3095              3100              3105

Lys Thr Val Met Asp Ile Ile Ser Arg Gln Asp Gln Arg Gly Ser
3110              3115              3120

Gly Gln Val Val Thr Tyr Ala Leu Asn Thr Phe Thr Asn Leu Val
3125              3130              3135

Val Gln Leu Ile Arg Asn Met Glu Ala Glu Glu Val Leu Glu Met
3140              3145              3150

Gln Asp Leu Trp Leu Leu Arg Arg Ser Glu Lys Val Thr Asn Trp
3155              3160              3165

Leu Gln Ser Asn Gly Trp Asp Arg Leu Lys Arg Met Ala Val Ser
3170              3175              3180

Gly Asp Asp Cys Val Val Lys Pro Ile Asp Asp Arg Phe Ala His
3185              3190              3195

Ala Leu Arg Phe Leu Asn Asp Met Gly Lys Val Arg Lys Asp Thr
3200              3205              3210

Gln Glu Trp Lys Pro Ser Thr Gly Trp Asp Asn Trp Glu Glu Val
3215              3220              3225

Pro Phe Cys Ser His His Phe Asn Lys Leu His Leu Lys Asp Gly
3230              3235              3240

Arg Ser Ile Val Val Pro Cys Arg His Gln Asp Glu Leu Ile Gly
3245              3250              3255

Arg Ala Arg Val Ser Pro Gly Ala Gly Trp Ser Ile Arg Glu Thr
3260              3265              3270

```
Ala Cys Leu Ala Lys Ser Tyr Ala Gln Met Trp Gln Leu Leu Tyr
3275             3280            3285

Phe His Arg Arg Asp Leu Arg Leu Met Ala Asn Ala Ile Cys Ser
    3290            3295            3300

Ser Val Pro Val Asp Trp Val Pro Thr Gly Arg Thr Thr Trp Ser
3305            3310            3315

Ile His Gly Lys Gly Glu Trp Met Thr Thr Glu Asp Met Leu Val
3320            3325            3330

Val Trp Asn Arg Val Trp Ile Glu Glu Asn Asp His Met Glu Asp
3335            3340            3345

Lys Thr Pro Val Thr Lys Trp Thr Asp Ile Pro Tyr Leu Gly Lys
3350            3355            3360

Arg Glu Asp Leu Trp Cys Gly Ser Leu Ile Gly His Arg Pro Arg
3365            3370            3375

Thr Thr Trp Ala Glu Asn Ile Lys Asn Thr Val Asn Met Val Arg
3380            3385            3390

Arg Ile Ile Gly Asp Glu Glu Lys Tyr Met Asp Tyr Leu Ser Thr
3395            3400            3405

Gln Val Arg Tyr Leu Gly Glu Glu Gly Ser Thr Pro Gly Val Leu
3410            3415            3420
```

<210> SEQ ID NO 80
<211> LENGTH: 28
<212> TYPE: DNA
<213> ORGANISM: Artificial Sequence
<220> FEATURE:
<223> OTHER INFORMATION: primer

<400> SEQUENCE: 80
ttaggatccg ttgttgatct gtgtgaat                                    28

<210> SEQ ID NO 81
<211> LENGTH: 26
<212> TYPE: DNA
<213> ORGANISM: Artificial Sequence
<220> FEATURE:
<223> OTHER INFORMATION: primer

<400> SEQUENCE: 81
taactcgagc gtacacaacc caagtt                                      26

<210> SEQ ID NO 82
<211> LENGTH: 27
<212> TYPE: DNA
<213> ORGANISM: Artificial Sequence
<220> FEATURE:
<223> OTHER INFORMATION: primer

<400> SEQUENCE: 82
ttaggatcct cactagacgt gggagtg                                     27

<210> SEQ ID NO 83
<211> LENGTH: 29
<212> TYPE: DNA
<213> ORGANISM: Artificial Sequence
<220> FEATURE:
<223> OTHER INFORMATION: primer

<400> SEQUENCE: 83
taactcgaga agccatgtcy gatattgat                                   29

```
<210> SEQ ID NO 84
<211> LENGTH: 26
<212> TYPE: DNA
<213> ORGANISM: Artificial Sequence
<220> FEATURE:
<223> OTHER INFORMATION: primer

<400> SEQUENCE: 84
ttaggatccg catacagcat caggtg                                              26

<210> SEQ ID NO 85
<211> LENGTH: 27
<212> TYPE: DNA
<213> ORGANISM: Artificial Sequence
<220> FEATURE:
<223> OTHER INFORMATION: primer

<400> SEQUENCE: 85
taactcgagt gtggagttcc ggtgtct                                             27

<210> SEQ ID NO 86
<211> LENGTH: 31
<212> TYPE: DNA
<213> ORGANISM: Artificial Sequence
<220> FEATURE:
<223> OTHER INFORMATION: primer

<400> SEQUENCE: 86
ttaggatccg aatagagcga argttgagat a                                        31

<210> SEQ ID NO 87
<211> LENGTH: 28
<212> TYPE: DNA
<213> ORGANISM: Artificial Sequence
<220> FEATURE:
<223> OTHER INFORMATION: primer

<400> SEQUENCE: 87
taactcgagt ggtgggtgat cttcttct                                            28

<210> SEQ ID NO 88
<211> LENGTH: 31
<212> TYPE: DNA
<213> ORGANISM: Artificial Sequence
<220> FEATURE:
<223> OTHER INFORMATION: primer

<400> SEQUENCE: 88
ttaggatcca gtcacagtgg aggtacagta c                                        31

<210> SEQ ID NO 89
<211> LENGTH: 27
<212> TYPE: DNA
<213> ORGANISM: Artificial Sequence
<220> FEATURE:
<223> OTHER INFORMATION: primer

<400> SEQUENCE: 89
taactcgagc rcagatacca tcttccc                                             27

<210> SEQ ID NO 90
<211> LENGTH: 28
<212> TYPE: DNA
<213> ORGANISM: Artificial Sequence
<220> FEATURE:
<223> OTHER INFORMATION: primer
```

<400> SEQUENCE: 90
ttaggatccc ttatgtgctt ggccttag                                       28

<210> SEQ ID NO 91
<211> LENGTH: 26
<212> TYPE: DNA
<213> ORGANISM: Artificial Sequence
<220> FEATURE:
<223> OTHER INFORMATION: primer

<400> SEQUENCE: 91
taactcgagt cttcagcctc catgtg                                         26

<210> SEQ ID NO 92
<211> LENGTH: 29
<212> TYPE: DNA
<213> ORGANISM: Artificial Sequence
<220> FEATURE:
<223> OTHER INFORMATION: primer

<400> SEQUENCE: 92
ttaggatcca atgcccactc aaacataga                                      29

<210> SEQ ID NO 93
<211> LENGTH: 30
<212> TYPE: DNA
<213> ORGANISM: Artificial Sequence
<220> FEATURE:
<223> OTHER INFORMATION: primer

<400> SEQUENCE: 93
taactcgagt cattctcttc ttcagccctt                                     30

<210> SEQ ID NO 94
<211> LENGTH: 26
<212> TYPE: DNA
<213> ORGANISM: Artificial Sequence
<220> FEATURE:
<223> OTHER INFORMATION: primer

<400> SEQUENCE: 94
ttaggatcca agggtgatcg aggaat                                         26

<210> SEQ ID NO 95
<211> LENGTH: 29
<212> TYPE: DNA
<213> ORGANISM: Artificial Sequence
<220> FEATURE:
<223> OTHER INFORMATION: primer

<400> SEQUENCE: 95
taactcgagt tcccttcaga gagaggagc                                      29

<210> SEQ ID NO 96
<211> LENGTH: 28
<212> TYPE: DNA
<213> ORGANISM: Artificial Sequence
<220> FEATURE:
<223> OTHER INFORMATION: primer

<400> SEQUENCE: 96
ttaggatcct cttttgcaaa ctgcgatc                                       28

```
<210> SEQ ID NO 97
<211> LENGTH: 27
<212> TYPE: DNA
<213> ORGANISM: Artificial Sequence
<220> FEATURE:
<223> OTHER INFORMATION: primer

<400> SEQUENCE: 97
taactcgagt ccagctgcaa agggtat                                              27

<210> SEQ ID NO 98
<211> LENGTH: 28
<212> TYPE: DNA
<213> ORGANISM: Artificial Sequence
<220> FEATURE:
<223> OTHER INFORMATION: primer

<400> SEQUENCE: 98
ttaggatccg tgtggacatg tacattga                                             28

<210> SEQ ID NO 99
<211> LENGTH: 26
<212> TYPE: DNA
<213> ORGANISM: Artificial Sequence
<220> FEATURE:
<223> OTHER INFORMATION: primer

<400> SEQUENCE: 99
taactcgagc ccattgccat aaagtc                                               26

<210> SEQ ID NO 100
<211> LENGTH: 28
<212> TYPE: DNA
<213> ORGANISM: Artificial Sequence
<220> FEATURE:
<223> OTHER INFORMATION: primer

<400> SEQUENCE: 100
ttaggatcct catactgtgg tccatgga                                             28

<210> SEQ ID NO 101
<211> LENGTH: 26
<212> TYPE: DNA
<213> ORGANISM: Artificial Sequence
<220> FEATURE:
<223> OTHER INFORMATION: primer

<400> SEQUENCE: 101
taactcgagg cccatctcaa cccttg                                               26

<210> SEQ ID NO 102
<211> LENGTH: 26
<212> TYPE: DNA
<213> ORGANISM: Artificial Sequence
<220> FEATURE:
<223> OTHER INFORMATION: primer

<400> SEQUENCE: 102
ttaggatcct agagggcttc cagtgc                                               26

<210> SEQ ID NO 103
<211> LENGTH: 31
<212> TYPE: DNA
<213> ORGANISM: Artificial Sequence
<220> FEATURE:
<223> OTHER INFORMATION: primer
```

<400> SEQUENCE: 103
taactcgaga tactcatctc caggtttgtt g        31

<210> SEQ ID NO 104
<211> LENGTH: 30
<212> TYPE: DNA
<213> ORGANISM: Artificial Sequence
<220> FEATURE:
<223> OTHER INFORMATION: primer

<400> SEQUENCE: 104
ttaggatccg aaaacaaaac atcaagagtg        30

<210> SEQ ID NO 105
<211> LENGTH: 31
<212> TYPE: DNA
<213> ORGANISM: Artificial Sequence
<220> FEATURE:
<223> OTHER INFORMATION: primer

<400> SEQUENCE: 105
taactcgagg aatctctctg tcatgtgtcc t        31

<210> SEQ ID NO 106
<211> LENGTH: 26
<212> TYPE: DNA
<213> ORGANISM: Artificial Sequence
<220> FEATURE:
<223> OTHER INFORMATION: primer

<400> SEQUENCE: 106
ttaggatcct tgatggcacg accaac        26

<210> SEQ ID NO 107
<211> LENGTH: 28
<212> TYPE: DNA
<213> ORGANISM: Artificial Sequence
<220> FEATURE:
<223> OTHER INFORMATION: primer

<400> SEQUENCE: 107
ttaggatccg ttgttgatct gtgtgaat        28

<210> SEQ ID NO 108
<211> LENGTH: 26
<212> TYPE: DNA
<213> ORGANISM: Artificial Sequence
<220> FEATURE:
<223> OTHER INFORMATION: primer

<400> SEQUENCE: 108
taactcgagc aggtcaatgt ccattg        26

<210> SEQ ID NO 109
<211> LENGTH: 30
<212> TYPE: DNA
<213> ORGANISM: Artificial Sequence
<220> FEATURE:
<223> OTHER INFORMATION: primer

<400> SEQUENCE: 109
ttaggatcct gttgtgttcc tattgctggt        30

```
<210> SEQ ID NO 110
<211> LENGTH: 25
<212> TYPE: DNA
<213> ORGANISM: Artificial Sequence
<220> FEATURE:
<223> OTHER INFORMATION: primer

<400> SEQUENCE: 110
taactcgagt gatcagrgcc ccagc                                         25

<210> SEQ ID NO 111
<211> LENGTH: 26
<212> TYPE: DNA
<213> ORGANISM: Artificial Sequence
<220> FEATURE:
<223> OTHER INFORMATION: primer

<400> SEQUENCE: 111
ttaggatcct gctgcccaga agagaa                                        26

<210> SEQ ID NO 112
<211> LENGTH: 26
<212> TYPE: DNA
<213> ORGANISM: Artificial Sequence
<220> FEATURE:
<223> OTHER INFORMATION: primer

<400> SEQUENCE: 112
taactcgagc accaacaygg gttctt                                        26

<210> SEQ ID NO 113
<211> LENGTH: 25
<212> TYPE: DNA
<213> ORGANISM: Artificial Sequence
<220> FEATURE:
<223> OTHER INFORMATION: primer

<400> SEQUENCE: 113
ttaggatcct caaggacggt gtggc                                         25

<210> SEQ ID NO 114
<211> LENGTH: 28
<212> TYPE: DNA
<213> ORGANISM: Artificial Sequence
<220> FEATURE:
<223> OTHER INFORMATION: primer

<400> SEQUENCE: 114
taactcgagc aatgatcttc atgttggg                                      28

<210> SEQ ID NO 115
<211> LENGTH: 26
<212> TYPE: DNA
<213> ORGANISM: Artificial Sequence
<220> FEATURE:
<223> OTHER INFORMATION: primer

<400> SEQUENCE: 115
ttaggatcct atgggggagg actggt                                        26

<210> SEQ ID NO 116
<211> LENGTH: 25
<212> TYPE: DNA
<213> ORGANISM: Artificial Sequence
<220> FEATURE:
<223> OTHER INFORMATION: primer
```

```
<400> SEQUENCE: 116
taactcgagc ccagaacctt ggatc                                      25

<210> SEQ ID NO 117
<211> LENGTH: 25
<212> TYPE: DNA
<213> ORGANISM: Artificial Sequence
<220> FEATURE:
<223> OTHER INFORMATION: primer

<400> SEQUENCE: 117
ttaggatcca gaccccccaag aaggc                                     25

<210> SEQ ID NO 118
<211> LENGTH: 26
<212> TYPE: DNA
<213> ORGANISM: Artificial Sequence
<220> FEATURE:
<223> OTHER INFORMATION: primer

<400> SEQUENCE: 118
taactcgagc ccctttggtc ttgtct                                     26

<210> SEQ ID NO 119
<211> LENGTH: 29
<212> TYPE: DNA
<213> ORGANISM: Artificial Sequence
<220> FEATURE:
<223> OTHER INFORMATION: primer

<400> SEQUENCE: 119
ttaggatcca ggaaggatgt atgcagatg                                  29

<210> SEQ ID NO 120
<211> LENGTH: 30
<212> TYPE: DNA
<213> ORGANISM: Artificial Sequence
<220> FEATURE:
<223> OTHER INFORMATION: primer

<400> SEQUENCE: 120
taactcgaga catttgcgca tatgattttg                                 30

<210> SEQ ID NO 121
<211> LENGTH: 28
<212> TYPE: DNA
<213> ORGANISM: Artificial Sequence
<220> FEATURE:
<223> OTHER INFORMATION: primer

<400> SEQUENCE: 121
ttaggatcca ggaaggacac acaagagt                                   28

<210> SEQ ID NO 122
<211> LENGTH: 26
<212> TYPE: DNA
<213> ORGANISM: Artificial Sequence
<220> FEATURE:
<223> OTHER INFORMATION: primer

<400> SEQUENCE: 122
taactcgaga caggctgcac agcttt                                     26
```

```
<210> SEQ ID NO 123
<211> LENGTH: 28
<212> TYPE: DNA
<213> ORGANISM: Artificial Sequence
<220> FEATURE:
<223> OTHER INFORMATION: primer

<400> SEQUENCE: 123
ttaggatcct ctctcatagg gcacagac                                    28
```